United States Patent
Stoit et al.

(10) Patent No.: US 10,179,791 B2
(45) Date of Patent: Jan. 15, 2019

(54) SPIRO-CYCLIC AMINE DERIVATIVES AS S1P MODULATORS

(75) Inventors: Axel Stoit, Hoofddorp (NL); Wouter I. Iwema Bakker, Hoofddorp (NL); Hein K. A. C. Coolen, Hoofddorp (NL); Maria J. P. van Dongen, Hoofddorp (NL); Nicolas J.-L. D. Leflemme, Hoofddorp (NL); Adrian Hobson, Worcester, MA (US)

(73) Assignees: AbbVie B.V., Hoofddorp (NL); AbbVie, Inc., North Chicago, IL (US)

( * ) Notice: Subject to any disclaimer, the term of this patent is extended or adjusted under 35 U.S.C. 154(b) by 0 days.

(21) Appl. No.: 13/808,903

(22) PCT Filed: Jul. 8, 2011

(86) PCT No.: PCT/EP2011/061599
§ 371 (c)(1),
(2), (4) Date: Apr. 18, 2013

(87) PCT Pub. No.: WO2012/004378
PCT Pub. Date: Jan. 12, 2012

(65) Prior Publication Data
US 2013/0196998 A1    Aug. 1, 2013

Related U.S. Application Data

(60) Provisional application No. 61/444,186, filed on Feb. 18, 2011, provisional application No. 61/362,782, filed on Jul. 9, 2010.

(30) Foreign Application Priority Data

Jul. 9, 2010 (EP) .................................... 10169104
Feb. 18, 2011 (EP) .................................... 11154961

(51) Int. Cl.
*C07D 491/107* (2006.01)
*C07D 265/36* (2006.01)
(Continued)

(52) U.S. Cl.
CPC .......... *C07D 491/107* (2013.01); *A61K 31/44* (2013.01); *C07D 265/34* (2013.01);
(Continued)

(58) Field of Classification Search
CPC ................ C07D 265/36; C07D 265/34; C07D 491/107; C07D 401/00; A61K 31/44
(Continued)

(56) References Cited

U.S. PATENT DOCUMENTS

2003/0203940 A1   10/2003   Yoshioka et al.
2005/0090520 A1   4/2005    Lindquist
(Continued)

FOREIGN PATENT DOCUMENTS

CN    101490017 A    7/2009
CN    101511783 A    8/2009
(Continued)

OTHER PUBLICATIONS

Ca plus Englis Abstract DN 152:12124, 2009 Efficient synthesis of 5-alkoxy-(3R)-hydroxy-2,3-dihydrospiro[indene-1,4'-pipendines]: a novel scaffold for renin inhibitors by Nakamura, Yuji.*
(Continued)

*Primary Examiner* — Rita J Desai
(74) *Attorney, Agent, or Firm* — Fish & Richardson P.C.

(57) ABSTRACT

The present invention relates to spiro-cyclic amine derivatives of the formula (I)

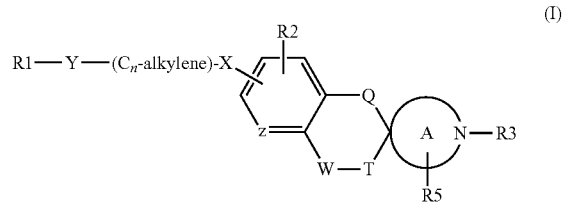

wherein
R1 is selected from
  cyano,
  (2-4C)alkenyl, (2-4C)alkynyl, (1-4C)alkyl each optionally substituted with CN or one or more fluoro atoms,
  (3-6C)cycloalkyl, (4-6C)cycloalkenyl or a (8-10C)bicyclic group, each optionally substituted with halogen or (1-4C)alkyl,
  phenyl, biphenyl, naphthyl, each optionally substituted with one or more substituents independently selected from halogen, cyano, (1-6C)alkyl optionally substituted with one or more fluoro atoms, (1-6C)alkoxy optionally substituted with one or more fluoro atoms, amino, di(1-4C)alkylamino and (3-6C)cycloalkyl optionally substituted with phenyl which may be substituted with (1-4C)alkyl or halogen,
  phenyl substituted with phenoxy, benzyl, benzyloxy, phenylethyl or monocyclic heterocycle, each optionally substituted with (1-4C)alkyl optionally substituted with one or more fluoro atoms,
  monocyclic heterocycle optionally independently substituted with halogen, (1-6C)alkyl optionally substituted with one or more fluoro atoms, (3-6C)cycloalkyl, or phenyl optionally substituted with (1-4C)alkyl or halogen,
and
  bicyclic heterocycle optionally substituted with halogen or (1-4C)alkyl optionally substituted with one or more fluoro atoms;
—Y—($C_n$-alkylene)-X— is a linking group wherein
(Continued)

Y is attached to R1 and selected from a bond, —O—, —CO—, —S—, —SO—, —SO$_2$—, —NH—, —CH═CH—, —C(CF$_3$)═CH—, —C≡C—, —CH$_2$—O—, —O—CO—, —CO—O—, —CO—NH—, —NH—CO—, and trans-cyclopropylene;

n is an integer from 0 to 10; and

X is attached to the phenylene/pyridyl moiety and selected from a bond, —O—, —S—, —SO—, —SO$_2$—, —NH—, —CO—, —CH═CH—, and trans-cyclopropylene;

R2 is H or independently selected from one or more substituents selected from halogen, (1-4C)alkoxy and (1-4C)alkyl optionally substituted with one or more fluor atoms; and R3 is (1-4C)alkylene-R4 wherein the alkylene group may be substituted with one or more halogen atoms or with (CH$_2$)$_2$ to form a cyclopropyl moiety, or R3 is (3-6C)cycloalkylene-R4, —CH$_2$-(3-6C)cycloalkylene-R4, (3-6C)cycloalkylene-CH$_2$—R4 or —CO—CH$_2$—R4, wherein R4 is —OH, —PO$_3$H$_2$, —OPO$_3$H$_2$, —COOH, —COO(1-4C)alkyl or tetrazol-5-yl;

Q is a bond or —O—;

—W-T- is selected from —CH═CH—, —CH$_2$—CH$_2$—, —CH$_2$—O—, —O—CH$_2$—, —O—CH$_2$—CH$_2$—, and —CO—O—;

R5 is H or independently selected from one or more halogens;

Z is CH, CR2 or N; and

A represents a morpholine ring structure or a 5-, 6- or 7-membered cyclic amine;

or a pharmaceutically acceptable salt, a solvate or hydrate thereof or one or more N-oxides thereof.

The compounds of the invention have affinity to S1P receptors and may be used in the treatment, alleviation or prevention of diseases and conditions in which (a) S1P receptor(s) is (are) involved.

22 Claims, 1 Drawing Sheet

(51) Int. Cl.
  *C07D 491/20* (2006.01)
  *A61K 31/44* (2006.01)
  *C07D 401/00* (2006.01)
  *C07D 265/34* (2006.01)
  *C07F 9/6561* (2006.01)

(52) U.S. Cl.
  CPC ......... *C07D 265/36* (2013.01); *C07D 401/00* (2013.01); *C07D 491/20* (2013.01); *C07F 9/6561* (2013.01)

(58) Field of Classification Search
  USPC .................. 546/17, 18; 544/71; 548/409; 514/238.8, 278
  See application file for complete search history.

(56) References Cited

U.S. PATENT DOCUMENTS

2005/0187251 A1  8/2005  Mahaney et al.
2006/0113010 A1  6/2006  Saitou et al.
2009/0023797 A1  1/2009  Azzaoui et al.
2009/0192154 A1  7/2009  Maekawara et al.
2009/0321144 A1  12/2009  Wyble et al.

FOREIGN PATENT DOCUMENTS

| CN | 101812058 A | 8/2010 |
|---|---|---|
| EP | 0431943 A2 | 6/1991 |
| EP | 2364976 A1 | 9/2011 |
| FR | 2822727 A1 | 10/2002 |
| GB | 2228432 A | 8/1990 |
| JP | H03206042 A | 9/1991 |
| JP | H06248350 A | 9/1994 |
| JP | H072848 A | 1/1995 |
| JP | H1072623 A | 3/1998 |
| JP | 2004211187 A | 7/2004 |
| JP | 2007046108 A | 2/2007 |
| JP | 2007063642 A | 3/2007 |
| SU | 1069387 A1 | 11/1985 |
| WO | WO 97/17350 | 5/1997 |
| WO | WO-2004111021 A1 | 12/2004 |
| WO | WO-2005058295 A2 | 6/2005 |
| WO | WO-2005105100 A1 | 11/2005 |
| WO | WO-2005105763 A1 | 11/2005 |
| WO | WO-2006047195 A2 | 5/2006 |
| WO | WO-2008012010 A1 | 1/2008 |
| WO | WO 2008/079382 A1 | 7/2008 |
| WO | WO-2008129029 A1 | 10/2008 |
| WO | 2009097309 | 8/2009 |
| WO | 2009097567 | 8/2009 |
| WO | WO-2011023795 A1 | 3/2011 |
| WO | WO-2011095579 A1 | 8/2011 |

OTHER PUBLICATIONS

CAS RN 1225504-67-5, STN entry date: May 28, 2010, 2-(6-chloro-5,7-dimethylspiro[chromane-2,3'-pyrrolidin]-1'-yl) acetic acid.

CAS RN 1216208-99-9, STN entry date: Apr. 4, 2010; 7-ethyl-3,4-dihydro-spiro]2H-1-benzopyran-2,4'-piperidine]-1'acetic acid, 7-ethyl-3,4-dihydro-.

CAS RN 1218487-49-0, STN entry date: Apr. 11, 2010, 2-(6-methylspiro[chromene-2,3'-pyrrolidin]-1'-yl)propanoic acid.

CAS RN 1216083-58-7, STN entry date: Apr. 4, 2010, 6-methyl-spiro[2H-1-benzopyran-2,4'-piperidine]-1'-acetic acid, 6-methyl-.

CAS RN 1215933-90-6, STN entry date: Apr. 4, 2010, 3-(7-methylspiro[chromene-2,3'-pyrrolidin]-1'-yl)propanoic acid.

CAS RN 1218530-23-4; STN entry date: Apr. 11, 2010, 2-(6-methoxyspiro[chomene-2,3'-pyrrolidin]-1'-yl)propanoic acid.

CAS RN 1216214-41-3; STN entry date: Apr. 4, 2010, 7-methoxy-spiro[2H-1-benzopyran-2,4'-piperidine]-1'-acetic acid, 7-methoxy-.

CAS RN1256794-00-9 STN Entry Date Dec. 16, 2010, Spiro[benzofuran-3(2H), 4'-piperidine], 5-bromo-.

Adlard P.A., et al., "A Novel Approach to Rapidly Prevent Age-Related Cognitive Decline," Aging Cell, 2014, vol. 13 (2), pp. 351-359.

Asle-Rousta.M., et al., "Activation of Sphingosine 1-Phosphate Receptor-1 by Sew2871 Improves Cognitive Function in Alzheimer'S Disease Model Rats," Excli Journal, 2013, vol. 12, pp. 449-461.

Bellettato C.M., et al., "Pathophysiology of Neuropathic Lysosomal Storage Disorders," Journal of Inherited Metabolic Disease, 2010, vol. 33 (4), pp. 347-362.

Blom T., et al., "FTY720 Stimulates 27-Hydroxycholesterol Production and Confers Atheroprotective Effects in Human Primary Macrophages," Circulation Research, 2010, vol. 106 (4), pp. 720-729.

Coste O., et al., "Antinociceptive Activity of the S1P-Receptor Agonist FTY720," Journal of Cellular and Molecular Medicine, 2008, vol. 12 (3), pp. 995-1004.

Cutler R.G., et al., "Involvement of Oxidative Stress-Induced Abnormalities in Ceramide and Cholesterol Metabolism in Brain Aging and Alzheimer'S Disease," Proceedings of the National Academy of Sciences of the United States of America, 2004, vol. 101 (7), pp. 2070-2075.

Deary I.J., et al., "Age-Associated Cognitive Decline," British Medical Bulletin, 2009, vol. 92, pp. 135-152.

Fukuzako H., et al., "Changes in Levels of Phosphorus Metabolites in Temporal Lobes of Drug-Naive Schizophrenic Patients," The American Journal of Psychiatry, 1999, vol. 156 (8), pp. 1205-1208.

(56) References Cited

OTHER PUBLICATIONS

Gottfries C.G., et al., "Therapy Options in Alzheimer's Disease," British Journal of Clinical Practice, 1994, vol. 48 (6), pp. 327-330.
Gregg J.P., et al., "Gene Expression Changes in Children with Autism," Genomics, 2008, vol. 91 (1), pp. 22-29.
Hait N.C., et al., "Regulation of Histone Acetylation in the Nucleus by Sphingosine-1-Phosphate," Science, 2009, vol. 325 (5945), pp. 1254-1257.
Han X., et al., "Substantial Sulfatide Deficiency and Ceramide Elevation in Very Early Alzheimer'S Disease: Potential Role in Disease Pathogenesis," Journal of Neurochemistry, 2002, vol. 82 (4), pp. 809-818.
Harada J., et al., "Sphingosine-1-Phosphate Induces Proliferation and Morphological Changes of Neural Progenitor Cells," Journal of Neurochemistry, 2004, vol. 88 (4), pp. 1026-1039.
Hicks A.A., et al., "Genetic Determinants of Circulating Sphingolipid Concentrations in European Populations," PLOS Genetics, 2009, vol. 5 (10), p. e1000672.
Hu Al-Xi., et al., "Synthesis and Characterization of 2-Arylmorpholine Hydrochloride," Journal of Hunan University (Natural Sciences), 2005, vol. 4, pp. 72.-76.
Hu A-X., et al., "Synthesis and Cyclooxygenase-2 Inhibitory Activity of 2-(2-Arylmorpholino)Ethyl Ester of Naproxen," Acta Chimica Sinica—Chinese Edition, 2008, vol. 66 (22), pp. 2553-2557.
International Search Report and Written Opinion for Application No. PCT/EP2011/006156, dated Mar. 8, 2012, 9 pages.
International Search Report and Written Opinion for Application No. PCT/EP2011/061586, dated Aug. 25, 2011, 17 pages.
International Search Report and Written Opinion for Application No. PCT/EP2011/061590, dated Aug. 12, 2011, 7 pages.
International Search Report and Written Opinion for Application No. PCT/EP2011/061599, dated Sep. 20, 2011, 12 pages.
International Search Report for Application No. PCT/EP2010/062552, dated Sep. 27, 2010, 3 pages.
Jaillard C., et al., "EDG8/S1P5: An Oligodendroglial Receptor with Dual Function on Process Retraction and Cell Survival," The Journal of Neuroscience : the Official Journal of the Society for Neuroscience, 2005, vol. 25 (6), pp. 1459-1469.
Jo S.K., et al., "Sphingosine-1-Phosphate Receptors: Biology and Therapeutic Potential in Kidney Disease," Kidney International, 2008, vol. 73 (11), pp. 1220-1230.
Kajimoto T., et al., "Involvement of Sphingosine-1-Phosphate in Glutamate Secretion in Hippocampal Neurons," Molecular and Cellular Biology, 2007, vol. 27 (9), pp. 3429-3440.
Kaneider N.C., et al., "The Immune Modulator FTY720 Targets Sphingosine-Kinase-Dependent Migration of Human Monocytes in Response to Amyloid Beta-Protein and its Precursor," The FASEB Journal, 2004, vol. 18 (11), pp. 1309-1311.
Kanno T., et al., "Regulation of Synaptic Strength by Sphingosine 1-Phosphate in the Hippocampus," Neuroscience, 2010, vol. 171 (4), pp. 973-980.
Kim W.S., et al., "Role of ATP-Binding Cassette Transporters in Brain Lipid Transport and Neurological Disease," Journal of Neurochemistry, 2008, vol. 104 (5), pp. 1145-1166.
Lahiri S., et al., "Ceramide Synthesis is Modulated by the Sphingosine Analog FTY720 Via a Mixture of Uncompetitive and Noncompetitive Inhibition in an Acyl-Coa Chain Length-Dependent Manner," The Journal of Biological Chemistry, 2009, vol. 284 (24), pp. 16090-16098.
Lee H., et al., "Bone Marrow-Derived Mesenchymal Stem Cells Prevent the Loss of Niemann-Pick Type C Mouse Purkinje Neurons by Correcting Sphingolipid Metabolism and Increasing Sphingosine-1-Phosphate," Stem Cells (Dayton, Ohio), 2010, vol. 28 (4), pp. 821-831.
Maceyka M., et al., "Sphingosine-1-Phosphate Signaling and Its Role in Disease," Trends in Cell Biology, 2012, vol. 22 (1), pp. 50-60.
Macqueen G.M., et al., "Neuropsychiatric Aspects of the Adult Variant of Tay-Sachs Disease," The Journal of Neuropsychiatry and Clinical Neurosciences, 1998, vol. 10 (1), pp. 10-19.

Mattes H., et al., "Design and Synthesis of Selective and Potent Orally Active S1P5 Agonists," ChemMedChem, 2010, vol. 5 (10), pp. 1693-1696.
Miron V.E., et al., "Central Nervous System-Directed Effects of FTY720 (Fingolimod)," Journal of the Neurological Sciences, 2008, vol. 274 (1-2), pp. 13-17.
Miron V.E., et al., "Cyclical and Dose-Dependent Responses of Adult Human Mature Oligodendrocytes to Fingolimod," The American Journal of Pathology, 2008, vol. 173 (4), pp. 1143-1152.
Miron V.E., et al., "Fingolimod (FTY720) Enhances Remyelination Following Demyelination of Organotypic Cerebellar Slices," The American Journal of Pathology, 2010, vol. 176 (6), pp. 2682-2694.
Narayan S., et al., "Evidence for Disruption of Sphingolipid Metabolism in Schizophrenia," Journal of Neuroscience Research, 2009, vol. 87 (1), pp. 278-288.
Novgorodov A.S., et al., "Activation of Sphingosine-1-Phosphate Receptor S1P5 Inhibits Oligodendrocyte Progenitor Migration," Faseb Journal : Official Publication of the Federation of American Societies for Experimental Biology, 2007, vol. 21 (7), pp. 1503-1514.
Pahnke J., et al., "Alzheimer'S Disease and Blood-Brain Barrier Function—Why have Anti-Beta-Amyloid Therapies Failed to Prevent Dementia Progression?," Neuroscience and Biobehavioral Reviews, 2009, vol. 33 (7), pp. 1099-1108.
Sanchez T., et al., "Phosphorylation and Action of the Immunomodulator FTY720 Inhibits Vascular Endothelial Cell Growth Factor-Induced Vascular Permeability," The Journal of Biological Chemistry, 2003, vol. 278 (47), pp. 47281-47290.
Sim-Selley L.J., et al., "Sphingosine-1-Phosphate Receptors Mediate Neuromodulatory Functions in the CNS," Journal of Neurochemistry, 2009, vol. 110 (4), pp. 1191-1202.
Takabe K., et al., "Inside-Out Signaling of Sphingosine-1-Phosphate: Therapeutic Targets," Pharmacological reviews, 2008, vol. 60 (2), pp. 181-195.
Takasugi N., et al., "Bace1 Activity is Modulated by Cell-Associated Sphingosine-1-Phosphate," The Journal of Neuroscience : the Official Journal of the Society for Neuroscience, 2011, vol. 31 (18), pp. 6850-6857.
Takasugi N., et al., "Fty720/Fingolimod, a Sphingosine Analogue, Reduces Amyloid-$\hat{1}^2$ Production in Neurons," Plos One, 2013, vol. 8 (5), pp. e64050.
Van Doorn R., et al., "Sphingosine 1-Phosphate Receptor 5 Mediates the Immune Quiescence of the Human Brain Endothelial Barrier," Journal of Neuroinflammation, 2012, vol. 20 (9), p. 133.
Walzer T., et al., "Natural Killer Cell Trafficking in Vivo Requires a Dedicated Sphingosine 1-Phosphate Receptor," Nature Immunology, 2007, vol. 8 (12), pp. 1337-1344.
Written Opinion for Application No. PCT/EP2010/062552, dated Oct. 14, 2010, 7 pages.
Yordanova., et al., "2-(Arylmorpholino) Ethanols and Some of their Derivatives," Farmatsiya, 1998, vol. 45 (1), pp. 3-11.
Yu N., et al., "Characterization of Lysophosphatidic Acid and Sphingosine-1-Phosphate-Mediated Signal Transduction in Rat Cortical Oligodendrocytes," Glia, 2004, vol. 45 (1), pp. 17-27.
Yutilov, et al., "Synthesis and Antiviral Activity of Spinaceamine Derivatives," Khimiko-Farmatsevticheskii Zhurnal, 1989, vol. 23 (1), pp. 56-59.
Yutilov, et al., "Synthesis and Biological Activity of N-4-beta-hydroxyethylspinaceamines," Khimiko-Farmatsevticheskii Zhurnal, 1989, vol. 23 (2), pp. 160-163.
Brailoiu, E., et al., Sphingosine 1-phosphate enhances spontaneous transmitter release at the frog neuromuscular junction, British Journal of Pharmacology, 2002, vol. 136, pp. 1093-1097.
Deogracias, R. et al., "Fingolimod, a sphingosine-1 phosphate receptor modulator, increases BDNF levels and improves symptoms of a mouse model of Rett syndrome," Proc Natl Arad Sci U S A, 2012, vol. 109(35), pp. 14230-14235.
Di Nuzzo, L., et al., "Antidepressant activity of fingolimod in mice," Pharmacol Res Perspect, 2015, col. 3(3), pp. 1-17.
Foster, C.A. et al, "FTY720 Rescue Therapy in the Dark Agouti Rat Model of Experimental Autoimmune Encephalomyelitis: Expres-

(56) References Cited

OTHER PUBLICATIONS sion of Central Nervous System Genes and Reversal of Blood-Brain-Barrier Damage," Brain Pathology, 2009, vol. 19, pp. 254-266.
Hait, N.C. et al., "Active, phosphorylated fingolimod inhibits histone deacetylases and facilitates fear extinction memory," Nat Neurosci., 2014, vol. 17(7), pp. 971-980.
Helquist, P. et al., "Treatment of Niemann-Pick Type C Disease by Histone Deacetylase Inhibitors," Neurotherapeutics, 2013, vol. 10, pp. 688-697.
Kornhuber, J. et al., "The role of ceramide in major depressive disorder," European Archives of Psychiatry and Clinical Neuroscience, 2009, vol. 259, pp. 199-204.
Subei, A.M. et al., "Sphingosine 1-Phosphate Receptor Modulators in Multiple Sclerosis," CNS Drugs, 2015, vol. 29(7), pp. 565-575.
Vidal, C.N. et al., "Mapping Corpus Callosum Deficits in Autism: An Index of Aberrant Cortical Connectivity," Biol Psychiatry, vol. 60(3), pp. 218-225.
Wang, H. et al., "Potential serum biomarkers from a metabolomics study of autism," J. Psychiatry Neurosci., 2016, vol. 41(1), pp. 27-37.
Zhang, Y. H., et al., Intracellular sphingosine 1-phosphate mediates the increased excitability produced by nerve growth factor in rat sensory neurons, J Physiol, 575(1): 101-113 (2006).
Clinical Study to Evaluate the Efficacy, Safety, and Tolerability of ACT-128800 in Patients With Relapsing-remitting Multiple Sclerosis. (2009) Retrieved from https://clinicaltrials.gov/ct2/show/NCT01006265?term=NCT01006265&rank=1 (Identification No. NCT01006265).
Safety, Tolerability, Efficacy and Optimal Dose Finding Study of BAF312 in Patients With Relapsing-remitting Multiple Sclerosis. (2009) Retrieved from https://clinicaltrials.gov/ct2/show/NCT00879658?term=NCT00879658&rank=1 (Identification No. NCT00879658).
Phase 2 Extension Trial in Patients With Relapsing-Remitting Multiple Sclerosis (RRMS) (DreaMS). (2010) Retrieved from https://clinicaltrials.gov/ct2/show/NCT01226745?term=NCT01226745&rank=1 (Identification No. NCT01226745).
A Study to Assess the Relative Bioavailability of Different Formulations of GSK2018682, a Sphingosine-1-phosphate Receptor Subtype 1 Agonist, in Healthy Volunteers. (P1A114919). (2011) Retrieved from https://clinicaltrials.gov/ct2/show/NCT01466322?term=NCT01466322&rank=1 (Identification No. NCT01466322).
European Search Report for Application No. EP16191215, dated Dec. 5, 2016, 7 pages.
Cieslik et al., The Molecular Mechanism of Amyloid β42 Peptide Toxicity: The Role of Sphingosine Kinase-1 and Mitochondrial Sirtuins, PLoS One, 10(9): e0137193. doi:10.1371/journal.pone.0137193.
Couttas et al., Loss of the neuroproteective factor Sphingosime-1-phosphate early in Alzheimer's disease pathogenesis, Acta Neuropathologica Communications, 2(9):1-13 (2014).
Doi et al., Fingolimod Phosphate Attenuates Oligomeric Amyloid β-Induced Neurotoxicity via Increased Brain-Derived Neurotrophic Factor Expression in Neurons, PLoS One, 8(4): e61988.doi:10.1371/journal.pone.0061988.
Farr et al., Spingosine-1-phosphate Receptor 5 Agonist A-971432 Improves Leaning and Memory in the SAMP8 Mouse Model of Alzheimer's Disease, Alzheimer's & Dementia, 13(7): Suppl. P949 (2017).
Fukumoto et al., Fingolimod increases brain-derived neurotrophic factor levels and ameliorates amyloid β-induced memory impairment, Behavioural Brain Res., 268: 88-93 (2014).
Gomez-Brouchet et al., Critical Role for Sphingosine Kinase-1 in Regulating Survival of Neuroblastoma Cells Exposed to Amyloid-β Peptide, Mol. Pharmacol., 72(2):341-349 (2007).
Hobson et al., Discovery of A-971432, An Orally Bioavailable Selective Sphingosine-1-phosphate receptor 5 (S1P5) Agonist for Potential Treatment of Neurodegenerative Disorders, J Med Chem, 58(23):9154-70 (2015).
Lloyd-Evans et al., Niemann-Pick disease type C1 is a sphingosine storage disease that causes deregulation of lysosomal calcium, Nature Medicine, 14(11): 1247-1255 (2008).
Malaplate-Armand et al., Soluble oligomers of amyloid-β peptide induce neuronal apoptosis by activating a cPLA2-dependent sphingomyelinase-ceramide pathway, Neurobiology of Disease, 23: 178-189 (2006).
Van der Kam et al., The Use of Selective Sphingosine-1-phosphate Receptor 5 Agonists for the Treatment of Neurodegenerative Disorders such as Alzheimer's Disease and Lysosomal Storage Diseases such as Niemann-Pick C Disease, Alzheimer's & Dementia, 10: P281 (2014).
Crooks et al., "The Synthesis and Analgesic Activities of Some Spiro[indan-1,3'-pyrrolidine] Derivatives Designed as Rigid Analogs of Profadol," American Pharmaceutical Association, vol. 71, No. 3, Mar. 1, 1982, pp. 291-294; XP-001041834.
International Search Report dated Sep. 20, 2011, PCT/EP2011/061599.

* cited by examiner

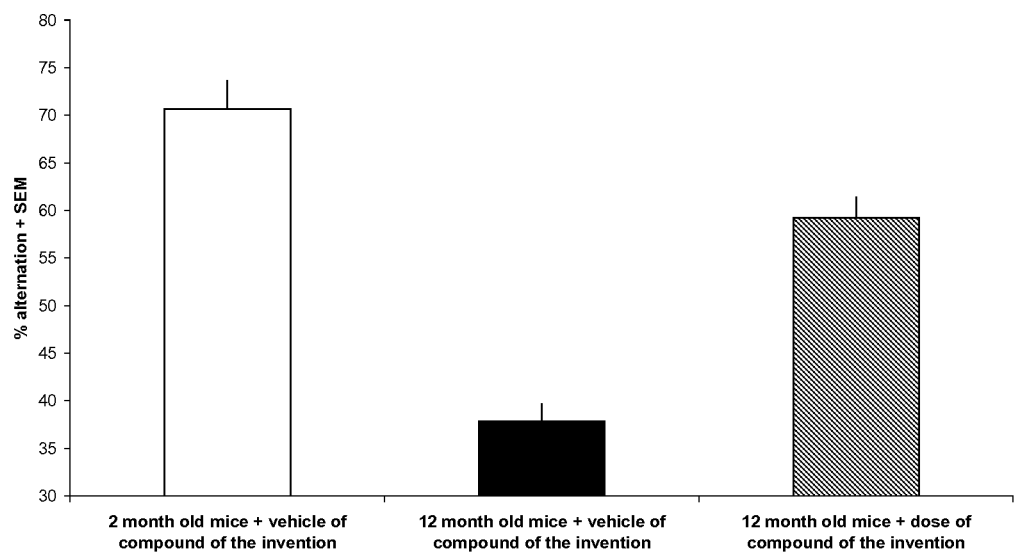

SPIRO-CYCLIC AMINE DERIVATIVES AS S1P MODULATORS

This application is a national stage entry under 35 U.S.C. § 371 of PCT/EP2011/061599, filed Jul. 8, 2011, which claims priority of U.S. Provisional Application No. 61/444,186, filed Feb. 18, 2011, U.S. Provisional Application No. 61/362,782, filed Jul. 9, 2010, European Patent Application No. 11154961.4, filed Feb. 18, 2011, and European Patent Application No. 10169104.6, filed Jul. 9, 2010, the disclosures of which are incorporated herein by reference in their entirety.

FIELD OF THE INVENTION

This invention relates to new spiro-cyclic amine derivatives having affinity to S1P receptors, a pharmaceutical composition containing said compounds, as well as the use of said compounds for the preparation of a medicament for treating, alleviating or preventing diseases and conditions in which any S1P receptor is involved or in which modulation of the endogenous S1P signaling system via any S1P receptor is involved.

BACKGROUND OF THE INVENTION

Sphingosine-1-phosphate (S1P) is a bioactive sphingolipid that mediates a wide variety of cellular responses, such as proliferation, cytoskeletal organization and migration, adherence- and tight junction assembly, and morphogenesis. S1P can bind with members of the endothelial cell differentiation gene family (EDG receptors) of plasma membrane-localized G protein-coupled receptors. To date, five members of this family have been identified as S1P receptors in different cell types, S1P1 (EDG-1), S1P2 (EDG-5), S1P3 (EDG-3), S1P4 (EDG-6) and S1P5 (EDG-8). S1P can produce cytoskeletal re-arrangements in many cell types to regulate immune cell trafficking, vascular homeostasis and cell communication in the central nervous system (CNS) and in peripheral organ systems.

It is known that S1P is secreted by vascular endothelium and is present in blood at concentrations of 200-900 nanomolar and is bound by albumin and other plasma proteins. This provides both a stable reservoir in extracellular fluids and efficient delivery to high-affinity cell-surface receptors. S1P binds with low nanomolar affinity to the five receptors S1P1-5. In addition, platelets also contain S1P and may be locally released to cause e.g. vasoconstriction. The receptor subtypes S1P1, S1P2 and S1P3 are widely expressed and represent dominant receptors in the cardiovascular system. Further, S1P1 is also a receptor on lymphocytes. S1P4 receptors are almost exclusively in the haematopoietic and lymphoid system. S1P5 is primarily (though not exclusively) expressed in central nervous system. The expression of S1P5 appears to be restricted to oligodendrocytes in mice, the myelinating cells of the brain, while in rat and man expression at the level of astrocytes and endothelial cells was found but not on oligodendrocytes.

S1P receptor modulators are compounds which signal as (ant)agonists at one or more S1P receptors. The present invention relates to modulators of the S1P5 receptor, in particular agonists, and preferably to agonists with selectivity over S1P1 and/or S1P3 receptors, in view of unwanted cardiovascular and/or immunomodulatory effects. It has now been found that S1P5 agonists can be used in the treatment of cognitive disorders, in particular age-related cognitive decline.

Although research is ongoing to develop therapeutics that can be used to treat age related cognitive decline and dementia, this has not yet resulted in many successful candidates. Therefore, there is a need for new therapeutics with the desired properties.

Description Of The Invention

It has now been found that spiro-cyclic amine derivatives of the formula (I)

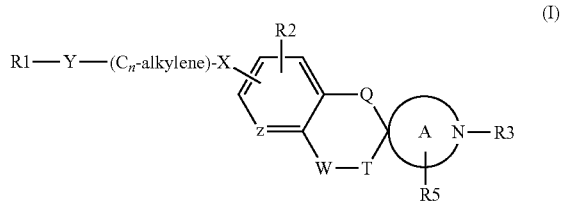

wherein
R1 is selected from
  cyano,
  (2-4C)alkenyl, (2-4C)alkynyl, (1-4C)alkyl each optionally substituted with CN or one or more fluoro atoms,
  (3-6C)cycloalkyl, (4-6C)cycloalkenyl or a (8-10C)bicyclic group, each optionally substituted with halogen or (1-4C)alkyl,
  phenyl, biphenyl, naphthyl, each optionally substituted with one or more substituents independently selected from halogen, cyano, (1-6C)alkyl optionally substituted with one or more fluoro atoms, (1-6C)alkoxy optionally substituted with one or more fluoro atoms, amino, di(1-4C)alkylamino and (3-6C)cycloalkyl optionally substituted with phenyl which may be substituted with (1-4C)alkyl or halogen,
  phenyl substituted with phenoxy, benzyl, benzyloxy, phenylethyl or monocyclic heterocycle, each optionally substituted with (1-4C)alkyl optionally substituted with one or more fluoro atoms,
  monocyclic heterocycle optionally independently substituted with halogen, (1-6C)alkyl optionally substituted with one or more fluoro atoms, (3-6C)cycloalkyl, or phenyl optionally substituted with (1-4C)alkyl or halogen,
  and
  bicyclic heterocycle optionally substituted with halogen or (1-4C)alkyl optionally substituted with one or more fluoro atoms;
—Y—($C_n$-alkylene)-X- is a linking group wherein
  Y is attached to R1 and selected from a bond, —O—, —CO—, —S—, —SO—, —SO$_2$—, —NH—, —CH=CH—, —C(CF$_3$)=CH—, —C≡C—, —CH$_2$—O—, —O—CO—, —CO—O—, —CO—NH—, —NH—CO—, and trans-cyclopropylene;
  n is an integer from 0 to 10; and
  X is attached to the phenylene/pyridyl moiety and selected from a bond, —O—, —S—, —SO—, —SO$_2$—, —NH—, —CO—, —CH=CH—, and trans-cyclopropylene;
R2 is H or independently selected from one or more substituents selected from halogen, (1-4C)alkoxy and (1-4C)alkyl optionally substituted with one or more fluor atoms; and
R3 is (1-4C)alkylene-R4 wherein the alkylene group may be substituted with one or more halogen atoms or with (CH$_2$)$_2$ to form a cyclopropyl moiety, or R3 is (3-6C)

cycloalkylene-R4, —CH$_2$-(3-6C)cycloalkylene-R4, (3-6C)cycloalkylene-CH$_2$—R4 or —CO—CH$_2$—R4, wherein R4 is —OH, —PO$_3$H$_2$, —OPO$_3$H$_2$, —COOH, —COO(1-4C)alkyl or tetrazol-5-yl;

Q is a bond or —O—;

—W-T- is selected from —CH═CH—, —CH$_2$—CH$_2$—, —CH$_2$—O—, —O—CH$_2$—, —O—CH$_2$—CH$_2$— and —CO—O—;

R5 is H or independently selected from one or more halogens;

Z is CH, CR2 or N; and

A represents a morpholine ring structure or a 5-, 6- or 7-membered cyclic amine;

or a pharmaceutically acceptable salt, a solvate or hydrate thereof or one or more N-oxides thereof, display affinity for S1P receptors. In particular, compounds of the invention show selective affinity for the S1P5 receptor over the S1P1 and/or S1P3 receptor(s).

In the prior art, structures of spiroindoline derivatives are disclosed showing some similiarties to the structures of the compounds of the present invention, e.g. in WO 2005063745. However, those compounds are modulators of the Mas receptor. There is no suggestion or teaching that the spiroindoline compounds of WO 2005063745 may display affinity for S1P receptors.

The compounds of the invention are modulators of the S1P receptor, in particular of the S1P5 receptor. More specifically, the compounds of the invention are S1P5 receptor agonists. The compounds of the invention are useful for treating, alleviating and preventing diseases and conditions in which (any) S1P receptor(s)—in particular S1P5—is (are) involved or in which modulation of the endogenous S1P signaling system via any S1P receptor is involved. In particular, the compounds of the present invention may be used to treat, alleviate or prevent CNS (central nervous system) disorders, such as neurodegenerative disorders, in particular—but not limited to—cognitive disorders (in particular age-related cognitive decline) and related conditions, Alzheimer's disease, (vascular) dementia, Nieman's Pick disease, and cognitive deficits in schizophrenia, obsessive-compulsive behavior, major depression, autism, multiple sclerosis and pain, etc. Preferably, the compounds of the present invention may be used to treat, alleviate or prevent cognitive disorders (in particular age-related cognitive decline) and related conditions.

In an embodiment of the invention, the compounds have formula (I) wherein R3 is selected from —(CH$_2$)$_2$—OH, —CH$_2$—COOH, —(CH$_2$)$_2$—COOH, —(CH$_2$)$_3$—COOH, —CH$_2$—CHCH$_3$—COOH, —CH$_2$—C(CH$_3$)$_2$—COOH, —CHCH$_3$—CH$_2$—COOH, —CH$_2$—CF$_2$—COOH, —CO—CH$_2$—COOH, 1,3-cyclobutylene-COOH, —(CH$_2$)$_2$—PO$_3$H$_2$, —(CH$_2$)$_3$—PO$_3$H$_2$, —(CH$_2$)$_2$—OPO$_3$H$_2$, —(CH$_2$)$_3$—OPO$_3$H$_2$, —CH$_2$-tetrazol-5-yl, —(CH$_2$)$_2$-tetrazol-5-yl and —(CH$_2$)$_3$-tetrazol-5-yl. Preferred R3 groups are selected from —(CH$_2$)$_2$—COOH, —CH$_2$—CHCH$_3$—COOH, —CH$_2$—C(CH$_3$)$_2$—COOH, —CHCH$_3$—CH$_2$—COOH, —CH$_2$—CF$_2$—COOH, —CO—CH$_2$—COOH and 1,3-cyclobutylene-COOH. Most preferred is —(CH$_2$)$_2$—COOH.

In another embodiment, Q is a bond.

In another embodiment, the compounds have formula (I) wherein R2 is H, methyl, chloro or fluoro. In further embodiments, R2 is H.

In a further embodiment of the invention, Z is CH or CR2.

In another embodiment, the compounds have formula (I)—W-T- is selected from —CH$_2$—O—, —O—CH$_2$—, —O—CH$_2$—CH$_2$— and —CO—O—. In preferred embodiments, —W-T- is —O—CH$_2$—.

Further, in an embodiment of the invention, in the group —Y—(C$_n$-alkylene)-X-, Y is selected from a bond, —O—, —CO—, —CH═CH—, —C(CF$_3$)═CH—, —C≡C—, and trans-cyclopropylene; n is an integer from 0 to 6. Preferably, Y is selected from a bond, —O—, —CH═CH—, —C≡C—, and trans-cyclopropylene. In further embodiments, X is selected from a bond, —O—, —S—, —SO—, —SO$_2$—, —NH—, —CO—, —CH═CH— and trans-cyclopropylene. Preferably, X is selected from a bond, —O—, —S—, —SO—, —SO$_2$—, —NH—, and —CO—. In preferred embodiments, the group —Y—(C$_n$-alkylene)-X- is selected from —CH$_2$—O—, —CH$_2$—S— and —CH═CH— and particular is —CH$_2$—O—.

In certain embodiments of the invention R1 is (1-4C)alkyl and Y is a bond, n is an integer selected from 1 to 6 and X is —O— or a bond. In further embodiments, R1 and —(CH$_2$)$_n$— together are a linear hexyl, heptyl or octyl group.

In other embodiments of the invention, R1 is selected from (1-4C)alkyl, cyclohexyl, cyclohexenyl, biphenyl optionally substituted with halogen, phenyl optionally substituted with one, two or three substituents independently selected from halogen, (1-4C)alkyl, (1-4C)alkoxy, trifluoromethyl, trifluoromethoxy, and cyclopropyl optionally substituted with phenyl, thienyl, pyridyl, tetrahydropyranyl, each optionally substituted with halogen, (1-4C)alkyl, cyclopropyl or phenyl optionally substituted with halogen, and indolyl, dihydrobenzofuranyl and benzdioxanyl, each optionally substituted with halogen or (1-4C)alkyl. In preferred embodiments of the invention, R1 is selected from phenyl, optionally substituted with one or more substituents independently selected from halogen, (1-4C)alkyl, cyclopropyl and trifluoromethyl. Further preferred, R1 is 2,6-dichlorophenyl.

In further embodiments of the invention, R5 is H.

In preferred embodiments of the invention, A represents a piperidine structure.

In another embodiment, the compounds of the invention have the structure (II)

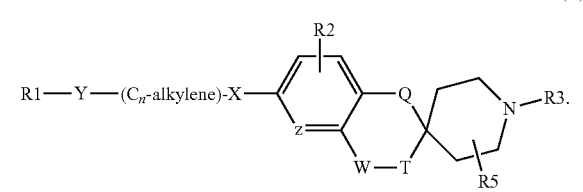

(II)

Compounds of the invention may suitably be prepared by methods available in the art, and as illustrated in the experimental section of this description. Some novel and useful intermediates have been found for the preparation of the compounds of this invention. They are further embodiments of the invention. Thus, another embodiment of the invention is a compound of the formula (III)

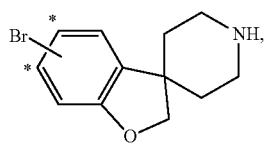

(III)

wherein Br is attached at one of the sites indicated with an asterisk.

Also, an embodiment of the invention is a compound of the formula (IV)

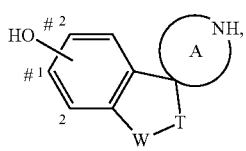

(IV)

wherein OH is attached at one of the sites indicated with #, and wherein, if OH is at the position indicated with $^1$, the compound may be independently substituted with (1-4C) alkyl or halogen selected from F or Cl at one or both positions indicated with $^2$; and W-T is —O—CH$_2$— or —CH$_2$—CH$_2$—; and A represents a morpholine ring structure or a 5- or 6-membered cyclic amine. Compounds of formula (III) are useful in the preparation of compounds of the formula (I) wherein —W-T- is —O—CH$_2$— and compounds of formula (IV) in the preparation of compounds of the formula (I) wherein —W-T- is —O—CH$_2$— or —CH$_2$—CH$_2$—.

According to a further embodiment of this invention, a very efficient process for the preparation of a compound of formula (I) wherein R2 is H or one or two substituents selected from fluoro, (1-4C)alkyl and (1-4C)alkoxy; —W-T- is —O—CH$_2$— and Z is CH or CR2, is a process, comprising an intramolecular Heck cyclization step wherein a compound of formula (V),

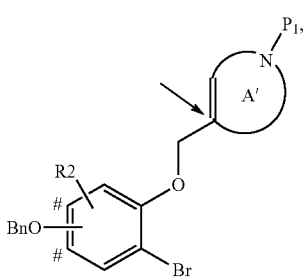

(V)

wherein A' represents a 5-, 6- or 7-membered cyclic amine with a double bond at the carbon atom indicated with an arrow, P1 is a protecting group selected from —CO$_2$-benzyl and —CO$_2$-(1-4C)alkyl (preferably —CO$_2$-benzyl), Bn is benzyl and the BnO-group may be attached at one of the sites indicated with #, is converted in a suitable solvent at elevated temperature (e.g. in N-Methyl-2-pyrrolidone (NMP) at 140° C.), in the presence of silver carbonate (preferably in 1-2 molar amounts with regard to the amount of compound V) and Herrmann-Beller catalyst (in 1-10 mol %, preferably 3-6 mol %) into a compound of formula (VI),

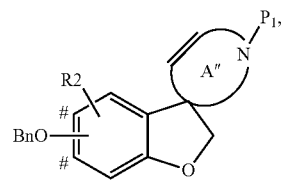

(VI)

wherein A" represents a 5-, 6- or 7-membered cyclic amine with a double bond at a position shifted one or (transiently) two positions—depending on the position of the nitrogen atom in the ring—with regard to ring A', whereafter further process steps follow (such as first deprotection and reduction to produce a compound according to formula (IV)) to produce a compound of formula (I).

The term halogen refers to fluoro, chloro, bromo, or iodo. Preferred halogens are fluoro and chloro, and in particular chloro.

The terms (1-6C) and (1-4C)alkyl mean a branched or unbranched alkyl group having 1-6 and 1-4 carbon atoms, respectively, for example methyl, ethyl, propyl, isopropyl and butyl. A preferred alkyl group is methyl.

The term (1-4C)alkoxy means an alkoxy group having 1-4 carbon atoms, wherein the alkyl moiety is as defined above. A preferred alkoxy group is methoxy.

The terms (1-4C)alkylene and (C$_n$-alkylene) mean a branched or unbranched alkylene group having 1-4 or n carbon atoms, respectively, for example methylene, —CHCH$_3$—, —C(CH$_3$)$_2$—, —CHCH$_3$CH$_2$—, and the like. In the definition of R3 which is (1-4C)alkylene-R4, one or more carbon atoms in the alkylene group may (amongst others) independently be substituted with (CH$_2$)$_2$ to form a cyclopropyl moiety, meaning to form a R3 group such as

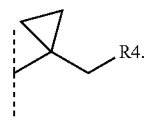

The term (2-4C)alkynyl means a branched or unbranched alkynyl group having 2-4 carbon atoms, wherein the triple bond may be present at different positions in the group, for example ethynyl, propargyl, 1-butynyl, 2-butynyl, etc.

The terms 5-, 6- or 7-membered cyclic amine as used in the definition of formula (I) refer to pyrrolidinyl, piperidinyl and hexamethyleneiminyl structures, respectively.

The term (3-6C)cycloalkyl means a cyclic alkyl group having 3-6 carbon atoms, thus cyclopropyl, cyclobutyl, cyclopentyl or cyclohexyl. Preferred are cyclopentyl and cyclohexyl.

The term (4-6C)cycloalkenyl means a cyclic alkenyl group having 4-6 carbon atoms and comprising one or two double bonds, for example cyclohexenyl.

The term (3-6C)cycloalkylene means a cyclic alkyl group having two attachment points. Preferred is 1,3-cyclobutylene, having the structure

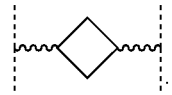

The term (8-10C)bicyclic group means a fused ring system of two groups selected from aromatic and non-aromatic ring structures having together 8-10 carbon atoms, for example—and in particular—the indane group.

The term monocyclic heterocycle encompasses monocyclic heteroaryl groups and non-aromatic heteromonocyclic groups, for example furanyl, thienyl, pyrrolyl, oxazolyl, thiazolyl, imidazolyl, pyrazolyl, isoxazolyl, isothiazolyl, triazolyl, oxadiazolyl, pyridyl, pyridazinyl, pyrimidinyl, pyrazinyl, triazinyl, tetrahydrofuranyl, tetrahydropyranyl, dioxanyl, morpholinyl, and the like.

The term bicyclic heterocycle encompasses bicyclic heteroaryl groups and non-aromatic heterobicyclic groups, for example indolyl, indazolyl, isoindolyl, indolizinyl, benzimidazolyl, imidazothiazolyl, imidazopyridinyl, benzfuranyl, dihydrobenzofuranyl, benzdioxanyl, quinolinyl, isoquinolinyl, quinolizinyl, tetrahydroisoquinolinyl, and the like.

With reference to substituents, the term "independently" means that the substituents may be the same or different from each other in the same molecule.

The compounds of the present invention may contain one or more asymmetric centers and can thus occur as racemates and racemic mixtures, single enantiomers, diastereomeric mixtures and individual diastereomers.

Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Compounds may exist as polymorphs and as such are intended to be included in the present invention. In addition, compounds may form solvates with water (i.e., hydrates) or common organic solvents, and such solvates are also intended to be encompassed within the scope of this invention.

Isotopically-labeled compound of formula (I) or pharmaceutically acceptable salts thereof, including compounds of formula (I) isotopically-labeled to be detectable by PET or SPECT, also fall within the scope of the invention. The same applies to compounds of formula (I) labeled with $[^{13}C]$—, $[^{14}C]$—, $[^{3}H]$—, $[^{18}F]$—, $[^{125}I]$—or other isotopically enriched atoms, suitable for receptor binding or metabolism studies.

The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when isolating and purifying the compounds of the invention, or separately by reacting them with pharmaceutically acceptable non-toxic bases or acids, including inorganic or organic bases and inorganic or organic acids.

The compounds of the invention may be administered enterally or parenterally. The exact dose and regimen of these compounds and compositions thereof will be dependent on the biological activity of the compound per se, the age, weight and sex of the patient, the needs of the individual subject to whom the medicament is administered, the degree of affliction or need and the judgment of the medical practitioner. In general, parenteral administration requires lower dosages than other methods of administration which are more dependent upon adsorption. However, the dosages for humans are preferably 0.001-10 mg per kg body weight. In general, enteral and parenteral dosages will be in the range of 0.1 to 1,000 mg per day of total active ingredients.

Mixed with pharmaceutically suitable auxiliaries, e.g. as described in the standard reference "Remington, The Science and Practice of Pharmacy" (21$^{st}$ edition, Lippincott Williams & Wilkins, 2005, see especially Part 5: Pharmaceutical Manufacturing) the compounds may be compressed into solid dosage units, such as pills or tablets, or be processed into capsules or suppositories. By means of pharmaceutically suitable liquids the compounds can also be applied in the form of a solution, suspension or emulsion.

For making dosage units, e.g. tablets, the use of conventional additives such as fillers, colorants, polymeric binders and the like, is contemplated. In general, any pharmaceutically suitable additive which does not interfere with the function of the active compounds can be used.

Suitable carriers with which the compounds of the invention can be administered include for instance lactose, starch, cellulose derivatives and the like, or mixtures thereof, used in suitable amounts. Compositions for intravenous administration may for example be solutions of the compounds of the invention in sterile isotonic aqueous buffer. Where necessary, the intravenous compositions may include for instance solubilizing agents, stabilizing agents and/or a local anesthetic to ease the pain at the site of the injection.

Pharmaceutical compositions of the invention may be formulated for any route of administration and comprise at least one compound of the present invention and pharmaceutically acceptable salts thereof, with any pharmaceutically suitable ingredient, excipient, carrier, adjuvant or vehicle.

By "pharmaceutically suitable" it is meant that the carrier, diluent or excipient must be compatible with the other ingredients of the formulation and not deleterious to the recipient thereof.

In an embodiment of the invention, a pharmaceutical pack or kit is provided comprising one or more containers filled with one or more pharmaceutical compositions of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described in this document.

LEGEND TO THE FIGURE

FIG. 1 Percentage of alternation of young and old C57BL/6J male mice in the T-maze with either vehicle (control groups) or compound of the invention (dose in mg/kg; p.o.)

The following examples are intended to further illustrate the invention in more detail.

Any novel intermediate as disclosed herein is a further embodiment of the present invention.

EXAMPLES

§ 1. (Analytical) Methods

Nuclear magnetic resonance spectra ($^1$H NMR) were determined in the indicated solvent using a Bruker Avance-I 400 with a 9.4T magnet ($^1$H: 400 MHz, $^{13}$C: 100 MHz), equipped with a BBI inversie broadband probehead with Z-gradient and ATM, or a Bruker Avance-DRX 600 with a 14.1T magnet, equipped with a TXI inverse triple resonance cryoprobehead with Z-gradient and ATM, at 300 K, unless indicated otherwise. The spectra were determined in deuterated chloroform (CDCl$_3$) with 99.8 atom % D; or in dimethylsulfoxide-d$_6$ (DMSO-d$_6$) containing 0.03 v/v % tetramethylsilane; both obtained from Aldrich Chemical shifts (δ) are given in ppm downfield from tetramethylsilane. Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiplet). NH and OH signals were identified after mixing the sample with a drop of D$_2$O.

Melting points were recorded on a Büchi B-545 melting point apparatus.

All reactions involving moisture sensitive compounds or conditions were carried out under an anhydrous nitrogen atmosphere.

Reactions were monitored by using thin-layer chromatography (TLC) on silica coated plastic sheets (Merck precoated silica gel 60 F254) with the indicated eluent. Spots were visualised by UV light (254 nm) or I$_2$.

Liquid Chromatography-Mass Spectrometry (LC-MS)

System A: Column: Acquity UPLC BEH C18 1.7 µm, 50×2.1 mm with 1.7 µm particles. The column is thermo stated in a column oven at 45° C.

Detection: Diode array between 210 and 260 nm

| step | total time (min) | flow (µl/min) | A (%) | B (%) |
|---|---|---|---|---|
| 0 | 0 | 800 | 95 | 5 |
| 1 | 0.1 | 800 | 95 | 5 |
| 2 | 4.5 | 800 | 10 | 90 |
| 3 | 5 | 800 | 10 | 90 |
| 4 | 5.01 | 800 | 95 | 5 |

A = 99.9% Water with 0.1% CH$_3$COOH
B = 99.9% CH$_3$CN with 0.1% CH$_3$COOH

System B: Column: Waters Sunfire C18, 30×4.6 mm with 2.5 µm particles. The column is thermo stated in a column oven at 23° C.

Detection: UV/VIS meter with the wavelength set to 254 nm+evaporative light scattering detector operating at 70° Celsius and 1.7 bar N$_2$ pressure.

| step | total time (min) | flow (ul/min) | A (%) | B (%) |
|---|---|---|---|---|
| 0 | 0 | 1800 | 95 | 5 |
| 1 | 1.8 | 1800 | 0 | 100 |
| 2 | 2.6 | 1800 | 0 | 100 |
| 3 | 2.8 | 1800 | 95 | 5 |
| 4 | 3.0 | 1800 | 95 | 5 |

A = 99.9% Water with 0.1% HCOOH
B = 99.9% CH$_3$CN with 0.1% HCOOH

The reported retention times (R$_t$), for System B, are for the peak in the Total Ion Current (TIC) chromatogram which showed the mass for [M+H]+ within 0.5 amu accuracy of the calculated exact MW and had an associated peak in the Evaporative Light Scattering (ELS) chromatogram with a relative area % (purity) of >85%.

§ 2. General Aspects of Syntheses

Abbreviations

ACE-Cl 1-Chloroethyl chloroformate
9-BBN 9-borabicyclo[3.3.1]nonane dimer
CHCl$_3$ Chloroform
CH$_2$Cl$_2$ Dichloromethane
CH$_3$CN Acetonitrile
CuBr$_2$ Copper(II) bromide
DBU 1,8-Diazabicyclo[5.4.0]undec-7-ene
DIAD Diisopropyl azodicarboxylate
DIPEA N,N-Diisopropylethylamine
DMF N,N-dimethylformamide
DMSO Dimethyl sulfoxide
Et$_3$N Triethylamine
Et$_2$O Diethyl ether
EtOH Ethanol
EtOAc Ethyl acetate
HCl Hydrogen chloride
K$_2$CO$_3$ Potassium carbonate
KHCO$_3$ Potassium bicarbonate
KI Potassium iodide
KOH Potassium hydroxide
KOtBu Potassium tert-butoxide
MeOH Methanol
NaBH$_4$ Sodium borohydride
NaHCO$_3$ Sodium bicarbonate
NaI Sodium iodide
NaOH Sodium hydroxide
NaOtBu Sodium tert-butoxide
Na$_2$SO$_4$ Sodium sulfate
NBS N-Bromosuccinimide
iPr$_2$O Diisopropyl ether
RT Room Temperature
SiO$_2$ Silica gel
TFA Trifluoroacetic acid
THF Tetrahydrofuran
TMSCl Chlorotrimethylsilane
TMSOTf Trimethylsilyl trifluoromethanesulfonate Suitable syntheses of claimed compounds and intermediates containing spiro-piperidine moieties follow routes as described below; see Scheme 1.

Scheme 1
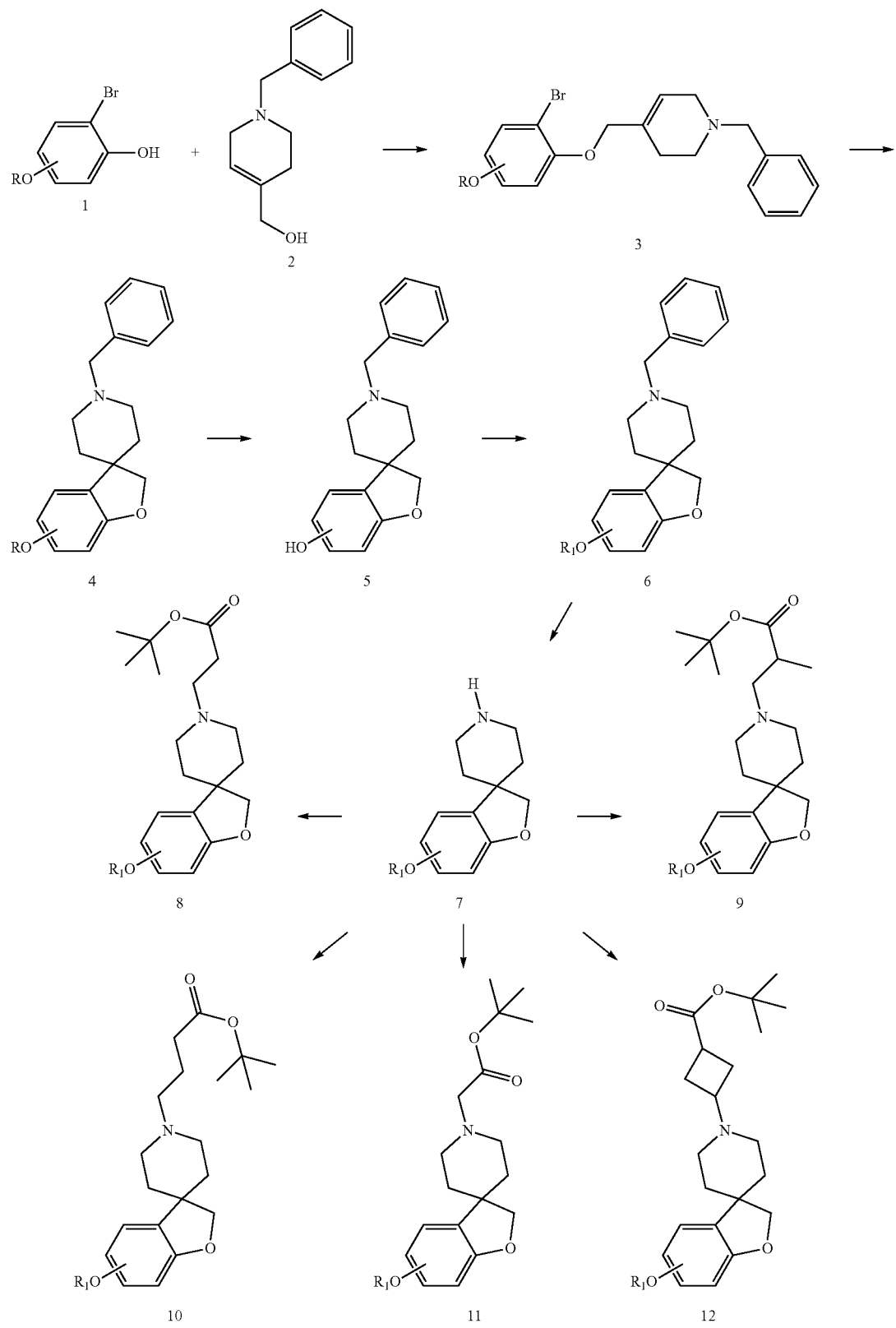
R = CH₃, CH₂Phenyl
R1 = defined in claim

The synthesis begins with a suitably substituted 2-bromophenol. Suitably substituted 2-bromophenols are commercially available or can be obtained from other commercially available 2-bromophenols. A compound of type 1 can be converted into 3, by reaction with (1-benzyl-1,2,3,6-tetrahydropyridin-4-yl)methanol, in the presence of triphenylphosphine, and a suitable azo-reagent, like diisopropyl azodicarboxylate, in a solvent such as tetrahydrofuran or dichloromethane. Subsequent conversion of 3 into 4, is through a Bu$_3$SnH mediated process, in the presence of AIBN and in a solvent like benzene or toluene under reflex conditions and or microwave conditions. Deprotection of the methoxy substituted derivatives (compound 4), can be done with HBr in acetic acid under relflux conditions, affording 1'-benzyl-2H-spiro[1-benzofuran-3,4'-piperidin]-6-ol and or the respective-5-ol analog (5). Subsequent O-alkylation can be done with a suitable alkylating agent like 1-bromooctane or benzyl bromide, in solvents such as dimethylsulfoxide (DMSO), acetone, methanol, or acetonitrile, in the presence of a base like potassium hydroxide or potassium carbonate, at temperatures between 0° C. and 60° C. Removal of the N-benzyl group in (for example) 1'-benzy-6-(octyloxy)-2H-spiro[1-benzofuran-3,4'-piperidin] (6) can be done by reaction with ACE-Cl in a solvent such as 1,2-dichloroethane, followed by reaction of the intermediate carbamate with methanol.

The obtained spiro-piperidines (7) can be reacted with an (meth)acrylic acid ester, in a so called Michael-addition, in a solvent such as acetonitrile, methanol, or N,N-dimethylformamide, at temperatures between room temperature and 85° C., and eventually with the addition of some base like triethylamine or 1,8-diazabicyclo[5.4.0]undec-7-ene, to afford the corresponding tert-butyl spiro-piperidine propanoates (8) and -2-methylpropanoates (9). The spiro-piperidines can also be reacted with a suitable alkylating reagent, such as tert-butyl bromoacatate or 4-bromo-butyric acid tert-butyl ester, in the presence of a base, such as potassium carbonate or cesium carbonate, in a solvent such as acetonitrile and/or tetrahydrofuran, at room temperature, to afford compounds of type 10 and 11.

Compounds of type 12 can be obtained through reductive amination with 3-oxocyclobutane-1-carboxylate in a solvent like dichloroethane or THF, in the presence of sodiumtriacetoxyborohydride.

Compounds of type 7-12, can be converted into the final compounds (I) by basic or acidic hydrolysis of the ester, depending on the nature of group R1. As an example, tert-butyl esters can be treated with an acid, such as trifluoroacetic acid or hydrogen chloride, in a solvent such as CH$_2$Cl$_2$ or 1,4-dioxane, at room temperature. As a further example, these esters can be treated with a base, such as sodium hydroxide or lithium hydroxide, in solvents such as ethanol, THF, and/or water, at temperatures between room temperature and 70° C.

As another example, removal of both benzyl groups in 1'-benzy-6-(benzyloxy)-2H-spiro[1-benzofuran-3,4'-piperidin] (4) (scheme 2), can be done by hydrogenation in a solvent such as ethanol and a catalyst like palladium hydroxide. The obtained spiro-piperidine (13) can be reacted with an (meth)acrylic acid ester, affording tert-butyl 3-{6-hydroxy-2H-spiro[1-benzofuran-3,4'-piperidin]-1'-yl}propanoate 14A) and tert-butyl 3-{6-hydroxy-2H-spiro[1-benzofuran-3,4'-piperidin]-1'-yl}-2-methylpropanoate (14B). Those compounds can be modified in the following way: By reaction with a suitable alkylating reagent, such as a alkyl bromide or an alkyl chloride, in the presence of a base, such as potassium carbonate or cesium carbonate, in a solvent such as acetonitrile and/or tetrahydrofuran, at room temperature, to afford compounds of type 8 and 9. Alternatively, 14A/B can be converted to type 8 and 9, by reaction with a suitable alcohol, in the presence of triphenylphosphine, and a suitable azo-reagent, like diisopropyl azodicarboxylate, in a solvent such as tetrahydrofuran or dichloromethane. Furthermore, 3-{6-hydroxy-2H-spiro[1-benzofuran-3,4'-piperidine]-1'-yl}propanoate can be converted into tert-butyl 3-{6-(6-phenoxy)-2H-spiro[1-benzo-furan-3,4'-piperidine]-1'-yl}propanoate (compound of type 15), using bromobenzene and a mixture of palladium (II) acetate, potassium phosphate tribasic monohydrate, 2-di-tert-butylphosphino-2',4',6'-triisopropylbiphenyl and phenylboronic acid at 100° C., preferentially overnight.

In another example, and for example from compound 14A, the corresponding tert-butyl 3-{6-[(trifluoromethane)-sulfonyloxy]-2H-spiro[1-benzofuran-3,4'-piperidine]-1'-yl] propanoate (16) can be obtained using trifluoromethanesulfonimide and a base like triethylamine in a solvent like chloroform, which can be converted into tert-butyl 3-[6-(acetylsulfanyl)-2H-spiro[1-benzofuran-3,4'-piperidine]-1'-yl]propanoate (20, scheme 3) (van den Hoogenband A. Tetrahedron Letters 2010, 51, 6877), using (R)-1-[(1S$_p$)-2-(dicyclohexylphos-phino)-ferrocenyl]ethyldi-ter-butyl-phosphine, (CyPF-t-Bu) and tris-(dibenzyliden-aceton)-di-palladium(0) in the presence of potassium thioacetate. This is done in a solvent like toluene at elevated temperatures. The S-acetyl protected derivative (20) can be hydrolyzed, for example with sodium hydroxide in ethanol, and treated subsequently in situ with a benzylhalide, for example, 1,3-dichloro-2-(chloromethyl)-4-methoxybenzene to afford 3-(6-{[2,6-dichloro-3-methoxy)-phenyl]methylsulfanyl}-2H-spiro[1-benzofuran-3,4'-piperidine]-1'-yl}propanoate (21, scheme 3), which can be hydrolyzed to afford a compound of formulae (I). Alternatively, a compound of type 21, the basic amine being protected as its hydrochloric acid, can be converted into the corresponding sulfon analog (22), using potassium peroxymonosulfate in a solvent like water at room temperature. A compound of type 16 (scheme 2), can be converted into its stannyl derivative (17), using hexa-N-butylditin in a solvent like 1,4-dioxane in the presence of lithium chloride and tetrakis(triphenylphosphine)-palladium(0) at higher temperatures. This tert-butyl 3-[6-(tributylstannyl)-2H-spiro[1-benzofuran-3,4'-piperidine]-1'-yl]propanoate can be converted into tert-butyl 3-{6-iodo-2H-spiro[1-benzofuran-3,4'-piperidine]-1'-yl}propanoate (18) using N-iodo-succinimide in a solvent like THF, preferable at low temperature. The bromo-analog (19, scheme 3), using N-bromosuccinimide, can be prepared accordingly. In another example, compounds of type 23 can be obtained using the stannyl analog 17 and the appropriate acid chloride in a solvent like dichloroethane at higher temperatures.

Scheme 2
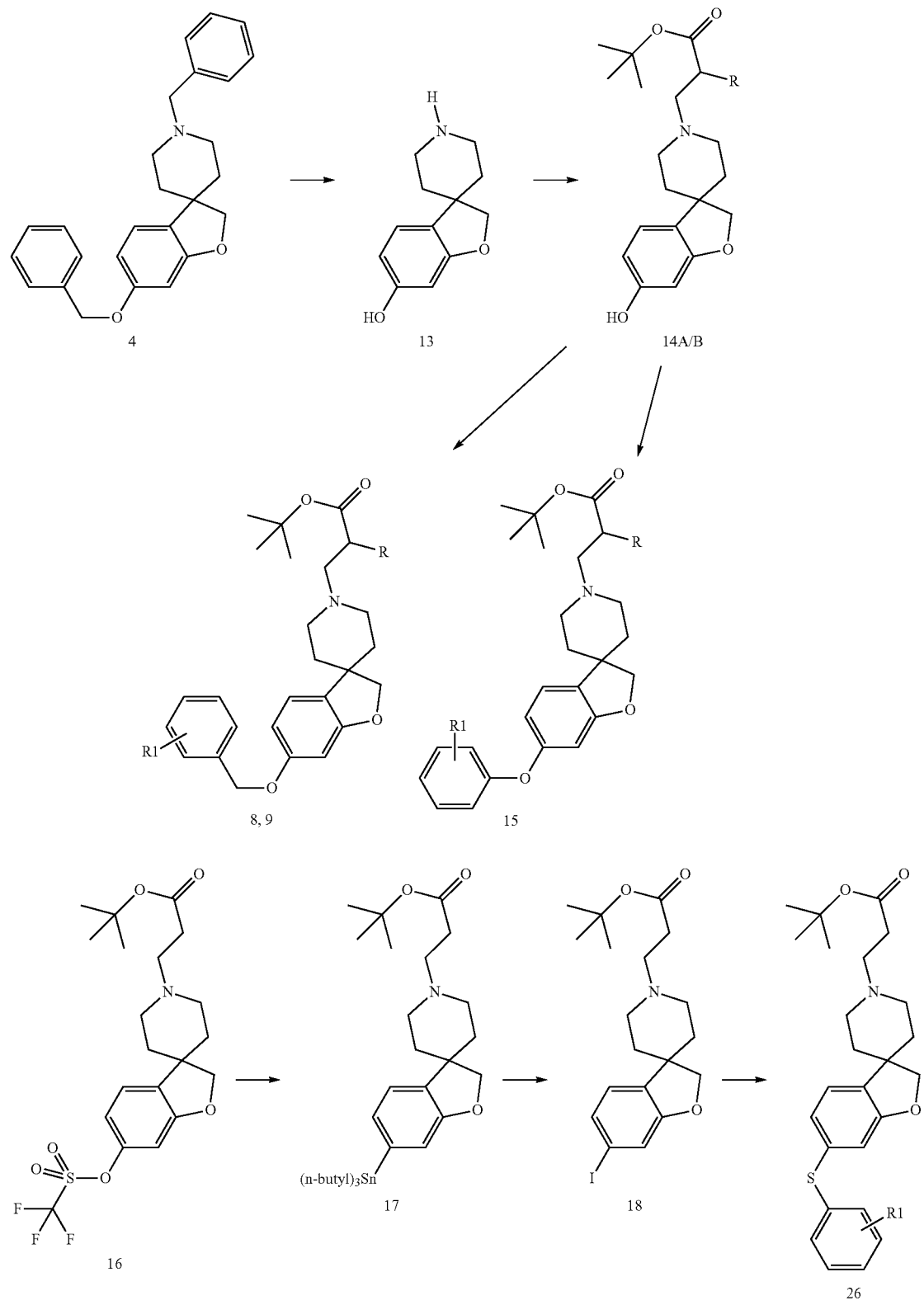
R = H, CH₃
R1 = defined in the claim

Scheme 3
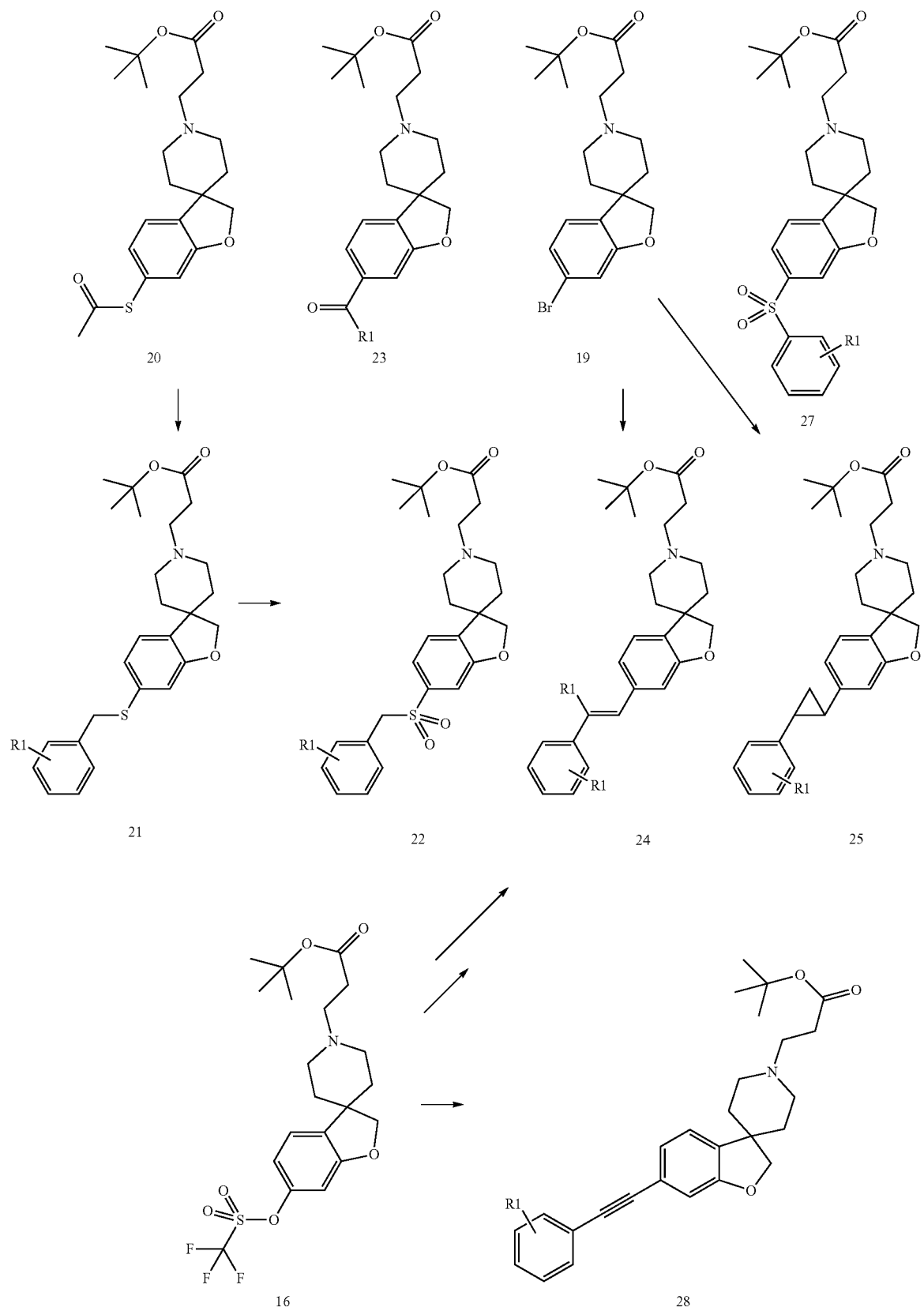

Tert-butyl 3-{6-iodo-2H-spiro[1-benzofuran-3,4'-piperidine]-1'-yl}propanoate (18) can be used for copper(I)iodide catalyzed reactions with for example 2-methyl-benzene-1-thiol in a solvent like 1,2-dimethoxyethane and in the presence of potassium carbonate at higher temperatures, affording an example of compound type 26 (scheme 2), which can be oxidized (into examples of type 27, scheme 3), using the conditions for the conversion of compound type 21 into 22. Tert-butyl 3-{6-bromo-2H-spiro[1-benzofuran-3,4'-piperidine]-1'-yl}propanoate (19) is a suitable precursor for the Suzuki-reaction. In a specific example, potassium 2-[(E)-2-(2,6-dichlorophenyl)-ethenyl]trifluoroboronate, cesium carbonate, and 1',1'-bis(diphenyl-phosphino)-ferrocene palladium(II)dichloride dichloromethane complex are reacted in a mixture of toluene and water at reflux overnight, affording tert-butyl 3-{6-[(E)-2-(2,6-dichlorophenyl)ethenyl]-2H-spiro[1-benzofuran-3,4'-piperidine]-1'-yl}propanoate as an example of compound type 24 (scheme 3). In another example, compounds of type 24 can be obtained using a compound of type 16 (scheme 2), which be converted into its vinyl derivative, using tributyl(ethenyl) stannane in a solvent like 1,4-dioxane in the presence of lithium chloride and tetrakis(triphenylphosphine)-palladium (0) at higher temperatures. This tert-butyl 3-{6-(ethenyl)-2H-spiro[1-benzofuran-3,4'-piperidine]-1'-yl}propanoate can be converted into compounds of type 24, using a suitable substituted phenylboronic acid in a solvent like N,N-dimethylforamide at higher temperatures (Karimi B, Synthesis 2010, 1399). In another embodiment of this invention, compounds of type 28 (scheme 3), can be obtained from tert-butyl 3-{-{6-[(trifluoro-methane)sulfonyloxy]-2H-spiro [1-benzofuran-3,4'-piperidine]-1'-yl]propano-ate (compound 16) and a suitable substituted phenylacetylene derivative in a solvent like dimethyl sulfoxide using a base like potassium phosphate tribasic monohydrate in the presence of palladium(II) acetate and triphenylphosphine at higher temperatures.

Using the methodology described for the conversion of compound 19 into examples of compound type 24, tert-butyl 4-{6-[2-(2,6-dichlorophenyl)cyclopropyl]-2H-spiro[1-benzofuran-3,4'-piperidine]-1'-yl}-propanoate (as an example of compound type 25) can be obtained from 19 and the potassium salt of [2-(2,6-dichlorophenyl)-cyclopropyl]-trifluoroboronate.

In another embodiment of this invention, compounds of type 35 (scheme 4), can be obtained as follows: 1-(benzyloxy)-4-bromo-2,3-difluoro-benzene (29) and 4-pyridinemethanol (30) are reacted in a solvent like NMP at 1000 C for 0.5 hr (Stephane G. Tetrahedron Letters 2009, 50, 3776), followed by quarterization with benzylbromide and reduction of the intermediate pyridine-1-ium bromide with sodium borohydride to afford compound 32. Cyclization (Bu₃SnH, in the presence of AIBN), in a solvent like benzene or toluene can be done under reflux conditions and or microwave conditions. Removal of both benzyl groups in r-benzy-6-(benzyloxy)-7-fluoro-2H-spiro[1-benzofuran-3,4'-piperidine] (33), can be done by hydrogenation in a solvent such as ethanol and a catalyst like palladium hydroxide. Compound 34 can be converted into compound type 35 as described before, followed by hydrolysis to afford compounds of formulae (I).

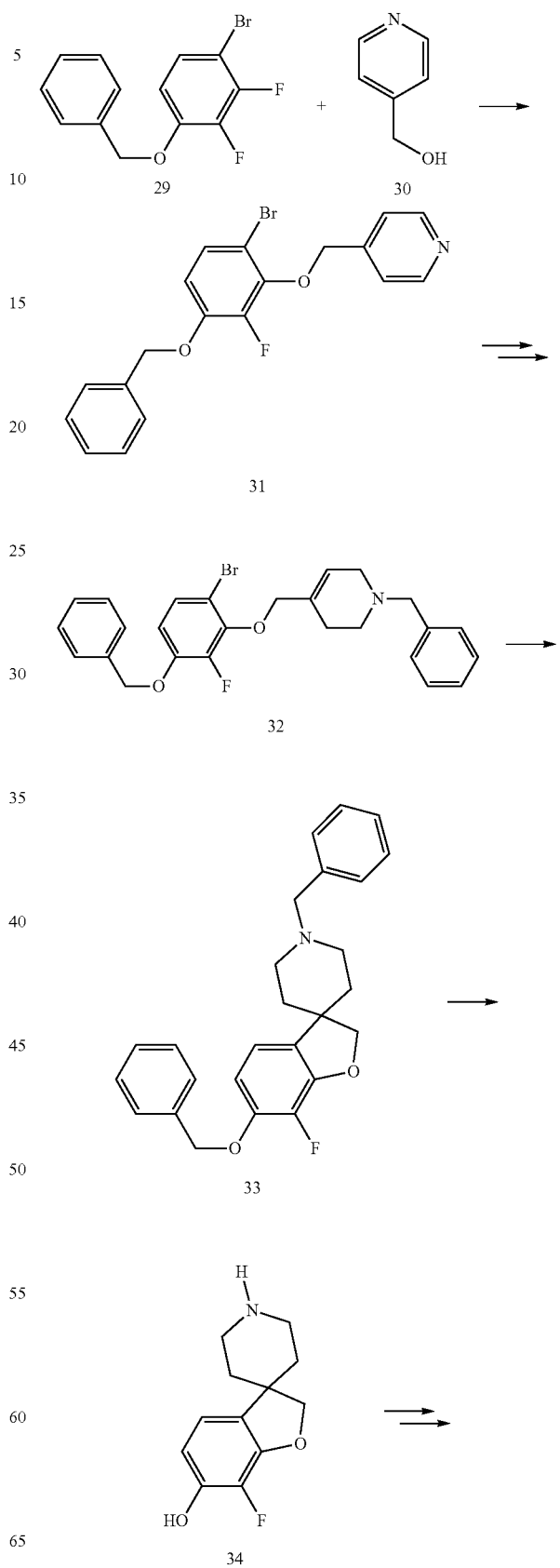

Scheme 4

-continued

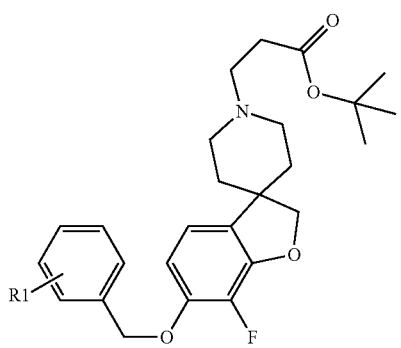
35

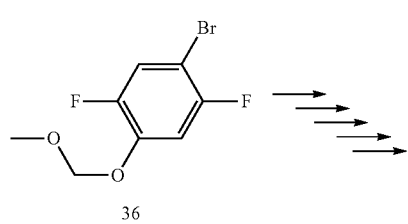
36

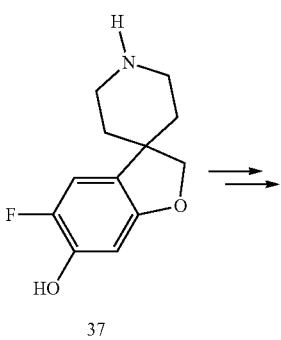
37

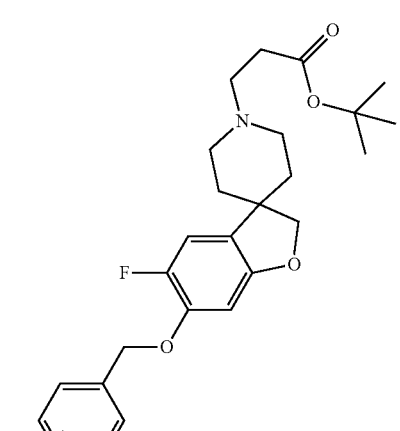
38

-continued

39

40

41

R1 = defined in the claim

Using this methodology (Tetrahedron Letters 2009), the appropriate (protected) fluorinated benzene derivatives can be converted into compounds of type 38 and 41.

6-Bromo-2H[1-benzofuran-3,4'-piperidine] (46, scheme 5), can be prepared in a similar manner. Removal of the N-benzyl can be done by the reaction with ACE-Cl in a solvent such as 1,2-dichloroethane, followed by reaction of the intermediate carbamate with methanol. Conversion of compound 46 into compound types 47, 48 and 49 are done in a similar manner as described in scheme 1 and 2.

Furthermore, treatment of compound 45 with n-butyl lithium at −75° C., in a solvent like tetrahydrofuran or diethyl ether, followed by quenching with a suitable isocyanate affords the corresponding amide, which can be debenzylated with ACE-Cl and converted to compounds of type 50. Hydrolysis will afford compounds of formulae (I).

Scheme 5
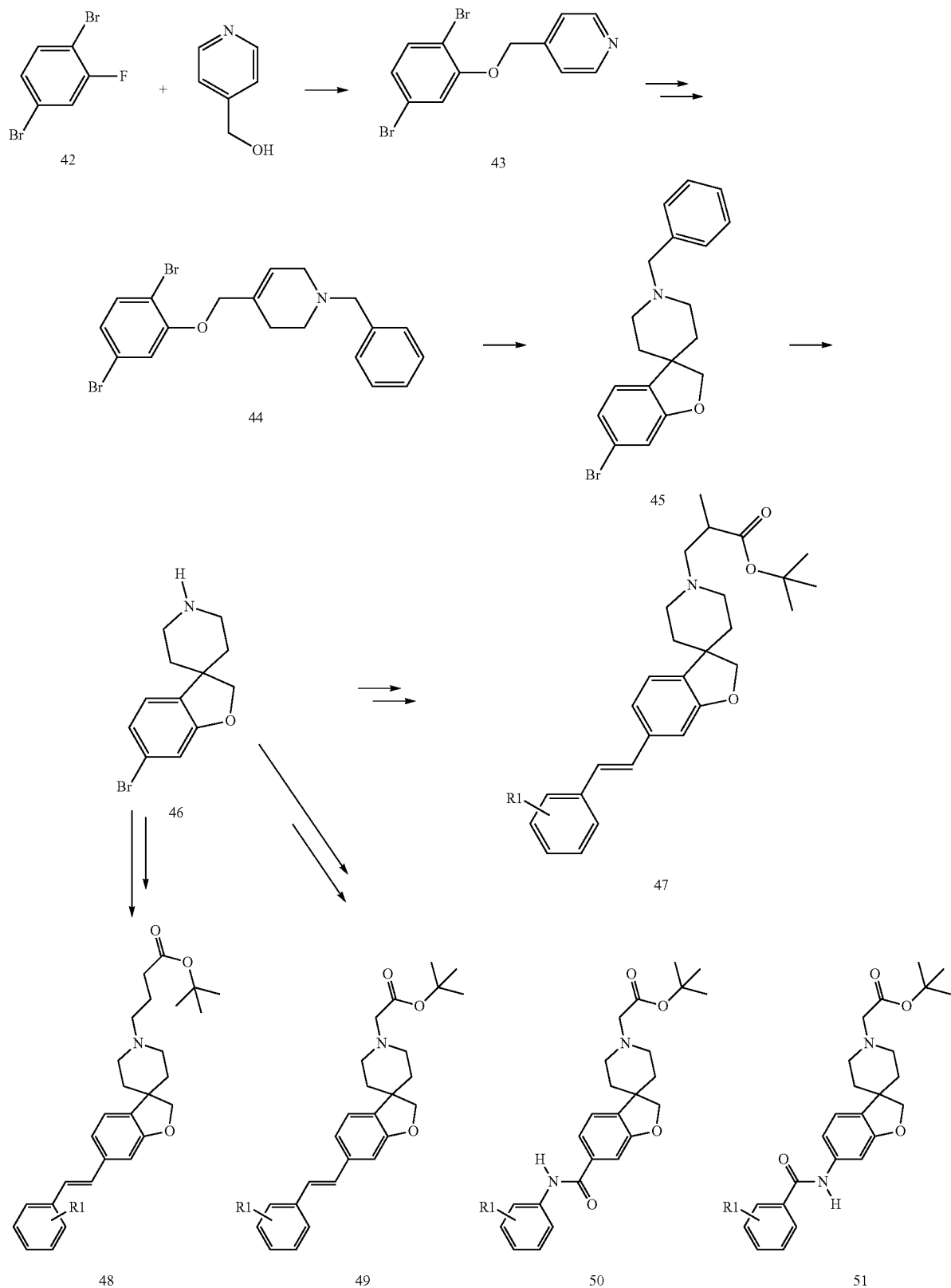
R1 = defined in the claim

Amides of compound type 51 (scheme 5) can be prepared using a suitable substituted benzamide, for example 2,6-dichlorobenzamide and tert-butyl 3-{-{6-[(trifluoromethane)sulfonyloxy]-2H-spiro[1-benzofuran-3,4'-piperidine]-1'-yl]-propano-ate (compound 16) in a solvent like tert-butyl alcohol and a base like potassium phosphate tribasic in the presence of tris-(dibenzylidenaceton)-dipalladium(0) and 2-di-t-butylphosphino-3,4,5,6-tetramethyl-2',4',6'-tri-1-propylbiphenyl at elevated temperatures. Hydrolysis will afford compounds of formulae (I).

As another example, compound 13 (scheme 2) can be protected (compound 52, scheme 6) at the nitrogen with a suitable protecting group (P. G. M. Wuts, T. W. Greene Protective groups in organic synthesis, 4th ed., John Wiley & Sons, 2006), such as tert-butyloxycarbonyl (BOC), by reaction with di-tert-butyl dicarbonate in a solvent such as acetonitrile at room temperature.

Subsequently, the phenolic group can be reacted with a suitable alkylating reagent in a solvent such as acetonitrile, in the presence of a base such as potassium carbonate, at room temperature, or by using the mitsunobu conditions and the appropriate alcohol. After which the tert-butyloxycarbonyl (BOC) group can be removed by the treatment with an acid, such as hydrogen chloride, in a solvent such as ethanol, at temperatures between room temperature and 60° C., to afford (in an alternative way) the already mentioned spiropiperidine of type 7.

Compounds of type 7 can also be modified on nitrogen with a 2,2-difluoro-propionic acid ester group (54), by the following sequence of steps (Cheguillaume A., Lacroix S., Marchand-Brynaert J. *Tetrahedron Letters* 2003, 44, 2375): First reaction with 1H-benzotriazole-1-methanol in a solvent such as ethanol, at temperatures around 50° C.; followed by reaction with a zinc reagent prepared from zinc dust, trimethylsilylchloride and a bromodifluoroacetate, in a solvent such as tetrahydrofuran, at temperatures around 70° C.

Compounds of formulae (I) I wherein R3= $(CH_2)_2OPO_3H_2$ can be synthesized as shown in scheme 6. Thus, compound 7 is reacted with 2-(2-chloro-ethoxy)tetrahydro-2H-pyran, in the presence of a base, such as potassium carbonate, and sodium iodide, in a solvent such as DMF, at a temperature around 100° C. The tetrahydro-2H-pyran group (in compound 55) is removed by treatment with an acid such as p-toluenesulfonic acid, in a solvent such as methanol, at room temperature. The formed alcohol (compound 56) is then treated with a phosphoramidite reagent such as di-tert-butyl N,N-diisopropyl-phosphoramidite, in the presence of tetrazole, in a mixture of solvents, such as THF, $CH_2Cl_2$, and $CH_3CN$, at room temperature, and subsequently oxidized with an oxidizing reagent such as hydrogen peroxide or tert-butylhydroperoxide in the same solvents, at room temperature, affording compounds of type 57. Hydrolysis of the phosphate esters can be done by treatment with an acid, such as TFA, in a solvent such as $CH_2Cl_2$, at room temperature.

Scheme 6

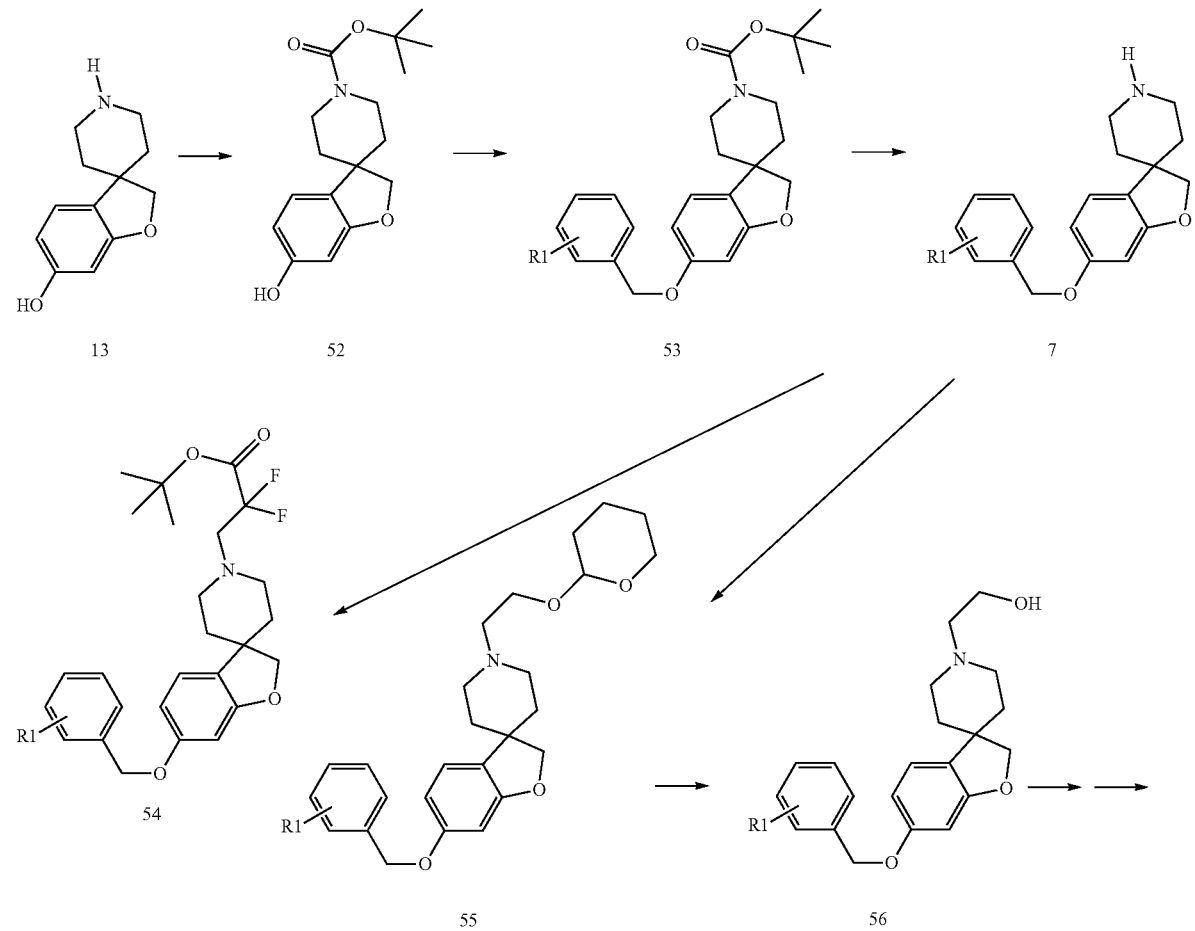

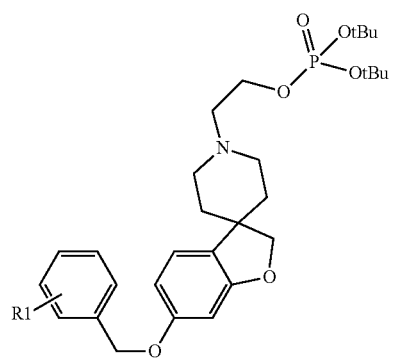

57

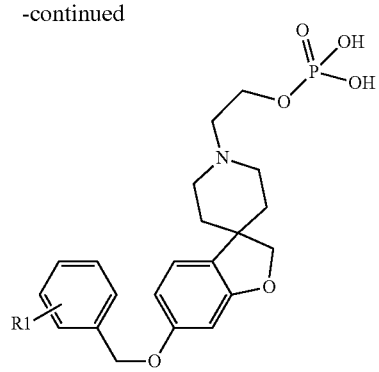

58

In another embodiment of this invention, compounds of type 64 (scheme 7), can be obtained as follows: 4-(benzyloxy)-1-bromo-2-fluoro-benzene and 3-pyridinemethanol (59) are reacted in a solvent like NMP at 100° C. for 0.5 hr, followed by quarterization with benzylbromide and reduction of the intermediate pyridine-1-ium bromide with sodium borohydride to afford 1-benzyl-5-[5-(benzyloxy)-2-bromophenoxymethyl]-1,2,3,6-tetra-hydropyridine. This can be converted to benzyl 5-[5-benzyloxy)-2-bromophenoxymethyl]-1,2,3,6-tetrahydropyridine-1-carboxylate (61) using a base like potassium bicarbonate in dichloromethane in the presence of benzylchloroformate at ambient temperature. Cyclization of compound 61 can be done in a solvent like NMP and in the presence of silver carbonate and Herrmann-Beller palladacycle (Lauren R. Tetrahedron, 2008, 64, 4468) preferentially at 140° C. Removal of both protective groups and reduction of the double bond in 6-(benzyloxy)-2',6'-dihydro-1'H,2H-spiro[1-benzofuran-3,3'-pyridine] (62), can be done by hydrogenation in a solvent mixture such as methanol and ethylacetate using a catalyst like palladium hydroxide. Compound 63 can be converted into compounds of type 64 and other structural analogs (for example compound type analogs of 24 and 28) as described before. Hydrolysis will afford compounds of formulae (I).

Scheme 7

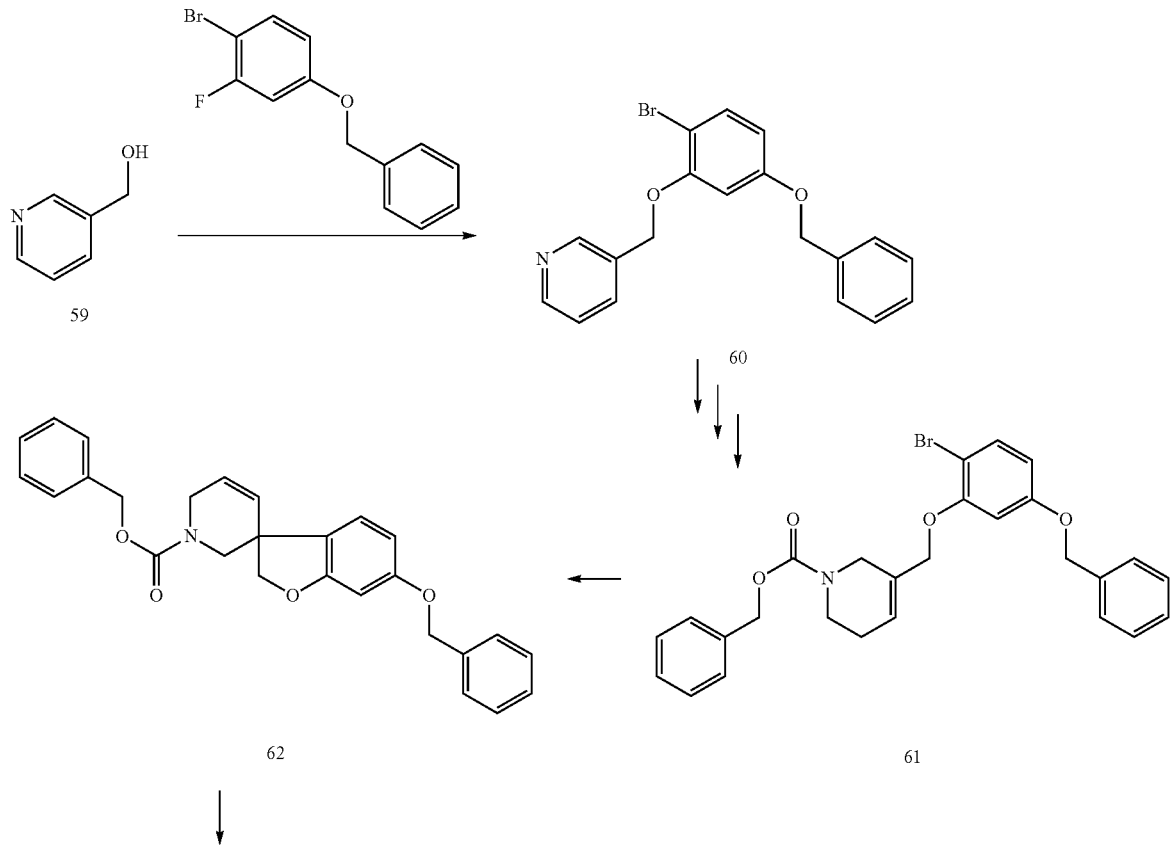

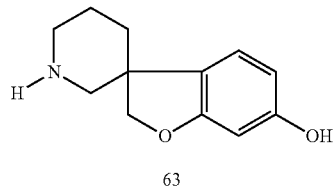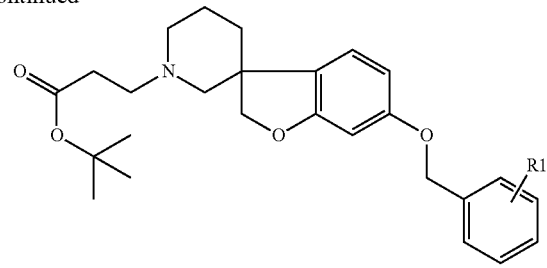

In another example of this invention, compounds of type 69 (scheme 8), can be obtained as follows: (1-benzyl-2,5-dihydro-1H-pyrrol-3-yl)methanol (US2010-0069351) and 4-(benzyloxy)-1-bromo-2-fluorobenzene are reacted in a solvent like NMP at 100° C. for 30 minutes affording 1-benzyl-3-[5-benzyloxy]-2-bromophenoxy-methyl]-2,5-dihydro-1H-pyrrole (66). Cyclization (Bu₃SnH, in the presence of AIBN), in a solvent like benzene or toluene can be done under microwave conditions (preferentially at 200° C.). Removal of both protective groups can be done by ammonium formate in a solvent such as methanol using a catalyst like palladium hydroxide. Compound 68 can be converted into compounds of type 69 (and analogs) as described before, followed by hydrolysis to afford compounds of formulae (I).

Scheme 8

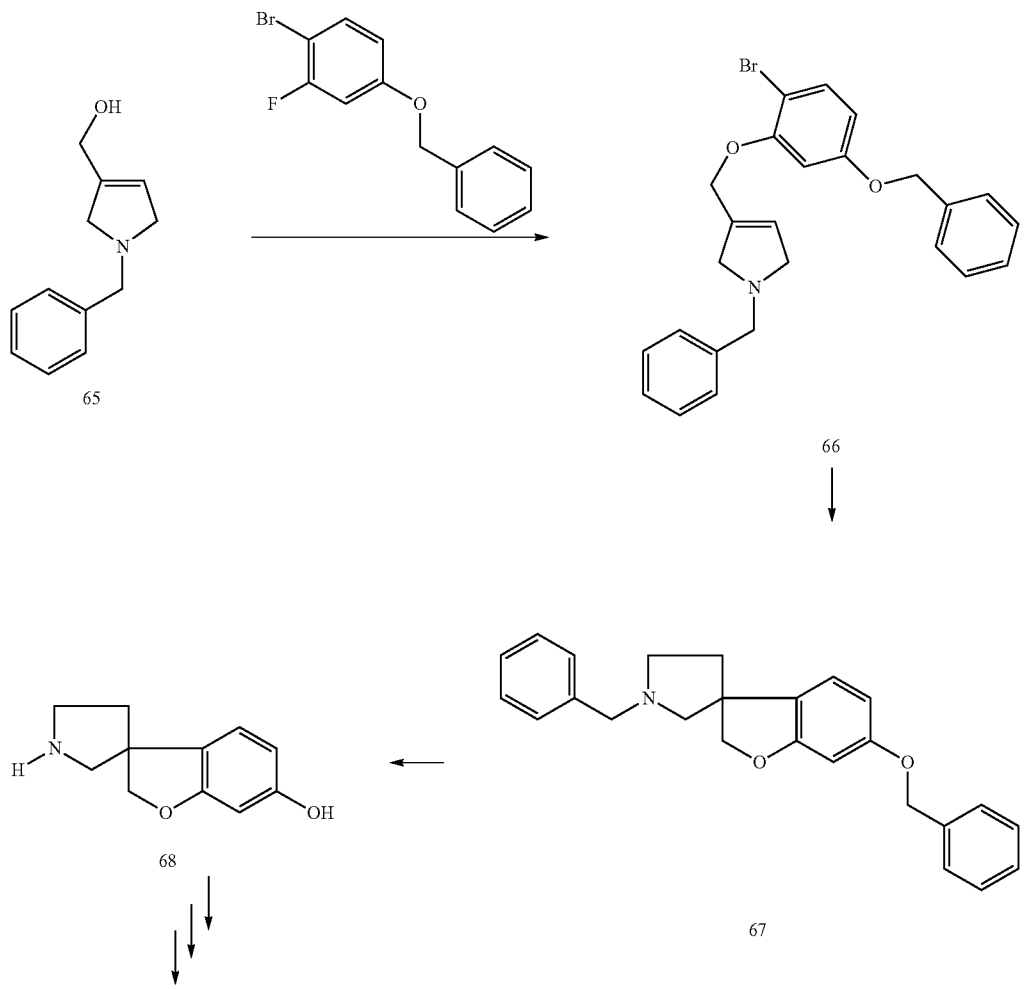

-continued

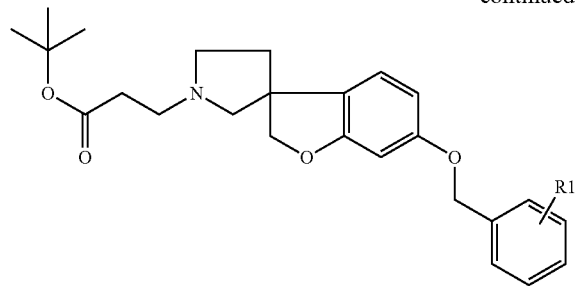

69

In yet another example of this invention, compounds of type 75 (scheme 9), can be prepared as follows: aminoalcohol 71 can be obtained by the reaction of 5-(benzyloxy)-2,3-dihydro-1H-inden-1-one (70) and trimethylsilyl cyanide in the presence of a lewis acid, like zinc iodide, at room temperature, in the neat. Subsequently followed by reduction of the intermediate cyanohydrin with a reducing agent like lithium aluminum hydride in a solvent like tetrahydrofuran. The amino alcohol (71) can be reacted with an activated chloroacetic acid or bromoacetic acid in a solvent such as dichloromethane with a base such as triethylamine, and subsequently cyclized in a solvent such as 2-propanol with a base such as potassium hydroxide to afford 5-(benzyloxy)-2,3-dihydrospiro[indene-1,2'-morpholine]-5'-one (72). This product can be reduced with a reducing agent such as borane in a solvent such as tetrahydrofuran, at temperatures between 0° C. and room temperature, to afford 5-(benzyloxy)-2,3-dihydrospiro[indene-1,2'-morpholine] (73). This product can be hydrogenated in a solvent like in MeOH and a catalyst like palladiumhydroxide to afford compound 74. Compound 74 can be converted into compounds of type 75 (and analogs) as described before, followed by hydrolysis to afford compounds of formulae (I).

Scheme 9

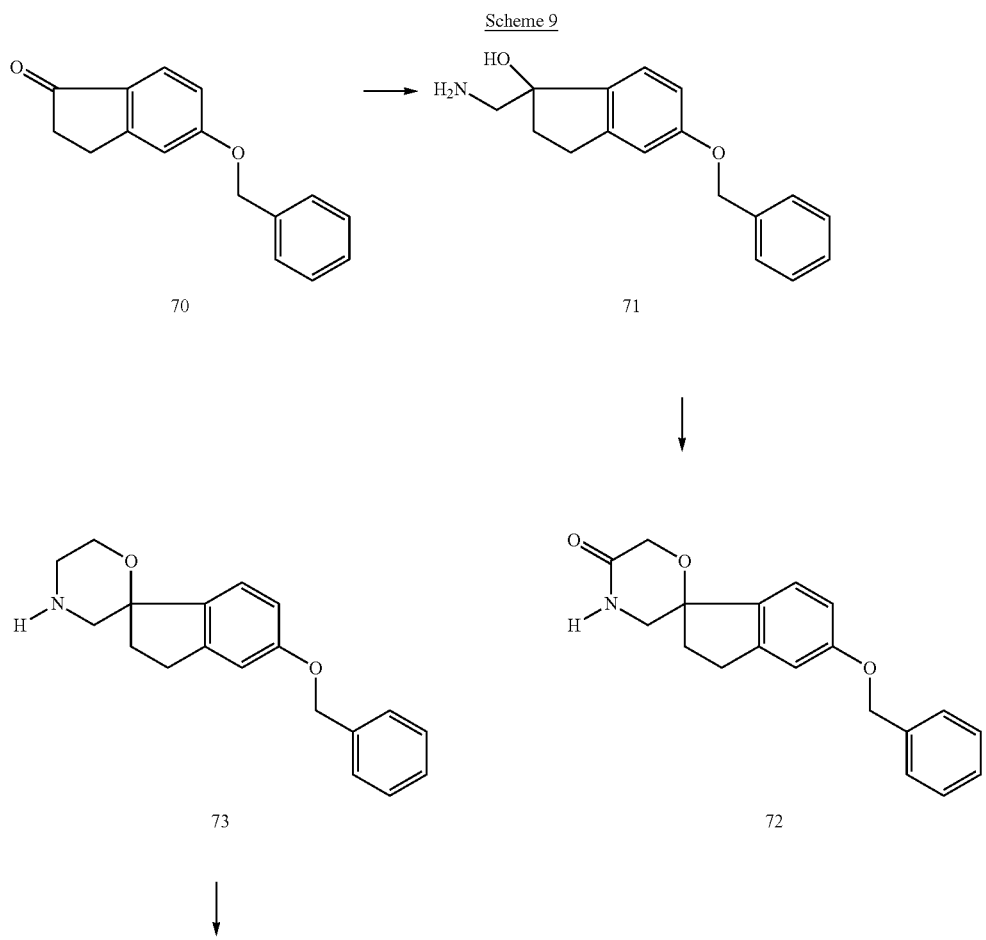

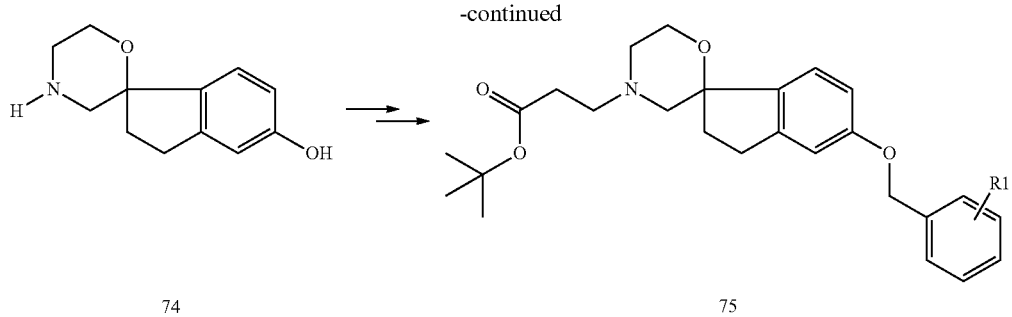

In another embodiment of this invention, compounds of type 82 (scheme 10), can be obtained as follows: 6-methoxy-2,3-dihydro-1H-inden-1-one (76) and sodium borohydride are reacted in a solvent like MeOH at room temperature, followed by dehydration, using an acidic catalyst like p-toluenesulfonic acid hydrate in the presence of hydroquinone in a solvent like toluene. This product: 5-methoxy-1H-indene (77) can be treated with lithium bis(trimethylsilyl)amide (LiHMDS) in a solvent like tetrahydrofuran (0° C.). The intermediate can be reacted with a suitable alkylating reagent, for example tert-butyl N,N-bis(2-chloroethyl)carbamate, in a solvent like tetrahydrofuran or diethyl ether, preferentially between 0° C. and room temperature. This product (78) can be hydrogenated in a solvent like MeOH and a catalyst like palladiumhydroxide to afford compound 79, which can be reacted with sodium ethanethiolate in a solvent like N,N-dimethylformamide at 130° C. for 60 hours. Deprotection can be done using for example 4N HCl in a solvent like dioxane to afford the HCl salt of 2,3-dihydro-spiro[indene-1,4'-piperidine]-5-ol (81), which can be converted into compounds of type 82 (and analogs) as described before. Hydrolysis will afford compounds of formulae (I).

Scheme 10

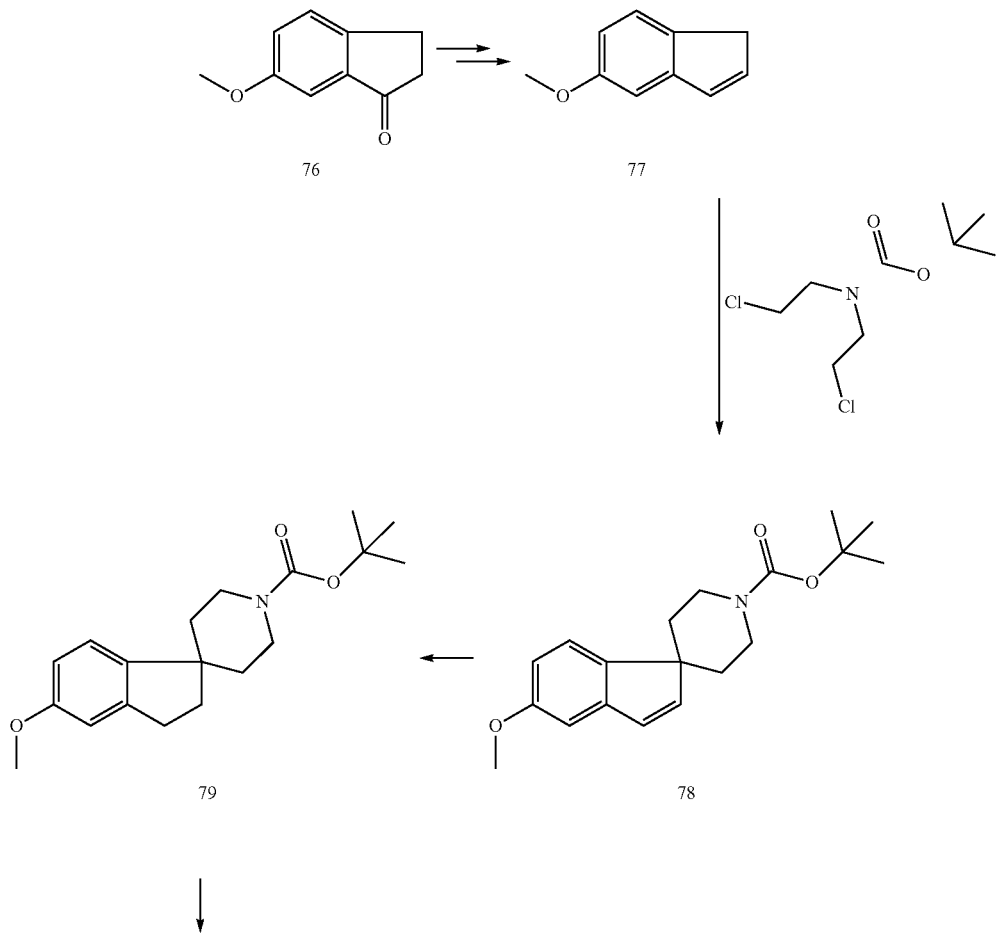

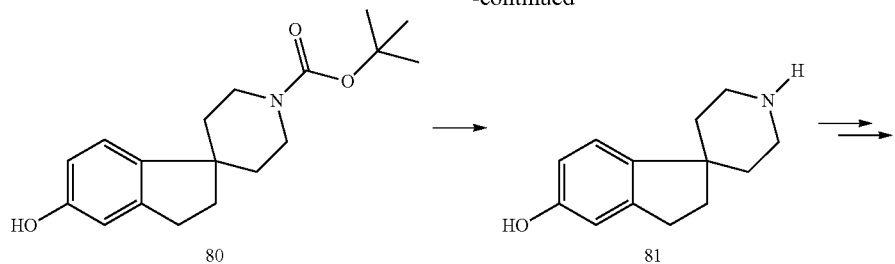

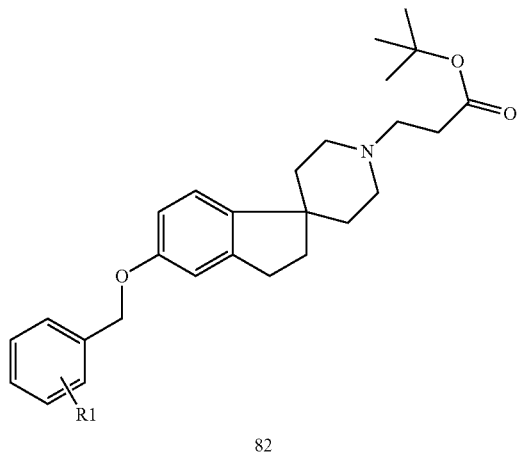

§ 3. Specific Syntheses

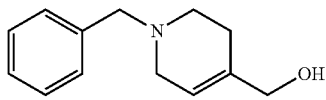 [SMILES: OCC1=CCN(Cc2ccccc2)CC1]

(1-Benzyl-1,2,3,6-tetrahydropyridin-4-yl)methanol. 4-Hydroxymethyl-pyridine (20 g, 183 mmol, 1.0 eq) was dissolved in DMF (80 mL) and benzylbromide (24.2 mL; 202 mmol) was added and the solution was stirred at 100° C. for 2 hours. The solution was allowed to cool to RT and diluted with EtOH (300 mL) and treated portionwise with NaBH$_4$ (8.7 g; 230 mmol) and stirred at reflux for 3 hours. The solution was allowed to cool to RT and concentrated largely. The residue was taken up in EtOAc and water and the organic phase was dried (Na$_2$SO$_4$), filtered and concentrated to give 35 g crude oil. The material was purified with a short plug (10 cm) of silica eluting with EtOAc to give the product (23.9 g; 64%) which was isolated as an oil.

$^1$H NMR (300 MHz, CDCl$_3$) δ ppm 7.39-7.2 (m, 5H), 5.69-5.63 (m, 1H), 4.03 (s, 2H), 3.58 (s, 2H), 3.0 (m, 2H), 2.6 (t, J=6 Hz, 2H), 2.21-2.11 (m, 2H).

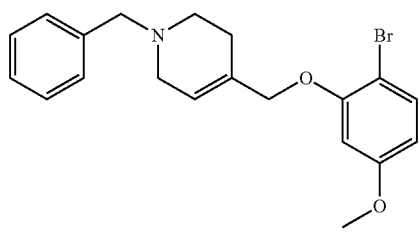 [SMILES: COc1ccc(Br)c(OCC2=CCN(Cc3ccccc3)CC2)c1]

1-Benzyl-4-((2-bromo-5-methoxyphenoxy)methyl)-1,2,3,6-tetrahydro-pyridine. (1-benzyl-1,2,3,6-tetrahydropyridin-4-yl)methanol (20.7 g; 102 mmol) was dissolved in THF (150 mL) and 2-bromo-5-methoxyphenol (20.7 g, 102 mmol) was added followed by PPh$_3$ (29.4 g; 112 mmol). The solution was cooled on ice and diisopropyl azodicarboxylate (22.2 mL; 112 mmol) was added dropwise keeping T<10° C. (period of ~2 hours) and stirred at RT overnight. The mixture was concentrated and the residue was stirred in heptanes (200-300 mL) for 20 minutes. The precipitate was filtered off and rinsed with heptanes. The filtrate was concentrated to give 36 g yellow oil. Heptanes (150 mL) was added and the mixture was stirred for 5 minutes and left standing for 2 minutes (oils out), the heptane phase was decanted from the oil and concentrated to give the product (25 g; 63%) which was isolated as a yellow oil.

$^1$H NMR (300 MHz, CDCl$_3$) δ ppm 7.42-7.2 (m, 6H), 6.48 (d, J=2Hz, 1H), 6.39 (dd, J=9 and 2Hz, 1H), 5.85-5.8 (m, 1H), 4.44 (s, 2H), 3.78 (s, 3H), 3.6 (s, 2H) 3.07-3.01 (m, 2H), 2.64 (t, J=6 Hz, 2H), 2.31-2.23 (m, 2H).

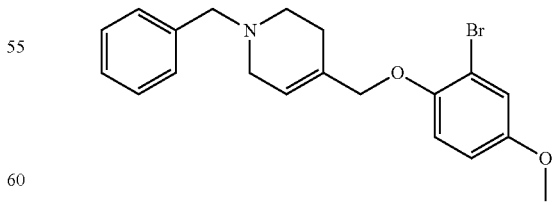

1-Benzyl-4-((2-bromo-4-methoxyphenoxy)methyl)-1,2,3,6-tetrahydro-pyridine. (1-benzyl-1,2,3,6-tetrahydropyridin-4-yl)methanol (18.9 g; 93 mmol) was dissolved in THF (150 mL) and 2-bromo-4-methoxyphenol (18.9 g; 93 mmol) was added followed by PPh$_3$ (26.8 g, 102 mmol). The solution was cooled on ice and diisopropyl azodicarboxylate (20.3 mL, 102 mmol) was added dropwise keeping T<10° C. (period of ~2 hours) and stirred at RT for 2 days. The mixture was concentrated. The residu was taken up in EtOAc and sat. NaHCO$_3$ and the organic phase was dried (Na$_2$SO$_4$), filtered and concentrated to give 50 g crude oil. The material was stirred in heptanes (200-300 mL) for 20 minutes. The precipitate was filtered off and rinsed with heptanes. The filtrate was concentrated to give 29 g yellow oil. The material was purified with a short plug (10 cm) of silica eluting with heptanes/EtOAc 6/1 to give the product (18.5 g; 51%) which was isolated as a yellow oil. $^1$H NMR (300 MHz, CDCl$_3$) δ ppm 7.38-7.2 (m, 5H), 7.12 (d, J=2Hz, 1H), 6.83 (m, 2H), 5.78 (m, 1H), 4.42 (s, 2H), 3.76 (s, 3H), 3.59 (s, 2H) 3.02 (m, 2H), 2.63 (t, J=6 Hz, 2H), 2.33-2.23 (m, 2H).

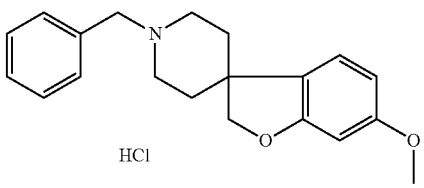 [SMILES: COc1ccc2c(c1)OCC21CCN(Cc2ccccc2)CC1 ; Cl]

1'-Benzyl-6-methoxy-2H-spiro[benzofuran-3,4'-piperidine]hydrochloride. 1-benzyl-4-((2-bromo-5-methoxyphenoxy)methyl)-1,2,3,6-tetrahydro-pyridine (25 g; 64.4 mmol) was dissolved in benzene (500 mL) and the solution was purged with nitrogen for 30 minutes. Bu$_3$SnH (24.97 g; 85.8 mmol) was added followed by AIBN (0.6 g) and the solution was stirred at reflux overnight. The reaction mixture was concentrated and taken up in EtOAc and sat. NaHCO$_3$. The organic phase was dried (Na$_2$SO$_4$), filtered and concentrated to give 46 g crude oil. A solution of 5-6 N HCl in i-PrOH (40 mL) was diluted with i-PrOH (200 mL) and added to the oil and stirred for 1 hour. The precipitate was filtered off and rinsed with TBME and dried in vacuo to give the product (15.1 g; 68%) which was isolated as a white solid. $^1$H NMR (free base, 300 MHz, CDCl$_3$) δ ppm 7.38-7.22 (m, 5H), 7.03 (d, J=9 Hz, 1H), 6.43 (dd, J=9 and 2Hz, 1H), 6.39 (d, J=2Hz, 1H), 4.37 (s, 2H), 3.77 (s, 3H), 3.53 (s, 2H), 2.94-2.83 (m, 2H), 2.1-1.88 (m, 4H), 1.74-1.67 (m, 2H).

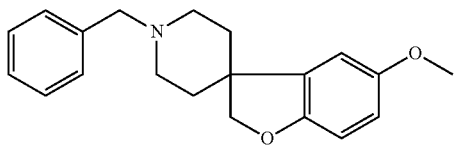 [SMILES: COc1ccc2c(c1)C1(CCN(Cc3ccccc3)CC1)CO2]

1'-Benzyl-5-methoxy-2H-spiro[1-benzofuran-3,4'-piperidine]. 1-benzyl-4-((2-bromo-4-methoxyphenoxy)methyl)-1,2,3,6-tetrahydro-pyridine (20 g; 51.5 mmol) was dissolved in benzene (400 mL) and the solution was purged with nitrogen for 30 minutes. Bu$_3$SnH (23.6 mL; 87 mmol) was added followed by AIBN (0.5 g) and the solution was stirred at reflux overnight. The reaction mixture was concentrated and taken up in EtOAc and sat. NaHCO$_3$. The organic phase was dried (Na$_2$SO$_4$), filtered and concentrated to give 40 g crude oil. The material was purified with a short plug (10 cm) of silica eluting with heptanes/EtOAc 4/1 to give the product (16.2 g; 91%) which was isolated as a light yellow solid. $^1$H NMR (300 MHz, CDCl$_3$) δ ppm 7.38-7.22 (m, 5H), 6.74-6.63 (m, 3H), 4.37 (s, 2H), 3.77 (s, 3H), 3.53 (s, 2H), 2.93-2.84 (m, 2H), 2.1-1.88 (m, 4H), 1.76-1.67 (m, 2H).

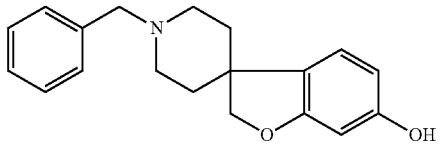 [SMILES: Oc1ccc2c(c1)OCC21CCN(Cc2ccccc2)CC1]

1'-Benzyl-2H-spiro[1-benzofuran-3,4'-piperidin]-6-ol. 1'-benzyl-6-methoxy-2H-spiro[benzofuran-3,4'-piperidine] hydrochloride (15 g; 0.58 mmol) was suspended in HOAc (160 mL) and 48% HBr (20 mL) was added and the solution was stirred at reflux for 24 hours. The mixture was concentrated and the residue was taken up in EtOAc and sat. NaHCO$_3$. The organic phase was dried (Na$_2$SO$_4$), filtered and concentrated to give the product (14 g). $^1$H NMR (300 MHz, CDCl$_3$) δ ppm 7.38-7.23 (m, 5H), 6.94 (d, J=8 Hz, 1H), 6.37-6.26 (m, 2H), 4.36 (s, 2H), 3.55 (s, 2H), 2.94-2.85 (m, 2H), 2.11-1.88 (m, 4H), 1.75-1.65 (m, 2H).

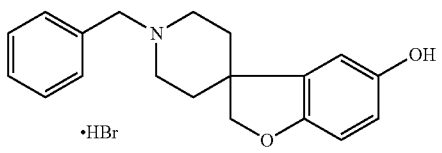 [SMILES: Oc1ccc2c(c1)C1(CCN(Cc3ccccc3)CC1)CO2 ; Br]

1'-Benzyl-2H-spiro[1-benzofuran-3,4'-piperidin]-5-ol hydrobromide. 1'-benzyl-5-methoxy-2H-spiro[benzofuran-3,4'-piperidine]. (16.2 g; 46.8 mmol) was suspended in HOAc (160 mL) and 48% HBr (20 mL) was added and the solution was stirred at reflux for 20 hours. The mixture was allowed to cool and partially concentrated. The precipitate was collected by filtration and dried in vacuo to give the product (14.7 g; 84%). $^1$H NMR (300 MHz, CD$_3$OD) δ ppm 7.6-7.46 (m, 5H), 6.64-6.57 (m, 3H), 4.43 (s, 2H), 4.35 (s, 2H), 3.48 (s, 2H), 3.21-3.04 (m, 2H), 2.23-2.08 (m, 2H), 2.02-1.92 (m, 2H).

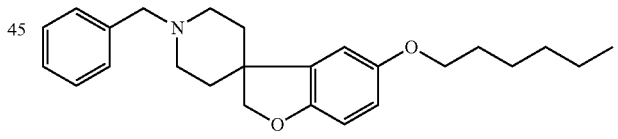

1'-Benzyl-5-(hexyloxy)-2H-spiro[1-benzofuran-3,4'-piperidine]. 1'-benzyl-2H-spiro[1-benzofuran-3,4'-piperidin]-5-ol hydrobromide (170 mg; 0.58 mmol) was dissolved in MeOH (3 mL) and NaOH (48 mg; 1.2 mmol) was added and the solution was stirred for 5 minutes. 1-bromohexane (0.1 mL; 0.7 mmol) was added and the solution was stirred at reflux overnight. The mixture was allowed to cool to RT and concentrated. The residue was taken up in EtOAc and H$_2$O, the organic phase was dried (Na$_2$SO$_4$), filtered and concentrated to give 160 mg oil. The material was subjected to column chromatography with heptanes/EtOAc 4/1 to give the product (102 mg; 60%) which was isolated as an oil. $^1$H-NMR (300 MHz, CDCl$_3$) δ ppm 7.38-7.22 (m, 5H), 6.74-6.66 (m, 3H), 4.36 (s, 2H), 3.87 (t, J=7 Hz, 2H), 3.55 (s, 2H), 2.95-2.85 (m, 2H), 2.11-1.9 (m, 4H), 1.8-1.68 (m, 2H), 1.5-1.4 (m, 2H), 1.4-1.22 (m, 6H), 0.89 (t, J=7.5 Hz, 3H).

The following compounds were obtained in a similar manner:

1'-Benzyl-5-(heptyloxy)-2H-spiro[1-benzofuran-3,4'-piperidine].

1'-Benzyl-5-(octyloxy)-2H-spiro[1-benzofuran-3,4'-piperidine].

In a similar manner and starting with 1'-benzyl-2H-spiro[1-benzofuran-3,4'-piperidin]-6-ol) the following compounds were obtained:

1'-Benzyl-6-(hexyloxy)-2H-spiro[1-benzofuran-3,4'-piperidine].

1'-Benzyl-6-(heptyloxy)-2H-spiro[1-benzofuran-3,4'-piperidine].

1'-Benzyl-6-(octyloxy)-2H-spiro[1-benzofuran-3,4'-piperidine].

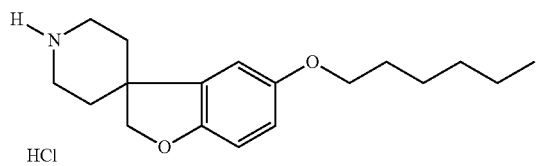 [SMILES: CCCCCCOc1ccc2c(c1)C1(CCNCC1)CO2 ; Cl]

5-(Hexyloxy)-2H-spiro[1-benzofuran-3,4'-piperidine]hydrochloride. 1'-benzyl-5-(hexyloxy)-2H-spiro[1-benzofuran-3,4'-piperidine] (2.7 g; 7.1 mmol) was dissolved in 1,2-DCE (20 mL) and the solution was stirred at 0° C. 1-Chloroethylchloroformate (3.07 mL; 28.4 mmol) was added dropwise and the solution was stirred for 10 minutes at 0° C. and at reflux for 6 h. The solution was allowed to cool to RT overnight and diluted with DCM and washed with brine. The organic phase was dried (Na$_2$SO$_4$), filtered and concentrated thoroughly to give the crude oil.

The oil was dissolved in MeOH (20 mL) and stirred at reflux for 1.5 hours. The mixture was concentrated largely and treated with TBME. Material oiled out and the solution was decanted off and the oil was dried in vacuo to give 0.5 g of the product. The decanted solution was concentrated and the residue dissolved in little MeOH. 1N HCl in i-PrOH (20 mL) was added and the solution was stirred for 30 minutes. The mixture was concentrated to volume and the precipitate was filtered off and dried in vacuo to give another 1.2 g. Pooling of the obtained fractions gave the product (1.7 g; 74%) which was obtained as a white solid. $^1$H NMR (300 MHz, CDCl$_3$) δ ppm 9.78 (s, 2H), 6.81-6.66 (m, 3H), 4.36 (s, 2H), 3.9 (t, J=7 Hz, 2H), 3.62-3.49 (m, 2H), 3.14-2.93 (m, 2H), 2.43-2.27 (m, 2H), 2.07-1.95 (m, 2H), 1.81-1.7 (m, 2H), 1.51-1.3 (m, 6H), 0.9 (t, J=7.5 Hz, 3H).

The following compounds were obtained in a similar manner:

5-(Heptyloxy)-2H-spiro[1-benzofuran-3,4'-piperidine]hydrochloride.

5-(Octyloxy)-2H-spiro[1-benzofuran-3,4'-piperidine]hydrochloride.

6-(Hexyloxy)-2H-spiro[1-benzofuran-3,4'-piperidine]hydrochloride.

6-(Heptyloxy)-2H-spiro[1-benzofuran-3,4'-piperidine]hydrochloride.

6-(Octyloxy)-2H-spiro[1-benzofuran-3,4'-piperidine]hydrochloride.

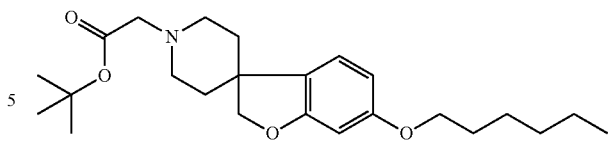

Tert-butyl 2-(6-(hexyloxy)-2H-spiro[1-benzofuran-3,4'-piperidin]-1'-yl)acetate. 6-(hexyloxy)-2H-spiro[1-benzofuran-3,4'-piperidine]hydrochloride (700 mg; 2.15 mmol) was suspended in CH$_3$CN (15 mL) and t-butylchloroacetate (0.37 mL; 2.58 mmol) was added followed by K$_2$CO$_3$ (714 mg; 4.3 mmol) and the solution was stirred at 55° C. overnight. The solution was allowed to cool to RT and concentrated. The residue was taken up in EtOAc and H$_2$O. The organic phase was dried (Na$_2$SO$_4$), filtered and concentrated to give the product (850 mg; 98%). $^1$H NMR (300 MHz, CDCl$_3$) δ ppm 7.0 (d, J=9 Hz, 1H), 6.42 (dd, J=9 Hz, 2Hz, 1H), 6.37 (d, J=2Hz, 1H), 4.37 (s, 2H), 3.9 (t, J=7.5 Hz, 2H), 3.17 (s, 2H), 2.99-2.9 (m, 2H), 2.34-2.2 (m, 2H), 2.09-1.95 (m, 2H), 1.8-1.65 (m, 4H), 1.48 (s, 9H), 1.34-1.26 (m, 6H), 0.9 (t, J=7.5 Hz, 3H).

The following compounds were obtained in a similar manner:

Tert-butyl 2-(6-(heptyloxy)-2H-spiro[1-benzofuran-3,4'-piperidin]-1'-yl)acetate.

Tert-butyl 2-(6-(octyloxy)-2H-spiro[1-benzofuran-3,4'-piperidin]-1'-yl)acetate.

Tert-butyl 2-(5-(hexyloxy)-2H-spiro[1-benzofuran-3,4'-piperidin]-1'-yl)acetate.

Tert-butyl 2-(5-(heptyloxy)-2H-spiro[1-benzofuran-3,4'-piperidin]-1'-yl)acetate.

Tert-butyl 2-(5-(octyloxy)-2H-spiro[1-benzofuran-3,4'-piperidin]-1'-yl)acetate.

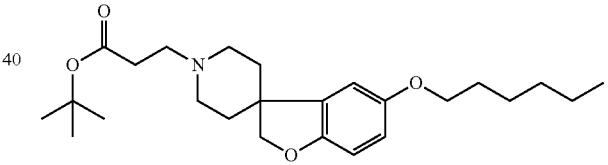

Tert-butyl 3-(5-(hexyloxy)-2H-spiro[1-benzofuran-3,4'-piperidin]-1'-yl)propano-ate. 6-(hexyloxy)-2H-spiro[1-benzofuran-3,4'-piperidine]hydrochloride (600 mg; 1.84 mmol) was suspended in THF (8 mL) and t-butylacrylate (0.32 mL; 2.2 mmol) was added followed by Et$_3$N (0.36 mL; 2.58 mmol). The solution was stirred at 70° C. overnight. The solution was allowed to cool to RT and poured in EtOAc and sat. NaHCO$_3$. The organic phase was dried (Na$_2$SO$_4$), filtered and concentrated to give the product (770 mg; 100%) which was obtained as an oil. $^1$H NMR (300 MHz, CDCl$_3$) δ ppm 7.19 (m, 1H), 6.73-6.66 (m, 2H), 4.34 (s, 2H), 3.87 (t, J=7.5 Hz, 2H), 2.94-2.84 (m, 2H), 2.69 (t, J=7.5 Hz, 2H), 2.44 (t, J=7.5 Hz, 2H), 2.16-1.87 (m, 4H), 1.8-1.64 (m, 4H), 1.46 (s, 9H), 1.52-1.29 (m, 6H), 0.9 (t, J=7.5 Hz, 3H).

The following compounds were obtained in a similar manner:

Tert-butyl 2-(5-(heptyloxy)-2H-spiro[1-benzofuran-3,4'-piperidin]-1'-yl)propanoate.

Tert-butyl 2-(5-(octyloxy)-2H-spiro[1-benzofuran-3,4'-piperidin]-1'-yl)propanoate.

Tert-butyl 2-(6-(hexyloxy)-2H-spiro[1-benzofuran-3,4'-piperidin]-1'-yl)propanoate.

Tert-butyl 2-(6-(heptyloxy)-2H-spiro[1-benzofuran-3,4'-piperidin]-1'-yl)propanoate.
Tert-butyl 2-(6-(octyloxy)-2H-spiro[1-benzofuran-3,4'-piperidin]-1'-yl)propanoate.

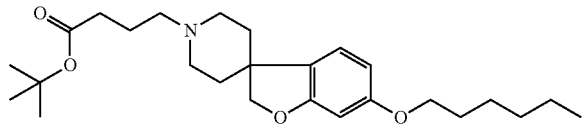 [SMILES: CCCCCCOc1ccc2c(c1)OCC21CCN(CCCC(=O)OC(C)(C)C)CC1]

Tert-butyl 4-(6-(heptyloxy)-2H-spiro[benzofuran-3,4'-piperidin]-1'-yl)butanoate. 6-(Hexyloxy)-2H-spiro[1-benzofuran-3,4'-piperidine]hydrochloride (700 mg; 2.06 mmol) was suspended in CH₃CN (15 mL) and t-butyl-4-bromobutyrate (551 mg; 2.47 mmol) was added followed by K₂CO₃ (684 mg; 4.12 mmol) and KI (342 mg; 2.47 mmol) and the solution was stirred at 75° C. overnight. The solution was allowed to cool to RT and concentrated. The residue was taken up in EtOAc and H₂O. The organic phase was dried (Na₂SO₄), filtered and concentrated to give the product (890 mg, 97%). ¹H NMR (300 MHz, CDCl₃) δ ppm 6.96 (d, J=9 Hz, 1H), 6.42 (dd, J=9 Hz, 2Hz, 1H), 6.37 (d, J=2Hz, 1H), 4.36 (s, 2H), 3.9 (t, J=7.5 Hz, 2H), 2.95-2.85 (m, 2H), 2.4-2.3 (m, 2H), 2.24 (t, J=8 Hz, 2H), 2.12-1.87 (m, 4H), 1.87-1.63 (m, 6H), 1.45 (s, 9H), 1.5-1.22 (m, 8H), 0.89 (t, J=7.5 Hz, 3H).

The following compounds were obtained in a similar manner:
Tert-butyl 2-(6-(heptyloxy)-2H-spiro[1-benzofuran-3,4'-piperidin]-1'-yl)butanoate.
Tert-butyl 2-(6-(octyloxy)-2H-spiro[1-benzofuran-3,4'-piperidin]-1'-yl)butanoate.
Tert-butyl 2-(5-(hexyloxy)-2H-spiro[1-benzofuran-3,4'-piperidin]-1'-yl)butanoate.
Tert-butyl 2-(5-(heptyloxy)-2H-spiro[1-benzofuran-3,4'-piperidin]-1'-yl)butanoate.
Tert-butyl 2-(5-(octyloxy)-2H-spiro[1-benzofuran-3,4'-piperidin]-1'-yl)butanoate.

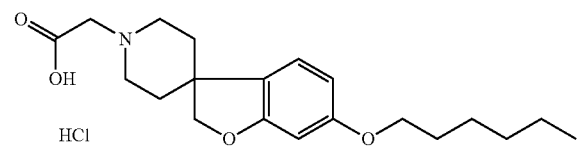 [SMILES: CCCCCCOc1ccc2c(c1)OCC21CCN(CC(=O)O)CC1 ; Cl]

Compound 1. 2-(6-(Hexyloxy)-2H-spiro[1-benzofuran-3,4'-piperidin]-1'-yl)acetic acid hydrochloride Tert-butyl 2-(6-(hexyloxy)-2H-spiro[1-benzofuran-3,4'-piperidin]-1'-yl)acetate (850 mg; 2.1 mmol) was stirred in 4N HCl in dioxane (10 mL) and stirred overnight. The precipitate was filtered off and rinsed with TBME. The solid was dried in vacuo to give the product (590 mg; 73%). ¹H NMR (300 MHz, CD₃OD) δ ppm 7.04 (s, 1H), 6.48-6.44 (dd, J=8 and 2Hz, 1H), 6.37 (d, J=2Hz, 1H), 4.47 (s, 2H), 4.11 (s, 2H), 3.91 (t, J=6.5 Hz, 2H), 3.75-3.6 (m, 2H), 3.4-3.1 (bs, 4H), 2.22 (s, 2H), 2.03-1.94 (m, 2H), 1.79-1.68 (m, 2H), 1.51-1.32 (m, 6H), 0.92 (t, J=7 Hz, 3H). DSC peak at 250° C.

The following compounds were obtained in a similar manner:

Compound 2. 2-(6-(Hexyloxy)-2H-spiro[1-benzofuran-3,4'-piperidin]-1'-yl)propanoic acid hydrochloride ¹H NMR (300 MHz, CD₃OD) δ ppm 7.07 (s, 1H), 6.48-6.44 (dd, J=8 Hz and 2Hz, 1H), 6.37 (d, J=2Hz, 1H), 4.47 (s, 2H), 3.92 (t, J=6.5 Hz, 2H), 3.67-3.56 (m, 2H), 3.47 (t, J=7 Hz, 2H), 3.3-3.1 (bs, 2H), 2.85 (t, J=7 Hz, 2H), 2.22-2.08 (m, 2H), 2.04-1.93 (m, 2H), 1.79-1.66 (m, 2H), 1.51-1.3 (m, 6H), 0.92 (t, J=7 Hz, 3H). DSC peak at 245.4° C.

Compound 3. 2-(6-(Hexyloxy)-2H-spiro[1-benzofuran-3,4'-piperidin]-P-yl)buta-noic acid hydrochloride ¹H NMR (300 MHz, CD₃OD) δ ppm 7.04 (s, 1H), 6.48-6.44 (dd, J=8 Hz, 2Hz, 1H), 6.37 (d, J=2Hz, 1H), 4.47 (s, 2H), 3.91 (t, J=6.5 Hz, 2H), 3.69-3.53 (m, 2H), 3.27-3.18 (m, 2H), 3.1 (s, 2H), 2.49 (t, J=7 Hz, 2H), 2.14-1.96 (m, 6H), 1.76-1.7 (m, 2H), 1.48-1.32 (m, 6H), 0.92 (t, J=7 Hz, 3H). DSC peak at 232.6° C.

Compound 4. 2-(6-(Heptyloxy)-2H-spiro[1-benzofuran-3,4'-piperidin]-1'-yl)acetic acid hydrochloride ¹H NMR (300 MHz, CD₃OD) δ ppm 7.03 (s, 1H), 6.48-6.44 (dd, J=8 Hz, 2Hz, 1H), 6.37 (d, J=2Hz, 1H), 4.47 (s, 2H), 4.14 (s, 2H), 3.91 (t, J=6.5 Hz, 2H), 3.76-3.6 (m, 2H), 3.4-3.1 (bs, 2H), 2.22 (t, 2H), 2.03-1.94 (m, 2H), 1.79-1.68 (m, 2H), 1.52-1.27 (m, 8H), 0.9 (t, J=7 Hz, 3H). DSC peak at 251.6° C.

Compound 5. 2-(6-(Heptyloxy)-2H-spiro[1-benzofuran-3,4'-piperidin]-1'-yl)propanoic acid hydrochloride ¹H NMR (300 MHz, CD₃OD) δ ppm 7.07 (s, 1H), 6.48-6.44 (dd, J=8 Hz, 2Hz, 1H), 6.37 (d, J=2Hz, 1H), 4.47 (s, 2H), 3.92 (t, J=6.5 Hz, 2H), 3.67-3.56 (m, 2H), 3.46 (t, J=7 Hz, 2H), 3.3-3.1 (m, 2H), 2.85 (t, J=7 Hz, 2H), 2.22-2.07 (m, 2H), 2.04-1.93 (m, 2H), 1.78-1.66 (m, 2H), 1.52-1.28 (m, 8H), 0.91 (t, J=7 Hz, 3H). DSC peak at 240.2° C.

Compound 6. 2-(6-(Heptyloxy)-2H-spiro[1-benzofuran-3,4'-piperidin]-P-yl)butanoic acid hydrochloride ¹H NMR (300 MHz, CD₃OD) δ ppm 7.04 (s, 1H), 6.48-6.44 (dd, J=8 Hz, 2Hz, 1H), 6.37 (d, J=2Hz, 1H), 4.47 (s, 2H), 3.91 (t, J=6.5 Hz, 2H), 3.68-3.55 (m, 2H), 3.27-3.18 (m, 2H), 3.1 (s, 2H), 2.49 (t, J=7 Hz, 2H), 2.22-1.94 (m, 6H), 1.8-1.68 (m, 2H), 1.51-1.32 (m, 8H), 0.91 (t, J=7 Hz, 3H). DSC peak at 229.1° C.

Compound 7. 2-(6-(Octyloxy)-2H-spiro[1-benzofuran-3,4'-piperidin]-1'-yl)acetic acid hydrochloride ¹H NMR (300 MHz, CD₃OD) δ ppm 7.03 (s, 1H), 6.48-6.44 (dd, J=8 and 2Hz, 1H), 6.37 (d, J=2Hz, 1H), 4.47 (s, 2H), 4.14 (s, 2H), 3.91 (t, J=6.5 Hz, 2H), 3.76-3.6 (m, 2H), 3.4-3.1 (bs, 2H), 2.22 (t, J=7 Hz, 2H), 2.03-1.94 (m, 2H), 1.79-1.67 (m, 2H), 1.51-1.26 (m, 10H), 0.9 (t, J=7 Hz, 3H). DSC peak at 247.6° C.

Compound 8. 2-(6-(Octyloxy)-2H-spiro[1-benzofuran-3,4'-piperidin]-1'-yl)propanoic acid hydrochloride ¹H NMR (300 MHz, CD₃OD) δ ppm 7.07 (s, 1H), 6.48-6.44 (dd, J=8 and 2Hz, 1H), 6.37 (d, J=2Hz, 1H), 4.47 (s, 2H), 3.92 (t, J=6.5 Hz, 2H), 3.67-3.56 (m, 2H), 3.46 (t, J=7 Hz, 2H), 3.3-3.1 (m, 2H), 2.85 (t, J=7 Hz, 2H), 2.22-2.07 (m, 2H), 2.04-1.93 (m, 2H), 1.78-1.66 (m, 2H), 1.51-1.28 (m, 10H), 0.91 (t, J=7 Hz 3H). DSC peak at 235.9° C.

Compound 9. 2-(6-(Octyloxy)-2H-spiro[1-benzofuran-3,4'-piperidin]-1'-yl)butanoic acid hydrochloride ¹H NMR (300 MHz, CD₃OD) δ ppm 7.04 (s, 1H), 6.48-6.44 (dd, J=8 and 2Hz, 1H), 6.37 (d, J=2Hz, 1H), 4.47 (s, 2H), 3.91 (t, J=6.5 Hz, 2H), 3.69-3.54 (m, 2H), 3.27-3.18 (m, 2H), 3.1 (s, 2H), 2.49 (t, J=7 Hz, 2H), 2.21-1.94 (m, 6H), 1.79-1.68 (m, 2H), 1.51-1.27 (m, 10H), 0.9 (t, J=7 Hz, 3H). DSC peak at 232° C.

Compound 10. 2-(5-(Hexyloxy)-2H-spiro[1-benzofuran-3,4'-piperidin]-1'-yl)acetic acid hydrochloride ¹H NMR (300 MHz, CD₃OD) δ ppm 6.82-6.67 (m, 3H), 4.47 (s, 2H), 4.14 (s, 2H), 3.91 (t, J=6.5 Hz, 2H), 3.78-3.63 (m, 2H), 3.3-3.1 (m, 2H), 2.33-2.18 (m, 2H), 2.07-1.96 (m, 2H), 1.8-1.67 (m, 2H), 1.53-1.42 (m, 2H), 1.42-1.3 (m, 4H), 0.92 (t, J=7 Hz, 3H).

Compound 11. 2-(5-(Hexyloxy)-2H-spiro[1-benzofuran-3,4'-piperidin]-1'-yl)propanoic acid hydrochloride ¹H NMR (300 MHz, CD₃OD) δ ppm 6.82-6.67 (m, 3H), 4.47 (s, 2H), 3.91 (t, J=6.5 Hz, 2H), 3.68-3.58 (m, 2H), 3.48 (t, J=7 Hz, 2H), 3.3-3.09 (m, 2H), 2.89 (t, J=7 Hz, 2H), 2.28-2.14 (m, 2H), 2.07-1.95 (m, 2H), 1.8-1.67 (m, 2H), 1.53-1.27 (m, 6H), 0.92 (t, J=7 Hz, 3H)

Compound 12. 2-(5-(Hexyloxy)-2H-spiro[1-benzofuran-3,4'-piperidin]-1'-yl)butanoic acid hydrochloride ¹H NMR (300 MHz, CD₃OD) δ ppm 6.82-6.67 (m, 3H), 4.47 (s, 2H), 3.92 (t, J=6.5 Hz, 2H), 3.7-3.58 (m, 2H), 3.25 (m, 2H), 3.1 (m, 2H), 2.5 (t, J=7 Hz, 2H), 2.28-1.92 (m, 6H), 1.8-1.68 (m, 2H), 1.53-1.4 (m, 2H), 1.42-1.27 (m, 6H), 0.92 (t, J=7 Hz, 3H). DSC peak at 235.4° C.

Compound 13. 2-(5-(Heptyloxy)-2H-spiro[1-benzofuran-3,4'-piperidin]-1'-yl)acetic acid hydrochloride ¹H NMR (300 MHz, CD₃OD) δ ppm 6.82-6.67 (m, 3H), 4.47 (s, 2H), 4.14 (s, 2H), 3.91 (t, J=6.5 Hz 2H), 3.75-3.63 (m, 2H), 3.3-3.12 (m, 2H), 2.33-2.18 (m, 2H), 2.07-1.96 (m, 2H), 1.8-1.67 (m, 2H), 1.53-1.27 (m, 8H), 0.92 (t, J=7 Hz, 3H).

Compound 14. 2-(5-(Heptyloxy)-2H-spiro[1-benzofuran-3,4'-piperidin]-1'-yl)propanoic acid hydrochloride ¹H NMR (300 MHz, CD₃OD) δ ppm 6.82-6.67 (m, 3H), 4.47 (s, 2H), 3.91 (t, J=6.5 Hz, 2H), 3.68-3.58 (m, 2H), 3.47 (t, J=7 Hz, 2H), 3.3-3.1 (m, 2H), 2.87 (t, J=7 Hz, 2H), 2.25-2.14 (m, 2H), 2.07-1.96 (m, 2H), 1.8-1.67 (m, 2H), 1.53-1.27 (m, 10H), 0.92 (t, J=7 Hz, 3H).

Compound 15. 2-(5-(Heptyloxy)-2H-spiro[1-benzofuran-3,4'-piperidin]-1'-yl)butanoic acid hydrochloride ¹H NMR (300 MHz, CD₃OD) δ pm 6.82-6.67 (m, 3H), 4.47 (s, 2H), 3.91 (t, J=6.5 Hz, 2H), 3.68-3.57 (m, 2H), 3.4-3.06 (m, 4H), 2.5 (t, J=7 Hz, 2H), 2.25-1.94 (m, 6H), 1.79-1.68 (m, 2H), 1.51-1.27 (m, 10H), 0.92 (t, J=7 Hz, 3H). DSC peak at 240° C.

Compound 16. 2-(5-(Octyloxy)-2H-spiro[1-benzofuran-3,4'-piperidin]-1'-yl)acetic acid hydrochloride ¹H NMR (300 MHz, CD₃OD) δ ppm 6.82-6.67 (m, 3H), 4.47 (s, 2H), 4.14 (s, 2H), 3.91 (t, J=6.5 Hz, 2H), 3.75-3.62 (m, 2H), 3.3-3.12 (m, 2H), 2.32-2.18 (m, 2H), 2.07-1.95 (m, 2H), 1.8-1.67 (m, 2H), 1.54-1.27 (m, 10H), 0.9 (t, J=7 Hz, 3H).

Compound 17. 2-(5-(Octyloxy)-2H-spiro[1-benzofuran-3,4'-piperidin]-1'-yl)propanoic acid hydrochloride ¹H NMR (300 MHz, CD₃OD) δ ppm 6.82-6.67 (m, 3H), 4.47 (s, 2H), 3.91 (t, J=6.5 Hz, 2H), 3.68-3.58 (m, 2H), 3.47 (t, J=7 Hz, 2H), 3.3-3.1 (m, 2H), 2.87 (t, J=7 Hz, 2H), 2.26-2.14 (m, 2H), 2.07-1.96 (m, 2H), 1.8-1.67 (m, 2H), 1.53-1.27 (m, 10H), 0.92 (t, J=7 Hz, 3H).

Compound 18. 2-(5-(Octyloxy)-2H-spiro[1-benzofuran-3,4'-piperidin]-1'-yl)butanoic acid hydrochloride ¹H NMR (300 MHz, CD₃OD) δ ppm 6.82-6.67 (m, 3H), 4.47 (s, 2H), 3.91 (t, J=6.5 Hz, 2H), 3.7-3.57 (m, 2H), 3.36-3.03 (m, 4H), 2.49 (t, J=7 Hz, 2H), 2.26-1.96 (m, 6H), 1.79-1.68 (m, 2H), 1.53-1.27 (m, 12H), 0.92 (t, J=7 Hz, 3H). DSC peak at 241.1° C.

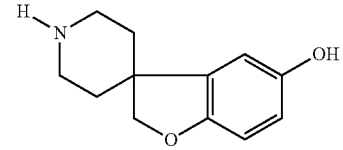 [SMILES: Oc1ccc2c(c1)C1(CCNCC1)CO2]

2H-spiro[1-Benzofuran-3,4'-piperidin]-5-ol. To a mixture of 1'-benzyl-2H-spiro[1-benzofuran-3,4'-piperidin]-5-ol hydrobromide (6 g, 15.9 mmol) in 120 ml MeOH was added 0.6 g Palladium hydroxide. The mixture was treated with H₂, at normal pressure overnight. The crude reaction mixture was concentrated till about 20 mL and filtered through a tosic acid solid phase extraction cartridge, washing with MeOH, and eluting with 2 N NH₃/MeOH. The product was concentrated to give 2.6 g (80%) as a white solid. ¹H-NMR (400 MHz, DMSO-d₆) δ ppm 8.8 (s, 1H), 6.57-6.51 (m, 2H), 6.47 (dd, J=8 and 2Hz, 1H), 4.29 (s, 2H), 2.9-2.84 (m, 2H), 2.55-2.47 (m, 2H), 1.68-1.59 (m, 2H), 1.54-1.47 (m, 2H).

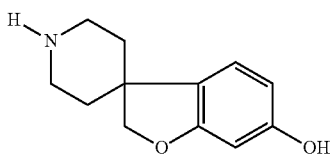 [SMILES: Oc1ccc2c(c1)OCC21CCNCC1]

2H-spiro[1-Benzofuran-3,4'-piperidin]-6-ol. To a mixture of 1'-benzyl-2H-spiro[1-benzofuran-3,4'-piperidin]-6-ol (2 g, 5.3 mmol) in 60 ml MeOH (containing 5 mL of 4 N HCl in MeOH) was added 0.2 g Palladium hydroxide. The mixture was treated with $H_2$, at normal pressure for 48 hours. The crude reaction mixture was concentrated till about 20 mL and filtered through a tosic acid solid phase extraction cartridge, washing with MeOH, and eluting with 2 N $NH_3$/MeOH. The product was concentrated to give 950 mg (90%) $^1$H NMR (400 MHz, DMSO-$d_6$) δ ppm 9.3 (bs, 1H), 6.91 (d, J=8 Hz, 1H), 6.50 (d, J=2Hz, 1H), 4.31 (s, 2H), 2.9-2.84 (m, 2H), 2.54-2.45 (m, 2H), 1.68-1.59 (m, 2H), 1.52-1.44 (m, 2H).

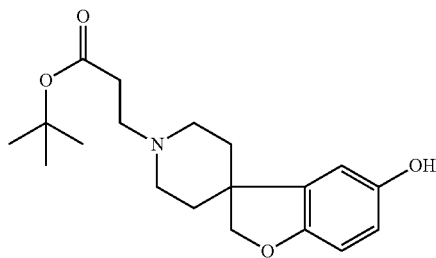 [SMILES: CC(C)(C)OC(=O)CCN1CCC2(CC1)COc1ccc(O)cc12]

Tert-butyl 3-{5-hydroxy-2H-spiro[1-benzofuran-3,4'-piperidine]-1'-yl}propanoate A mixture of 2H-spiro[1-benzofuran-3,4'-piperidin]-5-ol (3.85 g; 18.76 mmol), tert-butyl acrylate (3.28 ml; 22.51 mmol) and N,N-diisopropylamine in MeOH (175 mL) was heated under reflux overnight. After cooling to RT the mixture was concentrated in vacuo, and the residue was partitioned between EtOAc and 5% aqueous $NaHCO_3$ solution. The organic layer was dried ($Na_2SO_4$), filtered, concentrated in vacuo, and purified by column chromatography ($SiO_2$, $Et_2O$:hexanes 1:1 followed by $Et_2O$) to afford the product (4g), Rt 1.02 min (System B), [M+H]$^+$ 334.2

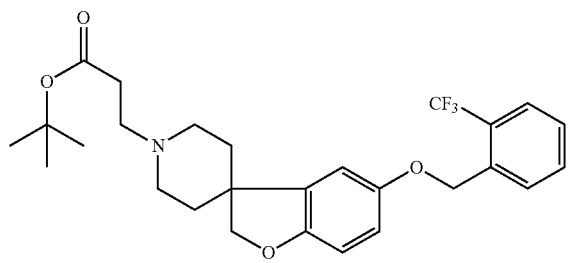 [SMILES: CC(C)(C)OC(=O)CCN1CCC2(CC1)COc1ccc(OCc3ccccc3C(F)(F)F)cc12]

Tert-butyl 3-(5-{[2-(trifluoromethyl)phenyl]methoxy}-2H-spiro[1-benzofuran-3,4'-piperidine]-1'-yl}propanoate.
To a solution of Tert-butyl 3-{5-hydroxy-2H-spiro[1-benzofuran-3,4'-piperidine]-1'-yl}propanoate (0.51 g; 1.53 mmol) in THF (10 mL) was added 2-(trifluoromethyl)benzyl alcohol (0.3 mL; 2.29 mmol), followed by DIAD (0.43 mL; 2.2 mmol) and triphenylphosphine (0.58 g; 2.2 mmol). The resulting mixture was stirred at RT for 3 days. Subsequently, the reaction mixture was concentrated in vacuo. The residue was purified by column chromatography ($SiO_2$, $Et_2O$:hexanes 2:1) to afford the product (0.38 g). Rt 1.42 min (System B), [M+H]$^+$ 492.2

The following compounds were obtained according to a similar manner:

Tert-butyl 3-[5-(cyclohexylmethoxy)-2H-spiro[1-benzofuran-3,4'-piperidine]-1'-yl]propanoate. Rt 1.49 min (System B), [M+H]$^+$ 430.3

Tert-butyl 3-(5-{[3-(trifluoromethyl)phenyl]methoxy}-2H-spiro[1-benzofuran-3,4'-piperidine]-1'-yl}propanoate. Rt 1.48 min (System B), [M+H]$^+$ 492.1

Tert-butyl 3-{5-[(2,6-dichlorophenyl)methoxy]-2H-spiro[1-benzofuran-3,4'-piperidine]-1'-yl}propanoate. Rt 1.45 min (System B), [M+H]$^+$ 492.1

Tert-butyl 3-{5-[(3,5-dichlorophenyl)methoxy]-2H-spiro[1-benzofuran-3,4'-piperidine]-1'-yl}propanoate. Rt 1.50 min (System B), [M+H]$^+$ 492.1

Tert-butyl 3-{5-[(2,6-difluorophenyl)methoxy]-2H-spiro[1-benzofuran-3,4'-piperidine]-1'-yl}propanoate.

Tert-butyl 3-{5-[(2-chlorophenyl)methoxy]-2H-spiro[1-benzofuran-3,4'-piperidine]-1'-yl}propanoate.

Tert-butyl 3-{5-[(2,4,6-trichlorophenyl)methoxy]-2H-spiro[1-benzofuran-3,4'-piperidine]-1'-yl}propanoate. Rt 1.53 min (System B), [M+H]$^+$ 528.0

Tert-butyl 3-{5-[(2-chloro-6-methylphenyl)methoxy]-2H-spiro[1-benzofuran-3,4'-piperidine]-1'-yl}propanoate. Rt 1.50 min (System B), [M+H]$^+$ 472.1

Compound 19. 3-(5-{[2-(Trifluoromethyl)phenyl]methoxy}-2H-spiro[1-benzo-furan-3,4'-piperidine]-1'-yl}propanoic acid hydrochloride Tert-butyl 3-(5-{[2-(trifluoromethyl)phenyl]-methoxy}-2H-spiro[1-benzofuran-3,4'-piperidine]-1'-yl}propanoate (0.21 g; 0.43 mmol) was dissolved in a 4M solution of HCl in 1,4-dioxane (3.2 mL; 12.82 mmol) and stirred overnight at RT. Subsequently, the solvent was removed in vacuo and the residue treated with $iPr_2O$, the precipitate was collected by filtration and dried overnight under reduced pressure to afford the product (0.17 g). $^1$H NMR (400 MHz, DMSO/TFA-$d_6$) δ ppm 9.5 (bs, 1H), 7.75 (d, J=8.2Hz, 2H), 7.68 (t, J=8.2Hz, 1H), 7.53 (t, J=7.7 Hz, 1H), 6.69-6.82 (m, 3H), 5.15 (s, 2H), 4.42 (bs, 2H), 3.45-3.60 (m, 2H), 3.29-3.41 (m, 2H), 2.98-3.18 (m, 2H), 2.78 (t, J=7.4 Hz, 2H), 2.02-2.18 (m, 2H), 1.80-1.91 (m, 2H). Rt 1.36 min (System B), [M+H]$^+$ 436.1

The following compounds were obtained according to a similar manner:

Compound 20. 3-[5-(Cyclohexylmethoxy)-2H-spiro[1-benzofuran-3,4'-piperidine]-1'-yl]propanoic acid hydrochloride Rt 1.40 min (System B), [M+H]$^+$ 374.2

Compound 21. 3-(5-{[3-(Trifluoromethyl)phenyl]methoxy}-2H-spiro[1-benzofuran-3,4'-piperidine]-1'-yl}propanoic acid hydrochloride Rt 1.77 min (System B), [M+H]$^+$ 436.1

Compound 22. 3-{5-[(2,6-Dichlorophenyl)methoxy]-2H-spiro[1-benzofuran-3,4'-piperidine]-1'-yl}propanoic acid hydrochloride Rt 1.49 min (System B), [M+H]+ 436.2

Compound 23. 3-{5-[(3,5-Dichlorophenyl)methoxy]-2H-spiro[1-benzofuran-3,4'-piperidine]-1'-yl}propanoic acid hydrochloride Rt 1.42 min (System B), [M+H]+ 436.0

Compound 24. 3-{5-[(2,6-Difluorophenyl)methoxy]-2H-spiro[1-benzofuran-3,4'-piperidine]-1'-yl}propanoic acid hydrochloride Rt 1.27 min (System B), [M+H]+ 404.1

Compound 25. 3-{5-[(2-Chlorophenyl)methoxy]-2H-spiro[1-benzofuran-3,4'-piperidine]-1'-yl}propanoic acid hydrochloride Rt 1.33 min (System B), [M+H]+ 402.1

Compound 26. 3-{5-[(2,4,6-Trichlorophenyl)methoxy]-2H-spiro[1-benzofuran-3,4'-piperidine]-1'-yl}propanoic acid hydrochloride $^1$H NMR (400 MHz, DMSO-d$_6$) δ ppm 12.63 (bs, 1H), 10.36 (bs, 1H), 7.79 (s, 2H), 6.98 (dd, J=8 and 2Hz, 1H), 6.76 (dd, J=8 and 2Hz, 2H), 5.14 (s, 2H), 4.46 (br s, 2H), 3.24-3.56 (m, 4H), 2.99-3.17 (m, 2H), 2.87 (t, J=8 Hz, 2H,) 2.12-2.29 (m, 2H), 1.84-1.94 (m, 2H).
Rt 1.47 min (System B), [M+H]+ 472.0

Compound 27. 3-{5-[(2-Chloro-6-methylphenyl)methoxy]-2H-spiro[1-benzofuran-3,4'-piperidine]-1'-yl}propanoic acid hydrochloride Rt 1.77 min (System B), [M+H]+ 416.1

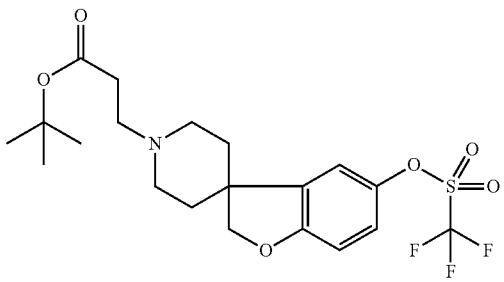 [SMILES: CC(C)(C)OC(=O)CCN1CCC2(CC1)COc1ccc(OS(=O)(=O)C(F)(F)F)cc12]

Tert-butyl 3-{5-[(trifluoromethane)sulfonyloxy]-2H-spiro[1-benzofuran-3,4'-piperidine]-1'-yl]propanoate. To a solution of tert-butyl 3-{5-hydroxy-2H-spiro[1-benzofuran-3,4'-piperidine]-1'-yl}propanoate (333 mg; 1.0 mmol) in 15 mL dichloro-methane and pyridine (90 mg; 1.1 eq) was added dropwise a solution of trifluoro-methanesulfonic anhydride (310 mg; 1.1 eq) dissolved in 5 ml dichlorometh-ane, at −10° C. The resulting reaction mixture was allowed to warm to RT and stirred overnight. The reaction was quenched by the addition of an 5% aqueous NH$_4$Cl solution. The resulting mixture was extracted with dichloromethane. The organic layers were dried (Na$_2$SO$_4$), filtered and con-centrated in vacuo to afford the product (390 mg), which was used as such in the next step. Rt 1.34 min (System B), [M+H]+ 466.1

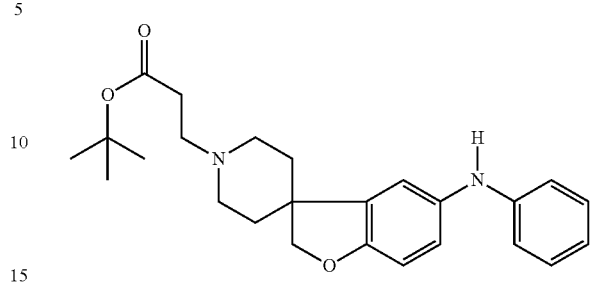

Tert-butyl 3-[5-(Phenylamino)-2H-spiro[1-benzofuran-3,4'-piperidine]-1'-yl]pro-panoate. To a degassed solution of tert-butyl 3-{5-[(trifluoromethane)sulfonyloxy]-2H-spiro[1-benzfuran-3,4'-piperidine]-1'-yl]propanoate (380 mg; 0.82 mmol) in toluene (20 mL) was aniline (91.23 mg; 0.98 mmol), cesiumcarbonate (372 mg, 1.14 mmol), palladium (II)acetate (9 mg, 0.04 mmol), 2-dicyclohexylphosphino-2',4',6'-triiso-propylbiphenyl (39 mg; 0.08 mmol) and 5 mg phenylboronic acid. The resulting mixture was heated to 100° C. overnight. After cooling to RT a 5% aqueous NaHCO$_3$ solution was added, and the product was extracted with EtOAc. The combined organic layers were dried (Na$_2$SO$_4$), filtered, and concentrated in vacuo. The residue was purified by column chromatography (SiO$_2$, dichlo-romehthane/MeOH 95:5) to afford the product (270 mg) which was used as such in the next step.

Compound 28. 3-[5-(Phenylamino)-2H-spiro[1-benzofuran-3,4'-piperidine]-1'-yl]propanoic acid hydrochloride Tert-butyl 3-[5-(phenylamino)-2H-spiro[1-benzfuran-3,4'-piperidine]-1'-yl]propanoate. (0.27 g; 0.66 mmol) was dissolved in a 4M solution of HCl in 1,4-dioxane (10 mL, 40 mmol) and stirred overnight at RT. Subsequently, the solvent was removed in vacuo and the residue treated with iPr$_2$O, the precipitate was collected by filtration and dried overnight under reduced pressure to afford the product (0.2 g). Rt 1.21 min (System B), [M+H]+ 353.1

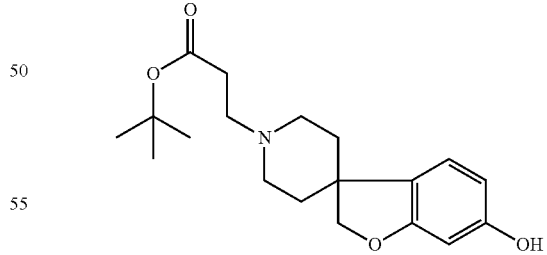

Tert-butyl 3-{6-hydroxy-2H-spiro[1-benzofuran-3,4'-pip-eridine]-1'-yl}propanoate. A mixture of 2H-spiro[1-benzo-furan-3,4'-piperidin]-6-ol (5.09 g; 18.76 mmol), tert-butyl acrylate (4 ml; 27.28 mmol) and N,N-diisopropylamine (5.31 ml, 31 mmol) in MeOH (100 mL) was heated under reflux overnight. After cooling to RT the mixture was concentrated in vacuo, and the residue was partitioned between EtOAc and 5% aqueous NaHCO$_3$ solution. The organic layer was dried (Na$_2$SO$_4$), filtered, and concentrated in vacuo to afford the product (7.54 g). $^1$H NMR (400 MHz, CDCl$_3$-d) δ ppm 6.92 (d, J=7.9 Hz, 1H), 6.28-6.35 (m, 2H), 5.40 (bs, 1H), 4.35 (s, 2H), 2.85-2.93 (m, 2H), 2.70 (t, J=7.4 Hz, 2H), 2.45 (t, J=7.4 Hz, 2H), 2.02-2.12 (m, 2H), 1.86-1.97 (m, 2H), 1.67-1.75 (m, 2H), 1.46 (s, 9H). Rt 0.97 min (System B), [M+H]$^+$ 334.2

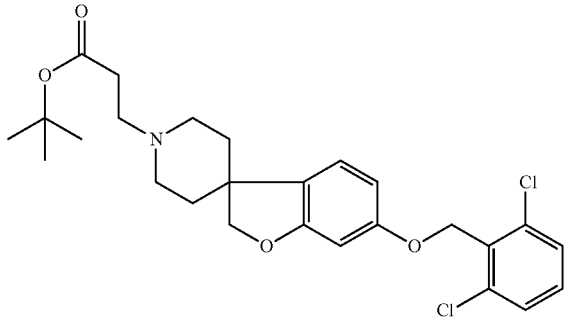 [SMILES: CC(C)(C)OC(=O)CCN1CCC2(CC1)COc1cc(OCc3c(Cl)cccc3Cl)ccc12]

Tert-butyl 3-{6-[(2,6-dichlorophenyl)methoxy]-2H-spiro[1-benzofuran-3,4'-piperidine]-1'-yl}propanoate. To a solution of (2,6-dichlorophenyl)methanol (0.79 g; 4.45 mmol) and tert-butyl 3-{6-hydroxy-2H-spiro[1-benzofuran-3,4'-piperidine]-1'-yl}propanoate (1 g, 2.97 mmol) in dichloromethane (60 mL) was added triphenyl-phosphine (1.95 g; 7.42 mmol), followed, after 30 minutes by DIAD (1.46 mL; 7.42 mmol). Subsequently, the resulting mixture was stirred at RT overnight, and concentrated in vacuo. The residue was purified by column chromatography (SiO$_2$, dichloromethane/acetone 95:5) to afford the crude product (2 g). This product was dissolved in Et$_2$O (60 mL) and 4 mL 1 M HCl/Ethanol was added. The formed white solid was isolated by filtration and washed with Et$_2$O and EtOAc, after which it was partitioned between 5% aqueous NaHCO$_3$ and dichloromethane. The organic layer was dried (Na$_2$SO$_4$), filtered, and concentrated in vacuo, to afford the product (1.10 g, 75%). $^1$H NMR (400 MHz, CHLOROFORM-d) δ ppm 7.36 (d, J=8 Hz, 2H,) 7.23 (d, J=8 Hz, 1H), 7.03 (d, J=8 Hz, 1H), 6.56 (dd, J=8 and 2Hz, 1H), 6.51 (d, J=2Hz, 1H), 5.22 (s, 2H), 4.37 (s, 2H), 2.85-2.92 (m, 2H), 2.70 (t, J=8 Hz, 2H), 2.45 (dt, J=8 and 2Hz, 2H), 2.03-2.11 (m, 2H), 1.89-1.98 (m, 2H), 1.69-1.77 (m, 2H), 1.46 (s, 9H). Rt 1.45 min (System B), [M+H]$^+$ 492.1.

The following compounds were obtained according to a similar manner:

Tert-butyl 3-{6-[(4-phenylpentyl)oxy]-2H-spiro[1-benzofuran-3,4'-piperidine]-1'-yl}propanoate.
Tert-butyl 3-{6-[(3-chlorophenyl)methoxy]-2H-spiro[1-benzofuran-3,4'-piperidine]-1'-yl}propanoate.
Tert-butyl 3-[6-(cyclohexylmethoxy)-2H-spiro[1-benzofuran-3,4'-piperidine]-1'-yl]propanoate.
Tert-butyl 3-[6-(oxan-2ylmethoxy)-2H-spiro[1-benzofuran-3,4'-piperidine]-1'-yl]propanoate.
Tert-butyl 3-{6-[(2,5-dichlorophenyl)methoxy]-2H-spiro[1-benzofuran-3,4'-piperidine]-1'-yl}propanoate.
Tert-butyl 3-(6-{[3-(trifluoromethyl)phenyl]methoxy}-2H-spiro[1-benzofuran-3,4'-piperidine]-1'-yl}propanoate.
Tert-butyl 3-(6-{[2-(trifluoromethyl)phenyl]methoxy}-2H-spiro[1-benzofuran-3,4'-piperidine]-1'-yl}propanoate.
Tert-butyl 3-{6-[(2,3-dichlorophenyl)methoxy]-2H-spiro[1-benzofuran-3,4'-piperidine]-1'-yl}propanoate.
Tert-butyl 3-{6-[(2-chloro-6-fluorphenyl)methoxy]-2H-spiro[1-benzofuran-3,4'-piperidine]-1'-yl}propanoate.
Tert-butyl 3-[6-(benzyloxy)-2H-spiro[1-benzofuran-3,4'-piperidine]-1'-yl]propanoate.
Tert-butyl 3-{6-[(2,4-dichlorophenyl)methoxy]-2H-spiro[1-benzofuran-3,4'-piperidine]-1'-yl}propanoate.
Tert-butyl 3-(6-{[2-chloro-6-(trifluoromethyl)phenyl]methoxy}-2H-spiro[1-benzofuran-3,4'-piperidine]-1'-yl}propanoate.
Tert-butyl 3-[6-(cyclohex-3-en-1ylmethoxy)-2H-spiro[1-benzofuran-3,4'-piperidine]-1'-yl]propanoate.
Tert-butyl 3-{6-[(3,5-dichloropyridin-4-yl)methoxy]-2H-spiro[1-benzofuran-3,4'-piperidine]-1'-yl}propanoate. The required (3,5-dichloro-pyridin-4-yl)-methanol was prepared as follows: To a solution of 3,5-dichloro-4-pyridinecarboxaldehyde (4.68 mL; 26.59 mmol) in MeOH (50 mL) was added NaBH$_4$ (1.01 g, 26.59 mmol), in small portions at 0° C. After the addition was complete, the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and EtOAc. The layers were separated and the organic layer was dried (Na$_2$SO$_4$), filtered and concentrated in vacuo to afford the product as an amorphous solid (4.04 g, 85%).

Tert-butyl 3-{6-[(2,4-dichloropyridin-3-yl)methoxy]-2H-spiro[1-benzofuran-3,4'-piperidine]-1'-yl}propanoate. The required (2,4-dichloro-pyridin-3-yl)-methanol was prepared as follows: To a solution of 2,4-dichloropyridine (3.00 mL; 27.8 mmol) in THF (25 mL) was added dropwise a solution of LDA (15.3 mL; 2.00 mol/l in THF/heptane/ethylbenzene; 30.6 mmol), at −78° C. The resulting mixture was stirred at −78° C. for 1 h. Subsequently, a solution of ethyl chloroformate (3.2 mL; 33.33 mmol) in THF (5 mL), was added dropwise, at −78° C. and the mixture was stirred for another 1 h at the same temperature. To the resulting mixture was added 5% aqueous NaHCO$_3$-solution, dropwise, at −78° C. The mixture was allowed to warm to RT and extracted with EtOAc. The organic layer was dried (Na$_2$SO$_4$) and concentrated in vacuo. The residue was purified by column chromatography (SiO$_2$, Et$_2$O: hexanes 1:3) to afford 2,4-dichloro-nicotinic acid ethyl ester (2.45 g). To a solution of 2,4-dichloro-nicotinic acid ethyl ester (2.35 g; 10.68 mmol) in THF (50 mL) was added dropwise diisobutylaluminum hydride (32.0 mL; 1.00 mol/l in THF, 32.0 mmol), at 4° C. After 15 minutes the ice-bath was removed and the reaction mixture was stirred at RT overnight. Subsequently, the resulting mixture was concentrated in vacuo and partitioned between 5% aqueous NaHCO$_3$ and EtOAc. The layers were separated and the organic layer was dried (Na$_2$SO$_4$) and concentrated in vacuo. The residue was purified by column chromatography (Et$_2$O: hexanes 1:1) to afford (2,4-dichloropyridin-3-yl)methanol (0.40 g).

Tert-butyl 3-{6-[(2,4,6-trichlorophenyl)methoxy]-2H-spiro[1-benzofuran-3,4'-piperidine]-1'-yl}propanoate.
Tert-butyl 3-{6-[(2,6-dichloro-4-iodophenyl)methoxy]-2H-spiro[1-benzofuran-3,4'-piperidine]-1'-yl}propanoate. The required (2,6-dichloro-4-iodophenyl)methanol was prepared as follows: To a solution of 3,5-dichloroiodobenzene (2.72 g; 9.97 mmol) in THF (25 mL) was added lithium diisopropylamide (5.48 mL; 2.00 mol/l; 10.98 mmol), at −78° C. The resulting mixture was stirred for 4.5 hour, and subsequently a solution of N,N-dimethylformamide (1.16 mL, 14.95 mmol) in THF (5 mL) was added dropwise, at −78° C. The resulting reaction mixture was stirred for 2 hours at −40° C. Subsequently, the reaction was quenched by the addition of a 5% aqueous NH$_4$Cl solution, at −20° C. The resulting mixture was extracted with Et$_2$O. The combined organic layers were dried (Na$_2$SO$_4$), filtered, and concentrated in vacuo. The residue was purified by column chromatography (SiO$_2$, Et$_2$O:hexanes 1:3) to afford the 2,6-dichloro-4-benzaldehyde (0.7 g, 23%). To a solution of 2,6-dichloro-4-benzaldehyde (450 mg, 1.27 mmol) in MeOH (15 mL) was added NaBH$_4$ (72.14 mg; 1.91 mmol), in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and EtOAc. The layers were separated and the organic layer was dried (Na$_2$SO$_4$), filtered and concentrated in vacuo. The residue was purified by column chromatography (dichloromethane/acetone 95:5) to afford (2,6-dichloro-4-iodophenyl)methanol (0.42 g) which was used as such.

Tert-butyl 3-{6-[(2,6-difluorophenyl)methoxy]-2H-spiro[1-benzofuran-3,4'-piperidine]-1'-yl}propanoate.

Tert-butyl 3-{6-[2-(2,6-dichlorphenyl)ethoxy]-2H-spiro[1-benzofuran-3,4'-piperidine]-1'-yl}propanoate.

Tert-butyl 3-{6-[2-(2-fluorophenyl)ethoxy]-2H-spiro[1-benzofuran-3,4'-piperidine]-1'-yl}propanoate.

Tert-butyl 3-{6-[(2-chloro-5-methylphenyl)methoxy]-2H-spiro[1-benzofuran-3,4'-piperidine]-1'-yl}propanoate. The required (2-chloro-5-methylphenyl)methanol was prepared as follows: To a solution of 2-chloro-5-methylbenzoic acid (2.05 g; 12.2 mmol) in THF (20 mL) was added borane-THF complex (1M, 24.03 mL; 24.3 mmol) dropwise and subsequently stirred for 2 hours at 60° C. To the reaction mixture was added 1 M HCl (30 mL), at 0° C., and the resulting mixture was stirred at RT for 10 minutes. The resulting mixture was concentrated in vacuo and the residue was partitioned between EtOAc and 5% aqueous NaHCO$_3$-solution. The organic layer was dried (Na$_2$SO$_4$), filtered, and concentrated in vacuo to afford the product (1.8 g, 95%), which was used as such in the next step.

Tert-butyl 3-{6-[(2-chloro-5-ethylphenyl)methoxy]-2H-spiro[1-benzofuran-3,4'-piperidine]-1'-yl}propanoate. The required (2-chloro-5-ethylphenyl)methanol was prepared as follows: To a nitrogen purged solution of ethyl 5-bromo-2-chlorobenzoate (4.26 mL, 25.05 mmol) in THF (100 mL) was added lithium chloride (2.12 g, 50.09 mmol) and [1,1'-bis(diphenylphosphino)ferrocene]dichloropalladium (II) (0.82 g, 1 mmol). Subsequently, the mixture was cooled to −78° C., and a solution of diethylzinc (37.57 mL; 1 mol/l; 37.57 mmol) in heptane was added dropwise. The reaction mixture was allowed to come to RT overnight. The resulting reaction mixture was cooled to −10° C. and diluted with 300 mL Et$_2$O. Subsequently, a 1 M HCl solution (150 mL) was added carefully. The organic layer was separated, dried (Na$_2$SO$_4$), filtered, and concentrated in vacuo. The residue was purified by column chromatography (SiO$_2$, Et$_2$O: hexanes 5:95) to afford ethyl 2-chloro-5-ethylbenzoate (4.61 g, 86%). To a nitrogen purged solution of ethyl 2-chloro5-ethyl-benzoate (1 g, 4.70 mmol) in THF (25 mL), cooled to −5° C., was added diisobutylaluminiumhydride (14.11 mL; 14.11 mmol) in toluene. The reaction mixture was allowed to come to RT and stirred overnight. The resulting reaction mixture was cooled to −10° C. and 5% aqueous NaHCO$_3$-solution (10 mL) was added. The organic layer was separated, dried (Na$_2$SO$_4$), filtered, and concentrated in vacuo. The residue was purified by column chromatography (SiO$_2$, Et$_2$O:hexanes 1:3 followed by Et$_2$O:hexanes 1:1) to afford (2-chloro-6-ethylphenyl)methanol (0.59 g, 75%) which was used as such.

Tert-butyl 3-{6-[(2-chloro-5-proylphenyl)methoxy]-2H-spiro[1-benzofuran-3,4'-piperidine]-1'-yl}propanoate. The required (2-chloro-5-propylphenyl)methanol was prepared as follows: To a nitrogen purged solution of ethyl 5-bromo-2-chlorobenzoate (2 g, 7.59 mmol) in THF (14 mL) was added 0.5 M lithium chloride in THF (30 mL) and [1,1'-bis(diphenylphosphino)ferrocene]dichloropalladium(II) (0.22 g, 0.3 mmol). Subsequently, the mixture was cooled to −78° C., and a solution of N-propylzinc bromide (30.36 mL; 0.5 mol/l; 15.18 mmol) was added dropwise. The reaction mixture was allowed to come to RT overnight. The resulting reaction mixture was cooled to −10° C. and diluted with 300 mL Et$_2$O. Subsequently, a 1 M HCl solution (150 mL) was added carefully. The organic layer was separated, dried (Na$_2$SO$_4$), filtered, and concentrated in vacuo. The residue was purified by column chromatography (SiO$_2$, Et$_2$O: hexanes 5:95 followed by Et$_2$O:hexanes 1:0) to afford ethyl 2-chloro-5-propylbenzoate (1.1 g, 63%). To a nitrogen purged solution of ethyl 2-chloro-5-propyl-benzoate (1.12 g, 4.94 mmol) in THF (28 mL), cooled to −5° C., was added diisobutylaluminiumhydride (14.82 mL; 14.82 mmol) in toluene. The reaction mixture was allowed to come to RT and stirred overnight. The resulting reaction mixture was cooled to −10° C. and 5% aqueous NaHCO$_3$-solution (10 mL) was added. The organic layer was separated, dried (Na$_2$SO$_4$), filtered, and concentrated in vacuo. The residue was purified by column chromatography (SiO$_2$, Et$_2$O: hexanes 1:3 followed by Et$_2$O:hexanes 1:1) to afford (2-chloro-6-propylphenyl)methanol (0.76 g, 83%) which was used as such.

Tert-butyl 3-{6-[3-(2-fluorophenyl)propoxy]-2H-spiro[1-benzofuran-3,4'-piperidine]-1'-yl}propanoate.

Tert-butyl 3-{6-[3-(2-chlorophenyl)propoxy]-2H-spiro[1-benzofuran-3,4'-piperidine]-1'-yl}propanoate.

Tert-butyl 3-{6-[(5,7-difluoro-2,3-dihydro-1H-inden-1-yl)oxy]-2H-spiro[1-benzofuran-3,4'-piperidine]-1'-yl}propanoate. The required 5,7-difluoro-2,3-dihydro-1H-inden-1-ol was prepared as follows: To a solution of 5,7-difluoro-1-indanone (1.20 g, 7.14 mmol) in EtOH (50 mL) was added NaBH$_4$ (283.5 mg; 7.49 mmol), in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and EtOAc. The layers were separated and the organic layer was dried (Na$_2$SO$_4$), filtered and concentrated in vacuo. The product: 5,7-difluoro-2,3-dihydro-1H-inden-1-ol (1.2 g; 99%) was used as such.

Tert-butyl 3-{6-[(5,7-dichloro-2,3-dihydro-1H-inden-1-yl)oxy]-2H-spiro[1-benzofuran-3,4'-piperidine]-1'-yl}propanoate. The required 5,7-chloro-2,3-dihydro-1H-inden-1-ol was prepared from 5,7-dichloro-1-indanone using the conditions described for 5,7-difluoro-2,3-dihydro-1H-inden-1-ol.

Tert-butyl 3-{6-[(1R)-(2,3-dihydro-1H-inden-1-yl)oxy]-2H-spiro[1-benzofuran-3,4'-piperidine]-1'-yl}propanoate.

Tert-butyl 3-{6-[(1S)-(2,3-dihydro-1H-inden-1-yl)oxy]-2H-spiro[1-benzofuran-3,4'-piperidine]-1'-yl}propanoate.

Tert-butyl 3-[6-(3-phenylpropoxy)-2H-spiro[1-benzofuran-3,4'-piperidine]-1'-yl]propanoate.

Tert-butyl 3-{6-[2-(2,4-dichlorphenyl)ethoxy]-2H-spiro[1-benzofuran-3,4'-piperidine]-1'-yl}propanoate.

Tert-butyl 3-{6-[2-(2-chlorphenyl)ethoxy]-2H-spiro[1-benzofuran-3,4'-piperidine]-1'-yl}propanoate.

Tert-butyl 3-(6-{[2,6-dichloro-4-(trifluoromethyl)phenyl]methoxy}-2H-spiro[1-benzofuran-3,4'-piperidine]-1'-yl)propanoate. The required [2,6-dichloro-4-(trifluoromethyl)phenyl]methanol was prepared as follows: To a solution of 1,3-dichloro-5-(trifluoromethyl)benzene (4.73 g; 22 mmol)

in THF (40 mL) was added N-butyllithim (8 mL; 2.50 mol/l; 20 mmol), at −78° C. The resulting mixture was stirred for 15 minutes and added onto dry ice in THF. The reaction mixture was acified to pH=3 (with 5 M HCl solution) and extracted with EtOAc. The organic layer was dried (Na$_2$SO$_4$), filtered, and concentrated in vacuo. The residue was purified by column chromatography (SiO$_2$, dichloromethane/MeOH 8:2) to afford 2,6-dichloro-4-(trifluoromethyl)benzoic acid (1.2 g). To a solution of this 2,6-dichloro-4-(trifluoromethyl)-benzoic acid (1.7 g; 6.56 mmol) in THF (20 mL) was added borane-THF complex (1M, 13.13 mL; 13.3 mmol) dropwise and subsequently stirred overnight at 60° C. To the reaction mixture was added 1 M HCl (30 mL), at 0° C., and the resulting mixture was stirred at RT for 10 minutes. The resulting mixture was concentrated in vacuo and the residue was partitioned between EtOAc and 5% aqueous NaHCO$_3$-solution. The organic layer was dried (Na$_2$SO$_4$), filtered, and concentrated in vacuo. The residue was purified by column chromatography (SiO$_2$, Et$_2$O:hexanes 1:3 followed by Et$_2$O:hexanes 1:1) to afford [2,6-dichloro-4-(trifluoromethyl)phenyl]methanol (1.3 g; 80%), which was used as such in the next step.

Tert-butyl 3-{6-[(2,6-dichloro-4-methylphenyl)methoxy]-2H-spiro[1-benzofuran-3,4'-piperidine]-1'-yl}propanoate. The required (2,6-dichloro-4-methylphenyl)methanol was prepared as follows: To a nitrogen purged solution of ethyl 1-bromo-3,5-dichlorobenzene (2.5 g, 11.07 mmol) in THF (14 mL) was added 0.5 M lithium chloride in THF (44.27 mL; 22.13 mmol) and [1,1'-bis(diphenyl-phosphino)-ferrocene]dichloropalladium(II) (0.32 g, 0.44 mmol). Subsequently, the mixture was cooled to −78° C., and a solution of methylzinc bromide (30.36 mL; 0.5 mol/l; 15.18 mmol) in THF was added dropwise. The reaction mixture was allowed to come to RT and was subsequently heated overnight (at 60° C.). The resulting reaction mixture was cooled to −10° C. and diluted with 300 mL Et$_2$O. Subsequently, a 1 M HCl solution (150 mL) was added carefully. The organic layer was separated, dried (Na$_2$SO$_4$), filtered, and concentrated in vacuo. The residue was purified by column chromatography (SiO$_2$, hexanes followed by dichloromethane/hexanes 1:9) to afford 1,3-dichloro-5-methylbenzene (1.0 g; 56%), which was reacted in THF with N-butyllithium, followed by adding into dry ice (as described for 1,3-dichloro-5-(trifluoromethyl)benzene). The product of this, 2,6-dichloro-4-methylbenzoic acid was reduced with borane-THF complex (as described for 2,6-dichloro-4-(trifluoromethyl)benzoic) to afford (2,6-dichloro-4-methylphenyl)methanol in 71% over two steps, which was used as such.

Tert-butyl 3-{6-[(5-bromo-2-chlorophenylphenyl)methoxy]-2H-spiro[1-benzofuran-3,4'-piperidine]-1'-yl}propanoate.

Tert-butyl 3-{6-[(2-chloro-5-phenyl)methoxy]-2H-spiro[1-benzofuran-3,4'-piperidine]-1'-yl}propanoate. To a degassed mixture of tert-butyl 3-{6-[(5-bromo-2-chlorophenyl)methoxy]-2H-spiro[1-benzfuran-3,4'-piperidine]-1'-yl}propanoate (100 mg; 0.56 mmol) in 3 mL 1,2-dimethoxyethane and sodiumbicarbonate (1.5 mL) was added subsequently, phenylboronic acid (80 mg; 0.67 mmol) and tetrakis(triphenylphosphine)palladium(0) (6 mg; 0.06 mmol). The resulting mixture was heated under reflux, overnight. After cooling to RT, the mixture was partitioned between EtOAc and 5% aqueous NaHCO$_3$. The organic layer was dried (Na$_2$SO$_4$), filtered, and concentrated in vacuo. The residue was purified by column chromatography (SiO$_2$, Et$_2$O:hexanes 1:3 followed by 1:1) to afford the product (180 mg; 60%).

Tert-butyl 3-{6-[(2-chloro-5-cyclopropylphenyl)methoxy]-2H-spiro[1-benzofuran-3,4'-piperidine]-1'-yl}propanoate. To a degassed mixture of tert-butyl 3-{6-[(5-bromo-2-chlorophenyl)methoxy]-2H-spiro[1-benzofuran-3,4'-piperidine]-1'-yl}pro-panoate (0.28 g; 0.52 mmol) in 9 mL toluene and 3 ml H$_2$O, was added subsequently, potassium cyclopropyltrifluoroboronate (0.9 g; 0.63 mmol), cesium carbonate (0.51 g; 1.56 mmol) and 1',1'-bis(diphenylphosphino)ferrocene palladium(II)dichloride dichloromethane complex (20 mg; 0.03 mmol). The resulting mixture was heated overnight (90° C.). After cooling to RT, the reaction mixture was diluted with EtOAc, filtered and washed with 5% aqueous NaHCO$_3$. The organic layer was dried (Na$_2$SO$_4$), filtered, and concentrated in vacuo. The residue was purified by column chromatography (SiO$_2$, Et$_2$O:hexanes 1:1) to afford the product (0.23 g; 88%).

Tert-butyl 3-[6-({2-chloro-5-[2-phenylcyclopropyl]phenyl}methoxy)-2H-spiro[1-benzofuran-3,4'-piperidine]-1'-yl]propanoate. To a degassed mixture of tert-butyl 3-{6-[(5-bromo-2-chlorophenyl)methoxy]-2H-spiro[1-benzofuran-3,4'-piperidine]-1'-yl}propanoate (0.3 g; 0.56 mmol) in 9 mL toluene and 3 ml H$_2$O, was added subsequently, potassium trifluoro(2-phenylcyclopropyl)boronate (0.9 g; 0.63 mmol), cesium carbonate (0.55 g; 1.68 mmol) and 1',1'-bis(diphenylphosphino)ferrocene palladium(II)dichloride dichloromethane complex (20 mg; 0.03 mmol). The resulting mixture was heated overnight (90° C.). After cooling to RT, the reaction mixture was diluted with EtOAc, filtered and washed with 5% aqueous NaHCO$_3$. The organic layer was dried (Na$_2$SO$_4$), filtered, and concentrated in vacuo. The residue was purified by column chromatography (SiO$_2$, Et$_2$O:hexanes 1:1) to afford the product (0.23 g; 71%). The required potassium trifluoro(2-phenylcyclopropyl)boronate was prepared from trans-2-(4,4,5,5-tetramethyl-1,3,2-dioxaborolan-2-yl)styrene using the Simmons-Smith conditions (J. Org. Chem., 2004, 69, 327 and J. Am. Chem. Soc, 2009, 131, 6516) to afford 4,4,5,5-tetramethyl-2-(2-phenylcyclopropyl)-1,3,2-dioxaborolane, which was converted to potassium trifluoro(2-phenylcyclopropyl)boronate using similar conditions described for the synthesis of potassium butyltrifluoroboronate (see also: J. Org. Chem., 2004, 69, 357)

Tert-butyl 3-{6-[(2-chloro-6-methylphenyl)methoxy]-2H-spiro[1-benzofuran-3,4'-piperidine]-1'-yl}propanoate.

Tert-butyl 3-(6-{[(2E)-3-(4-chlorophenyl)prop-2-en-1-yl]oxy}-2H-spiro[1-benzofuran-3,4'-piperidine]-1'-yl)propanoate. The required (2E)-3-(4-chlorophenyl)prop-2-en-1-ol (J.O.C., 2006, 71, 1969-76) was prepared as follows: To a nitrogen purged solution of ethyl (2E)-3-(4-chlorophenyl)prop-2-enoate (3.32 g; 16.88 mmol) in dichloromethane (60 mL), cooled to −78° C., was added diisobutyl-aluminiumhydride (49 mL; 49 mmol) in toluene, dropwise in 30 minutes. The reaction mixture was allowed to come to 0° C. (in 1 hour). MeOH (15 mL) was added dropwise, maintaining a steady state of gas evolution. The resulting reaction mixture was stirred for another 30 minutes at RT, subsequently followed by the addition of a saturated aqueous solution of potassiumnatriumtartrate. The organic layer was separated and the aqueous phase was extracted 2 times with dichloromethane. The organic layers were dried (Na$_2$SO$_4$), filtered, and concentrated in vacuo. The residue was purified by column chromatography (SiO$_2$, Et$_2$O:hexanes 1:1) to afford the product (2.5 g; 87.8%) which was used as such.

Tert-butyl 3-{6-[(3-phenyl)prop-2-yn-1-yl]oxy}-2H-spiro [1-benzofuran-3,4'-piperidine]-1'-yl}propanoate.

Tert-butyl 3-[6-(2,3-dihydro-1-benzfuran-3-yloxy)-2H-spiro[1-benzofuran-3,4'-piperidine]-1'-yl]propanoate. The required 2,3-dihydro-1-benzofuran-3-ol was prepared as follows: To a solution of 3-coumaranone (2.82 g, 21 mmol) in EtOH (50 mL) was added NaBH$_4$ (2.39 g; 63 mmol), in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and EtOAc. The layers were separated and the organic layer was dried (Na$_2$SO$_4$), filtered and concentrated in vacuo. The product: 2,3-dihydro-1-benzfuran-3-ol (2.59 g, 90%) was used as such.

Tert-butyl 3-(6-{[(2E)-3-(2,6-dichlorophenyl)prop-2-en-1-yl]oxy}-2H-spiro[1-benzofuran-3,4'-piperidine]-1'-yl) propanoate. The required (2E)-3-(2,6-dichlorophenyl)prop-2-en-1-ol was prepared (in 91%) as described for the preparation of (2E)-3-(4-chlorophenyl)prop-2-en-1-ol.

Tert-butyl 3-(6-{3-[2-(trifluoromethyl)phenyl]propoxy}-2H-spiro[1-benzofuran-3,4'-piperidine]-1'-yl)propanoate.

Tert-butyl 3-(6-{[(2E)-3-phenylprop-2-en-1-yl]oxy}-2H-spiro[1-benzfuran-3,4'-piperidine]-1'-yl)propanoate.

Tert-butyl 3-{6-[3-(2,3-difluorophenyl)propoxy]-2H-spiro [1-benzofuran-3,4'-piperidine]-1'-yl}propanoate.

Tert-butyl 3-{6-[(7-chloro-2,3-dihydro-1H-inden-1-yl)oxy]-2H-spiro[1-benzofuran-3,4'-piperidine]-1'-yl}propanoate.

Tert-butyl 3-{6-[3-(2-chloro-6-fluorophenyl)propoxy]-2H-spiro[1-benzofuran-3,4'-piperidine]-1'-yl}propanoate.

Tert-butyl 3-{6-[3-(2,6-dichlorophenyl)propoxy]-2H-spiro [1-benzofuran-3,4'-piperidine]-1'-yl}propanoate.

Tert-butyl 3-{6-[3-(4-chlorophenyl)propoxy]-2H-spiro[1-benzofuran-3,4'-piperidine]-1'-yl}propanoate.

Tert-butyl 3-(6-{[(3-(4-chlorophenyl)prop-2-yn-1-yl]oxy}-2H-spiro[1-benzofuran-3,4'-piperidine]-1'-yl)propanoate.

Tert-butyl 3-(6-{[(2E)-3-(2-fluororophenyl)prop-2-en-1-yl]oxy}-2H-spiro[1-benzofuran-3,4'-piperidine]-1'-yl)propanoate. The required (2E)-3-(2-fluorophenyl)prop-2-en-1-ol was prepared (in 66%) as described for the preparation of (2E)-3-(4-chlorophenyl)prop-2-en-1-ol.

Tert-butyl 3-{6-[(4-bromothiophen-2yl)methoxy]-2H-spiro[1-benzofuran-3,4'-piperidine]-1'-yl}propanoate. The required (4-bromothiophen-2-yl)methanol was prepared as follows: To a solution of 4-bromo-thiophenecarboxyaldehyde (2.5 g; 13.09 mmol) in EtOH (50 mL) was added NaBH$_4$ (0.74 g; 19.63 mmol), in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and EtOAc. The layers were separated and the organic layer was dried (Na$_2$SO$_4$), filtered and concentrated in vacuo to afford the product: (2.12 g, 83%) which was used as such.

Tert-butyl 3-{6-[(4-butylthiophen-2yl)methoxy]-2H-spiro[1-benzofuran-3,4'-piperidine]-1'-yl}propanoate. N-butylboronic acid was converted to its potassium butyltrifluoroboronate using a protocol from Org. Biomol. Chem., 2005, 941. A mixture of n-butylboronic acid in THF (40 mL), water (10 mL), and potassium bifluoride (4.6 g; 58.9 mmol) was stirred at RT for 4 hours. Subsequently, the solvents were removed in vacuo and the residue treated with toluene and concentrated in vacuo. The latter steps were repeated three times to remove all the water. The obtained solid was treated with hot acetone (20 mL) amd the acetone was decanted. This was repeated with another 20 mL acetone. The combined aceton layers were concentrated in vacuo and the residue was treated with Et$_2$O. The formed precipitate was collected by filtration and dried in vacuo to afford potassium butyltrifluoroboronate (1.4 g, 87%), which was used as such.

To a degassed mixture of Tert-butyl 3-{6-[(4-bromothiophen-2yl)methoxy]-2H-spiro[1-benzfuran-3,4'-piperidine]-1'-yl}propanoate (100 mg; 0.2 mmol) in 20 mL toluene was added subsequently, potassium butyltrifluoroboronate (35.2 mg; 0.22 mmol), palladium(II) acetate (2.2 mg; 0.01 mmol), potassium phosphate tribasic mono-hydrate (158.5 mg; 0.69 mmol) and 2-dicyclohexylphosphino-2',6'-diisopropoxy-1', 1'-biphenyl (9.2 mg; 0.02 mmol). The resulting mixture was heated under reflux, overnight (Pyrex bottle). After cooling to RT, the mixture was concentrated in vacuo and partitioned between EtOAc and 5% aqueous NaHCO$_3$. The organic layer was dried (Na$_2$SO$_4$), filtered, and concentrated in vacuo. The residue was purified by column chromatography (SiO$_2$, Et$_2$O:hexanes 1:1) to afford the product (65 mg; 68%)

Tert-butyl 3-{6-[(4-cyclopropylmethylthiophen-2yl) methoxy]-2H-spiro[1-benzofuran-3,4'-piperidine]-1'-yl}propanoate. To a degassed mixture of tert-butyl 3-{6-[(4-bromothiophen-2yl)methoxy]-2H-spiro[1-benzfuran-3,4'-piperidine]-1'-yl}propanoate (350 mg; 0.69 mmol) in 20 mL toluene was added subsequently, potassium cyclopropyltrifluoroboronate (112 mg; 0.76 mmol), palladium(II) acetate (7.8 mg; 0.03 mmol), powdered potassium phosphate tribasic monohydrate (554.7 mg; 2.41 mmol) and 2-dicyclohexylphosphino-2',6'-diisopropoxy-1',1'-biphenyl (32 mg; 0.07 mmol). The resulting mixture was heated under reflux, overnight (Pyrex bottle). After cooling to RT, the mixture was concentrated in vacuo and partitioned between EtOAc and 5% aqueous NaHCO$_3$. The organic layer was dried (Na$_2$SO$_4$), filtered, and concentrated in vacuo. The residue was purified by column chromatography (SiO$_2$, Et$_2$O: hexanes 1:1) to afford the product (230 mg; 74%)

Tert-butyl 3-(6-{[4-(2-fluorophenyl)thiophen-2yl] methoxy}-2H-spiro[1-benzofuran-3,4'-piperidine]-1'-yl}propanoate. To a degassed mixture of tert-butyl 3-{6-[(4-bromothiophen-2yl)methoxy]-2H-spiro[1-benzfuran-3,4'-piperidine]-1'-yl}propanoate (100 mg; 0.2 mmol) in 20 mL toluene was added subsequently, 2-fluoro-phenylboronic acid (30.2 mg; 0.22 mmol), palladium(II) acetate (2.2 mg; 0.01 mmol), potassium phosphate tribasic monohydrate (158.5 mg; 069 mmol) and dicyclohexylphosphino-2',6'-diisopropoxy-1',1'-biphenyl (9.2 mg; 0.02 mmol). The resulting mixture was heated under reflux, overnight (Pyrex bottle). After cooling to RT, the mixture was concentrated in vacuo and partitioned between EtOAc and 5% aqueous NaHCO$_3$. The organic layer was dried (Na$_2$SO$_4$), filtered, and concentrated in vacuo. The residue was purified by column chromatography (SiO$_2$, Et$_2$O:hexanes 2:1) to afford the product (98 mg; 95%).

The following compound was obtained in a similar way:
Tert-butyl 3-{6-[(4-phenylthiophen-2yl)methoxy]-2H-spiro [1-benzofuran-3,4'-piperidine]-1'-yl}propanoate.

Tert-butyl 3-{6-[(4-bromo-3-methylthiophen-2yl) methoxy]-2H-spiro[1-benzofuran-3,4'-piperidine]-1'-yl}propanoate. The required (4-bromo-3-methylthiophen-2-yl)methanol was prepared as follows: To a solution of 4-bromo-3-methylthiophenecarboxylic acid (2 g; 0.95 mmol) in THF (20 mL) was added borane-THF complex (1M, 18.19 mL; 18.19 mmol) dropwise, at 0° C. Subsequently, the reaction mixture was stirred for 1 hour at 60° C. To this reaction mixture was added 1 M HCl (30 mL), at 0° C., and the resulting mixture was stirred at RT for 10 minutes. The resulting mixture was concentrated in vacuo and the residue was partitioned between EtOAc and 5% aqueous NaHCO$_3$-solution. The organic layer was dried (Na$_2$SO$_4$), filtered, and concentrated in vacuo, affording the product (2.2 g; 100%), which was used as such.

The above described intermediate: tert-butyl 3-{6-[(4-bromo-3-methylthiophen-2yl)methoxy]-2H-spiro[1-benzofuran-3,4'-piperidine]-1'-yl}propanoate was used to synthesize the following 2 compounds:

Tert-butyl 3-{6-[(3-methyl-4-phenylthiophen-2yl)methoxy]-2H-spiro[1-benzofuran-3,4'-piperidine]-1'-yl}propanoate. To a degassed mixture of tert-butyl 3-{6-[(4-bromo-3-methylthiophen-2yl)methoxy]-2H-spiro[1-benzofuran-3,4'-piperidine]-1'-yl}propanoate (200 mg; 0.38 mmol) in 10 mL toluene was added subsequently, phenylboronic acid (56 mg; 0.46 mmol), palladium(II) acetate (4.3 mg; 0.02 mmol), potassium phosphate tribasic monohydrate (308.5 mg; 1.34 mmol) and 2-dicyclohexylphosphino-2',6'-diisopropoxy-1',1'-biphenyl (15.7 mg; 0.04 mmol). The resulting mixture was heated under reflux, overnight (Pyrex bottle). After cooling to RT, the mixture was concentrated in vacuo and partitioned between EtOAc and 5% aqueous NaHCO$_3$. The organic layer was dried (Na$_2$SO$_4$), filtered, and concentrated in vacuo. The residue was purified by column chromatography (SiO$_2$, Et$_2$O:hexanes 2:1) to afford the product (200 mg; 100%).

Tert-butyl 3-{6-[(4-butyl-3-methylthiophen-2yl)methoxy]-2H-spiro[1-benzofuran-3,4'-piperidine]-1'-yl}propanoate. To a degassed mixture of tert-butyl 3-{6-[(4-bromo-3-methylthiophen-2yl)methoxy]-2H-spiro[1-benzofuran-3,4'-piperidine]-1'-yl}propanoate (200 mg; 0.38 mmol) in 10 mL toluene was added subsequently, potassium butyltrifluoroboronate (68.6 mg; 0.42 mmol), palladium(II) acetate (4.3 mg; 0.02 mmol), potassium phosphate tribasic monohydrate (308.5 mg; 1.34 mmol) and 2-dicyclohexylphosphino-2',6'-diisopropoxy-1',1'-biphenyl (15.7 mg; 0.04 mmol). The resulting mixture was heated under reflux, overnight (Pyrex bottle). After cooling to RT, the mixture was concentrated in vacuo and partitioned between EtOAc and 5% aqueous NaHCO$_3$. The organic layer was dried (Na$_2$SO$_4$), filtered, and concentrated in vacuo. The residue was purified by column chromatography (SiO$_2$, Et$_2$O:hexanes 1:1) to afford the product (126 mg; 65%).

Tert-butyl 3-{6-[(2,6-dichloro-3-ethylphenyl)methoxy]-2H-spiro[1-benzofuran-3,4'-piperidine]-1'-yl}propanoate. The required (2,6-dichloro-3-ethylphenyl)-methanol was prepared as follows: To a mixture of 2',4'-dichloroacetophenone (4.85 g; 25.66 mmol) suspended in diethylene glycol (20 mL) was added potassium hydroxide (2.37 g; 35.92 mmol) and hydrazine hydrate (2.93 mL). The resulting mixture was heated at 100° C. (for 1 hour) and subsequently overnight (at 200° C.). After cooling to RT, the mixture was partitioned between Et$_2$O and H$_2$O. The organic layer was dried (Na$_2$SO$_4$), filtered, and concentrated in vacuo. The residue was purified by column chromatography (SiO$_2$, hexanes) to afford the product: 2,4-dichloro-1-ethylbenzene (2.24 g; 50%). To a solution 2,2,6,6-tetramethylpiperidine (2.36 mL; 14 mmol), dissolved in THF (40 ml) was added n-butyllithium (5.61 mL; 2.50 mol/l; 14 mmol), at at −78° C. The reaction mixture was stirred for 90 minutes, allowing the temperature to reach 0° C. Subsequently, a solution of 2,4-dichloro-1-ethylbenzene (2.23 g; 12.74 mmol), dissolved in THF (5 mL) was added at −78° C. The resulting mixture was stirred for 2.5 hours. Subsequently, a solution of N,N-dimethylformamide (1.48 mL; 19.11 mmol) was added dropwise and the resulting reaction mixture was stirred for 30 minutes. The reaction was quenched by the addition of a saturated aqueous NaH$_4$Cl solution, at −50° C. The resulting mixture was extracted with Et$_2$O. The combined organic layers were dried (Na$_2$SO$_4$), filtered, and concentrated in vacuo to afford the crude 2,6-dichloro-3-ethylbenzaldehyde, which was redissolved in MeOH (100 mL). Subsequently, NaBH$_4$ (1.45 g; 38.22 mmol) was added, in small portions, at 0° C. After the addition was complete, the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and Et$_2$O. The layers were separated and the organic layer was dried (Na$_2$SO$_4$), filtered and concentrated in vacuo. The residue was purified by column chromatography (SiO$_2$, Et$_2$O:hexanes 1:7 followed by 1:1) to afford the product: (2,6-dichloro-3-ethylphenyl)methanol (2.11 g; 80%)

Tert-butyl 3-{6-[(4-butyl-2,6-dichlorophenyl)methoxy]-2H-spiro[1-benzofuran-3,4'-piperidine]-1'-yl}propanoate. The required (4-butyl-2,6-dichlorophenyl)-methanol was prepared as follows: To a degassed mixture of 1-bromo-3,5-dichloro-benzene (4.42 g; 19.57 mmol) in 90 mL toluene and 30 ml H$_2$O, was added subsequently, potassium butyltrifluoroboronate (4.01 g; 24.45 mmol), cesium carbonate (19.13 g; 58.7 mmol) and 1',1'-bis(diphenylphosphino)ferrocene palladium(II)-dichloride dichloromethane complex (0.8 g; 0.98 mmol). The resulting mixture was heated during 48 hours (90° C.). After cooling to RT, the reaction mixture was diluted with EtOAc, filtered and washed with H$_2$O. The organic layer was dried (Na$_2$SO$_4$), filtered, and concentrated in vacuo. The residue was purified by column chromatography (SiO$_2$, Et$_2$O:hexanes 1:1) to afford 1-butyl-3,5-dichlorobenzene (3.39 g; 85%). This product was converted to (4-butyl-2,6-dichlorophenyl)methanol (overall yield: 71%), by the sequence described for the conversion of 2,4-dichloro-1-ethylbenzene into (2,6-dichloro-3-ethylphenyl)methanol.

Tert-butyl 3-{6-[(2,6-dichloro-4-cyclopropylphenyl)methoxy]-2H-spiro[1-benzofuran-3,4'-piperidine]-1'-yl}propanoate. The required (2,6-dichloro-4-cyclopropylphenyl)methanol was prepared as follows: To a solution 2,2,6,6-tetramethylpiperidine (2.36 mL; 14 mmol), dissolved in THF (40 ml) was added n-butyllithium (5.61 mL; 2.50 mol/l; 14 mmol), at −78° C. The reaction mixture was stirred for 90 minutes, allowing the temperature to reach 0° C. Subsequently, a solution of 3,5-dichloroiodobenzene (6.82 g; 25 mmol), dissolved in THF (10 mL) was added at −78° C. The resulting mixture was stirred for 2.5 hours. Subsequently, a solution of N,N-dimethylformamide (2.9 mL; 37.5 mmol) was added dropwise and the resulting reaction mixture was stirred for 30 minutes. The reaction was quenched by the addition of a saturated aqueous NaH$_4$Cl solution, at −50° C. The resulting mixture was extracted with Et$_2$O. The combined organic layers were dried (Na$_2$SO$_4$), filtered, and concentrated in vacuo. The residue was purified by column chromatography (SiO$_2$, dichloromethane:hexanes 1:1) to afford the product: 2,6-dichloro-4-iodo-benzaldehyde (5.11 g; 64). Subsequently, 2.7 g; 8.52 mmol of this aldehyde was redissolved in MeOH (100 mL) and NaBH$_4$ (0.45 g; 12.79 mmol) was added, in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and Et$_2$O. The layers were separated and the organic layer was dried (Na$_2$SO$_4$), filtered and concentrated in vacuo. The residue was purified by column chromatography (SiO$_2$, dichloromethane:acetone 95:5) to afford the product: (2,6-dichloro-4-iodophenyl)methanol (2.2 g; 81%). To a degassed mixture of (2,6-dichloro-4-iodophenyl)methanol (303 mg; 1 mmol) in 9 mL toluene and 3 ml H$_2$O, was added subsequently, potassium butyltrifluoroboronate (117 mg; 1.2 mmol), cesium carbonate (977 mg; 3 mmol) and 1',1'-bis(diphenylphosphino)-ferrocene palladium(II)dichloride dichloromethane complex (0.037 g; 0.05 mmol). The resulting mixture was heated during 72 hours (90° C.). After cooling to RT, the reaction mixture was diluted with EtOAc, filtered and washed with H$_2$O. The organic layer was dried (Na$_2$SO$_4$), filtered, and concentrated in vacuo. The residue was purified by column chromatography (SiO$_2$, dichloromethane:acetone 95:5) to afford (2,6-dichloro-4-cyclopropylphenyl)methanol (130 mg; 59%).

Tert-butyl 3-{6-[(2-chloro-6-ethylphenyl)methoxy]-2H-spiro[1-benzofuran-3,4'-piperidine]-1'-yl}propanoate. The required (2-chloro-6-ethylphenyl)methanol was prepared as follows: To a solution of 2-chloro-6-ethylbenzaldehyde (1.8 g, 10.67 mmol), prepared according to US2007/197621, (see also WO2007/85556 and US6380387) in MeOH (50 mL) was added NaBH$_4$ (1.21 g; 32.02 mmol), in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and EtOAc. The layers were separated and the organic layer was dried (Na$_2$SO$_4$), filtered and concentrated in vacuo. The residue was purified by column chromatography (SiO$_2$, Et$_2$O:hexanes 1:7 followed by Et$_2$O:hexanes 3:1) yielding (2-chloro-6-ethylphenyl)methanol (1.2 g; 66%).

Tert-butyl 3-(6-{[2-chloro-6-(propan-2-yl)phenyl]methoxy}-2H-spiro[1-benzofuran-3,4'-piperidine]-1'-yl)propanoate. The required [2-chloro-6-(popan-2-yl)phenyl]methanol was obtained from a NaBH$_4$ reduction of 2-chloro-6-(propan-2-yl)benzaldehyde in MeOH, which was prepared in a similar manner as 2-chloro-6-ethylbenzaldehyde.

Tert-butyl 3-{6-[(2-chloro-6-cyclopropyl)phenyl)methoxy]-2H-spiro[1-benzofuran-3,4'-piperidine]-1'-yl}propanoate. The required (2-chloro-6-cyclopropylphenyl)methanol was obtained from a NaBH$_4$ reduction of 2-chloro-6-cyclopropylbenzaldehyde in MeOH, which was prepared in a similar manner as 2-chloro-6-ethylbenzaldehyde.

Tert-butyl 3-(6-{[2-chloro-6-(2-methylpropyl)phenyl]methoxy}-2H-spiro[1-benzofuran-3,4'-piperidine]-1'-yl)propanoate. The required [2-chloro-6-(2-methylpropyl)phenyl)methanol was obtained from a NaBH$_4$ reduction of 2-chloro-6-(2-methylpropyl)benzaldehyde in MeOH, which was prepared in a similar manner as 2-chloro-6-ethylbenzaldehyde.

Tert-butyl 3-{6-[(2,6-dichloro-3-methoxyphenyl)methoxy]-2H-spiro[1-benzo-furan-3,4'-piperidine]-1'-yl}propanoate. The required (2,6-dichloro-3-methoxy-phenyl)methanol was obtained as follows: A mixture of 2,4-dichlorophenol (4.8 g; 29.45 mmol), potassium carbonate (5.09 g; 36.8 mmol) and iodomethane in acetone (75 mL) was heated under reflux for 3.5 hours. After cooling to RT the mixture was concentrated in vacuo, and the residue was partitioned between Et$_2$O and H$_2$O. The organic layer was dried (Na$_2$SO$_4$), filtered, and concentrated in vacuo to afford the 2,4-dichloro-1-methoxybenzene (4.88 g; 93%). To a solution of 2,2,6,6-tetramethylpiperidine (3.73 mL; 9.32 mmol), dissolved in THF (50 ml) was added n-butyllithium (5.61 mL; 2.50 mol/l; 14 mmol), at at −78° C. The reaction mixture was stirred for 90 minutes, allowing the temperature to reach 0° C. Subsequently, a solution of 2,4-dichloro-1-methoxybenzene (1.5 g; 8.47 mmol), dissolved in THF (5 mL) was added at −78° C. The resulting mixture was stirred for 2.5 hours. Subsequently, a solution of N,N-dimethylformamide (0.99 mL; 12.71 mmol) was added dropwise and the resulting reaction mixture was stirred for 30 minutes. The reaction was quenched by the addition of a saturated aqueous NaH$_4$Cl solution, at −50° C. The resulting mixture was extracted with Et$_2$O. The combined organic layers were dried (Na$_2$SO$_4$), filtered, and concentrated in vacuo. The crude 2,6-dichloro-3-methoxybenaldehyde was dissolved in MeOH (50 mL) and NaBH$_4$ (0.96 g; 25.4 mmol) was added, in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and Et$_2$O. The layers were separated and the organic layer was dried (Na$_2$SO$_4$), filtered and concentrated in vacuo. The residue was purified by column chromatography (SiO$_2$, Et$_2$O:hexanes 1:1) to afford the product: (2,6-dichloro-3-methoxyphenyl)methanol (1.35 g; 77%).

Tert-butyl 3-(6-{[2-chloro-6-(trifluoromethoxy)phenyl]methoxy}-2H-spiro[1-benzofuran-3,4'-piperidine]-1'-yl)propanoate. The required [2-chloro-6-(trifluoro-methoxy)phenyl]methanol was obtained from 1-chloro-3-(trifluoromethoxy)benzene, using the sequence LiTMP/N,N-dimethylformamide, followed by NaBH$_4$/MeOH, overall yield 71% (similar to (2,6-dichloro-3-methoxyphenyl)methanol)).

Tert-butyl 3-(6-{[2-fluoro-6-(propan-2-yl)phenyl]methoxy}-2H-spiro[1-benzofuran-3,4'-piperidine]-1'-yl)propanoate. The required [2-fluoro-6-(propan-2-yl)-phenyl]methanol was obtained analogous to the sequence described for compound 273.

Tert-butyl 3-{6-[(2-cyclopropyl-6-fluorophenyl)methoxy]-2H-spiro[1-benzofuran-3,4'-piperidine]-1'-yl}propanoate. The required (2-cyclopropyl-6-fluorophenyl)-methanol was obtained as described for compound 273.

Tert-butyl 3-{6-[(2-ethyl-6-fluorophenyl)methoxy]-2H-spiro[1-benzo-furan-3,4'-piperidine]-1'-yl}propanoate. The required (2-ethyl-6-fluorophenyl)methanol was obtained analogous to the sequence described for compound 273.

Tert-butyl 3-(6-{[2-fluoro-6-(trifluoromethyl)phenyl]methoxy}-2H-spiro[1-benzofuran-3,4'-piperidine]-1'-yl) propanoate.

Tert-butyl 3-{6-[(4-chloro-2,6-difluorophenyl)methoxy]-2H-spiro[1-benzofuran-3,4'-piperidine]-1'-yl}propanoate.

Tert-butyl 3-{6-[1-(2,6-dichlorophenyl)ethoxy]-2H-spiro[1-benzofuran-3,4'-piperidine]-1'-yl}propanoate.

Tert-butyl 3-{6-[(2,6-diethylphenyl)methoxy]-2H-spiro[1-benzofuran-3,4'-piperidine]-1'-yl}propanoate. The required (2,6-diethylphenyl)methanol was prepared as follows: To a cooled solution (0° C.) of (E)-butyl[(2,6-difluorophenyl)methylidene]amine (1.97 g; 9.99 mmol), prepared according to US2007/197621, (see also WO2007/85556 and US6380387), dissolved in THF (35 mL), was added ethylmagnesium bromide (3M, 7.32 mL; 21.97 mmol) dropwise. Subsequently, the reaction mixture was stirred for 2 hour at RT. To this reaction mixture was added 3 mL H$_2$O and the resulting mixture was partitioned between EtOAc and 5% aqueous NaHCO$_3$-solution. The organic layer was dried (Na$_2$SO$_4$), filtered, and concentrated in vacuo. The residue was purified by column chromatography (SiO$_2$, Et$_2$O: hexanes 1:7) affording (E)-butyl[(2,6-diethylphenyl)-methylidene]amine (1.18 g; 54%). This product (1.70 g; 7.82 mmol) was dissolved in 20 mL H$_2$O and sulfuric acid (5 mL; 93.90 mmol) and heated to reflux for 2 hours. After cooling to RT, the resulting mixture was partitioned between EtOAc and 5% aqueous NaHCO$_3$-solution. The organic layer was dried (Na$_2$SO$_4$), filtered, and concentrated in vacuo. The residue was purified by column chromatography (SiO$_2$, Et$_2$O:hexanes 1:7 followed by Et$_2$O:hexanes 1:7) yielding (2,6-diethylbenzaldehyde (1.27 g; 95%).

This product was reduced in MeOH (50 mL) with NaBH$_4$ (0.71 g; 18.8 mmol), at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and EtOAc. The layers were separated and the organic layer was dried (Na$_2$SO$_4$), filtered and concentrated in vacuo. The residue was purified by column chromatography (SiO$_2$, Et$_2$O:hexanes 1:1) yielding (2,6-diethylphenyl)-methanol (0.68 g; 55%).

Tert-butyl 3-(6-{[2-(propan-2-yl)phenyl]methoxy}-2H-spiro[1-benzo-furan-3,4'-piperidine]-1'-yl)propanoate.

Tert-butyl 3-(6-{[2-ethyl-6-(trifluoromethyl)phenyl]methoxy}-2H-spiro[1-benzofuran-3,4'-piperidine]-1'-yl)propanoate. The required (2-ethyl-6-(trifluorophenyl)-methanol was obtained as described for compound 273 (starting from 2-fluoro-6-(trifluoromethyl)benzaldehyde).

Tert-butyl 3-(6-{[2-chloro-6-(difluoromethoxy)phenyl]methoxy}-2H-spiro[1-benzofuran-3,4'-piperidine]-1'-yl)propanoate. The required (2-chloro-6-difluoromethoxy-phenyl)methanol was prepared as follows: To a solution of 2-chloro-6-hydroxy-benzaldehyde (1.00 g; 6.39 mmol) and KOH (7.17 g; 127.7 mmol) in CH$_3$CN (20 mL) and water (20 mL) was added bromodifluoromethyl diethylphosphonate (1.25 ml; 7.03 mmol), at −15° C. After 30 minutes the mixture was allowed to warm to RT, stirred for another 30 min. and then treated with 1M aqueous HCl and extracted with Et$_2$O. The combined organic layers were dried (Na$_2$SO$_4$), filtered and concentrated in vacuo. The residue was purified by column chromatography (SiO$_2$, Et$_2$O/hexanes 1:3), to afford 2-chloro-6-difluoromethoxy-benzaldehyde (0.68 g). To a solution of 2-chloro-6-difluoromethoxy-benzaldehyde (0.65 g; 3.15 mmol) in MeOH (10 mL) was added NaBH$_4$ (357.13 mg; 9.44 mmol), at −15° C. After complete addition the mixture was allowed to warm to RT and stirred for 30 minutes. Subsequently, water (5 mL) was added and the volatiles were removed in vacuo. The residue was partitioned between Et$_2$O and 5% aqueous NaHCO$_3$. The layers were separated and the organic layer was dried (Na$_2$SO$_4$), filtered, and concentrated in vacuo to afford (2-chloro-6-difluoromethoxy-phenyl)-methanol (0.52 g), which was used as such.

Tert-butyl 3-{6-[(2-fluoro-6-methoxyphenyl)methoxy]-2H-spiro[1-benzofuran-3,4'-piperidine]-1'-yl}propanoate.

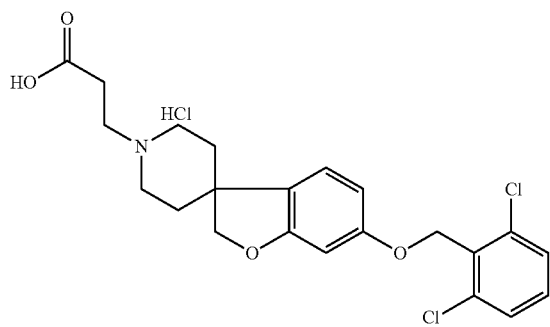 [SMILES: O=C(O)CCN1CCC2(CC1)COc1cc(OCc3c(Cl)cccc3Cl)ccc12 ; Cl]

Compound 29. 3-{6-[(2,6-Dichlorophenyl)methoxy]-2H-spiro[1-benzofuran-3,4'-piperidine]-1'-yl}propanoic acid hydrochloride Tert-butyl 3-{6-[(2,6-dichloro-phenyl)methoxy]-2H-spiro[1-benzfuran-3,4'-piperidine]-1'-yl}propanoate (1.10 g, 2.23 mmol) was dissolved in a 4M solution of HCl in 1,4-dioxane (20 mL; 4 mol/l; 80 mmol) and stirred overnight at 50° C. Subsequently, the solvent was removed in vacuo and the residue treated with iPr$_2$O, the precipitate was collected by filtration and dried overnight under reduced pressure to afford the product (1.0 g, 89%). $^1$H NMR (400 MHz, DMSO-d$_6$) δ ppm 12.9 (bs, 1H), 10.5 (bs, 1H), 7.54-7.58 (m, 2H), 7.44-7.50 (m, 1H), 7.04-6.95 (m, 1H), 6.56-6.62 (m, 2H), 5.18 (s, 2H), 4.48 (bs, 2H), 3.42-3.56 (m, 2H), 3.24-3.41 (m, 2H), 2.96-3.18 (m, 2H), 2.86 (t, J=8.0 Hz, 2H), 2.10-2.30 (m, 2H), 1.80-1.91 (m, 2H). Rt 1.57 min (System B), [M+H]$^+$ 436.0

The following compounds were obtained according to a similar manner:

Compound 30. 3-{6-[(4-Phenylpentyl)oxy]-2H-spiro[1-benzofuran-3,4'-piperidine]-1'-yl}propanoic acid hydrochloride Rt 1.46 min (System B), [M+H]$^+$ 424.1

Compound 31. 3-{6-[(3-Chlorophenyl)methoxy]-2H-spiro[1-benzofuran-3,4'-piperidine]-1'-yl}propanoic acid hydrochloride $^1$H NMR (400 MHz, DMSO-d$_6$) δ ppm 12.20 (bs, 1H) 11.30 (bs, 1H) 7.37-7.51 (m, 4H), 6.94-7.08 (m, 1H), 6.50-6.58 (m, 2H), 5.09 (s, 2H), 4.46 (s, 2H), 3.24-3.49 (m, 4H), 2.97-3.13 (m, 2H), 2.87 (t, J=7.8 Hz, 2H), 2.13-2.26 (m, 2H), 1.79-1.89 (m, 2H).

Compound 32. 3-[6-(Cyclohexylmethoxy)-2H-spiro[1-benzofuran-3,4'-piperidine]-1'-yl]propanoic acid hydrochloride Rt 1.42 min (System B), [M+H]$^+$ 374.2

Compound 33. 3-[6-(Oxan-2-ylmethoxy)-2H-spiro[1-benzofuran-3,4'-piperidine]-1'-yl]propanoic acid hydrochloride Rt 1.13 min (System B), [M+H]$^+$ 376.2

Compound 34. 3-{6-[(2,5-Dichlorophenyl)methoxy]-2H-spiro[1-benzofuran-3,4'-piperidine]-1'-yl}propanoic acid hydrochloride Rt 1.40 min (System B), [M+H]$^+$ 436.1

Compound 35. 3-(6-{[3-(Trifluoromethyl)phenyl]methoxy}-2H-spiro[1-benzofuran-3,4'-piperidine]-1'-yl)propanoic acid hydrochloride $^1$H NMR (400 MHz, DMSO/TFA-d$_6$) δ ppm 10.0 (bs, 1H), 7.69-7.78 (m, 2H), 7.56-7.66 (m, 2H), 7.00 (d, J=8.4 Hz, 1H), 6.49-6.58 (m, 2H), 5.15 (s, 2H), 4.50 (bs, 2H), 3.45-3.60 (m, 2H), 3.29-3.41 (m, 2H), 2.95-3.18 (m, 2H), 2.86 (t, J=7.4 Hz, 2H), 2.18-2.33 (m, 2H), 1.85-1.94 (m, 2H). Rt 1.38 min (System B), [M+H]$^+$ 436.1

Compound 36. 3-(6-{[2-(Trifluoromethyl)phenyl]methoxy}-2H-spiro[1-benzofuran-3,4'-piperidine]-1'-yl)propanoic acid hydrochloride Rt 1.37 min (System B), [M+H]$^+$ 436.1

Compound 37. 3-{6-[(2,3-Dichlorophenyl)methoxy]-2H-spiro[1-benzofuran-3,4'-piperidine]-1'-yl}propanoic acid hydrochloride Rt 1.40 min (System B), [M+H]$^+$ 436.0

Compound 38. 3-{6-[(2-Chloro-6-fluorphenyl)methoxy]-2H-spiro[1-benzofuran-3,4'-piperidine]-1'-yl}propanoic acid hydrochloride $^1$H NMR (400 MHz, DMSO/TFA-d) δ ppm 9.80 (bs, 1H), 7.40-7.48 (m, 1H), 7.34 (d, J=8.9 Hz, 1H), 7.20 (t, J=. 8.9 Hz, 1H), 7.01 (d, J=8. Hz, 1H), 6.52-6.58 (m, 2H), 5.15 (s, 2H), 4.51 (bs, 1H), 3.35-3.63 (m, 4H), 3.06-3.20 (m, 2H), 2.84 (t, J=7.5 Hz, 2H), 2.18-2.28 (m, 2H), 1.85-1.93 (m, 2H). Rt 1.31 min (System B), [M+H]$^+$ 420.1

Compound 39. 3-[6-(Benzyloxy)-2H-spiro[1-benzofuran-3,4'-piperidine]-1'-yl]-propanoic acid hydrochloride Rt 1.57 min (System B), [M+H]$^+$ 368.1

Compound 40. 3-{6-[(2,4-Dichlorophenyl)methoxy]-2H-spiro[1-benzofuran-3,4'-piperidine]-1'-yl}propanoic acid hydrochloride Rt 1.42 min (System B), [M+H]$^+$ 436.1

Compound 41. 3-(6-{[2-Chloro-6-(trifluoromethyl)phenyl]methoxy}-2H-spiro[1-benzofuran-3,4'-piperidine]-1'-yl)propanoic acid hydrochloride Rt 1.37 min (System B), [M+H]$^+$ 470.1

Compound 42. 3-[6-(Cyclohex-3-en-1ylmethoxy)-2H-spiro[1-benzofuran-3,4'-piperidine]-1'-yl]propanoic acid hydrochloride Rt 1.38 min (System B), [M+H]$^+$ 372.2

Compound 43. 3-{6-[(3,5-Dichloropyridin-4-yl)methoxy]-2H-spiro[1-benzofuran-3,4'-piperidine]-1'-yl}propanoic acid hydrochloride Rt 1.23 min (System B), [M+H]$^+$ 437.0

Compound 44. 3-{6-[(2,4-Dichloropyridin-3-yl)methoxy]-2H-spiro[1-benzofuran-3,4'-piperidine]-1'-yl}propanoic acid hydrochloride Rt 1.19 min (System B), [M+H]$^+$ 437.0

Compound 45. 3-{6-[(2,4,6-Trichlorophenyl)methoxy]-2H-spiro[1-benzofuran-3,4'-piperidine]-1'-yl}propanoic acid hydrochloride $^1$H NMR (400 MHz, DMSO-d$_6$) δ ppm 12.64 (bs, 1H), 10.09 (bs, 1H), 7.78 (s, 2H), 7.02 (bs, 1H), 6.54-6.59 (m, 2H), 5.13 (s, 2H), 4.46 (s, 2H), 3.21-3.50 (m, 4H), 2.92-3.11 (m, 2H), 2.80 (t, J=8 Hz, 2H), 2.04-2.15 (m, 2H), 1.81-1.89 (m, 2H). Rt 1.45 min (System B), [M+H]$^+$ 471.9

Compound 46. 3-{6-[(2,6-Dichloro-4-iodophenyl)methoxy]-2H-spiro[1-benzofuran-3,4'-piperidine]-1'-yl}propanoic acid hydrochloride $^1$H NMR (400 MHz, DMSO-d$_6$) δ ppm 12.82 (bs, 1H), 10.18 (bs, 1H), 7.98 (s, 2H), 7.00 (bs, 1H), 6.55-6.60 (m, 2H), 5.12 (s, 2H), 4.47 (bs, 2H), 3.26-3.51 (m, 4H), 3.10-3.19 (m, 2H), 2.83 (t, J=8 Hz, 2H), 2.08-2.19 (m, 2H), 1.82-1.90 (m, 2H). Rt 1.47 min (System B), [M+H]$^+$ 561.8.

Compound 47. 3-{6-[(2,6-Difluorophenyl)methoxy]-2H-spiro[1-benzofuran-3,4'-piperidine]-1'-yl}propanoic acid hydrochloride Rt 1.28 min (System B), [M+H]$^+$ 404.0.

Compound 48. 3-{6-[2-(2,6-Dichlorphenyl)ethoxy]-2H-spiro[1-benzofuran-3,4'-piperidine]-1'-yl}propanoic acid hydrochloride $^1$H NMR (400 MHz, DMSO-d$_6$) δ ppm 12.80 (bs, H), 10.70 (b, 1H), 7.49 (d, J=8.1 Hz, 2H), 7.28-7.39 (m, 1H), 6.88-7.08 (m, 1H), 6.41-6.51 (m, 2H), 4.41-4.49 (m, 2H), 4.08-4.18 (m, 2H), 3.25-3.48 (m, 6H), 3.06 (bs, 2H), 2.82-2.92 (m, 2H), 2.1-2.3 (m, 2H) 1.78-1.83 (m, 2H). Rt 1.41 min (System B), [M+H]$^+$ 450.0

Compound 49. 3-{6-[2-(2-Fluororphenyl)ethoxy]-2H-spiro[1-benzofuran-3,4'-piperidine]-1'-yl}propanoic acid hydrochloride Rt 1.32 min (System B), [M+H]$^+$ 400.0

Compound 50. 3-{6-[(2-Chloro-5-methylphenyl)methoxy]-2H-spiro[1-benzofuran-3,4'-piperidine]-1'-yl}propanoic acid hydrochloride Rt 1.40 min (System B), [M+H]$^+$ 416.1

Compound 51. 3-{6-[(2-Chloro-5-ethylphenyl)methoxy]-2H-spiro[1-benzofuran-3,4'-piperidine]-1'-yl}propanoic acid hydrochloride $^1$H NMR (400 MHz, DMSO-d$_6$) δ ppm 12.70 (bs., 1H) 10.55 (bs, 1H), 7.43 (d, J=2.2Hz, 1H), 7.40 (d, J=8.2Hz, 1H), 7.24 (dd, J=8.2 and 2.2Hz, 1H), 6.94-7.03 (m, 1H), 6.51-6.61 (m, 2H), 5.06 (s, 2H), 4.47 (bs., 2H), 3.22-3.55 (m, 4H), 2.95-3.15 (m, 2H), 2.86 (t, J=7.6 Hz, 2H), 2.61 (q, J=7.6 Hz, 2H), 2.10-2.30 (m, 2H), 1.79-1.91 (m, 2H), 1.16 (t, J=7.6 Hz, 3H). Rt 1.45 min (System B), [M+H]$^+$ 430.1.

Compound 52. 3-{6-[(2-Chloro-5-proylphenyl)methoxy]-2H-spiro[1-benzofuran-3,4'-piperidine]-1'-yl}propanoic acid hydrochloride Rt 1.52 min (System B), [M+H]$^+$ 444.1

Compound 53. 3-{6-[3-(2-Fluorophenyl)propoxy]-2H-spiro[1-benzofuran-3,4'-piperidine]-1'-yl}propanoic acid hydrochloride $^1$H NMR (600 MHz, DMSO-d$_6$) δ ppm 12.80 (bs, 1H), 10.70 (bs, 1H), 7.27-7.32 (m, 1H), 7.20-7.27 (m, 1H), 7.09-7.15 (m, 2H), 6.88-6.98 (m, 1H), 6.44 (d, J=7.6 Hz, 1H), 6.38 (d, J=2.2Hz, 1H), 4.45 (bs., 2H), 3.91 (t, J=6.2Hz, 2H), 3.19-3.52 (m, H), 3.01 (m, 2H), 2.85 (t, J=7.7 Hz, 2H), 2.74 (t, J=7.6 Hz, 2H), 2.14-2.28 (m, 2H), 1.91-1.99 (m, 2H), 1.73-1.88 (m, 2H).

Compound 54. 3-{6-[3-(2-Chlorophenyl)propoxy]-2H-spiro[1-benzofuran-3,4'-piperidine]-1'-yl}propanoic acid hydrochloride Rt 1.44 min (System B), [M+H]$^+$ 430.1

Compound 55. 3-[6-(3-Phenylpropoxy]-2H-spiro[1-benzofuran-3,4'-piperidine]-1'-yl}propanoic acid hydrochloride Rt 1.45 min (System B), [M+H]$^+$ 396.2

Compound 56. 3-{6-[2-(2,4-Dichlorophenyl)ethoxy]-2H-spiro[1-benzfuran-3,4'-piperidine]-1'-yl}propanoic acid hydrochloride Rt 1.47 min (System B), [M+H]$^+$ 450.0

Compound 57. 3-{6-[2-(2-Chlorophenyl)ethoxy]-2H-spiro[1-benzofuran-3,4'-piperidine]-1'-yl}propanoic acid hydrochloride Rt 1.39 min (System B), [M+H]$^+$ 416.0

Compound 58. 3-(6-{[2,6-Dichloro-4-(trifluoromethyl)phenyl]methoxy}-2H-spiro[1-benzofuran-3,4'-piperidine]-1'-yl)propanoic acid hydrochloride Rt 1.49 min (System B), [M+H]$^+$ 504.0

Compound 59. 3-{6-[(2,6-Dichloro-4-methylphenyl)methoxy]-2H-spiro[1-benzofuran-3,4'-piperidine]-1'-yl)propanoic acid hydrochloride $^1$H NMR (400 MHz, DMSO-d$_6$) δ ppm 12.64 (bs, 1H), 9.90 (bs, 1H), 7.42 (s, 2H), 7.01 (bs, 1H), 6.56-6.61 (m, 2H), 5.14 (s, 2H), 4.49 (br s, 2H), 3.31-3.53 (m, 4H), 3.01-3.11 (m, 2H), 2.81-2.87 (m, 2H), 2.35 (s, 3H), 2.09-2.19 (m, 2H), 1.84-1.92 (m, 2H). Rt 1.43 min (System B), [M+H]$^+$ 450.0

Compound 60. 3-{6-[(5-Bromo-2-chlorophenyl)methoxy]-2H-spiro[1-benzofuran-3,4'-piperidine]-1'-yl}propanoic acid hydrochloride Rt 1.52 min (System B), [M+H]$^+$ 480.0

Compound 61. 3-{6-[(2-Chloro-6-methylphenyl)methoxy]-2H-spiro[1-benzofuran-3,4'-piperidine]-1'-yl}propanoic acid hydrochloride Rt 1.42 min (System B), [M+H]$^+$ 416.1

Compound 62. 3-(6-{3-[2-(Trifluoromethyl)phenyl]propoxy}-2H-spiro[1-benzofuran-3,4'-piperidine]-1'-yl)propanoic acid hydrochloride Rt 1.48 min (System B), [M+H]$^+$ 464.1

Compound 63. 3-{6-[3-(2,3-Difluorophenyl)propoxy]-2H-spiro[1-benzofuran-3,4'-piperidine]-1'-yl}propanoic acid hydrochloride Rt 1.42 min (System B), [M+H]$^+$ 432.1

Compound 64. 3-{6-[3-(2-Chloro-6-fluorophenyl)propoxy]-2H-spiro[1-benzofuran-3,4'-piperidine]-1'-yl}propanoic acid hydrochloride Rt 1.42 min (System B), [M+H]$^+$ 432.1

Compound 65. 3-{6-[3-(2,6-Dichlorophenyl)propoxy]-2H-spiro[1-benzofuran-3,4'-piperidine]-1'-yl}propanoic acid hydrochloride $^1$H NMR (400 MHz, DMSO-d$_6$) δ ppm 12.70 (bs., 1H), 10.70 (bs., 1H), 7.46 (d, J=8.3 Hz, 2H), 7.27 (dd, J=8.3 and 7.6 Hz, 1H), 6.95 (d, J=8.0 Hz, 1H), 6.46 (dd, J=8.0 and 2.0 Hz, 1H), 6.40 (d, J=2.0 Hz, 1H), 4.47 (bs., 2H), 3.99 (t, J=6.1 Hz, 2H), 3.46 (m, 2H), 3.29 (m, 2H), 2.98-3.10 (m, 4H), 2.87 (t, J=7.7 Hz, 2H), 2.15-2.30 (m, 2H), 1.90-1.99 (m, 2H), 1.78-1.88 (m, 2H). Rt 1.49 min (System B), [M+H]$^+$ 464.0.

Compound 66. 3-{6-[3-(4-Chlorophenyl)propoxy]-2H-spiro[1-benzofuran-3,4'-piperidine]-1'-yl}propanoic acid hydrochloride Rt 1.46 min (System B), [M+H]$^+$ 430.1

Compound 67. 3-{6-[(2-Chloro-5-phenylphenyl)methoxy]-2H-spiro[1-benzofuran-3,4'-piperidine]-1'-yl}propanoic acid hydrochloride Rt 1.90 min (System B), [M+H]$^+$ 478.0

Compound 68. 3-{6-[(2,6-Dichloro-3-ethylphenyl)methoxy]-2H-spiro[1-benzofuran-3,4'-piperidine]-1'-yl}propanoic acid hydrochloride $^1$H NMR (400 MHz, DMSO-d$_6$) δ ppm 12.80 (bs., 1H), 10.30 (bs., 1H), 7.50 (d, J=8.1 Hz, 1H), 7.45 (d, J=8.1 Hz, 1H) 6.95-7.07 (m, 1H), 6.58-6.62 (m, 2H), 5.19 (s, 2H), 4.48 (bs, 2H), 3.20-3.52 (m, 4H), 2.95-3.20 (m, 2H), 2.85 (t, J=7.7 Hz, 2H) 2.75 (q, J=7.6 Hz, 2H), 2.10-2.28 (m, 2H), 1.80-1.90 (m, 2H), 1.18 (t, J=7.6 Hz, 3H).

Compound 69. 3-{6-[(4-Butyl-2,6-dichlorophenyl)methoxy]-2H-spiro[1-benzofuran-3,4'-piperidine]-1'-yl}propanoic acid hydrochloride $^1$H NMR (400 MHz, DMSO-d$_6$) δ ppm 12.55 (bs, 1H), 10.27 (bs, 1H), 7.37 (s, 2H), 6.95 (bs, 1H), 6.51-6.58 (m, 2H), 5.09 (s, 2H), 4.44 (bs, 2H), 3.22-3.50 (m, 4H), 2.94-3.18 (m, 2H), 2.81 (t, J=8 and 2Hz, 2H), 2.57 (t, J=8 Hz, 2H), 2.07-2.19 (m, 2H), 1.78-1.86 (m, 2H), 1.48-1.56 (m, 2H), 1.21-1.30 (m, 2H), 0.84-0.89 (t, J=8 Hz, 3H). Rt 1.92 min (System B), [M+H]$^+$ 492.0

Compound 70. 3-{6-[(2,6-Dichloro-4-cyclorpropylphenyl)methoxy]-2H-spiro[1-benzofuran-3,4'-piperidine]-1'-yl}propanoic acid hydrochloride $^1$H NMR (400 MHz, DMSO-d$_6$) δ ppm 12.55 (bs, 1H), 10.09 (bs, 1H), 7.27 (s, 2H), 7.00 (br s, 1H), 6.55-6.60 (m, 2H), 5.11 (s, 2H), 4.49 (bs, 2H), 3.26-3.52 (m, 4H), 2.97-3.12 (m, 2H), 2.84 (t, J=8 Hz, 2H), 2.08-2.22 (m, 2H), 1.97-2.02 (m, 1H), 1.83-1.91 (m, 2H), 0.99-1.06 (m, 2H), 0.78-0.82 (m, 2H). Rt 1.65 min (System B), [M+H]$^+$ 476.0.

Compound 71. 3-{6-[(2-Chloro-5-cyclopropylphenyl)methoxy]-2H-spiro[1-benzofuran-3,4'-piperidine]-1'-yl}propanoic acid hydrochloride Rt 1.68 min (System B), [M+H]+ 442.1

Compound 72. 3-[6-({2-Chloro-5-[2-phenylcyclopropyl]phenyl}methoxy)-2H-spiro[1-benzofuran-3,4'-piperidine]-1'-yl]propanoic acid hydrochloride Rt 1.72 min (System B), [M+H]+ 518.0

Compound 73. 3-{6-[(2-Chloro-6-ethylphenyl)methoxy]-2H-spiro[1-benzofuran-3,4'-piperidine]-1'-yl}propanoic acid hydrochloride $^1$H NMR (400 MHz, DMSO-d$_6$) δ ☐ppm 12.80 (bs, 1H), 10.30 (bs, 1H), 7.35-7.37 (m, 2H), 7.26-7.30 (m, 1H), 6.95-7.40 (m, 1H), 6.56-6.63 (m, 2H), 5.10 (s, 2H), 4.49 (bs, 2H) 3.24-3.54 (m, 4H), 2.96-3.14 (m, 2H), 2.87 (t, J=8.2Hz, 2H), 2.71 (q, J=7.6 Hz, 2H), 2.18-2.33 (m, 2H), 1.80-1.90 (m, 2H), 1.17 (t, J=7.6 Hz, 3H). Rt 1.40 min (System B), [M+H]+ 430.0

Compound 74. 3-(6-{[2-Chloro-6-(propan-2-yl)phenyl]methoxy}-2H-spiro[1-benzofuran-3,4'-piperidine]-1'-yl)propanoic acid hydrochloride $^1$H NMR (400 MHz, DMSO-d$_6$) δ ppm 12.80 (bs, 1H), 10.90 (bs, 1H), 7.33-7.41 (m, 3H), 6.94-7.04 (m, 1H), 6.56-6.63 (m, 2H), 5.15 (s, 2H), 4.49 (bs, 2H), 3.24-3.54 (m, 4H), 3.14-3.22 (m, 1H), 2.95-3.14 (m, 2H), 2.88 (t, J=8.0 Hz, 2H), 2.14-2.33 (m, 2H), 1.80-1.90 (m, 2H), 1.19 (d, J=6.7 Hz, 6H). Rt 1.40 min (System B), [M+H]+ 430.0.

Compound 75. 3-{6-[(2-Chloro-6-cyclopropyl)phenyl)methoxy]-2H-spiro[1-benzofuran-3,4'-piperidine]-1'-yl}propanoic acid hydrochloride $^1$H NMR (400 MHz, DMSO-d$_6$) δ ppm 12.90 (bs, 1H), 10.10 (bs, 1H), 7.29-7.37 (m, 2H), 6.94-7.09 (m, 2H), 6.56-6.62 (m, 2H), 5.26 (s, 2H), 4.49 (bs, 2H), 3.42-3.56 (m, 2H), 3.24-3.41 (m, 2H), 2.96-3.18 (m, 2H), 2.84 (t, J=7.7 Hz, 2H), 2.00-2.23 (m, 3H), 1.80-1.91 (m, 2H), 0.88-0.96 (m, 2H), 0.73-0.65 (m, 2H). Rt 1.43 min (System B), [M+H]+ 442.0

Compound 76. 3-{6-[(2,6-Dichloro-3-methoxyphenyl)methoxy]-2H-spiro[1-benzofuran-3,4'-piperidine]-1'-yl}propanoic acid hydrochloride Rt 1.35 min (System B), [M+H]+ 465.9

Compound 77. 3-(6-{[2-Chloro-6-(trifluoromethoxy)phenyl]methoxy}-2H-spiro[1-benzofuran-3,4'-piperidine]-1'-yl)propanoic acid hydrochloride $^1$H NMR (400 MHz, DMSO-d$_6$) δ ppm 12.90 (bs, 1H) 10.50 (bs, 1H) 7.58-7.65 (m, 2H), 7.46-7.51 (m, 1H), 6.95-7.03 (m, 1H), 6.56-6.62 (m, 2H), 5.10 (s, 2H), 4.49 (bs, 2H), 3.42-3.56 (m, 2H), 3.24-3.41 (m, 2H), 2.96-3.18 (m, 2H), 2.84 (t, J=7.7 Hz, 2H), 2.13-2.28 (m, 2H), 1.83-1.91 (m, 2H). Rt 1.41 min (System B), [M+H]+ 486.0

Compound 78. 3-(6-{[2-Chloro-6-(2-methylpropyl)phenyl]methoxy}-2H-spiro[1-benzofuran-3,4'-piperidine]-1'-yl)propanoic acid hydrochloride $^1$H NMR (400 MHz, DMSO-d$_6$) δ ppm 12.9 (bs, 1H), 10.1 (bs, 1H), 7.31-7.42 (m, 2H), 7.20-7.24 (m, 1H), 6.96-7.03 (m, 1H), 6.56-6.62 (m, 2H), 5.08 (s, 2H), 4.49 (bs, 2H), 3.45-3.56 (m, 2H), 3.24-3.41 (m, 2H), 2.96-3.18 (m, 2H), 2.84 (t, J=7.7 Hz, 2H), 2.58 (d, J=7.4 Hz, 2H), 2.00-2.23 (m, 3H), 1.80-1.91 (m, 2H), 0.85 (d, J=6.8 Hz, 6H).

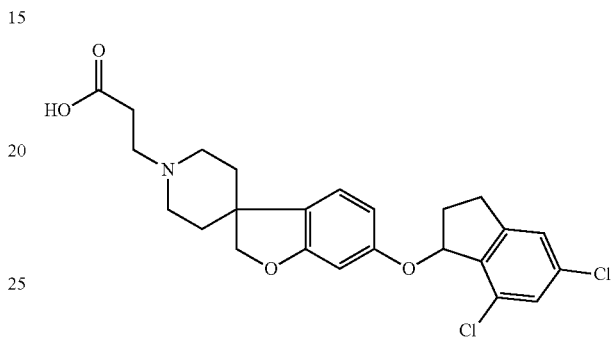

Compound 79. 3-{6-[(5,7-Dichloro-2,3-dihydro-1H-inden-1-yl)oxy]-2H-spiro[1-benzofuran-3,4'-piperidine]-1'-yl}propanoic acid A mixture of 3-{6-[(5,7-dichloro-2,3-dihydro-benzofuran-3,4'-piperidine]-1'-yl}propanoate (0.27 g; 0.52 mmol), 2M aqueous NaOH (5 mL; 10 mmol) and ethanol (40 mL) was stirred for 3 hours at 50° C. and subsequently cooled to 0° C. To this reaction mixture was added aqueous HCl (10 mL; 1 mol/l), dropwise, after which it was concentrated in vacuo. The residue was treated with saturated brine and dichloromethane. The water layer was washed with dichloromethane (twice). Subsequently, the organic layer was dried (Na$_2$SO$_4$), filtered, and concentrated in vacuo, followed by treated with iPr$_2$O. The formed precipitate was collected by filtration, washed with iPr$_2$O and dried in vacuo to yield the product (209 mg; 81.8%). $^1$H NMR (400 MHz, CDCl$_3$-d) δ ppm 7.25 (s, 1H), 7.19 (s, 1H), 7.06 (d, J=8.2Hz, 1H), 6.53 (dd, J=8.2 and 2.1 Hz, 1H), 6.47 (d, J=2.1 Hz, 1H), 5.70 (d, J=5.1 Hz, 1H), 4.40 (s, 2H), 3.14-3.28 (m, 3H), 2.84-2.98 (m, 3H), 2.60 (t, J=5.9 Hz, 2H), 2.27-2.46 (m, 4H), 2.09 (t, J=11.4 Hz, 2H), 1.89 (bd, J=13.8 Hz, 2H). Rt 1.47 min (System B), [M+H]+ 462.0

The following compounds were obtained according to a similar manner:

Compound 80. 3-{6-[(5,7-Difluoro-2,3-dihydro-1H-inden-1-yl)oxy]-2H-spiro[1-benzofuran-3,4'-piperidine]-1'-yl}propanoic acid Rt 1.39 min (System B), [M+H]+ 430.1

Compound 81. 3-{6-[(1R)-(2,3-dihydro-1H-inden-1-yl)oxy]-2H-spiro[1-benzofuran-3,4'-piperidine]-1'-yl}propanoic acid Rt 1.34 min (System B), [M+H]+ 394.1

Compound 82. 3-{6-[(1S)-(2,3-dihydro-1H-inden-1-yl)oxy]-2H-spiro[1-benzofuran-3,4'-piperidine]-1'-yl}propanoic acid ¹H NMR (400 MHz, CDCl₃-d) δ ppm 7.42 (d, J=7.3 Hz, 1H), 7.21-7.34 (m, 3H), 7.05 (d, J=8.2Hz, 1H), 6.57 (dd, J=8.2 and 2.0 Hz, 1H), 6.51 (d, J=2.0 Hz, 1H), 5.71 (dd, J=6.5 and 4.4 Hz, 1H), 4.40 (s, 2H), 3.08-3.19 (m, 3H), 2.87-2.97 (m, 1H), 2.84 (t, J=6.1 Hz, 2H), 2.50-2.62 (m, 3H), 2.30-2.46 (m, 2H), 2.15-2.25 (m, 1H), 2.00-2.11 (m, 2H), 1.84-1.93 (m, 2H). Rt 1.34 min (System B), [M+H]⁺ 394.1

Compound 83. 3-(6-{[(2E)-3-(4-Chlorophenyl)prop-2-en-1-yl]oxy}-2H-spiro[1-benzofuran-3,4'-piperidine]-1'-yl}propanoic acid Rt 1.48 min (System B), [M+H]⁺ 428.0

Compound 84. 3-{6-[(3-Phenyl)prop-2-yn-1-yl]oxy}-2H-spiro[1-benzofuran-3,4'-piperidine]-1'-yl}propanoic acid Rt 1.37 min (System B), [M+H]⁺ 392.1

Compound 85. 3-[6-(2,3-Dihydro-1-benzfuran-3-yloxy)-2H-spiro[1-benzofuran-3,4'-piperidine]-1'-yl]propanoic acid Rt 1.95 min (System B), [M+H]⁺ 396.1

Compound 86. 3-(6-{[(2E)-3-(2,6-dichlorophenyl)prop-2-en-1-yl]oxy}-2H-spiro[1-benzofuran-3,4'-piperidine]-1'-yl)propanoic acid ¹H NMR (400 MHz, DMSO-d₆) δ ppm 7.48-7.52 (m, 2H), 7.32 (t, J=8.1 Hz, 1H), 7.10 (d, J=8.1 Hz, 1H), 6.72-6.60 (m, 1H), 6.53-6.46 (m, 2H), 6.31-6.39 (m, 1H), 4.75 (dd, J=5.1 and 2.0 Hz, 2H), 4.37 (s, 2H), 2.87-2.95 (m, 2H), 2.64-2.71 (m, 2H) 2.40-2.46 (m, 2H), 2.12-2.22 (m, 2H), 1.78-1.88 (m, 2H), 1.59-1.67 (m, 2H). Rt 1.51 min (System B), [M+H]⁺ 462.1

Compound 87. 3-(6-{[(2E)-3-phenylprop-2-en-1-yl]oxy}-2H-spiro[1-benzofuran-3,4'-piperidine]-1'-yl)propanoic acid Rt 1.37 min (System B), [M+H]⁺ 394.1

Compound 88. 3-{6-[(7-Chloro-2,3-dihydro-1H-inden-1-yl)oxy]-2H-spiro[1-benzofuran-3,4'-piperidine]-1'-yl}propanoic acid Rt 1.37 min (System B), [M+H]⁺ 428.0

Compound 89. 3-(6-{[(3-(4-Chlorophenyl)prop-2-yn-1-yl]oxy}-2H-spiro[1-benzofuran-3,4'-piperidine]-1'-yl)propanoic acid Rt 1.43 min (System B), [M+H]⁺ 426.0

Compound 90. 3-(6-{[(2E)-3-(2-fluororophenyl)prop-2-en-1-yl]oxy}-2H-spiro[1-benzofuran-3,4'-piperidine]-1'-yl)propanoic acid Rt 1.41 min (System B), [M+H]⁺ 412.1

Compound 91. 3-{6-[(4-Bromothiophen-2yl)methoxy]-2H-spiro[1-benzofuran-3,4'-piperidine]-1'-yl}propanoic acid Rt 1.57 min (System B), [M+H]⁺ 452.0

Compound 92. 3-{6-[(4-Butylthiophen-2yl)methoxy]-2H-spiro[1-benzofuran-3,4'-piperidine]-1'-yl}propanoic acid Rt 1.67 min (System B), [M+H]⁺ 430.1

Compound 93. 3-(6-{[4-(2-Fluorophenyl)thiophen-2-yl]methoxy}-2H-spiro[1-benzofuran-3,4'-piperidine]-1'-yl}propanoic acid Rt 1.68 min (System B), [M+H]⁺ 468.0

Compound 94. 3-{6-[(4-Phenylthiophen-2yl)methoxy]-2H-spiro[1-benzofuran-3,4'-piperidine]-1'-yl}propanoic acid Rt 1.99 min (System B), [M+H]⁺ 450.0

Compound 95. 3-{6-[(4-Bromo-3-methylthiophen-2yl)methoxy]-2H-spiro[1-benzofuran-3,4'-piperidine]-1'-yl}propanoic acid ¹H NMR (400 MHz, DMSO-d₆) δ ppm 12.60 (bs., 1H), 7.68 (s, 1H), 7.08-7.13 (m, 1H), 6.45-6.51 (m, 2H), 5.18 (s, 2H), 4.36 (s, 2H), 2.81-2.89 (m, 2H), 2.61 (t, J=7.2Hz, 2H), 2.39 (t, J=7.2Hz, 2H), 2.17 (s, 3H), 2.02-2.12 (m, 2H), 1.74-1.86 (m, 2H), 1.56-1.64 (m, 2H). Rt 1.72 min (System B), [M+H]⁺ 467.9

Compound 96. 3-{6-[(4-Cyclopropylmethylthiophen-2yl)methoxy]-2H-spiro[1-benzfuran-3,4'-piperidine]-1'-yl}propanoic acid ¹H NMR (400 MHz, DMSO-d₆) δ ppm 7.06-7.10 (m, 2H), 6.91 (d, J=1.2Hz, 1H), 6.44-6.49 (m, 2H), 5.12 (s, 2H), 4.35 (s, 2H), 2.89-2.83 (m, 2H), 2.63 (t, J=7.0 Hz, 2H), 2.40 (t, J=7.0 Hz, 2H), 2.04-2.14 (m, 2H), 1.90 (dt, J=8.4, 5.0 Hz, 1H), 1.74-1.85 (m, 2H), 1.57-1.64 (m, 2H), 0.82-0.89 (m, 2H), 0.56-0.61 (m, 2H). Rt 1.69 min (System B), [M+H]⁺ 414.1.

Compound 97. 3-{6-[(3-Methyl-4-phenylthiophen-2yl)methoxy]-2H-spiro[1-benzofuran-3,4'-piperidine]-1'-yl}propanoic acid Rt 1.69 min (System B), [M+H]⁺ 464.0

Compound 98. 3-{6-[(4-Butyl-3-methylthiophen-2yl)methoxy]-2H-spiro[1-benzofuran-3,4'-piperidine]-1'-yl}propanoic acid Rt 1.82 min (System B), [M+H]⁺ 444.1

Compound 252. 3-(6-{[2-fluoro-6-(propan-2-yl)phenyl]methoxy}-2H-spiro[1-benzofuran-3,4'-piperidine]-1'-yl)propanoic acid ¹H NMR (400 MHz, DMSO-d₆) δ ppm 7.37-7.46 (m, 1H), 7.23 (d, J=7.8 Hz, 1H), 7.03-7.14 (m, 2H), 6.47-6.54 (m, 2H), 5.05 (s, 2H), 4.37 (s, 2H), 3.12-3.22 (d, 1H), 2.82-2.91 (m, 2H), 2.63 (t, J=7.1 Hz, 2H), 2.40 (t, J=7.1 Hz, 2H), 2.10 (t, J=11.1 Hz, 1H), 1.76-1.88 (m, 2H), 1.62 (d, J=13.1 Hz, 2H), 1.20 (d, J=6.8 Hz, 6H). Rt 1.45 min (System B), [M+H]+ 429.3

Compound 253. 3-{6-[(2-cyclopropyl-6-fluorophenyl)methoxy]-2H-spiro[1-benzofuran-3,4'-piperidine]-1'-yl}propanoic acid $^1$H NMR (400 MHz, DMSO-d$_6$) □ δ ppm 7.29-7.37 (m, 1H), 7.02-7.14 (m, 2H), 6.85 (d, J=7.8 Hz, 1H), 6.50-6.56 (m, 2H), 5.16 (s, 2H), 4.37 (s, 2H), 2.86-2.92 (m, 2H), 2.64 (t, J=7.2Hz, 2H), 2.41 (t, J=7.2Hz, 2H), 2.00-2.18 (m, 3H), 1.77-1.88 (m, 2H), 1.62 (d, J=12.6 Hz, 2H), 0.89-0.98 (m, 2H), 0.66-0.72 (m, 2H). Rt 1.40 min (System B), [M+H]+ 426.2

Compound 254. 3-{6-[(2-ethyl-6-fluorophenyl)methoxy]-2H-spiro[1-benzofuran-3,4'-piperidine]-1'-yl}propanoic acid $^1$H NMR (400 MHz, DMSO-d$_6$) □ δ ppm 7.33-7.42 (m, 1H), 7.04-7.17 (m, 3H), 6.48-6.56 (m, 2H), 5.02 (s, 2H), 4.37 (s, 2H), 2.87-2.97 (m, 2H), 2.62-2.74 (m, 5H), 2.45 (t, J=7.2 Hz, 2H), 2.11-2.23 (m, 2H), 1.80-1.92 (m, 2H), 1.64 (d, J=12.4 Hz, 2H), 1.16 (t, J=7.5 Hz, 3H). Rt 1.41 min (System B), [M+H]+ 414.3

Compound 255. 3-(6-{[2-fluoro-6-(trifluoromethyl)phenyl]methoxy}-2H-spiro[1-benzofuran-3,4'-piperidine]-1'-yl)propanoic acid $^1$H NMR (400 MHz, DMSO-d$_6$) □ δ ppm 7.63-7.75 (m, 3H), 7.12 (d, J=8.0 Hz, 1H), 6.47-6.53 (m, 2H), 5.09 (s, 2H), 4.37 (s, 2H), 2.86 (d, J=11.7 Hz, 2H), 2.62 (t, J=7.2 Hz, 2H), 2.40 (t, J=7.2Hz, 2H), 2.04-2.13 (m, 2H), 1.77-1.86 (m, 2H), 1.62 (d, J=13.1 Hz, 2H). Rt 1.50 min (System B), [M+H]+ 454.2

Compound 256. 3-{6-[(4-chloro-2,6-difluorophenyl)methoxy]-2H-spiro[1-benzofuran-3,4'-piperidine]-1'-yl}propanoic acid $^1$H NMR (400 MHz, DMSO-d$_6$) □ δ ppm 7.43-7.49 (m, 2H), 7.07-7.12 (m, 1H), 6.47 (s, 2H), 5.01 (s, 2H), 4.34 (s, 2H), 2.73-2.79 (m, 2H), 2.40-2.47 (m, 2H), 1.85-1.98 (m, 4H), 1.74-1.84 (m, 2H), 1.51-1.58 (m, 2H). Rt 1.36 min (System B), [M+H]+ 439.2

Compound 257. 3-{6-[1-(2,6-dichlorophenyl)ethoxy]-2H-spiro[1-benzo-furan-3,4'-piperidine]-1'-yl}propanoic acid $^1$H NMR (400 MHz, DMSO-d$_6$) □ δ 7.45 (d, J=8.1 Hz, 2H), 7.28-7.34 (m, 1H), 7.02 (d, J=8.1 Hz, 1H), 6.29 (dd, J=8.1, 2.1 Hz, 1H), 6.21 (d, J=2.1 Hz, 1H), 5.93 (q, J=6.6 Hz, 1H), 4.30 (s, 2H), 2.81 (d, J=11.9 Hz, 2H), 2.57 (t, J=7.2Hz, 2H), 2.37 (t, J=7.2Hz, 2H), 2.02 (t, J=11.2Hz, 2H), 1.69-1.78 (m, 2H), 1.67 (d, J=6.6 Hz, 3H), 1.55 (d, J=11.9 Hz, 2H). Rt 1.41 min (System B), [M+H]+ 450.1

Compound 258. 3-{6-[(2,6-diethylphenyl)methoxy]-2H-spiro[1-benzo-furan-3,4'-piperidine]-1'-yl}propanoic acid $^1$H NMR (400 MHz, DMSO-d$_6$) □ δ ppm 7.22-7.27 (m, 1H), 7.07-7.15 (m, 3H), 6.49-6.55 (m, 2H), 4.96 (s, 2H), 4.37 (s, 2H), 2.85 (d, J=11.7 Hz, 2H), 2.56-2.69 (m, 6H), 2.36 (t, J=7.0 Hz, 2H), 2.01-2.10 (m, 2H), 1.77-1.86 (m, 2H), 1.62 (d, J=12.9 Hz, 2H), 1.14 (t, J=7.5 Hz, 6H). Rt 1.47 min (System B), [M+H]+ 424.2

Compound 259. 3-(6-{[2-(propan-2-yl)phenyl]methoxy}-2H-spiro[1-benzofuran-3,4'-piperidine]-1'-yl)propanoic acid $^1$H NMR (400 MHz, DMSO-d$_6$) □ δ ppm 7.30-7.40 (m, 3H), 7.15-7.22 (m, 1H), 7.08 (d, J=8.0 Hz, 1H), 6.47-6.54 (m, 2H), 5.04 (s, 2H), 4.39 (s, 2H), 3.10-3.19 (m, 1H), 3.02 (d, J=11.9 Hz, 2H), 2.81 (t, J=7.0 Hz, 2H), 2.54 (t, J=7.0 Hz, 2H), 2.32-2.43 (m, 2H), 1.89-2.00 (m, 2H), 1.68 (d, J=13.3 Hz, 2H), 1.16-1.22 (m, 6H). Rt 1.45 min (System B), [M+H]+ 410.7

Compound 260. 3-(6-{[2-ethyl-6-(trifluoromethyl)phenyl]methoxy}-2H-spiro[1-benzofuran-3,4'-piperidine]-1'-yl)propanoic acid $^1$H NMR (400 MHz, DMSO-d$_6$) □ δ ppm 7.61-7.67 (m, 2H), 7.53-7.60 (m, 1H), 7.12 (d, J=7.8 Hz, 1H), 6.48-6.55 (m, 2H), 5.04 (s, 2H), 4.35 (s, 2H), 2.79 (d, J=11.2Hz, 2H), 2.73 (q, J=7.5 Hz, 2H), 2.45-2.5 (m, 2H), 2.05 (t, J=7.6 Hz, 2H), 1.87-1.97 (m, 2H), 1.77-1.86 (m, 2H), 1.58 (d, J=12.1 Hz, 2H), 1.17-1.23 (m, 3H). Rt 1.47 min (System B), [M+H]+ 464.2

Compound 261. 3-(6-{[2-Chloro-6-(difluoromethoxy)phenyl]methoxy}-2H-spiro[1-benzofuran-3,4'-piperidine]-1'-yl)propanoic acid $^1$H NMR (400 MHz, DMSO-d$_6$) δ ppm 7.43-7.56 (m, 2H), 7.27-7.32 (m, 1H), 7.06-7.13 (m, 1H), 6.49-6.57 (m, 2H), 5.06 (s, 2H), 4.40 (s, 2H), 3.04 (d, J=11.7 Hz, 2H), 2.83 (t, J=7.1 Hz, 2H), 2.56 (t, J=7.1 Hz, 2H), 2.40 (m, 3H), 1.89-2.02 (m, 2H), 1.69 (d, J=13.5 Hz, 2H).

Compound 262. 3-{6-[(2-Fluoro-6-methoxyphenyl)methoxy]-2H-spiro[1-benzofuran-3,4'-piperidine]-1'-yl}propanoic acid $^1$H NMR (400 MHz, DMSO-d$_6$) δ ppm 7.37-7.47 (m, 1H), 7.09 (d, J=7.9 Hz, 1H), 6.93 (d, J=8.4 Hz, 1H), 6.85 (t, J=8.8 Hz, 1H), 6.42-6.52 (m, 2H), 4.95 (s, 2H), 4.35 (s, 2H), 3.83 (s, 3H), 2.86 (d, J=11.7 Hz, 2H), 2.61 (t, J=7.1 Hz, 2H), 2.38 (t, J=7.1 Hz, 2H), 2.08 (t, J=11.2Hz, 2H) 1.81 (dt, J=12.8, 3.5 Hz, 2H), 1.61 (d, J=12.8 Hz, 2H). Rt 1.27 min (System B), [M+H]+ 416.7

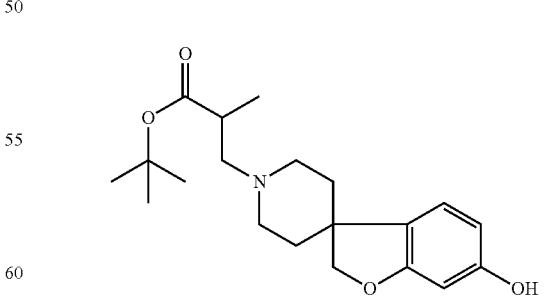

Tert-butyl 3-{6-hydroxy-2H-spiro[1-benzofuran-3,4'-piperidine]-1'-yl}-2-methyl-propanoate. To a solution of 2H-spiro[1-benzofuran-3,4'-piperidin]-6-ol (565 mg; 2.76 mmol) in N,N-dimethylformamide (5.00 mL) was added tert-butyl methacrylate (0.9 mL; 5.52 mmol) and DBU (1.24 mL; 8.28 mmol) The resulting mixture was heated at 140° C. in a sealed flask overnight. After cooling to RT the reaction mixture was partitioned between 5% aqueous NaHCO₃ solution and EtOAc. The layers were separated and the organic layer was dried (Na₂SO₄), filtered, and concentrated. The residue was purified by column chromatography (SiO₂, Et₂O: hexanes 1:1) to afford the product (0.45 g, 47%). ¹H NMR (400 MHz, CDCl₃-d) δ ppm 6.91 (d, J=8.0 Hz, 1H), 6.29-6.36 (m, 2H) 5.80 (bs, 1H), 4.34 (s, 2H), 2.88-2.96 (m, 1H), 2.75-2.84 (m, 1H), 2.51-2.66 (m, 2H), 2.26-2.35 (m, 1H), 1.96-2.10 (m, 2H), 1.83-1.93 (m, 2H), 1.65-1.69 (m, 2H), 1.48 (s, 9H), 1.11 (d, J=8.5 Hz, 3H). Rt 1.13 min (System B), [M+H]⁺ 348.1

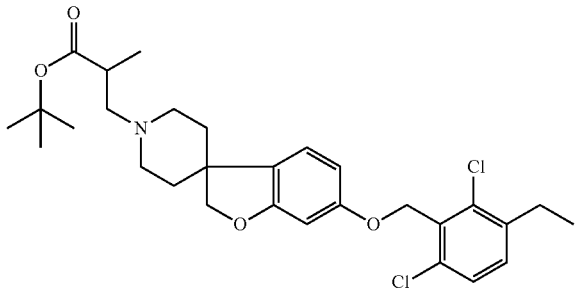 [SMILES: CCc1ccc(Cl)c(COc2ccc3c(c2)OCC32CCN(CC(C)C(=O)OC(C)(C)C)CC2)c1Cl]

Tert-butyl 3-{6-[(2,6-dichloro-3-ethylphenyl)methoxy]-2H-spiro[1-benzofuran-3,4'-piperidine]-1'-yl}-2-methylpropanoate. To a solution of (2,6-dichloro-3-ethylphenyl)methanol (324 mg; 1.58 mmol) and tert-butyl 3-{6-hydroxy-2H-spiro[1-benzofuran-3,4'-piperidine]-1'-yl}-2-methylpropanoate (0.44 g, 1.27 mmol) in dichloromethane (20 mL) was added triphenylphosphine (415 mg; 1.58 mmol), followed, after 30 minutes by DIAD (0.31 mL; 1.58 mmol). Subsequently, the resulting mixture was stirred at RT overnight, and concentrated in vacuo.

Subsequently, the reaction mixture was partitioned between 5% aqueous NaHCO₃ solution and EtOAc. The layers were separated and the organic layer was dried (Na₂SO₄), filtered, and concentrated. The residue was purified by column chromatography (SiO₂, Et₂O: hexanes 1:1) to afford the product (670 mg, 98%). Rt 1.62 min (System B), [M+H]⁺ 534.0.

The following compounds were obtained according to a similar manner:

Tert-butyl 3-{6-[(2,6-dichloro-3-ethylphenyl)methoxy]-2H-spiro[1-benzofuran-3,4'-piperidine]-1'-yl}-2-methylpropanoate.
Tert-butyl 3-{6-[(2,6-dichlorophenyl)methoxy]-2H-spiro[1-benzofuran-3,4'-piperidine]-1'-yl}-2-methylpropanoate.
Tert-butyl 3-{6-[(2-chloro-6-ethylphenyl)methoxy]-2H-spiro[1-benzofuran-3,4'-piperidine]-1'-yl}-2-methylpropanoate.
Tert-butyl 2-methyl-3-{6-[(2,4,6-trichlorophenyl)methoxy]-2H-spiro[1-benzofuran-3,4'-piperidine]-1'-yl}propanoate.
Tert-butyl 3-{6-[(2,6-dichloro-4-methylphenyl)methoxy]-2H-spiro[1-benzofuran-3,4'-piperidine]-1'-yl}-2-methylpropanoate.
Tert-butyl 3-{6-[(2,6-dichloro-3-methoxyphenyl)methoxy]-2H-spiro[1-benzofuran-3,4'-piperidine]-1'-yl}-2-methylpropanoate.
Tert-butyl 3-{6-[(4-butyl-2,6-dichlorophenyl)methoxy]-2H-spiro[1-benzofuran-3,4'-piperidine]-1'-yl}-2-methylpropanoate.
Tert-butyl 3-{6-[(2-chloro-6-cyclopropylphenyl)methoxy]-2H-spiro[1-benzofuran-3,4'-piperidine]-1'-yl}-2-methylpropanoate.
Tert-butyl 3-(6-{[2-chloro-6-(2-methylpropyl)phenyl]methoxy}-2H-spiro[1-benzofuran-3,4'-piperidine]-1'-yl)-2-methylpropanoate.
Tert-butyl 3-(6-{[2-chloro-6-(2-trifluoromethoxy)phenyl]methoxy}-2H-spiro[1-benzofuran-3,4'-piperidine]-1'-yl)-2-methylpropanoate.
Tert-butyl 3-{6-[(2-chloro-5-ethylphenyl)methoxy]-2H-spiro[1-benzofuran-3,4'-piperidine]-1'-yl}-2-methylpropanoate.
Tert-butyl 3-{6-[(2-ethyl-6-fluorophenyl)methoxy]-2H-spiro[1-benzofuran-3,4'-piperidine]-1'-yl}-2-methylpropanoate. The required [2-ethyl-6-fluorophenyl]-methanol was obtained analogous to the sequence described for compound 273.
Tert-butyl 3-{6-[(2-cyclopropyl-6-fluorophenyl)methoxy]-2H-spiro[1-benzofuran-3,4'-piperidine]-1'-yl}-2-methylpropanoate.
Tert-butyl 3-(6-{[2-fluoro-6-(propan-2-yl)phenyl]methoxy}-2H-spiro[1-benzofuran-3,4'-piperidine]-1'-yl)-2-methylpropanoate.
Tert-butyl 2-methyl-3-(6-{[2-(trifluoromethyl)phenyl]methoxy}-2H-spiro[1-benzofuran-3,4'-piperidine]-1'-yl)-2-methylpropanoate.

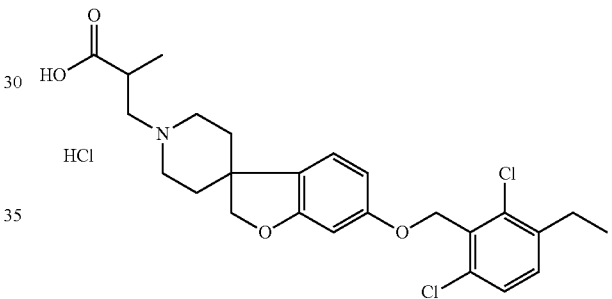

Compound 99. 3-{6-[(2,6-Dichloro-3-ethylphenyl)methoxy]-2H-spiro[1-benzofuran-3,4'-piperidine]-1'-yl}-2-methylpropanoic acid hydrochloride Tert-butyl 3-{6-[(2,6-dichlorophenyl)methoxy]-2H-spiro[1-benzfuran-3,4'-piperidine]-1'-yl}-2-methylpropanoate (0.62 g, 1.16 mmol) was dissolved in a 4M solution of HCl in 1,4-dioxane (10 mL; 4 mol/l; 40 mmol) and stirred for 48 hours at RT. Subsequently, the solvent was removed in vacuo and the residue treated with iPr₂O, the precipitate was collected by filtration and dried overnight under reduced pressure to afford the product (0.44 g, 66%). ¹H NMR (400 MHz, DMSO-d₆) δ ppm 12.90 (bs, 1H), 10.00 (bs, 1H), 7.50 (d, J=8.4 Hz, 1H), 7.44 (d, J=8.4 Hz, 1H), 6.96-7.04 (m, 1H), 6.56-6.62 (m, 2H), 5.19 (s, 2H), 4.48 (bs, 2H), 3.30-3.55 (m, 4H), 2.94-3.18 (m, 3H), 2.75 (q, J=7.4 Hz, 2H), 2.17-2.37 (m, 2H), 1.80-1.91 (m, 2H), 1.24 (d, J=7.0 Hz, 3H), 1.18 (t, J=7.4 Hz, 3H). Rt 1.60 min (System B), [M+H]⁺ 478.0

The following compounds were obtained according to a similar manner:

Compound 100. 3-{6-[(2,6-Dichlorophenyl)methoxy]-2H-spiro[1-benzofuran-3,4'-piperidine]-1'-yl}-2-methylpropanoic acid hydrochloride ¹H NMR (400 MHz, DMSO-d₆) δ ppm 12.90 (bs, 1H), 9.80 (bs, 1H), 7.54-7.58 (m, 2H) 7.46 (dd, J=8.1 and 6.2Hz, 1H) 7.10 (bs, 1H), 6.58-6.62 (m, 2H), 5.17 (s, 2H), 4.48 (bs, 2H), 3.44-3.53 (m, 4H) 2.95-3.20 (m, 3H), 2.10-2.29 (m, 2H), 1.80-1.91 (m, 2H), 1.24 (d, J=7.8 Hz, 3H). Rt 1.42 min (System B), [M+H]$^+$ 450.0

Compound 101. 3-{6-[(2-Chloro-6-ethylphenyl)methoxy]-2H-spiro[1-benzofuran-3,4'-piperidine]-1'-yl}-2-methylpropanoic acid hydrochloride $^1$H NMR (400 MHz, DMSO-d$_6$) δ ppm 12.90 (bs, 1H), 10.0 (bs, 1H), 7.32-7.39 (m, 2H), 7.25-7.29 (m, 1H), 6.96-7.04 (m, 1H), 6.56-6.62 (m, 2H), 5.10 (s, 2H), 4.48 (bs, 2H), 3.30-3.54 (m, 4H), 2.95-3.17 (m, 3H), 2.71 (q, J=7.4 Hz, 2H), 2.17-2.37 (m, 2H), 1.80-1.91 (m, 2H), 1.24 (d, J=7.0 Hz, 3H), 1.16 (t, J=7.4 Hz, 3H). Rt 1.49 min (System B), [M+H]$^+$ 444.0.

Compound 102. 2-Methyl-3-{6-[(2,4,6-trichlorophenyl)methoxy]-2H-spiro[1-benzofuran-3,4'-piperidine]-1'-yl}propanoic acid hydrochloride $^1$H NMR (400 MHz, DMSO-d$_6$) δ ppm 12.90 (bs, 1H), 10.10 (bs, 1H), 7.80 (s, 2H), 6.96-7.06 (m, 1H), 6.56-6.62 (m, 2H), 5.14 (s, 2H), 4.48 (bs, 2H), 2.98-3.55 (m, 7H), 2.20-2.37 (m, 2H), 1.80-1.91 (m, 2H), 1.24 (d, J=7 Hz, 3H). Rt 1.55 min (System B), [M+H]$^+$ 485.9

Compound 103. 3-{6-[(2,6-Dichloro-4-methylphenyl)methoxy]-2H-spiro[1-benzofuran-3,4'-piperidine]-1'-yl}-2-methylpropanoic acid hydrochloride Rt 1.50 min (System B), [M+H]$^+$ 463.9

Compound 104. 3-{6-[(2,6-Dichloro-3-methoxyphenyl)methoxy]-2H-spiro[1-benzofuran-3,4'-piperidine]-1'-yl}-2-methylpropanoic acid hydrochloride $^1$H NMR (400 MHz, DMSO-d$_6$) δ ppm 12.90 (bs, 1H), 10.10 (bs, 1H), 7.52 (d, J=9.1 Hz, 1, 1H), 7.25 (d, J=9.1 Hz, 1H), 6.95-7.09 (m, 1H), 6.56-6.62 (m, 2H), 5.17 (s, 2H), 4.48 (bs, 2H), 3.90 (s, 3H), 3.35-3.54 (m, 3H), 2.94-3.19 (m, 4H), 2.14-2.32 (m, 2H), 1.80-1.90 (m, 2H), 1.24 (t, J=7.0 Hz, 3H). Rt 1.41 min (System B), [M+H]$^+$ 480.0.

Compound 105. 3-{6-[(4-Butyl-2,6-dichlorophenyl)methoxy]-2H-spiro[1-benzofuran-3,4'-piperidine]-1'-yl}-2-methylpropanoic acid hydrochloride $^1$H NMR (400 MHz, DMSO-d$_6$) δ ppm 12.90 (bs, 1H), 9.80 (bs, 1H), 7.41 (s, 2H), 6.95-7.05 (m, 1H), 6.56-6.62 (m, 2H), 5.12 (s, 2H), 4.48 (bs, 2H), 3.35-3.54 (m, 3H), 2.98-3.19 (m, 4H), 2.62 (t, J=7.7 Hz, 2H), 2.12-2.31 (m, 2H), 1.80-1.90 (m, 2H), 1.50-1.62 (m, 2H), 1.20-1.35 (m, 5H), 0.90 (t, J=7.6 Hz, 3H). Rt 1.76 min (System B), [M+H]$^+$ 506.0

Compound 106. 3-(6-{[2-Chloro-6-(2-methylpropyl)phenyl]methoxy}-2H-spiro[1-benzofuran-3,4'-piperidine]-1'-yl)-2-methylpropanoic acid hydrochloride $^1$H NMR (400 MHz, DMSO-d$_6$) δ ppm 12.90 (bs, 1H), 9.90 (bs, 1H), 7.31-7.39 (m, 2H), 7.25-7.20 (m, 1H) 6.97-7.06 (m, 1H), 6.56-6.62 (m, 2H), 5.08 (s, 2H), 4.47 (bs, 2H), 3.24-3.58 (m, 3H), 2.88-3.18 (m, 4H), 2.58 (d, J=7.6 Hz, 2H), 2.11-2.38 (m, 2H), 1.80-1.91 (m, 3H), 1.25 (d, J=7.6 Hz, 3H), 0.85 (d, J=7.6 Hz, 6H). Rt 1.60 min (System B), [M+H]$^+$ 472.1

Compound 107. 3-(6-{[2-Chloro-6-(2-trifluoromethoxy)phenyl]methoxy}-2H-spiro[1-benzofuran-3,4'-piperidine]-1'-yl)-2-methylpropanoic acid hydrochloride $^1$H NMR (400 MHz, DMSO-d$_6$) δ ppm 12.9 (bs, 1H), 9.8 (bs, 1H), 7.58-7.65 (m, 2H), 7.47-7.52 (m, 1H), 7.06-6.97 (m, 1H), 6.56-6.62 (m, 2H), 5.10 (s, 2H), 4.47 (bs, 2H), 3.28-3.54 (m, 4H), 2.95-3.18 (m, 3H), 2.11-2.25 (m, 2H), 1.80-1.91 (m, 2H), 1.22 (d, J=7.6 Hz, 3H).

Compound 108. 3-{6-[(2-Chloro-5-ethylphenyl)methoxy]-2H-spiro[1-benzofuran-3,4'-piperidine]-1'-yl}-2-methylpropanoic acid hydrochloride Rt 1.54 min (System B), [M+H]$^+$ 444.1.

Compound 263. 3-{6-[(2-ethyl-6-fluorophenyl)methoxy]-2H-spiro[1-benzofuran-3,4'-piperidine]-1'-yl}-2-methylpropanoic acid hydrochloride The required [2-ethyl-6-fluorophenyl]-methanol was obtained analogous to the sequence described for compound 273. $^1$H NMR (400 MHz, DMSO-d$_6$) δ ppm 12.88 (br. s., 1H), 10.29 (br. s., 1H), 7.34-7.42 (m, 1H), 6.98-7.16 (m, 3H), 6.53-6.60 (m, 2H), 5.04 (s, 2H), 4.47 (br. s., 2H), 3.29-3.54 (m, 4H), 2.95-3.22 (m, 3H), 2.70 (q, J=7.5 Hz, 2H), 2.24-2.38 (m, 2H), 1.80-1.89 (m, 2H), 1.26 (d, J=7.1 Hz, 3H), 1.17 (t, J=7.5 Hz, 3H). Rt 1.44 min (System B), [M+H]$^+$ 428.8.

Compound 264. 3-{6-[(2-cyclopropyl-6-fluorophenyl)methoxy]-2H-spiro[1-benzofuran-3,4'-piperidine]-1'-yl}-2-methylpropanoic acid hydrochloride $^1$H NMR (400 MHz, DMSO-d$_6$) δ ppm 12.92 (br. s., 1H), 10.07 (br. s., 1H), 7.30-7.37 (m, 1H), 6.95-7.09 (m, 2H), 6.86 (d, J=7.8 Hz, 1H), 6.55-6.62 (m, 2H), 5.17 (s, 2H), 4.47 (br. s., 2H), 3.39-3.49 (m, 4H), 2.98-3.18 (m, 3H), 2.18-2.34 (m, 2H), 2.00-2.09 (m, 1H), 1.78-1.88 (m, 2H), 1.25 (d, J=7.1 Hz, 3H), 0.90-0.98 (m, 2H), 0.64-0.73 (m, 2H). Rt 1.42 min (System B), [M+H]$^+$ 440.7.

Compound 265. 3-(6-{[2-fluoro-6-(propan-2-yl)phenyl]methoxy}-2H-spiro[1-benzofuran-3,4'-piperidine]-1'-yl)-2-methylpropanoic acid hydrochloride $^1$H NMR (400 MHz, DMSO-d$_6$) δ ppm 12.91 (br. s., 1H), 10.03 (br. s., 1H), 7.38-7.46 (m, 1H), 7.24 (d, J=7.8 Hz, 1H), 6.97-7.10 (m, 2H), 6.53-6.60 (m, 2H), 5.06 (s, 2H), 4.47 (br. s., 2H), 3.31-3.48 (m, 4H), 2.96-3.23 (m, 4H), 2.18-2.35 (m, 2H), 1.80-1.91 (m, 2H), 1.24 (d, J=7.1 Hz, 3H), 1.20 (d, J=6.8 Hz, 6H). Rt 1.49 min (System B), [M+H]$^+$ 442.7.

Compound 266. 2-methyl-3-(6-{[2-(trifluoromethyl)phenyl]methoxy}-2H-spiro[1-benzofuran-3,4'-piperidine]-1'-yl)propanoic acid hydrochloride $^1$H NMR (400 MHz, DMSO-d$_6$) δ ppm 12.91 (br. s., 1H), 10.23 (br. s., 1H), 7.80 (d, J=7.8 Hz, 1H), 7.69-7.76 (m, 2H), 7.56-7.62 (m, 1H), 7.00 (br. s., 1H), 6.54 (d, J=8.1 Hz, 1H), 6.49 (d, J=2.0 Hz, 1H), 5.19 (s, 2H), 4.47 (br. s., 2H), 3.31-3.54 (m, 4H), 2.96-3.17 (m, 3H), 2.21-2.40 (m, 2H), 1.77-1.89 (m, 2H), 1.25 (d, J=7.1 Hz, 3H). Rt 1.43 min (System B), [M+H]+ 450.6.

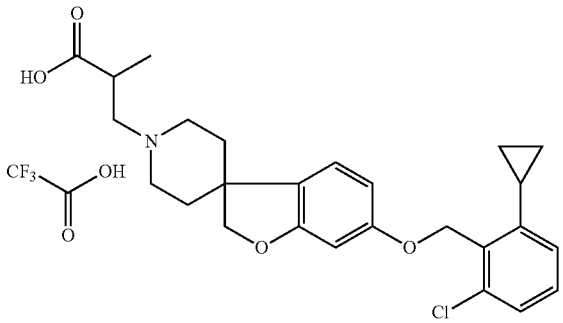

Compound 109. 3-{6-[(2-Chloro-6-cyclopropylphenyl)methoxy]-2H-spiro[1-benzofuran-3,4'-piperidine]-1'-yl}-2-methylpropanoic acid 2,2,2-trifluoroacetic acid Tert-butyl 3-{6-[(2-chloro-6-cyclopropylphenyl)methoxy]-2H-spiro[1-benzofuran-3,4'-piperidine]-1'-yl}-2-methylpropanoate (350 mg; 0.68 mmol) was dissolved in dichloromethane (10 mL). Trifluoroacetic acid (2 mL; 25.9 mmol) was added and the reaction mixture was stirred for 18 hours at RT. Subsequently, the solvent was removed in vacuo and the residue treated with iPr$_2$O, the precipitate was collected by filtration and dried overnight under reduced pressure to afford the product (0.15 g, 35.8%). $^1$H NMR (400 MHz, DMSO-d$_6$) δ ppm 12.90 (bs, 1H), 9.50 (bs, 1H), 7.29-7.37 (m, 2H), 7.01-7.20 (m, 2 H), 6.56-6.62 (m, 2 H), 5.26 (s, 2 H), 4.47 (bs, 2H), 3.24-3.54 (m, 3H), 2.88-3.18 (m, 4H), 2.01-2.18 (m, 3H), 1.80-1.91 (m, 2H), 1.20 (d, J=7.6 Hz, 3H), 0.88-0.96 (m, 2H), 0.73-0.65 (m, 2H). Rt 1.50 min (System B), [M+H]+ 456.0.

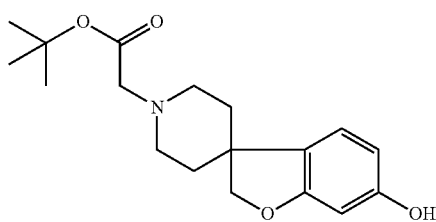 [SMILES: CC(C)(C)OC(=O)CN1CCC2(CC1)COc1cc(O)ccc12]

Tert-butyl 2-{6-hydroxy-2H-spiro[1-benzofuran-3,4'-piperidine]-1'-yl}acet To a solution of 2H-spiro[1-benzofuran-3,4'-piperidin]-6-ol (1.05 g; 5.12 mmol) in CH$_3$CN (15 mL) and N-ethyldiisopropylamine (2.19 mL) was added tert-butyl bromoacetate (0.79 mL; 5.37 mmol). The resulting mixture was heated at 65° C. overnight.

After cooling to RT, the reaction mixture was partitioned between 5% aqueous NaHCO$_3$ solution and EtOAc. The layers were separated and the organic layer was dried (Na$_2$SO$_4$), filtered, and concentrated. The residue was purified by column chromatography (SiO$_2$, Et$_2$O) to afford the product (1.45 g, 88.7%). $^1$H NMR (400 MHz, CDCl$_3$-d) δ ppm 6.94 (d, J=7.9 Hz, 1H), 6.34 (dd, 7.9 and 2.2 Hz, 1H), 6.31 (d, J=2.2Hz, 1H), 5.05-5.28 (m, 1H), 4.36 (s, 2H), 3.17 (s, 2H), 2.92-3.01 (m, 2H), 2.22-2.32 (m, 2H), 1.97-2.07 (m, 2H), 1.62-1.74 (m, 2H), 1.48 (s, 9H). Rt 0.95 min (System B), [M+H]+ 320.1.

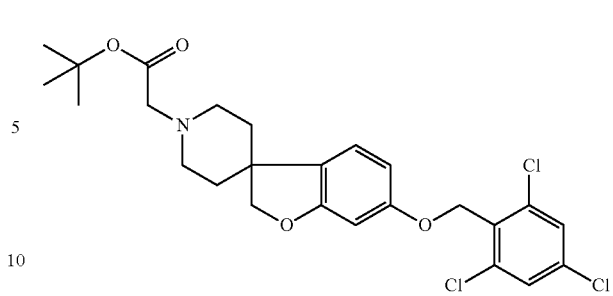

Tert-butyl 2-{6-[(2,4,6-trichlorophenyl)methoxy]-2H-spiro[1-benzofuran-3,4'-piperidine]-1'-yl}acetate. To a solution of (2,4,6-trichloro-phenyl)methanol (248 mg; 1.17 mmol) and Tert-butyl 3-{6-hydroxy-2H-spiro[1-benzofuran-3,4'-piperidine]-1'-yl}acetate (300 mg; 0.94 mmol) in dichloromethane (20 mL) was added triphenylphosphine (308 mg; 1.17 mmol), followed, after 30 minutes by DIAD (0.23 mL; 1.17 mmol). Subsequently, the resulting mixture was stirred at RT overnight, and concentrated in vacuo. Subsequently, the reaction mixture was partitioned between 5% aqueous NaHCO$_3$ solution and EtOAc. The layers were separated and the organic layer was dried (Na$_2$SO$_4$), filtered, and concentrated. The residue was purified by column chromatography (SiO$_2$, Et$_2$O: hexanes 1:1) to afford the product (410 mg, 85%). Rt 1.63 min (System B), [M+H]+ 514.0.

The following compounds were obtained according to a similar manner:

Tert-butyl 2-{6-[(2-chloro-6-ethylphenyl)methoxy]-2H-spiro[1-benzofuran-3,4'-piperidine]-1'-yl}acetate.

Tert-butyl 2-{6-[(2-chloro-6-cyclopropylphenyl)methoxy]-2H-spiro[1-benzofuran-3,4'-piperidine]-1'-yl}acetate.

Tert-butyl 2-{6-[(4-butyl-2,6-dichlorophenyl)methoxy]-2H-spiro[1-benzofuran-3,4'-piperidine]-1'-yl}acetate.

Tert-butyl 2-{6-[(2-chloro-5-ethylphenyl)methoxy]-2H-spiro[1-benzofuran-3,4'-piperidine]-1'-yl}acetate.

Tert-butyl 2-(6-{[2-chloro-6-(propan-2-yl)phenyl]methoxy}-2H-spiro[1-benzofuran-3,4'-piperidine]-1'-yl) acetate.

Tert-butyl 2-{6-[(2,6-dichloro-3-ethylphenyl)methoxy]-2H-spiro[1-benzofuran-3,4'-piperidine]-1'-yl}acetate.

Tert-butyl 2-(6-{[2-chloro-6-(trifluoromethoxy)phenyl]methoxy}-2H-spiro[1-benzofuran-3,4'-piperidine]-1'-yl) acetate.

Tert-butyl 2-{6-[(2,6-dichlorophenyl)methoxy]-2H-spiro[1-benzofuran-3,4'-piperidine]-1'-yl}acetate.

Tert-butyl 2-{6-[(2,6-dichloro-3-methoxyphenyl)methoxy]-2H-spiro[1-benzofuran-3,4'-piperidine]-1'-yl}acetate.

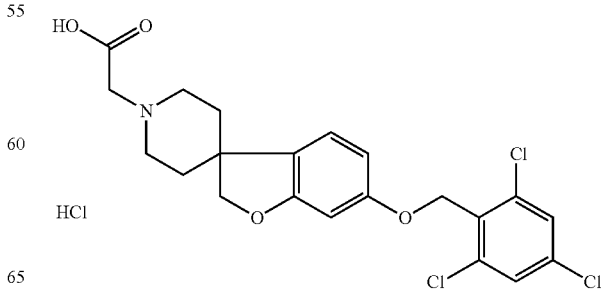

Compound 110. 2-{6-[(2,4,6-Trichlorophenyl)methoxy]-2H-spiro[1-benzofuran-3,4'-piperidine]-1'-yl}acetic acid hydrochloride Tert-butyl 2-{6-[(2,4,6-trichloro-phenyl)methoxy-]-2H-spiro[1-benzofuran-3,4'-piperidine]-1'-yl}acetate (0.41 g, 0.8 mmol) was dissolved in a 4M solution of HCl in 1,4-dioxane (20 mL; 4 mol/l; 80 mmol) and stirred for 48 hours at RT.

Subsequently, the solvent was removed in vacuo and the residue treated with iPr$_2$O, the precipitate was collected by filtration and dried overnight under reduced pressure to afford the product (0.29 g, 70%). $^1$H NMR (400 MHz, DMSO-d$_6$) δ ppm 13.90 (bs, 1 H), 10.30 (bs, 1H), 7.79 (s, 2H), 7.03-7.19 (m, 1H), 6.56-6.62 (m, 2H), 5.15 (s, 2H), 4.47 (bs, 2H) 4.17 (bs, 2H), 3.46-3.56 (m, 2H), 3.15-3.28 (m, 2H), 2.13-2.28 (m, 2H), 1.83-1.91 (m, 2H). Rt 1.73 min (System B), [M+H]$^+$ 457.9

The following compounds were obtained according to a similar manner:

Compound 111. 2-{6-[(2-Chloro-6-ethylphenyl)methoxy]-2H-spiro[1-benzofuran-3,4'-piperidine]-1'-yl}acetic acid hydrochloride $^1$H NMR (400 MHz, DMSO-d$_6$) δ ppm 13.9 (bs, 1H) 10.90 (bs, 1H) 7.34-7.39 (m, 2H), 7.25-7.31 (m, 1H), 7.17-7.20 (m, 1H), 6.56-6.62 (m, 2H), 5.10 (s, 2H), 4.47 (bs, 2H), 4.17 (bs, 2H), 3.46-3.58 (m, 2H), 3.15-3.28 (m, 2H), 2.71 (q, J=7.4 Hz, 2H), 2.13-2.28 (m, 2H), 1.83-1.91 (m, 2H), 1.16 (t, J=7.4 Hz, 3H). Rt 1.65 min (System B), [M+H]$^+$ 416.0

Compound 112. 2-{6-[(2-Chloro-6-cyclopropylphenyl)methoxy]-2H-spiro[1-benzofuran-3,4'-piperidine]-1'-yl}acetic acid hydrochloride $^1$H NMR (400 MHz, DMSO-d$_6$) □ ppm 13.80 (bs, 1H), 10.40 (bs, 1H), 7.28-7.38 (m, 2H), 7.08-7.23 (m, 1H) 7.04 (dd, J=7.0 and 2.0 Hz, 1H), 6.56-6.62 (m, 2H), 5.27 (s, 2H), 4.47 (bs, 2H) 4.13 (bs, 2H), 3.06-3.56 (m, 4H), 2.13-2.28 (m, 2H), 2.00-2.10 (m, 1H), 1.83-1.91 (m, 2H), 0.95-0.87 (m, 2H), 0.73-0.65 (m, 2H). Rt 1.67 min (System B), [M+H]$^+$ 428.0.

Compound 113. 2-{6-[(4-Butyl-2,6-dichlorophenyl)methoxy]-2H-spiro[1-benzofuran-3,4'-piperidine]-1'-yl}acetic acid hydrochloride Rt 1.99 min (System B), [M+H]$^+$ 478.0

Compound 114. 2-{6-[(2-Chloro-5-ethylphenyl)methoxy]-2H-spiro[1-benzofuran-3,4'-piperidine]-1'-yl}acetic acid hydrochloride Rt 1.71 min (System B), [M+H]$^+$ 416.1

Compound 115. 2-(6-{[2-Chloro-6-(propan-2-yl)phenyl]methoxy}-2H-spiro[1-benzofuran-3,4'-piperidine]-1'-yl)acetic acid hydrochloride $^1$H NMR (400 MHz, DMSO-d$_6$) δ ppm 14.0 (bs, 1H), 10.30 (bs, 1H), 7.31-7.42 (m, 3H), 7.18-7.05 (m, 1H), 6.56-6.62 (m, 2H), 5.15 (s, 2H), 4.45 (bs, 2H), 4.15 (bs, 2H), 3.45-3.56 (m, 2H), 3.12-3.27 (m, 3H), 2.15-2.27 (m, 2H), 1.80-1.91 (m, 2H), 1.20 (d, J=7.2Hz, 6H). Rt 1.72 min (System B), [M+H]$^+$ 430.1

Compound 116. 2-{6-[(2,6-Dichloro-3-ethylphenyl)methoxy]-2H-spiro[1-benzofuran-3,4'-piperidine]-1'-yl}acetic acid hydrochloride $^1$H NMR (400 MHz, DMSO-d$_6$) δ ppm 13.9 (bs, 1H), 10.40 (bs, 1H), 7.50 (d, J=8.4 Hz, 1H), 7.45 (d, J=8.4 Hz, 1H), 7.19-7.03 (m, 1H), 6.56-6.62 (m, 2H), 5.20 (s, 2H), 4.47 (bs, 2H), 4.17 (bs, 2H), 3.08-3.56 (m, 4H), 2.75 (q, J=7.2Hz, 2H), 2.13-2.28 (m, 2H), 1.83-1.91 (m, 2H), 1.18 (t, J=7.2Hz, 3H). Rt 1.75 min (System B), [M+H]$^+$ 450.1

Compound 117. 2-(6-{[2-Chloro-6-(trifluoromethoxy)phenyl]methoxy}-2H-spiro[1-benzofuran-3,4'-piperidine]-1'-yl)acetic acid hydrochloride Rt 1.64 min (System B), [M+H]$^+$ 472.0.

Compound 118. 2-{6-[(2,6-Dichlorophenyl)methoxy]-2H-spiro[1-benzofuran-3,4'-piperidine]-1'-yl}acetic acid hydrochloride $^1$H NMR (400 MHz, DMSO-d$_6$) δ ppm 14.10 (bs, 1H), 10.10 (bs, 1H), 7.54-7.60 (m, 2H), 7.46 (dd, J=8.1 and 6.2Hz, 1H) 7.08 (bs, 1H), 6.58-6.62 (m, 2H), 5.18 (s, 2H), 4.48 (bs, 2H), 4.18 (bs, 2H), 3.48-3.55 (m, 2H), 3.15-3.30 (m, 2H), 2.13-2.30 (m, 2H), 1.82-1.92 (m, 2H). Rt 2.02 min (System B), [M+H]$^+$ 422.0

Compound 267. 2-{6-[(2,6-dichloro-3-methoxyphenyl)methoxy]-2H-spiro[1-benzofuran-3,4'-piperidine]-1'-yl}acetic acid hydrochloride $^1$H NMR (400 MHz, DMSO-d$_6$) δ ppm 13.90 (br. s., 1H), 10.20 (br. s., 1H), 7.52 (d, J=9.0 Hz, 1H), 7.26 (d, J=9.0 Hz, 1H), 6.55-6.62 (m, 2H), 5.17 (s, 2H), 4.47 (br. s., 1H), 4.17 (br. s., 1H), 3.90 (s, 3H), 3.12-3.60 (m, 6H), 2.10-2.32 (m, 2H), 1.82-1.93 (m, 2H). Rt 1.53 min (System B), [M+H]$^+$ 452.1

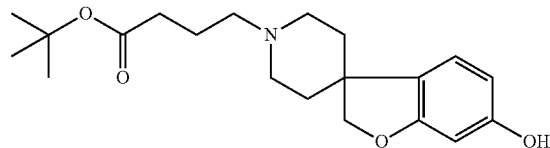 [SMILES: CC(C)(C)OC(=O)CCCN1CCC2(CC1)COc1cc(O)ccc12]

Tert-butyl 4-{6-hydroxy-2H-spiro[1-benzofuran-3,4'-piperidine]-1'-yl}butanoate. To a suspension of 2H-spiro[1-benzofuran-3,4'-piperidin]-6-ol (2 g; 9.74 mmol) in CH$_3$CN (50 mL) was added potassiumcarbonate (4.04 g; 29.23 mmol), followed by 4-bromo-butyric acid tert-butyl ester (2.39 g; 10.72 mmol) (prepared according to Tetrahedron, 1992, 48 (42), 9277). The resulting mixture was heated at 65° C. overnight.

After cooling to RT, the reaction mixture was partitioned between 5% aqueous NaHCO$_3$ solution and EtOAc. The layers were separated and the organic layer was dried (Na$_2$SO$_4$), filtered, and concentrated. The residue was purified by column chromatography (SiO$_2$, Et$_2$O) to afford the product (2.95 g, 75%). $^1$H NMR (400 MHz, CDCl$_3$-d) δ ppm 6.93 (d, J=8.0 Hz, 1H), 6.33 (dd, J=8.0, 2.1 Hz, 1H), 6.30 (d, J=2.1 Hz, 1H), 5.80 (bs, 1H), 4.35 (s, 2H), 2.89-2.94 (m, 2H), 2.35-2.41 (m, 2H), 2.26 (t, J=7.4 Hz, 2H), 1.89-2.07 (m, 4H), 1.77-1.86 (m, 2H), 1.67-1.74 (m, 2H), 1.45 (s, 9H). Rt 1.08 min (System B), [M+H]$^+$ 348.1

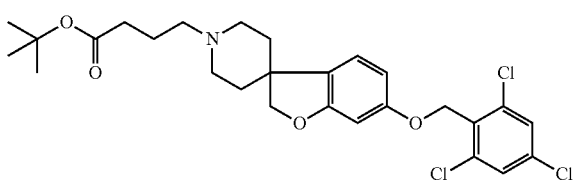 [SMILES: CC(C)(C)OC(=O)CCCN1CCC2(CC1)COc1cc(OCc3c(Cl)cc(Cl)cc3Cl)ccc12]

Tert-butyl 4-{6-[(2,4,6-trichlorophenyl)methoxy]-2H-spiro[1-benzofuran-3,4'-piperidine]-1'-yl}butanoate. To a solution of (2,4,6-trichlorophenyl)methanol (164.5 mg; 0.78 mmol) and tert-butyl 4-{6-hydroxy-2H-spiro[1-benzofuran-3,4'-piperidine]-1'-yl}butanoate (250 mg; 0.62 mmol) in dichloromethane (20 mL) was added triphenylphosphine (204 mg; 0.78 mmol), followed, after 30 minutes by DIAD (0.15 mL; 0.78 mmol). Subsequently, the resulting mixture was stirred at RT overnight, and concentrated in vacuo. Subsequently, the reaction mixture was partitioned between 5% aqueous NaHCO$_3$ solution and EtOAc. The layers were separated and the organic layer was dried (Na$_2$SO$_4$), filtered, and concentrated. The residue was purified by column chromatography (SiO$_2$, Et$_2$O: hexanes 1:2) to afford the product (174 mg, 52%). Rt 1.59 min (System B), [M+H]$^+$ 542.0.

The following compounds were obtained according to a similar manner:
Tert-butyl 4-{6-[(2-chloro-6-ethylphenyl)methoxy]-2H-spiro[1-benzofuran-3,4'-piperidine]-1'-yl}butanoate.
Tert-butyl 4-{6-[(2-chloro-6-cyclopropylphenyl)methoxy]-2H-spiro[1-benzofuran-3,4'-piperidine]-1'-yl}butanoate.
Tert-butyl 4-{6-[(2,6-dichloro-3-ethylphenyl)methoxy]-2H-spiro[1-benzofuran-3,4'-piperidine]-1'-yl}butanoate.
Tert-butyl 4-{6-[(2-chloro-5-ethylphenyl)methoxy]-2H-spiro[1-benzofuran-3,4'-piperidine]-1'-yl}butanoate.
Tert-butyl 4-{6-[(2,6-dichloro-3-methoxyphenyl)methoxy]-2H-spiro[1-benzofuran-3,4'-piperidine]-1'-yl}butanoate.
Tert-butyl 4-{6-[(4-butyl-2,6-dichlorophenyl)methoxy]-2H-spiro[1-benzofuran-3,4'-piperidine]-1'-yl}butanoate.
Tert-butyl 4-(6-{[2-chloro-6-(trifluoromethoxy)phenyl]methoxy}-2H-spiro[1-benzofuran-3,4'-piperidine]-1'-yl)butanoate.
Tert-butyl 4-(6-{[2-chloro-6-(propan-2-yl)phenyl]methoxy}-2H-spiro[1-benzofuran-3,4'-piperidine]-1'-yl)butanoate.
Tert-butyl 4-{6-[(2,6-dichlorophenyl)methoxy]-2H-spiro[1-benzofuran-3,4'-piperidine]-1'-yl}butanoate.

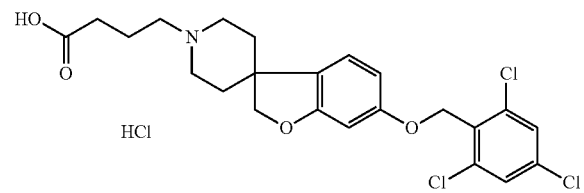 [SMILES: O=C(O)CCCN1CCC2(CC1)COc1cc(OCc3c(Cl)cc(Cl)cc3Cl)ccc12 ; Cl]

Compound 119. 4-{6-[(2,4,6-Trichlorophenyl)methoxy]-2H-spiro[1-benzofuran-3,4'-piperidine]-1'-yl}butanoic acid hydrochloride Tert-butyl 4-{6-[(2,4,6-trichlorophenyl)methoxy-]-2H-spiro[1-benzofuran-3,4'-piperidine]-1'-yl}butanoate (172 mg, 0.32 mmol) was dissolved in a 4M solution of HCl in 1,4-dioxane (10 mL; 4 mol/l; 40 mmol) and stirred for 48 hours at RT. Subsequently, the solvent was removed in vacuo and the residue treated with iPr$_2$O, the precipitate was collected by filtration and dried overnight under reduced pressure to afford the product (144 mg, 82%). $^1$H NMR (400 MHz, DMSO-d$_6$) δ ppm 14.10 (bs, 1H), 10.30 (bs, 1H), 7.54 (d, J=8.0 Hz, 2H), 7.33 (t, J=8.0 Hz, 1H), 7.00-7.25 (m, 5H), 4.50 (s, 2H), 4.19 (bs, 2H), 3.50-3.58 (m, 2H), 3.19-3.31 (m, 2H), 2.20-2.31 (m, 2H), 1.87-1.95 (m, 2H). Rt 1.46 min (System B), [M+H]$^+$ 485.9.

The following compounds were obtained in a similar manner:

Compound 120. 4-{6-[(2-Chloro-6-ethylphenyl)methoxy]-2H-spiro[1-benzofuran-3,4'-piperidine]-1'-yl}butanoic acid hydrochloride $^1$H NMR (400 MHz, DMSO-d$_6$) δ ppm 12.20 (bs, 1H), 10.30 (bs, 1H), 7.34-7.38 (m, 2H), 7.25-7.31 (m, 1H), 7.00 (d, J=8.1 Hz, 1H), 6.55-6.62 (m, 2H), 5.10 (s, 2H), 4.50 (s, 2H), 3.49 (m, 2H), 2.95-3.12 (m, 4H), 2.71 (q, J=7.5 Hz, 2H), 2.37 (t, J=7.2Hz, 2H), 2.20-2.30 (m, 2H), 1.81-2.00 (m, 4H), 1.16 (t, J=7.5 Hz, 3H). Rt 1.38 min (System B), [M+H]$^+$ 444.0.

Compound 268. 1'-(3-Carboxypropyl)-6-[(2-Chloro-6-ethylphenyl)methoxy]-2H-spiro[1-benzofuran-3,4'-piperidin]-1'-ium-1'-olate 4-{6-[(2-Chloro-6-ethyl-phenyl)methoxy]-2H-spiro[1-benzofuran-3,4'-piperidine]-1'-yl}butanoic acid hydro-chloride (210 mg; 0.38 mmol) was filtered through a tosic acid solid phase extraction cartridge, washing with dioxane, and eluting with 2 N NH$_3$/MeOH. The product was concentrated and dissolved in DCM (10 mL). Subsequently was added m-CPBA (95 mg; 0.38 mmol) and the resulting mixture was stirred overnight at RT. The residue (after evaporation of the solvent) was purified by column chromatography (Inertsil ODS-3 (25×5), H$_2$O:CH$_3$CN 4:6 to pure CH$_3$CN) to afford the product (40 mg; 22%). $^1$H NMR (400 MHz, DMSO-d$_6$) δ ppm 7.56-7.65 (m, 1H) 7.48 (m, 1H) 7.28 (d, J=5.1 Hz, 1H) 7.16 (d, J=8.2Hz, 1H) 6.51-6.63 (m, 2H) 5.10 (s, 2H) 4.48 (s, 2 H) 3.63 (s, 2H) 3.35-3.56 (m, 4H) 2.71 (q, J=7.5 Hz, 2H) 2.36-2.56 (m, 4H) 1.97-2.09 (m, 2H) 1.71 (d, J=13.8 Hz, 2H) 1.16 (t, J=7.5 Hz, 3H). Rt 1.41 min (System B), [M+H]$^+$ 460.6.

Compound 121. 4-{6-[(2-Chloro-6-cyclopropylphenyl)methoxy]-2H-spiro[1-benzofuran-3,4'-piperidine]-1'-yl}butanoic acid hydrochloride $^1$H NMR (400 MHz, DMSO-d$_6$) δ ppm 12.30 (bs, 1H), 10.30 (bs, 1H) 7.29-7.37 (m, 2H), 7.04 (dd, J=7.0, 2.0 Hz, 1H), 7.00 (m, 1H), 6.56-6.64 (m, 2H), 5.27 (s, 2H) 4.49 (bs, 2H), 3.48 (m, 2H), 3.04 (m, 4H), 2.37 (t, J=7.1 Hz, 2H), 2.20-2.30 (m, 2H), 2.06 (dt, J=8.4, 5.3 Hz, 1H), 1.90-2.00 (m, 2H), 1.80-1.90 (m, 2H), 0.89-0.96 (m, 2H), 0.66-0.73 (m, 2H). Rt 1.43 min (System B), [M+H]$^+$ 456.0.

Compound 122. 4-{6-[(2,6-Dichloro-3-ethylphenyl)methoxy]-2H-spiro[1-benzofuran-3,4'-piperidine]-1'-yl}butanoic acid hydrochloride Rt 1.57 min (System B), [M+H]$^+$ 478.0.

Compound 123. 4-{6-[(2-Chloro-5-ethylphenyl)methoxy]-2H-spiro[1-benzofuran-3,4'-piperidine]-1'-yl}butanoic acid hydrochloride $^1$H NMR (400 MHz, DMSO-d$_6$) δ ppm 12.30 (bs, 1H), 10.40 (bs, 1H), 7.38-7.44 (m, 2 H), 7.24 (dd, J=8.2, 2.2Hz, 1H), 6.96-7.02 (m, 1H), 6.51-6.60 (m, 2H), 5.06 (s, 2H), 4.48 (bs, 2H), 3.42-3.52 (m, 2H), 2.95-3.12 (m, 4H), 2.61 (q, J=7.6 Hz, 2H), 2.36 (t, J=7.2Hz, 2H), 2.22-2.30 (m, 2H), 1.79-2.00 (m, 4H), 1.17 (t, J=7.6 Hz, 3H). Rt 1.45 min (System B), [M+H]$^+$ 444.0.

Compound 124. 4-{6-[(2,6-Dichloro-3-methoxyphenyl)methoxy]-2H-spiro[1-benzofuran-3,4'-piperidine]-1'-yl}butanoic acid hydrochloride Rt 1.34 min (System B), [M+H]$^+$ 480.0

Compound 125. 4-{6-[(4-Butyl-2,6-dichlorophenyl)methoxy]-2H-spiro[1-benzofuran-3,4'-piperidine]-1'-yl}butanoic acid hydrochloride Rt 1.62 min (System B), [M+H]$^+$ 506.0

Compound 126. 4-(6-{[2-Chloro-6-(trifluoromethoxy)phenyl]methoxy}-2H-spiro[1-benzofuran-3,4'-piperidine]-1'-yl)butanoic acid hydrochloride $^1$H NMR (400 MHz, DMSO-d$_6$) δ ppm 12.30 (bs, 1H), 10.45 (bs, 1H), 7.57-7.66 (m, 2H), 7.48 (dt, J=7.6, 1.6 Hz, 1H), 7.00 (d, J=8.0 Hz, 1H), 6.53-6.62 (m, 2H), 5.10 (s, 2H), 4.50 (s, 2H), 3.43-3.52 (m, 2H), 2.96-3.11 (m, 4H), 2.37 (t, J=7.1 Hz, 2H), 2.21-2.32 (m, 2H), 1.95 (quin, J=7.6 Hz, 2H), 1.81-1.89 (m, 2H). Rt 1.41 min (System B), [M+H]$^+$ 500.0.

Compound 127. 4-(6-{[2-Chloro-6-(propan-2-yl)phenyl]methoxy}-2H-spiro[1-benzofuran-3,4'-piperidine]-1'-yl)butanoic acid hydrochloride $^1$H NMR (400 MHz, DMSO-d$_6$) δ ppm 12.30 (bs, 1H), 10.60 (bs, 1H), 7.33-7.41 (m, 3H), 6.99 (d, J=7.4 Hz, 1H), 6.55-6.63 (m, 2H), 5.15 (s, 2H), 4.49 (bs, 2H), 3.44-3.52 (m, 2H), 3.14-3.22 (m, 1H), 2.95-3.11 (m, 4H), 2.23-2.40 (m, 4H), 1.96 (quin, J=7.6 Hz, 2H), 1.81-1.88 (m, 2H), 1.20 (d, J=6.8 Hz, 6H).

Compound 128. 4-{6-[(2,6-Dichlorophenyl)methoxy]-2H-spiro[1-benzofuran-3,4'-piperidine]-1'-yl}butanoic acid hydrochloride $^1$H NMR (400 MHz, DMSO-d$_6$) δ ppm 12.10 (bs, 1H), 10.50 (bs, 1H), 7.54-7.58 (m, 2H), 7.45-7.51 (m, 1H), 6.97-7.12 (m, 1H), 6.56-6.62 (m, 2H), 5.21 (s, 2H), 4.48 (bs, 2H), 3.38-3.54 (m, 2H), 2.94-3.35 (m, 4H), 2.38 (t, J=7.5 Hz, 2H), 2.20-2.37 (m, 2H), 1.94-2.03 (m, 2H), 1.82-1.93 (m, 2H). Rt 1.37 min (System B), [M+H]$^+$ 450.0.

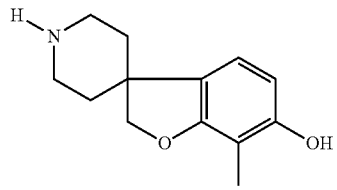

7-Methyl-2H-spiro[1-benzofuran-3,4'-piperidine]-6-ol

A mixture of 2H-spiro[1-benzofuran-3,4'-piperidin]-6-ol (0.78 g; 5.24 mmol), sodium triacetoxyborohydride (2.22 g; 10.48 mmol) and benzaldehyde (0.76 mL; 7.49 mmol) in 1,2-dichloroethane (25 mL) was stirred overnight at RT. Subsequently, the reaction mixture was diluted with dichloromethane and extracted with a 5% aqueous NaHCO$_3$ solution. The organic layer was dried (Na$_2$SO$_4$), filtered, concentrated in vacuo, and purified by column chromatography (SiO$_2$, Et$_2$O/hexanes 1:1) to afford 1'-benzyl-2H-spiro[1-benzofuran-3,4'-piperidine]-6-ol (1.03 g; 93.1%), Rt 1.00 min (System B), [M+H]$^+$ 296.1. To a suspension of NaH (60% in oil) (179 mg; 4.47 mmol) in 5 mL THF was added 1'-benzyl-2H-spiro[1-benzofuran-3,4'-piperidine]-6-ol (660 mg; 2.23 mmol), dissolved in 5 mL THF, dropwise at 0° C. The resulting mixture was stirred at 15° C. (for 15 min) and cooled down again. Subsequently, chloromethylmethylether (0.24 mL; 3.35 mmol) was added, dissolved in 5 mL THF, and the resulting mixture was stirred overnight. To this reaction mixture was added H$_2$O and Et$_2$O. The layers were separated and the aqueous layer was extracted once more with Et$_2$O. The organic layer was dried (Na$_2$SO$_4$), filtered, concentrated in vacuo, and purified by column chromatography (SiO$_2$, Et$_2$O/hexanes 1:1) to afford 1'-benzyl-6-(methoxymethoxy)-2H-spiro[1-benzofuran-3,4'-piperidine (0.54 g; 71.2%), Rt 1.16 min (System B), [M+H]$^+$ 340.1. $^1$H NMR (400 MHz, CDCl$_3$-d) δ ppm 7.23-7.36 (m, 5H), 7.02 (d, J=8.2Hz, 1H), 6.51-6.57 (m, 2H), 5.12 (s, 2H), 4.36 (s, 2H), 3.53 (s, 2H), 3.46 (s, 3H), 2.85-2.91 (m, 2H), 1.91-2.07 (m, H), 1.67-1.73 (m, 2H).

To a solution 1'-benzyl-6-(methoxymethoxy)-2H-spiro[1-benzofuran-3,4'-piperidine (0.6 g; 1.77 mmol) in Et$_2$O (25 ml) was added n-butyllithium (1.56 mL; 2.50 mol/l; 3.89 mmol) at 0° C. The reaction mixture was refluxed for 90 minutes. Subsequently, the mixture was cooled to 0° C. and a solution of 1,2-dibromotetra-chloroethane (1.27 g; 3.89 mmol) was added. The resulting mixture was stirred for 15 minutes and diluted with EtOAc and H$_2$O. The layers were separated and the aqueous layer was extracted once more with EtOAc. The organic layer was dried (Na$_2$SO$_4$), filtered, concentrated in vacuo, and purified by column chromatography (SiO$_2$, Et$_2$O/hexanes 1:1) to afford 1'-benzyl-7-bromo-6-(methoxymethoxy)-2H-spiro[1-benzofuran-3,4'-piperidine (0.36 g; 49.2%). $^1$H NMR (400 MHz, CDCl$_3$-d) δ ppm 7.24-7.36 (m, 5H,) 6.97 (d, J=8.2Hz, 1H), 6.67 (d, J=8.2Hz, 1H), 5.21 (s, 2H), 4.48 (s, 2H), 3.50-3.55 (m, 5H), 2.85-2.92 (m, 2H), 1.89-2.07 (m, 4H), 1.70-1.77 (m, 2H).

To a nitrogen purged mixture of 1'--benzyl-7-bromo-6-(methoxymethoxy)-2H-spiro[1-benzofuran-3,4'-piperidine (0.33 g; 0.81 mmol) in 9 mL anhydrous 1,4-dioxane, was added subsequently, potassium carbonate (336 mg; 2.43 mmol), trimethylboroxine (0.11 mL.; 0.81 mmol), and tetrakis(triphenylphosphine)palladium(0) (93 mg; 0.08 mmol). The resulting mixture was heated for 28 hours at 115° C. (in a pyrex bottle). After cooling to RT, the reaction mixture was diluted with EtOAc, filtered and washed with 5% aqueous NaHCO$_3$. The organic layer was dried (Na$_2$SO$_4$), filtered, and concentrated in vacuo. The residue was purified by column chromatography (SiO$_2$, Et$_2$O:hexanes 1:1) to afford 1'-benzyl-6-(methoxymethoxy)-7-methyl-2H-spiro[1-benzofuran-3,4'-piperidine] (0.25 g; 87%). $^1$H NMR (400 MHz, CDCl$_3$-d) δ ppm 7.24-7.36 (m, 5H), 6.89 (d, J=8.2Hz, 1H), 6.60 (d, J=8.2Hz, 1H), 5.15 (s, 2H), 4.36 (s, 2H), 3.53 (s, 2H), 3.48 (s, 3H), 2.85-2.91 (m, 2H), 2.10 (s, 3H), 1.90-2.08 (m, 4H), 1.67-1.73 (m, 2H). Rt 1.25 min (System B), [M+H]$^+$ 354.1. The compound was dissolved in a 1M solution of HCl in EtOH and stirred for 90 minutes at 50° C. Subsequently, the solvent was removed in vacuo and the residu was treated with iPr$_2$O. The precipitate was collected by filtration and dried overnight to afford 1'-benzyl-7- methyl-2H-spiro[1-benzofuran-3,4'-piperidine]-6-ol hydrochloride (220 mg; 97%) Rt 1.07 min (System B), [M+H]+ 310.1

To a mixture of 1'-benzyl-7-methyl-2H-spiro[1-benzofuran-3,4'-piperidin]-6-ol hydrochloride (0.22 g;, 0.64 mmol) in 10 ml MeOH was added palladium hydroxide (44 mg; 0.06 mmol). The mixture was treated with $H_2$, for 72 hours. The crude reaction mixture was concentrated till about 5 mL and filtered through a tosic acid solid phase extraction cartridge, washing with MeOH, and eluting with 2 N $NH_3$/MeOH. The product was concentrated to give 7-methyl-2H-spiro[1-benzofuran-3,4'-piperidine]-6-ol (137 mg; 98%) $^1$H NMR (400 MHz, $CDCl_3$-d) δ ppm 6.81 (d, J=8.0 Hz, 1H), 6.32 (d, J=8.0 Hz, 1H), 4.41 (s, 2H), 3.11 (dt, J=12.7, 3.6 Hz, 2H), 2.64-2.73 (m, 2H), 2.11 (s, 3H), 1.78-1.87 (m, 2H), 1.66-1.73 (m, 2 H). Rt 0.88 min (System B), [M+H]+ 220.1

7-methyl-2H-spiro[1-benzofuran-3,4'-piperidine]-6-ol was converted into:

Compound 129. 3-{6-[(2,6-Dichlorophenyl)methoxy]-7-methyl-2H-spiro[1-benzofuran-3,4'-piperidine]-1'-yl}propanoic acid hydrochloride In a similar manner as described for compound 29. $^1$H NMR (400 MHz, DMSO-$d_6$) δ ppm 12.60 (bs., 1H), 10.70 (bs., 1H), 7.54-7.60 (m, 2H), 7.44-7.50 (m, 1H), 6.90 (bs., 1H), 6.75 (d, J=8.2Hz, 1H), 5.19 (s, 2H) 4.46 (bs., 2H), 3.40-3.52 (m, 2H), 3.24-3.39 (m, 2H), 2.98-3.14 (m, 2H), 2.87 (t, J=7.5 Hz, 2H), 2.14-2.28 (m, 2H), 1.91 (s, 3H), 1.88 (br. s., 2H). Rt 1.41 min (System B), [M+H]+ 450.0

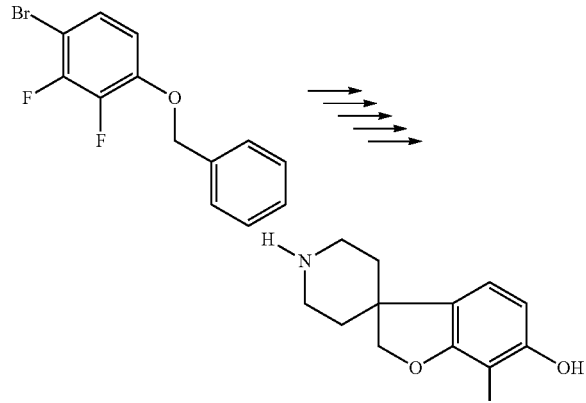

7-Fluoro-2H-spiro[1-benzofuran-3,4'-piperidine]-6-ol

4-Pyridinemethanol (1.7 g; 15.62 mmol) was dissolved in 1-methyl-2-pyrrolidinone (50 mL) and sodium hydride (60% in mineral oil; 0.62 g; 15.62 mmol) was added. The mixture was stirred for 30 minutes at ambient temperature. Subsequently, 1-(benzyloxy)-4-bromo-2,3-difluoro-benzene (4.45 g; 14.88 mmol), dissolved in 1-methyl-2-pyrrolidinone (30 mL) was added and the reaction mixture was heated to 100° C. TLC showed a complete conversion within 15 minutes. After cooling to RT, the reaction mixture was diluted with EtOAc, and washed with a 5% aqueous $NaHCO_3$ solution. The organic layer was washed several times with $H_2O$, dried ($Na_2SO_4$), filtered, and concentrated in vacuo. The residue was purified by column chromatography ($SiO_2$, $Et_2O$:hexanes 2:1 to pure $Et_2O$) to afford 4-[3-(benzyloxy)-6-bromo-2-fluorophenoxymethyl]pyridine (4.81 g; 83%), $^1$H NMR (400 MHz, $CDCl_3$-d) δ ppm 8.62-8.66 (m, 2H), 7.32-7.48 (m, 7H), 7.21 (dd, J=9.0, 2.4 Hz, 1H), 6.69 (dd, J=9.0, 8.0 Hz, 1H), 5.17 (s, 2H), 5.13 (s, 2H), which was dissolved in acetone (72 mL). To this reaction mixture was added benzyl bromide (1.85 mL; 15.45 mmol) and stirred overnight at 40° C. Subsequently, the mixture was concentrated in vacuo yielding 1-benzyl-4-[3-(benzyloxy)-6-bromo-2-fluorophenoxymethyl]pyridin-1-ium bromide (7.55 g; 99%), which was dissolved in MeOH (100 mL). To this cooled (−10° C.) reaction mixture was added sodium borohydride (1.16 g; 30.71 mmol). After the addition was complete the mixture was allowed to warm to RT and stirred for 4 hours. Subsequently, the mixture was cooled to 0° C., water was added, and the MeOH evaporated in vacuo. To the aqueous solution was added a 5% aqueous $NaHCO_3$ solution and $Et_2O$. The layers were separated and the organic layer was dried ($Na_2SO_4$), filtered and concentrated in vacuo. The residue was purified by column chromatography ($SiO_2$, $Et_2O$:hexanes 1:1) to afford the product: 1-benzyl-4-[3-(benzyloxy)-6-bromo-2-fluorophenoxymethyl]-1,2,3,6-tetrahydropyridine (3.73 g; 63%). $^1$H NMR (400 MHz, $CDCl_3$-d) δ ppm 7.23-7.44 (m, 10H), 7.16 (dd, J=9.0, 2.3 Hz, H), 6.63 (dd, J=9.0, 7.9 Hz, 1H), 5.78-5.82 (m, 1H), 5.11 (s, 2H), 4.51 (s, 2H), 3.60 (s, 2H), 3.00-3.04 (m, 2H), 2.64 (t, J=5.7 Hz, 2H), 2.36-2.42 (m, 2H). Rt 1.48 min (System B), [M+H]+ 483.9.

To a intensively degassed mixture of 1-benzyl-4-[3-(benzyloxy)-6-bromo-2-fluorophenoxymethyl]-1,2,3,6-tetrahydropyridine (3.73 g; 7.73 mmol) in 45 mL benzene was added subsequently, 2,2'-azobis(2-methylpropionitrile) (0.05 g; 0.31 mmol) and tri-n-butyltinhydride (3.13 mL; 11.60 mmol). The reaction mixture was heated under microwave conditions (using silicon carbide) for 1 hour at 175° C. After cooling to RT, the mixture was concentrated in vacuo during which precipitation occurred of the product. The precipitate was collected by filtration and purified by column chromatography ($SiO_2$, $Et_2O$:hexanes 2:1) to afford the product: r-benzyl-6-(benzyloxy)-7-fluoro-2H-spiro[1-benzofuran-3,4'-piperidine] (2.34 g; 72%), $^1$H NMR (400 MHz, $CDCl_3$-d) δ ppm 7.24-7.46 (m, 10H), 6.75 (dd, J=8.2, 1.4 Hz, 1H), 6.51 (dd, J=8.2, 6.9 Hz, 1H), 5.10 (s, 2H), 4.46 (s, 2H), 3.53 (s, 2H), 2.84-2.92 (m, 2H), 1.88-2.07 (m, 4H), 1.69-1.75 (m, 2H), which was dissolved in MeOH (50 mL). Subsequently, ammonium formate (1.44 g; 22.8 mmol) and palladiumhydroxide (0.04 g; 0.29 mmol) were added. The reaction mixture was stirred overnight (at 60° C.). The crude reaction mixture was concentrated till about 5 mL and filtered through a tosic acid solid phase extraction cartridge, washing with MeOH, and eluting with 2 N $NH_3$/MeOH. The product was concentrated to give 7-fluoro-2H-spiro[1-benzofuran-3,4'-piperidine]-6-ol (1.23 g; 96%) $^1$H NMR (400 MHz, DMSO-$d_6$) δ ppm 6.73 (dd, J=8.1, 1.2Hz, 1H), 6.39-6.44 (m, 1H), 4.45 (s, 2H), 2.87 (dt, J=12.6, 3.5 Hz, 2H), 2.44-2.55 (m, 2H), 1.59-1.70 (m, 2H), 1.48-1.57 (m, 2H). Rt 0.40 min (System B), [M+H]+ 224.1

In a similar manner and as described for compound 29, 7-fluoro-2H-spiro[1-benzofuran-3,4'-piperidine]-6-ol was converted to tert-butyl 3-{7-fluoro-6-hydroxy-2H-spiro[1-benzofuran-3,4'-piperidine]-1'-yl]propanoate, $^1$H NMR (400 MHz, $CDCl_3$-d) δ ppm 6.70 (dd, J=8.1, 1.2Hz, 1H), 6.47 (dd, J=8.1, 7.3 Hz, 1H), 4.45 (s, 2H), 2.91 (d, J=12.0 Hz, 2H), 2.71 (t, J=7.2Hz, 2H), 2.46 (t, J=7.2Hz, 2H), 2.03-2.12 (m, 2H), 1.89-1.98 (m, 2H), 1.70-1.77 (m, 2H), 1.45 (s, 9H), subsequently followed by the Mitsunobu chemistry and acidic hydrolysis yielding the following compounds:

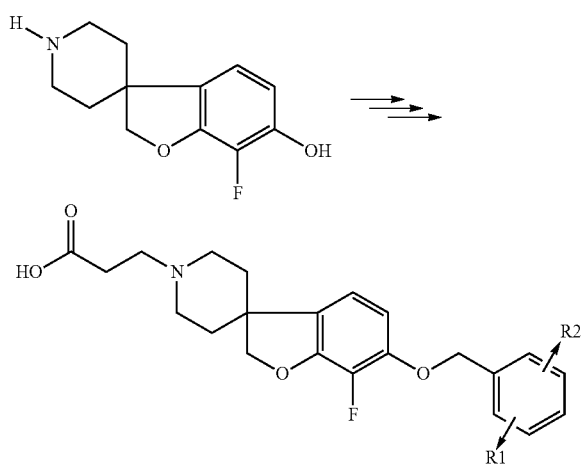

Compound 130. 3-{6-[(2,6-Dichlorophenyl)methoxy]-7-fluor-2H-spiro[1-benzofuran-3,4'-piperidine]-1'-yl}propanoic acid hydrochloride ¹H NMR (400 MHz, DMSO-d₆) δ ppm 12.70 (bs, 1H), 10.50 (bs, 1H), 7.56-7.61 (m, 2H), 7.46-7.52 (m, 1H), 6.81-6.94 (m, 2H), 5.26 (s, 2H), 4.60 (bs, 2H), 3.43-3.53 (m, 2H), 3.25-3.37 (m, 2H), 3.00-3.11 (m, 2H), 2.86 (t, J=7.5 Hz, 2H), 2.13-2.29 (m, 2H), 1.89-2.96 (m, 2H). Rt 1.37 min (System B), [M+H]⁺ 454.0

Compound 131. 3-{6-[(2,6-Dichloro-4-methylphenyl)methoxy]-7-fluoro-2H-spiro[1-benzofuran-3,4'-piperidine]-1'-yl}propanoic acid hydrochloride ¹H NMR (400 MHz, DMSO-d₆) δ ppm 12.50 (bs, 1H), 10.90 (bs, 1H), 7.42 (s, 2H), 6.85-6.93 (m, 2H), 5.21 (s, 2H), 4.59 (s, 2H), 3.41-3.52 (m, 2H), 3.37-3.26 (m, 2H), 3.00-3.15 (m, 2H), 2.86 (t, J=7.6 Hz, 2H), 2.34 (s, 3H), 2.16-2.29 (m, 2H), 1.88-1.96 (m, 2H). Rt 1.44 min (System B), [M+H]⁺ 468.1

Compound 132. 3-{7-Fluoro-6-[(2,4,6-trichlorophenyl)methoxy]-2H-spiro[1-benzofuran-3,4'-piperidine]-1'-yl}propanoic acid hydrochloride ¹H NMR (400 MHz, DMSO-d₆) δ ppm 12.90 (bs., 1H), 10.40 (bs., 1H), 7.81 (s, 2H), 6.85-6.93 (m, 2H), 5.23 (s, 2H), 4.60 (bs., 2H), 3.40-3.55 (m, 2H), 3.25-3.37 (m, 2H), 2.96-3.15 (m, 2H), 2.85 (t, J=7.3 Hz, 2H), 2.12-2.25 (m, 2H), 1.88-1.97 (m, 2H). Rt 1.44 min (System B), [M+H]⁺ 490.0.

Compound 133. 3-{6-[(2,6-Dichloro-3-methoxyphenyl)methoxy]-7-fluor-2H-spiro[1-benzofuran-3,4'-piperidine]-1'-yl}propanoic acid hydrochloride ¹H NMR (400 MHz, DMSO-d₆) δ ppm 12.80 (bs, 1H), 10.50 (bs., 1H), 7.54 (d, J=9.0 Hz, 1H), 7.28 (d, J=9.0 Hz, 1H), 6.84-6.94 (m, 2H), 5.25 (s, 2H), 4.60 (bs, 2H), 3.90 (s, 3H), 3.41-3.54 (m, 2H), 3.25-3.35 (m, 2H), 2.97-3.16 (m, 2H), 2.86 (t, J=7.6 Hz, 2H), 2.13-2.28 (m, 2H), 1.94 (m, 2H). Rt 1.36 min (System B), [M+H]⁺ 484.1

Compound 134. 3-{6-[(4-Butyl-2,6-dichlorophenyl)methoxy]-7-fluor-2H-spiro[1-benzofuran-3,4'-piperidine]-1'-yl}propanoic acid hydrochloride ¹H NMR (400 MHz, DMSO-d₆) δ ppm 12.80 (bs, 1H), 10.70 (bs, 1H), 7.43 (s, 2H), 6.81-6.93 (m, 2H), 5.21 (s, 2H), 4.60 (bs, H), 3.42-3.54 (m, 2H), 3.26-3.35 (m, 2H), 2.98-3.12, (m, 2H), 2.87 (t, J=7.6 Hz, 2H), 2.62 (t, J=7.6 Hz, 2H), 2.18-2.30 (m, 2H), 1.92 (d, J=13.7 Hz, 2H), 1.51-1.62 (m, 2H), 1.24-1.35 (m, 2H), 0.90 (t, J=7.4 Hz, 3H). Rt 1.67 min (System B), [M+H]⁺ 510.1. Rt 0.97 min (System B), [M+H]⁺ 448.0

Compound 135. 3-{6-[(2-Chloro-5-ethylphenyl)methoxy]-7-fluoro-2H-spiro[1-benzofuran-3,4'-piperidine]-1'-yl}propanoic acid hydrochloride Compound 136. 3-{6-[(2-Chloro-6-ethylphenyl)methoxy]-7-fluoro-2H-spiro[1-benzofuran-3,4'-piperidine]-1'-yl}propanoic acid hydrochloride ¹H NMR (400 MHz, DMSO-d₆) δ ppm 12.80 (bs, 1H), 11.80 (bs, 1H), 7.35-7.40 (m, 2H), 7.29-7.32 (m, 1H), 6.82-6.96 (m, 2H), 5.19 (s, 2H), 4.60 (bs, 2H), 3.43-3.54 (m, 2H), 3.24-3.34 (m, 2H), 2.98-3.12 (m, 2H), 2.87 (t, J=7.6 Hz, 2H), 2.73 (q, J=7.8 Hz, 2H), 2.15-2.30 (m, 2H), 1.88-1.97 (m, 2H), 1.17 (t, J=7.8 Hz, 3H). Rt 1.47 min (System B), [M+H]⁺ 448.1

Compound 137. 3-(6-{[2-Chloro-6-(trifluoromethoxy)phenyl]methoxy}-7-fluoro-2H-spiro[1-benzofuran-3,4'-piperidine]-1'-yl}propanoic acid hydrochloride Rt 1.44 min (System B), [M+H]⁺ 504.0.

Compound 269. 3-{6-[(2-Chloro-6-ethylophenyl)methoxy]-7-fluoro-2H-spiro[1-benzofuran-3,4'-piperidine]-1'-yl}propanoic acid hydrochloride ¹H NMR (400 MHz, DMSO-d₆) δ ppm 12.70 (br. s., 1H), 10.60 (br. s., 1H), 7.35-7.41 (m, 2H), 7.27-7.33 (m, 1H), 6.80-6.97 (m, 2H), 5.19 (s, 2H) 4.60 (br. s., 2H), 3.25-3.55 (m, 4H), 3.00-3.12 (m, 2H), 2.87 (t, J=7.5 Hz, 2H), 2.73 (q, J=7.5 Hz, 2H), 2.18-2.30 (m, 2H), 1.88-1.97 (m, 2H), 1.17 (t, J=7.5 Hz, 3H). Rt 1.47 min (System B), [M+H]⁺ 448.1.

Compound 270. 3-{6-[(2-Chloro-6-fluorophenyl)methoxy]-7-fluoro-2H-spiro[1-benzofuran-3,4'-piperidine]-1'-yl}propanoic acid A mixture of tert-butyl 3-{6-[(2-Chloro-6-fluorophenyl)methoxy]-7-fluoro-2H-spiro[1-benzofuran-3,4'-piperidine]-1'-yl}propanoate (178 mg; 0.36 mmol), 2M aqueous NaOH (5 mL; 10 mmol) and ethanol (40 mL) was stirred for 3 hours at 50° C. and subsequently cooled to 0° C. To this reaction mixture was added aqueous HCl (10 mL; 10 mmol), dropwise, after which it was concentrated in vacuo. The residue was treated with saturated brine and dichloromethane. The water layer was washed with dichloromethane (twice). Subsequently, the organic layer was dried (Na₂SO₄), filtered, and concentrated in vacuo, followed by treated with iPr₂O. The formed precipitate was collected by filtration, washed with iPr₂O and dried in vacuo to yield the product (142 mg; 85.5%). ¹H NMR (400 MHz, DMSO-d₆) δ ppm 7.49-7.56 (m, 1H), 7.43 (d, J=8.0 Hz, 1H), 7.33 (t, J=8.8 Hz, 1H), 7.00 (d, J=8.0 Hz, 1H), 6.80 (t, J=7.6 Hz, 1H), 5.16 (d, J=1.4 Hz, 2H), 4.48 (s, 2H), 2.86 (d, J=11.7 Hz, 2H), 2.61 (t, J=7.0 Hz, 2H), 2.41 (t, J=7.0 Hz, 2H), 2.06 (t, J=11.7 Hz, 2H), 1.78-1.88 (m, 2H) 1.67 (d, J=12.5 Hz, 2H). Rt 1.34 min (System B), [M+H]⁺ 438.1.

The following compounds were obtained according to a similar manner:

Compound 271. 3-{6-[(2-Chloro-6-(propan-2-yl)phenyl]methoxy}-7-fluoro-2H-spiro[1-benzofuran-3,4'-piperidine]-1'-yl}propanoic acid $^1$H NMR (400 MHz, DMSO-d$_6$) δ ppm 7.35-7.45 (m, 3H), 7.01 (d, J=8.5 Hz, 1H), 6.84 (t, J=7.4 Hz, 1H), 5.22 (s, 2H), 4.48 (s, 2H), 3.16-3.25 (m, 1H), 2.84-2.89 (m, 2H), 2.61 (t, J=7.0 Hz, 2H), 2.40 (t, J=7.0 Hz, 2H), 2.02-2.11 (m, 2H), 1.80-1.89 (m, 2H), 1.67 (d, J=12.9 Hz, 2H), 1.20 (d, J=6.8 Hz, 6H). Rt 1.49 min (System B), [M+H]$^+$ 462.2.

Compound 272. 3-{6-[(2-Chloro-6-cyclopropylphenyl)methoxy]-7-fluoro-2H-spiro[1-benzofuran-3,4'-piperidine]-1'-yl}propanoic acid $^1$H NMR (400 MHz, DMSO-d$_6$) δ ppm 7.30-7.38 (m, 2H), 7.06 (dd, J=6.9, 1.9 Hz, 1H), 7.01 (d, J=8.0 Hz, 1H), 6.86 (t, J=7.3 Hz, 1H), 5.34 (s, 2H), 4.49 (s, 2H), 2.87-2.94 (m, 2H), 2.65 (t, J=7.0 Hz, 2H), 2.42 (t, J=7.0 Hz, 2H), 2.04-2.16 (m, 3H), 1.80-1.90 (m, 2H), 1.68 (d, J=12.8 Hz, 2H), 0.89-0.96 (m, 2H), 0.66-0.72 (m, 2H). Rt 1.44 min (System B), [M+H]$^+$ 460.2.

Compound 273. 3-{6-[(2-Cyclopropyl-6-fluorophenyl)methoxy]-7-fluoro-2H-spiro[1-benzofuran-3,4'-piperidine]-1'-yl}propanoic acid $^1$H NMR (400 MHz, DMSO-d$_6$) δ ppm 7.31-7.38 (m, 1H), 7.07 (t, J=9.1 Hz, 1H), 6.99 (d, J=8.2Hz, 1H), 6.80-6.90 (m, 2H), 5.25 (s, 2H), 4.48 (s, 2H), 2.87 (d, J=12.1 Hz, 2H), 2.62 (t, J=7.2Hz, 2H), 2.40 (t, J=7.2Hz, 2H), 2.03-2.12 (m, 3H), 1.78-1.89 (m, 2H), 1.66 (d, J=12.6 Hz, 2H), 0.90-0.98 (m, 2H), 0.66-0.72 (m, 2H). Rt 1.42 min (System B), [M+H]$^+$ 444.2.

The required (2-cyclopropyl-6-fluorophenyl)methanol was prepared as follows: To a cooled solution (0° C.) of (E)-butyl[(2,6-difluorophenyl)methylidene]amine (4.45 g; 22.56 mmol), prepared according to US2007/197621, (see also WO2007/85556 and US6380387), dissolved in THF (100 mL), was added cyclopropylmagnesium bromide (0.5M, 51.9 mL; 25.95 mmol) dropwise. Subsequently, the reaction mixture was stirred for 2 hour at RT. To this reaction mixture was added 3 mL H$_2$O and the resulting mixture was partitioned between EtOAc and 5% aqueous NaHCO$_3$-solution. The organic layer was dried (Na$_2$SO$_4$), filtered, and concentrated in vacuo, affording (E)-butyl[(2-cyclopropyl-6-fluorophenyl)methylidene]amine (5.07 g; 100%), which was dissolved in 24 mL H$_2$O and sulfuric acid (8 mL) and heated to reflux for 2 hours. After cooling to RT, the resulting mixture was partitioned between EtOAc and 5% aqueous NaHCO$_3$-solution. The organic layer was dried (Na$_2$SO$_4$), filtered, and concentrated in vacuo. The residue was purified by column chromatography (SiO$_2$, Et$_2$O:hexanes 1:7 followed by Et$_2$O:hexanes 1:7) yielding (2-cyclopropyl-6-fluorobenzaldehyde (2.37 g; 66%). $^1$H NMR (400 MHz, CDCl$_3$-d) δ ppm 10.64 (s, 1H), 7.39-7.45 (m, 1H), 6.92-6.99 (m, 1H), 6.83 (d, J=7.9 Hz, 1H), 2.81-2.90 (m, 1H), 1.04-1.11 (m, 2H), 0.70-0.77 (m, 2H). To (2-cyclopropyl-6-fluorobenzaldehyde (2.37 g; 14.44 mmol) in MeOH (50 mL) was added NaBH$_4$ (1.21 g; 32.02 mmol), in small portions, at 0° C. After the addition was complete the mixture was allowed to warm to RT and stirred for one hour. Subsequently, the mixture was cooled to 0° C., water was added, and the MeOH evaporated in vacuo. To the aqueous solution was added a 5% aqueous NaHCO$_3$ solution and EtOAc. The layers were separated and the organic layer was dried (Na$_2$SO$_4$), filtered and concentrated in vacuo. The residue was purified by column chromatography (SiO$_2$, Et$_2$O:hexanes 1:7 followed by Et$_2$O:hexanes 1:3) yielding (2-cyclopropyl-6-fluorophenyl)methanol (2.02 g; 84%). $^1$H NMR (400 MHz, CDCl$_3$-d) δ ppm 7.13-7.22 (m, 1H) 6.86-6.94 (m, 1H) 6.79 (d, J=7.8 Hz, 1H) 4.95 (d, J=3.9 Hz, 2H) 2.15 (m, 1H) 1.74 (t, J=5.5 Hz, 1H) 0.97-1.04 (m, 2H) 0.68-0.75 (m, 2H).

Compound 274. 3-(7-fluoro-6-{[2-fluoro-6-(propan-2-yl)phenyl]methoxy}-2H-spiro[1-benzofuran-3,4'-piperidine]-1'-yl)propanoic acid $^1$H NMR (400 MHz, DMSO-d$_6$) δ ppm 7.43 (m, 1H), 7.25 (d, J=7.9 Hz, 1H), 7.08 (t, J=9.0 Hz, 1H), 7.00 (d, J=7.5 Hz, 1H), 6.82 (t, J=7.5 Hz, 1H), 5.13 (d, J=1.1 Hz, 2H), 4.48 (s, 2H), 3.14-3.24 (m, 1H), 2.87 (d, J=11.9 Hz, 2H), 2.61 (t, J=7.0 Hz, 2H), 2.40 (t, J=7.0 Hz, 2H), 2.07 (t, J=11.4 Hz, 2H), 1.78-1.88 (m, 2H), 1.66 (d, J=12.7 Hz, 2H), 1.20 (d, J=6.8 Hz, 6H). Rt 1.46 min (System B), [M+H]$^+$ 446.3.

Compound 275. 3-[7-fluoro-6-(hexyloxy)-2H-spiro[1-benzofuran-3,4'-piperidine]-1'-yl]propanoic acid To a mixture of tert-butyl 3-{7-fluoro-6-hydroxy-2H-spiro[1-benzofuran-3,4'-piperidine]-1'-yl]propanoate, CH$_3$CN (10 mL), 1-bromohexane (0.123 mL; 0.88 mmol) was added followed by K$_2$CO$_3$ (400 mg; 2.92 mmol) and the solution was stirred at 75° C. overnight. The solution was allowed to cool to RT and concentrated. The residue was taken up in EtOAc and H$_2$O. The organic phase was dried (Na$_2$SO$_4$), filtered and concentrated. The residue was purified by column chromatography (SiO$_2$, Et$_2$O:hexanes 1:1) yielding tert-butyl 3-{7-fluoro-6-(hexyloxy)-2H-spiro[1-benzofuran-3,4'-piperidine]-1'-yl]propanoate (100 mg; 100%), which was dissolved 2M aqueous NaOH (2 mL; 4 mmol) and ethanol (10 mL). The reaction mixture was stirred for 3 hours at 500 C and subsequently cooled to 0° C. To this reaction mixture was added aqueous HCl (4 mL; 1 mol/l), dropwise, after which it was concentrated in vacuo. The residue was treated with saturated brine and dichloromethane. The water layer was washed with dichloromethane (twice). Subsequently, the organic layer was dried (Na$_2$SO$_4$), filtered, and concentrated in vacuo, followed by treated with iPr$_2$O. The formed precipitate was collected by filtration, washed with iPr$_2$O and dried in vacuo to yield the product (150 mg; 67.1%). $^1$H NMR (400 MHz, DMSO-d$_6$) δ ppm 6.93 (d, J=8.3 Hz, 1H), 6.57-6.62 (m, 1H), 4.46 (s, 2H), 3.97 (t, J=6.5 Hz, 2H), 2.85 (d, J=11.9 Hz, 2H), 2.60 (t, J=7.2Hz, 2H), 2.39 (t, J=7.2Hz, 2H), 2.06 (t, J=11.3 Hz, 2H), 1.76-1.86 (m, 2H), 1.61-1.73 (m, 4H), 1.35-1.44 (m, 2H), 1.25-1.33 (m, 4H), 0.84-0.90 (m, 3H). Rt 1.45 min (System B), [M+H]$^+$ 380.3.

The following compounds were obtained in a similar manner:

Compound 276. 3-[7-fluoro-6-(heptyloxy)-2H-spiro[1-benzofuran-3,4'-piperidine]-1'-yl]propanoic acid $^1$H NMR (400 MHz, DMSO-d$_6$) δ ppm 6.93 (d, J=8.3 Hz, 1H), 6.57-6.63 (m, 1H), 4.47 (s, 2H), 3.97 (t, J=6.5 Hz, 2H), 2.86 (d, J=11.9 Hz, 2H), 2.61 (t, J=6.9 Hz, 2H), 2.40 (t, J=6.9 Hz, 2H), 2.08 (t, J=11.2Hz, 2H), 1.81 (td, J=12.6, 3.4 Hz, 2H), 1.61-1.73 (m, 4H), 1.20-1.43 (m, 8H), 0.86 (t, J=6.7 Hz, 3H). Rt 1.56 min (System B), [M+H]+ 394.3.

Compound 277. 3-[7-fluoro-6-(octyloxy)-2H-spiro[1-benzofuran-3,4'-piperidine]-1'-yl]propanoic acid ¹H NMR (400 MHz, DMSO-d₆) δ ppm 6.92 (dd, J=8.3, 1.2Hz, 1H), 6.55-6.63 (m, 1H), 4.46 (s, 2H), 3.97 (t, J=6.5 Hz, 2H), 2.85 (d, J=12.0 Hz, 2H), 2.60 (t, J=7.2Hz, 2H), 2.39 (t, J=7.2Hz, 2H), 2.00-2.11 (m, 2H), 1.81 (td, J=12.6, 3.8 Hz, 2H), 1.60-1.73 (m, 4H), 1.18-1.43 (m, 10H), 0.86 (t, J=6.8 Hz, 3H). Rt 1.64 min (System B), [M+H]+ 408.3.

Compound 278. 3-[7-fluoro-6-(hex-5-en-1-yloxy)-2H-spiro[1-benzofuran-3,4'-piperidine]-1'-yl]propanoic acid ¹H NMR (400 MHz, DMSO-d₆) δ ppm 6.92 (dd, J=8.3, 1.3 Hz, 1H), 6.57-6.63 (m, 1H), 5.82 (ddt, J=17.2, 10.2, 6.6, 6.6 Hz, 1H), 4.94-5.06 (m, 2H), 4.46 (s, 2H), 3.99 (t, J=6.6 Hz, 2 H), 2.85 (d, J=12.0 Hz, 2H), 2.61 (t, J=7.1 Hz, 2H), 2.39 (t, J=7.1 Hz, 2H), 2.02-2.12 (m, 4H), 1.81 (td, J=12.6, 3.8 Hz, 2H), 1.61-1.75 (m, 4H), 1.44-1.54 (m, 2H). Rt 1.45 min (System B), [M+H]+ 378.3.

Compound 279. 3-[7-fluoro-6-(oct-7-en-1-yloxy)-2H-spiro[1-benzofuran-3,4'-piperidine]-1'-yl]propanoic acid ¹H NMR (400 MHz, DMSO-d₆) δ ppm 6.92 (dd, J=8.2, 1.2Hz, 1H), 6.56-6.62 (m, 1H), 5.80 (ddt, J=17.1, 10.3, 6.7, 6.7 Hz, 1H), 4.91-5.04 (m, 2H), 4.46 (s, 2H), 3.97 (t, J=6.6 Hz, 2H), 2.81-2.88 (m, 2H), 2.60 (t, J=7.0 Hz, 2H), 2.38 (t, J=7.0 Hz, 2H), 1.98-2.11 (m, 4H), 1.76-1.86 (m, 2H), 1.60-1.73 (m, 4H), 1.27-1.44 (m, 6H). Rt 1.59 min (System B), [M+H]+ 406.3.

Compound 280. 3-[7-fluoro-6-(hept-6-en-1-yloxy)-2H-spiro[1-benzofuran-3,4'-piperidine]-1'-yl]propanoic acid ¹H NMR (400 MHz, DMSO-d₆) δ ppm 6.92 (d, J=8.2Hz, 1H), 6.57-6.63 (m, 1H), 5.74-5.86 (m, 1H), 4.92-5.05 (m, 2H), 4.46 (s, 2H), 3.97 (t, J=6.3 Hz, 2H), 2.85 (d, J=11.9 Hz, 2H), 2.60 (t, J=7.0 Hz, 2H), 2.39 (t, J=7.0 Hz, 2H), 2.00-2.11 (m, 4H), 1.76-1.86 (m, 2H), 1.61-1.74 (m, 4H), 1.40 (dt, J=6.6, 3.5 Hz, 4H). Rt 1.29 min (System B), [M+H]+ 392.3.

Compound 281. 3-{7-fluoro-6-[(5,6,6-trifluorohex-5-en-1-yl)oxy]-2H-spiro[1-benzofuran-3,4'-piperidine]-1'-yl}propanoic acid ¹H NMR (400 MHz, DMSO-d₆) δ ppm 6.92 (d, J=8.2Hz, 1H), 6.57-6.63 (m, 1H), 5.74-5.86 (m, 1H), 4.92-5.05 (m, 2H), 4.46 (s, 2H), 3.97 (t, J=6.3 Hz, 2H), 2.85 (d, J=11.9 Hz, 2H), 2.60 (t, J=7.0 Hz, 2H), 2.39 (t, J=7.0 Hz, 2H), 2.00-2.11 (m, 4H), 1.76-1.86 (m, 2H), 1.61-1.74 (m, 4H), 1.40 (dt, J=6.6, 3.5 Hz, 4H). Rt 1.39 min (System B), [M+H]+ 432.3.

Compound 282. 3-{7-fluoro-6-[(4,4,5,5,5-pentafluoropentyl)oxy]-2H-spiro[1-benzofuran-3,4'-piperidine]-1'-yl}propanoic acid ¹H NMR (400 MHz, CDCl₃-d) δ ppm 6.79 (d, J=8.2Hz, 1H), 6.50 (dd, J=8.2, 7.0Hz, 1H), 4.49 (s, 2H), 4.08 (t, J=5.9 Hz, 2H), 3.16 (d, J=12.0 Hz, 2H), 2.83 (t, J=6.2Hz, 2H), 2.58 (t, J=6.2Hz, 2H), 2.20-2.41 (m, 4H), 1.99-2.15 (m, 4H), 1.85-1.94 (m, 2H). Rt 1.38 min (System B), [M+H]+ 456.2.

Compound 283. 3-{7-fluoro-6-[(5,5,6,6,6-pentafluorohexyl)oxy]-2H-spiro[1-benzofuran-3,4'-piperidine]-1'-yl}propanoic acid ¹H NMR (400 MHz, DMSO-d₆) δ ppm 6.94 (d, J=8.2Hz, 1H), 6.59-6.64 (m, 1H), 4.47 (s, 2H), 4.03 (t, J=6.2Hz, 2H), 2.86 (d, J=11.8 Hz, 2H), 2.60 (t, J=7.1 Hz, 2H), 2.21-2.43 (m, 4H), 2.06 (t, J=11.2Hz, 2H), 1.76-1.87 (m, 4H), 1.60-1.72 (m, 4H). Rt 1.44 min (System B), [M+H]+ 470.2.

Compound 284. 3-[7-fluoro-6-(4,4,4-trifluorobutoxy]-2H-spiro[1-benzofuran-3,4'-piperidine]-1'-yl}propanoic acid ¹H NMR (400 MHz, DMSO-d₆) δ ppm 6.95 (dd, J=8.3, 1.1 Hz, 1H), 6.58-6.65 (m, 1H), 4.48 (s, 2H), 4.06 (t, J=6.2Hz, 2H), 2.85 (d, J=11.9 Hz, 2H), 2.60 (t, J=7.1 Hz, 2H), 2.34-2.48 (m, 4H), 2.05 (t, J=11.0 Hz, 2H), 1.88-1.98 (m, 2H), 1.81 (td, J=12.6, 3.6 Hz, 2H), 1.65 (d, J=12.8 Hz, 2H). Rt 1.28 min (System B), [M+H]+ 406.2

Compound 285. 3-[6-(Cyclohexylethoxy)-7-fluoro-2H-spiro[1-benzofuran-3,4'-piperidine]-1'-yl]propanoic acid ¹H NMR (400 MHz, DMSO-d₆) δ ppm 6.93 (d, J=8.1 Hz, 1H), 6.90-6.94 (m, 1H), 4.46 (s, 2H), 4.01 (t, J=6.6 Hz, 2H), 2.85 (d, J=11.4 Hz, 2H), 2.60 (t, J=7.0 Hz, 2H), 2.38 (t, J=7.0 Hz, 2H), 2.05 (t, J=11.4 Hz, 2H), 1.55-1.86 (m, 12H), 1.38-1.50 (m, 1H), 1.07-1.27 (m, 2H), 0.87-1.00 (m, 2H). Rt 1.51 min (System B), [M+H]+ 406.7

Compound 286. 3-{6-[(2-Ethylhexyl)oxy]-7-fluoro-2H-spiro[1-benzofuran-3,4'-piperidine]-1'-yl}propanoic acid ¹H NMR (400 MHz, DMSO-d₆) δ ppm 6.93 (d, J=8.2Hz, 1H), 6.58-6.64 (m, 1H), 4.46 (s, 2H), 3.87 (d, J=5.7 Hz, 2H), 2.85 (d, J=11.7 Hz, 2H), 2.60 (t, J=7.0 Hz, 2H), 2.39 (t, J=7.0 Hz, 2H), 2.06 (t, J=11.7 Hz, 2H), 1.75-1.87 (m, 2H), 1.59-1.71 (m, 3H), 1.22-1.49 (m, 8H), 0.82-0.92 (m, 6H). Rt 1.57 min (System B), [M+H]+ 408.7

Compound 287. 3-{7-Fluoro-6-[(3,5,5-trimethylhexyl)oxy]-2H-spiro[1-benzofuran-3,4'-piperidine]-1'-yl}propanoic acid ¹H NMR (400 MHz, DMSO-d₆) δ ppm 6.93 (d, J=8.2Hz, 1H), 6.61 (t, J=7.7 Hz, 1H), 4.46 (s, 2H), 4.00 (t, J=6.1 Hz, 2H), 2.85 (d, J=11.9 Hz, 2H), 2.60 (t, J=7.0 Hz, 2H), 2.39 (t, J=7.0 Hz, 2H), 2.01-2.11 (m, 2H), 1.75-1.86 (m, 2H), 1.60-1.74 (m, 3H), 1.55 (s, 1H), 1.27 (dd, J=14.0, 3.2Hz, 1H), 1.02-1.09 (m, 1H), 0.94 (d, J=6.3 Hz, 3H), 0.87 (s, 9H). Rt 1.59 min (System B), [M+H]+ 422.8

Compound 288. 3-[6-(3-Cyclohexylpropoxy)-7-fluoro-2H-spiro[1-benzofuran-3,4'-piperidine]-1'-yl]propanoic acid ¹H NMR (400 MHz, DMSO-d₆) δ ppm 6.92 (d, J=8.2Hz, 1H), 6.59 (t, J=7.7 Hz, 1H), 4.46 (s, 2H), 3.95 (t, J=6.5 Hz, 2H), 2.85 (d, J=11.7 Hz, 2H), 2.60 (t, J=7.0 Hz, 2H), 2.39 (t, J=7.0 Hz, 2H), 2.06 (t, J=11.2Hz, 2H), 1.81 (td, J=12.5, 3.4 Hz, 2H), 1.57-1.75 (m, 9H), 1.05-1.32 (m, 6H), 0.80-0.93 (m, 2H).

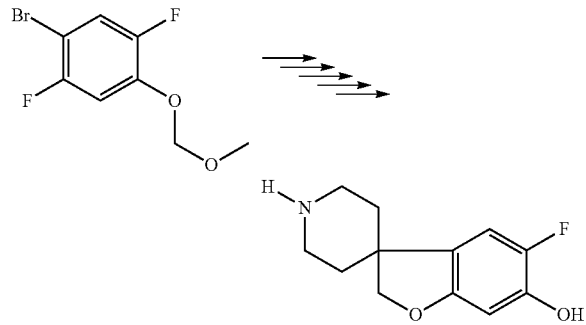

5-Fluoro-2H-spiro[1-benzofuran-3,4'-piperidine]-6-ol

4-Pyridinemethanol (7.9 g; 32.37 mmol) was dissolved in 1-methyl-2-pyrrolidinone (200 mL) and sodium hydride (60% in mineral oil; 2.89 g; 72.37 mmol) was added. The mixture was stirred for 30 minutes at ambient temperature. Subsequently, 1-bromo-2,5-difluoro-4-(methoxy-methoxy) benzene (17.44 g; 68.92 mmol), dissolved in 1-methyl-2-pyrrolidinone (150 mL) was added and the reaction mixture was heated to 100° C. TLC showed a complete conversion within 15 minutes. After cooling to RT, the reaction mixture was diluted with EtOAc, and washed with a 5% aqueous NaHCO$_3$ solution. The organic layer was washed several times with H$_2$O, dried (Na$_2$SO$_4$), filtered, and concentrated in vacuo. The residue was purified by column chromatography (SiO$_2$, Et$_2$O:hexanes 2:1 to pure Et$_2$O) to afford 4-[2-bromo-4-fluoro-5-(methoxymethoxy)phenoxymethyl]-pyridine (10.23 g; 29.81 mmol; 43.38%), $^1$HNMR (400 MHz, CDCl$_3$-d) δ ppm 8.61-8.66 (m, 2H) 7.39-7.43 (m, 2H) 7.33 (d, J=10.1 Hz, 1H) 6.84 (d, J=7.2Hz, 1H) 5.16 (s, 2H) 5.10 (s, 2H) 3.49 (s, 3H), which was dissolved in acetone (153 mL). To this reaction mixture was added benzyl bromide (4.46 mL; 37.26 mmol) and the mixture was stirred overnight at 40° C. Subsequently, the mixture was concentrated in vacuo yielding 1-benzyl-4-[2-bromo-4-fluoro-5-(methoxymethoxy)phenoxy)-methyl)pyridin-1-ium bromide (17.29 g; 99%), which was dissolved in MeOH (200 mL). To this cooled (−10° C.) reaction mixture was added sodium borohydride (2.8 g; 74.12 mmol). After the addition was complete the mixture was allowed to warm to RT and stirred for 4 hours. Subsequently, the mixture was cooled to 0° C., water was added, and the MeOH evaporated in vacuo. To the aqueous solution was added a 5% aqueous NaHCO$_3$ solution and Et$_2$O. The layers were separated and the organic layer was dried (Na$_2$SO$_4$), filtered and concentrated in vacuo. The residue was purified by column chromatography (SiO$_2$, Et$_2$O) to afford the product: 1-benzyl-4-[2-bromo-4-fluoro-5-(methoxymethoxy)phenoxymethyl]-1,2,3,6-tetrahydropyridine (8.47 g; 67.8%). $^1$H NMR (400 MHz, CDCl$_3$-d) δ ppm 7.23-7.37 (m, 6H) 6.83 (d, J=7.3 Hz, 1H) 5.80-5.83 (m, 1H) 5.18 (s, 2H) 4.43 (s, 2H) 3.60 (s, 2H) 3.51 (s, 3H) 3.03 (br. s., 2H) 2.63 (t, J=5.7 Hz, 2H) 2.24-2.29 (m, 2H). Rt 1.49 min (System B), [M+H]$^+$ 438.1.

To a intensively degassed mixture of 1-benzyl-4-[2-bromo-4-fluoro-5-(methoxy-methoxy)phenoxymethyl]-1,2,3,6-tetrahydropyridine (5.78 g; 13.25 mmol) in benzene (75 mL) was added subsequently, 2,2'-azobis(2-methylpropionitrile) (0.09 g; 0.53 mmol) and tri-n-butyltinhydride (5.36 mL; 19.87 mmol; 1.5 eq). The reaction mixture (divided into 5 batches) was heated under microwave conditions (using silicon carbide) for 1 hour at 175° C. After cooling to RT, the mixture was concentrated in vacuo and purified by column chromatography (SiO$_2$, Et$_2$O:hexanes 2:1). The residu was dissolved in Et$_2$O (150 mL) and washed 25 mL 10% aqueous KF, dried and concentrated to afford the product: 1'-benzyl-5-fluoro-6-(methoxymethoxy)-2H-spiro[1-benzofuran-3,4'-piperidine] (3.80 g; 80.26%), $^1$H NMR (400 MHz, CDCl$_3$-d) δ ppm 7.24-7.36 (m, 5H) 6.86 (d, J=10.3 Hz, 1H) 6.66 (d, J=6.6 Hz, 1H) 5.14-5.17 (m, 2H) 4.35 (s, 2H) 3.53 (s, 2H) 3.51 (s, 3H) 2.83-2.91 (m, 2H) 1.98-2.07 (m, 2H) 1.91 (td, J=12.6, 3.8 Hz, 2H) 1.67-1.73 (m, 2H). Rt 1.13 min (System B), [M+H]$^+$ 358.2, which was dissolved in 1,2-dichloroethane (20 mL) at 0° C. Subsequently, 1-chloroethyl chloroformate (0.82 mL; 7.55 mmol) was added and the reaction mixture was stirred for 1 hour (at RT). Methanol (20 mL) was added and the reaction mixture was stirred overnight and concentrated in vacuo to give 5-fluoro-6-(methoxymethoxy)-2H-spiro[1-benzofuran-3,4'-piperidine] (0.83 g; 90%). $^1$H NMR (400 MHz, DMSO-d$_6$) δ ppm 9.20 (br. s., 1H) 9.00 (br. s., 1H) 7.02 (d, J=10.3 Hz, 1H) 6.75 (d, J=6.7 Hz, 1H) 5.19 (s, 2H) 4.48 (s, 2H) 3.22-3.42 (m, 5H) 2.89-3.03 (m, 2H) 1.99-2.10 (m, 2H) 1.80 (d, J=14.1 Hz, 2H), which was suspended in hydrochloric acid (25 mL, 1M) and 25 mL ethanol. The reaction mixture was stirred at reflux for 1 hour. The residu was concentrated in vacuo, yielding the hydrochloride salt of 5-Fluoro-2H-spiro[1-benzofuran-3,4'-piperidine]-6-ol (0.68 g), $^1$H NMR (400 MHz, DMSO-d$_6$) δ ppm 9.90 (s., 1H), 9.05 (br. s., 1H), 8.85 (br. s., 1H), 6.91 (d, J=10.4 Hz, 1H), 6.41 (d, J=7.0 Hz, 1H), 4.42 (s, 2H), 3.26 (d, J=13.0 Hz, 2H), 2.87-3.02 (m, 2H), 1.92-2.05 (m, 2H), 1.77 (d, J=14.2Hz, 2H), which was filtered through a tosic acid solid phase extraction cartridge, washing with MeOH, and eluting with 2 N NH$_3$/MeOH. The product was concentrated to give 5-fluoro-2H-spiro[1-benzofuran-3,4'-piperidine]-6-ol (0.57 g; 97%). Rt 0.41 min (System B), [M+H]$^+$ 224.2

In a similar manner and as described for compound 29, 5-fluoro-2H-spiro[1-benzofuran-3,4'-piperidine]-6-ol was converted to tert-butyl 3-{5-fluoro-6-hydroxy-2H-spiro[1-benzofuran-3,4'-piperidine]-1'-yl]propanoate, $^1$H NMR (400 MHz, CDCl$_3$-d) δ ppm 6.79 (d, J=9.7 Hz, 1H), 6.44 (d, J=7.0 Hz, 1H), 4.34 (s, 2H), 2.88 (d, J=12.0 Hz, 2H), 2.69 (t, J=7.3 Hz, 2H), 2.45 (t, J=7.3 Hz, 2H), 2.02-2.10 (m, 2H), 1.83-1.92 (m, 2H), 1.68-1.75 (m, 2H), 1.46 (s, 9H).

Subsequently, followed by the Mitsunobu chemistry and hydrolysis (as described for compound 270), to afford the following compounds:

Compound 289. 3-{6-[(2,6-Dichlorophenyl) methoxy]-5-fluoro-2H-spiro[1-benzofuran-3,4'-piperidine]-1'-yl}propanoic acid $^1$H NMR (400 MHz, DMSO-d$_6$) δ ppm 7.54-7.60 (m, 2H), 7.46-7.51 (m, 1H), 7.17 (d, J=10.7 Hz, 1H), 6.88 (d, J=6.9 Hz, 1H), 5.23 (s, 2H), 4.38 (s, 2H), 2.86 (d, J=11.8 Hz, 2H), 2.60 (t, J=7.1 Hz, 2H), 2.39 (t, J=7.1 Hz, 2H), 2.06 (t, J=11.8 Hz, 2H), 1.83 (td, J=12.7, 3.6 Hz, 2H), 1.62 (d, J=12.7 Hz, 2H). Rt 1.36 min (System B), [M+H]$^+$ 454.1

Compound 290. 3-{6-[(2-Chloro-6-ethylphenyl) methoxy]-5-fluoro-2H-spiro[1-benzofuran-3,4'-piperidine]-1'-yl}propanoic acid $^1$H NMR (400 MHz, DMSO-d$_6$) δ ppm 7.37 (d, J=4.4 Hz, 2H) 7.26-7.31 (m, 1H) 7.16 (d, J=10.7 Hz, 1H) 6.89 (d, J=6.9 Hz, 1H) 5.16 (s, 2H) 4.38 (s, 2H) 2.85 (d, J=11.7 Hz, 2H) 2.72 (q, J=7.5 Hz, 2H) 2.59 (t, J=7.0 Hz, 2H) 2.36 (t, J=7.0 Hz, 2H) 2.04 (t, J=11.7 Hz, 2H) 1.83 (td, J=12.6, 3.3 Hz, 2H) 1.61 (d, J=12.6 Hz, 2H) 1.16 (t, J=7.5 Hz, 3H). Rt 1.39 min (System B), [M+H]$^+$ 448.6

Compound 336. 315-Fluoro-6-(hexyloxy)-2H-spiro [1-benzofuran-3,4'-piperidine]-1'-yl}propanoic acid $^1$H NMR (400 MHz, DMSO-d$_6$) □ ppm 6.78-7.03 (m, 1H) 6.69 (d, J=6.9 Hz, 1H) 4.45 (br. s., 2H) 3.98 (t, J=6.4 Hz, 2H) 3.20-3.61 (m, 4H) 2.96-3.19 (m, 2H) 2.89 (t, J=7.7 Hz, H) 2.23 (m, 2H) 1.86 (d, J=13.1 Hz, 2H) 1.62-1.74 (m, 2H) 1.21-1.46 (m, 6H) 0.87 (t, J=6.4 Hz, 3H)

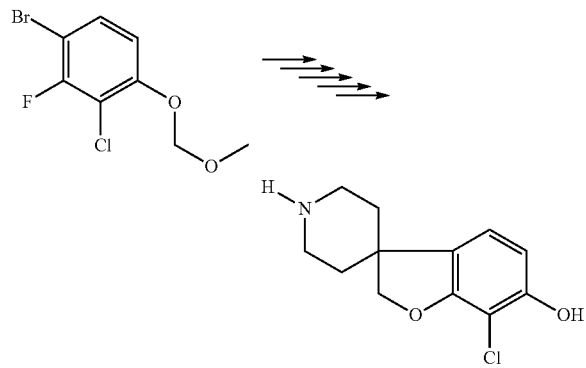

7-Chloro-2H-spiro[1-benzofuran-3,4'-piperidine]-6-ol

This compound was synthesized according to the procedure of 5-Fluoro-2H-spiro[1-benzofuran-3,4'-piperidine]-6-ol (see compound 289), starting from 1-bromo-3-chloro-2-fluoro-4-(methoxy-methoxy)benzene in comparable or better yields.

Some examples to illustrate this are:

4-[6-bromo-2-chloro-3-(methoxymethoxy)phenoxymethyl]pyridine (76%)

$^1$H NMR (400 MHz, CDCl$_3$-d) δ ppm 8.62-8.68 (m, 2H), 7.50 (d, J=5.4 Hz, 2H), 7.42 (d, J=9.0 Hz, 1H), 6.95 (d, J=9.0 Hz, 1H), 5.25 (s, 2H), 5.06 (s, 2H), 3.52 (s, 3H).

1-benzyl-4-[6-bromo-2-chloro-3-(methoxymethoxy) phenoxymethyl]-1,2,3,6-tetra-hydropyridine (74%)

$^1$H NMR (400 MHz, CDCl$_3$-d) δ ppm 7.23-7.39 (m, 6H), 6.88 (d, J=9.0 Hz, 1H), 5.85-5.88 (m, 1H), 5.23 (s, 2H), 4.40 (s, 2H), 3.62 (s, 2H), 3.51 (s, 3H), 3.04-3.08 (m, 2H), 2.67 (t, J=5.7 Hz, 2H), 2.42-2.48 (m, 2H)

7-chloro-6-(methoxymethoxy)-2H-spiro[1-benzofuran-3,4'-piperidine] (100%)

$^1$H NMR (400 MHz, DMSO-d$_6$) δ ppm 9.20 (br. s., 1H), 9.00 (br. s., 1H), 7.01 (d, J=8.3 Hz, 1H), 6.78 (d, J=8.3 Hz, 1H), 5.24 (s, 2H), 4.60 (s, 2H), 3.40 (s, 3H), 3.28 (d, J=13.1 Hz, 2H), 2.90-3.03 (m, 2H), 2.07 (td, J=13.1, 4.2Hz, 2H), 1.84 (d, J=14.3 Hz, 2H).

7-Chloro-2H-spiro[1-benzofuran-3,4'-piperidine]-6-ol $^1$H NMR (400 MHz, DMSO-d$_6$) δ ppm 6.88 (d, J=8.2Hz, 1H) 6.45 (d, J=8.2Hz, 1H) 4.43 (s, 2H) 2.86-2.92 (m, 2H) 2.48-2.55 (m, 2H) 1.66 (dt, J=11.6, 4.2Hz, 2H) 1.84 (d, J=13.0 Hz, 2H). Rt 0.60 min (System B), [M+H]$^+$ 240.1.

In a similar manner and as described for compound 29, 7-chloro-2H-spiro[1-benzofuran-3,4'-piperidine]-6-ol was converted to tert-butyl 3-{7-chloro-6-hydroxy-2H-spiro[1-benzofuran-3,4'-piperidine]-1'-yl]propanoate.

Subsequently, followed by the Mitsunobu chemistry and hydrolysis (as described for compound 270), to afford the following compounds:

Compound 291. 3-{7-Chloro-6-[(2-chloro-6-cyclopropylphenyl)methoxy]-2H-spiro[1-benzofuran-3,4'-piperidine]-1'-yl}propanoic acid $^1$H NMR (400 MHz, DMSO-d$_6$) δ ppm 7.31-7.38 (m, 2H) 7.17 (d, J=8.2Hz, 1H) 7.06 (dd, J=7.0, 1.8 Hz, 1H) 6.88 (d, J=8.2Hz, 1H) 5.34 (s, 2H) 4.48 (s, 2H) 2.84-2.91 (m, 2H) 2.62 (t, J=7.0 Hz, 2H) 2.40 (t, J=7.0 Hz, 2H) 2.03-2.13 (m, 3H) 1.85 (t, J=11.5 Hz, 2H) 1.68 (d, J=12.8 Hz, 2H) 0.88-0.95 (m, 2H) 0.67-0.73 (m, 2H). Rt 1.48 min (System B), [M+H]$^+$ 476.2

Compound 292. 3-(7-Chloro-6-{[2-fluoro-6-(propan-2-yl)phenyl]methoxy}-2H-spiro[1-benzofuran-3,4'-piperidine]-1'-yl)propanoic acid $^1$H NMR (400 MHz, DMSO-d$_6$) δ ppm 7.36-7.43 (m, 1H), 7.07-7.19 (m, 3H), 6.84 (d, J=8.3 Hz, 1H), 5.12 (s, 2H), 4.48 (s, 2H), 2.87 (d, J=11.7 Hz, 2H), 2.72 (q, J=7.5 Hz, 2H), 2.61 (t, J=7.0 Hz, 2H), 2.40 (t, J=7.0 Hz, 2H), 2.07 (t, J=11.4 Hz, 2H), 1.79-1.89 (m, 2H), 1.67 (d, J=12.8 Hz, 2H), 1.18 (t, J=7.5 Hz, 3H). Rt 1.43 min (System B), [M+H]$^+$ 448.2

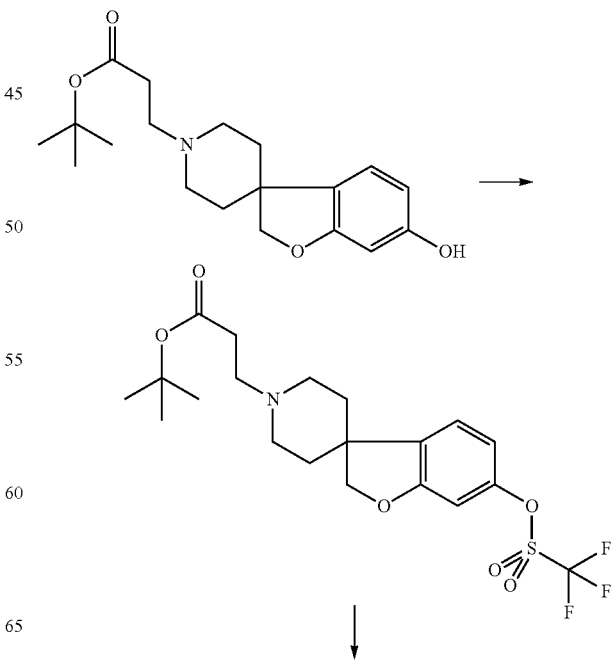

-continued

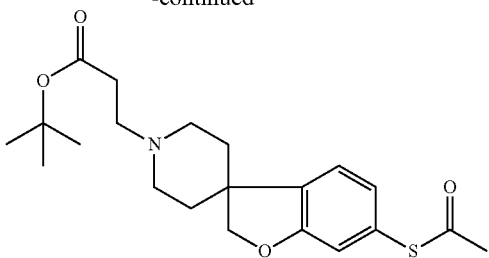

Tert-butyl 3-[6-(acetylsulfanyl)-2H-spiro[1-benzofuran-3,4'-piperidine]-1'-yl]propanoate. To a solution of tert-butyl 3-{6-hydroxy-2H-spiro[1-benzofuran-3,4'-piperidine]-1'-yl}propanoate (7.9 g, 23.7 mmol) in 15 mL chloroform, was added triethylamine (4.93 mL; 35.54 mmol), 4-dimethylaminopyridine (290 mg, 2.37 mmol) and a solution of trifluoromethanesulfonimide (10.16 g, 28.43 mmol) dissolved in 5 ml chloroform. The resulting reaction mixture was heated, at 60° C., and stirred overnight. Subsequently, the mixture was cooled to 0° C., water was added, followed by a 5% NaHCO$_3$ solution and the mixture was extracted with chloroform. The organic layer was dried (Na$_2$SO$_4$), filtered and concentrated in vacuo. The residue was purified by column chromatography (SiO$_2$, dichloromethane:acetone 9:1) to afford tert-butyl 3-{6-[(trifluoromethane)sulfonyloxy]-2H-spiro[1-benzofuran-3,4'-piperidine]-1'-yl]pro-panoate (9.5 g; 86%). $^1$H NMR (400 MHz, CDCl$_3$-d) δ ppm 7.11 (d, J=8.2 Hz, 1 H), 6.77 (dd, J=8.2 and 2.3 Hz, 1H), 6.68 (d, J=2.3 Hz, 1H), 4.34 (s, 2H), 2.85-2.94 (m, 2H), 2.69 (t, J=7.6 Hz, 2H), 2.45 (t, J=7.6 Hz, 2H), 2.02-2.10 (m, 2H), 1.86-1.97 (m, 2H), 1.72-1.75 (m, 2H), 1.46 (s, 9H).

To a nitrogen purged solution of tert-butyl 3-{-{6-[(trifluoromethane)sulfonyloxy]-2H-spiro[1-benzofuran-3,4'-piperidine]-1'-yl]propanoate (1.4 g, 3.01 mmol) in toluene (30 mL) was added (R)-1-[(1S$_p$)-2-(dicyclohexylphosphino)ferrocenyl]ethyldi-ter-butylphosphine (Strem chemicals; catalogue number 88733), (CyPF-t-Bu) (83.4 mg; 0.15 mmol), followed by tris-(dibenzylidenaceton)-dipalladium(0) (68.85 mg; 0.08 mmol). This mixture was stirred for 5 min. Subsequently, potassium thioacetate (0.69 g; 6.02 mmol) was added and the resulting mixture was heated at 110° C. for 24 hours. Subsequently, the reaction mixture was cooled, diluted with Et$_2$O and filtered. The remaining organic layer was dried and concentrated in vacuo. The residue was purified by column chromatography (SAX, dichloromethane:acetone 9:1) to afford tert-butyl 3-[6-(acetylsulfanyl)-2H-spiro[1-benzofuran-3,4'-piperidine]-1'-yl]pro-panoate (0.95 g; 80%). $^1$H NMR (400 MHz, CDCl$_3$-d) δ ppm 7.14 (d, J=8 Hz, 1H), 6.93 (dd, J=8 and 2Hz, 1H), 6.84 (d, J=2Hz, 1H), 4.39 (s, 2H), 2.86-2.94 (m, 2H), 2.69 (t, J=8 Hz, 2H), 2.44 (t, J=8 Hz, 2H), 2.40 (s, 3H), 2.02-2.11 (m, 2H), 1.90-1.99 (m, 2H), 1.72-1.79 (m, 2H), 1.46 (s, 9H). Rt 1.53 min (System B), [M+H]$^+$ 538.0

Tert-butyl 3-(6-{[(2,6-dichloro-3-methoxy)phenyl]methyl]sulfanyl}-2H-spiro[1-benzofuran-3,4'-piperidine]-1'-yl)propanoate. Under ice-bath cooling, a solution of NaOH (22 mg; 0.55 mmol) in 5 EtOH (5 mL) was added to tert-butyl 3-[6-(acetyl-sulfanyl)-2H-spiro[1-benzofuran-3,4'-piperidine]-1'-yl]propanoate (0.18 g; 0.46 mmol) dissolved in EtOH (5 mL) and stirring was continued during 30 minutes in which LCMS showed the complete deprotection of the S-acetyl. To this reaction mixture was added 1,3-dichloro-2-(chloromethyl)-4-methoxybenzene (160 mg; 0.53 mmol) dissolved in EtOH (2 mL) and stirred for another 20 minutes at 0° C. Subsequently, the reaction mixture was diluted with EtOAc and washed with brine. The remaining organic layer was dried (Na$_2$SO$_4$), and concentrated in vacuo. The residue was purified by column chromatography (SiO$_2$, dichloromethane:acetone 9:1) to afford 3-(6-{[2,6-dichloro-3-methoxy)phenyl]methylsulfanyl}-2H-spiro[1-benzofuran-3,4'-piperidine]-1'-yl}propanoate 220 mg; 80%.

The required 1,3-dichloro-2-(chloromethyl)-4-methoxybenzene was obtained from (the already described) (2,6-dichloro-3-methoxyphenyl)methanol using thionyl chloride (14 eq) in benzene (75%).

The following compounds were obtained according to a similar manner. The corresponding benzylic chlorides were obtained from the aforementioned benzylic alkohols:

Tert-butyl 3-(6-{[(4-butyl-2,6-dichlorophenyl)methyl]sulfanyl}-2H-spiro[1-benzofuran-3,4'-piperidine]-1'-yl}propanoate.

Tert-butyl 3-(6-{[(2-chloro-6-ethylphenyl)methyl]sulfanyl}-2H-spiro[1-benzofuran-3,4'-piperidine]-1'-yl}propanoate.

Tert-butyl 3-(6-{[(2-chloro-6-cyclopropylphenyl)methyl]sulfanyl}-2H-spiro[1-benzofuran-3,4'-piperidine]-1'-yl}propanoate.

Tert-butyl 3-(6-{[(2,6-dichloro-3-ethylphenyl)methyl]sulfanyl}-2H-spiro[1-benzofuran-3,4'-piperidine]-1'-yl}propanoate.

Tert-butyl 3-(6-{[(2,4,6-trichlorophenyl)methyl]sulfanyl}-2H-spiro[1-benzofuran-3,4'-piperidine]-1'-yl}propanoate.

Tert-butyl 3-(6-{[(2,6-dichlorophenyl)methyl]sulfanyl}-2H-spiro[1-benzofuran-3,4'-piperidine]-1'-yl}propanoate.

Tert-butyl 3-(6-{[(2-chlorophenyl)methyl]sulfanyl}-2H-spiro[1-benzofuran-3,4'-piperidine]-1'-yl}propanoate.

Tert-butyl 3-(6-{[(2-methylphenyl)methyl]sulfanyl}-2H-spiro[1-benzofuran-3,4'-piperidine]-1'-yl}propanoate.

Tert-butyl 3-[6-(benzylsulfanyl)-2H-spiro[1-benzofuran-3,4'-piperidine]-1'-yl]propanoate.

Tert-butyl 3-(6-{[(2-cyclopropyl-6-fluorophenyl)methyl]sulfanyl}-2H-spiro[1-benzofuran-3,4'-piperidine]-1'-yl}propanoate.

Tert-butyl 3-[6-({[2-fluoro-6-(propan-2-yl)phenyl]methyl}sulfanyl)-2H-spiro[1-benzofuran-3,4'-piperidine]-1'-yl]propanoate.

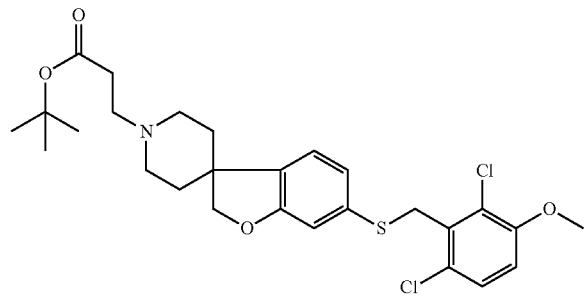 [SMILES: COc1ccc(Cl)c(CSc2ccc3c(c2)OCC32CCN(CCC(=O)OC(C)(C)C)CC2)c1Cl]

Compound 138. 3-(6-{[(2,6-Dichloro-3-methoxy) phenyl)methyl]sulfanyl}-2H-spiro[1-benzofuran-3, 4'-piperidine]-1'-yl}propanoic acid hydrochloride Tert-butyl 3-(6-{[(2,6-dichloro-3-methoxy)phenyl) methyl]sulfanyl}-2H-spiro[1-benzofuran-3,4'-piperidine]-1'-yl}propanoate (190 mg, 0.35 mmol) was dissolved in a 4M solution of HCl in 1,4-dioxane (10 mL; 4 mol/l; 40 mmol) and stirred for 48 hours at RT. Subsequently, the solvent was removed in vacuo and the residue treated with iPr$_2$O, the precipitate was collected by filtration and dried overnight under reduced pressure to afford the product (144 mg, 82%). Rt 1.45 min (System B), [M+H]$^+$ 482.0

The following compounds were obtained according to a similar manner:

Compound 139. 3-(6-{[(4-Butyl-2,6-dichlorophenyl)methyl]sulfanyl}-2H-spiro[1-benzofuran-3,4'-piperidine]-1'-yl}propanoic acid hydrochloride Rt 1.75 min (System B), [M+H]$^+$ 508.0

Compound 140. 3-(6-{[(2-Chloro-6-ethylphenyl) methyl]sulfanyl}-2H-spiro[1-benzofuran-3,4'-piperidine]-1'-yl}propanoic acid hydrochloride $^1$H NMR (400 MHz, DMSO-d$_6$) δ ppm 12.73 (bs, 1H), 10.27 (bs, 1H), 7.19-7.35 (m, 3H), 7.06 (bs, 1H), 6.94 (d, J=8 Hz, 1H), 6.88 (s, 1H), 4.50 (bs, 2H)m 4.31 (s, 2H), 3.27-3.54 (m, 4H), 2.99-3.15 (m, 2H), 2.85 (t, J=8 Hz, 2H), 2.66-2.74 (m, 2H), 2.12-2.26 (m, 2H), 1.84-1.94 (m, 2H), 1.18 (t, J=8 Hz, 3H).

Compound 141. 3-(6-{[(2-Chloro-6-cyclopropylphenyl)methyl]sulfanyl}-2H-spiro[1-benzofuran-3,4'-piperidine]-1'-yl}propanoic acid hydrochloride $^1$H NMR (400 MHz, DMSO-d$_6$) δ ppm 12.82 (bs, 1H), 9.91 (bs, 1H), 7.36 (d, J=8 Hz, 1H), 7.28 (t, J=8 Hz, 1H), 7.13 (bs, 1H), 7.03 (t, J=8 Hz, 2H), 6.96 (d, J=2Hz, 1H), 4.56 (bs, 4H), 3.37-3.59 (m, 4H), 3.19-3.25 (m, 2H), 2.88 (t, J=8 Hz, 2H), 2.17-2.23 (m, 2H), 2.09-2.13 (m, 1H), 1.92-1.99 (m, 2H), 0.96-1.12 (m, 2H), 0.64-0.80 (m, 2H). Rt 1.52 min (System B), [M+H]$^+$ 458.0.

Compound 142. 3-(6-{[(2,6-Dichloro-3-ethylphenyl)methyl]sulfanyl}-2H-spiro[1-benzofuran-3,4'-piperidine]-1'-yl}propanoic acid hydrochloride Rt 1.57 min (System B), [M+H]$^+$ 480.0

Compound 143. 3-(6-{[(2,4,6-Trichlorophenyl) methyl]sulfanyl}-2H-spiro[1-benzofuran-3,4'-piperidine]-1'-yl}propanoic acid hydrochloride $^1$H NMR (400 MHz, DMSO-d$_6$) δ ppm 12.82 (bs, 1H), 10.09 (bs, 1H), 7.71 (s, 2H), 7.05 (bs, 1H), 6.94 (d, J=8 Hz, 1H), 6.88 (d, J=2Hz, 1H), 4.50 (bs, 2H), 4.34 (s, 2H), 3.26-3.54 (m, 4H), 2.99-3.12 (m, 2H), 2.83 (t, J=8 Hz, 2H), 2.10-2.22 (m, 2H), 1.85-1.92 (m, 2H). Rt 1.55 min (System B), [M+H]$^+$ 487.9

Compound 144. 3-(6-{[(2,6-Dichlorophenyl)methyl] sulfanyl}-2H-spiro[1-benzofuran-3,4'-piperidine]-1'-yl}propanoic acid hydrochloride $^1$H NMR (400 MHz, DMSO-d$_6$) δ ppm 12.55 (bs, 1H), 10.18 (bs, 1H), 7.50 (d, J=8 Hz, 2H), 7.35 (t, J=8 Hz, 1H), 7.06 (bs, 1H), 6.95 (bd, J=8 Hz, 1H), 6.89 (s, 1H), 4.50 (bs, 2H), 4.39 (s, 2H), 3.27-3.54 (m, 4H), 2.99-3.12 (m, 2H), 2.84 (t, J=8 Hz, 2H), 2.09-2.24 (m, 2H), 1.85-1.92 (m, 2H). Rt 1.44 min (System B), [M+H]$^+$ 451.9

Compound 145. 3-(6-{[(2-Chlorophenyl)methyl] sulfanyl}-2H-spiro[1-benzofuran-3,4'-piperidine]-1'-yl}propanoic acid hydrochloride $^1$H NMR (400 MHz, DMSO-d$_6$) δ ppm 12.82 (bs, 1H), 10.00 (bs, 1H), 7.41-7.48 (m, 2H), 7.25-7.33 (m, 2H), 7.03 (bs, 1H), 6.88 (d, J=8 Hz, 1H), 6.84 (s, 1H), 4.47 (bs, 2H), 4.28 (s, 2H), 3.18-3.55 (m, 4H), 2.97-3.12 (m, 2H), 2.83 (t, J=8 Hz, 2H), 2.06-2.21 (m, 2H), 1.81-1.91 (m, 2H). Rt 2.31 min (System B), [M+H]$^+$ 418.0.

Compound 146. 3-(6-{[(2-Methylphenyl)methyl] sulfanyl}-2H-spiro[1-benzofuran-3,4'-piperidine]-1'-yl}propanoic acid hydrochloride Rt 1.72 min (System B), [M+H]$^+$ 398.1

Compound 147. 3-[6-(Benzylsulfanyl)-2H-spiro[1-benzofuran-3,4'-piperidine]-1'-yl}propanoic acid hydrochloride $^1$H NMR (400 MHz, DMSO-d$_6$) □ ppm . . . . Rt 1.35 min (System B), [M+H]$^+$ 384.1

Compound 293. 3-(6-{[(2-Cyclopropyl-6-fluorophenyl)methyl]sulfanyl}-2H-spiro[1-benzofuran-3,4'-piperidine]-1'-yl}propanoic acid hydrochloride $^1$H NMR (400 MHz, DMSO-d$_6$) δ ppm 12.73 (br s, 1H), 10.27 (br s, 1H), 7.20-7.25 (m, 1H), 6.97-7.06 (m, 2H), 6.93 (d, J=8 Hz, 1H), 6.88 (s, 1H), 6.80 (d, J=8 Hz, 1H), 4.49 (br s, 2H), 4.35 (s, 2H), 3.25-3.53 (m, 4H), 3.01-3.13 (m, 2H), 2.83 (t, J=8 Hz, 2H), 2.11-2.22 (m, 2H), 2.01-2.08 (m, 1H), 1.87 (d, J=8 Hz, 2H), 0.91-0.98 (m, 2H), 0.64-0.68 (m, 2H). Rt 1.47 min (System B), [M+H]$^+$ 442.2.

Compound 294. 3-[6-({[2-Fluoro-6-(propan-2-yl) phenyl]methyl}sulfanyl)-2H-spiro[1-benzofuran-3, 4'-piperidine]-1'-yl]propanoic acid hydrochloride $^1$H NMR (400 MHz, DMSO-d$_6$) δ ppm 7.27-7.46 (m, 1H), 6.93-7.14 (m, 5H), 4.50 (br s, 2H), 4.22 (br s, 2H), 3.32-3.53 (m, 4H), 3.12-3.17 (m, 2H), 2.81-2.86 (m, 3H), 2.13-2.18 (m, 2H), 1.85-1.91 (m, 2H), 1.16 (d, J=8 Hz, 6H). Rt 1.48 min (System B), [M+H]$^+$ 444.3.

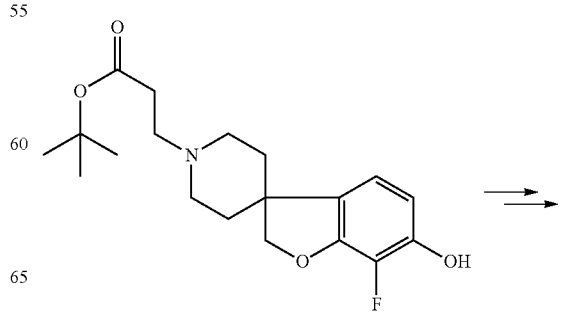

-continued

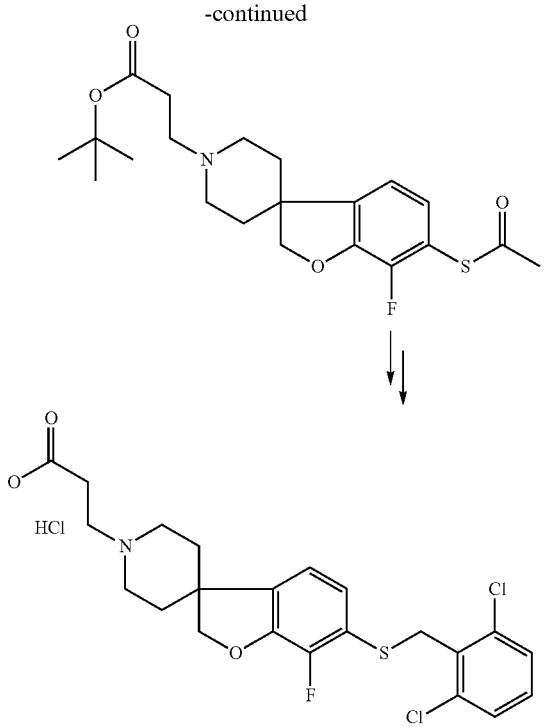

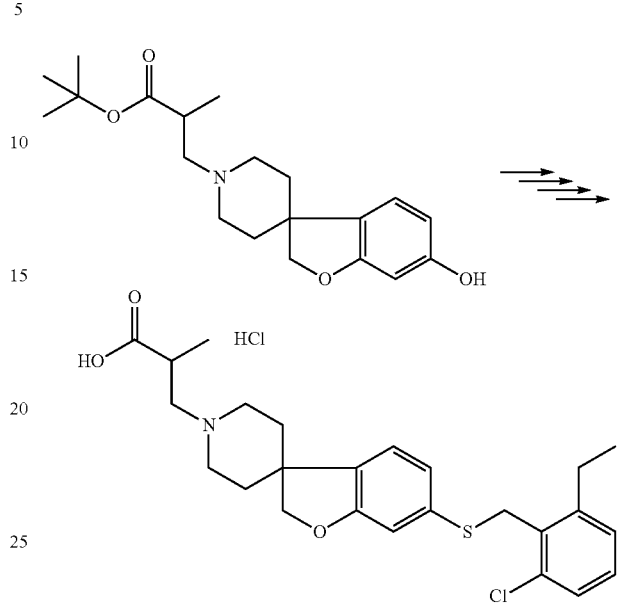

(br s, 2H), 3.26-3.54 (m, 4H), 2.91 (t, J=8 Hz, 2H), 2.85 (t, J=8 Hz, 2H), 2.14-2.25 (m, 2H), 1.89-1.97 (m, 2H), 1.50-1.59 (m, 2H), 1.23-1.40 (m, 6H), 0.91 (t, J=8 Hz, 3H). Rt 1.43 min (System B), [M+H]$^+$ 382.7.

Tert-butyl 3-{7-fluoro-6-hydroxy-2H-spiro[1-benzofuran-3,4'-piperidine]-1'-yl}-propanoate was converted to tert-butyl 3-[6-(acetylsulfanyl)-7-fluoro-2H-spiro[1-benzofuran-3,4'-piperidine]-1'-yl]propanoate, $^1$H NMR (400 MHz, CDCl$_3$-d) δ ppm 6.86-6.94 (m, 3H), 4.50 (s, 2H), 2.88-2.94 (m, 2H), 2.67-2.72 (t, J=8 Hz, 2H), 2.44 (t, J=8 Hz, 5H), 2.01-2.10 (m, 2H), 1.91-1.99 (m, 2H), 1.78-1.82 (m, 2H), 1.46 (s, 9H) and converted to the following compounds (in a similar manner and as described for compound 138):

Compound 295. 3-(6-{[(2,6-Dichlorophenyl)methyl]sulfanyl}-2H-spiro[1-benzofuran-3,4'-piperidine]-1'-yl}propanoic acid hydrochloride $^1$H NMR (400 MHz, DMSO-d$_6$) δ ppm 12.64 (br s, 1H), 9.82 (br s, 1H), 7.47 (d, J=8 Hz, 2H), 7.31-7.36 (m, 1H), 6.95-6.99 (m, 1H), 6.88-6.91 (m, 1H), 4.64 (br s, 2H), 4.33 (s, 2H), 3.31-3.52 (m, 4H), 3.03-3.12 (m, 2H), 2.82 (t, J=8 Hz, 2H), 2.11-2.19 (m, 2H), 1.92-1.98 (m, 2H). Rt 1.49 min (System B), [M+H]$^+$ 470.1.

Compound 296. 3-(6-{[(2-Chloro-6-ethylphenyl)methyl]sulfanyl}-2H-spiro[1-benzofuran-3,4'-piperidine]-1'-yl}propanoic acid hydrochloride $^1$H NMR (400 MHz, DMSO-d$_6$) δ ppm 12.64 (br s, 1H), 9.90 (br s, 1H), 7.18-7.32 (m, 3H), 7.00-7.05 (m, 1H), 6.87-6.94 (m, 1H), 4.63 (br s, 2H), 4.27 (s, 2H), 3.25-3.54 (m, 4H), 2.96-3.13 (m, 2H), 2.83 (t, J=8 Hz, 2H), 2.63-2.72 (m, 2H), 2.11-2.20 (m, 2H), 1.89-2.00 (m, 2H), 1.15 (t, J=8 Hz, 3H). Rt 1.67 min (System B), [M+H]$^+$ 464.1.

Compound 297. 3-[7-Fluoro-6-(pentylsulfanyl)-2H-spiro[1-benzofuran-3,4'-piperidine]-1'-yl]propanoic acid hydrochloride $^1$H NMR (400 MHz, DMSO-d$_6$) δ ppm 12.63 (br s, 1H), 10.27 (br s, 1H), 6.94-6.99 (m, 2H), 6.89-6.92 (m, 1H), 4.63

The following compounds, starting from tert-butyl 3-{6-hydroxy-2H-spiro[1-benzofuran-3,4'-piperidine]-1'-yl}-2-methyl-propanoate, were obtained according to the procedure described for compound 138.

The corresponding benzylic chlorides were obtained from the already described benzylic alcohols:

Compound 148. 2-Methyl-3-(6-{[(2,4,6-trichlorophenyl)methyl]sulfanyl}-2H-spiro[1-benzofuran-3,4'-piperidine]-1'-yl}propanoic acid hydrochloride $^1$H NMR (400 MHz, DMSO-d$_6$) δ ppm 13.00 (bs, 1H), 9.64 (bs, 1H), 7.82 (s, 2H), 7.06 (d, J=8 Hz, 1H), 7.18 (bs, 1H), 7.01 (d, J=2 Hz, 1H), 4.61 (bs, 2H), 4.46 (s, 2H), 3.41-3.65 (m, 4H), 3.16-3.27 (m, 2H), 3.07-3.14 (m, 1H), 2.25-2.39 (m, 2H), 1.95-2.05 (m, 2H), 1.35 (d, J=8 Hz, 3H). Rt 1.65 min (System B), [M+H]$^+$ 502.0.

Compound 149. 3-(6-{[(2,6-Dichloro-3-methoxyphenyl)methyl]sulfanyl}-2H-spiro[1-benzofuran-3,4'-piperidine]-1'-yl}-2-methylpropanoic acid hydrochloride $^1$H NMR (400 MHz, DMSO-d$_6$) δ ppm 12.91 (bs, 1H), 9.82 (bs, 1H), 7.45 (d, J=8 Hz, 1H), 7.14 (d, J=8 Hz, 1H), 7.05 (bs, 1H), 6.95 (d, J=8 Hz, 1H), 6.89 (d, J=2Hz, 1H), 4.49 (bs, 2H), 4.37 (s, 2H), 3.86 (s, 3H), 3.42-3.55 (m, 3H), 2.98 (m, 4H), 2.18-2.29 (m, 2H), 1.83-1.91 (m, 2H), 1.24 (d, J=8 Hz, 3H).

Compound 150. 3-(6-{[(2,6-Dichloro-4-methylphenyl)methyl]sulfanyl}-2H-spiro[1-benzofuran-3,4'-piperidine]-1'-yl}-2-methylpropanoic acid hydrochloride Rt 1.55 min (System B), [M+H]$^+$ 487.9

Compound 151. 3-(6-{[(2-Chloro-6-ethylphenyl)methyl]sulfanyl}-2H-spiro[1-benzofuran-3,4'-piperidine]-1'-yl}-2-methylpropanoic acid hydrochloride Rt 1.57 min (System B), [M+H]+ 460.1

Compound 152. 3-[6-({[2-Chloro-6-(propan-2-yl)phenyl]methyl}sulfanyl)-2H-spiro[1-benzofuran-3,4'-piperidine]-1'-yl}-2-methylpropanoic acid hydrochloride 1H NMR (400 MHz, DMSO-d6) δ ppm 12.82 (bs, 1H), 9.82 (bs, 1H), 7.27-7.33 (m, 3H), 7.01-7.09 (bs, 1H), 6.94 (d, J=8 Hz, 1H), 6.88 (s, 1H), 4.49 (bs, 2H), 4.34 (s, 2H), 3.31-3.52 (m, 4H), 2.99-3.21 (m, 4H), 2.19-2.33 (m, 2H), 1.82-1.92 (m, 2H), 1.24 (d, J=8 Hz, 3H), 1.16 (d, J=8 Hz, 6H).

Compound 153. 3-(6-{[(2,6-Dichlorophenyl)methyl]sulfanyl}-2H-spiro[1-benzofuran-3,4'-piperidine]-1'-yl}-2-methylpropanoic acid hydrochloride 1H NMR (400 MHz, DMSO-d6) δ ppm 12.82 (bs, 1H), 9.82 (bs, 1H), 7.49 (d, J=8 Hz, 2H), 7.38 (t, J=8 Hz, 1H), 7.06 (bs, 1H), 6.95 (d, J=8 Hz, 1H), 6.88 (s, 1H), 4.49 (bs, 2H), 4.38 (s, 2H), 3.30-3.53 (m, 4H), 2.98-3.17 (m, 3H), 2.18-2.35 (m, 2H), 1.82-1.93 (m, 2H), 1.24 (d, J=8 Hz, 3H).

Compound 298. 3-(6-{[(2-Chloro-6-cyclopropylphenyl)methyl]sulfanyl}-2H-spiro[1-benzofuran-3,4'-piperidine]-1'-yl}-2-methylpropanoic acid hydrochloride 1H NMR (400 MHz, DMSO-d6) δ ppm 12.87 (br s, 1H), 9.80 (br s, 1H), 7.31 (d, J=4 Hz, 1H), 7.23 (t, J=4 Hz, 1H), 7.04 (br s, 1H), 6.98 (t, J=4 Hz, 2H), 6.90 (s, 1H), 4.46 (s, 4H), 3.30-3.55 (m, 4H), 3.00-3.15 (m, 3H), 2.20-2.30 (m, 2H), 2.02-2.10 (m, 1H), 1.84-1.91 (m, 2H), 1.23 (d, J=4 Hz, 3H), 0.91-0.95 (m, 2H), 0.66-0.70 (m, 2H). Rt 1.58 min (System B), [M+H]+ 472.1

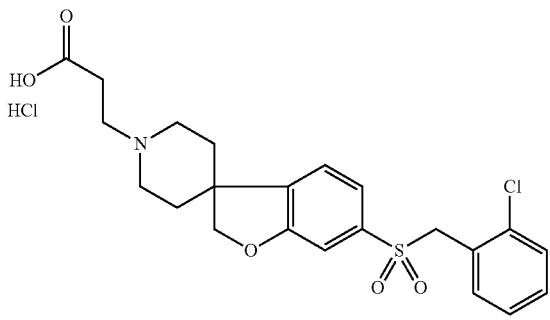 [SMILES: Cl ; O=C(O)CCN1CCC2(CC1)COc1cc(S(=O)(=O)Cc3ccccc3Cl)ccc12]

Compound 154. 3-(6-{[(2-Chlorophenyl)methane]sulfonyl}-2H-spiro[1-benzofuran-3,4'-piperidine]-1'-yl}propanoic acid hydrochloride Tert-butyl 3-(6-{[(2-chlorophenyl)methyl]sulfanyl}-2H-spiro[1-benzofuran-3,4'-piperidine]-1'-yl}pro-panoate. (237 mg, 0.50 mmol) was dissolved in a 4M solution of HCl in 1,4-dioxane (10 mL; 4 mol/l; 40 mmol) and stirred for 5 minutes at RT. Subsequently, the solvent was removed in vacuo and the residue treated with iPr2O, the precipitate was collected by filtration. To this HCl salt, dissolved in MeOH (7.50 mL) at 0° C., was added potassium peroxymonosulfate (922 mg; 1.50 mmol) in H2O (7.50 mL) and the reaction mixture was stirred for 2 hour. Subsequently, the reaction mixture was diluted with dichloromethane and washed with 5% aqueous NaHCO3 and brine. The remaining organic layer was dried (Na2SO4), and concentrated in vacuo. The residue was purified by column chromatography (SiO2, dichloro-methane:acetone 9:1) to afford tert-butyl 3-(6-{[(2-chlorophenyl)methane]sulfonyl}-2H-spiro[1-benzofuran-3,4'-piperidine]-1'-yl}propanoate (220 mg; 72.5%) which was dissolved in a 4M solution of HCl in 1,4-dioxane (10 mL; 4 mol/l; 40 mmol) and stirred for 48 hours at RT. Subsequently, the solvent was removed in vacuo and the residue treated with iPr2O, the precipitate was collected by filtration and dried overnight under reduced pressure to afford the product (150 mg, 70%). 1H NMR (400 MHz, DMSO-d6) δ ppm 12.55 (bs, 1H), 10.27 (bs, 1H), 7.24-7.44 (m, 6H), 7.08 (s, 1H), 4.74 (s, 2H), 4.59 (br s, 2H), 3.24-3.54 (m, 4H), 3.01-3.14 (m, 2H), 2.81-2.89 (t, J=8 Hz, 2H), 2.15-2.28 (m, 2H), 1.89-1.96 (m, 2H). Rt 1.36 min (System B), [M+H]+ 450.0

The following compound was obtained according to a similar manner:

Compound 299. 3-(6-{[(2,6-Dichlorophenyl)methane]sulfonyl}-2H-spiro[1-benzofuran-3,4'-piperidine]-1'-yl}propanoic acid hydrochloride 1H NMR (400 MHz, DMSO-d6) δ ppm 12.64 (br s, 1H), 10.27 (br s, 1H), 7.52 (d, J=8 Hz, 2H), 7.40-7.45 (m, 2H), 7.32-7.39 (m, 2H), 4.87 (s, 2H), 4.63 (s, 2H), 3.26-3.56 (m, 4H), 3.01-3.16 (m, 2H), 2.84 (t, J=8 Hz, 2H), 2.17-2.28 (m, 2H), 1.91-1.99 (m, 2H). Rt 1.24 min (System B), [M+H]+ 484.1

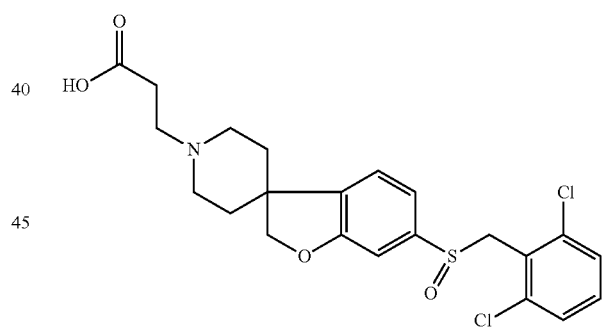

Compound 300. 3-(6-{[(2,6-Dichlorophenyl)methane]sulfinyl}-2H-spiro[1-benzofuran-3,4'-piperidine]-1'-yl}propanoic acid hydrochloride To tert-butyl 3-(6-{[(2,6-dichlorophenyl)-methyl]sulfanyl}-2H-spiro[1-benzofuran-3,4'-piperidine]-1'-yl}-propanoate hydro-chloride. (210 mg, 0.41 mmol), dissolved in MeOH (7.50 mL) at 0° C., was added potassium peroxymonosulfate (254 mg; 0.41 mmol) in H2O (7.50 mL) and the reaction mixture was stirred for 2 hour. Subsequently, the reaction mixture was diluted with EtOAc and washed with 5% aqueous NaHCO3 and brine. The remaining organic layer was dried (Na2SO4), and concentrated in vacuo. The residue was purified by column chromatography (SiO2, dichloro-methane:acetone 95:5) to afford tert-butyl 3-(6-{[(2,6-dichlorophenyl)methane]sulfinyl}-2H-spiro[1-benzofuran-3,4'-piperidine]-1'-yl}propanoate (130 mg), which was dissolved in 2M aqueous NaOH (1 mL; 2 mmol) and ethanol (10 mL). The reaction mixture was stirred for 3 hours at 60° C. and subsequently cooled to 0° C. To this reaction mixture was added aqueous HCl (2 mL; 1 mol/l), dropwise, after which it was concentrated in vacuo. The residue was treated with saturated brine and dichloromethane. The water layer was washed with dichloromethane (twice). Subsequently, the organic layer was dried ($Na_2SO_4$), filtered, and concentrated in vacuo, followed by treated with $iPr_2O$. The formed precipitate was collected by filtration, washed with $iPr_2O$ and dried in vacuo to yield the product (100 mg; 70%). $^1$H NMR (400 MHz, DMSO-$d_6$) δ ppm 7.57 (d, J=8 Hz, 2H), 7.44-7.49 (m, 2H), 7.03-7.09 (m, 2H), 4.56 (d, J=12Hz, 3H), 4.39 (d, J=12Hz, 1H), 2.92-3.01 (m, 2H), 2.71 (t, J=8 Hz, 2H), 2.48 (t, J=8 Hz, 2H), 2.15-2.23 (m, 2H), 1.89-1.99 (m, 2H), 1.71-1.79 (m, 2H). Rt 1.35 min (System B), [M+H]$^+$ 468.1

2.45 (t, J=7.8 Hz, 2H), 2.02-2.12 (m, 2H), 1.93-2.01 (m, 2H), 1.72-1.77 (m, 2H), 1.47-1.68 (m, 6H), 1.46 (s, 9H), 1.26-1.39 (m, 6H), 0.99-1.04 (m, 6H), 0.89 (t, J=7.2Hz, 9H). To a ice-bath cooled solution of Tert-butyl 3-[6-(tributylstannyl)-2H-spiro[1-benzofuran-3,4'-piperidine]-1'-yl]propanoate (3 g; 4.95 mmol), dissolved in THF (50 mL), was added N-iodosuccinimide (1.67 g; 7.42 mmol) (portionwise). The resulting reaction mixture was stirred for 75 minutes (at 0° C.). Subsequently, the reaction mixture was diluted with EtOAc and $Na_2S2O_3$. The organic layer was washed with brine, dried ($Na_2SO_4$), and concentrated in vacuo. The residue was purified by column chromatography ($SiO_2$, dichloromethane:acetone 9:1) to afford tert-butyl 3-{6-iodo-2H-spiro[1-benzofuran-3,4'-piperidine]-1'-yl}propanoate (1.55 g; 70%). Rt 1.32 min (System B), [M+H]$^+$ 444.0

Tert-butyl 3-{6-bromo-2H-spiro[1-benzofuran-3,4'-piperidine]-1'-yl}propanoate. Was prepared from 3-[6-(tributyl-

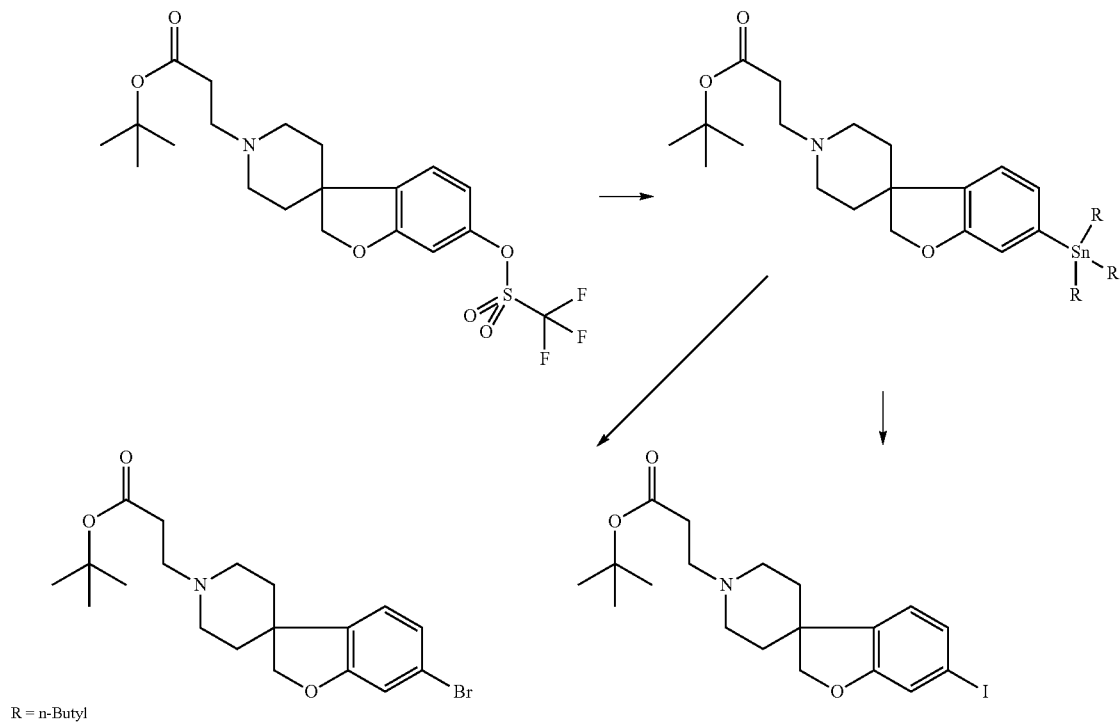

R = n-Butyl

Tert-butyl 3-{6-iodo-2H-spiro[1-benzofuran-3,4'-piperidine]-1'-yl}propanoate. To a nitrogen purged solution of tert-butyl 3-{-{6-[(trifluoromethane)sulfonyloxy]-2H-spiro [1-benzofuran-3,4'-piperidine]-1'-yl]propanoate (5 g, 10.74 mmol) and hexa-N-butylditin (12.46 g; 21.48 mmol) in 1,4-dioxane (25 mL) was added lithium chloride (2.28 g; 53.7 mmol) and tetrakis(triphenylphosphine)palladium(0). This mixture was stirred for 72 hours at 108° C. Subsequently, the reaction mixture was cooled, diluted with $Et_2O$ and extracted with a solution of KF in $H_2O$ (5 mol/l). The organic layer was dried ($Na_2SO_4$) and concentrated in vacuo. The residue was purified by column chromatography ($SiO_2$, $Et_2O$:hexanes 1:3) to afford tert-butyl 3-[6-(tributylstannyl)-2H-spiro[1-benzofuran-3,4'-piperidine]-1'-yl]propanoate (4.29 g; 66%). $^1$H NMR (400 MHz, CDCl$_3$-d) δ ppm 7.11 (d, J=8.2Hz, 1H), 6.96 (d, J=8.2Hz, 1H), 6.91 (s, 1H), 4.34 (s, 2H), 2.85-2.94 (m, 2H), 2.69 (t, J=7.8 Hz, 2H), stannyl)-2H-spiro[1-benzofuran-3,4'-piperidine]-1'-yl]propanoate in a similar manner, using N-bromosuccinimide (57%).

Tert-butyl 3-{6-[(2-methylphenyl)sulfanyl]-2H-spiro[1-benzofuran-3,4'-piperidine]-1'-yl}propanoate. To a nitrogen purged solution of tert-butyl 3-{6-iodo-2H-spiro[1-benzofuran-3,4'-piperidine]-1'-yl}propanoate (0.2 g, 0.43 mmol) in 1,2-dimethoxyethane (5 mL) was added 2-methylbenzene-1-thiol (0.05 mL; 0.43 mmol) and potassium carbonate (118 mg; 0.86 mmol) and finally copper(I)iodide (9 mg; 0.045 mmol). This mixture was stirred for 24 hours at 93° C. Additional 2-methylbenzene-1-thiol (0.01 mL) and copper (I)iodide (10 mg) were added and the reaction mixture was stirred for another 4 hours. Subsequently, the reaction mixture was cooled, diluted with EtOAc and extracted with a saturated $NH_4Cl$ solution and brine. The organic layer was dried ($Na_2SO_4$) and concentrated in vacuo. The residue was purified by column chromatography (SiO$_2$, dichloromethane:acetone 9:1) to afford tert-butyl 3-{6-[(2-methylphenyl)sulfanyl]-2H-spiro[1-benzofuran-3,4'-piperidine]-1'-yl}propanoate (0.14 g; 74%). Rt 1.47 min (System B), [M+H]$^+$ 444.1

The following compound was obtained according to a similar manner:

Tert-butyl 3-{6-[(2,6-dichlorophenyl)sulfanyl]-2H-spiro[1-benzofuran-3,4'-piperidine]-1'-yl}propanoat Tert-butyl 3-{6-[(2-methylbenzene)sulfonyl]-2H-spiro[1-benzofuran-3,4'-piperidine]-1'-yl}propanoate. This compound was prepared from tert-butyl 3-{6-[(2-methylphenyl)sulfanyl]-2H-spiro[1-benzofuran-3,4'-piperidine]-1'-yl}propanoate using the methodology of compound 154.

Tert-butyl 3-{6-[(2,6-dichlorobenzene)sulfonyl]-2H-spiro[1-benzofuran-3,4'-piperidine]-1'-yl}propanoate. To a solution tert-butyl 3-[6-(tributylstannyl)-2H-spiro[1-benzofuran-3,4'-piperidine]-1'-yl]propanoate (450 mg; 0.74 mmol), dissolved in THF (15 ml) was added n-butyllithium (0.45 mL; 2.50 mol/l; 1.11 mmol), at at −78° C. The reaction mixture was stirred for 30 minutes. Subsequently, a solution of 2,6-dichlorobenzene-1-sulfonyl fluoride (0.2 g; 0.87 mmol), dissolved in THF (7 mL) was added at −78° C. The resulting mixture was stirred and allowed to warm to RT overnight. The reaction was quenched by the addition of a saturated aqueous NaH$_4$Cl solution. The resulting mixture was extracted with Et$_2$O and washed with 10 mL KF (10% in H$_2$O). The organic layer was dried (Na$_2$SO$_4$), filtered, and concentrated in vacuo. The residue was purified by column chromatography (SiO$_2$, dichloromethane:acetone 9:1) to afford the product (75 mg; 19%) Rt 1.35 min (System B), [M+H]$^+$ 525.9

The following compound was obtained according to a similar manner:

Tert-butyl 3-[6-(benzenesulfonyl)-2H-spiro[1-benzofuran-3,4'-piperidine]-1'-yl}propanoate.

Compound 155. 3-{6-[(2-Methylphenyl)sulfanyl]-2H-spiro[1-benzofuran-3,4'-piperidine]-1'-yl}propanoic acid hydrochloride Tert-butyl 3-{6-[(2-methylphenyl)sulfanyl]-2H-spiro[1-benzofuran-3,4'-piperidine]-1'-yl}propanoate (120 mg, 0.25 mmol) was dissolved in a 4M solution of HCl in 1,4-dioxane (10 mL; 4 mol/l; 40 mmol) and stirred for 48 hours at RT. Subsequently, the solvent was removed in vacuo and the residue treated with iPr$_2$O, the precipitate was collected by filtration and dried overnight under reduced pressure to afford the product (90 mg, 82%). $^1$H NMR (400 MHz, DMSO-d$_6$) δ ppm 12.73 (bs, 1H), 10.27 (bs, 1H), 7.18-7.38 (m, 4H), 7.08 (bs, 1H), 6.74 (d, J=8 Hz, 1H), 6.55 (s, 1H), 4.48 (bs, 2H), 3.23-3.55 (m, 4H), 2.95-3.15 (m, 2H), 2.80-2.88 (m, 2H), 2.32 (s, 3H), 2.08-2.23 (m, 2H), 1.84-1.93 (m, 2H). Rt 1.40 min (System B), [M+H]$^+$ 384.1

The following compound was obtained according to a similar manner:

Compound 156. 3-{6-[(2,6-Dichlorophenyl)sulfanyl]-2H-spiro[1-benzofuran-3,4'-piperidine]-1'-yl}propanoic acid hydrochloride $^1$H NMR (400 MHz, DMSO-d$_6$) δ ppm 12.73 (bs, 1H), 10.18 (bs, 1H), 7.70 (d, J=8 Hz, 2H), 7.56 (t, J=8 Hz, 1H), 7.04 (bs, 1H), 6.59 (dd, J=8 and 2Hz, 1H), 6.44 (s, 1H), 4.47 (bs, 2H), 3.25-3.53 (m, 4H), 2.96-3.11 (m, 2H), 2.82 (t, J=8 Hz, 2H), 2.06-2.18 (m, 2H), 1.83-1.92 (m, 2H). Rt 1.39 min (System B), [M+H]$^+$ 437.9.

Compound 157. 3-{6-[(2-Methylbenzene)sulfonyl]-2H-spiro[1-benzofuran-3,4'-piperidine]-1'-yl}propanoic acid hydrochloride Rt 1.21 min (System B), [M+H]$^+$ 416.0

Compound 158. 3-{6-[(2,6-Dichlorobenzene)sulfonyl]-2H-spiro[1-benzofuran-3,4'-piperidine]-1'-yl}propanoic acid hydrochloride Rt 1.63 min (System B), [M+H]$^+$ 469.9

Compound 159. 3-[6-(Benzenesulfonyl)-2H-spiro[1-benzofuran-3,4'-piperidine]-1'-yl}propanoic acid hydrochloride Rt 1.40 min (System B), [M+H]$^+$ 384.1

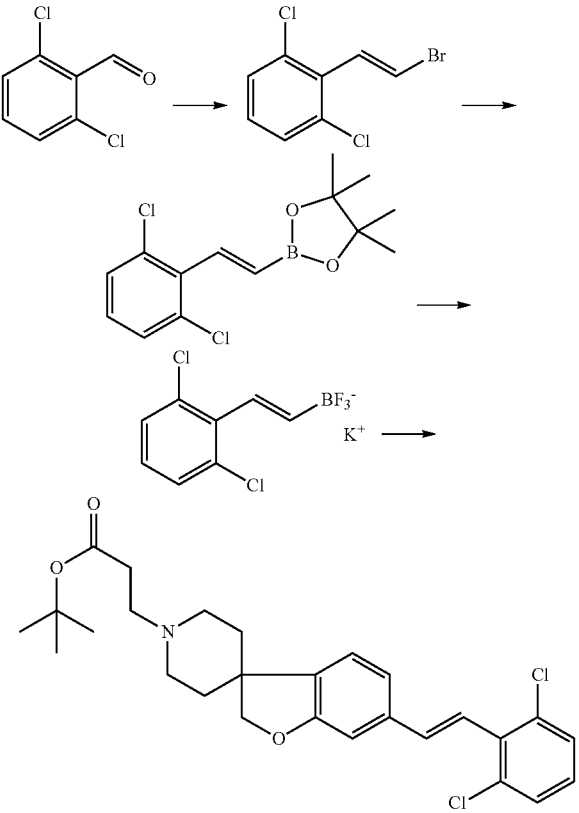

Tert-butyl 3-{6-[(E)-2-(2,6-dichlorophenyl)ethenyl]-2H-spiro[1-benzofuran-3,4'-piperidine]-1'-yl}propanoate. To a solution (bromomethyl)triphenylphosphonium bromide (23.92 g; 54.85 mmol), dissolved in THF (150 ml) was added a suspension of potassium tert-butoxide (6.16 g; 54.85 mmol) in THF (50 mL), at −78° C. (Adv. Synth. Catal., 2006, 348, 851). The reaction mixture was stirred for 2 hours. Subsequently, a solution of 2,6-dichlorobenzaldehyde (8 g; 45.71 mmol), dissolved in THF (50 mL) was added dropwise at −78° C. The resulting mixture was stirred and allowed to warm to RT overnight. The reaction was quenched by the addition of a saturated aqueous NaH$_4$Cl solution. The resulting mixture was extracted with Et$_2$O and washed with brine. The organic layer was dried (Na$_2$SO$_4$), filtered, and concentrated in vacuo. The residue was purified by column chromatography (SiO$_2$, hexanes) to afford 2-[(E)-

2-bromoethenyl]-1,3-dichlorobenzene (7.22 g; 62%) $^1$H NMR (400 MHz, CDCl$_3$-d) δ ppm 7.32 (d, J=8.0 Hz, 2H), 7.12-7.20 (m, 2H), 6.97 (d, J=14.2Hz, 1H)

To a nitrogen purged mixture of 2-[(E)-2-bromoethenyl]-1,3-dichlorobenzene (7.22 g; 28.66 mmol) in 1,4-dioxane (200 mL), was added subsequently, Bis(pinacolato)diboron (8.01 g; 31.52 mmol), potassium acetate (8.44 g; 85.97 mmol), 1',1'-bis(diphenyl-phosphino)-ferrocene palladium (II)dichloride dichloromethane complex (0.7 g; 0.86 mmol) and (additional) 1',1'-bis(diphenylphosphino)-ferrocene (0.48 g; 0.86 mmol) The resulting mixture was heated overnight (85° C.). After cooling to RT, the reaction mixture was diluted with EtOAc, filtered and washed with H$_2$O. The organic layer was dried (Na$_2$SO$_4$), filtered, and concentrated in vacuo. The residue was purified by column chromatography (SiO$_2$, Et$_2$O:hexanes 1:7) to afford of 2-[(E)-2-(2,6-dichloro-phenyl)ethenyl]-4,4,5,5-tetramethyl-1,3,2-dioxaborolane (6.24 g; 72%). $^1$H NMR (400 MHz, CDCl$_3$-d) δ ppm 7.39 (d, J=18.8 Hz, 1H), 7.31 (d, J=8.0 Hz, 2H), 7.11 (d, J=8.0 Hz, 1H), 6.24 (d, J=18.8 Hz, H), 1.33 (s, 12H). To a mixture of 2-[(E)-2-(2,6-dichlorophenyl)ethenyl]-4,4,5,5-tetramethyl-1,3,2-dioxaborolane (2.5 g; 8.36 mmol) in MeOH (60 mL) and water (15 mL), was added potassium bifluoride (4.57 g; 58.3 mmol) was stirred at RT overnight. Subsequently, the solvents were removed in vacuo and the residue treated with toluene and concentrated in vacuo. The latter steps were repeated three times to remove all the water. The obtained solid was treated with hot acetonitrile (20 mL) and the acetonitrile was decanted. This was repeated 3 times. The combined acetonitrile layers were concentrated in vacuo and the residue was treated with Et$_2$O. The formed precipitate was collected by filtration and dried in vacuo to afford the potassium 2-[(E)-2-(2,6-dichlorophenyl)ethenyl]-trifluoroboronate (2.31 g, 99%). $^1$H NMR (400 MHz, DMSO-d$_6$) δ ppm 7.39 (d, J=8.0 Hz, 2H), 7.16 (t, J=8.0 Hz, 1H), 6.42 (d, J=18.6 Hz, 1H), 6.08-6.17 (m, 1H).

To a degassed mixture of tert-butyl 3-{6-bromo-2H-spiro[1-benzofuran-3,4'-piperidine]-1'-yl}propanoate (1.26 g; 3.18 mmol) and potassium 2-[(E)-2-(2,6-dichlorophenyl)ethenyl]-ltrifluoroboronate (1.06 g, 3.82 mmol) in toluene (45 mL) and water (15 mL), was added subsequently, cesium carbonate (3.54 g; 10.87 mmol), and 1',1'-bis(diphenylphosphino)-ferrocene palladium(II)dichloride dichloromethane complex (0.13 g; 0.16 mmol). The resulting mixture was heated overnight (100° C.). After cooling to RT, the reaction mixture was diluted with EtOAc, filtered and washed with 5% aqueous NaHCO$_3$. The organic layer was dried (Na$_2$SO$_4$), filtered, and concentrated in vacuo. The residue was purified by column chromatography (SiO$_2$, Et$_2$O:hexanes 1:1 followed by 2:1) to afford tert-butyl 3-{6-[(E)-2-(2,6-dichlorophenyl)ethenyl]-2H-spiro[1-benzofuran-3,4'-piperidine]-1'-yl}pro-panoate (1.04 g; 67%). $^1$H NMR (400 MHz, CDCl$_3$-d) δ ppm 7.34 (d, J=8.0 Hz, 2H), 7.01-7.15 (m, 6H), 4.40 (s, 2H), 2.88-2.94 (m, 2H), 2.67-2.74 (m, 2H), 2.42-2.48 (m, 2H), 2.04-2.13 (m, 2H), 1.92-2.20 (m, 2H), 1.72-1.88 (m, 2H), 1.47 (s, 9H). Rt 1.58 min (System B), [M+H]$^+$ 488.1

The following compounds were obtained according to a similar manner. The aldehydes are commercially available and or described before:

Tert-butyl 3-{6-[(E)-2-(2-chlorophenyl)ethenyl]-2H-spiro[1-benzofuran-3,4'-piperidine]-1'-yl}propanoate.

Tert-butyl 3-{6-[(E)-2-phenylethenyl]-2H-spiro[1-benzofuran-3,4'-piperidine]-1'-yl}propanoate.

Tert-butyl 3-{6-[(E)-2-(4-fluorphenyl)ethenyl]-2H-spiro[1-benzofuran-3,4'-piperidine]-1'-yl}propanoate.

Tert-butyl 3-{6-[(E)-2-(2,6-dichloro-3-ethylphenyl)ethenyl]-2H-spiro[1-benzofuran-3,4'-piperidine]-1'-yl}propanoate.

Tert-butyl 3-{6-[(E)-2-(2,6-dichloro-4-cyclopropylphenyl)ethenyl]-2H-spiro[1-benzofuran-3,4'-piperidine]-1'-yl}propanoate.

Tert-butyl 3-{6-[(E)-2-(4-butyl-2,6-dichlorophenyl)ethenyl]-2H-spiro[1-benzofuran-3,4'-piperidine]-1'-yl}propanoate.

Tert-butyl 3-{6-[(1Z)-3,3,3-trifluoro-2-phenylprop-1-en-1-yl]-2H-spiro[1-benzofuran-3,4'-piperidine]-1'-yl}propanoate. The required potassium trifluoro[(1Z)-3,3,3-trifluoro-2-phenylprop-1-en-1yl]boronate was prepared as follows: 2,2,2-trifluoro-1-phenylethan-1-one was converted to [(1E)-1-bromo-3,3,3-trifluoroprop-1-en-2-yl]benzene and [(1Z)-1-bromo-3,3,3-trifluoroprop-1-en-2-yl]benzene (4:1) and in a similar manner as 2-[(E)-2-bromoethenyl]-1,3-dichlorobenzene. This mixture was converted into a mixture of the potassium trifluoro[(1E and Z)-3,3,3-trifluoro-2-phenylprop-1-en-1yl]boronates, which was reacted with tert-butyl 3-{6-bromo-2H-spiro[1-benzofuran-3,4'-piperidine]-1'-yl}propanoate to afford a mixture, which was purified (HPLC) to afford the title compound. $^1$H NMR (400 MHz, CDCl$_3$-d) δ ppm 7.37-7.43 (m, 3 H), 7.27-7.31 (m, 2 H), 7.12-7.15 (m, 1 H), 6.93 (d, J=7.8 Hz, 1 H), 6.62 (dd, J=7.8, 1.2 Hz, 1 H), 6.33 (d, J=1.2Hz, 1 H), 4.28 (s, 2 H), 2.82-2.89 (m, 2 H), 2.67 (t, J=7.4 Hz, 2 H), 2.42 (t, J=7.4 Hz, 2H), 1.97-2.07 (m, 2H), 1.83-1.92 (m, 2 H), 1.63-1.69 (m, 2 H), 1.45 (s, 9 H). HPLC conditions were: Chiralpak AD 20 um, 60 mL/min. Eluens heptane:EtOH (8:2).

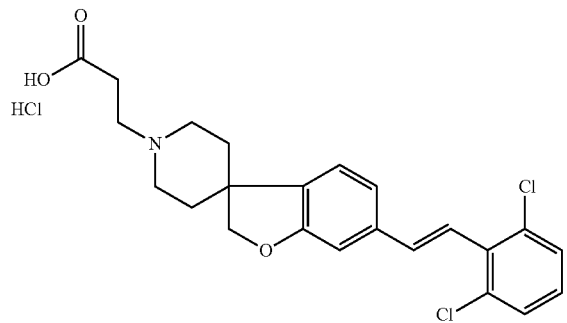 [SMILES: Cl ; O=C(O)CCN1CCC2(CC1)COc1cc(/C=C/c3c(Cl)cccc3Cl)ccc12]

Compound 160. 3-{6-[(E)-2-(2,6-Dichlorophenyl)ethenyl]-2H-spiro[1-benzofuran-3,4'-piperidine]-1'-yl}propanoic acid hydrochloride Tert-butyl 3-{6-[(E)-2-(2,6-dichlorophenyl)ethenyl]-2H-spiro[1-benzofuran-3,4'-piperidine]-1'-yl}propanoate (1.04 g, 2.13 mmol) was dissolved in a 4M solution of HCl in 1,4-dioxane (20 mL; 4 mol/l; 80 mmol) and stirred for 48 hours at RT. Subsequently, the solvent was removed in vacuo and the residue treated with iPr$_2$O, the precipitate was collected by filtration and dried overnight under reduced pressure to afford the product (0.93 g, 89.4%). $^1$H NMR (400 MHz, DMSO-d$_6$) δ ppm 12.70 (bs, 1H), 10.30 (bs, 1H), 7.53 (d, J=8.1 Hz, 2H), 7.30-7.35 (m, 1H), 6.99-7.25 (m, 5H), 4.51 (s, 2H), 3.41-3.55 (m, 2H), 3.30-3.39 (m, 2H), 3.01-3.19 (m, 2H), 2.85 (t, J=7.5 Hz, 2H), 2.13-2.25 (m, 2H), 1.86-1.95 (m, 2H). Rt 1.49 min (System B), [M+H]$^+$ 432.1

The following compounds were obtained according to a similar manner.

Compound 161. 3-{6-[(E)-2-(2-Chlorophenyl)ethenyl]-2H-spiro[1-benzofuran-3,4'-piperidine]-1'-yl}propanoic acid hydrochloride Rt 1.42 min (System B), [M+H]+ 398.0

Compound 162. 3-{6-[(E)-2-Phenylethenyl]-2H-spiro[1-benzofuran-3,4'-piperidine]-1'-yl}propanoic acid hydrochloride 1H NMR (400 MHz, DMSO-d6) δ ppm 12.64 (bs, 1H), 10.55 (bs, 1H), 7.59 (d, J=8 Hz, 2H), 7.38 (t, J=8 Hz, 2H), 7.27 (t, J=8 Hz, 1H), 7.22 (s, 2H), 7.10-7.17 (m, 3H), 4.50 (bs, 2H), 3.28-3.52 (m, 4H), 3.01-3.18 (m, 2H), 2.86 (t, J=8 Hz, 2H), 2.16-2.28 (m, 2H), 1.87-1.95 (m, 2H).

Compound 163. 3-{6-[(E)-2-(4-Fluorphenyl)ethenyl]-2H-spiro[1-benzofuran-3,4'-piperidine]-1'-yl}propanoic acid hydrochloride 1H NMR (400 MHz, DMSO-d6) δ ppm 12.70 (bs, 1H), 10.10 (bs, 1H), 7.63 (dd, J=8.6, 5.5 Hz, 2H), 7.04-7.28 (m, 7H), 4.49 (bs, 2H), 3.42-3.54 (m, 2H), 3.30-3.38 (m, 2H), 3.01-3.15 (m, 2H), 2.83 (t, J=7.6 Hz, 2H), 2.12-2.22 (m, 2H), 1.86-1.94 (m, 2H).

Compound 164. 3-{6-[(E)-2-(2,6-Dichloro-3-ethylphenyl)ethenyl]-2H-spiro[1-benzofuran-3,4'-piperidine]-1'-yl}propanoic acid hydrochloride Rt 1.54 min (System B), [M+H]+ 460.0

Compound 165. 3-{6-[(E)-2-(2,6-Dichloro-4-cyclopropylphenyl)ethenyl]-2H-spiro[1-benzofuran-3,4'-piperidine]-1'-yl}propanoic acid hydrochloride Rt 1.56 min (System B), [M+H]+ 472.0

Compound 166. 3-{6-[(E)-2-(4-Butyl-2,6-dichlorophenyl)ethenyl]-2H-spiro[1-benzofuran-3,4'-piperidine]-1'-yl}propanoic acid hydrochloride Rt 1.70 min (System B), [M+H]+ 488.0

Compound 167. 3-{6-[(1Z)-3,3,3-Trifluoro-2-phenylprop-1-en-1-yl]-2H-spiro[1-benzofuran-3,4'-piperidine]-1'-yl}propanoic acid hydrochloride 1H NMR (400 MHz, DMSO-d6) δ ☐ ppm 12.70 (bs., 1 H), 9.60 (bs., 1 H), 7.41-7.52 (m, 5 H), 7.30 (s, 1 H), 7.15-7.25 (m, 1 H), 7.01 (d, J=7.7 Hz, 1 H), 6.90 (s, 1 H), 4.53 (s, 2 H), 3.48-3.56 (m, 2 H), 3.30-3.41 (m, 2 H), 3.02-3.20 (m, 2 H), 2.80 (t, J=7.4 Hz, 3 H), 2.06-2.17 (m, 2 H), 1.94 (bd, J=14.1 Hz, 2H). Rt 1.55 min (System B), [M+H]+ 432.0

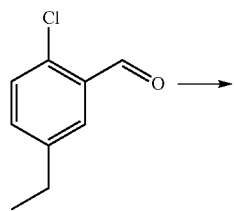

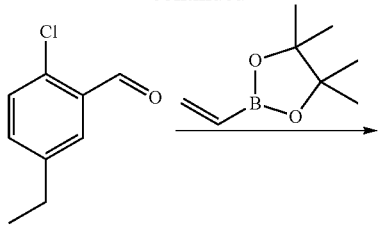

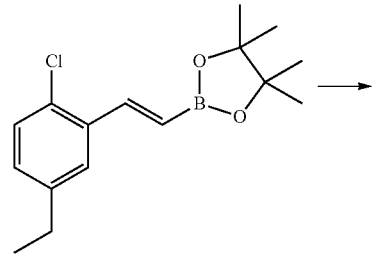

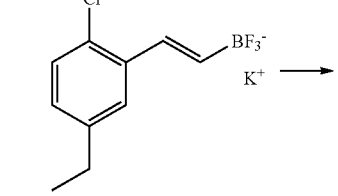

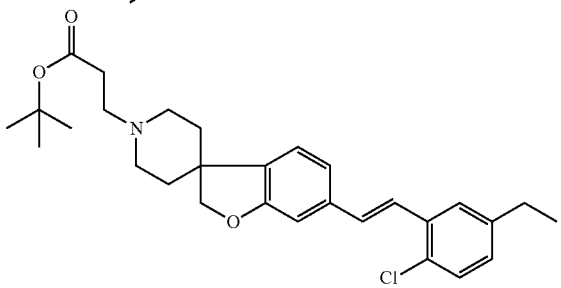

Tert-butyl 3-{6-[(E)-2-(2-Chloro-5-ethylphenyl)ethenyl]-2H-spiro[1-benzofuran-3,4'-piperidine]-1'-yl}propanoate.

To a solution of Methyltriphenylphosphonium bromide (5.77 g; 16.15 mmol), dissolved in THF (25 ml) was added potassium tert-butoxide (1.81 g; 16.15 mmol) in THF (50 mL), at −78° C. (Adv. Synth. Catal., 2006, 348, 851). The reaction mixture was stirred for 1.5 hours. Subsequently, a solution of 2-chloro-5-ethylbenzaldehyde (2.27 g; 13.45 mmol) (obtained from the already described 2-chloro-5-ethylbenzaldehyde by oxidation (Manganese dioxide in acetonitrile (69%)), dissolved in THF (30 mL), was added dropwise at −78° C. The resulting mixture was stirred and allowed to warm to RT overnight. The reaction was quenched by the addition of a saturated aqueous NaH4Cl solution. The resulting mixture was extracted with Et2O and washed with brine. The organic layer was dried (Na2SO4), filtered, and concentrated in vacuo. The residue was purified by column chromatography (SiO2, hexanes) to afford 1-chloro-2-ethenyl-4-ethylbenzene (2.11 g; 94%)

To a degassed mixture of 1-chloro-2-ethenyl-4-ethylbenzene (2.1 g; 12.6 mmol) in dichloromethane (50 mL), was added subsequently Vinylboronic acid pinacol ester (1.94 mL; 11.46 mmol) and Hoveyda-Grubbs catalyst 2nd generation (0.36 g; 0.57 mmol) (Tetrahedron, (65), 2009, 3130). The resulting mixture was heated overnight (40° C.). After cooling to RT, the reaction mixture was diluted with EtOAc and washed with H2O. The organic layer was dried (Na2SO4), filtered, and concentrated in vacuo. The residue was purified by column chromatography (SiO₂, hexanes) to afford of 2-[(E)-2-(2-chloro-5-ethylphenyl)ethenyl]-4,4,5,5-tetramethyl-1,3,2-dioxaborolane (2.32 g; 69%), which was used as such for the conversion to tert-butyl 3-{6-[(E)-2-(2-chloro-5-ethylphenyl)ethenyl]-2H-spiro[1-benzofuran-3,4'-piperidine]-1'-yl}propane-ate using similar conditions as described for the precursor of compound 160.

The following compounds were obtained according to a similar manner.

Tert-butyl 3-{6-[(E)-2-(2,5-dichlorophenyl)ethenyl]-2H-spiro[1-benzofuran-3,4'-piperidine]-1'-yl}propanoate.

Tert-butyl 3-{6-[(E)-2-(3-methylphenyl)ethenyl]-2H-spiro [1-benzofuran-3,4'-piperidine]-1'-yl}propanoate.

Tert-butyl 3-{6-[(E)-2-(2-fluorophenyl)ethenyl]-2H-spiro [1-benzofuran-3,4'-piperidine]-1'-yl}propanoate.

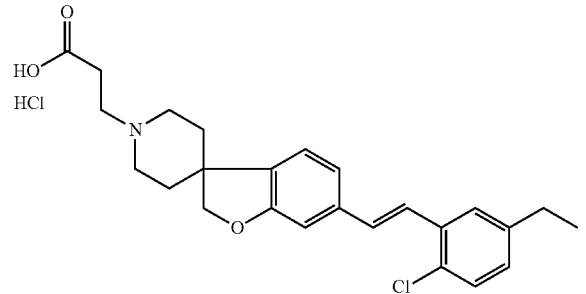 [SMILES: Cl ; CCc1ccc(Cl)c(/C=C/c2ccc3c(c2)OCC32CCN(CCC(=O)O)CC2)c1]

Compound 168. 3-{6-[(E)-2-(2-Chloro-5-ethylphenyl)ethenyl]-2H-spiro[1-benzofuran-3,4'-piperidine]-1'-yl}propanoic acid hydrochloride Tert-butyl 3-{6-[(E)-2-(2,6-dichlorophenyl)ethenyl]-2H-spiro[1-benzofuran-3,4'-piperidine]-1'-yl}propanoate (1.04 g, 2.13 mmol) was dissolved in a 4M solution of HCl in 1,4-dioxane (20 mL; 4 mol/l; 80 mmol) and stirred for 48 hours at RT. Subsequently, the solvent was removed in vacuo and the residue treated with iPr₂O, the precipitate was collected by filtration and dried overnight under reduced pressure to afford the product (0.93 g, 89.4%). Rt 1.53 min (System B), [M+H]⁺ 426.0.

The following compounds were obtained according to a similar manner.

Compound 169. 3-{6-[(E)-2-(2,5-Dichlorophenyl)ethenyl]-2H-spiro[1-benzofuran-3,4'-piperidine]-1'-yl}propanoic acid hydrochloride ¹H NMR (400 MHz, DMSO-d₆) δ ppm 12.90 (bs, 1H), 10.20 (bs, 1H), 7.94 (d, J=3.0 Hz, 1H), 7.52 (d, J=8.1 Hz, 1H), 7.27-7.46 (m, 3H), 7.09-7.23 (m, 3H), 4.52 (bs, 2H), 3.46-3.56 (m, 2H), 3.26-3.35 (m, 2H), 3.00-3.14 (m, 2H), 2.86 (t, J=7.7 Hz, 2H), 2.16-2.30 (m, 2H), 1.85-1.95 (m, 2H). Rt 1.50 min (System B), [M+H]⁺ 432.0.

Compound 170. 3-{6-[(E)-2-(3-Methylphenyl)ethenyl]-2H-spiro[1-benzofuran-3,4'-piperidine]-1'-yl}propanoic acid hydrochloride Rt 1.37 min (System B), [M+H]⁺ 378.1

Compound 171. 3-{6-[(E)-2-(2-Fluorophenyl)ethenyl]-2H-spiro[1-benzofuran-3,4'-piperidine]-1'-yl}propanoic acid hydrochloride ¹H NMR (400 MHz, DMSO-d₆) δ ppm 12.90 (bs, 1H), 10.50 (bs, 1H), 7.78 (t, J=7.7 Hz, 1H), 7.01-7.40 (m, 8H), 4.50 (br. s., 2H), 3.42-3.56 (m, 2H), 3.26-3.39 (m, 2H), 3.00-3.14 (m, 2H), 2.87 (t, J=7.7 Hz, 2H), 2.16-2.32 (m, 2H), 1.83-1.95 (m, 2H). Rt 1.34 min (System B), [M+H]⁺ 382.1.

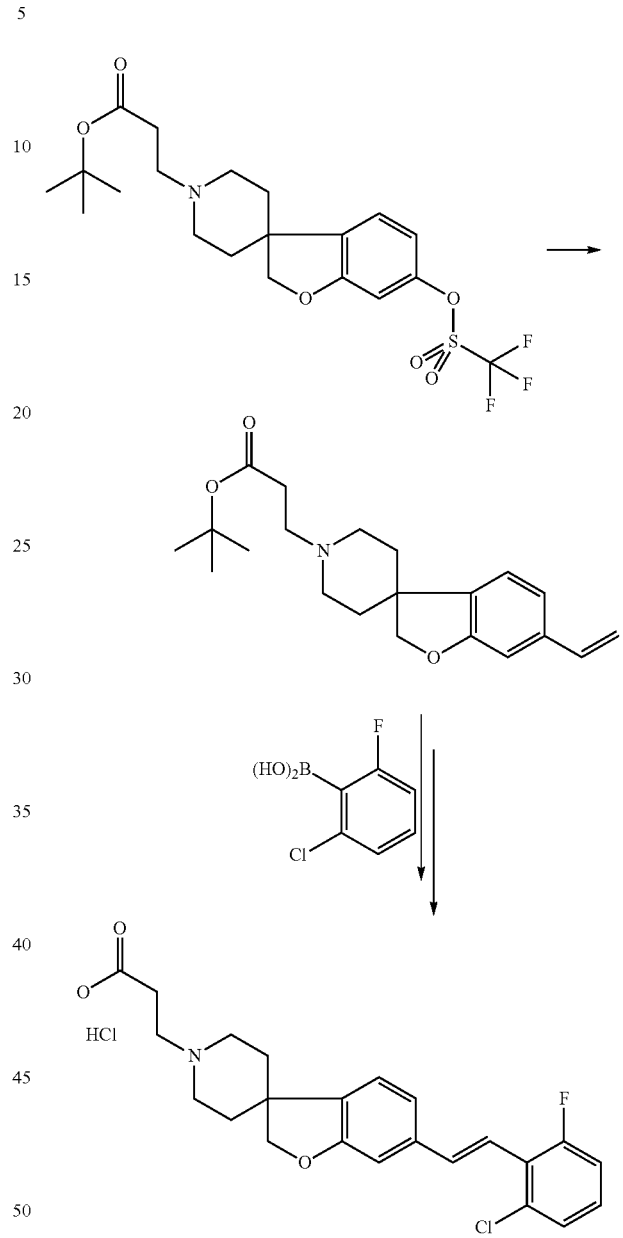

Compound 301. 3-{6-[(E)-2-(2-Chloro-6-fluorophenyl)ethenyl]-2H-spiro[1-benzofuran-3,4'-piperidine]-1'-yl}propanoic acid hydrochloride To a nitrogen purged solution of tert-butyl 3-{-{6-[(trifluoromethane)sulfonyloxy]-2H-spiro[1-benzofuran-3,4'-piperidine]-1'-yl]propanoate (600 mg, 1.29 mmol) and tributyl-(ethenyl)stannane (0.37 mL; 1.29 mmol) in 1,4-dioxane (25 mL) was added lithium chloride (164 mg; 3.87 mmol) followed by tetrakis(triphenylphosphine)palladium(0) (149 mg; 0.13 mmol) (Tetrahedron Letters, 48 (2007), 323-326). This mixture was stirred in a pre-heated oilbath (110° C.) for 70 min. Subsequently, the reaction mixture was cooled, diluted with Et₂O and filtered. The organic layer was washed with 5% aqueous KF, dried (Na₂SO₄), filtered, and concentrated in vacuo. The residue was purified by column chromatography (SiO₂, dichloromethane:acetone 9:1) to afford tert-butyl 3-{6-(ethenyl-2H-spiro[1-benzofuran-3,4'-piperidine]-1'-yl}propanoate (330 mg; 74.5%). ¹H NMR (400 MHz, CDCl₃-d) δ ppm 7.07 (d, J=8 Hz, 1H), 6.91 (dd, J=8 and 2Hz, 1H), 6.87 (d, J=2Hz, 1H), 6.66 (dd, J=10 and 10 Hz, 1H), 5.68 (d, J=18 Hz, 1H), 5.19 (d, J=10 Hz, 1H), 4.36 (s, 2H), 2.86-2.93 (m, 2H), 2.69 (t, J=8 Hz, 2H), 2.45 (t, J=8 Hz, 2H), 2.03-2.11 (m, 2H), 1.91-1.99 (m, 2H), 1.69-1.76 (m, 2H), 1.46 (s, 9H). For the Oxidative Heck cross-coupling (Synthesis (2010), 1399-1427), a mixture of tert-butyl 3-{6-(ethenyl-2H-spiro[1-benzofuran-3,4'-piperidine]-1'-yl}propanoate (100 mg; 0.29 mmol), palladium acetate (10 mg; 0.04 mmol), BIAN (bis(aryl)acenaphthequinodiimine) (J. Org. Chemistry in press (2011) (24 mg; 0.06 mmol) and 2-chloro-6-fluorophenylboronic acid (76 mg; 0.44 mmol) were dissolved in 5 ml N,N-dimethylformamide. The (open vessel) reaction mixture was stirred overnight (90° C.). Additional palladium acetate (5 mg), BIAN (bis(aryl)acenaphthe-quinodiimine) (12 mg) and 2-chloro-6-fluorophenylboronic acid (50 mg) were added and the reaction mixture was stirred for another 24 hours (90° C.). Subsequently, the reaction mixture was cooled, diluted with EtOAc and washed with 5% aqueous NaHCO₃, dried (Na₂SO₄), filtered, and concentrated in vacuo. The residue was purified by column chromatography (SiO₂, dichloromethane:acetone 9:1) to afford tert-butyl 3-{6-[(E)-2-(2-Chloro-6-fluorophenyl)ethenyl]-2H-spiro[1-benzofuran-3,4'-piperidine]-1'-yl}propanoate (70 mg; 43.3%). Rt 1.50 min (System B), [M+H]⁺ 472.2, which was converted to 3-{6-[(E)-2-(2-Chloro-6-fluorophenyl)ethenyl]-2H-spiro[1-benzofuran-3,4'-piperidine]-1'-yl}-propanoic acid hydrochloride (69%) (as described for compound 168). ¹H NMR (400 MHz, DMSO-d₆) δ ppm 12.73 (br s, 1H), 10.91 (br s, 1H), 7.10-7.41 (m, 8H), 4.51 (br s, 2H), 3.29-3.52 (m, 4H), 3.02-3.13 (m, 2H), 2.83 (t, J=8 Hz, 2H), 2.12-2.22 (m, 2H), 1.87-1.95 (m, 2H). Rt 1.42 min (System B), [M+H]⁺ 416.2

Compound 302. 3-{6-[(E)-2-(2-Cyclopropyl-6-fluorophenyl)ethenyl]-2H-spiro[1-benzofuran-3,4'-piperidine]-1'-yl}propanoic acid hydrochloride Tert-butyl 3-{6-[(E)-2-(2-bromo-6-fluorophenyl)ethenyl]-2H-spiro[1-benzofuran-3,4'-piperidine]-1'-yl}-propanoate (prepared according to the synthesis of compound 301), Rt 1.42 min (System B), [M+H]⁺ 518.5, was reacted with potassium cyclopropyltrifluoroboronate (Tetrahedron Letters, 2008, 4122-4124), using the conditions described for compound 71 (53%) to afford tert-butyl 3-{6-[(E)-2-(2-cyclopropyl-6-fluorophenyl)ethenyl]-2H-spiro[1-benzofuran-3,4'-piperidine]-1'-yl}propanoate. Rt 1.53 min (System B), [M+H]⁺ 478.7, which was converted to 3-{6-[(E)-2-(2-cyclopropyl-6-fluorophenyl)ethenyl]-2H-spiro[1-benzofuran-3,4'-piperidine]-1'-yl}pro-panoic acid hydrochloride (69%) (as described for compound 168). ¹H NMR (400 MHz, DMSO-d₆) δ ppm 11.73 (br s, 1H), 10.09 (br s, 1H), 7.39 (d, J=16 Hz, 1H), 7.04-7.22 (m, 6H), 6.91 (d, J=8 Hz, 1H), 4.52 (br s, 2H), 3.48-3.58 (m, 2H), 3.03-3.13 (m, 2H), 2.85 (t, J=8 Hz, 2H), 2.09-2.25 (m, 5H), 1.87-1.95 (m, 2H), 0.97-1.02 (m, 2H), 0.70-0.74 (m, 2H). Rt 1.46 min (System B), [M+H]⁺ 422.7

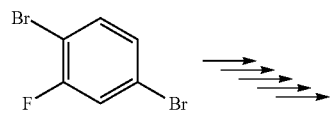

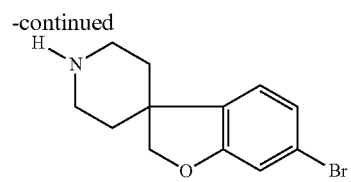

6-Bromo-2H-spiro[1-benzofuran-3,4'-piperidine]

4-Pyridinemethanol (17.56 g; 160.9 mmol) was dissolved in 1-methyl-2-pyrrolidinone (150 mL) and sodium hydride (60% in mineral oil; 6.44 g; 160.9 mmol) was added. The mixture was stirred for 10 minutes at ambient temperature. This mixture was subsequently added to 1,4-dibromo-2-fluorobenzene (20.43 g; 80.47 mmol), dissolved in 1-methyl-2-pyrrolidinone (250 mL). The resulting reaction mixture was heated to 100° C. TLC showed a complete conversion within 5 minutes. After cooling to RT, the reaction mixture was diluted with EtOAc, and washed with a 5% aqueous NaHCO₃ solution. The organic layer was washed several times with H₂O, dried (Na₂SO₄), filtered, and concentrated in vacuo. The residue was purified by column chromatography (SiO₂, Et₂O:hexanes 2:1 to pure Et₂O) to afford 4-(2,5-dibromophenoxymethyl)pyridine (17.4 g; 63%), which was dissolved in acetone (260 mL). To this reaction mixture was added benzyl bromide (6.37 mL; 53.26 mmol) and the mixture was stirred overnight at 40° C. Subsequently, the mixture was concentrated in vacuo yielding 1-benzyl-4-(2,5-dibromophenoxymethyl)pyridin-1-ium bromide (24.9 g; 95%), which was dissolved in MeOH (225 mL). To this cooled (−10° C.) reaction mixture was added sodium borohydride (4.51 g; 119.50 mmol). After the addition was complete the mixture was allowed to warm to RT and stirred for 4 hours. Subsequently, the mixture was cooled to 0° C., water was added, and the MeOH evaporated in vacuo. To the aqueous solution was added a 5% aqueous NaHCO₃ solution and Et₂O. The layers were separated and the organic layer was dried (Na₂SO₄), filtered and concentrated in vacuo. The residue was purified by column chromatography (SiO₂, Et₂O:hexanes 1:1) to afford the product: 1-benzyl-4-(2,5-dibromophenoxymethyl)-1,2,3,6-tetrahydropyridine (19.78 g; 94%). Rt 1.37 min (System B), [M+H]⁺ 437.8.

To a intensively degassed mixture of 1-benzyl-4-(2,5-dibromophenoxy-methyl)-1,2,3,6-tetrahydropyridine (8 g; 18.3 mmol) in 75 mL benzene was added subsequently, 2,2'-azobis(2-methylpropionitrile) (0.12 g; 0.73 mmol) and tri-n-butyltinhydride (7.4 mL; 27.45 mmol). The reaction mixture was heated for 72 hour at 115° C. After cooling to RT, the mixture was diluted with Et₂O and washed with 10% aqueous KF. The organic layer was dried (Na₂SO₄), filtered and concentrated in vacuo. The residue was purified by repeated column chromatography (SiO₂, Et₂O:hexanes 1:1) to afford the product: 1'-benzyl-6-bromo-2H-spiro[1-benzofuran-3,4'-piperidine] (1.3 g; 20%), ¹H NMR (400 MHz, CDCl₃-d) δ ppm 7.24-7.35 (m, 5H), 6.97-7.02 (m, 2H), 6.91-6.94 (m, 1H), 4.38 (s, 2H), 3.53 (s, 2H), 2.85-2.92 (m, 2H), 1.90-2.07 (m, 4H), 1.67-1.74 (m, 2H). This product was dissolved in 1,2-dichloroethane (20 mL) at 0° C. Subsequently, 1-chloroethyl chloroformate (0.98 mL; 9.07 mmol) was added and the reaction mixture was stirred for 15 minutes. The crude reaction mixture was concentrated in vacuo. Toluene (100 mL) was added and the mixture was concentrated. This last step was repeated twice. MeOH (20 mL) was added and the mixture was stirred overnight. The reaction mixture was concentrated in vacuo to afford 6-bromo-2H-spiro[1-benzofuran-3,4'-piperidine]hydrochloride (1.1 g; 99%). $^1$H NMR (400 MHz, DMSO-d$_6$) δ ppm 8.80-9.15 (m, 2H), 7.05-7.11 (m, 3H), 4.53 (s, 2H), 3.25-3.32 (m, 2H), 2.92-3.03 (m, 2H), 2.05 (dt, J=13.6, 4.2Hz, 2H), 1.78-1.85 (m, 2H). The product was dissolved in MeOH (5 mL) and filtered through a tosic acid solid phase extraction cartridge, washing with MeOH, and eluting with 2 N NH$_3$/MeOH. The product was concentrated to give 5.42 mol) was added tert-butyl bromoacetate (0.42 g; 2.17 mmol). The resulting mixture was heated at 65° C. overnight.

After cooling to RT, the reaction mixture was partitioned between 5% aqueous NaHCO$_3$ solution and EtOAc. The layers were separated and the organic layer was dried (Na$_2$SO$_4$), filtered, and concentrated. The residue was purified by column chromatography (SiO$_2$, Et$_2$O:hexanes 1:1) to afford the product (0.46 g, 66.7%). Rt 2.59 min (System B), [M+H]$^+$ 383.9

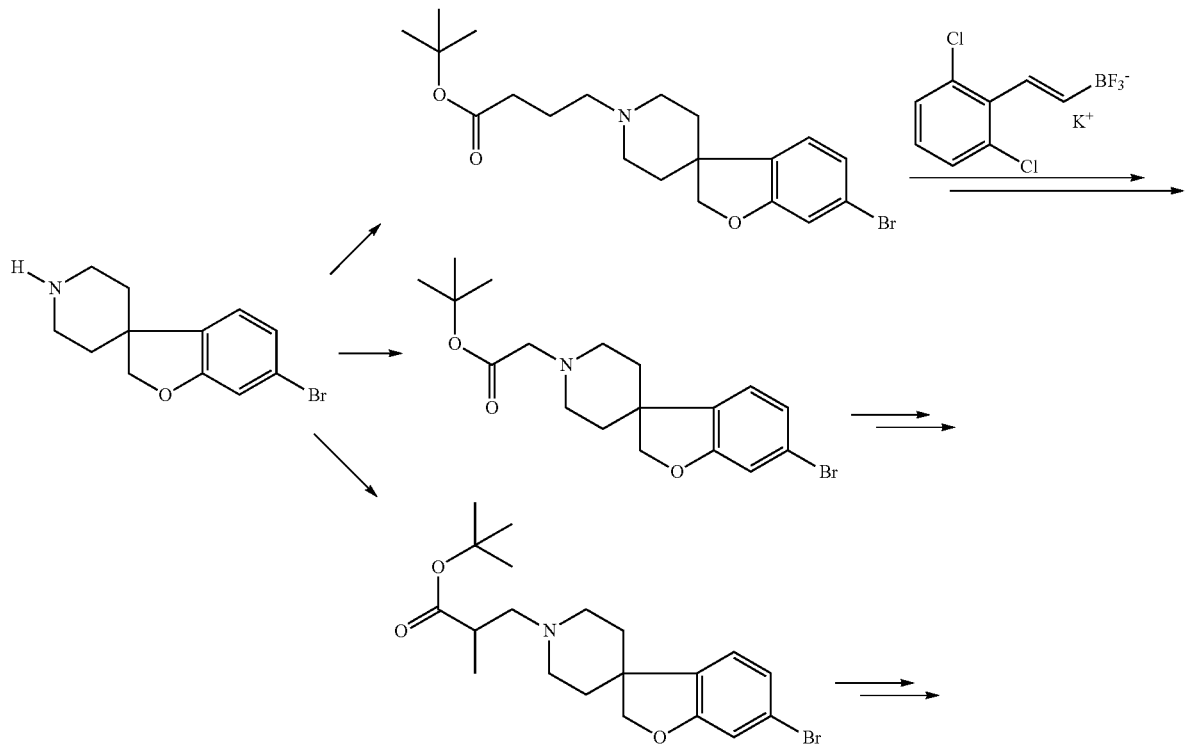

6-bromo-2H-spiro[1-benzofuran-3,4'-piperidine] (0.8 g). Rt 1.05 min (System B), [M+H]$^+$ 270.0

Tert-butyl 4-{6-bromo-2H-spiro[1-benzofuran-3,4'-piperidine]-1'-yl}butanoate. To a suspension of 6-bromo-2H-spiro[1-benzofuran-3,4'-piperidine]hydrochloride (0.55 g; 1.81 mmol) in CH$_3$CN (35 mL) was added potassiumcarbonate (0.75 g; 5.42 mmol), potassium iodide (0.36 g; 2.17 mmol), followed by 4-bromo-butyric acid tert-butyl ester (0.48 g; 2.17 mmol). The resulting mixture was heated at 65° C. overnight.

After cooling to RT, the reaction mixture was partitioned between 5% aqueous NaHCO$_3$ solution and EtOAc. The layers were separated and the organic layer was dried (Na$_2$SO$_4$), filtered, and concentrated. The residue was purified by column chromatography (SiO$_2$, Et$_2$O:hexanes 2:1) to afford the product (0.54 g, 72%). $^1$H NMR (400 MHz, CHLOROFORM-d) δ ppm 7.00 (dd, J=7.8, 1.5 Hz, 1H), 6.97 (d, J=7.8 Hz, 1H) 6.93 (d, J=1.5 Hz, 1H), 4.37 (s, 2H), 2.88-2.94 (m, 2H), 2.34-2.40 (m, 2H), 2.27 (t, J=7.4 Hz, 2H), 1.89-2.03 (m, 4H) 1.69-1.85 (m, 4H), 1.45 (s, 9H). Rt 1.30 min (System B), [M+H]$^+$ 412.0.

Tert-butyl 2-{6-bromo-2H-spiro[1-benzofuran-3,4'-piperidine]-1'-yl}acetate. To a suspension of 6-bromo-2H-spiro[1-benzofuran-3,4'-piperidine]hydrochloride (0.55 g; 1.81 mmol) in CH$_3$CN (35 mL) and potassium carbonate (0.75 g;

Tert-butyl 3-{6-bromo-2H-spiro[1-benzofuran-3,4'-piperidine]-1'-yl}-2-methyl-propanoate. To a suspension of 6-bromo-2H-spiro[1-benzofuran-3,4'-piperidine]hydrochloride (0.53 g; 1.74 mmol) in N,N-dimethylformamide (7 mL) was added tert-butyl methacrylate (0.57 mL; 3.48 mmol) and DBU (0.78 mL; 5.22 mmol) The resulting mixture was heated at 140° C. in a sealed flask overnight.

After cooling to RT the reaction mixture was partitioned between 5% aqueous NaHCO$_3$ solution and EtOAc. The layers were separated and the organic layer was dried (Na$_2$SO$_4$), filtered, and concentrated. The residue was purified by column chromatography (SiO$_2$, Et$_2$O: hexanes 1:1) to afford the product (436 mg, 61%).
Rt 1.36 min (System B), [M+H]$^+$ 412.0.

Tert-butyl 4-{6-[(E)-2-(2,6-dichlorophenyl)ethenyl]-2H-spiro[1-benzofuran-3,4'-piperidine]-1'-yl}butanoate. To a degassed mixture of tert-butyl 3-{6-bromo-2H-spiro[1-benzofuran-3,4'-piperidine]-1'-yl}butanoate (0.26 g; 0.63 mmol) and potassium 2-[(E)-2-(2,6-dichlorophenyl)ethenyl]-1trifluoroboronate (0.21 g, 0.76 mmol) in toluene (9 mL) and water (3 mL), was added subsequently, cesium carbonate (0.71 g; 2.17 mmol), and 1',1'-bis(diphenyl-phosphino)-ferrocene palladium(II)di-chloride dichloromethane complex (26 mg; 0.03 mmol). The resulting mixture was heated overnight (100° C.). After cooling to RT, the reaction mixture was diluted with EtOAc, filtered and washed with 5% aqueous NaHCO₃. The organic layer was dried (Na₂SO₄), filtered, and concentrated in vacuo. The residue was purified by column chromatography (SiO₂, Et₂O:hexanes 1:1 followed by 3:1) to afford tert-butyl 3-{6-[(E)-2-(2,6-dichlorophenyl)ethenyl]-2H-spiro[1-benzofuran-3,4'-piperidine]-1'-yl}buta-noate (257 mg; 80%). Rt 1.57 min (System B), [M+H]⁺ 502.2

Tert-butyl 2-{6-[(E)-2-(2,6-dichlorophenyl)ethenyl]-2H-spiro[1-benzofuran-3,4'-piperidine]-1'-yl}acetate. To a degassed mixture of tert-butyl 3-{6-bromo-2H-spiro[1-benzofuran-3,4'-piperidine]-1'-yl}acetate (244 mg; 0.59 mmol) and potassium 2-[(E)-2-(2,6-dichlorophenyl)ethenyl]-ltrifluoroboronate (196 mg, 0.76 mmol) in toluene (9 mL) and water (3 mL), was added subsequently, cesium carbonate (0.65 g; 2 mmol), and 1',1'-bis(diphenyl-phosphino)-ferrocene palladium(II)dichloride dichloromethane complex (24 mg; 0.03 mmol). The resulting mixture was heated overnight (100° C.). After cooling to RT, the reaction mixture was diluted with EtOAc, filtered and washed with 5% aqueous NaHCO₃. The organic layer was dried (Na₂SO₄), filtered, and concentrated in vacuo. The residue was purified by column chromatography (SiO₂, Et₂O:hexanes 1:1 followed by 3:1) to afford Tert-butyl 3-{6-[(E)-2-(2,6-dichlorophenyl)ethenyl]-2H-spiro[1-benzofuran-3,4'-piperidine]-1'-yl}butanoate (187 mg; 67%). ¹H NMR (400 MHz, CHLOROFORM-d) δ ppm 6.96-7.02 (m, 2H), 6.93 (d, J=1.1 Hz, 1H), 4.38 (s, 2H), 3.17 (s, 2H), 2.93-2.99 (m, 2H), 2.27 (dt, J=12.5 and 2.5 Hz, 2H), 2.03 (dt, J=12.5, 4.0 Hz, 2H), 1.68-1.76 (m, 2H), 1.48 (s, 9H). Rt 1.62 min (System B), [M+H]⁺ 474.2.

Tert-butyl 3-{6-[(E)-2-(2,6-dichlorophenyl)ethenyl]-2H-spiro[1-benzofuran-3,4'-piperidine]-1'-yl}-2-methylpropanoate. To a degassed mixture of tert-butyl 3-{6-bromo-2H-spiro[1-benzofuran-3,4'-piperidine]-1'-yl}-2-methylpropanoate (218 mg; 0.53 mmol) and potassium 2-[(E)-2-(2,6-dichlorophenyl)ethenyl]-ltrifluoroboronate (178 mg, 0.64 mmol) in toluene (9 mL) and water (3 mL), was added subsequently, cesium carbonate (520 mg; 1.59 mmol), and 1',1'-bis(diphenyl-phosphino)-ferrocene palladium(II)dichloride dichloromethane complex (22 mg; 0.03 mmol). The resulting mixture was heated overnight (1000 C). After cooling to RT, the reaction mixture was diluted with EtOAc, filtered and washed with 5% aqueous NaHCO₃. The organic layer was dried (Na₂SO₄), filtered, and concentrated in vacuo. The residue was purified by column chromatography (SiO₂, Et₂O:hexanes 1:2) to afford tert-butyl 3-{6-[(E)-2-(2,6-dichlorophenyl)ethenyl]-2H-spiro[1-benzofuran-3,4'-piperidine]-1'-yl}-2-methyl-propanoate (197 mg; 31.6%). Rt 1.63 min (System B), [M+H]⁺ 502.0.

Compound 172. 4-{6-[(E)-2-(2,6-Dichlorophenyl) ethenyl]-2H-spiro[1-benzofuran-3,4'-piperidine]-1'-yl}butanoic acid hydrochloride Tert-butyl 3-{6-[(E)-2-(2,6-dichlorophenyl)ethenyl]-2H-spiro[1-benzofuran-3,4'-piperidine]-1'-yl}butanoate (257 mg, 0.51 mmol) was dissolved in a 4M solution of HCl in 1,4-dioxane (10 mL; 4 mol/l; 40 mmol) and stirred for 48 hours at RT. Subsequently, the solvent was removed in vacuo and the residue treated with iPr₂O, the precipitate was collected by filtration and dried overnight under reduced pressure to afford the product (233 mg, 89.6%). ¹H NMR (400 MHz, DMSO-d₆) δ ppm 12.85 (bs., 1H), 9.90 (bs., 1H), 7.54 (d, J=8.1 Hz, 2H), 7.33 (t, J=8.1 Hz, 1H), 6.99-7.18 (m, 5H), 4.52 (bs., 2H), 3.41-3.55 (m, 2H), 3.00-3.17 (m, 4H), 2.24-2.40 (m, 4H), 1.84-2.01 (m, 4H). Rt 1.44 min (System B), [M+H]⁺ 446.0.

The following compounds were obtained according to a similar manner.

Compound 173. 2-{6-[(E)-2-(2,6-Dichlorophenyl) ethenyl]-2H-spiro[1-benzofuran-3,4'-piperidine]-1'-yl}acetic acid hydrochloride ¹H NMR (400 MHz, DMSO-d₆) δ ppm 14.10 (bs., 1H), 10.30 (bs., 1H), 7.54 (d, J=8.0 Hz, 2H), 7.33 (t, J=8.0 Hz, 1H), 7.00-7.25 (m, 5H), 4.50 (s, 2H), 4.19 (bs., 2H), 3.50-3.58 (m, 2H), 3.19-3.31 (m, 2H), 2.20-2.31 (m, 2H), 1.87-1.95 (m, 2H). Rt 1.67 min (System B), [M+H]⁺ 418.0.

Compound 174. 3-{6-[(E)-2-(2,6-Dichlorophenyl) ethenyl]-2H-spiro[1-benzofuran-3,4'-piperidine]-1'-yl}-2-methylpropanoic acid hydrochloride Rt 1.53 min (System B), [M+H]⁺ 446.0.

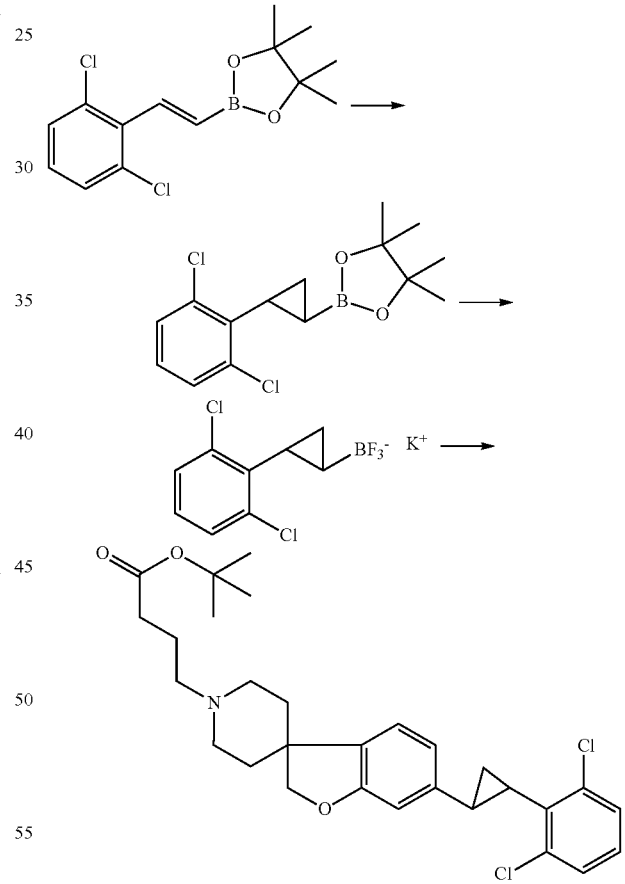

Tert-butyl 4-{6-[2-(2,6-dichlorophenyl)cyclopropyl]-2H-spiro[1-benzofuran-3,4'-piperidine]-1'-yl}butanoate. The required potassium [2-(2,6-dichlorophenyl)-cyclopropyl]-ltrifluoroboronate was prepared as follows: To freshly distilled dichloromethane (10 mL) was added Et₂Zn (6.02 mL; 1 mil in hexanes; 6.02 mmol) at 0° C. (J. Org. Chem., 69, (2), 2004, 327). To this solution was added (very slowly) trifluoroacetic acid (0.46 mL; 6.02 mmol) dissolved in dichloromethane (20 mL). After the addition was completed (75 minutes), the reaction mixture was stirred for 30 minutes at 0° C. Subsequently, a solution of diiodomethane (0.48 mL; 6.02 mmol) dissolved in dichloromethane (10 mL) was added and the resulting reaction mixture was stirred for an additional 20 minutes at 0° C. To this reaction mixture was added 2-[(E)-2-(2,6-dichlorophenyl)ethenyl]-4,4,5,5-tetramethyl-1,3,2-dioxaborolane (0.9 g; 3.01 mmol) in dichloromethane (10 mL), and allowed to warm to RT and stirred overnight. The reaction mixture was quenched with saturated aqueous NH$_4$Cl and diluted with EtOAc, filtered and washed with 5% aqueous NaHCO$_3$. The organic layer was dried (Na$_2$SO$_4$), filtered, and concentrated in vacuo. The residue was purified by column chromatography (SiO$_2$, Et$_2$O:hexanes 1:7) to afford 2-[2-(2,6-dichloro-phenyl)cyclopropyl]-4,4,5,5-tetramethyl-1,3,2-dioxaborolane.potassium (0.7 g; 74%), which was dissolved in MeOH (8 mL) and water (2 mL). Subsequently, potassium bifluoride (1.19 g; 15.21 mmol) was added and the reaction mixture was stirred at RT overnight. Subsequently, the solvents were removed in vacuo and the residue treated with toluene and concentrated in vacuo. The latter steps were repeated three times to remove all the water. The obtained solid was treated with hot acetonitrile (20 mL) and the acetonitrile was decanted. This was repeated 3 times. The combined acetonitrile layers were concentrated in vacuo and the residue was treated with Et$_2$O. The formed precipitate was collected by filtration and dried in vacuo to afford the potassium [2-(2,6-dichlorophenyl)cyclopropyl]-trifluoroboronate (0.41 g; 64%). $^1$H NMR (400 MHz, DMSO-d$_6$) δ ppm 7.3 (d, J=8.0 Hz, 2H), 7.13 (t, J=8.0 Hz, 1H), 1.37-1.44 (m, 1H), 0.65-0.71 (m, 1H), 0.36-0.43 (m, 1H), −0.09-0.01 (m, 1H). To a nitrogen purged mixture of tert-butyl 3-{6-bromo-2H-spiro[1-benzofuran-3,4'-piperidine]-1'-yl}butanoate (0.26 g; 0.63 mmol) and potassium [2-(2,6-dichlorophenyl)cyclopropyl]-ltrifluoroboronate (0.22 g, 0.76 mmol) in toluene (9 mL) and water (3 mL), was added subsequently, cesium carbonate (0.71 g; 2.17 mmol), and 1',1'-bis(diphenyl-phosphino)-ferrocene palladium(II)dichloride dichloromethane complex (26 g; 0.03 mmol) (Org. Lett., Vol 6, No 3, 2004, 357). The resulting mixture was heated overnight (100° C.). After cooling to RT, the reaction mixture was diluted with EtOAc, filtered and washed with 5% aqueous NaHCO$_3$. The organic layer was dried (Na$_2$SO$_4$), filtered, and concentrated in vacuo. The residue was purified by column chromatography (SiO$_2$, Et$_2$O) to afford Tert-butyl 4-{6-[2-(2,6-dichlorophenyl)-cyclopropyl]-2H-spiro[1-benzofuran-3,4'-piperidine]-1'-yl]butanoate (268 mg; 82%). Rt 1.61 min (System B), [M+H]$^+$ 516.0.

The following compounds were obtained according to a similar manner.

Tert-butyl 2-{6-[2-(2,6-dichlorophenyl)cyclopropyl]-2H-spiro[1-benzofuran-3,4'-piperidine]-1'-yl}acetate.

Tert-butyl 3-{6-[2-(2,6-dichlorophenyl)cyclopropyl]-2H-spiro[1-benzofuran-3,4'-piperidine]-1'-yl}-2-methylpropanoate.

Tert-butyl 3-{6-[2-(2,6-dichlorophenyl)cyclopropyl]-2H-spiro[1-benzofuran-3,4'-piperidine]-1'-yl}propanoate.

For the following compounds, the required potassium analogs of [2-(substituted-phenyl)cyclopropyl]-trifluoroboronates were obtained through the sequence described above from the corresponding 2-[(E)-2-(substituted-phenyl)ethenyl]-4,4,5,5-tetramethyl-1,3,2-dioxaborolane analogs;

Tert-butyl 3-[6-(2-phenylcyclopropyl)-2H-spiro[1-benzofuran-3,4'-piperidine]-1'-yl}propanoate.

Tert-butyl 3-{6-[2-(2-fluorophenyl)cyclopropyl]-2H-spiro[1-benzofuran-3,4'-piperidine]-1'-yl}propanoate.

Tert-butyl 3-{6-[2-(2-chlorophenyl)cyclopropyl]-2H-spiro[1-benzofuran-3,4'-piperidine]-1'-yl}propanoate. $^1$H NMR (400 MHz, CDCl$_3$-d) δ ppm 7.30-7.26 (m, 2H) 7.04-7.13 (m, 2H), 6.79 (dd, J=7.7 and 1.6 Hz, 1H), 6.66 (d, J=1.6 Hz, 1H), 4.36 (s, 2H), 2.87-2.94 (m, 2H), 2.71 (t, J=7.6 Hz, 2H), 2.46 (t, J=7.6 Hz, 2H), 2.19-2.24 (m, 1H), 1.92-2.16 (m, 5H), 1.72-1.79 (m, 2H), 1.54-1.61 (m, 1H), 1.46 (s, 9H), 1.37-1.41 (m, 1H).

Tert-butyl 3-{6-[2-(2-chloro-5-ethylphenyl)cyclopropyl]-2H-spiro[1-benzofuran-3,4'-piperidine]-1'-yl}propanoate.

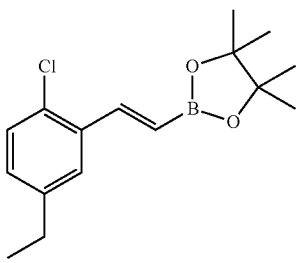

A

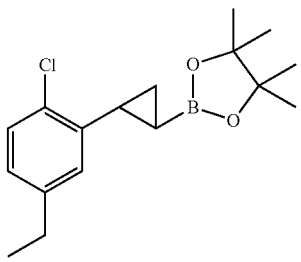

B

As an example, NMR data are given for A and B:

A: $^1$H NMR (400 MHz, CDCl$_3$-d) δ ppm 7.76 (d, J=18.4 Hz, 1H), 7.46 (d, J=2.1 Hz, 1H), 7.26 (d, J=8.2Hz, 1H), 7.06 (dd, J=8.2, 2.1 Hz, 1H), 6.17 (d, J=18.4 Hz, 1H), 2.62 (q, J=7.6 Hz, 2H), 1.32 (s, 12H), 1.22 (t, J=7.6 Hz, 3H).

B: $^1$H NMR (400 MHz, CDCl$_3$-d) δ □ ppm 7.23 (d, J=8.1 Hz, 1H), 6.93 (dd, J=8.1 and 2.0 Hz, 1H), 6.80 (d, J=2.0 Hz, 1H), 2.55 (q, J=7.6 Hz, 2H), 2.34 (dt, J=8.1 and 5.7 Hz, 1H) 1.26 (s, 12H), 1.15-1.23 (m, 4H), 1.00-1.06 (m, 1H), 0.15-0.23 (m, 1H)

Tert-butyl 3-{6-[2-(4-butyl-2,6-dichlorophenyl)cyclopropyl]-2H-spiro[1-benzo-furan-3,4'-piperidine]-1'-yl}propanoate.

Compound 175. 4-{6-[2-(2,6-Dichlorophenyl)cyclopropyl]-2H-spiro[1-benzo-furan-3,4'-piperidine]-1'-yl}butanoic acid hydrochloride Tert-butyl 4-{6-[2-(2,6-dichlorophenyl)cyclopropyl]-2H-spiro[1-benzofuran-3,4'-piperidine]-1'-yl}butanoate (268 mg, 0.52 mmol) was dissolved in a 4M solution of HCl in 1,4-dioxane (10 mL; 4 mol/l; 40 mmol) and stirred for 48 hours at RT. Subsequently, the solvent was removed in vacuo and the residue treated with iPr$_2$O, the precipitate was collected by filtration and dried overnight under reduced pressure to afford the product (239 mg, 92.7%). Rt 1.44 min (System B), [M+H]$^+$ 460.0.

The following compounds were obtained according to a similar manner:

Compound 176. 2-{6-[2-(2,6-Dichlorophenyl)cyclopropyl]-2H-spiro[1-benzo-furan-3,4'-piperidine]-1'-yl}acetic acid hydrochloride Rt 1.70 min (System B), [M+H]⁺ 431.9

Compound 177. 3-{6-[2-(2,6-Dichlorophenyl)cyclopropyl]-2H-spiro[1-benzo-furan-3,4'-piperidine]-1'-yl}-2-methylpropanoic acid hydrochloride Rt 1.53 min (System B), [M+H]⁺ 460.0.

Compound 178. 3-{6-[2-(2,6-Dichlorophenyl)cyclopropyl]-2H-spiro[1-benzo-furan-3,4'-piperidine]-1'-yl}propanoic acid hydrochloride $^1$H NMR (400 MHz, DMSO-$d_6$) δ ppm 12.80 (bs, 1H), 10.20 (bs, 1H), 7.45 (d, J=8.1 Hz, 2H), 7.30 (t, J=8.1 Hz, 1, 1H), 6.67-7.30 (m, 1H), 6.82 (d, J=8.4 Hz, 1, 1H), 6.68 (s, 1H), 4.47 (bs, 2H), 3.42-3.55 (m, 2H), 3.21-3.42 (m, 2H), 2.95-3.14 (m, 2H), 2.86 (t, J=8.3 Hz, 2H), 2.08-2.28 (m, 4H), 1.82-1.95 (m, 2H), 1.54-1.62 (m, 1H), 1.32-1.41 (m, 1H). Rt 1.45 min (System B), [M+H]⁺ 446.0.

Compound 179. 3-[6-(2-Phenylcyclopropyl)-2H-spiro[1-benzofuran-3,4'-piperidine]-1'-yl}propanoic acid hydrochloride Rt 1.33 min (System B), [M+H]⁺ 378.2.

Compound 180. 3-{6-[2-(2-Fluorophenyl)cyclopropyl]-2H-spiro[1-benzofuran-3,4'-piperidine]-1'-yl}propanoic acid hydrochloride $^1$H NMR (400 MHz, DMSO-$d_6$) δ ppm 12.70 (bs, 1H), 10.90 (bs, 1H), 7.09-7.29 (m, 4H), 6.95-7.05 (m, 1H), 6.78 (d, J=7.8 Hz, 1H), 6.65 (s, 1H), 4.45 (bs, 2H), 3.38-3.56 (m, 2H), 3.24-3.39 (m, 2H), 2.96-3.20 (m, 2H), 2.88 (t, J=7.8 Hz, 2H), 2.12-2.40 (m, 4H), 1.78-1.95 (m, 2H), 1.41-1.55 (m, 2H). Rt 1.35 min (System B), [M+H]⁺ 396.0.

Compound 181. 3-{6-[2-(2-Chlorophenyl)cyclopropyl]-2H-spiro[1-benzofuran-3,4'-piperidine]-1'-yl}propanoic acid hydrochloride $^1$H NMR (400 MHz, DMSO-$d_6$) δ ppm 12.90 (bs, 1H), 10.50 (bs, 1H), 7.46 (d, J=4.1 Hz, 1H), 7.40-7.44 (m, 1H), 7.12-7.34 (m, 3H), 6.93-7.08 (m, 1H), 6.82 (d, J=6.2Hz, 1H), 6.70 (s, 1H), 4.48 (bs, 2H), 3.42-3.56 (m, 2H), 3.26-3.39 (m, 2H), 3.00-3.14 (m, 2H), 2.86 (t, J=7.7 Hz, 2H) 2.32-2.42 (m, 1H) 2.08-2.32 (m, 3H) 1.81-1.95 (m, 2H) 1.49-1.56 (m, 1H), 1.39-1.49 (m, 1H). Rt 1.40 min (System B), [M+H]⁺ 412.0.

Compound 182. 3-{6-[2-(2-Chloro-5-ethylphenyl)cyclopropyl]-2H-spiro[1-benzofuran-3,4'-piperidine]-1'-yl}propanoic acid hydrochloride $^1$H NMR (400 MHz, DMSO-$d_6$) δ ppm 12.70 (bs., 1H), 10.70 (bs., 1H), 7.31 (d, J=8.1 Hz, 1H), 7.06 (dd, J=8.1, 2.0 Hz, 1H), 6.95-7.10 (m, 2H), 6.79 (dd, J=8.1 and 1.2Hz, 1H), 6.67 (d, J=1.2Hz, 1H), 4.47 (bs., 2H), 3.43-3.52 (m, 2H), 3.25-3.30 (m, 2H), 2.99-3.11 (m, 2H), 2.88 (t, J=7.6 Hz, 2H), 2.58 (q, J=7.6 Hz, 2H), 2.34 (dt, J=8.8 and 5.4 Hz, 1H), 2.20-2.30 (m, 2H), 2.11 (dt, J=8.8 and 5.4 Hz, 1H), 1.82-1.90 (m, 2H), 1.54 (dt, J=8.8 and 5.4 Hz, 1H), 1.43 (dt, J=8.8 and 5.4 Hz, 1H), 1.16 (t, J=7.6 Hz, 3H). Rt 1.40 min (System B), [M+H]⁺ 440.1.

Compound 183. 3-{6-[2-(4-Butyl-2,6-dichlorophenyl)cyclopropyl]-2H-spiro[1-benzofuran-3,4'-piperidine]-1'-yl}propanoic acid hydrochloride Rt 1.77 min (System B), [M+H]⁺ 502.0.

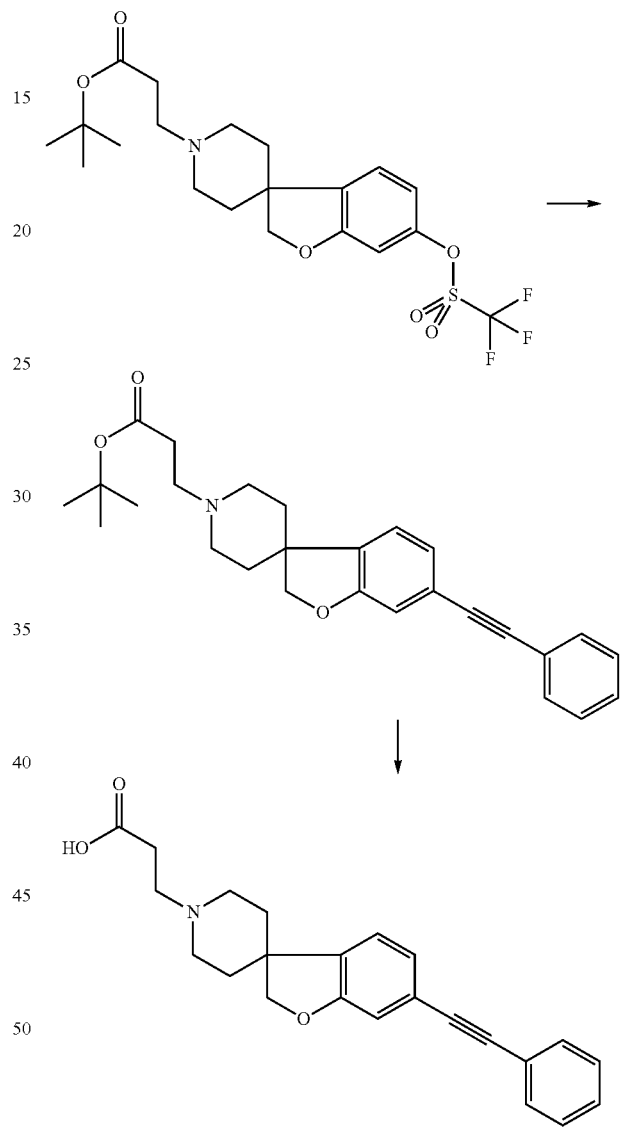

Compound 303. 3-[6-(2-Phenylethynyl)-2H-spiro[1-benzofuran-3,4'-piperidine]-1'-yl]propanoic acid hydrochloride To a degassed mixture of tert-butyl 3-{-{6-[(trifluoromethane)sulfonyloxy]-2H-spiro[1-benzofuran-3,4'-piperidine]-1'-yl]pro-panoate (235 mg, 0.5 mmol) and phenylacetylene (0.08 mL; 0.76 mmol) in dimethyl sulfoxide (5 mL), was added potassium phosphate tribasic monohydrate (128 mg; 0.61 mmol). Subsequently was added palladium (II) acetate (6 mg; 0.03 mmol) and triphenylphosphine (26.5 mg; 0.1 mmol). The resulting mixture was heated for 1 hour in an oilbath (80° C.). After cooling to RT, the mixture was diluted with EtOAc. The reaction mixture was partitioned between EtOAc and 5% aqueous NaHCO$_3$. The organic layer was dried (Na$_2$SO$_4$), filtered, and concentrated in vacuo. The residue was purified by column chromatography (SiO$_2$, dichloromethane:MeOH 95:5 to 9:1) to afford tert-butyl 3-[6-(2-phenylethynyl)-2H-spiro[1-benzofuran-3,4'-piperidine]-1'-yl]propanoate (190 mg; 90%). Rt 1.44 min (System B), [M+H]$^+$ 418.3. This product (170 mg; 0.41 mmol) was dissolved in a 4M solution of HCl in 1,4-dioxane (10 mL; 4 mol/l; 40 mmol) and heated for 1.5 hour in an oilbath (50° C.). Subsequently, the solvent was removed in vacuo and the residue treated with iPr$_2$O, the precipitate was collected by filtration and dried overnight under reduced pressure to afford the product (120 mg, 70%). $^1$H NMR (400 MHz, DMSO-d$_6$) δ ppm 12.55 (br s, 1H), 10.18 (br s, 1H), 7.39-7.45 (m, 2H), 7.28-7.33 (m, 3H), 7.02 (s, 2H), 6.87 (s, 1H), 4.42 (s, 2H), 3.14-3.44 (m, 4H), 2.89-3.01 (m, 2H), 2.73 (t, J=8 Hz, 2H), 2.05-2.17 (m, 2H), 1.75-1.84 (m, 2H). Rt 1.37 min (System B), [M+H]$^+$ 363.2.

The following compound was obtained according to a similar manner:

Compound 304. 3-{6-[2--(2-Chlorophenyl)ethynyl)-2H-spiro[1-benzofuran-3,4'-piperidine]-1'-yl}propanoic acid hydrochloride $^1$H NMR (400 MHz, DMSO-d$_6$) δ ppm 7.52-7.56 (m, 1H), 7.40-7.44 (m, 1H), 7.22-7.26 (m, 2H), 7.07-7.14 (m, 2H), 6.97 (s, 1H), 4.39 (s, 2H), 2.88-2.95 (m, 2H), 2.70 (t, J=8 Hz, 2H), 2.45 (t, J=8 Hz, 2H), 2.03-2.12 (m, 2H), 1.91-2.01 (m, 2H), 1.71-1.78 (m, 2H), 1.46 (s, 9H). Rt 1.39 min (System B), [M+H]$^+$ 396.2.

Tert-butyl 3-{6-benzyl-2H-spiro[1-benzofuran-3,4'-piperidine]-1'-yl}propanoate. To a degassed mixture of B-benzyl-9-BBN (279.3 mg; 1.32 mmol) (0.5 mil in THF (15 mL) was added potassium phosphate tribasic monohydrate (420 mg; 1.98 mmol) and the reaction mixture was stirred for 15 minutes. Subsequently were added tert-butyl 3-{-{6-[(trifluoromethane)sulfonyloxy]-2H-spiro[1-benzo-furan-3,4'-piperidine]-1'-yl}propanoate (307 mg, 0.66 mmol), palladium(II) acetate (6 mg; 0.03 mmol) and 2-dicyclohexylphosphino-2',6'-dimethoxy-1',1'-biphenyl (22 mg; 0.05 mmol). The resulting mixture was heated for 1 hour under reflux. After cooling to RT, the mixture was diluted with EtOAc. The reaction mixture was partitioned between EtOAc and 5% aqueous NaHCO$_3$.

The organic layer was dried (Na$_2$SO$_4$), filtered, and concentrated in vacuo. The residue was purified by column chromatography (SiO$_2$, dichloromethane:MeOH 95:1) to afford the product (200 mg; 74.4%). Rt 1.40 min (System B), [M+H]$^+$ 408.2.

Tert-butyl 3-[6-(2-phenylethyl)-2H-spiro[1-benzofuran-3,4'-piperidine]-1'-yl]propanoate. To a degassed mixture of potassium phenethyltrifluoroboronate (209 mg; 0.99 mmol) in toluene (15 mL) and H$_2$O (1.5 mL), was added potassium phosphate tribasic monohydrate (630 mg; 3 mmol), and the resulting reaction mixture was stirred for 15 minutes. Subsequently was added tert-butyl 3-{-{6-[(trifluoro-methane)sulfonyloxy]-2H-spiro[1-benzofuran-3,4'-piperidine]-1'-yl]propanoate (307 mg, 0.66 mmol), palladium(II) acetate (7 mg; 0.03 mmol) and 2-dicyclohexylphosphino-2',6'-di-isopropoxy-1',1'-biphenyl (30 mg; 0.07 mmol). The resulting mixture was heated for 1 hour in a pre-heated oilbath (100° C.). After cooling to RT, the mixture was diluted with EtOAc. The reaction mixture was partitioned between EtOAc and 5% aqueous NaHCO$_3$. The organic layer was dried (Na$_2$SO$_4$), filtered, and concentrated in vacuo. The residue was purified by repeated column chromatography (SiO$_2$, dichloromethane:MeOH 95:5) to afford the product (190 mg; 68.4%). Rt 1.43 min (System B), [M+H]$^+$ 422.2.

Tert-butyl 3-{6-[(2-(2,dichlorophenyl)ethyl]-2H-spiro[1-benzofuran-3,4'-piperidine]-1'-yl}propanoate. To a degassed solution of potassium [2-(2,6-dichlorophenyl)ethyl]trifluoroborate (0.3 g; 1.07 mmol) in toluene (10 mL) and water (1 mL) was added potassium phosphate tribasic (0.68 g; 3.2 mmol) and the reaction mixture was stirred for 10 minutes. Subsequently was added tert-butyl 3-{-{6-[(trifluoromethane)sulfonyloxy]-2H-spiro[1-benzofuran-3,4'-piperidine]-1'-yl}pro-panoate (382 mg, 0.82 mmol), palladium(II) acetate (7.3 mg; 0.03 mmol), and 2-dicyclohexylphosphino-2',6'-diisopropoxy-1,1'-biphenyl (30 mg; 0.07 mmol). The resulting mixture was heated under reflux, overnight. After cooling to RT, the mixture was concentrated in vacuo and partitioned between EtOAc and 5% aqueous NaHCO$_3$. The organic layer was dried (Na$_2$SO$_4$), filtered, and concentrated in vacuo. The residue was purified by column chromatography (SiO$_2$, Et$_2$O:hexanes 1:1) to afford the product (0.21 g; 52.1%). Rt 1.52 min (System B), [M+H]$^+$ 490.0

The required potassium [2-(2,6-dichlorophenyl)ethyl]trifluoroborate was prepared as follows: To a solution of 2,6-dichlorostyrene (1.58 mL; 11.6 mmol) in THF (15 mL) was added chloro(1,5-cyclooctadiene)Iridium(I) dimer (38.8 mg; 0.06 mmol), 1,2-bis(diphenylphosphino)ethane (46.1 mg; 0.12 mmol) and pinacolborane (11.6 mL; 1M in THF; 11.6 mmol). The resulting mixture was stirred at RT, overnight, subsequently, concentrated in vacuo and purified by column chromatography (SiO$_2$, Et$_2$O:hexanes 1:3). The obtained product was treated with MeOH (56 mL), water (14 mL), and potassium bifluoride (3.43 g; 43.9 mmol) and stirred at RT overnight. Subsequently, the solvents were removed in vacuo and the residue treated with toluene and concentrated in vacuo. The latter steps were repeated three times to remove all the water. The obtained solid was treated with CH$_3$CN, and heated at 50° C. The precipitate was removed by filtration and washed with CH$_3$CN. The combined CH$_3$CN layers were concentrated in vacuo and the residue was treated with Et$_2$O. The formed precipitate was collected by filtration and dried in vacuo to afford potassium [2-(2,6-dichlorophenyl)ethyl]trifluoroborate (1.12 g), which was used as such.

Tert-butyl 3-{6-[(2-(2-fluorophenyl)ethyl]-2H-spiro[1-benzofuran-3,4'-piperidine]-1'-yl}propanoate. To tert-butyl 3-{6-[(E)-2-(2-fluorophenyl)ethenyl]-2H-spiro[1-benzofuran-3,4'-piperidine]-1'-yl}propanoate (compound 171) (80 mg; 0.18 mmol) in 10 ml MeOH was added palladium hydroxide (3 mg; 0.02 mmol). The mixture was treated with H$_2$, overnight. The crude reaction mixture was filtered through Celite to afford the product (80 mg; 99%). Rt 1.39 min (System B), [M+H]$^+$ 440.1.

Tert-butyl 3-[6-(phenoxymethyl)-2H-spiro[1-benzofuran-3,4'-piperidine]-1'-yl]propanoate. To a degassed solution of potassium trifluoro(phenoxymethyl)]-borane (0.3 g; 1.07 mmol) (Org. Lett., 2008, Vol 10, No 11, 2135) in toluene (20 mL) and water (2 mL) was added potassium phosphate tribasic (0.64 g; 3 mmol) and the reaction mixture was stirred for 10 minutes. Subsequently was added tert-butyl 3-{-{6-[(trifluoromethane)sulfonyloxy]-2H-spiro[1-benzofuran-3,4'-piperidine]-1'-yl}propanoate (325 mg, 0.7 mmol), palladium(II) acetate (15.6 mg; 0.07 mmol), and 2-dicyclohexylphosphino-2',6'-diisopropoxy-1,1'-biphenyl (65 mg; 0.14 mmol). The resulting mixture was heated under reflux for 70 hours. After cooling to RT, the mixture was concentrated in vacuo and partitioned between EtOAc and 5% aqueous NaHCO$_3$. The organic layer was dried (Na$_2$SO$_4$), filtered, and concentrated in vacuo. The residue was purified by column chromatography (SiO$_2$, dichloromethane:acetone 9:1) to afford the product (0.25 g; 84.1%). Rt 1.29 min (System B), [M+H]$^+$ 424.4.

Tert-butyl 3-[6-(phenylamino)-2H-spiro[1-benzofuran-3,4'-piperidine]-1'-yl]propanoate. To a degassed solution of Aniline (84 mg: 0.9 mmol) in toluene (15 mL) was added and cesium carbonate (342 mg; 1.05 mmol), tert-butyl 3-{-{6-[(trifluoromethane)sulfonyloxy]-2H-spiro[1-benzofuran-3,4'-piperidine]-1'-yl]pro-panoate (350 mg, 0.75 mmol), palladium(II) acetate (8.44 mg; 0.04 mmol), phenylboronic acid (4.5 mg; 0.04 mmol) and 2-dicyclohexylphosphino-2',6'-diisopropoxy-1,1'-biphenyl (35 mg; 0.08 mmol). The resulting mixture was heated at 100° C. overnight. After cooling to RT, the mixture was concentrated in vacuo and partitioned between EtOAc and 5% aqueous NaHCO$_3$. The organic layer was dried (Na$_2$SO$_4$), filtered, and concentrated in vacuo. The residue was purified by column chromatography (SiO$_2$, dichloromethane:acetone 97:3) to afford the product (0.27 g; 87.9%). Rt 1.33 min (System B), [M+H]$^+$ 409.2.

Compound 184. 3-{6-Benzyl-2H-spiro[1-benzofuran-3,4'-piperidine]-1'-yl}propanoic acid hydrochloride Tert-butyl 3-{6-benzyl-2H-spiro[1-benzofuran-3,4'-piperidine]-1'-yl}propanoate (180 mg, 0.44 mmol) was dissolved in a 4M solution of HCl in 1,4-dioxane (10 mL; 4 mol/l; 40 mmol) and stirred for 48 hours at RT. Subsequently, the solvent was removed in vacuo and the residue treated with iPr$_2$O, the precipitate was collected by filtration and dried overnight under reduced pressure to afford the product (120 mg, 66.5%). Rt 1.29 min (System B), [M+H]$^+$ 352.2.

The following compounds were obtained according to a similar manner:

Compound 185. 3-[6-(2-Phenylethyl)-2H-spiro[1-benzofuran-3,4'-piperidine]-1'-yl]propanoic acid hydrochloride Rt 1.37 min (System B), [M+H]$^+$ 366.2.

Compound 186. 3-{6-[(2-(2,Dichlorophenyl)ethyl]-2H-spiro[1-benzofuran-3,4'-piperidine]-1'-yl}propanoic acid hydrochloride Rt 1.36 min (System B), [M+H]$^+$ 384.1.

Compound 187. 3-{6-[(2-(2-Fluorophenyl)ethyl]-2H-spiro[1-benzofuran-3,4'-piperidine]-1'-yl}propanoic acid hydrochloride $^1$H NMR (400 MHz, DMSO-d$_6$) δ ppm 12.90 (bs, 1H), 10.20 (bs, 1H), 7.42-7.48 (m, 2H), 7.27-7.32 (m, 1H), 7.04 (bs, 1H), 6.82 (d, J=6.2Hz, 1H), 6.69 (s, 1H), 4.48 (bs, 2H), 3.42-3.56 (m, 2H), 3.26-3.39 (m, 2H), 3.00-3.14 (m, 4H), 2.86 (t, J=7.7 Hz, 2H), 2.68-2.75 (m, 2H), 2.16-2.30 (m, 2H), 1.85-1.95 (m, 2H). Rt 1.42 min (System B), [M+H]$^+$ 433.9.

Compound 188. 3-[6-(Phenoxymethyl)-2H-spiro[1-benzofuran-3,4'-piperidine]-1'-yl]propanoic acid hydrochloride $^1$H NMR (400 MHz, DMSO-d$_6$) δ ppm 12.64 (bs, 1H), 10.18 (bs, 1H), 7.29 (t, J=8 Hz, 2H), 7.12 (bs, 1H), 6.88-7.03 (m, 5H), 5.05 (s, 2H), 4.49 (s, 2H), 3.27-3.54 (m, 4H), 3.00-3.16 (m, 2H), 2.84 (t, J=8 Hz, 2H), 2.12-2.27 (m, 2H), 1.85-1.94 (m, 2H). Rt 1.32 min (System B), [M+H]$^+$ 368.2

Compound 189. 3-[6-(Phenylamino)-2H-spiro[1-benzofuran-3,4'-piperidine]-1'-yl]propanoic acid hydrochloride Rt 1.24 min (System B), [M+H]$^+$ 353.2

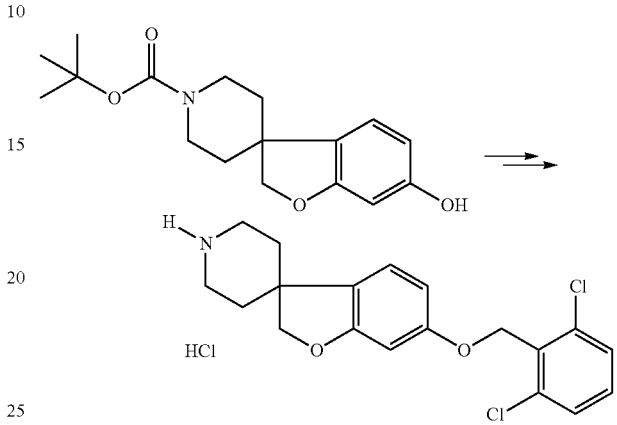

Compound 190. 6-[(2,6-Dichlorophenyl)methoxy]-2H-spiro[1-benzofuran-3,4'-piperidine]hydrochloride A mixture of 2H-spiro[1-benzofuran-3,4'-piperidine]-6-ol (2.6 g; 12.7 mmol) and di-tert-butyl dicarbonate (3.04 g; 13.9 mmol) in dichloro-methane (50 mL) was stirred at RT overnight. Subsequently, the resulting mixture was concentrated in vacuo and the residue was purified by column chromatography (SiO$_2$, Et$_2$O; hexanes) to afford tert-butyl 6-hydroxy-2H-spiro[1-benzofuran-3,4'-piperidine]-1'-carboxylate (2.5 g; 81%). Rt 1.89 min (System B), [M+H]$^+$ 306.1. To a solution of (2,6-dichlorophenyl)methanol (0.24 g; 1.38 mmol) and tert-butyl 6-hydroxy-2H-spiro[1-benzofuran-3,4'-piperidine]-1'-carboxylate (0.28 g, 0.92 mmol) in dichloromethane (10 mL) was added triphenylphosphine (0.36 g; 1.38 mmol), followed, after 30 minutes by DIAD (0.27 mL; 1.38 mmol). Subsequently, the resulting mixture was stirred at RT overnight, and diluted with dichloromethane, washed with 5% aqueous NaHCO$_3$, dried (Na$_2$SO$_4$), and filtered. The residue was purified by column chromatography (SiO$_2$, Et$_2$O:hexanes 1:1) to afford tert-butyl 6-[(2,6-dichlorophenyl)methoxy]-2H-spiro[1-benzofuran-3,4'-piperidine]-1'-carboxylate (430 mg; 100%).

Tert-butyl 3-{6-[(2,6-dichlorophenyl)methoxy]-2H-spiro[1-benzfuran-3,4'-piperidine]-1'-carboxylate (3.68 g, 7.92 mmol) was dissolved in a 1M solution of HCl in EtOH (30 mL) and stirred for 2 hours at 50° C. Subsequently, the solvent was removed in vacuo and the residue treated with iPr$_2$O, the precipitate was collected by filtration and dried overnight under reduced pressure to afford 6-[(2,6-dichlorophenyl)methoxy]-2H-spiro[1-benzfuran-3,4'-piperidine] hydrochloride (1.89 g, 59%). $^1$H NMR (400 MHz, DMSO-d$_6$) δ ppm 7.55-7.58 (m, 2H) 7.46 (dd, J=8.1 and 6.2Hz, 1H) 7.05 (d, J=8.1 Hz, 1 H) 6.57-6.61 (m, 2H), 5.18 (s, 2H), 4.49 (bs, 2H), 3.23-3.32 (m, 2H), 2.91-3.03 (m, 2H), 1.98-2.10 (m, 2H), 1.77-1.82 (m, 2H).

Compound 191. 6-[(2,6-Dichlorophenyl)methoxy]-1'-methyl-2H-spiro[1-benzofuran-3,4'-piperidine]

To a solution of 6-[(2,6-dichlorophenyl)methoxy]-2H-spiro[1-benzofuran-3,4'-piperidine] (220 mg; 0.55 mmol) and N-ethyldiisopropylamine (0.19 mL; 1.10 mmol) in MeOH (20 mL), was added formaldehyde (0.08 mL; 1.1 mmol; 37% in $H_2O$) and sodiumtriacetoxyborohydride (232 mg; 1.1 mmol). Subsequently, the resulting mixture was stirred at RT overnight. Subsequently, the mixture was diluted with EtOAc, washed with 5% aqueous $NaHCO_3$, dried ($Na_2SO_4$), and filtered. The residue was purified by column chromatography ($SiO_2$, MeOH) to afford the product (160 mg; 67.5%). Rt 1.36 min (System B), $[M+H]^+$ 378.0.

Compound 192. 3-{6-[(2,6-Dichlorophenyl) methoxy]-2H-spiro[1-benzofuran-3,4'-piperidine]-1'-yl}butanoic acid hydrochloride To a mixture of 6-[(2,6-dichlorophenyl)methoxy]-2H-spiro[1-benzfuran-3,4'-piperidine] (0.6 g; 1.5 mmol) in dichloroethane (12 mL), was added tert-butyl acetoacetate (1 mL; 6 mmol), sodiumtriacetoxyborohydride (232 mg; 1.1 mmol) and a drop of acetic acid. Subsequently, the resulting mixture was stirred at RT overnight. Subsequently, the mixture was diluted with EtOAc, washed with 5% aqueous $NaHCO_3$, dried ($Na_2SO_4$), and filtered. The residue was purified by column chromatography ($SiO_2$, $Et_2O$:hexanes 1:3) to afford Tert-butyl 3-{6-[(2,6-dichlorophenyl) methoxy]-2H-spiro[1-benzofuran-3,4'-piperidine]-1'-yl}butanoate (0.76 g; 72.5%). Rt 1.70 min (System B), $[M+H]^+$ 506.0, which was hydrolyzed using the 4M solution of HCl in 1,4-dioxane conditions, affording the product (90%). $^1H$ NMR (400 MHz, DMSO-$d_6$) δ ppm 12.80 (bs, 1H), 10.70 (bs, 1H), 7.55-7.59 (m, 2H), 7.46 (dd, J=8.1 and 6.2Hz, 1, 1H) 7.05 (bs, 1H), 6.55-6.62 (m, 2H), 5.18 (s, 2H), 4.52 (bs, 2H), 3.62-3.72 (m, 1H), 3.30-3.48 (m, 2H), 2.98-3.20 (m, 3H), 2.52-2.63 (m, 1H) 2.30-2.48 (m, 2H). 1.80-1.90 (m, 2H) 1.33 (d, J=7.8 Hz, 3H). Rt 1.70 min (System B), $[M+H]^+$ 450.0.

Compound 193. 3-{6-[(2,6-Dichlorophenyl) methoxy]-2H-spiro[1-benzofuran-3,4'-piperidine]-1'-yl}-2,2-difluoropropanoic To a solution of 6-[(2,6-dichlorophenyl)methoxy]-2H-spiro[1-benzfuran-3,4'-piperidine] (1 g; 2.5 mmol) in EtOH (10 mL) was added 1H-benzotriazole-1-methanol (0.37 g; 2.5 mmol), and the reaction mixture was heated at 50° C. for 20 minutes. After cooling to RT, the solvent was removed in vacuo to afford 6-[(2,6-dichlorophenyl)methoxy]-2H-spiro [1-benzfuran-3,4'-piperidine]-1H-benzotriazole; which was used as such.

To a suspension of zinc dust (0.33 g; 4.99 mmol) in dry THF (10 mL) was added chlorotrimethylsilane (0.32 mL; 2.5 mmol) and ethyl bromodifluoroacetate (0.48 ml; 3.74 mmol), this mixture was heated under reflux for 10 min. and then cooled to RT. To the resulting mixture was added drop-wise a solution of 6-[(2,6-dichlorophenyl)-methoxy]-2H-spiro[1-benzfuran-3,4'-piperidine]-1H-benzotriazole in THF (5 mL). After the addition is complete the resulting mixture is heated under reflux for 2 hours. After cooling to RT the reaction mixture was filtered over Kieselguhr and the filter-cake was washed with ethanol. The solvents were removed in vacuo and the residu was purified by column chromatography ($SiO_2$, $Et_2O$: hexanes 1:1) to afford Tert-butyl 3-{6-[(2,6-dichlorophenyl) methoxy]-2H-spiro[1-benzofuran-3,4'-piperidine]-1'-yl}-2, 2-difluoropropanoate (0.21 g; 16.8%). Rt 2.61 min (System B), $[M+H]^+$ 500.0, which was dissolved in EtOH (15 mL). Sodium hydroxide was added (3.0 mL; 2 mol/l; 6 mmol; 14.3 eq) and the reaction mixture was stirred for 3 hours at 50° C. and subsequently cooled to 0° C. To this reaction mixture was added aqueous HCl (6 mL; 1 mol/l), dropwise, after which it was concentrated in vacuo. The residue was treated with saturated brine and dichloromethane. The water layer was washed with dichloromethane (twice). Subsequently, the organic layer was dried ($Na_2SO_4$), filtered, and concentrated in vacuo, followed by treated with $iPr_2O$. The formed precipitate was collected by filtration, washed with $iPr_2O$ and dried in vacuo to yield the product (100 mg; 50.4%). $^1H$ NMR (400 MHz, DMSO-$d_6$) δ ppm 7.56-7.59 (m, 2H), 7.47 (dd, J=8.1 and 6.2 Hz, 1H), 7.12 (d, J=8.0 Hz, 1H), 6.58-6.62 (m, 2H), 5.17 (s, 2H), 4.45 (bs, 2H), 3.87 (t, J=15.1 Hz, 2H), 3.35-3.42 (m, 2H), 3.03-3.18 (m, 2H) 2.08-2.19 (m, 2H), 1.79-1.85 (m, 2H). Rt 1.77 min (System B), $[M+H]^+$ 472.0.

Compound 194. 3-{6-[(2,6-Dichlorophenyl) methoxy]-2H-spiro[1-benzofuran-3,4'-piperidine]-1'-yl}-2,2-methylpropanoic acid To a mixture of 6-[(2,6-dichlorophenyl)methoxy]-2H-spiro[1-benzfuran-3,4'-piperidine] (0.42 g; 1.05 mmol) in dichloroethane (10 mL), was added Tert-butyl 2,2-dimethyl-3-oxopropanoate (0.35 g; 2.1 mmol), sodiumtriacetoxyborohydride (0.6 g; 3 mmol), and the resulting mixture was stirred at RT for 72 hours. Subsequently, the mixture was diluted with EtOAc, washed with 5% aqueous $NaHCO_3$, dried ($Na_2SO_4$), and filtered. The residue was purified by column chromatography ($SiO_2$, $Et_2O$:hexanes 1:1) to afford Tert-butyl 3-{6-[(2,6-dichlorophenyl)methoxy]-2H-spiro[1-benzofuran-3,4'-piperidine]-1'-yl-2,2-methylpropanoate (0.54 g). Rt 1.70 min (System B), $[M+H]^+$ 506.0, which was suspended in THF (11 mL). To this suspension was added lithium hydroxide (82 mg; 3.39 mmol) and the mixture was stirred at 50° C. for 48 hours. To this mixture (at RT) were added, 3 mL 1M HCl, 50 mL $H_2O$ and 25 mL phosphate buffer (pH 7). This mixture was washed with dichloromethane (3 times). Subsequently, the organic layer was dried ($Na_2SO_4$), filtered en concentrated in vacuo and to afford the product (490 mg; 93%). $^1H$ NMR (400 MHz, $CDCl_3$-d) δ ppm 7.36-7.39 (m, 2H) 7.25 (dd, J=8.1 and 6.2Hz, 1H), 7.08 (d, J=8.3 Hz, 1H), 6.60 (dd, J=8.2 and 2.3 Hz, 1H) 6.53 (d, J=2.2Hz, 1H), 5.23 (s, 2H), 4.39 (s, 2H), 3.08-3.18 (m, 2H), 2.45-2.62 (m, 4H), 2.01-2.11 (m, 2H), 1.80-1.88 (m, 2H), 1.27 (s, 6H). Rt 1.64 min (System B), $[M+H]^+$ 464.0.

Compound 305. 4-{6-[(2,6-Dichlorophenyl) methoxy]-2H-spiro[1-benzofuran-3,4'-piperidine]-1'-yl}-3-methylbutanoic acid A mixture of 6-[(2,6-dichlorophenyl)methoxy]-2H-spiro [1-benzfuran-3,4'-piperidine] (0.45 g; 1.12 mmol), $K_2CO_3$ (0.47 g; 3.37 mmol), methyl 4-chloro-3-methylbutanoate and potassium iodide (0.22 g; 1.35 mmol) in $CH_3CN$ (20 mL) was refluxed during 72 hours. After cooling to RT the reaction mixture was partitioned between 5% aqueous $NaHCO_3$ solution and $Et_2O$. The organic layer was dried ($Na_2SO_4$), filtered, and concentrated in vacuo. The residue was purified by column chromatography ($SiO_2$, $Et_2O$) to afford tert-butyl 4-{6-[(2,6-Dichlorophenyl)methoxy]-2H-spiro[1-benzofuran-3,4'-piperidine]-1'-yl}-3-methyl-butanoate (0.16 g; 30%). Rt 1.36 min (System B), $[M+H]^+$ 478.6.

A mixture of this product (150 mg; 0.31 mmol), 2M aqueous NaOH (2 mL; 4 mmol) and ethanol (10 mL) was stirred for 3 hours at 50° C. and subsequently cooled to 0° C. To this reaction mixture was added aqueous HCl (4 mL;

1 mol/l), dropwise, after which it was concentrated in vacuo. The residue was treated with saturated brine and dichloromethane. The water layer was washed with dichloromethane (twice). Subsequently, the organic layer was dried (Na$_2$SO$_4$), filtered, and concentrated in vacuo, followed by treated with iPr$_2$O. The formed precipitate was collected by filtration, washed with iPr$_2$O and dried in vacuo to yield 4-{6-[(2,6-Dichlorophenyl)methoxy]-2H-spiro[1-benzofuran-3,4'-piperidine]-1'-yl}-3-methyl-butanoic acid (50 mg; 32.6%). $^1$H NMR (400 MHz, DMSO-d$_6$) δ ppm 7.53-7.58 (m, 2H), 7.43-7.50 (m, 1H), 7.12 (d, J=8.1 Hz, 1H), 6.51-6.57 (m, 2H), 5.16 (s, 2H), 4.37 (s, 2H), 2.76-2.92 (m, 2H), 2.37 (dd, J=15.1, 6.0 Hz, 1H), 2.18-2.24 (m, 2H), 2.07-2.17 (m, 2H), 1.98-2.06 (m, 2H), 1.78-1.89 (m, 2 H), 1.62 (d, J=12.9 Hz, 2H), 0.89 (d, J=6.4 Hz, 3H). Rt 1.39 min (System B), [M+H]$^+$ 464.6.

Compound 306. 4-{6-[(2,6-Dichlorophenyl)methoxy]-2H-spiro[1-benzofuran-3,4'-piperidine]-1'-yl}pentanoic acid To a mixture of 6-[(2,6-dichlorophenyl)-methoxy]-2H-spiro[1-benzfuran-3,4'-piperidine] (0.63 g; 1.57 mmol) in dichloroethane (12 mL), was added ethyl levulinate (0.67 mL; 4.72 mmol), sodiumtriacetoxy-borohydride (0.93 g; 4.4 mmol) and a few drops of acetic acid. The resulting mixture was stirred at RT for 72 hours.

Subsequently, the mixture was diluted with EtOAc, washed with 5% aqueous NaHCO$_3$, dried (Na$_2$SO$_4$), and filtered. The residue was purified by column chromatography (SiO$_2$, Et$_2$O:hexanes 1:1) to afford ethyl 4-{6-[(2,6-Dichlorophenyl)methoxy]-2H-spiro[1-benzofuran-3,4'-piperidine]-1'-yl}pentanoate (0.14 g; 18.8%). Rt 1.40 min (System B), [M+H]$^+$ 492.6, which was hydrolyzed to the acid as described for compound 305 (100 mg; 70%). $^1$H NMR (400 MHz, DMSO-d$_6$) δ ppm 7.54-7.59 (m, 2H), 7.44-7.50 (m, 1H), 7.07 (d, J=8.1 Hz, 1H), 6.53-6.60 (m, 2H), 5.17 (s, 2H), 4.41-4.48 (m, 2H), 2.97-3.10 (m, 2H), 2.72-2.82 (m, 1H), 2.58-2.69 (m, 1H), 2.25-2.41 (m, 2H), 1.91-2.13 (m, 4H), 1.75 (d, J=12.9 Hz, 2H), 1.52-1.63 (m, 1H), 1.12 (d, J=6.4 Hz, 3H). Rt 1.35 min (System B), [M+H]$^+$ 464.6.

Compound 195. 3-{6-[(2,6-Dichlorophenyl)methoxy]-2H-spiro[1-benzofuran-3,4'-piperidine]-1'-yl}ethan-1-ol hydrochloride A mixture of 6-[(2,6-dichlorophenyl)methoxy]-2H-spiro[1-benzfuran-3,4'-piperidine] (1.61 g; 4.02 mmol), 2-(2-chloroethoxy)tetrahydro-2H-pyran (0.71 mL; 4.82 mmol), K$_2$CO$_3$ (1.67 g; 12.05 mmol) and NaI (0.12 g; 0.8 mmol) in DMF 215 mL) was heated to 100° C. overnight. After cooling to RT the reaction mixture was partitioned between 5% aqueous NaHCO$_3$ solution and Et$_2$O. The organic layer was dried (Na$_2$SO$_4$), filtered, and concentrated in vacuo. The residue was purified by column chromatography (SiO$_2$, Et$_2$O) to afford 6-[(2,6-dichlorophenyl)methoxy]-1'-[2-(oxan-3-yloxy)ethyl-2H-spiro[1-benzfuran-3,4'-piperidine] (1 g; 50%), which was dissolved in MeOH (20 mL). To this reaction mixture was added p-toluenesulfonic acid monohydrate (0.39 g; 2 mmol) and the resulting mixture was stirred at 50° C. for 1 hour. The reaction mixture was partitioned between 5% aqueous NaHCO$_3$ solution and EtOAc. The organic layer was dried (Na$_2$SO$_4$), filtered, and concentrated in vacuo. The residue was purified by column chromatography (SiO$_2$, MeOH) to afford the product (0.46 g), which was converted into its HCl salt by treatment of the product in 1 M HCl in EtOH followed by concentration in vacuo (70 mg; 7.7%). $^1$H NMR (400 MHz, DMSO-d$_6$) δ ppm 9.70 (bs., 1H), 7.54-7.80 (m, 2H), 7.44-7.50 (m, 1H), 7.0 (d, J=7.9 Hz, 1H), 6.55-6.62 (m, 2H), 5.37 (m, 1H), 5.17 (s, 2H), 4.50 (s, 2H), 3.74-3.82 (m, 2H), 3.49-3.57 (m, 2H), 3.14-3.20 (m, 2H), 3.00-3.12 (m, 2H), 2.13-2.27 (m, 2H), 1.81-1.89 (m, 2H).

Compound 196. (2-{6-[(2,6-Dichlorophenyl)methoxy]-2H-spiro[1-benzofuran-3,4'-piperidine]-1'-yl}ethoxy)phosphonic acid To a solution of 3-{6-[(2,6-dichlorophenyl)methoxy]-2H-spiro[1-benzofuran-3,4'-piperidine]-1'-yl}ethan-1-ol (0.36 g; 0.88 mmol) in N,N-dimethylformamide (3 mL), was added a tetrazole solution in CH$_3$CN ((7.84 mL; 0.45 mmol) at RT. The resulting mixture was stirred for 30 minutes and subsequently di-tert-butyl N,N-diisopropylphosphoramidite (0.56 ml; 1.76 mmol) was added and stirred and the reaction mixture was stirred for 1.5 hour. Subsequently, the mixture was cooled to 0° C., and a solution of tert-butyl hydroperoxide in nonane (0.24 ml; ~5.5 mol/L, 1.32 mmol) was added. Thereafter the mixture was stirred at RT for another 30 min. The reaction was quenched by the addition of an 5% aqueous NaHCO$_3$ solution and extracted with EtOAc. The organic layer was dried (Na$_2$SO$_4$), filtered and concentrated in vacuo. The residue was purified by column chromatography (SiO$_2$, EtOAc followed by MeOH) to afford di-tert-butyl (2-{6-[(2,6-dichlorophenyl)methoxy]-2H-spiro[1-benzofuran-3,4'-piperidine]-1'-yl}ethyl)phosphonate (0.30 g; 62.5%). Rt 2.03 min (System B), [M+H]$^+$ 544.0, which was dissolved in hydrochloric acid (5 mL; 4 mol/l; 20 mmol). The reaction was stirred at RT overnight. Subsequently, the solvent was removed in vacuo and the residue treated with iPr$_2$O, the precipitate was collected by filtration and dried overnight under reduced pressure to afford the product (0.23 g, 81%). $^1$H NMR (400 MHz, DMSO-d$_6$) δ ppm 11.30 (bs, 1H), 7.55-7.59 (m, 2H), 7.46 (dd, J=8.1 and 6.2Hz, 1H), 7.10 (bs, 1H), 6.55-6.62 (m, 2H), 5.18 (s, 2H), 4.48 (bs, 2H), 4.18-4.24 (m, 2H), 3.30-3.48 (m, 2H), 3.44-3.53 (m, 2H), 3.35-3.43 (m, 2H), 3.09-3.2 (m, 2H), 2.13-2.24 (m, 2H), 1.84-1.91 (m, 2H). Rt 2.03 min (System B), [M+H]$^+$ 487.9.

Compound 197. 6-[(2,6-Dichlorophenyl)methoxy]-1'12-(1H-1,2,3,4-tetrazol-5-yl)ethyl-2H-spiro[1-benzofuran-3,4'-piperidine]

To a mixture of 6-[(2,6-dichlorophenyl)methoxy]-2H-spiro[1-benzfuran-3,4'-piperidine] (0.51 g; 1.27 mmol) in MeOH (10 mL), was added N-ethyldiisopropylamine (0.27 mL; 1.59 mmol) and acrylonitrile (0.11 mL; 2.8 mmol) and the resulting mixture was stirred at 80° C. for 4 hours (in a closed pyrex bottle). Subsequently, the mixture was concentrated in vacuo and the residue was purified by column chromatography (SiO$_2$, Et$_2$O) to afford 3-{6-[(2,6-dichlorophenyl)methoxy]-2H-spiro[1-benzfuran-3,4'-piperidine]-1'-yl}pro-panenitrile (0.31 g; 58%). Rt 1.80 min (System B), [M+H]$^+$ 417.0, which was dissolved in toluene (10 mL).

Subsequently was added azidotrimethyltin (0.39 g; 1.8 mmol) and the reaction mixture was heated for 72 hours at 100° C. Subsequently, the mixture was concentrated in vacuo and the residue was purified by column chromatography (SiO$_2$, EtOAc:MeOH 9:1, followed by MeOH) to afford the product (0.09 g; 29.3%). Rt 1.54 min (System B), [M+H]$^+$ 460.0.

Compound 198. (3-{6-[(2,6-Dichlorophenyl) methoxy]-2H-spiro[1-benzofuran-3,4'-piperidine]-1'-yl}propyl)phosphonic acid A mixture of 6-[(2,6-dichlorophenyl)methoxy]-2H-spiro [1-benzfuran-3,4'-piperidine] (0.59 g; 1.47 mmol), diethyl (3-bromopropyl)phosphonate (0.34 mL; 1.77 mmol), NaI (0.04 g; 0.29 mmol), and $K_2CO_3$ (0.61 g; 4.42 mmol) in $CH_3CN$ (10 mL) was heated under reflux for 2 hours. After cooling to RT the mixture was partitioned between 5% aqueous $NaHCO_3$ solution and $Et_2O$. The organic layer was dried ($Na_2SO_4$), filtered and concentrated in vacuo. The residue was purified by column chromatography ($SiO_2$, EtOAc:MeOH 90:10) to afford diethyl (3-{6-[(2,6-dichlorophenyl)methoxy]-2H-spiro[1-benzofuran-3,4'-piperidine]-1'-yl}propyl)phosphonate (0.8 g; 85.1%). Rt 1.62 min (System B), $[M+H]^+$ 542.0,. To a solution of diethyl (3-{6-[(2,6-dichlorophenyl)methoxy]-2H-spiro[1-benzofuran-3,4'-piperidine]-1'-yl}propyl)phosphonate (0.68 g; 1.25 mmol) in $CH_2Cl_2$ (15 mL) was added bromotrimethylsilane (1.32 ml; 10 mmol) and the reaction mixture was stirred at RT overnight. Subsequently the mixture was concentrated in vacuo, redissolved in MeOH (10 mL), and stirred for 2 hours at RT. The resulting mixture was concentrated in vacuo and treated with $iPr_2O$. The precipitate was collected by filtration and dried under vacuum to give the product (0.65 g; 86.8%). $^1H$ NMR (400 MHz, DMSO-$d_6$) δ ppm 9.10-11.10 (m, 2H), 7.54-7.59 (m, 2H), 7.46 (dd, J=8.1 and 6.2Hz, 1H), 7.10 (bs, 1H), 6.55-6.62 (m, 2H), 5.18 (s, 2H), 4.52 (bs, 2H), 3.40-3.58 (m, 2H), 3.12-3.24 (m, 2H), 2.97-3.12 (m, 2H), 2.02-2.13 (m, 2H), 1.83-1.97 (m, 4H), 1.59-1.70 (m, 2H). Rt 1.61 min (System B), $[M+H]^+$ 485.9.

Compound 199. 3-{6-[(2,6-Dichlorophenyl) methoxy]-2H-spiro[1-benzofuran-3,4'-piperidine]-1'-yl}-3-oxopropanoic acid To a suspension of 6-[(2,6-dichlorophenyl)methoxy]-2H-spiro[1-benzofuran-3,4'-piperidine] (0.62 g; 1.55 mmol), and N-ethyldiisopropylamine (0.79 mL; 4.64 mmol) dichloromethane (15 mL) was added dropwise ethyl malonyl chloride (0.3 ml; 2.32 mmol) at 0° C. The resulting mixture was stirred at RT overnight. Subsequently, the reaction mixture was partitioned between 5% aqueous $NaHCO_3$ solution and dichloromethane. The organic layer was dried ($Na_2SO_4$), filtered, and concentrated in vacuo. The residue was purified by column chromatography ($SiO_2$, $Et_2O$) to afford ethyl 3-{6-[(2,6-dichlorophenyl)methoxy]-2H-spiro [1-benzofuran-3,4'-piperidine]-1'-yl}-3-oxopropanoate (0.46 g; 62.1%). Rt 2.44 min (System B), $[M+H]^+$ 478.0, which was dissolved in EtOH (15 mL) and sodium hydroxide (3 mL; 2 mol/l; 6 mmol) and the mixture was stirred at 50° C. overnight. After cooling to RT the resulting mixture was loaded onto a PE-AX column [ISOLUTE (Biotage AB); 0.58 mmol/g, 10 g]. The column was washed with $CH_3CN$ and than the required compound was eluted with 20 v/v % TFA in $CH_3CN$. The compound containing fractions were concentrated in vacuo to afford the product (60 mg; 14.8%). Rt 2.62 min (System B), $[M+H]^+$ 450.0.

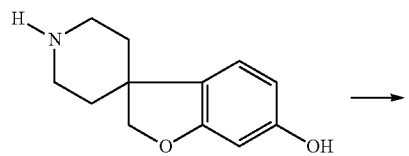

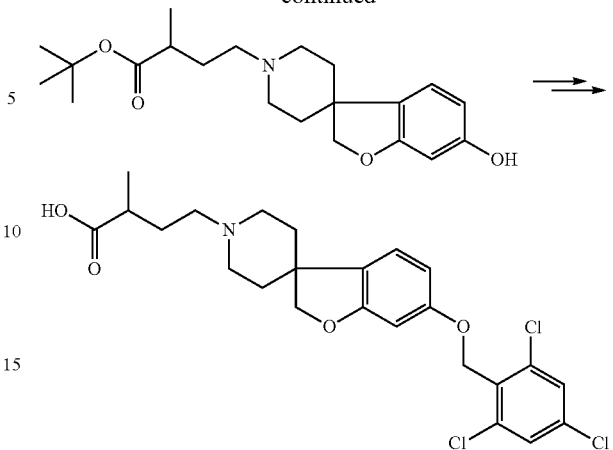

Compound 307. 2-Methyl-4-{6-[(2,4,6-trichlorophenyl)methoxy]-2H-spiro[1-benzofuran-3,4'-piperidine]-1'-yl}butanoic acid A mixture of 2H-spiro[1-benzfuran-3,4'-piperidine]-6-ol (1.06 g; 5.16 mmol), N-ethyldiisopropylamine (2.65 mL; 15.49 mmol), potassium iodide (0.86 g; 5.16 mmol) and 4-chloro-2-methylbutyric acid methyl ester in $CH_3CN$ (50 mL) was refluxed for 72 hours. After cooling to RT the reaction mixture was partitioned between 5% aqueous $NaHCO_3$ solution and $Et_2O$. The organic layer was dried ($Na_2SO_4$), filtered, and concentrated in vacuo. The residue was purified by column chromatography ($SiO_2$, $Et_2O$) to afford tert-butyl 4-{6-hydroxy-2H-spiro[1-benzofuran-3,4'-piperidine]-1'-yl}-2-methylbutanoate (0.82 g; 50%). $^1H$ NMR (400 MHz, $CDCl_3$-d) δ ppm 6.93 (d, J=8.3 Hz, 1H), 6.28-6.36 (m, 2H), 4.35 (s, 2H), 3.69 (s, 3H), 2.88-2.94 (m, 2H), 2.47-2.55 (m, 1H), 2.32-2.41 (m, 2H), 1.86-2.06 (m, 5H), 1.57-1.75 (m, 3H), 1.18 (d, J=7.6 Hz, 3H). To a solution of (2,4,6-trichlorophenyl)methanol (0.24 g; 1.13 mmol) and tert-butyl 4-{6-hydroxy-2H-spiro[1-benzofuran-3,4'-piperidine]-1'-yl}-2-methylbutanoate (0.29 g, 0.91 mmol) in dichloromethane (20 mL) was added triphenylphosphine (0.3 g; 1.13 mmol), followed, after 30 minutes by DIAD (0.22 mL; 1.13 mmol). Subsequently, the resulting mixture was stirred at RT overnight, and diluted with dichloromethane, washed with 5% aqueous $NaHCO_3$, dried ($Na_2SO_4$), and filtered. The residue was purified by column chromatography ($SiO_2$, $Et_2O$:hexanes 1:1) to afford tert-butyl 2-methyl-4-{6-[(2,4,6-trichlorophenyl)methoxy]-2H-spiro [1-benzofuran-3,4'-piperidine]-1'-yl}butanoate acid (280 mg; 60%). Rt 1.51 min (System B), $[M+H]^+$ 514.1.

A mixture of this product (270 mg; 0.53 mmol), 2M aqueous NaOH (2 mL; 4 mmol) and ethanol (10 mL) was stirred for 3 hours at 50° C. and subsequently cooled to 0° C. To this reaction mixture was added aqueous HCl (4 mL; 1 mol/l), dropwise, after which it was concentrated in vacuo. The residue was treated with saturated brine and dichloromethane. The water layer was washed with dichloromethane (twice). Subsequently, the organic layer was dried ($Na_2SO_4$), filtered, and concentrated in vacuo, followed by treated with $iPr_2O$. The formed precipitate was collected by filtration, washed with $iPr_2O$ and dried in vacuo to yield the product (160 mg; 60%). $^1H$ NMR (400 MHz, DMSO-$d_6$) δ ppm 7.79 (s, 2H), 7.11 (d, J=8.0 Hz, 1H), 6.49-6.55 (m, 2H), 5.13 (s, 2H), 4.36 (s, 2H), 2.80-2.88 (m, 2H), 2.31-2.42 (m, 3H), 1.96-2.10 (m, 2H), 1.72-1.87 (m, 3H), 1.61 (d, J=12.4 Hz, 2H), 1.45-1.55 (m, 1H), 1.07 (d, J=7.0 Hz, 3H). Rt 1.49 min (System B), [M+H]+ 500.1.

The following compounds were obtained according to a similar manner:

Compound 308. 4-{6-[(2,6-Dichlorophenyl)methoxy]-2H-spiro[1-benzofuran-3,4'-piperidine]-1'-yl}-2-methylbutanoic acid $^1$H NMR (400 MHz, DMSO-d$_6$) δ ppm 7.54-7.59 (m, J=7.6 Hz, 2H), 7.44-7.50 (m, 1H), 6.92-7.18 (m, 1H), 6.56-6.62 (m, 2H), 5.17 (s, 2H), 4.47 (s, 2H), 3.25-3.54 (m, 3H), 2.91-3.19 (m, 3H), 2.42-2.49 (m, 1H), 2.12-2.29 (m, 2H), 1.94-2.09 (m, 1H), 1.75-1.91 (m, 3H), 1.13 (d, J=8.5 Hz, 3H). Rt 1.34 min (System B), [M+H]+ 464.1.

Compound 309. 4-{6-[(2-Chloro-6-ethylphenyl)methoxy]-2H-spiro[1-benzofuran-3,4'-piperidine]-1'-yl}-2-methylbutanoic acid $^1$H NMR (400 MHz, DMSO-d$_6$) δ ppm 7.33-7.38 (m, 2H), 7.24-7.30 (m, 1H), 7.11 (d, J=7.5 Hz, 1H), 6.50-6.57 (m, 2H), 5.09 (s, 2H), 4.38 (s, 2H), 2.88-2.99 (m, 2H), 2.71 (q, J=8.1 Hz, 2H), 2.36-2.44 (m, 1H), 2.15-2.23 (m, 1H), 1.74-1.93 (m, 3H), 1.65 (d, J=12.9 Hz, 2H), 1.49-1.60 (m, 1H), 1.16 (t, J=8.1 Hz, 3H), 1.09 (d, J=7.1 Hz, 3H). Rt 1.39 min (System B), [M+H]+ 458.2.

Compound 310. 4-{6-[(2-Chloro-6-fluorophenyl)methoxy]-2H-spiro[1-benzofuran-3,4'-piperidine]-1'-yl}-2-methylbutanoic acid $^1$H NMR (400 MHz, DMSO-d$_6$) δ ppm 7.47-7.54 (m, 1H), 7.39-7.45 (d, J=8.4 Hz, 1H), 7.28-7.35 (t, 1H), 7.11 (d, J=7.8 Hz, 1H), 6.48-6.56 (m, 2H), 5.08 (d, J=1.6 Hz, 2H), 4.36 (s, 2H), 2.79-2.89 (m, 2H), 2.31-2.43 (m, 3H), 1.96-2.10 (m, 2H), 1.72-1.88 (m, 3H), 1.61 (d, J=12.7 Hz, 2H), 1.45-1.54 (m, 1H), 1.07 (d, J=7.6 Hz, 3H). Rt 1.31 min (System B), [M+H]+ 448.2.

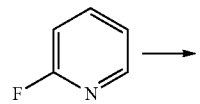

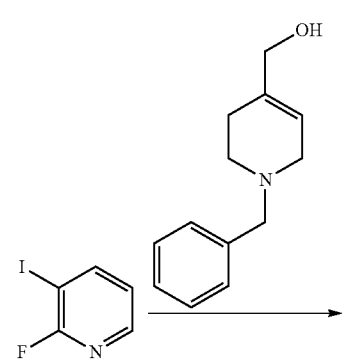

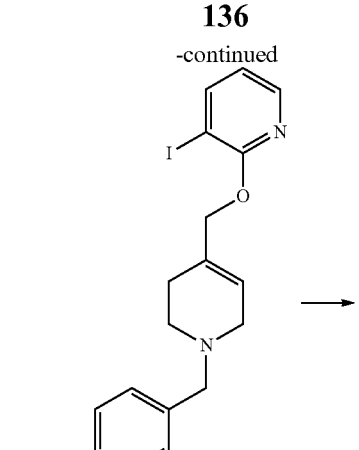

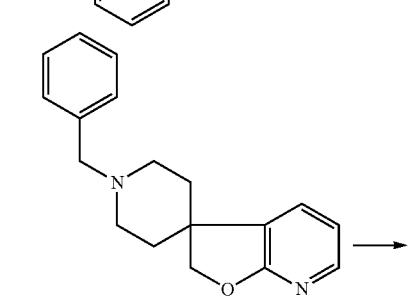

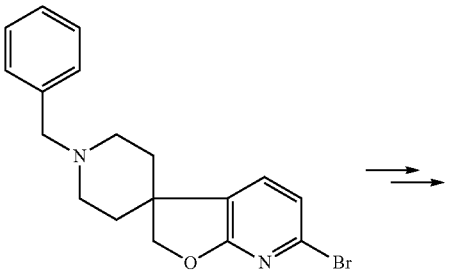

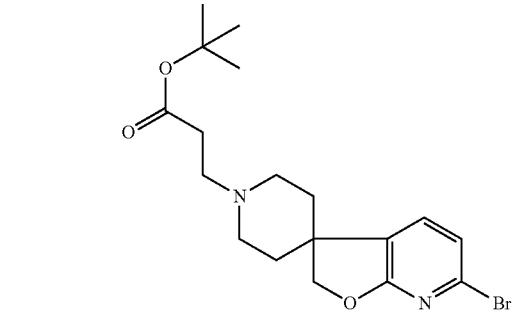 [SMILES: CC(C)(C)OC(=O)CCN1CCC2(CC1)COc1nc(Br)ccc12]

Tert-butyl 3-{5-bromo-2H-spiro[furo[2,3-b]pyridine-1,4'-piperidine]-1'-yl}pro-panoate. To a solution of 2,2,6,6-tetramethylpiperidine (16.1 mL; 95.5 mmol) in tetra-hydrofuran (370 mL) (−78° C.) was added n-butyllithium (38.19 mL, 2.5 mol/l in hexane, 95.5 mmol). The reaction mixture was stirred for 90 minutes, allowing the temperature to reach 0° C. Subsequently (at −70° C.), a solution of 2-fluoropyridine (8.2 ml; 95.5 mmol) dissolved in THF (10 mL) was added dropwise. During the addition, the temperature of the reaction mixture was kept below −60° C. The reaction mixture was stirred at −70° C. for one hour, after which iodine (29 g; 114.6 mmol) in tetrahydrofuran (50 mL) was added dropwise. The resulting reaction mixture was stirred at −70° C. for 2 hours. The reaction mixture was allowed to warm to 0° C., and subsequently quenched by the addition of a saturated aqueous NH$_4$Cl solution, followed by Et$_2$O. The organic phase was separated and extracted with a sodium bisulphite solution, followed by an aqueous NaHCO₃ solution. The organic layer was dried (Na₂SO₄), filtered, and concentrated in vacuo. The residue was purified by column chromatography (SiO₂, Et₂O:hexanes 5:95) to afford 2-Fluoro-3-iodopyridine (15.59 g; 73%). ¹H-NMR (CDCl₃, 400 MHz) δ ppm 8.21-8.13 (m, 2H), 7.01-6.95 (m, 1H). Rt 1.55 min (System B), [M+H]⁺ 224.0.

To a stirred solution of (1-benzyl-1,2,3,6-tetrahydropyridin-4-yl)methanol (WO2007/057775) (11.73 g; 57.7 mmol) in N,N-dimethylformamide (114 mL) was added sodium hydride dispersion in mineral oil (2.32 g) (portion wise). The reaction mixture for 1 hour at ambient temperature and added to a solution of 2-Fluoro-3-iodopyridine (11.39 g; 51 mmol), dissolved in N,N-dimethylformamide (100 mL). The reaction mixture was stirred at RT overnight. The reaction mixture was poured into a 5% sodium bicarbonate solution and extracted with diethyl ether. The organic layer was washed with water (3 times) and brine. The organic layer was dried (Na₂SO₄), filtered, and concentrated in vacuo. The residue was purified by column chromatography (SiO₂, Et₂O:hexanes 1:1) to afford 2-[(1-benzyl-1,2,3,6-tetrahydropyridin-4-yl)methoxy]-3-iodopyridine (17.5 g; 84.31%). ¹H-NMR (CDCl₃, 400 MHz) δ ppm: 8.07 (d, J=5.8 Hz, 1H), 8.00 (d, J=3.0 Hz, 1H), 7.36-7.23 (m, 5H), 6.63 (t, J=4.8 Hz, 1H), 5.87-5.80 (m, 1H), 4.76 (s, 2H), 3.07-3.00 (s, 2H), 3.03 (s, 2H), 2.64 (t, J=5.8 Hz, 2H), 2.32-2.24 (m, 2H). Rt 1.19 min (System B), [M+H]⁺ 407.1.

To a intensively degassed solution of 2-[(1-benzyl-1,2,3,6-tetrahydropyridin-4-yl)methoxy]-3-iodopyridine (3.5 g; 8.62 mmol) in toluene (500 mL) was added subsequently, 2,2'-azobis(2-methylpropionitrile) (0.28 g; 1.72 mmol) and tri-n-butyltinhydride (6.95 mL; 28.85 mmol). The reaction mixture was heated for 24 hours at 110° C. After cooling to RT, the mixture was diluted with Et₂O and washed with 10% aqueous KF. The organic layer was dried (Na₂SO₄), filtered and concentrated in vacuo. The residue was purified by column chromatography (SiO₂, Et₂O) to afford 1'-benzyl-2H-spiro[furo[2,3-b]pyridine-1,4'-piperidine] (2.42 g; 70%), ¹H-NMR (CDCl₃, 400 MHz) δ ppm: 8.01 (d, J=3.5 Hz, 1H), 7.42 (d, J=5.5 Hz, 1H), 7.35-7.25 (m, 5H), 6.81 (t, J=5.3 Hz, 1H), 4.39 (s, 2H), 3.54 (s, 2H), 2.91-2.83 (m, 2H), 2.13-2.03 (m, 2H), 2.01-1.91 (m, 2H), 1.80-1.71 (m, 2H). Rt 0.89 min (System B), [M+H]⁺ 281.1.

A solution of N,N-dimethylethanolamine (1.64 mL; 16.26 mmol) in THF (10 mL) was cooled to −5° C., after which n-butyllithium (13 mL, 2.5 M in hexane; 32.52 mmol) was added drop wise (Chem. Rev., 1993, 93, 2317). The resulting yellow mixture was stirred at 0° C. for 30 minutes. Subsequently, the reaction mixture was cooled to −78° C., and a solution of 1'-benzyl-2H-spiro[furo[2,3-b]pyridine-1,4'-piperidine] (1.52 g; 5.42 mmol) in THF (10 mL) was added. The resulting reaction mixture was stirred for 1 hour. Subsequently, a solution of 1,2-dibromotetrafluoroethane (2.58 mL; 21.7 mmol) dissolved in THF (40 mL) was added to this reaction mixture. After addition, the reaction mixture was allowed to warm slowly and stirred overnight at RT. The reaction mixture was quenched by the addition of a saturated aqueous NH₄Cl solution, followed by Et₂O. The organic phase was separated and extracted with an aqueous NaHCO₃ solution. The organic layer was dried (Na₂SO₄), filtered, and concentrated in vacuo. The residue was purified by column chromatography (SiO₂, Et₂O:hexanes:triethylamine 35:60:5) to afford 1'-benzyl-5-bromo-2H-spiro[furo[2,3-b]pyridine-1,4'-piperidine] (0.65 g; 33.3%). ¹H-NMR (CDCl₃, 400 MHz) δ ppm: 7.36-7.25 (m, 6H), 7.00 (d, J=7.3 Hz, 1H), 4.43 (s, 2H), 3.55 (s, 2H), 2.90-2.82 (m, 2H), 1.98-1.87 (m, 2H), 1.78-1.71 (m, 2 H). Rt 1.09 min (System B), [M+H]⁺ 361.1.

To a solution of 1'-benzyl-5-bromo-2H-spiro[furo[2,3-b]pyridine-1,4'-piperidine] (0.9 g; 2.56 mmol) in 1,2-dichloroethane (20 mL) at 0° C., was added 1-chloroethyl chloroformate (0.3 mL; 2.74 mmol). The reaction mixture was stirred for 3 hours at 60° C. The crude reaction mixture was concentrated in vacuo. Toluene (100 mL) was added and the mixture was concentrated. This last step was repeated twice. MeOH (20 mL) was added and the mixture was stirred overnight. The reaction mixture was concentrated in vacuo to afford 5-bromo-2H-spiro[furo[2,3-b]pyridine-1,4'-piperidine]hydrochloride (0.85 g; >100%). ¹H-NMR (DMSO-d₆, 400 MHz) δ ppm: 9.17-9.03 (m, 1H), 7.55 (d, J=7.5 Hz, 1H), 7.18 (d, J=7.5 Hz, 1H), 4.58 (s, 2H), 3.65-3.25 (m, 3H), 3.07-2.92 (m, 2H), 2.15-2.03 (m, 2H), 1.93-1.84 (m, 2H). Rt 0.85 min (System B), [M+H]⁺ 269.0

To a suspension of 5-bromo-2H-spiro[furo[2,3-b]pyridine-1,4'-piperidine]hydro-chloride (0.85 g; 2.78 mmol) in MeOH (20 mL) was added tert-butyl methacrylate (0.48 mL; 3.34 mmol) and N,N-diisopropylethylamine (1 mL; 5.84 mmol). The resulting mixture was heated at 140° C. in a sealed flask overnight. After cooling to RT the reaction mixture was partitioned between 5% aqueous NaHCO₃ solution and EtOAc. The layers were separated and the organic layer was dried (Na₂SO₄), filtered, and concentrated. The residue was purified by column chro-matography (SiO₂, Et₂O) to afford tert-butyl 3-{5-bromo-2H-spiro[furo[2,3-b]pyridine-1,4'-piperidine]-1'-yl}propanoate (630 mg; 57%). ¹H-NMR (CDCl₃, 400 MHz) δ ppm: 7.26 (d, J=7.5 Hz, 1H), 7.01 (d, J=7.5 Hz, 1H), 4.42 (s, 2H), 2.90-2.82 (m, 2H), 2.69 (t, J=7.3 Hz, 2H), 2.43 (t, J=7.3 Hz, 2H), 2.15-2.05 (m, 2H), 1.95-1.85 (m, 2H), 1.46 (s, 9H). Rt 1.15 min (System B), [M+H]⁺ 399.0

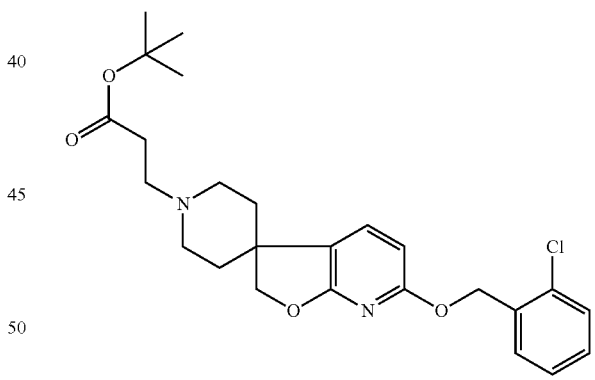

Tert-butyl 3-{5-[(2-chlorophenyl)methoxy-2H-spiro[furo[2,3-b]pyridine-1,4'-piperidine]-1'-yl)propanoate. To a degassed solution of tert-butyl 3-{5-bromo-2H-spiro[furo[2,3-b]pyridine-1,4'-piperidine]-1'-yl}propanoate (300 mg, 0.76 mmol) and (2-chlorophenyl)methanol (215.32 mg; 1.51 mmol) in toluene (2.67 mL) was added cesium carbonate (0.37 g, 1.13 mmol), palladium(II)acetate (3.39 mg, 0.02 mmol), and 2-di-tert-butylphosphino-3,4,5,6-tetramethyl-2',4',6'-triisopropyl-1,1'-biphenyl (7.26 mg, 0.02 mmol). The reaction mixture was stirred at 70° C. overnight. After one night, additional palladium(II) acetate (3.39 mg, 0.02 mmol) and 2-di-tert-butylphosphino-3,4,5,6-tetramethyl-2',4',6'-triisopropyl-1,1'-biphenyl (7.26 mg; 0.02 mmol) were added to the reaction mixture. The resulting mixture was stirred for another and 3 hours. After cooling to RT, the reaction mixture was diluted with EtOAc, filtered and washed with 5% aqueous NaHCO₃. The organic layer was dried (Na₂SO₄), filtered, and concentrated in vacuo. The residue was purified by column chromatography (SiO₂, Et₂O: hexanes:triethylamine 50:49:1) to afford tert-butyl 3-{5-[(2-chlorophenyl)-methoxy-2H-spiro[furo[2,3-b]pyridine-1,4'-piperidine]-1'-yl)propanoate (220 mg; 63%). ¹H-NMR (CDCl₃, 400 MHz) δ ppm: 7.54-7.52 (m, 1H), 7.39-7.36 (m, 2H), 7.28-7.24 (m, 2H), 6.36 (d, J=7.8 Hz, 1H), 5.42 (s, 2H), 4.40 (s, 2H), 2.90-2.81 (m, 2H), 2.68 (t, J=7.5 Hz, 2H), 2.44 (t, J=7.5 Hz, 2H), 2.15-2.05 (m, 2H), 1.96-1.86 (m, 2H), 1.70-1.78 (m, 2H), 1.46 (s, 9H). Rt 1.38 min (System B), [M+H]⁺ 459.0.

The following compound was obtained in a similar manner:

Tert-butyl 3-{5-[(2,6-dichlorophenyl)methoxy-2H-spiro[furo[2,3-b]pyridine-1,4'-piperidine]-1'-yl]propanoate. ¹H-NMR (CDCl₃, 400 MHz) δ ppm: 7.21-7.37 (m, 4H), 6.31 (d, J=7.8 Hz, 1H), 5.54 (s, 2H), 4.42 (s, 2H), 2.90-2.82 (m, 2H), 2.70 (t, J=7.5 Hz, 2H), 2.44 (t, J=7.5 Hz, 2H), 2.17-2.06 (m, 2H), 1.97-1.87 (m, 2H), 1.79-1.69 (m, 2H), 1.46 (s, 9H). Rt 1.40 min (System B), [M+H]⁺ 493.0.

Tert-butyl 3-[5-(2,6-dimethylphenoxy)-2H-spiro[furo[2,3-b]pyridine-1,4'-piperidine]-1'-yl]propanoate. To a degassed solution of tert-butyl 3-{5-bromo-2H-spiro[furo[2,3-b]pyridine-1,4'-piperidine]-1'-yl}propanoate (250 mg; 0.63 mmol)

In xylene (3 mL), was added subsequently, 2,6-dimethylphenol (76.78 mg; 0.63 mmol), potassium carbonate (173.92 mg; 1.26 mmol), 1-butylimidazole (0.50 mL; 3.8 mmol) and copper(I) iodide (23.97 mg; 0.13 mmol). The reaction mixture was heated at 140° C. and stirred overnight After cooling to RT, the reaction mixture was diluted with EtOAc, filtered and washed with 5% aqueous NaHCO₃. The organic layer was dried (Na₂SO₄), filtered, and concentrated in vacuo. The residue was purified by column chromatography (SiO₂, Et₂O:hexanes:triethylamine 50:49:1) to afford the product (70 mg, 25%). ¹H-NMR (CDCl₃, 400 MHz) δ ppm: 7.33 (d, J=7.8 Hz, 1H), 7.07-7.02 (m, 3H), 6.09 (d, J=7.8 Hz, 1H), 4.38 (s, 2H), 2.89-2.81 (m, 2H), 2.69 (t, J=7.5 Hz, 1H), 2.43 (t, J=7.5 Hz, 2H), 2.13 (s, 6H), 2.10-2.03 (m, 2H), 1.95-1.85 (m, 2H), 1.78-1.71 (m, 2H), 1.45 (s, 9H). Rt 1.35 min (System B), [M+H]⁺ 493.1.

Compound 200. 3-{5-[(2-Chlorophenyl)methoxy-2H-spiro[furo[2,3-b]pyridine-1,4'-piperidine]-1'-yl}propanoic acid hydrochloride Tert-butyl 3-{5-[(2-chlorophenyl)methoxy-2H-spiro[furo[2,3-b]pyridine-1,4'-piperidine]-1'-yl)propanoate (200 mg, 0.44 mmol) was dissolved in a 4M solution of HCl in 1,4-dioxane (10 mL; 4 mol/l; 40 mmol) and stirred for 48 hours at RT. Subsequently, the solvent was removed in vacuo and the residue treated with iPr₂O, the precipitate was collected by filtration and dried overnight under reduced pressure to afford the product (170 mg, 88%). ¹H NMR (400 MHz, DMSO-d₆) δ ppm 12.08 (bs, 1H), 10.9 (bs, 1H), 7.56-7.48 (m, 3H), 7.41-7.36 (m, 2H), 6.45 (d, 1H), 5.32 (s, 2H), 4.56-4.55 (m, 2H), 3.5-3.4 (m, 2H), 3.37-3.27 (m, 2H), 3.20-3.01 (m, 2H), 2.87 (t, J=7.4 Hz, 2H), 2.30-2.10 (m, 2H), 1.96-1.87 (m, 2H). Rt 1.30 min (System B), [M+H]⁺ 403.0

In a similar manner were made:

Compound 201. 3-{5-[(2,6-Dichlorophenyl)methoxy-2H-spiro[furo[2,3b]pyri-dine-1,4'-piperidine]-1'-yl)propanoic acid hydrochloride ¹H-NMR (DMSO-d₆, 400 MHz) δ ppm: 12.08 (bs, 1H), 10.03 (bs, 1H), 7.58-7.41 (m, 4H), 6.40-6.36 (m, 2H), 5.39 (s, 2H), 4.59-4.53 (m, 2H), 3.55-3.4 (m, 2H), 3.34-3.22 (m, 2H), 3.15-2.99 (m, 2H), 2.85 (t, J=7.3 Hz, 2H), 2.28-2.13 (m, 2H), 1.96-1.87 (m, 2H). Rt 1.32 min (System B), [M+H]⁺ 436.9

Compound 202. 3-[5-(2,6-Dimethylphenoxy)-2H-spiro[furo[2,3-b]pyridine-1,4'-piperidine]-1'-yl]propanoic acid hydrochloride ¹H-NMR (DMSO-d₆, 400 MHz) δ ppm: 12.08 (bs, 1H), 10.03 (bs, 1H), 7.52 (s, 1H), 7.15-7.04 (m, 3H), 6.40-6.36 (m, 2H), 4.53-4.40 (m, 2H), 3.52-3.40 (m, 2H), 3.39-3.25 (m, 2H), 3.13-2.93 (m, 2H), 2.84 (t, J=7.3 Hz, 2H), 2.20-2.08 (m, 2H), 2.03 (s, 6H), 1.97-1.87 (m, 2H). Rt 1.24 min (System B), [M+H]⁺ 383.1

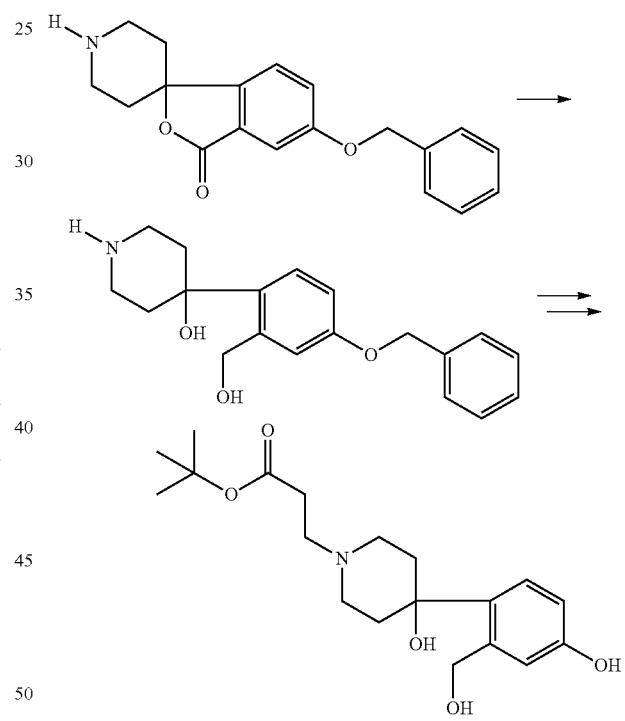

Tert-butyl 3-{4-hydroxy-4-[4-hydroxy-2-(hydroxymethyl)phenyl]piperidin-1-yl}propanoate. 5-(Benzyloxy)-3H-spiro[2-benzofuran-1,4'-piperidine]-3-one (5 g, mp 138-142° C.), made according to J. Org. Chem., 40, 10, 1975, 1427 was reduced to 4-[4-(benzyloxy)-2-(hydroxymethyl)phenyl]piperidin-4-ol (U.S. Pat. No. 3,962,259) (4.3 g, mp 198-202° C.) which was converted into tert-butyl 3-{4-[4-(benzyloxy)-2-(hydroxymethyl)-phenyl]-4-hydroxypiperidin-1-yl}propanoate (2.3 g), using the conditions described before (tert-butyl acrylate, N,N-diisopropylamine in MeOH). This intermediate was debenzylated using the following conditions:

(Pd(OH)₂/H₂/MeOH (overnight at RT) to afford the title compound (1.6 g, mp 68-70° C.). ¹H NMR (400 MHz, DMSO-d₆) δ ppm 9.1 (bs, 1H), 7.09 (bd, J=8 Hz, 1H), 6.97

(bs, 1H), 6.54 (bd, J=8 Hz, 1H), 5.69 (bs, 1H), 4.99 (bs, 1H), 4.74 (bs, 2H), 2.66-2.31 (m, 8H), 1.92-1.73 (m, 4H), 1.41 (s, 9H).

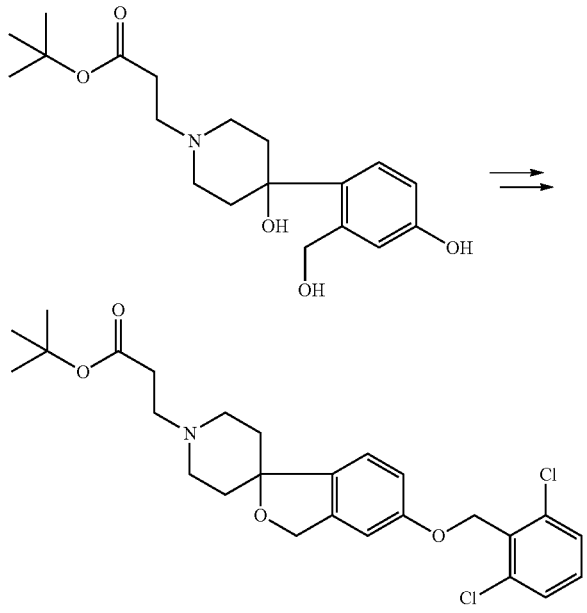

Tert-butyl 3-{5-[(2,6-dichlorophenyl)methoxy]-3-H-spiro[2-benzofuran-1,4'-piperidine]-1'-yl}propanoate. A mixture of tert-butyl 3-{4-hydroxy-4-[4-hydroxy-2-(hydroxymethyl)phenyl]piperidin-1-yl}propanoate (0.41 g; 1.17 mmol), K$_2$CO$_3$ (1.61 g; 11.67 mmol) and 2-(bromoethyl)-1,3-dichlorobenzene (0.28 g; 1.17 mmol) in acetone (50 mL) was heated at 35° C. overnight. After cooling to RT the reaction mixture was partitioned between an aqueous NaHCO$_3$ solution and DCM. The organic layer was dried (Na$_2$SO$_4$), filtered, and concentrated in vacuo. The residue was purified by column chromatography (SiO$_2$, DCM followed by EtOAc) to afford tert-butyl 3-(4-{4-[(2,6-dichlorophenyl)-methoxy]-2-(hydroxymethyl)phenyl}-4-hydroxypiperidin-1-yl)propanoate (0.49 g; 84.8%) Rt 1.32 min (System B), [M+H]$^+$ 510.1, which was dissolved in DCM (100 mL). Subsequently were added, triethylamine (0.54 mL; 4 mmol) and methanesulfonyl chloride (0.16 mL; 2.06 mmol) and the resulting mixture was stirred at RT for 72 hours. The reaction mixture was partitioned between an aqueous NaHCO$_3$ solution and DCM. The organic layer was dried (Na$_2$SO$_4$), filtered, and concentrated in vacuo. The residue was purified by column chromatography (SiO$_2$, DCM:EtOAc 3:1 followed by 1:1) to afford tert-butyl 3-{5-[(2,6-dichlorophenyl)-methoxy]-3-H-spiro[2-benzofuran-1, 4'-piperidine]-1'-yl}propanoate (0.26 g; 56.1%). Rt 1.45 min (System B), [M+H]$^+$ 492.1.

The following compounds were obtained in a similar manner:

Tert-butyl 3-[5-(cyclohexylmethoxy)-3-H-spiro[2-benzofuran-1,4'-piperidine]-1'-yl}propanoate.
Tert-butyl 3-{5-[(2-chlorophenyl)methoxy]-3-H-spiro[2-benzofuran-1,4'-piperidine]-1'-yl}propanoate.
Tert-butyl 3-(5-{[2-(trifluoromethyl)phenyl]methoxy}-3-H-spiro[2-benzofuran-1,4'-piperidine]-1'-yl}propanoate.
Tert-butyl 3-[5-(oxan-2-ylmethoxy)-3-H-spiro[2-benzofuran-1,4'-piperidine]-1'-yl}propanoate.
Tert-butyl 3-{5-[(3-chlorophenyl)methoxy]-3-H-spiro[2-benzofuran-1,4'-piperidine]-1'-yl}propanoate.
Tert-butyl 3-{5-[(2,3-dichlorophenyl)methoxy]-3-H-spiro[2-benzofuran-1,4'-piperidine]-1'-yl}propanoate.
Tert-butyl 3-(5-{[3-(trifluoromethyl)phenyl]methoxy}-3-H-spiro[2-benzofuran-1,4'-piperidine]-1'-yl}propanoate.
Tert-butyl 3-{5-[(2,5-dichlorophenyl)methoxy]-3-H-spiro[2-benzofuran-1,4'-piperidine]-1'-yl}propanoate.
Tert-butyl 3-{5-[(3,5-dichlorophenyl)methoxy]-3-H-spiro[2-benzofuran-1,4'-piperidine]-1'-yl}propanoate.

Compound 203. 3-{5-[(2,6-Dichlorophenyl)methoxy]-3-H-spiro[2-benzofuran-1,4'-piperidine]-1'-yl}propanoic acid hydrochloride Tert-butyl 3-{5-[(2,6-dichlorophenyl)methoxy]-3-H-spiro[2-benzofuran-1,4'-piperidine]-1'-yl}propanoate (260 mg, 0.53 mmol) was dissolved in a 4M solution of HCl in 1,4-dioxane (8 mL; 4 mol/l; 32 mmol) and stirred for 72 hours at RT. Subsequently, the solvent was removed in vacuo and the residue treated with iPr$_2$O, the precipitate was collected by filtration and dried overnight under reduced pressure to afford the product (220 mg, 95.5%). $^1$H NMR (400 MHz, DMSO-d$_6$) δ ppm 12.70 (bs., 1H), 10.40 (bs, 1H), 7.56-7.60 (m, 2H), 7.46-7.51 (m, 1H), 7.00-7.18 (m, 3H), 5.22 (s, 2H), 5.02 (s, 2H), 3.42-3.49 (m, 2H), 3.30-3.39 (m, 2H), 3.11-3.21 (m, 2H), 2.84 (t, J=7.6 Hz, 2H), 2.21-2.31 (m, 2H), 1.78-1.86 (m, 2H). Rt 1.35 min (System B), [M+H]$^+$ 436.1.

The following compounds were obtained in a similar manner:

Compound 204. 3-[5-(Cyclohexylmethoxy)-3-H-spiro[2-benzofuran-1,4'-piperidine]-1'-yl}propanoic acid hydrochloride Rt 1.41 min (System B), [M+H]$^+$ 374.2.

Compound 205. 3-{5-[(2-Chlorophenyl)methoxy]-3-H-spiro[2-benzofuran-1,4'-piperidine]-1'-yl}propanoic acid hydrochloride Rt 1.35 min (System B), [M+H]$^+$ 402.1.

Compound 206. 3-(5-{[2-(Trifluoromethyl)phenyl]methoxy}-3-H-spiro[2-benzofuran-1,4'-piperidine]-1'-yl}propanoic acid hydrochloride Rt 1.36 min (System B), [M+H]$^+$ 436.1.

Compound 207. 3-[5-(Oxan-2-ylmethoxy)-3-H-spiro[2-benzofuran-1,4'-piperidine]-1'-yl}propanoic acid hydrochloride Rt 1.17 min (System B), [M+H]$^+$ 376.2.

Compound 208. 3-{5-[(3-Chlorophenyl)methoxy]-3-H-spiro[2-benzofuran-1,4'-piperidine]-1'-yl}propanoic acid hydrochloride Rt 1.34 min (System B), [M+H]$^+$ 402.1.

Compound 209. 3-{5-[(2,3-Dichlorophenyl)methoxy]-3-H-spiro[2-benzofuran-1,4'-piperidine]-1'-yl}propanoic acid hydrochloride $^1$H NMR (400 MHz, DMSO-d$_6$) δ ppm 12.70 (bs, 1H), 10.40 (bs, 1H), 7.65-7.79 (m, 1H), 7.56-7.60 (m, 1H), 7.43

(t, J=7.5 Hz, 1H), 6.98-7.13 (m, 3H), 5.20 (s, 2H), 5.01 (s, 2H), 3.43-3.51 (m, 2H), 3.31-3.39 (m, 2H), 3.12-3.23 (m, 2H), 2.85 (t, J=7.6 Hz, 2H). 2.21-2.31 (m, 2H), 1.78-1.86 (m, 2H). Rt 1.40 min (System B), [M+H]$^+$ 436.1.

Compound 210. 3-(5-{[3-(Trifluoromethyl)phenyl]methoxy}-3-H-spiro[2-benzofuran-1,4'-piperidine]-1'-yl}propanoic acid hydrochloride Rt 1.40 min (System B), [M+H]$^+$ 436.1.

Compound 211. 3-{5-[(2,5-Dichlorophenyl)methoxy]-3-H-spiro[2-benzofuran-1,4'-piperidine]-1'-yl}propanoic acid hydrochloride Rt 1.43 min (System B), [M+H]$^+$ 436.1.

Compound 212. 3-{5-[(3,5-Dichlorophenyl)methoxy]-3-H-spiro[2-benzofuran-1,4'-piperidine]-1'-yl}propanoic acid hydrochloride $^1$H NMR (400 MHz, DMSO-d$_6$) δ ppm 12.80 (bs, 1H), 10.50 (bs, 1H), 7.58-7.61 (m, 1H), 7.50-7.53 (m, 2H), 6.96-7.10 (m, 3H), 5.13 (s, 2H), 4.99 (s, 2H), 3.44-3.53 (m, 2H), 3.30-3.39 (m, 2H), 3.11-3.22 (m, 2H), 2.86 (t, J=7.6 Hz, 2H), 2.21-2.32 (m, 2H), 1.76-1.85 (m, 2H).

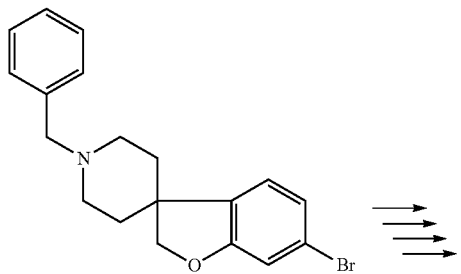

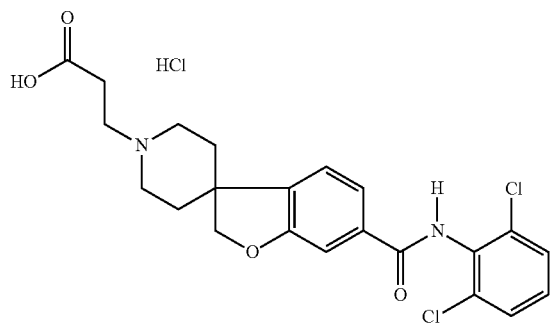

Compound 213. 3-{6-[((2,6-Dichlorophenyl)carbamoyl)-2H-spiro[1-benzofuran-3,4'-piperidine]-1'-yl}propanoic acid hydrochloride To a solution of 1'-benzyl-6-bromo-2H-spiro[1-benzofuran-3,4'-piperidine] (0.51 g; 0.87 mmol) in tetrahydrofuran (50 mL) was cooled to −78° C. and n-butyllithium (0.35 mL, 2.5 mol/l in hexane, 0.87 mmol) was added. Subsequently (at −78° C.), a solution of 1,3-dichloro-2-isocyanatobenzene (0.18 g; 0.96 mmol), dissolved in THF (10 mL), was added dropwise. The reaction mixture was stirred at −70° C. for 30 minutes. The reaction mixture was allowed to warm to 0° C., and subsequently quenched by the addition of a saturated aqueous NH$_4$Cl solution, followed by Et$_2$O. The organic phase was separated and extracted with an aqueous NaHCO$_3$ solution. The organic layer was dried (Na$_2$SO$_4$), filtered, and concentrated in vacuo. The residue was purified by column chromatography (SiO$_2$, Et$_2$O:hexanes 1:2) to afford 1'-benzyl-N-(2,6-dichlorophenyl)-2H-spiro[1-benzofuran-3,4'-piperi-dine]-6-carboxamide (0.17 g; 41.8%). Rt 1.22 min (System B), [M+H]$^+$ 467.1.

To a solution of r-benzyl-N-(2,6-dichlorophenyl)-2H-spiro[1-benzofuran-3,4'-piperidine]-6-carboxamide (0.17 g; 0.36 mmol) in 1,2-dichloroethane (10 mL) at 0° C., was added 1-chloroethyl chloroformate (0.08 mL; 0.76 mmol) and a few drops of triethylamine. The reaction mixture was stirred for 3 hours at RT. The crude reaction mixture was concentrated in vacuo. Toluene (100 mL) was added and the mixture was concentrated. This last step was repeated twice. MeOH (20 mL) was added and the mixture was stirred overnight. The reaction mixture was concentrated in vacuo and filtered through a tosic acid solid phase extraction cartridge, washing with MeOH, and eluting with 2 N NH$_3$/MeOH. The product was concentrated to afford N-(2,6-dichlorophenyl)-2H-spiro[1-benzofuran-3,4'-piperidine]-6-carboxamide (0.14 g; 100%)

Rt 1.05 min (System B), [M+H]$^+$ 377.1, which was dissolved in MeOH (10 mL). Subsequently was added tert-butylacrylate (0.06 mL; 0.44 mmol) and N,N-diisopropylethylamine (0.09 mL; 0.50 mmol). The resulting mixture was heated at 140° C. in a sealed flask overnight. After cooling to RT, the reaction mixture was partitioned between 5% aqueous NaHCO$_3$ solution and EtOAc. The layers were separated and the organic layer was dried (Na$_2$SO$_4$), filtered, and concentrated. The residue was purified by column chromatography (SiO$_2$, Et$_2$O) to afford Tert-butyl 3-{6-[((2,6-dichlorophenyl)carbamoyl)-2H-spiro[1-benzofuran-3,4'-piperidine]-1'-yl}propanoate (160 mg, 79%). Rt 1.25 min (System B), [M+H]$^+$ 505.1, which was dissolved in a 4M solution of HCl in 1,4-dioxane (10 mL; 4 mol/l; 40 mmol) and stirred for 48 hours at RT. Subsequently, the solvent was removed in vacuo and the residue treated with iPr$_2$O, the precipitate was collected by filtration and dried overnight under reduced pressure to afford the title compound (140 mg, 80.9%). Rt 1.09 min (System B), [M+H]$^+$ 449.1.

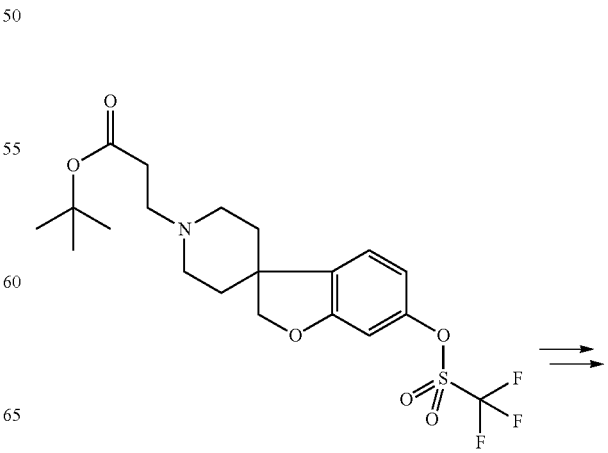

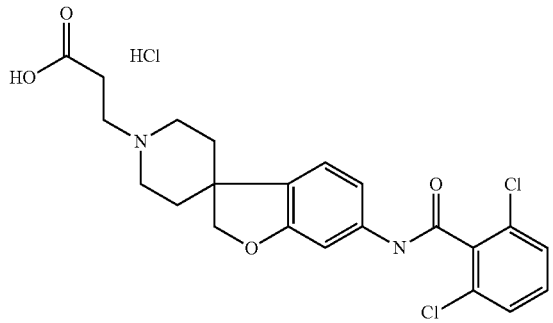

Compound 311. 3-{6-[((2,6-Dichlorobenzene)amido]-2H-spiro[1-benzofuran-3,4'-piperidine]-1'-yl}propanoic acid hydrochloride To a degassed solution of 2,6-dichlorobenzamide (113 mg; 0.6 mmol) and tert-butyl 3-{-{6-[(trifluoromethane)sulfonyloxy]-2H-spiro[1-benzofuran-3,4'-piperidine]-1'-yl]-propanoate (232 mg, 0.5 mmol) in tert-butyl alcohol (7.5 mL), was added potassium phosphate tribasic (0.16 g; 0.75 mmol). Subsequently were added tris-(dibenzylidenaceton)-dipalladium(0) (9.1 mg; 0.01 mmol), and 2-di-t-butylphosphino-3,4,5,6-tetramethyl-2',4',6'-tri-1-propylbiphenyl (24 mg; 0.05 mmol). The resulting mixture was heated under reflux, overnight. After cooling to RT, the mixture was concentrated in vacuo and partitioned between EtOAc and 5% aqueous NaHCO$_3$. The organic layer was dried (Na$_2$SO$_4$), filtered, and concentrated in vacuo. The residue was purified by column chromatography (SiO$_2$, dichloromethane:aceton 9:1) to afford the product (0.18 g; 71%). $^1$H NMR (400 MHz, CHCl$_3$-d) δ ppm 7.56 (br s, 1H), 7.38-7.45 (m, 1H), 7.22 (d, J=2Hz, 1H), 6.96-7.10 (m, 3H), 5.90 (br s, 1H), 4.39 (s, 2H), 2.87-2.94 (m, 2H), 2.70 (t, J=8 Hz, 2H), 2.45 (t, J=8 Hz, 2H), 2.03-2.12 (m, 2H), 1.90-1.99 (m, 2H), 1.71-1.77 (m, 2H), 1.48 (s, 9H), Rt 1.31 min (System B), [M+H]$^+$ 505.2, which was dissolved in a 4M solution of HCl in 1,4-dioxane (20 mL; 4 mol/l; 80 mmol) and stirred for 3 hours at 65° C. Subsequently, the solvent was removed in vacuo and the residue treated with iPr$_2$O, the precipitate was collected by filtration and dried overnight under reduced pressure to afford the product (80 mg, 49%). $^1$H NMR (400 MHz, DMSO-d$_6$) δ ppm 10.73 (s, 1H), 7.46-7.62 (m, 3H), 7.28 (br s, 1H), 7.13-7.18 (m, 2H), 4.49 (br s, 2H), 3.30-3.51 (m, 4H), 3.00-3.20 (m, 2H), 2.81-2.87 (m, 2H), 2.12-2.19 (m, 2H), 1.86-1.92 (m, 2H). Rt 1.25 min (System B), [M+H]$^+$ 449.2

Compound 312. 3-{6-[((2,6-Difluorobenzene)amido]-2H-spiro[1-benzofuran-3,4'-piperidine]-1'-yl}propanoic acid hydrochloride $^1$H NMR (400 MHz, DMSO-d$_6$) δ ppm 12.64 (br s, 1H), 10.82 (s, 1H), 10.27 (br s, 1H), 7.56-7.63 (m, 1H), 7.04-7.29 (m, 5H), 4.51 (br s, 2H), 3.29-3.55 (m, 4H), 3.05-3.12 (m, 2H), 2.82-2.89 (m, 2H), 2.15-2.24 (m, 2H), 1.84-1.93 (m, 2H).

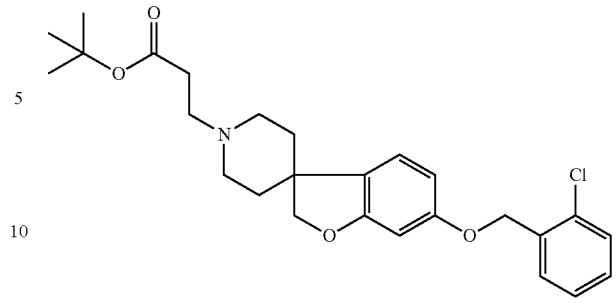

Tert-butyl 3-{6-[(2-chlorophenyl)methoxy]-2H-spiro[1-benzofuran-3,4'-piperidine]-1'-yl}propanoate. Cs$_2$CO$_3$ (240 mg; 0.735 mmol) and NaI (4 mg; 0.025 mmol) are placed as solid in a 16×100 mm glass tube reactor fitted with a magnetic stir bar. A solution of tert-butyl 3-{6-hydroxy-2H-spiro[1-benzofuran-3,4'-piperidine]-1'-yl}propanoate (81 mg; 0.245 mmol) in CH$_3$CN/THF/DMF 1.5:1:1.5 (0.061M) is added and the mixture is stirred at RT for 2 hours. To this reaction mixture is added 1-(bromoethyl)-2-chlorobenzene (61.77 mg; 0.3 mmol) in 0.5 mL DMF (0.6M) and the resulting mixture is warmed at 80° C. for 20 hours. The reaction is cooled down and the solvents are removed using a Genevac HT4 at 40° C. for 14 hours (full vacuum). The workup involves addition of 2 mL of K$_2$CO$_3$ 1M and 4 mL of DCM/MeOH 95:5 followed by stirring for 15 min. The phases are separated through phase separation cartridge 1PS. The aqueous layer is extracted again with 2 mL of DCM/MeOH 95:5 and organic layers are combined and dried through phase separation cartridge 1PS. Crude compounds are obtained after solvent removal using a Genevac HT4 at full vacuum 40° C. for 14 h and are used as such in the next step.

The following compounds were obtained in a similar manner:
Tert-butyl 3-[6-(benzyloxy)-2H-spiro[1-benzofuran-3,4'-piperidine]-1'-yl]propanoate.
Tert-butyl 3-{6-[(4-chlorophenyl)methoxy]-2H-spiro[1-benzofuran-3,4'-piperidine]-1'-yl}propanoate.
Tert-butyl 3-{6-[(6-cyanohexyl)oxy-2H-spiro[1-benzofuran-3,4'-piperidine]-1'-yl}propanoate.
Tert-butyl 3-[6-(4-phenylbutoxy)-2H-spiro[1-benzofuran-3,4'-piperidine]-1'-yl]propanoate.
Tert-butyl 3-[6-(2,3-dihydro-1-benzofuran-2-ylmethoxy)-2H-spiro[1-benzofuran-3,4'-piperidine]-1'-yl]propanoate.
Tert-butyl 3-[6-(2-phenoxyethoxy)-2H-spiro[1-benzofuran-3,4'-piperidine]-1'-yl]propanoate.
Tert-butyl 3-[6-(2-phenoxypropoxy)-2H-spiro[1-benzofuran-3,4'-piperidine]-1'-yl]propanoate.
Tert-butyl 3-[6-(2-phenoxybutoxy)-2H-spiro[1-benzofuran-3,4'-piperidine]-1'-yl]propanoate.
Tert-butyl 3-{6-[3-(benzyloxy)propoxy]-2H-spiro[1-benzofuran-3,4'-piperidine]-1'-yl}propanoate.
Tert-butyl 3-[6-(2-, 3-dihydro-1,4-benzodioxin-2-ylmethoxy)-2H-spiro[1-benzofuran-3,4'-piperidine]-1'-yl]propanoate.
Tert-butyl 3-(6-{[3-(4-tert-butylphenyl)-1,2,4-oxadiazol-5-yl]methoxy}-2H-spiro[1-benzofuran-3,4'-piperidine]-1'-yl)propanoate.
Tert-butyl 3-(6-{[4-(5-methyl-1,2,4-oxadiazol-3-yl)phenyl]methoxy}-2H-spiro[1-benzofuran-3,4'-piperidine]-1'-yl)propanoate.
Tert-butyl 3-(6-{[4-(1H-pyrazol-1-yl)phenyl]methoxy}-2H-spiro[1-benzofuran-3,4'-piperidine]-1'-yl)propanoate.

Tert-butyl 3-(6-{[4-(1H-1,2,4-triazol-1-yl)phenyl]methoxy}-2H-spiro[1-benzofuran-3,4'-piperidine]-1'-yl}propanoate.

Tert-butyl 3-{6-[(2-methyl-1,3-thiazol-4-yl)methoxy]-2H-spiro[1-benzofuran-3,4'-piperidine]-1'-yl}propanoate.

Tert-butyl 3-{6-[(1-methyl-1H-pyrazol-3-yl)methoxy]-2H-spiro[1-benzofuran-3,4'-piperidine]-1'-yl}propanoate.

Tert-butyl 3-[6-({6-methylimidazol[1,2-a]pyridin-2-yl}methoxy)-2H-spiro[1-benzofuran-3,4'-piperidine]-1'-yl]propanoate.

Tert-butyl 3-[6-(hex-5-yn-1-yloxy)-2H-spiro[1-benzofuran-3,4'-piperidine]-1'-yl]propanoate.

Tert-butyl 3-{6-[(5-oxohexyl)oxy]-2H-spiro[1-benzofuran-3,4'-piperidine]-1'-yl}propanoate.

Tert-butyl 3-{6-[2-(naphtalen-2-yloxy)ethoxy]-2H-spiro[1-benzofuran-3,4'-piperidine]-1'-yl}propanoate.

Tert-butyl 3-(6-{3-[(2-propyl-1,3-thiazol-5-yl)oxy]propoxy}-2H-spiro[1-benzofuran-3,4'-piperidine]-1'-yl)propanoate.

Tert-butyl 3-{6-[(7-methoxyheptyl)oxy]-2H-spiro[1-benzofuran-3,4'-piperidine]-1'-yl}propanoate.

Tert-butyl 3-{6-[(phenylcarbamoyl)methoxy]-2H-spiro[1-benzofuran-3,4'-piperidine]-1'-yl}propanoate.

Tert-butyl 3-{6-[2-(benzyloxy)ethoxy]-2H-spiro[1-benzofuran-3,4'-piperidine]-1'-yl}propanoate.

Tert-butyl 3-{6-[(4-methanesulfonylphenyl)methoxy]-2H-spiro[1-benzofuran-3,4'-piperidine]-1'-yl}propanoate.

Compound 214. 3-{6-[(2-Chlorophenyl)methoxy)-2H-spiro[1-benzofuran-3,4'-piperidine]-1'-yl}propanoic acid trifluoroacetic acid The crude Tert-butyl 3-{6-[(2-chlorophenyl)methoxy)-2H-spiro[1-benzofuran-3,4'-piperidine]-1'-yl}propanoate was treated with a mixture of TFA/DCM 2:1 and stirred at RT for 2 h. Subsequently, the volatiles were removed using a nitrogen flow and subsequently a Genevac HT4 full vacuum at 40° C. for 14 hours. The crude product was purified by preparative HPLC to afford the title compound; $R_t$=1.38 min. (System A), [M+H]$^+$ Found: 403.21; Calc: 402.14. Conditions for the preparative LC-MS: Injection of the crude product dissolved in 600 □L DMSO/CH$_3$CN 1:2; column ACQUITY UPLC BEH C18 1.7 μm (50×2.1 mm×1.7 μm) at 45° C. Mobile phase A=water+0.1% CH$_3$COOH and B=CH$_3$CN+0.1% CH$_3$COOH, from 5% B to 90% B in 5 minutes. C18 flow rate 0.8 mL/minute, detection with UV 210-260 nm.

The following compounds were obtained similarly:

Compound 215. 3-[6-(Benzyloxy)-2H-spiro[1-benzofuran-3,4'-piperidine]-1'-yl]propanoic acid trifluoroacetic acid $R_t$=1.28 min. (System A), [M+H]$^+$ Found: 368.23; Calc: 368.18.

Compound 216. 3-{6-[(4-Chlorophenyl)methoxy)-2H-spiro[1-benzofuran-3,4'-piperidine]-1'-yl}propanoic acid trifluoroacetic acid $R_t$=1.42 min. (System A), [M+H]$^+$ Found: 403.21; Calc: 402.14.

Compound 217. 3-{6-[(6-Cyanohexyl)oxy-2H-spiro[1-benzofuran-3,4'-piperidine]-1'-yl}propanoic acid trifluoroacetic acid $R_t$=1.18 min. (System A), [M+H]$^+$ Found: 387.28; Calc: 387.22.

Compound 218. 3-[6-(4-Phenylbutoxy)-2H-spiro[1-benzofuran-3,4'-piperidine]-1'-yl]propanoic acid trifluoroacetic acid $R_t$=1.54 min. (System A), [M+H]$^+$ Found: 410.30; Calc: 410.23.

Compound 219. 3-[6-(2,3-Dihydro-1-benzofuran-2-ylmethoxy)-2H-spiro[1-benzofuran-3,4'-piperidine]-1'-yl]propanoic acid trifluoroacetic acid $R_t$=1.32 min. (System A), [M+H]$^+$ Found: 410.25; Calc: 410.19.

Compound 220. 3-[6-(2-Phenoxyethoxy)-2H-spiro[1-benzofuran-3,4'-piperidine]-1'-yl]propanoic acid trifluoroacetic acid $R_t$=1.38 min. (System A), [M+H]$^+$ Found: 398.27; Calc: 398.19.

Compound 221. 3-[6-(2-Phenoxypropoxy)-2H-spiro[1-benzofuran-3,4'-piperidine]-1'-yl]propanoic acid trifluoroacetic acid $R_t$=1.49 min. (System A), [M+H]$^+$ Found: 412.28; Calc: 412.21.

Compound 222. 3-[6-(2-Phenoxybutoxy)-2H-spiro[1-benzofuran-3,4'-piperidine]-1'-yl]propanoic acid trifluoroacetic acid $R_t$=1.62 min. (System A), [M+H]$^+$ Found: 426.30; Calc: 426.22.

Compound 223. Tert-butyl 3-{6-[3-(Benzyloxy)propoxy]-2H-spiro[1-benzofuran-3,4'-piperidine]-1'-yl}propanoic acid trifluoroacetic acid Rt=1.51 min. (System A), [M+H]$^+$ Found: 426.31; Calc: 426.22.

Compound 224. 3-[6-(2-,3-Dihydro-1,4-benzodioxin-2-ylmethoxy)-2H-spiro[1-benzofuran-3,4'-piperidine]-1'-yl]propanoic acid trifluoroacetic acid $R_t$=1.44 min. (System A), [M+H]$^+$ Found: 426.27; Calc: 426.19.

Compound 225. 3-(6-{[3-(4-Tert-butylphenyl)-1,2,4-oxadiazol-5-yl]methoxy}-2H-spiro[1-benzofuran-3,4'-piperidine]-1'-yl)propanoic acid trifluoroacetic acid $R_t$=1.89 min. (System A), [M+H]$^+$ Found: 492.32; Calc: 492.24.

Compound 226. 3-(6-{[4-(5-Methyl-1,2,4-oxadi-azol-3-yl)phenyl]methoxy}-2H-spiro[1-benzofuran-3,4'-piperidine]-1'-yl)propanoic acid trifluoroacetic acid R$_t$=1.33 min. (System A), [M+11]$^+$ Found: 450.29; Calc: 450.20.

Compound 227. 3-(6-{[4-(1H-Pyrazol-1-yl)phenyl]methoxy}-2H-spiro[1-benzofuran-3,4'-piperidine]-1'-yl)propanoic acid trifluoroacetic acid Rt=1.33 min. (System A), [M+H]$^+$ Found: 434.28; Calc: 434.20.

Compound 228. 3-(6-{[4-(1H-1,2,4-Triazol-1-yl)phenyl]methoxy}-2H-spiro[1-benzofuran-3,4'-piperidine]-1'-yl)propanoic acid trifluoroacetic acid R$_t$=1.09 min. (System A), [M+H]$^+$ Found: 435.29; Calc: 435.20.

Compound 229. 3-{6-[(2-Methyl-1,3-thiazol-4-yl)methoxy]-2H-spiro[1-benzofuran-3,4'-piperidine]-1'-yl}propanoic acid trifluoroacetic acid Rt=1.05 min. (System A), [M+H]$^+$ Found: 389.21; Calc: 389.15.

Compound 230. 3-{6-[(1-Methyl-1H-pyrazol-3-yl)methoxy]-2H-spiro[1-benzofuran-3,4'-piperidine]-1'-yl}propanoic acid trifluoroacetic acid Rt=0.92 min. (System A), [M+H]$^+$ Found: 372.25; Calc: 372.19.

Compound 231. 3-[6-({6-Methylimidazol[1,2-a]pyridin-2-yl}methoxy)-2H-spiro[1-benzofuran-3,4'-piperidine]-1'-yl]propanoic acid trifluoroacetic acid R$_t$=0.77 min. (System A), [M+H]$^+$ Found: 421.28; Calc: 422.20.

Compound 232. 3-[6-(Hex-5-yn-1-yloxy)-2H-spiro[1-benzofuran-3,4'-piperidine]-1'-yl]propanoic acid trifluoroacetic acid R$_t$=1.3 min. (System A), [M+H]$^+$ Found: 358.26; Calc: 358.20.

Compound 233. 3-{6-[(5-Oxohexyl)oxy]-2H-spiro[1-benzofuran-3,4'-piperidine]-1'-yl}propanoic acid trifluoroacetic acid R$_t$=1.06 min. (System A), [M+H]$^+$ Found: 376.27; Calc: 376.21. Compound 234. 3-{6-[2-(Naphtalen-2-yloxy)ethoxy]-2H-spiro[1-benzofuran-3,4'-piperidine]-1'-yl}propanoic acid trifluoroacetic acid R$_t$=1.65 min. (System A), [M+H]$^+$ Found: 448.29; Calc: 448.21.

Compound 235. 3-(6-{3-[(2-Propyl-1,3-thiazol-5-yl)oxy]propoxy}-2H-spiro[1-benzofuran-3,4'-piperidine]-1'-yl)propanoic acid trifluoroacetic acid Rt=1.48 min. (System A), [M+H]$^+$ Found: 461.29; Calc: 461.21.

Compound 236. 3-{6-[(7-Methoxyheptyl)oxy]-2H-spiro[1-benzofuran-3,4'-piperidine]-1'-yl}propanoic acid trifluoroacetic acid R$_t$=1.49 min. (System A), [M+H]+Found: 406.33; Calc: 406.25.

Compound 237. 3-{6-[(Phenylcarbamoyl)methoxy]-2H-spiro[1-benzofuran-3,4'-piperidine]-1'-yl}propanoic acid trifluoroacetic acid Rt=1.12 min. (System A), [M+H]$^+$ Found: 411.27; Calc: 411.19.

Compound 238. 3-{6-[2-(Benzyloxy)ethoxy]-2H-spiro[1-benzofuran-3,4'-piperidine]-1'-yl}propanoic acid trifluoroacetic acid R$_t$=1.38 min. (System A), [M+H]$^+$ Found: 412.28; Calc: 412.21.

Compound 239. 3-{6-[(4-Methanesulfonylphenyl)methoxy]-2H-spiro[1-benzofuran-3,4'-piperidine]-1'-yl}propanoic acid trifluoroacetic acid Rt=1.06 min. (System A), [M+H]$^+$ Found: 446.26; Calc: 446.16.

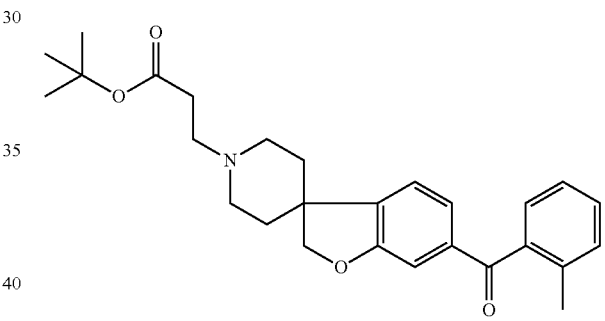

Tert-butyl 3-{6-[(2-Methylphenyl)carbonyl)-2H-spiro[1-benzofuran-3,4'-piperidine]-1'-yl}propanoate. To a nitrogen purged solution of Tert-butyl 3-[6-(tributylstannyl)-2H-spiro[1-benzofuran-3,4'-piperidine]-1'-yl]propanoate (0.3 g; 0.49 mmol) dissolved in dichloroethane (5 mL) was added 2-methylbenzoyl chloride (0.1 mL; 0.74 mmol). The resulting reaction mixture was stirred for 72 hour at 70° C. Subsequently, the reaction mixture was cooled and diluted with EtOAc and brine. The organic layer was washed with a solution of KF H$_2$O (5 mol/l), dried (Na$_2$SO$_4$), and concentrated in vacuo. The residue was purified by column chromatography (SiO$_2$, dichloromethane:acetone 9:1) to afford the product (120 mg; 55.7%). Rt 1.47 min (System B), [M+H]$^+$ 436.2.

The following compounds were obtained in a similar manner:
Tert-butyl 3-{6-benzoyl-2H-spiro[1-benzofuran-3,4'-piperidine]-1'-yl}propanoate.
Tert-butyl 3-{6-[(2-chlorophenyl)carbonyl)-2H-spiro[1-benzofuran-3,4'-piperidine]-1'-yl}propanoate.
Tert-butyl 3-{6-[(2E)-3-phenylprop-2-enoyl]-2H-spiro[1-benzofuran-3,4'-piperidine]-1'-yl}propanoate.
Tert-butyl 3-{6-[(2E)-3-(2-chlorophenyl)prop-2-enoyl]-2H-spiro[1-benzofuran-3,4'-piperidine]-1'-yl}propanoate.

Tert-butyl 3-{6-[(1-benzofuran-2-yl)carbonyl]-2H-spiro[1-benzofuran-3,4'-piperidine]-1'-yl}propanoate.

Tert-butyl 3-{6-[(2-phenylcyclopropyl)carbonyl]-2H-spiro[1-benzofuran-3,4'-piperidine]-1'-yl}propanoate.

Tert-butyl 3-[6-(3-phenylpropanoyl)-2H-spiro[1-benzofuran-3,4'-piperidine]-1'-yl]propanoate.

Compound 240. 3-{6-[(2-Methylphenyl)carbonyl)-2H-spiro[1-benzofuran-3,4'-piperidine]-1'-yl}propanoic acid hydrochloride Tert-butyl 3-{6-[(2-chlorophenyl)carbonyl)-2H-spiro[1-benzofuran-3,4'-piperidine]-1'-yl}propanoate (100 mg, 0.23 mmol) was dissolved in a 4M solution of HCl in 1,4-dioxane (20 mL; 4 mol/l; 80 mmol) and stirred for 48 hours at RT. Subsequently, the solvent was removed in vacuo and the residue treated with iPr₂O, the precipitate was collected by filtration and dried overnight under reduced pressure to afford the product (0.7 g, 73%). Rt 1.36 min (System B), [M+H]⁺ 380.1.

The following compounds were obtained obtained in a similar manner:

Compound 241. 3-{6-Benzoyl-2H-spiro[1-benzofuran-3,4'-piperidine]-1'-yl}propanoic acid hydrochloride Rt 1.45 min (System B), [M+H]⁺ 366.2.

Compound 242. 3-{6-[(2-Chlorophenyl)carbonyl)-2H-spiro[1-benzofuran-3,4'-piperidine]-1'-yl}propanoic acid hydrochloride ¹H NMR (400 MHz, DMSO-d₆) δ ppm 12.72 (bs, 1H), 10.20 (bs, 1H), 7.58-7.63 (m, 2H), 7.46-7.52 (m, 2H), 7.39-7.42 (m, 1H), 7.22-7.26 (m, 1H), 7.15 (bs, 1H), 4.59 (bs, 2H), 3.29-3.56 (m, 4H), 3.04-3.13 (m, 2H), 2.81-2.88 (m, 2H), 2.15-2.25 (m, 2H), 1.92-2.01 (m, 2H). Rt 1.55 min (System B), [M+H]⁺ 400.0

Compound 243. 3-{6-[(2E)-3-Phenylprop-2-enoyl]-2H-spiro[1-benzofuran-3,4'-piperidine]-1'-yl}propanoic acid trifluoroacetic acid Tert-butyl 3-{6-[(2E)-3-phenylprop-2-enoyl]-2H-spiro[1-benzofuran-3,4'-piperidine]-1'-yl}propanoate (200 mg, 0.45 mmol) was dissolved DCM (6 mL) and trifluoroacetic acid was added (2 mL; 25.96 mmol) and stirred at RT overnight. Subsequently, the solvent was removed in vacuo and the residue treated with iPr₂O, the precipitate was collected by filtration and dried overnight under reduced pressure to afford the product (0.21 g; 88.3%). Rt 1.35 min (System B), [M+H]⁺ 392.1.

The following compounds were obtained obtained in a similar manner:

Compound 244. 3-{6-[(2E)-3-(2-Chlorophenyl)prop-2-enoyl]-2H-spiro[1-benzofuran-3,4'-piperidine]-1'-yl}propanoic acid trifluoroacetic acid Rt 1.38 min (System B), [M+H]⁺ 426.0.

Compound 245. 3-{6-[(1-Benzofuran-2-yl)carbonyl]-2H-spiro[1-benzofuran-3,4'-piperidine]-1'-yl}propanoic acid trifluoroacetic acid Rt 1.26 min (System B), [M+H]⁺ 406.1.

Compound 246. 3-{6-[(2-Phenylcyclopropyl)carbonyl]-2H-spiro[1-benzofuran-3,4'-piperidine]-1'-yl}propanoic acid trifluoroacetic acid Rt 1.31 min (System B), [M+H]⁺ 406.1.

Compound 247. 3-[6-(3-phenylpropanoyl)-2H-spiro[1-benzofuran-3,4'-piperidine]-1'-yl]propanoic acid trifluoroacetic acid Rt 1.30 min (System B), [M+H]⁺ 394.1

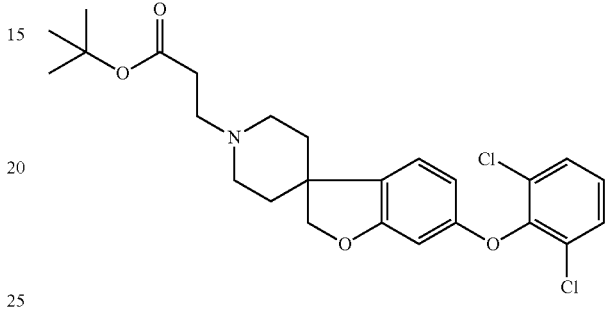

Tert-butyl 3-[6-(2,6-dichlorophenoxy)-2H-spiro[1-benzofuran-3,4'-piperidine]-1'-yl]propanoate. To a solution of 3-{6-hydroxy-2H-spiro[1-benzofuran-3,4'-piperidine]-1'-yl}propanoate (250 mg; 0.75 mmol) and 2,6-dichlorofluorobenzene (123.7 mg; 0.075 mmol), dissolved in DMF (5 mL) was added K₂CO₃ (155 mg; 1.2 mmol). The resulting reaction mixture was stirred for 48 hour minutes at 100° C. Subsequently, the reaction mixture was cooled and diluted with EtOAc and brine. The organic layer was washed with a aqueous solution of NaHCO₃, dried (Na₂SO₄), and concentrated in vacuo. The residue was purified by column chromatography (SiO₂, DCM:MeOH 95:1) to afford the product (130 mg; 36.2%). Rt 1.44 min (System B), [M+H]⁺ 478.1.

Tert-butyl 3-{6-(6-phenoxy)-2H-spiro[1-benzofuran-3,4'-piperidine]-1'-yl}propanoate. To a nitrogen purged solution of 3-{6-hydroxy-2H-spiro[1-benzofuran-3,4'-piperidine]-1'-yl}propanoate (237 mg; 0.71 mmol) in 20 mL toluene was added subsequently, bromobenzene (111.6 mg; 0.71 mmol), palladium(II) acetate (8 mg; 0.04 mmol), potassium phosphate tribasic monohydrate (302 mg; 1.42 mmol), 2-di-tert-butylphosphino-2',4',6'-triisopropylbiphenyl (23 mg; 0.05 mmol) and phenylboronic acid (4.3 mg: 0.04 mmol). The resulting mixture was heated at 100° C. overnight. After cooling to RT, the mixture was concentrated in vacuo and partitioned between EtOAc and 5% aqueous NaHCO₃. The organic layer was dried (Na₂SO₄), filtered, and concentrated in vacuo. The residue was purified by column chromatography (SiO₂, DCM:MeOH 97:3) to afford the product (150 mg; 51%). Rt 1.38 min (System B), [M+H]⁺ 410.2.

The following compound was obtained in a similar manner:

Tert-butyl 3-[6-(2,6-dimethylphenoxy)-2H-spiro[1-benzofuran-3,4'-piperidine]-1'-yl]propanoate.

Compound 248. 3-[6-(2,6-Dichlorophenoxy)-2H-spiro[1-benzofuran-3,4'-piperidine]-1'-yl]propanoic acid hydrochloride Tert-butyl 3-[6-(2,6-dichlorophenoxy)-2H-spiro[1-benzofuran-3,4'-piperidine]-1'-yl]propanoate (120 mg, 0.25 mmol) was dissolved in a 4M solution of HCl in 1,4-dioxane (10 mL; 4 mol/l; 40 mmol) and stirred for 2 hours at 50° C. Subsequently, the solvent was removed in vacuo and the residue treated with iPr$_2$O, the precipitate was collected by filtration and dried overnight under reduced pressure to afford the product (0.1 g, 86.9%). $^1$H NMR (400 MHz, DMSO-d$_6$) δ ppm 12.70 (bs, 1H), 10.10 (bs, 1H), 7.64 (d, J=8.2Hz, 2H), 7.38 (t, J=8.2Hz, 1H), 6.97-7.06 (m, 1H), 6.24-6.33 (m, 2H), 4.51 (bs, 2H), 3.43-3.52 (m, 2H), 3.26-3.37 (m, 2H), 2.96-3.09 (m, 2H), 2.83 (t, J=7.5 Hz, 2H), 2.07-2.18 (m, 2H), 1.86-1.93 (m, 2H)Rt 1.33 min (System B), [M+H]$^+$ 422.0.

The following compounds were obtained in a similar manner:

Compound 249. 3-{6-(6-Phenoxy)-2H-spiro[1-benzofuran-3,4'-piperidine]-1'-yl}propanoic acid hydrochloride Rt 1.27 min (System B), [M+H]$^+$ 354.1.

Compound 250. 3-[6-(2,6-Dimethylphenoxy)-2H-spiro[1-benzofuran-3,4'-piperidine]-1'-yl]propanoic acid hydrochloride Rt 1.36 min (System B), [M+H]$^+$ 382.2

Compound 251. 3-{6-[(2,6-Dichlorophenyl)methoxy]-2H-spiro[1-benzofuran-3,4'-piperidine]-1'-yl}cyclobutane-1-carboxylic acid hydrochloride To a mixture of 6-[(2,6-dichlorophenyl)methoxy]-2H-spiro[1-benzfuran-3,4'-piperidine] (0.5 g; 1.25 mmol) in dichloroethane (30 mL), was added tert-butyl 3-oxocyclobutane-1-carboxylate (276 mg; 1.62 mmol), sodiumtriacetoxyborohydride (423 mg; 2 mmol) and the resulting mixture was stirred at RT overnight. Subsequently, the mixture was diluted with EtOAc, washed with 5% aqueous NaHCO$_3$, dried (Na$_2$SO$_4$), and filtered. The residue was purified by column chromatography (SiO$_2$, Et$_2$O:hexanes 1:1) to afford Tert butyl 3-{6-[(2,6-dichlorophenyl)methoxy]-2H-spiro[1-benzofuran-3,4'-piperidine]-1'-yl}cyclobutane-1-carboxylate (0.42 g; 65%). Rt 1.50 min (System B), [M+H]$^+$ 518.0, which was hydrolyzed using the 4M solution of HCl in 1,4-dioxane conditions, affording the product (340 mg; 80%). $^1$H NMR (400 MHz, DMSO-d$_6$) δ ppm 12.5 (bs, 1H), 10.10 (bs, 1H), 7.55-7.58 (m, 2H), 7.47 (dd, J=8.1 and 6.2Hz, 1H), 6.98-7.02 (m, 1H), 6.56-6.62 (m, 2H), 5.18 (s, 2H), 4.48 (bs, 2H), 3.57-3.62 (m, 1H), 3.26-3.44 (m, 2H), 2.78-2.93 (m, 3H), 2.35-2.53 (m, 2H), 1.78-2.18 (m, 4H). Rt 1.33 min (System B), [M+H]$^+$ 461.9.

Compound 313. 2-{6-[(2,6-Dichlorophenyl)methoxy]-2H-spiro[1-benzofuran-3,4'-piperidine]-1'-yl}cyclopentane-1-carboxylic acid Ethyl 2-{6-[(2,6-dichlorophenyl)methoxy]-2H-spiro[1-benzofuran-3,4'-piperidine]-1'-yl}cyclopentane-1-carboxylate, was prepared from 6-[(2,6-dichlorophenyl)methoxy]-2H-spiro[1-benzfuran-3,4'-piperidine] and ethyl 2-oxocyclopentane-1-carboxylate (accordingly to compound 251). $^1$H NMR (400 MHz, CDCl$_3$-d) δ ppm 7.33-7.40 (m, 2H), 7.20-7.28 (m, 1H), 7.00 (d, J=8.2 Hz, 1H), 6.47-6.59 (m, 2H), 5.22 (s, 2H), 4.31-4.42 (m, 2H), 4.17 (qd, J=7.1, 1.1 Hz, 2H), 3.23 (d, J=11.1 Hz, 1H), 3.01-3.10 (m, 1H), 2.93 (d, J=11.1 Hz, 1H), 2.58-2.72 (m, 1H), 1.76-2.13 (m, 9H), 1.54-1.73 (m, 3H), 1.29 (t, J=7.0 Hz, 3H). This product was converted into compound 313 using the conditions described for compound 79. $^1$H NMR (400 MHz, DMSO-d$_6$) δ ppm 7.53-7.59 (m, 2H) 7.44-7.50 (m, 1H) 7.15 (d, J=7.9 Hz, 1H) 6.50-6.58 (m, 2H) 5.17 (s, 2H) 4.41 (s, 2H) 3.14-3.58 (m, 3H) 3.03 (d, J=11.9 Hz, 1H) 2.85-2.95 (m, 2H) 2.31-2.49 (m, 2H) 2.00-2.11 (m, 1H) 1.63-1.94 (m, 7H) 1.47-1.62 (m, 2H). Rt 1.33 min (System B), [M+H]$^+$ 476.6.

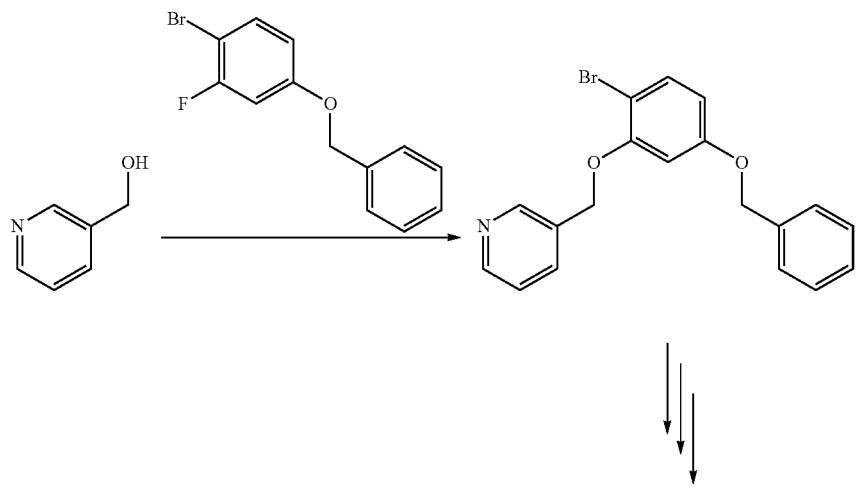

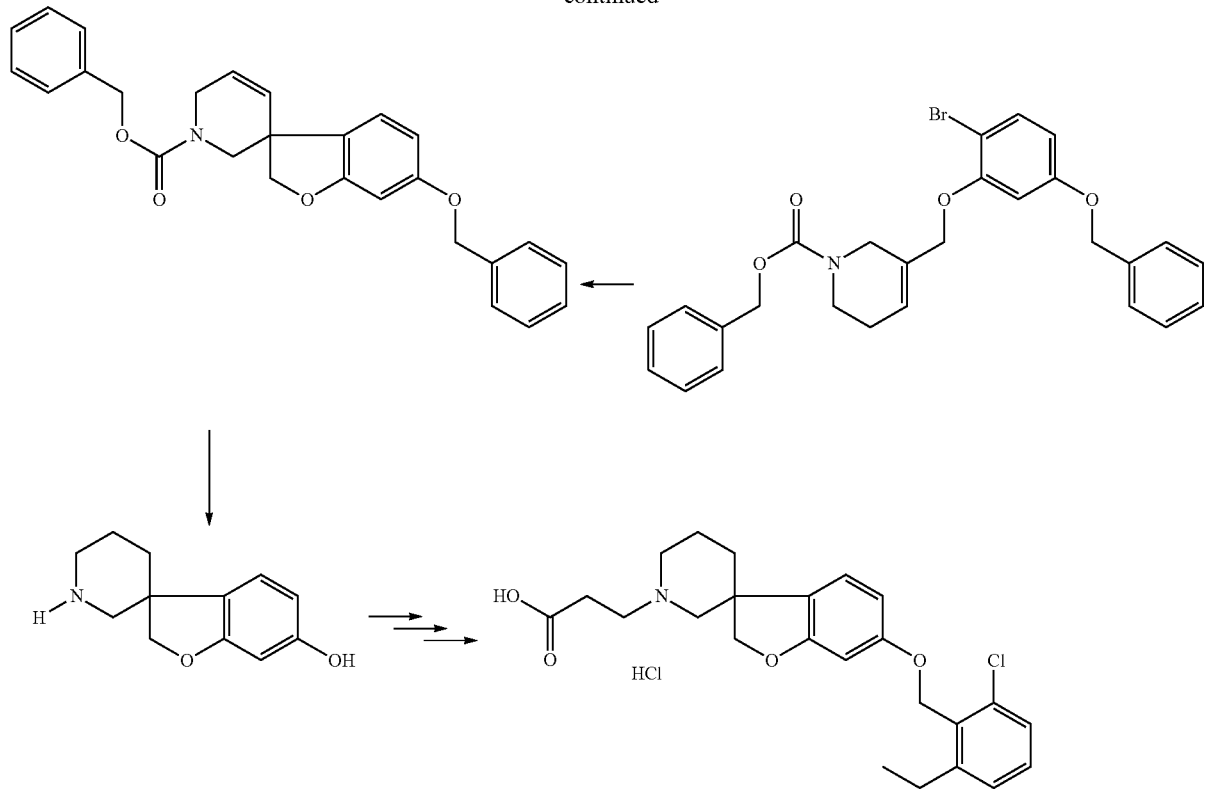

Compound 314. 3-{6-[(2-Chloro-6-ethylphenyl)methoxy]-2H-spiro[1-benzofuran-3,3'-piperidine]-1'-yl}propanoic acid hydrochloride 3-Pyridinemethanol (7.22 mL; 74.34 mmol) was dissolved in 1-methyl-2-pyrrolidinone (25 mL) and sodium hydride (60% in mineral oil; 2.97 g; 74.34 mmol) was added. The mixture was stirred for 30 minutes at ambient temperature. Subsequently, 4-(benzyloxy)-1-bromo-2-fluorobenzene (10.45 g; 37.17 mmol), dissolved in 1-methyl-2-pyrrolidinone (20 mL) was added and the reaction mixture was heated to 100° C. TLC showed a complete conversion within 30 minutes. After cooling to RT, the reaction mixture was diluted with EtOAc, and washed with a 5% aqueous NaHCO₃ solution. The organic layer was washed several times with H₂O, dried (Na₂SO₄), filtered, and concentrated in vacuo. The residue was purified by column chromatography (SiO₂, Et₂O:hexanes 1:1) to afford 3-[5-(benzyloxy)-2-bromophenoxymethyl]pyridine (13.71 g; 99%), $^1$H NMR (400 MHz, CDCl₃-d) δ ppm 8.70 (d, J=2.0 Hz, 1H) 8.59 (dd, J=4.9, 2.0 Hz, 1H) 7.81-7.87 (m, 1H) 7.30-7.46 (m, 6H) 6.62 (d, J=2.8 Hz, 1H) 6.52 (dd, J=8.7, 2.8 Hz, 1H) 5.11 (s, 2 H) 5.03 (s, 2 H), which was dissolved in acetone (200 mL). To this reaction mixture was added benzyl bromide (4.64 mL; 38.82 mmol) and stirred overnight at 40° C. Subsequently, the mixture was concentrated in vacuo yielding 1-benzyl-3-[5-(benzyloxy)-2-bromophenoxy)methyl)pyridin-1-ium bromide (19.7 g; 98%). 14.68 g; (27.12 mmol) of this product was dissolved in MeOH/THF (1:1; 400 mL). To this cooled (−60° C.) reaction mixture was added sodium borohydride (2.57 g; 67.80 mmol). After the addition was complete the mixture was allowed to warm to RT and stirred for another hour. Subsequently, the mixture was cooled to 0° C., water was added, and the MeOH evaporated in vacuo. To the aqueous solution was added a 5% aqueous NaHCO₃ solution and Et₂O. The layers were separated and the organic layer was dried (Na₂SO₄), filtered and concentrated in vacuo. The residue was purified by column chromatography (SiO₂, Et₂O:hexanes 1:1) to afford the product: 1-benzyl-5-[5-(benzyloxy)-2-bromophenoxymethyl]-1,2,3,6-tetrahydropyridine (10.54 g; 83%). $^1$H NMR (400 MHz, CDCl₃-d) δ ppm 7.23-7.43 (m, 11H), 6.54 (d, J=2.7 Hz, 1H), 6.46 (dd, J=8.7, 2.7 Hz, 1H), 5.88 (m, 1H), 5.02 (s, 2H), 4.40 (s, 2H), 3.63 (s, 2H), 3.09 (d, J=1.9 Hz, 2H), 2.58 (t, J=5.7 Hz, 2H), 2.18-2.25 (m, 2H). To a mixture of 1-benzyl-5-[5-(benzyloxy)-2-bromophenoxymethyl]-1,2,3,6-tetra-hydropyridine (1.40 g; 3.01 mmol) and potassium bicarbonate (0.30 g; 3.01 mmol) in 10 mL dichloromethane was added benzylchloroformate (2.04 mL; 13.57 mmol). The reaction mixture was stirred overnight at RT. Subsequently, ice-water and a 5% aqueous NaHCO₃ solution were added followed by dichloromethane. The layers were separated and the organic layer was dried (Na₂SO₄), filtered and concentrated in vacuo. The precipitate was collected by filtration and purified by column chromatography (SiO₂, Et₂O:hexanes 1:3) to afford the product: benzyl 5-[5-benzyloxy)-2-bromophenoxymethyl]-1,2,3,6-tetrahydropyridine-1-carboxylate (1.33 g; 86.78%), $^1$H NMR (400 MHz, CDCl₃-d) δ ppm 7.30-7.43 (m, 11H), 6.54 (d, J=2.6 Hz, 1H), 6.48 (dd, J=8.7, 2.6 Hz, 1H), 5.94-5.99 (m, 1H), 5.16 (s, 2H), 5.03 (s, 2H), 4.44 (s, 2H), 4.11 (br. s., 2H), 3.58 (t, J=5.7 Hz, 2H), 2.16-2.28 (m, 2H). To an intensively degassed mixture of the aforementioned product (0.66 g; 1.30 mmol) and silver carbonate (0.45 g; 1.62 mmol) in 1-methyl-2-pyrrolidinone (6 mL), was added Herrmann-Beller palladacycle (0.06 g; 0.06 mmol) (Tetrahedron, 64 (2008), 4468). The reaction mixture was heated for 18 hours at 140° C. After cooling to RT, the mixture was diluted with water and EtOAc. The layers were separated and the organic layer was dried (Na$_2$SO$_4$), filtered and concentrated in vacuo to afford benzyl 6-(benzyloxy)-2',6'-dihydro-1'H,2H-spiro[1-benzofuran-3,3'-pyridine]-1'-carboxylate (0.50 g; 90%), which was dissolved in MeOH (10 mL) and EtOAc (20 mL). Palladiumhydroxide (20 mg; 0.12 mmol) was added and the mixture was treated with H$_2$ at 50 psi overnight. The crude reaction mixture was concentrated till about 5 mL and filtered through a tosic acid solid phase extraction cartridge, washing with MeOH, and eluting with 2 N NH$_3$/MeOH. The product was concentrated to give 2H-spiro[1-benzofuran-3,3'-piperidine]-6-ol (220 mg; 91%). $^1$H NMR (400 MHz, DMSO-d$_6$) δ ppm 9.20 (br. s., 1H), 6.92 (d, J=8.0 Hz, 1H), 6.11-6.26 (m, 2H), 4.55 (d, J=8.8 Hz, 1H), 4.18 (d, J=8.8 Hz, 1H), 2.78-2.88 (m, 1H), 2.43-2.65 (m, 3H), 1.48-1.74 (m, 3H), 1.23-1.39 (m, 1H).

In a similar manner and as described for compound 29, 2H-spiro[1-benzofuran-3,3'-piperidine]-6-ol was converted to tert-butyl 3-{6-hydroxy-2H-spiro[1-benzofuran-3,3'-piperidine]-1'-yl}propanoate (59%). $^1$H NMR (400 MHz, CDCl$_3$-d) δ ppm 6.90-6.96 (d, J=9.7 Hz, 1H) 6.28-6.34 (m, 2H) 4.60 (d, J=8.8 Hz, 1H) 4.25 (dd, J=8.8, 1.2Hz, 1H) 2.77-2.86 (m, 1H) 2.62-2.71 (m, 2H) 2.55-2.61 (m, 1H) 2.32-2.40 (t, J=8.8 Hz, 2H) 2.05-2.14 (m, 2H) 1.46-1.75 (m, 4H) 1.44 (s, 9H), followed by the Mitsunobu chemistry yielding ter-butyl 3-{6-[(2-Chloro-6-ethylphenyl)methoxy]-2H-spiro[1-benzofuran-3,3'-piperidine]-1'-yl}propanoate. This product (340 mg; 0.7 mmol) was dissolved in a 4M solution of HCl in 1,4-dioxane (20 mL; 4 mol/l; 40 mmol) and stirred for 2 hours at 50° C. Subsequently, the solvent was removed in vacuo and the residue treated with iPr$_2$O, the precipitate was collected by filtration and dried overnight under reduced pressure to afford the product (0.25 g, 72.8%). $^1$H NMR (400 MHz, DMSO-d$_6$) δ ppm 12.70 (br. s., 1H), 10.55 (br. s., 1H), 7.33-7.41 (m, 2H), 7.25-7.32 (m, 1H), 7.17 (d, J=8.3 Hz, 1H), 6.57-6.64 (m, 2H), 5.11 (s, 2H), 4.93 (d, J=9.6 Hz, 1H), 4.34 (d, J=9.6 Hz, 1H), 3.17-3.47 (m, 6H), 2.83-2.97 (m, 2H), 2.71 (q, J=7.2Hz, 2H), 1.74-1.94 (m, 4H), 1.15 (t, J=7.2 Hz, 3H). Rt 1.48 min (System B), [M+H]$^+$ 430.0.

The following compounds were obtained in a similar manner:

Compound 315. 3-{6-[(2-Cyclopropyl-6-fluorophenyl)methoxy]-2H-spiro[1-benzofuran-3,3'-piperidine]-1'-yl}propanoic acid hydrochloride $^1$H NMR (400 MHz, DMSO-d$_6$) δ ppm 12.80 (br. s., 1H), 10.60 (br. s., 1H), 7.33 (td, J=8.0, 6.2Hz, 1H), 7.16 (d, J=8.0 Hz, 1H), 7.06 (t, J=8.0 Hz, 1H), 6.86 (d, J=7.7 Hz, 1H), 6.58-6.64 (m, 2H), 5.18 (d, J=1.2Hz, 2H), 4.99 (d, J=9.9 Hz, 1H), 4.32 (d, J=9.7 Hz, 1H), 3.15-3.52 (m, 6H), 2.86-2.98 (m, 2H), 1.99-2.10 (m, 1H), 1.71-1.90 (m, 4H), 0.89-0.98 (m, 2H), 0.66-0.74 (m, 2H). Rt 1.42 min (System B), [M+H]$^+$ 426.2.

Compound 316. 3-(6-{[2-Chloro-6-(propan-2-yl)phenyl]methoxy}-2H-spiro[1-benzofuran-3,3'-piperidine]-1'-yl)propanoic acid hydrochloride $^1$H NMR (400 MHz, DMSO-d$_6$) δ ppm 12.80 (br. s., 1H), 10.60 (br. s., 1H), 7.32-7.45 (m, 3H), 7.17 (d, J=8.0 Hz, 1H), 6.56-6.65 (m, 2H), 5.15 (s, 2H), 4.99 (d, J=9.5 Hz, 1H), 4.33 (d, J=9.5 Hz, 1H), 3.11-3.47 (m, 6H), 2.86-2.99 (m, 3H), 1.74-1.93 (m, 5H), 1.20 (d, J=6.7 Hz, 6H). Rt 1.53 min (System B), [M+H]$^+$ 444.0.

Compound 317. 3-{6-[(2-Chloro-6-cyclopropylphenyl)methoxy]-2H-spiro[1-benzofuran-3,3'-piperidine]-1'-yl}propanoic acid hydrochloride $^1$H NMR (400 MHz, DMSO-d$_6$) δ ppm 12.80 (br. s., 1H), 10.20 (br. s., 1H), 7.28-7.37 (m, 2H), 7.12-7.21 (m, 1H), 7.04-7.09 (m, 1H), 6.58-6.66 (m, 2H), 5.28 (s, 2H), 4.87 (d, J=9.6 Hz, 1H), 4.34 (d, J=9.6 Hz, 2H), 3.18-3.46 (m, 6H), 2.79-3.09 (m, 2H), 2.01-2.11 (m, 1H), 1.73-1.93 (m, 4H), 0.88-0.96 (m, 2H), 0.64-0.73 (m, 2H). Rt 1.49 min (System B), [M+H]$^+$ 442.0.

Compound 318. 3-{6-[(2-Chloro-6-fluorophenyl)methoxy]-2H-spiro[1-benzofuran-3,3'-piperidine]-1'-yl}propanoic acid hydrochloride $^1$H NMR (400 MHz, DMSO-d$_6$) δ ppm 12.80 (br. s., 1H), 10.40 (br. s., 1H), 7.48-7.56 (m, 1H), 7.40-7.45 (m, 1H), 7.29-7.36 (m, 1H), 7.17 (d, J=7.9 Hz, 1H), 6.57-6.63 (m, 2H), 5.10 (s, 2H), 4.93 (d, J=9.5 Hz, 1H), 4.34 (d, J=9.5 Hz, 1H), 3.16-3.46 (m, 6H), 2.84-2.95 (m, 2H), 1.71-1.95 (m, 4H). Rt 1.35 min (System B), [M+H]$^+$ 420.2.

Compound 319. 3-{6-[(2,6-Dichloro-3-ethylphenyl)methoxy]-2H-spiro[1-benzofuran-3,3'-piperidine]-1'-yl}propanoic acid hydrochloride $^1$H NMR (400 MHz, DMSO-d$_6$) δ ppm 12.80 (br. s., 1H), 10.50 (br. s., 1H), 7.46 (dd, J=7.5 Hz, 2H), 7.18 (d, J=7.8 Hz, 1H), 6.57-6.65 (m, 2H), 5.20 (s, 2H), 4.96 (d, J=9.6 Hz, 1H), 4.34 (d, J=9.6 Hz, 1H), 3.16-3.47 (m, 6H), 2.83-2.98 (m, 2H), 2.75 (q, J=7.5 Hz, 2H), 1.75-1.92 (m, 4H), 1.18 (t, J=7.5 Hz, 3H). Rt 1.55 min (System B), [M+H]$^+$ 464.0.

Compound 320. 3-{6-[(4-Butyl-2,6-dichlorophenyl)methoxy]-2H-spiro[1-benzofuran-3,3'-piperidine]-1'-yl}propanoic acid hydrochloride $^1$H NMR (400 MHz, DMSO-d$_6$) δ ppm 12.80 (br. s., 1H), 10.40 (br. s., 1H), 7.42 (s, 2H), 7.17 (d, J=7.9 Hz, 1H), 6.57-6.64 (m, 2H), 5.13 (s, 2H), 4.98 (d, J=9.5 Hz, 1H), 4.33 (d, J=9.5 Hz, 1H), 3.33-3.47 (m, 2H), 3.16-3.32 (m, 2H), 2.82-2.99 (m, 2H), 2.61 (t, J=7.6 Hz, 2H), 1.74-1.94 (m, 4H), 1.56 (m, 2H), 1.29 (m, 2H), 0.90 (t, J=7.6 Hz, 3H) Rt 1.72 min (System B), [M+H]$^+$ 492.0

Compound 321. 3-{6-[(2,6-Dichlorophenyl)methoxy]-2H-spiro[1-benzofuran-3,3'-piperidine]-1'-yl}propanoic acid hydrochloride $^1$H NMR (400 MHz, DMSO-d$_6$) δ ppm 12.80 (br. s., 1H), 10.10 (br. s., 1H), 7.57 (d, J=8.1 Hz, 2H), 7.44-7.52 (m, 1H), 7.17 (d, J=8.4 Hz, 1H), 6.58-6.65 (m, 2H), 5.18 (s, 2H), 4.91 (d, J=9.9 Hz, 1H), 4.34 (d, J=9.9 Hz, 1H), 3.32-3.47 (m, 4H), 3.18-3.32 (m, 2H), 2.82-3.00 (m, 2H), 1.74-1.92 (m, 4H). Rt 1.41 min (System B), [M+H]$^+$ 435.9.

Compound 322. 3-{6-[(2,4,6-Trichlorophenyl)methoxy]-2H-spiro[1-benzofuran-3,3'-piperidine]-1'-yl}propanoic acid hydrochloride $^1$H NMR (400 MHz, DMSO-d$_6$) δ ppm 12.80 (br. s., 1H), 10.30 (br. s., 1H), 7.80 (s, 2H) 7.17 (d, J=8.5 Hz, 1H), 6.57-6.64 (m, 2H), 5.15 (s, 2H), 4.94 (d, J=9.6 Hz, 1H), 4.34 (d, J=9.6 Hz, 1H), 3.34-3.48 (m, 4H), 3.16-3.32 (m, 2H), 2.83-2.97 (m, 2H), 1.74-1.94 (m, 4H). Rt 1.54 min (System B), [M+H]$^+$ 471.9.

Compound 323. 3-{6-[(3,5-Dichlorophenyl)methoxy]-2H-spiro[1-benzofuran-3,3'-piperidine]-1'-yl}propanoic acid Tert-butyl 3-{6-[(3,5-dichlorophenyl)-methoxy]-2H-spiro[1-benzofuran-3,3'-piperidine]-1'-yl}propanoate. (270 mg; 0.55 mmol), 2M aqueous NaOH (2 mL; 10 mmol) and ethanol (10 mL) was stirred for 3 hours at 50° C. and subsequently cooled to 0° C. To this reaction mixture was added aqueous HCl (10 mL; 1 mol/l), dropwise, after which it was concentrated in vacuo. The residue was treated with saturated brine and dichloromethane. The water layer was washed with dichloromethane (twice). Subsequently, the organic layer was dried ($Na_2SO_4$), filtered, and concentrated in vacuo, followed by treated with $iPr_2O$. The formed precipitate was collected by filtration, washed with $iPr_2O$ and dried in vacuo to yield the product (40 mg; 15.4%). $^1$H NMR (400 MHz, DMSO-$d_6$) δ ppm 7.57 (s, 1H), 7.48 (s, 2H), 7.08 (d, J=8.7 Hz, 1H), 6.43-6.50 (m, 2H), 5.07 (s, 2H), 4.46 (d, J=8.8 Hz, 1H), 4.24 (d, J=8.8 Hz, 1H), 2.68-2.79 (m, 1H), 2.43-2.65 (m, 3H), 2.21 (t, J=7.2Hz, 2H), 2.00-2.16 (m, 2H), 1.52-1.66 (m, 3H), 1.36-1.53 (s, 1H).

The following compounds were obtained according to a similar manner:

Compound 324. 3-{6-[(2,5-Dichlorophenyl)methoxy]-2H-spiro[1-benzofuran-3,3'-piperidine]-1'-yl}propanoic acid $^1$H NMR (400 MHz, DMSO-$d_6$) δ ppm 7.64 (s, 1H), 7.55 (d, J=1.5 Hz, 1H), 7.45 (m, 1H), 7.08 (d, J=8.7 Hz, 1H), 6.43-6.50 (m, 2H), 5.07 (s, 2H), 4.46 (d, J=9.0 Hz, 1H), 4.24 (d, J=9.0 Hz, 1H), 2.68-2.79 (m, 1H), 2.43-2.67 (m, 3H), 2.35 (t, J=7.2Hz, 2H), 2.00-2.18 (m, 2H), 1.52-1.66 (m, 3H), 1.36-1.51 (m, 1H). Rt 1.46 min (System B), [M+H]$^+$ 436.1.

Compound 325. 3-{6-[(2-Chloro-6-methylphenyl)methoxy]-2H-spiro[1-benzofuran-3,3'-piperidine]-1'-yl}propanoic acid $^1$H NMR (400 MHz, DMSO-$d_6$) δ ppm 12.10 (br. s., 1H), 7.06-7.38 (m, 4H), 6.47-6.54 (m, 2H), 5.10 (s, 2H), 4.48 (d, J=8.8 Hz, 1H), 4.25 (d, J=8.8 Hz, 1H), 2.71-2.80 (m, 1H), 2.47-2.67 (m, 3H), 2.30-2.44 (m, 5H), 2.02-2.18 (m, 2H), 1.55-1.69 (m, 3H), 1.37-1.53 (m, 1H). Rt 1.42 min (System B), [M+H]$^+$ 416.2

Compound 326. 3-(6-{[2-Chloro-6-(trifluoromethyl)phenyl]methoxy}-2H-spiro[1-benzofuran-3,3'-piperidine]-1'-yl)propanoic acid $^1$H NMR (400 MHz, DMSO-$d_6$) δ ppm 12.29 (br. s., 1H), 7.92 (d, J=8.1 Hz, 1H), 7.83 (d, J=8.1 Hz, 1H), 7.64-7.71 (m, 1H), 7.09-7.13 (m, 1H), 6.48-6.54 (m, 2H), 5.13 (s, 2H), 4.48 (d, J=8.8 Hz, 1H), 4.26 (d, J=8.8 Hz, 1H), 2.74-2.80 (m, 1H), 2.52-2.66 (m, 3H), 2.31-2.39 (m, 2H), 2.05-2.27 (m, 2H), 1.56-1.69 (m, 3H), 1.40-1.51 (m, 1H). Rt 1.42 min (System B), [M+H]$^+$ 416.2

Compound 327. 3-{6-[1-(2,6-Dichlorophenyl)ethoxy]-2H-spiro[1-benzofuran-3,3'-piperidine]-1'-yl}propanoic acid $^1$H NMR (400 MHz, DMSO-$d_6$) δ ppm 12.19 (br. s., 1H), 7.45 (d, J=8.0 Hz, 2H), 7.28-7.34 (m, 1H), 7.00 (d, J=8.0 Hz, 1H), 6.29 (dd, J=8.2, 2.1 Hz, 1H), 6.21 (d, J=2.1 Hz, 1H), 5.93 (q, J=6.6 Hz, 1H), 4.41 (d, J=8.8 Hz, 1H), 4.18 (d, J=8.8 Hz, 1H), 2.69-2.77 (m, 2H), 2.44-2.62 (m, 4H), 2.28-2.35 (m, 2H), 1.99-2.09 (m, 3H), 1.67 (d, J=6.6 Hz, 3H), 1.48-1.63 (m, 3H), 1.34-1.48 (m, 1H). Rt 1.42 min (System B), [M+H]$^+$ 416.2

Compound 328. 3-(6-{[2-Fluoro-6-(trifluoromethyl)phenyl]methoxy}-2H-spiro[1-benzofuran-3,3'-piperidine]-1'-yl)propanoic acid $^1$H NMR (400 MHz, DMSO-$d_6$) δ ppm 7.62-7.77 (m, 3H), 7.11 (d, J=8.8 Hz, 1H), 6.45-6.53 (m, 2H), 5.09 (s, 2H), 4.48 (d, J=9.0 Hz, 1H), 4.25 (d, J=9.0 Hz, 1H), 2.71-2.81 (m, 1H), 2.52-2.66 (m, 3H), 2.35 (t, J=6.9 Hz, 2H), 2.05-2.18 (m, 2H), 1.53-1.70 (m, 3H), 1.37-1.52 (m, 1H). Rt 1.45 min (System B), [M+H]$^+$ 454.2

Compound 329. 3-[6-(Oct-7-en-1-yloxy)-2H-spiro[1-benzofuran-3,3'-pi-peridine]-1'-yl)propanoic acid Was prepared from tert-butyl 3-{6-hydroxy-2H-spiro[1-benzofuran-3,3'-piperidine]-1'-yl}propanoate using the method described for compound 275. $^1$H NMR (400 MHz, CDCl$_3$-d) δ ppm 12.10 (br. s., 1H), 7.04 (d, J=8.1 Hz, 1H), 6.32-6.41 (m, 2H), 5.73-5.84 (m, 1H), 4.95 (m, 2H), 4.46 (d, J=8.8 Hz, 1H), 4.22 (d, J=8.8 Hz, 1H), 3.88 (t, J=6.5 Hz, 2H), 2.72-2.80 (m, 1H), 2.51-2.67 (m, 3H), 2.31-2.40 (t, J=6.9 Hz, 2H), 1.97-2.18 (m, 3H), 1.53-1.71 (m, 6H), 1.26-1.50 (m, 7H). Rt 1.37 min (System B), [M+H]$^+$ 388.3

The following compounds were obtained according to a similar manner:

Compound 330. 3-[6-(Hept-6-en-1-yloxy)-2H-spiro[1-benzofuran-3,3'-pi-peridine]-1'-yl)propanoic acid $^1$H NMR (400 MHz, CDCl$_3$-d) δ ppm 12.10 (br. s., 1H), 7.04 (d, J=8.1 Hz, 1H), 6.32-6.40 (m, 2H), 5.80 (ddt, J=17.0, 10.3, 6.7, 6.7 Hz, 1H), 4.90-5.06 (m, 2H), 4.45 (d, J=8.8 Hz, 1H), 4.22 (d, J=8.9 Hz, 1H), 3.88 (t, J=6.5 Hz, 2H), 2.69-2.80 (m, 1H), 2.51-2.65 (m, 3H), 2.29-2.39 (m, 2H), 1.98-2.16 (m, 4H), 1.52-1.73 (m, 5H), 1.33-1.48 (m, 5H). Rt 1.53 min (System B), [M+H]$^+$ 374.3

Compound 331. 3-[6-(Hex-5-en-1-yloxy)-2H-spiro[1-benzofuran-3,3'-pi-peridine]-1'-yl)propanoic acid $^1$H NMR (400 MHz, CDCl$_3$-d) δ ppm 12.10 (br. s., 1H), 7.04 (d, J=8.1 Hz, 1H), 6.29-6.42 (m, 2H), 5.69-5.91 (m, 1H), 4.90-5.10 (m, 2H), 4.45 (d, J=9.4 Hz, 1H), 4.22 (d, J=9.4 Hz, 1H), 3.84-3.94 (m, 2H), 2.69-2.83 (m, 1H), 2.60-2.68 (s, 3H), 2.28-2.41 (m, 2H), 2.00-2.18 (m, 3H), 1.33-1.77 (m, 9H). Rt 1.53 min (System B), [M+H]$^+$ 360.3

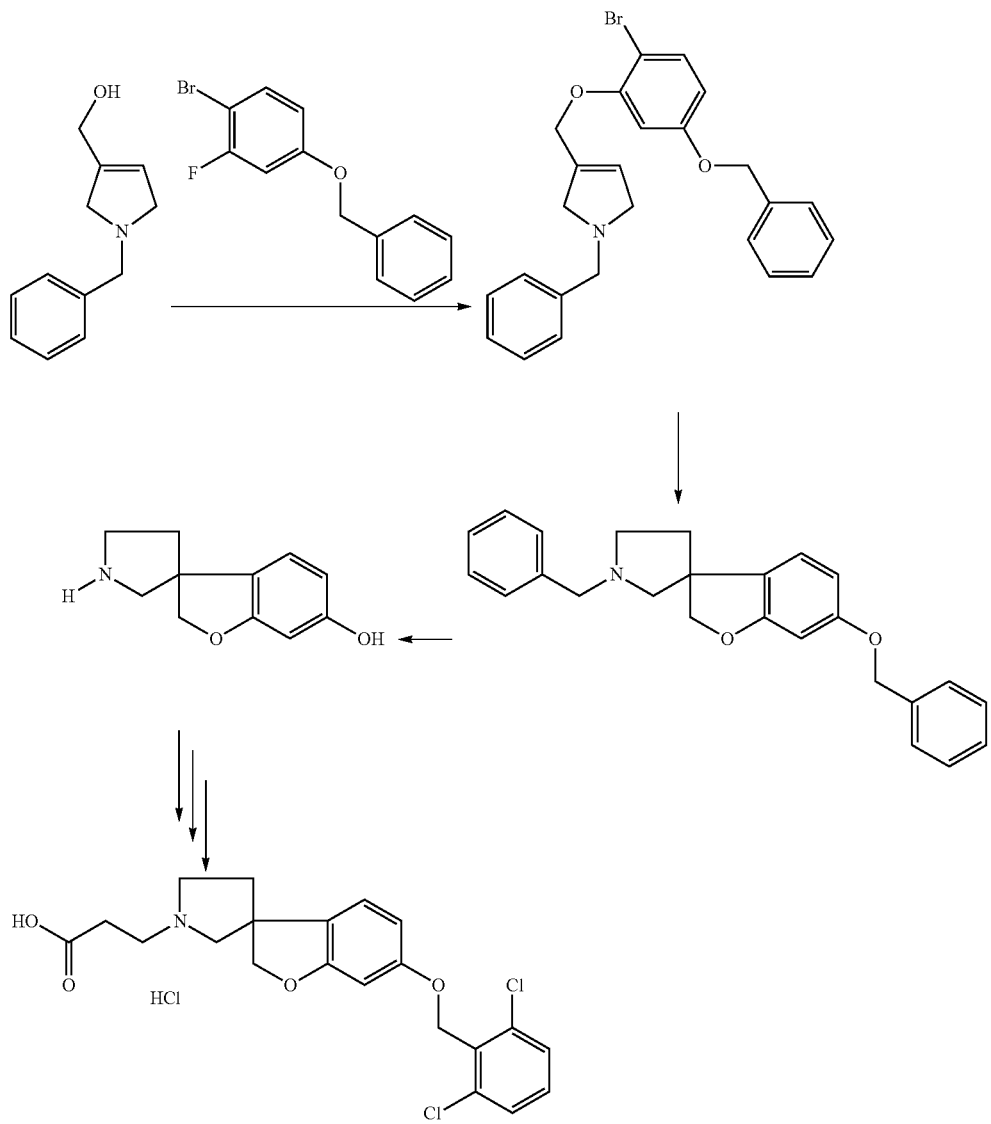

Compound 332. 3-{6-[(2,6-Dichlorophenyl)methoxy]-2H-spiro[1-benzofuran-3,3'-pyrrolidine]-1'-yl}propanoic acid hydrochloride (1-benzyl-2,5-dihydro-1H-pyrrol-3-yl)methanol (US2010/0069351) (0.47 g; 2.49 mmol) was dissolved in 1-methyl-2-pyrrolidinone (5 mL) and sodium hydride (60% in mineral oil; 0.1 g; 2.49 mmol) was added. The mixture was stirred for 30 minutes at ambient temperature. Subsequently, 4-(benzyloxy)-1-bromo-2-fluorobenzene (0.35 g; 1.25 mmol), dissolved in 1-methyl-2-pyrrolidinone (3 mL) was added and the reaction mixture was heated to 100° C. for 30 minutes. After cooling to RT, the reaction mixture was diluted with EtOAc, and washed with a 5% aqueous NaHCO₃ solution. The organic layer was washed several times with H₂O, dried (Na₂SO₄), filtered, and concentrated in vacuo. The residue was purified by column chromatography (SiO₂, Et₂O:hexanes 1:1 to pure Et₂O) to afford 1-benzyl-3-[5-benzyloxy]-2-bromophenoxymethyl]-2,5-dihydro-1H-pyrrole (0.48 g; 85%). Rt 1.45 min (System B), [M+H]⁺ 452.5.

To a intensively degassed mixture of 1-benzyl-3-[5-benzyloxy]-2-bromophenoxy-methyl]-2,5-dihydro-1H-pyrrole (0.46 g; 7.73 mmol) in 5 mL benzene was added subsequently, 2,2'-azobis(2-methylpropionitrile) (17 mg; 0.1 mmol) and tri-n-butyltinhydride (0.41 mL; 1.53 mmol). The reaction mixture was heated under microwave conditions for 2 hours at 200° C. After cooling to RT, the reaction mixture was diluted with EtOAc, and washed with a 5% aqueous NaHCO₃ solution, dried (Na₂SO₄), filtered, and concentrated in vacuo. The residue was purified by column chromatography (SiO₂, Et₂O:hexanes 1:1) to afford 1'-benzyl-6-(benzyloxy)-2H-spiro[1-benzofuran-3,3'-pyrrolidine] (0.26 g; 68%). $^1$H NMR (400 MHz, CDCl₃-d) δ ppm 7.20-7.45 (m, 10H), 7.10 (d, J=8.2Hz, 1H), 6.52 (dd, J=8.2, 2.2Hz, 1H), 6.43 (d, J=2.2Hz, 1H), 5.01 (s, 2H), 4.51 (d, J=8.8 Hz, 1H), 4.34 (d, J=8.8 Hz, 1H), 3.68 (d, J=13.1 Hz, 1H), 3.59 (d, J=13.1 Hz, 1H), 2.87 (dt, J=8.7, 5.0 Hz, 1H), 2.79 (d, J=9.2Hz, 1H), 2.61 (dt, J=8.9, 6.9 Hz, 1H), 2.48 (d, J=9.2Hz, 1H), 2.20 (ddd, J=13.4, 8.9, 5.0 Hz, 1H), 1.95-2.07 (m, 1H). Rt 1.35 min (System B), [M+H]⁺ 372.6. A mixture of this product (260 mg; 0.7 mmol), ammonium formate (0.18 g; 2.8 mmol) and palladiumhydroxide (5 mg; 0.03 mmol) in methanol (25 ml) was stirred overnight (at 60° C). The crude reaction mixture was concentrated till about 5 mL and filtered through a tosic acid solid phase extraction cartridge, washing with MeOH, and eluting with 2 N NH$_3$/MeOH. The product was concentrated to give 2H-spiro[1-benzofuran-3,3'-pyrrolidine]-6-ol (0.13 g; 97%). $^1$H NMR (400 MHz, DMSO-d$_6$) δ ppm 7.08 (d, J=8.1 Hz, 1H), 6.31 (dd, J=8.1, 2.1 Hz, 1H), 6.21 (d, J=2.1 Hz, 1H), 4.46 (d, J=9.0 Hz, 1H), 4.32 (d, J=9.0 Hz, 1H), 3.04-3.30 (m, 3H), 3.01 (d, J=11.4 Hz, 1H), 1.95-2.11 (m, 2H).

In a similar manner and as described for compound 29, 2H-spiro[1-benzofuran-3,3'-pyrrolidine]-6-ol was converted to tert-butyl 3-{6-hydroxy-2H-spiro[1-benzofuran-3,3'-pyrrolidine]-1'-yl}propanoate. $^1$H NMR (400 MHz, CDCl$_3$-d) δ ppm 6.99 (d, J=8.1 Hz, 1H), 6.34 (dd, J=8.1, 2.2Hz, 1H), 6.28 (d, J=2.2Hz, 1H), 4.47 (d, J=8.8 Hz, 1H), 4.30 (d, J=8.8 Hz, 1H), 2.84-2.94 (m, 2H), 2.79 (t, J=7.4 Hz, 2H), 2.55-2.63 (m, 2H), 2.46 (t, J=7.4 Hz, 2H), 2.10-2.21 (m, 1H), 1.94-2.05 (m, 1H) 1.45 (s, 9H), subsequently followed by the Mitsunobu chemistry and acidic hydrolysis yielding the product: 3-{6-[(2,6-dichlorophenyl)methoxy]-2H-spiro[1-benzofuran-3,3'-pyrrolidine]-1'-yl}propanoic acid hydrochloride. NMR (400 MHz, DMSO-d$_6$) δ ppm 12.70 (br. s., 1H), 11.55 (br. s., 1H), 7.57 (d, J=7.4 Hz, 2H), 7.36-7.52 (m, 2H), 6.65 (dd, J=8.3, 2.2Hz, 1H), 6.60 (d, J=2.2Hz, 1H), 5.19 (s, 2H), 4.23-4.81 (m, 2H), 3.14-3.91 (m, 6H), 2.84 (t, J=7.7 Hz, 2H), 2.10-2.40 (m, 2H).

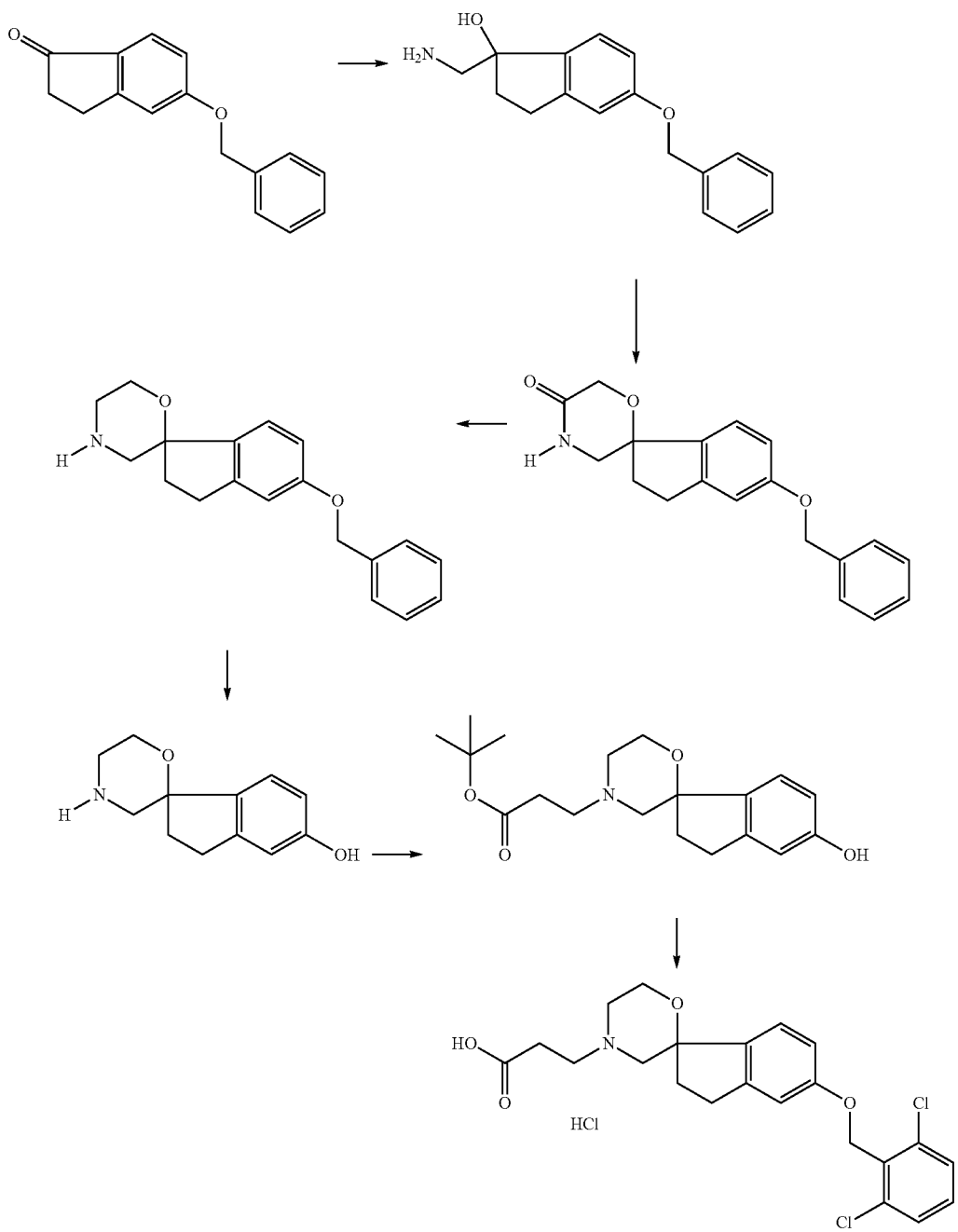

Compound 333. 3-{5-[(2,6-Dichlorophenyl)methoxy]-2,3-dihydrospiro[indene-1,2'-morpholine]-4'-yl}propanoic acid hydrochloride A mixture of 5-(benzyloxy)-2,3-dihydro-1H-inden-1-one (13.11 g; 55.02 mmol), zinc iodide (0.35 g; 1.1 mmol), and trimethylsilyl cyanide (22.71 mL; 181.5 mmol) was stirred overnight at RT. Subsequently, the excess trimethylsilyl cyanide was removed in vacuo, and the residue dissolved in THF (250 mL). The resulting solution was added, dropwise, to a mixture of lithium aluminum hydride (8.56 g; 225.57 mmol) in THF (200 mL). The resulting mixture was heated under reflux for 2 h. Next, the mixture was cooled to 0° C. and treated successively with water (10 mL), 2M aqueous NaOH (20 mL), and water (10 mL). Thereafter the mixture was heated under reflux for 15 minutes, cooled again to RT, filtered over Kieselguhr, and concentrated in vacuo. The residue was purified by column chromatography ($SiO_2$, MeOH) to afford 1-(aminomethyl)-5-(benzyloxy)-2,3-dihydro-1H-inden-1-ol (10.7 g; 72%). To a solution of 1-(aminomethyl)-5-(benzyloxy)-2,3-dihydro-1H-inden-1-ol (10.50 g; 40 mmol) and $Et_3N$ (6.52 mL; 46.78 mmol) in a mixture of $CH_2Cl_2$ (100 mL) and MeOH (16 mL) was added dropwise a solution of chloroacetyl chloride (3.42 mL; 42.9 mmol) in $CH_2Cl_2$ (10 mL), at 0° C. After 1 hour at 0° C. the reaction mixture was quenched with 1M aqueous HCl (200 mL). The layers were separated and the organic layer washed with a 5% aqueous $NaHCO_3$ solution, dried ($Na_2SO_4$) and concentrated yielding N-{[5-(benzyloxy)-1-hydroxy-2,3-dihydro-1H-inden-1-yl]methyl}-2-chloroacetamide (10.5 g; 78%). The residue was dissolved in 2-propanol (100 mL) and potassium tert-butoxide (3.71 g; 33 mmol) was added. The resulting mixture was stirred at RT for 1 hour and subsequently concentrated in vacuo. The crude product was partitioned between EtOAc and 0.5 M aqueous HCl. The layers were separated and the organic layer was washed with 5% aqueous $NaHCO_3$ solution, dried ($Na_2SO_4$) and evaporated in vacuo. The residue was purified by column chromatography ($SiO_2$, EtOAc:MeOH 9:1) to afford 5-(benzyloxy)-2,3-dihydrospiro[indene-1,2'-morpholine]-5'-one (5.1 g; 54.8%). $^1$H NMR (400 MHz, $CDCl_3$-d) δ ppm 7.29-7.45 (m, 6H), 7.05 (br. s., 1H), 6.83-6.91 (m, 2H), 5.06 (s, 2H), 4.15-4.30 (m, 2H), 3.61 (dd, J=12.2, 1.9 Hz, 1H), 3.46 (dd, J=12.2, 2.9 Hz, 1H), 3.05-3.15 (m, 1H), 2.84 (dt, J=16.1, 6.7 Hz, 1H), 2.30 (t, J=6.7 Hz, 2H).

To a solution of the aforementioned product (0.7 g; 2.26 mmol) in THF (10 mL) was added borane-THF complex (1M, 11.3 mL; 11.3 mmol) dropwise, at 0° C. After 1 hour the mixture was allowed to warm to RT and stirred overnight. To the reaction mixture was added MeOH (10 mL), at 0° C., and the resulting mixture was stirred at RT for 30 minutes, and subsequently concentrated in vacuo. The residue was suspended in MeOH (10 mL.) and 1 M aqueous NaOH (25 mL) was added and heated under reflux for 1 hour. The resulting mixture was concentrated in vacuo and the residue was partitioned between EtOAc and 5% aqueous $NaHCO_3$-solution. The organic layer was dried ($Na_2SO_4$), filtered, and concentrated in vacuo. The residue was purified by column chromatography ($SiO_2$, EtOAc:MeOH 9:1 to 1:9) to afford 5-(benzyloxy)-2,3-dihydrospiro[indene-1,2'-morpholine] (0.47 g; 70.3%). $^1$H NMR (400 MHz, $CDCl_3$-d) δ ppm 7.29-7.45 (m, 6H), 6.82-6.88 (m, 2H), 5.05 (s, 2H), 3.78 (dd, J=7.0, 2.8 Hz, 2H), 2.95-3.05 (m, 3H), 2.86-2.93 (m, 1H), 2.74-2.84 (m, 2H), 2.48 (ddd, J=13.0, 8.4, 4.4 Hz, 1H), 2.23 (dddd, J=13.0, 8.4, 7.0, 1.2Hz, 1H). Rt 1.19 min (System B), [M+H]$^+$ 296.1

5-(Benzyloxy)-2,3-dihydrospiro[indene-1,2'-morpholine] (0.46 g; 1.56 mmol) was dissolved in MeOH (20 mL). Palladiumhydroxide (11 mg; 0.16 mmol) was added and the mixture was treated with $H_2$ overnight. The reaction mixture was concentrated yielding 2,3-dihydrospiro[indene-1,2'-morpholine]-5-ol (310 mg; 97%). $^1$H NMR (400 MHz, DMSO-$d_6$) δ ppm 9.30 (br. s., 1H) 7.22 (d, J=8.0 Hz, 1H) 6.54-6.59 (m, 2H) 3.56 (dd, J=5.8, 3.7 Hz, 2H) 2.55-2.85 (m, 6H) 2.41 (ddd, J=13.0, 8.0, 4.5 Hz, 1H) 1.91-2.00 (m, 1H). Rt 0.30 min (System B), [M+H]$^+$ 206.1

A mixture of 2,3-dihydrospiro[indene-1,2'-morpholine]-5-ol (0.3 g; 1.46 mmol), tert-butyl acrylate (0.64 ml; 4.38 mmol) and N,N-diisopropylamine (0.76 ml, 4.46 mmol) in MeOH (20 mL) was heated under reflux overnight (closed pyrex bottle). After cooling to RT the mixture was concentrated in vacuo, and the residue was partitioned between EtOAc and 5% aqueous $NaHCO_3$ solution. The organic layer was dried ($Na_2SO_4$), filtered, and concentrated in vacuo. The residue was purified by column chromatography ($SiO_2$, $Et_2O$) to afford ter-butyl 3-{5-hydroxy-2,3-dihydrospiro[indene-1,2'-morpholine]-4'-yl}propanoate (0.32 g; 65.5%). $^1$H NMR (400 MHz, $CDCl_3$-d) δ ppm 7.46 (d, J=8.1 Hz, 1H), 6.60-6.68 (m, 2H), 4.97 (s, 1H), 3.69-3.81 (m, 2H), 2.93-3.03 (m, 1H), 2.33-2.79 (m, 10H), 2.08-2.17 (m, 1H), 1.46 (s, 9H). Rt 1.04 min (System B), [M+H]$^+$ 334.1

A mixture of tert-butyl 3-{5-hydroxy-2,3-dihydrospiro[indene-1,2'-morpholine]-4'-yl}propanoate (315 mg; 0.94 mmol), $K_2CO_3$ (0.39 g; 2.83 mmol) and 2,6-dichlorobenzylbromide (250 mg; 1.04 mmol) in $CH_3CN$ (10 mL) was stirred overnight (at RT). The reaction mixture was partitioned between 5% aqueous $NaHCO_3$ solution and $Et_2O$. The organic layer was dried ($Na_2SO_4$), filtered, and concentrated in vacuo. The residue was purified by column chromatography ($SiO_2$, $Et_2O$:hexanes 4:6) to afford tert-butyl 3-{5-[(2,6-Dichlorophenyl)methoxy]-2,3-dihydrospiro[indene-1,2'-morpholine]-4'-yl}propanoate (0.387 g; 83%). Rt 1.68 min (System B), [M+H]$^+$ 492.0., which was dissolved in a 1M solution of HCl in 1,4-dioxane (10 mL) and stirred for 2 hours at 70° C. Subsequently, the solvent was removed in vacuo and the residue treated with $iPr_2O$, the precipitate was collected by filtration and dried overnight under reduced pressure to afford 3-{5-[(2,6-dichlorophenyl)methoxy]-2,3-dihydrospiro[indene-1,2'-morpholine]-4'-yl}propanoic acid hydrochloride (300 mg, 83%). $^1$H NMR (400 MHz, DMSO-d) δ ppm 12.80 (bs, 1H), 11.20 (bs, 1H), 7.58 (d, J=8.0 Hz, 2H), 7.47 (t, J=8.0 Hz, 1H), 7.29 (d, J=8.8 Hz, 1H), 7.02 (s, 1H), 6.95 (d, J=8.8 Hz, 1H), 5.22 (s, 2H), 3.98 (d, J=7.5 Hz, 2H), 2.88-3.54 (m, 11H), 2.08-2.18 (m, 1H). Rt 1.45 min (System B), [M+H]$^+$ 435.9.

The following compounds were obtained according to a similar manner:

Compound 334. 3-[5-(Octyloxy)-2,3-dihydrospiro[indene-1,2'-morpholine]-4'-yl}propanoic acid hydrochloride $^1$H NMR (400 MHz, DMSO-d) δ ppm 12.80 (bs, 1H), 11.20 (bs, 1H), 7.23 (d, J=8.8 Hz, 1H), 6.78-6.86 (m, 2H), 3.85-4.03 (m, 4H), 3.24-3.50 (m, 4H), 3.05-3.23 (m, 2H), 2.80-3.03 (m, 5H), 2.04-2.18 (m, 1H), 1.62-1.75 (m, 2H), 1.18-1.45 (m, 10H), 0.85-0.95 (m, 3H).

Compound 335. 3-[5-(2,6-Dichlorophenoxy)-2,3-dihydrospiro[indene-1,2'-morpholine]-4'-yl}propanoic acid hydrochloride $^1$H NMR (400 MHz, DMSO-d) δ ppm 12.80 (bs, 1H), 10.60 (bs, 1H), 7.66 (d, J=8.0 Hz, 2H), 7.38 (t, J=8.0 Hz, 1H), 7.32 (d, J=8.8 Hz, 1H), 6.69-6.75 (m, 2H), 3.87-3.99 (m, 2H), 3.05-3.53 (m, 8H), 2.82-2.92 (m, 3H), 2.08-2.18 (m, 1H).

1H), 6.92 (d, J=6 Hz, 1H), 6.85 (dd, J=8, 2Hz, 1H), 6.66 (d, J=6 Hz, 1H), 3.90 (s, 3H), 3.42 (s, 2H). To a solution of this crude 5-methoxy-1H-indene (15.0 g; 75% pure, 60 mmol) in

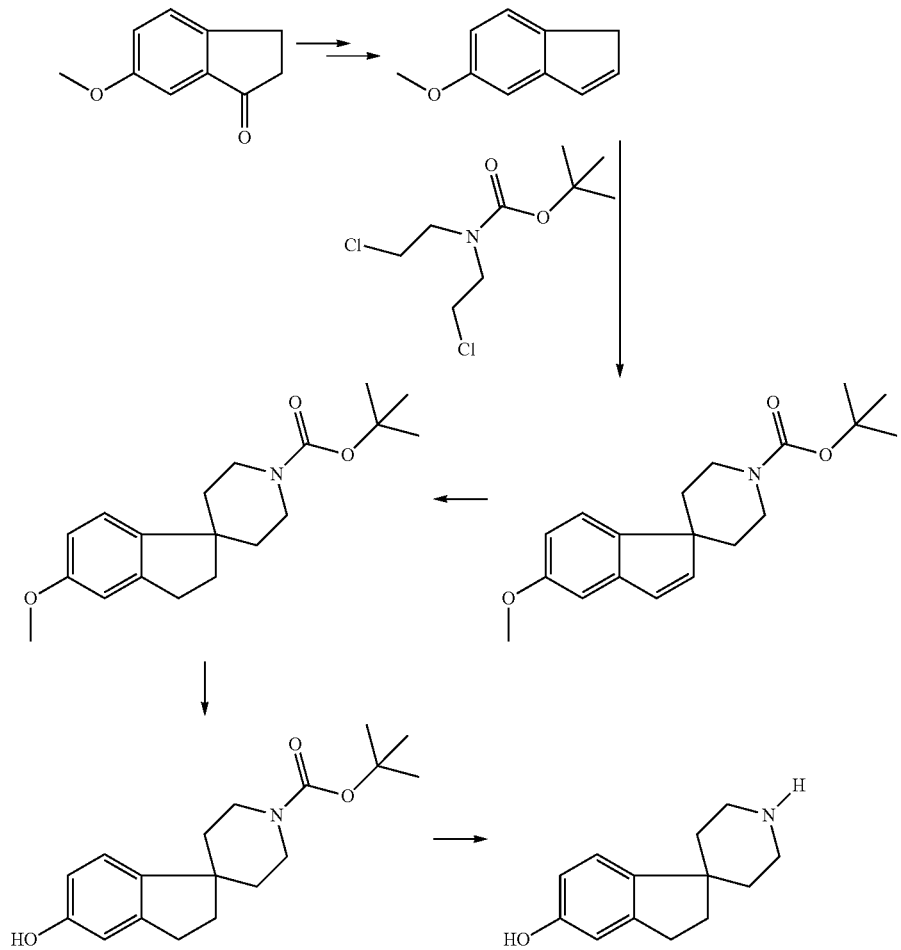

2,3-Dihydrospiro[indene-1,4'-piperidine]-5-ol

To a solution of 6-methoxy-2,3-dihydro-1H-inden-1-one (25 g; 154 mmol) in MeOH (400 mL) was added NaBH$_4$ (7.0 g; 185 mmol), portionwise at RT. The mixture was stirred for 1 hour at RT. Subsequently, water (100 mL) was added, followed by 2N hydrochloric acid (150 mL). The mixture was stirred for 1.5 hour at RT and then extracted with MTBE (2-methoxy-2-methylpropane). The combined organic layers were washed with brine, dried (NaSO$_4$), and concentrated in vacuo to give 6-methoxy-2,3-dihydro-1H-inden-1-ol as an oil, 25 g (99%). $^1$H NMR (300 MHz, CDCl$_3$-d) δ ppm 7.15 (d, J=8 Hz, 1H), 6.95 (d, J=2Hz, 1H), 6.80 (d, J=8 Hz, 1H), 4.82-4.78 (m, 1H), 3.80 (s, 3H), 3.05-2.95 (m, 1H), 2.80-2.70 (m, 1H), 2.40-2.30 (m, 1H), 2.15-2.05 (m, 1H). A mixture of 6-methoxy-2,3-dihydro-1H-inden-1-ol (18.5 g; 113 mmol), p-toluenesulfonic acid hydrate (0.1 g; 0.5 mmol), hydroquinone (0.1 g; 1 mmol), and toluene (150 mL) was heated to reflux for 1 hour. After cooling to room temperature the mixture was diluted with MTBE (50 mL), washed with saturated sodium bicarbonate, then with brine, dried (NaSO$_4$), and concentrated to give 5-methoxy-1H-indene (15.5 g; purity 75%), $^1$H NMR (300 MHz, CDCl$_3$-d) δ ppm 7.43 (d, J=8 Hz, 1H), 7.06 (d, J=2Hz, THF (50 mL at 0° C.), was added lithium bis(trimethylsilyl) amide (LiHMDS, 1 M solution in THF/ethylbenzene, 200 mL; 200 mmol). The resulting brown solution was added dropwise in 20 min to a solution of tert-butyl N,N-bis(2-chloroethyl)carbamate (23 g; 95 mmol) in THF (100 mL). The mixture was stirred for 1 hour at 0° C. and then for 1 hour at ambient temperature. The mixture was concentrated in vacuo and purified by column chromatography (SiO$_2$, EtOAc:hexanes 1:9) to afford an oil, 23 g. Crystallization from pentane gave tert-butyl 5-methoxyspiro[indene-1,4'-piperidine]-1'-carboxylate (9.4 g; (50%). $^1$H NMR (300 MHz, CDCl$_3$-d) δ ppm 7.22 (d, J=8 Hz, 1H), 6.88 (d, J=2Hz, 1H), 6.78 (dd, J=8, 2Hz, 1H), 6.72 (s, 2H), 4.30-4.10 (m, 2H), 3.80 (s, 3H), 3.10 (t, J=12Hz, 2H), 1.98 (dt, J=12, 4 Hz, 2H), 1.50 (s, 9H), 1.30 (d, J=12Hz, 2H). A mixture of tert-butyl 5-methoxyspiro[indene-1,4'-piperidine]-1'-carboxylate (3.15 g; 10 mmol), 10% Pd/C (0.6 g; 0.6 mmol), and ethanol (50 mL) was hydrogenated at 5 bar for 4 hour. The catalyst was removed by filtration over Celite and the filtrate was concentrated in vacuo to give tert-butyl 5-methoxy-2,3-dihydrospiro[indene-1,4'-piperidine]-1'-carboxylate (2.8 g; 88%). $^1$H NMR (400 MHz, CDCl$_3$-d) δ ppm 7.13 (d, J=8 Hz, 1H), 6.75 (dd, J=8, 2Hz, 1H), 6.70 (d, J=2Hz, 1H), 4.15-4.05 (m, 2H), 3.80 (s, 3H), 2.95 (t, J=12Hz, 2H), 2.85 (t, J=7 Hz, 2H), 2.05 (t, J=7 Hz, 2H), 1.80 (dt, J=12, 4 Hz, 2H), 1.55 (d, J=12Hz, 2H), 1.50 (s, 9H). To a solution of tert-butyl 5-methoxy-2,3-dihydrospiro[indene-1,4'-piperidine]-1'-carboxylate (320 mg; 1.0 mmol) in N,N-dimethylformamide (15 mL) was added sodium ethanethiolate (360 mg; 4.0 mmol). The mixture was heated at 130° C. for 60 hours. The mixture was cooled to room temperature and saturated ammonium chloride solution (50 mL) was added. The resulting mixture was extracted with dichloromethane. The combined extracts were washed with brine, dried (NaSO$_4$), and concentrated. The residue was purified by column chromatography (SiO$_2$, EtOAc:hexanes 1:2) to afford tert-butyl 5-hydroxy-2,3-dihydrospiro[indene-1,4'-piperidine]-1'-carboxylate (110 mg (37%). $^1$H NMR (300 MHz, CDCl$_3$-d) δ ppm 7.07 (d, J=8 Hz, 1H), 6.67 (dd, J=8, 2Hz, 1H), 6.63 (d, J=2Hz, 1H), 4.15-4.05 (m, 2H), 2.95 (t, J=12Hz, 2H), 2.85 (t, J=7 Hz, 2H), 2.07 (t, J=7 Hz, 2H), 1.75 (dt, J=12Hz, 2Hz, 2H), 1.55 (d, J=12Hz, 2H), 1.52 (s, 9H), which was dissolved in 4 N HCl in dioxane (4 mL). The precipitate (formed after 1 hour) was collected by filtration, washed with Et$_2$O and dried to afford the HCl salt of 2,3-dihydrospiro[indene-1,4'-piperidine]-5-ol (65 mg; 75%). $^1$H NMR (300 MHz, D$_2$O) δ ppm 7.20 (d, J=8 Hz, 1H), 6.82-6.78 (m, 2H), 3.46 (d, J=12Hz, 2H), 3.23 (t, J=12Hz, 2H), 2.88 (t, J=7 Hz, 2H), 2.14 (t, J=7 Hz, 2H), 2.02 (dt, J=12, 4 Hz, 2H), 1.78 (d, J=12Hz, 2H). In the following Table the structures of compounds 1-336 according to the invention are depicted.

In these structures, the structural element represents a COOH group.

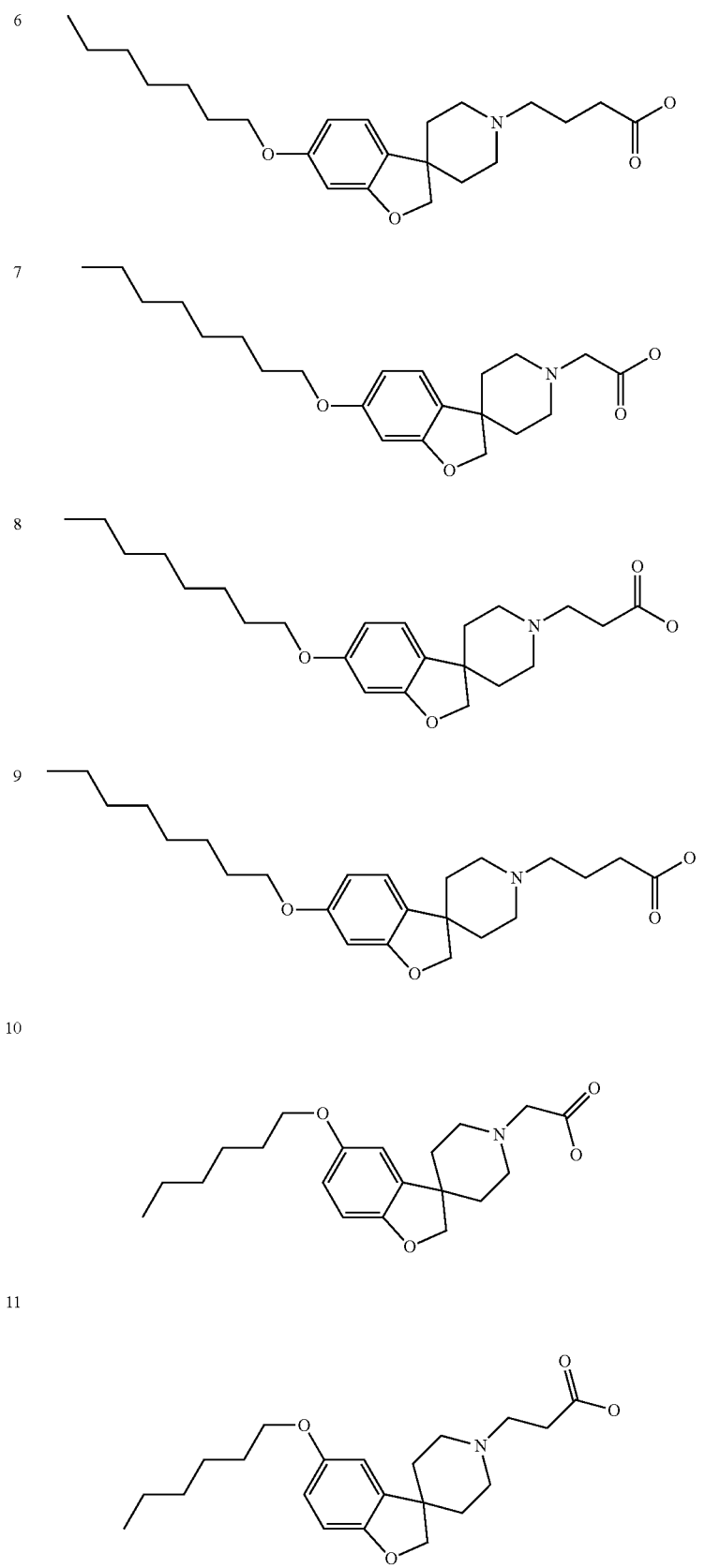

-continued
12
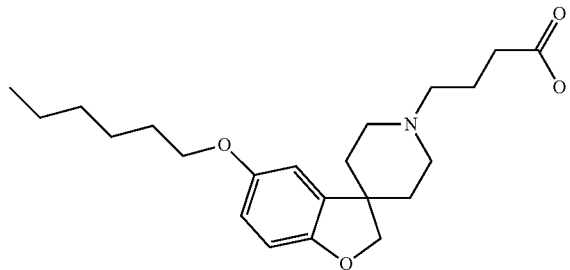 [SMILES: CCCCCCOc1ccc2c(c1)C1(CCN(CCCC(=O)O)CC1)CO2]
13
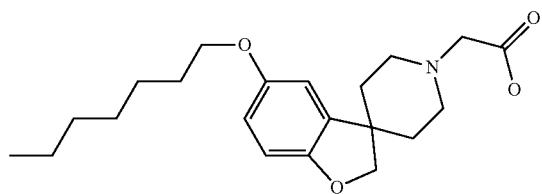 [SMILES: CCCCCCCOc1ccc2c(c1)C1(CCN(CC(=O)O)CC1)CO2]
14
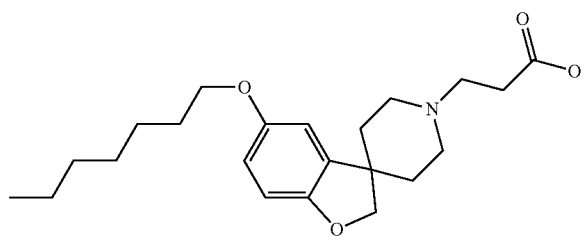 [SMILES: CCCCCCCOc1ccc2c(c1)C1(CCN(CCC(=O)O)CC1)CO2]
15
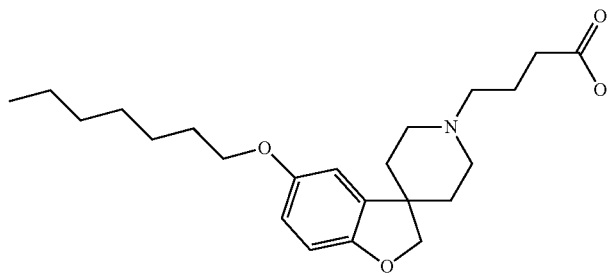 [SMILES: CCCCCCCOc1ccc2c(c1)C1(CCN(CCCC(=O)O)CC1)CO2]
16
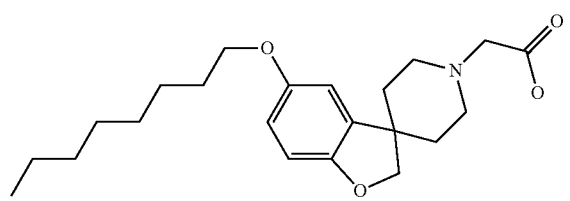 [SMILES: CCCCCCCCOc1ccc2c(c1)C1(CCN(CC(=O)O)CC1)CO2]
17
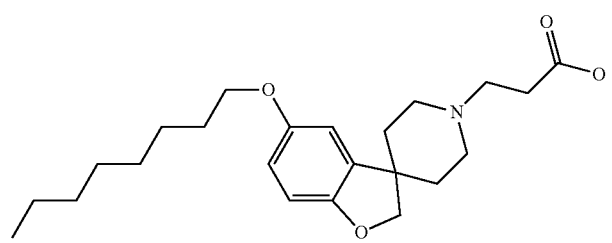 [SMILES: CCCCCCCCOc1ccc2c(c1)C1(CCN(CCC(=O)O)CC1)CO2]

-continued
18 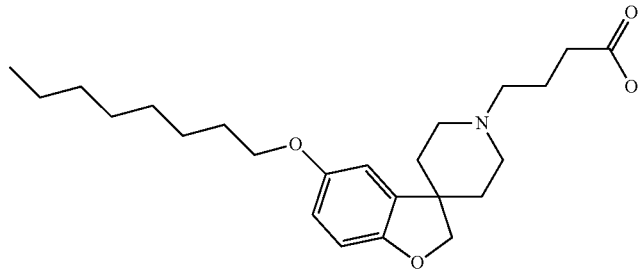 [SMILES: CCCCCCCCOc1ccc2c(c1)C1(CCN(CCCC(=O)O)CC1)CO2]
19 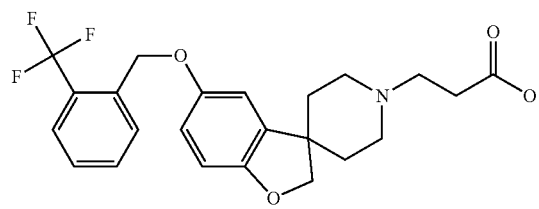 [SMILES: O=C(O)CCN1CCC2(CC1)COc1ccc(OCc3ccccc3C(F)(F)F)cc12]
20 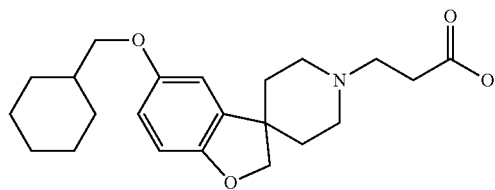 [SMILES: O=C(O)CCN1CCC2(CC1)COc1ccc(OCC3CCCCC3)cc12]
21 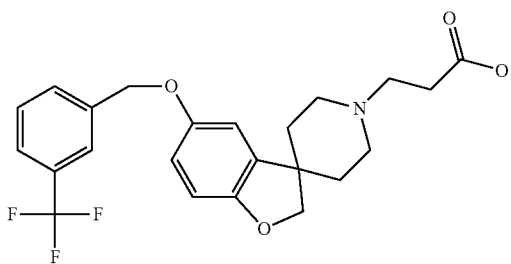 [SMILES: O=C(O)CCN1CCC2(CC1)COc1ccc(OCc3cccc(C(F)(F)F)c3)cc12]
22 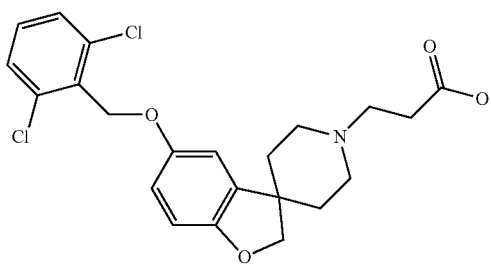 [SMILES: O=C(O)CCN1CCC2(CC1)COc1ccc(OCc3c(Cl)cccc3Cl)cc12]
23 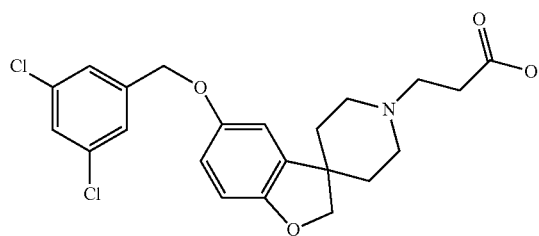 [SMILES: O=C(O)CCN1CCC2(CC1)COc1ccc(OCc3cc(Cl)cc(Cl)c3)cc12]

24 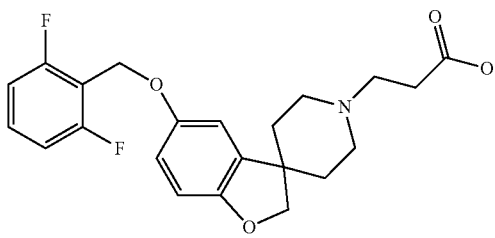 [SMILES: O=C(O)CCN1CCC2(CC1)COc1ccc(OCc3c(F)cccc3F)cc12]
25 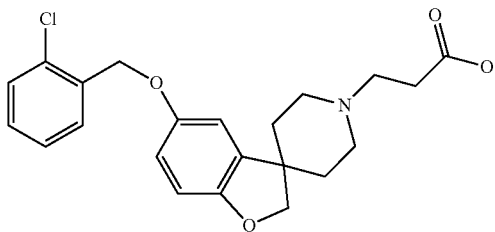 [SMILES: O=C(O)CCN1CCC2(CC1)COc1ccc(OCc3ccccc3Cl)cc12]
26 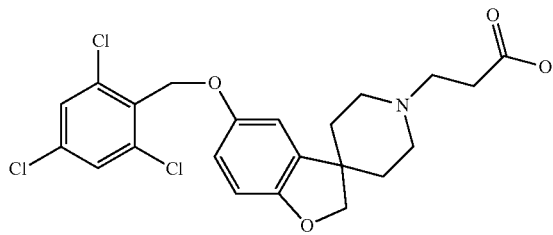 [SMILES: O=C(O)CCN1CCC2(CC1)COc1ccc(OCc3c(Cl)cc(Cl)cc3Cl)cc12]
27 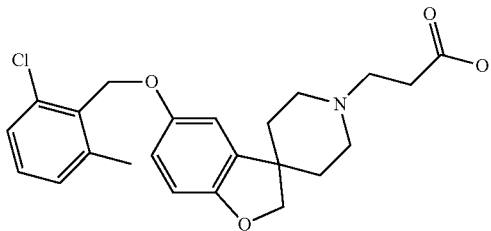 [SMILES: Cc1cccc(Cl)c1COc1ccc2c(c1)C1(CCN(CCC(=O)O)CC1)CO2]
28 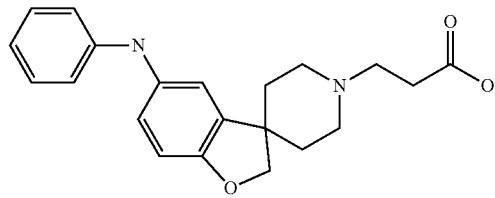 [SMILES: O=C(O)CCN1CCC2(CC1)COc1ccc(Nc3ccccc3)cc12]
29 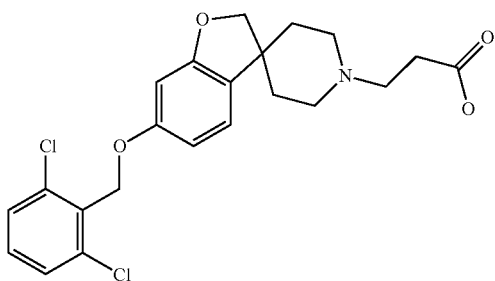 [SMILES: O=C(O)CCN1CCC2(CC1)COc1cc(OCc3c(Cl)cccc3Cl)ccc12]

-continued
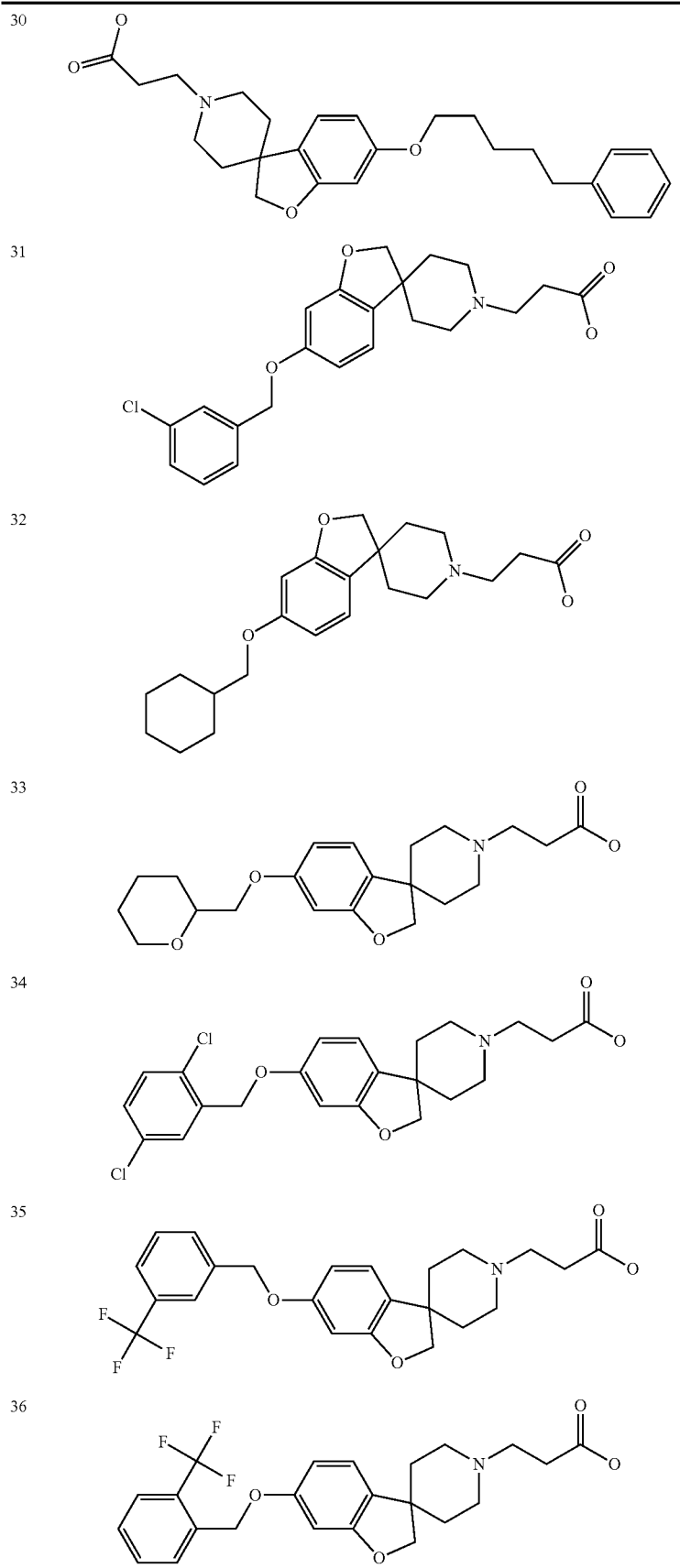

-continued
37
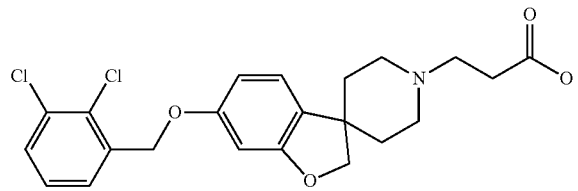 [SMILES: O=C(O)CCN1CCC2(CC1)COc1cc(OCc3cccc(Cl)c3Cl)ccc12]
38
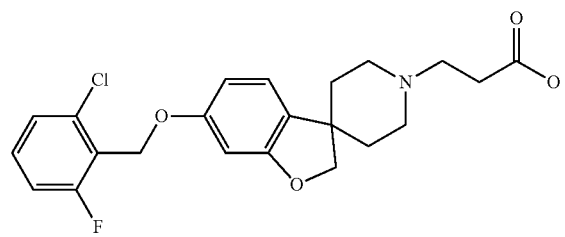 [SMILES: O=C(O)CCN1CCC2(CC1)COc1cc(OCc3c(F)cccc3Cl)ccc12]
39
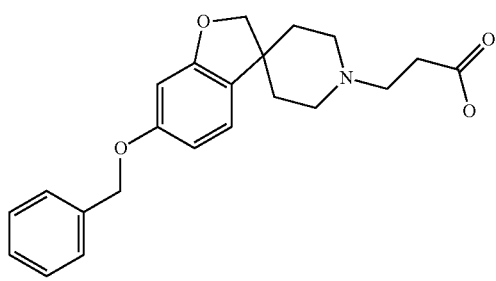 [SMILES: O=C(O)CCN1CCC2(CC1)COc1cc(OCc3ccccc3)ccc12]
40
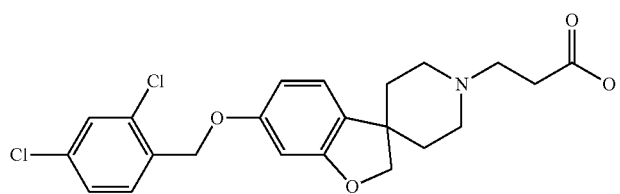 [SMILES: O=C(O)CCN1CCC2(CC1)COc1cc(OCc3ccc(Cl)cc3Cl)ccc12]
41
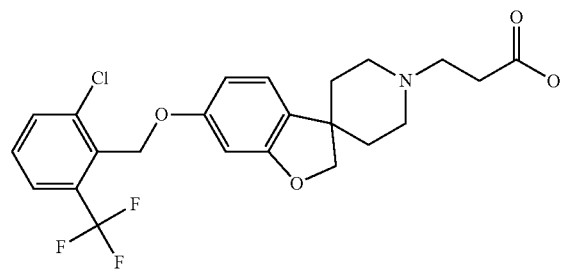 [SMILES: O=C(O)CCN1CCC2(CC1)COc1cc(OCc3c(Cl)cccc3C(F)(F)F)ccc12]
42
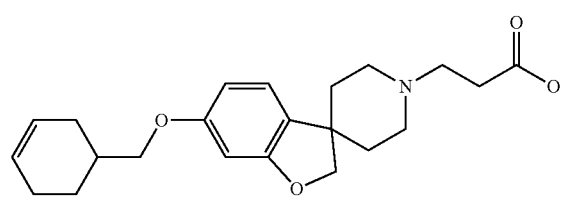 [SMILES: O=C(O)CCN1CCC2(CC1)COc1cc(OCC3CC=CCC3)ccc12]

-continued
43
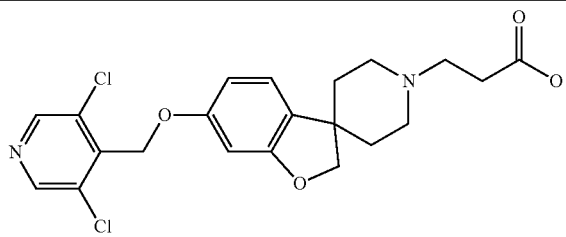
44
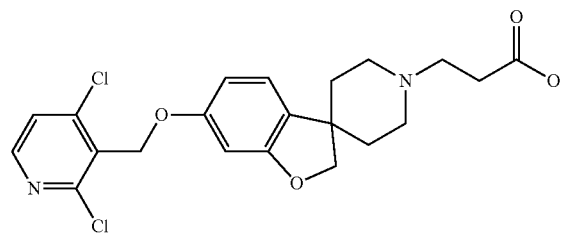 [SMILES: O=C(O)CCN1CCC2(CC1)COc1cc(OCc3c(Cl)ccnc3Cl)ccc12]
45
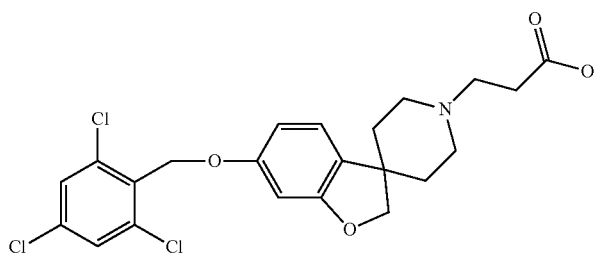 [SMILES: O=C(O)CCN1CCC2(CC1)COc1cc(OCc3c(Cl)cc(Cl)cc3Cl)ccc12]
46
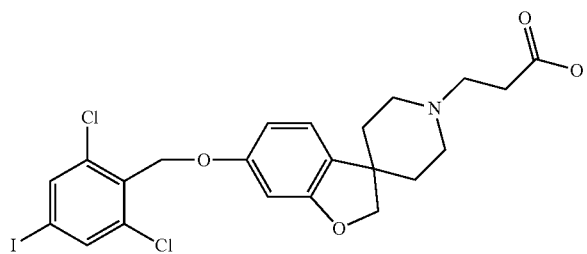 [SMILES: O=C(O)CCN1CCC2(CC1)COc1cc(OCc3c(Cl)cc(I)cc3Cl)ccc12]
47
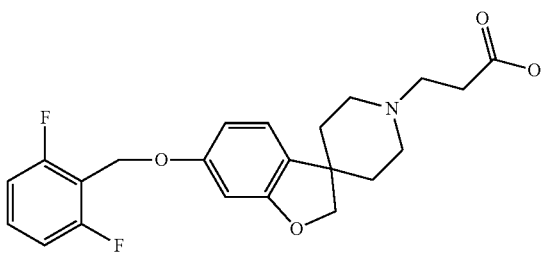 [SMILES: O=C(O)CCN1CCC2(CC1)COc1cc(OCc3c(F)cccc3F)ccc12]
48
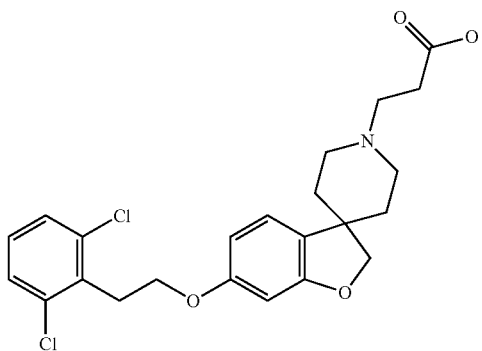 [SMILES: O=C(O)CCN1CCC2(CC1)COc1cc(OCCc3c(Cl)cccc3Cl)ccc12]

-continued
| | |
|---|---|
| 49 | 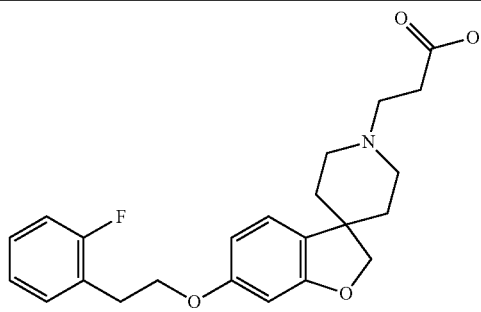 |
| 50 | 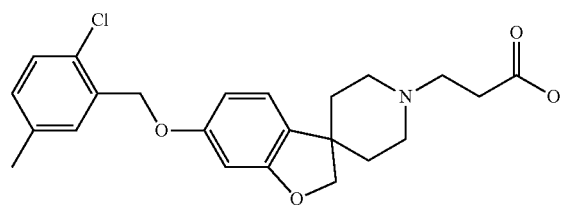 [SMILES: Cc1ccc(Cl)c(COc2ccc3c(c2)OCC32CCN(CCC(=O)O)CC2)c1] |
| 51 | 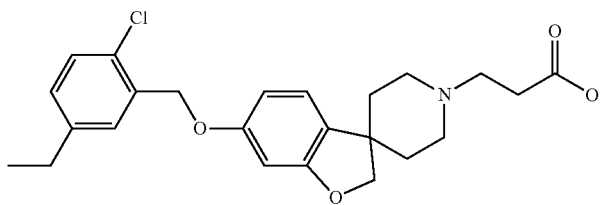 [SMILES: CCc1ccc(Cl)c(COc2ccc3c(c2)OCC32CCN(CCC(=O)O)CC2)c1] |
| 52 | 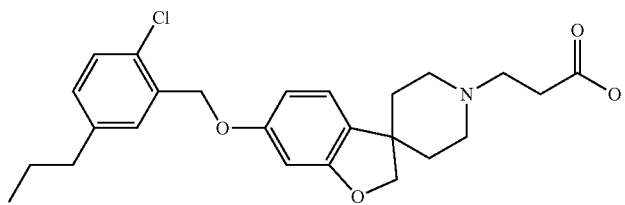 [SMILES: CCCc1ccc(Cl)c(COc2ccc3c(c2)OCC32CCN(CCC(=O)O)CC2)c1] |
| 53 | 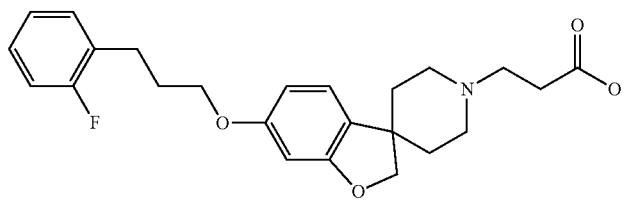 [SMILES: O=C(O)CCN1CCC2(CC1)COc1cc(OCCCc3ccccc3F)ccc12] |
| 54 | 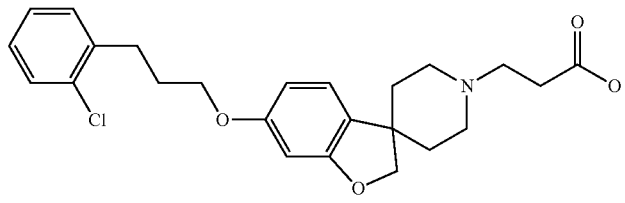 [SMILES: O=C(O)CCN1CCC2(CC1)COc1cc(OCCCc3ccccc3Cl)ccc12] |
| 55 | 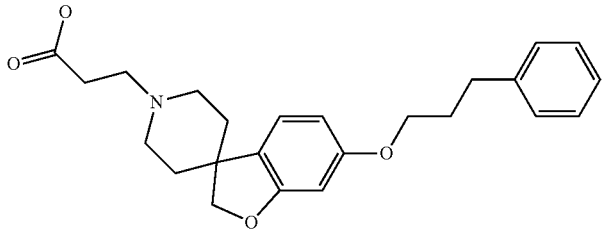 |

| | |
|---|---|
| 56 | 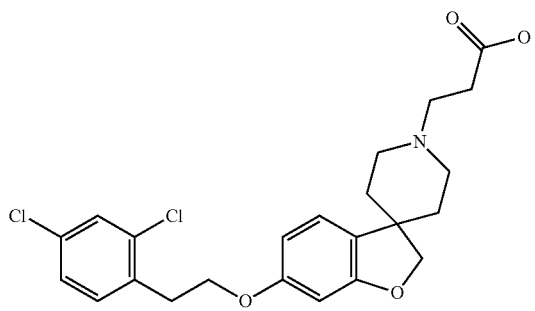 [SMILES: O=C(O)CCN1CCC2(CC1)COc1cc(OCCc3ccc(Cl)cc3Cl)ccc12] |
| 57 | 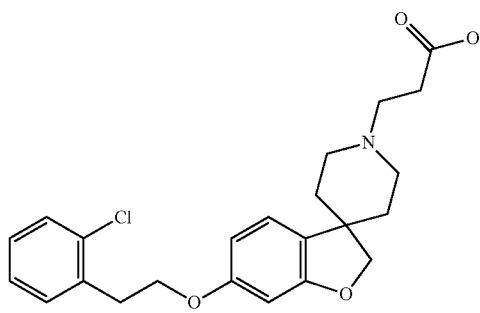 [SMILES: O=C(O)CCN1CCC2(CC1)COc1cc(OCCc3ccccc3Cl)ccc12] |
| 58 | 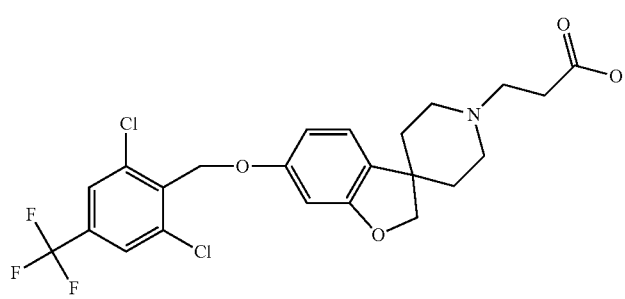 [SMILES: O=C(O)CCN1CCC2(CC1)COc1cc(OCc3c(Cl)cc(C(F)(F)F)cc3Cl)ccc12] |
| 59 | 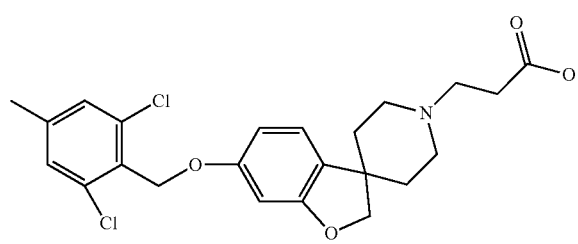 [SMILES: Cc1cc(Cl)c(COc2ccc3c(c2)OCC32CCN(CCC(=O)O)CC2)c(Cl)c1] |
| 60 | 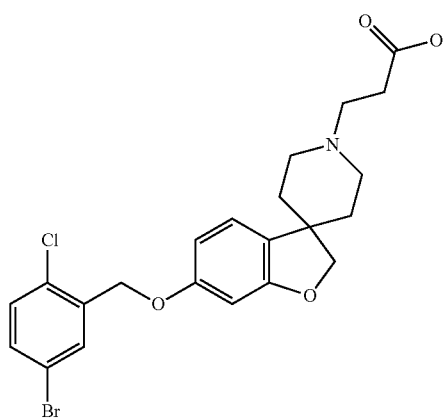 [SMILES: O=C(O)CCN1CCC2(CC1)COc1cc(OCc3cc(Br)ccc3Cl)ccc12] |

| 61 | 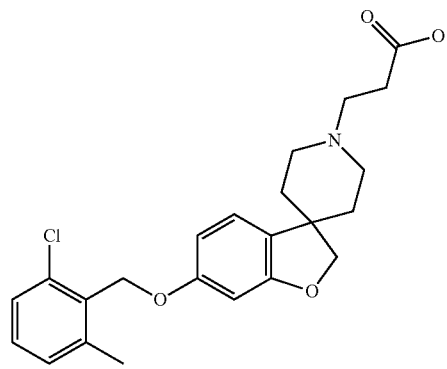 [SMILES: Cc1cccc(Cl)c1COc1ccc2c(c1)OCC21CCN(CCC(=O)O)CC1] |
| 62 | 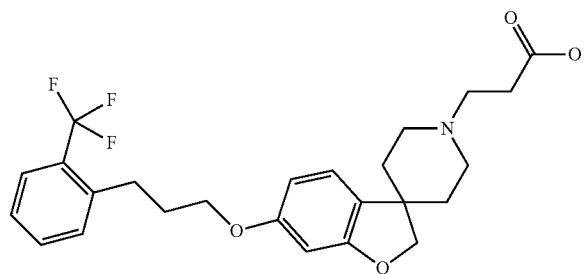 [SMILES: O=C(O)CCN1CCC2(CC1)COc1cc(OCCCc3ccccc3C(F)(F)F)ccc12] |
| 63 | 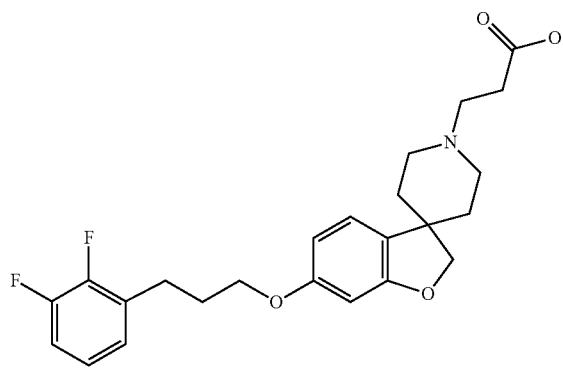 [SMILES: O=C(O)CCN1CCC2(CC1)COc1cc(OCCCc3cccc(F)c3F)ccc12] |
| 64 | 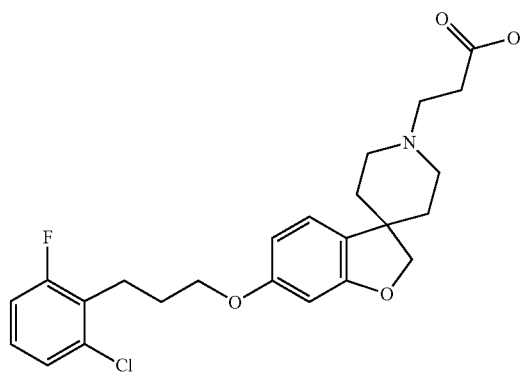 [SMILES: O=C(O)CCN1CCC2(CC1)COc1cc(OCCCc3c(F)cccc3Cl)ccc12] |

65
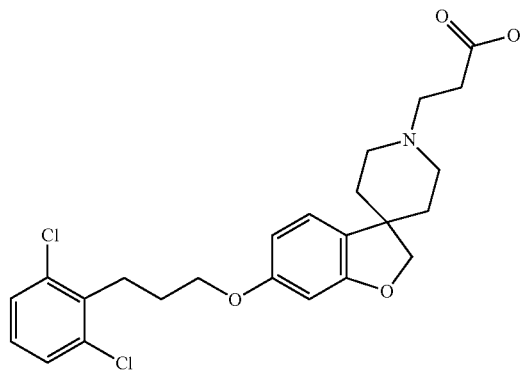
66
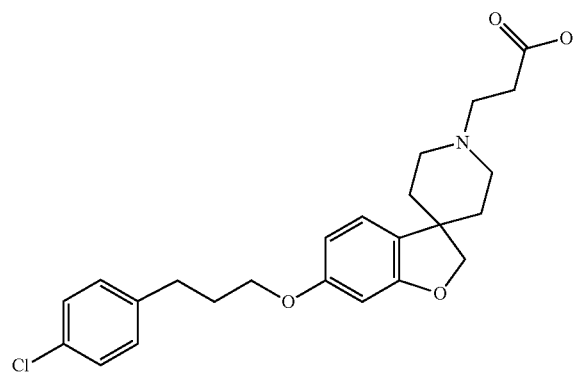 [SMILES: O=C(O)CCN1CCC2(CC1)COc1cc(OCCCc3ccc(Cl)cc3)ccc12]
67
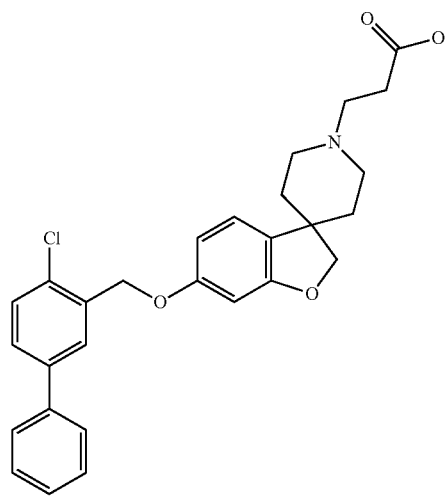 [SMILES: O=C(O)CCN1CCC2(CC1)COc1cc(OCc3cc(-c4ccccc4)ccc3Cl)ccc12]

| | |
|---|---|
| 68 | 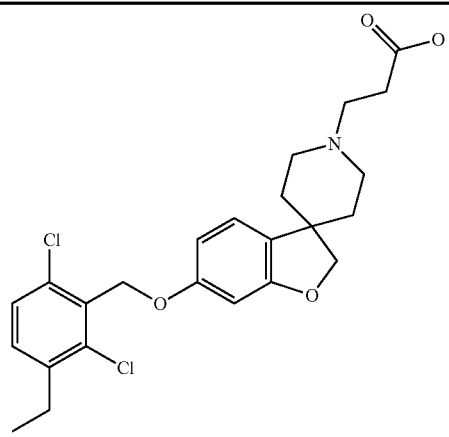 |
| 69 | 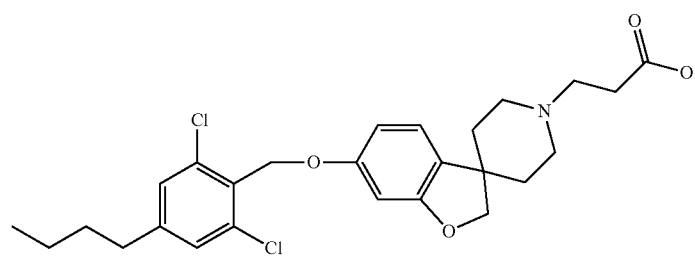 [SMILES: CCCCc1cc(Cl)c(COc2ccc3c(c2)OCC32CCN(CCC(=O)O)CC2)c(Cl)c1] |
| 70 | 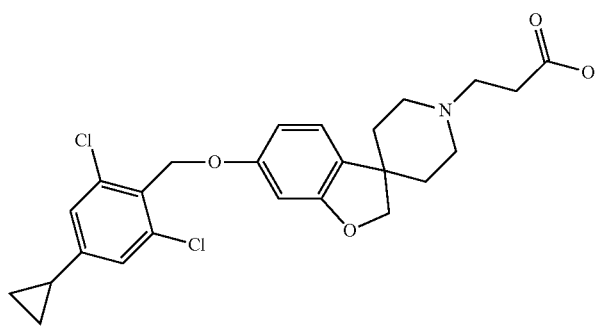 [SMILES: O=C(O)CCN1CCC2(CC1)COc1cc(OCc3c(Cl)cc(C4CC4)cc3Cl)ccc12] |
| 71 | 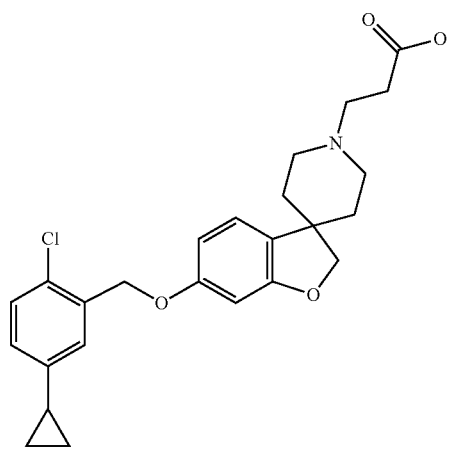 [SMILES: O=C(O)CCN1CCC2(CC1)COc1cc(OCc3cc(C4CC4)ccc3Cl)ccc12] |

72 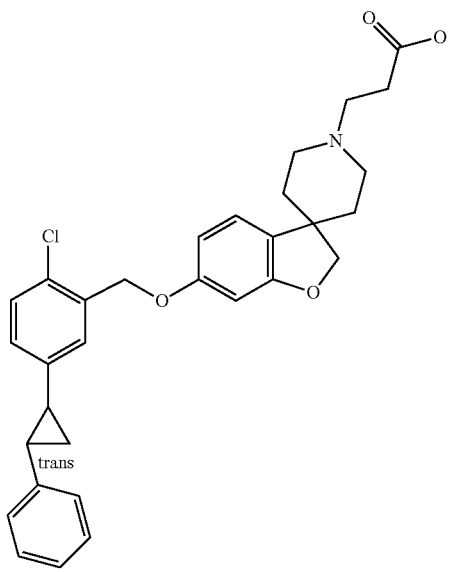 [SMILES: O=C(O)CCN1CCC2(CC1)COc1cc(OCc3cc(C4CC4c4ccccc4)ccc3Cl)ccc12]
73 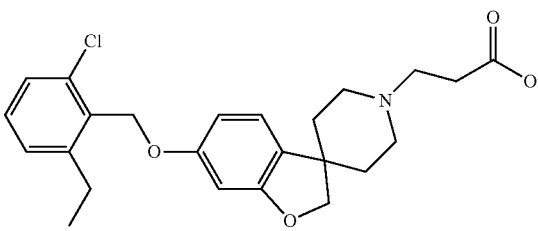 [SMILES: CCc1cccc(Cl)c1COc1ccc2c(c1)OCC21CCN(CCC(=O)O)CC1]
74 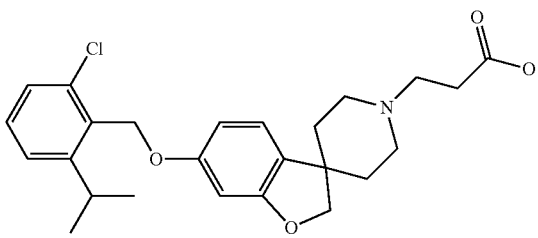
75 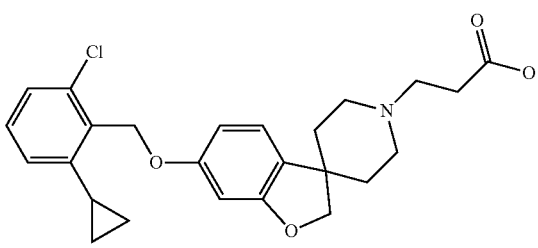
76 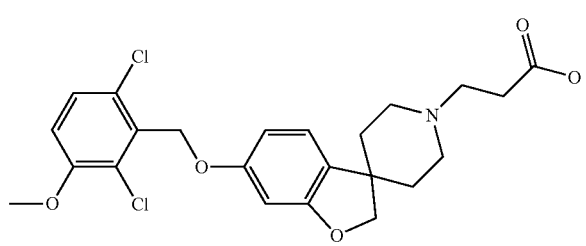

77 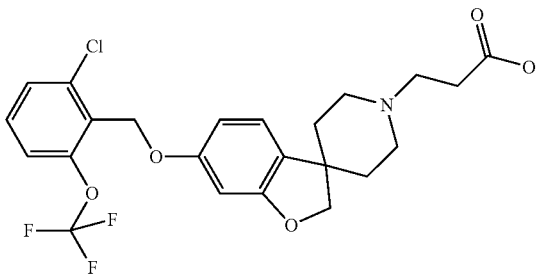 [SMILES: O=C(O)CCN1CCC2(CC1)COc1cc(OCc3c(Cl)cccc3OC(F)(F)F)ccc12]
78 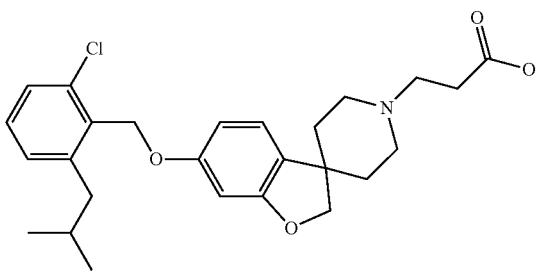 [SMILES: CC(C)Cc1cccc(Cl)c1COc1ccc2c(c1)OCC21CCN(CCC(=O)O)CC1]
79 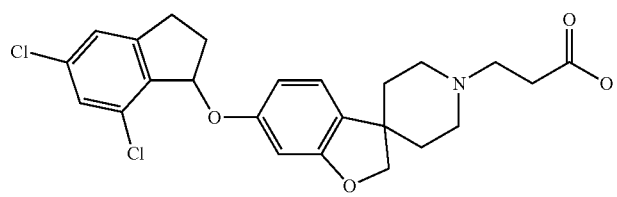 [SMILES: O=C(O)CCN1CCC2(CC1)COc1cc(OC3CCc4cc(Cl)cc(Cl)c43)ccc12]
80 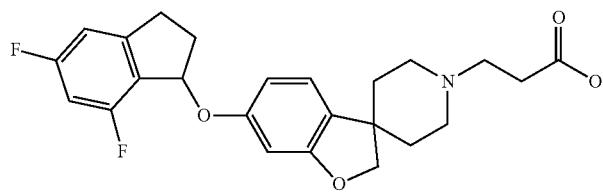 [SMILES: O=C(O)CCN1CCC2(CC1)COc1cc(OC3CCc4cc(F)cc(F)c43)ccc12]
81 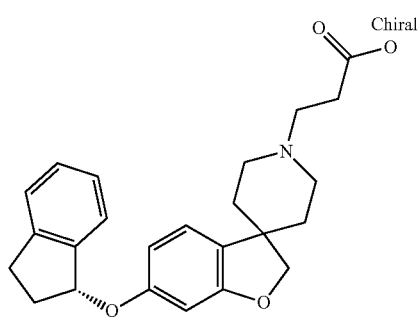 [SMILES: O=C(O)CCN1CCC2(CC1)COc1cc(O[C@@H]3CCc4ccccc43)ccc12]
82 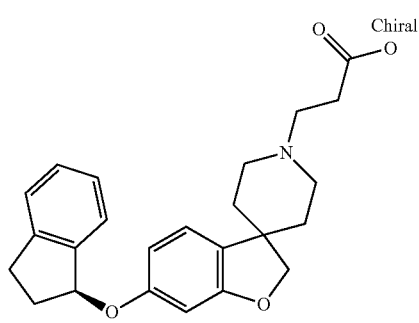 [SMILES: O=C(O)CCN1CCC2(CC1)COc1cc(O[C@H]3CCc4ccccc43)ccc12]

83
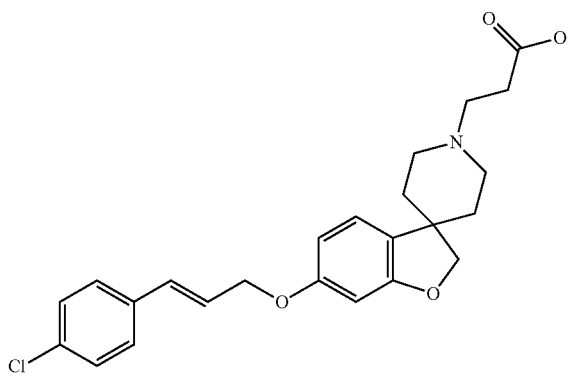 [SMILES: O=C(O)CCN1CCC2(CC1)COc1cc(OC/C=C/c3ccc(Cl)cc3)ccc12]
84
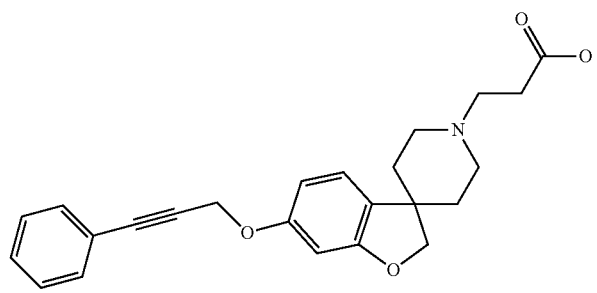 [SMILES: O=C(O)CCN1CCC2(CC1)COc1cc(OCC#Cc3ccccc3)ccc12]
85
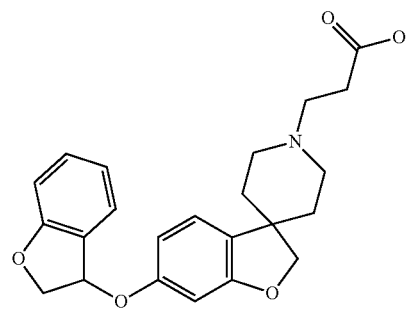 [SMILES: O=C(O)CCN1CCC2(CC1)COc1cc(OC3COc4ccccc43)ccc12]
86
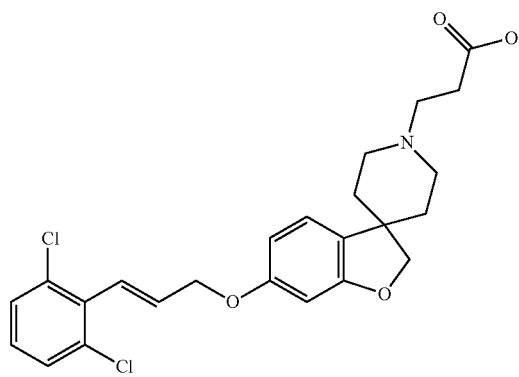 [SMILES: O=C(O)CCN1CCC2(CC1)COc1cc(OC/C=C/c3c(Cl)cccc3Cl)ccc12]

87
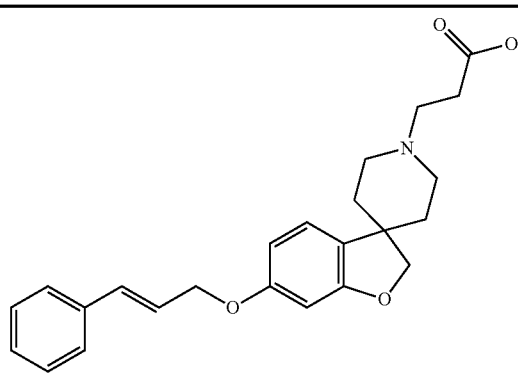
88
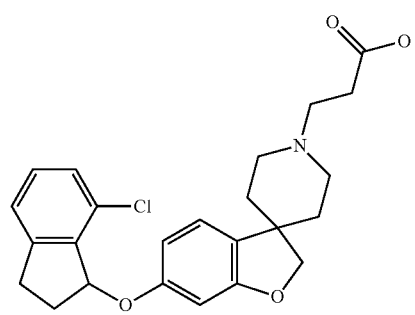 [SMILES: O=C(O)CCN1CCC2(CC1)COc1cc(OC3CCc4cccc(Cl)c43)ccc12]
89
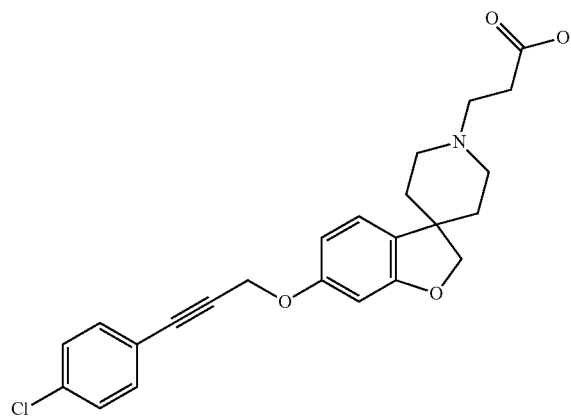 [SMILES: O=C(O)CCN1CCC2(CC1)COc1cc(OCC#Cc3ccc(Cl)cc3)ccc12]
90
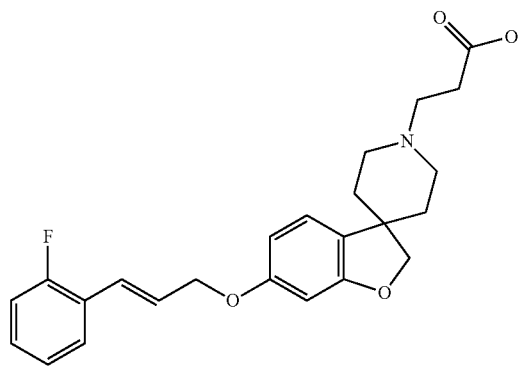 [SMILES: O=C(O)CCN1CCC2(CC1)COc1cc(OC/C=C/c3ccccc3F)ccc12]

91
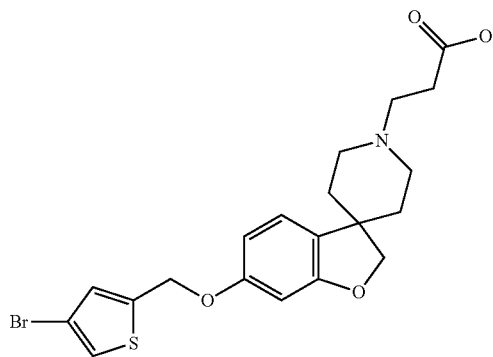 [SMILES: O=C(O)CCN1CCC2(CC1)COc1cc(OCc3cc(Br)cs3)ccc12]
92
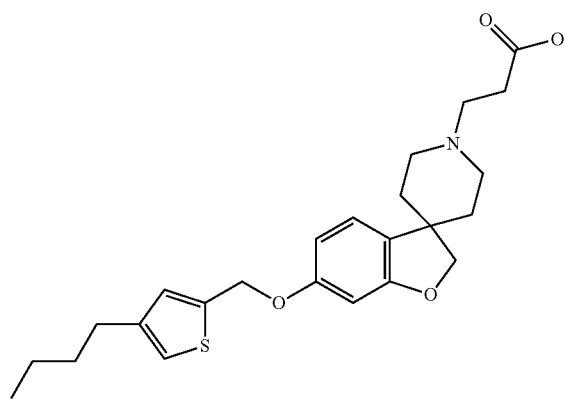 [SMILES: CCCCc1csc(COc2ccc3c(c2)OCC32CCN(CCC(=O)O)CC2)c1]
93
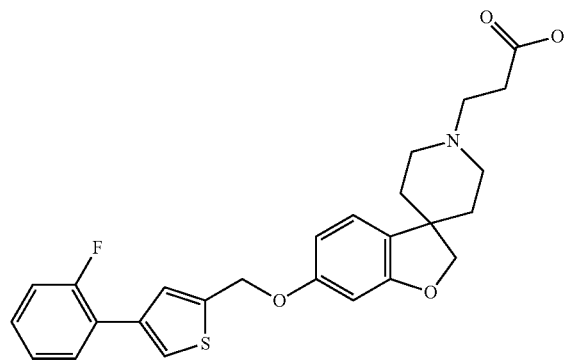 [SMILES: O=C(O)CCN1CCC2(CC1)COc1cc(OCc3cc(-c4ccccc4F)cs3)ccc12]
94
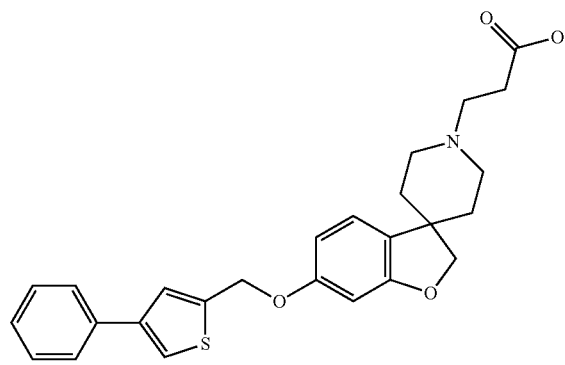 [SMILES: O=C(O)CCN1CCC2(CC1)COc1cc(OCc3cc(-c4ccccc4)cs3)ccc12]

95
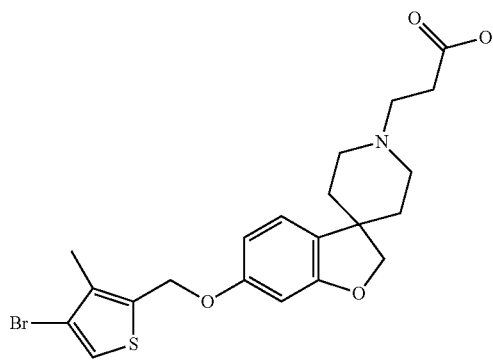 [SMILES: Cc1c(Br)csc1COc1ccc2c(c1)OCC21CCN(CCC(=O)O)CC1]
96
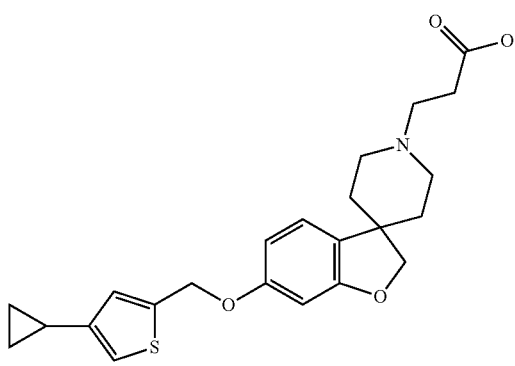 [SMILES: O=C(O)CCN1CCC2(CC1)COc1cc(OCc3cc(C4CC4)cs3)ccc12]
97
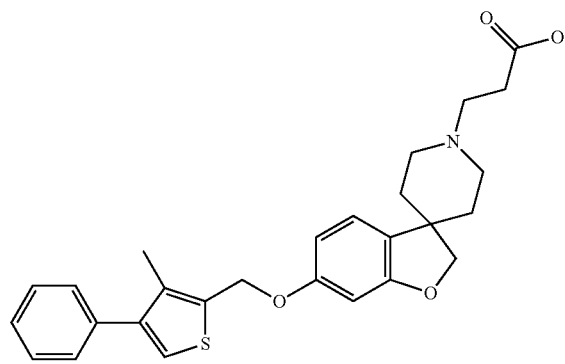 [SMILES: Cc1c(-c2ccccc2)csc1COc1ccc2c(c1)OCC21CCN(CCC(=O)O)CC1]
98
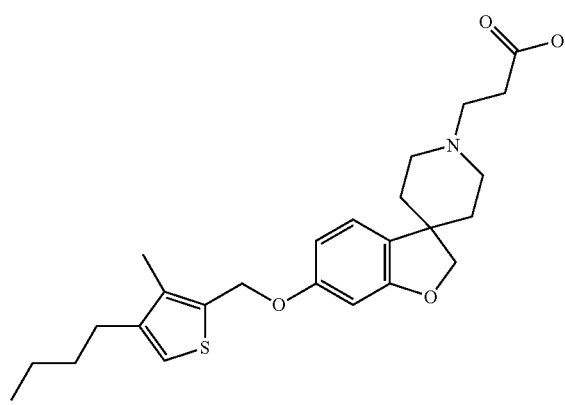 [SMILES: CCCCc1csc(COc2ccc3c(c2)OCC32CCN(CCC(=O)O)CC2)c1C]

-continued
99
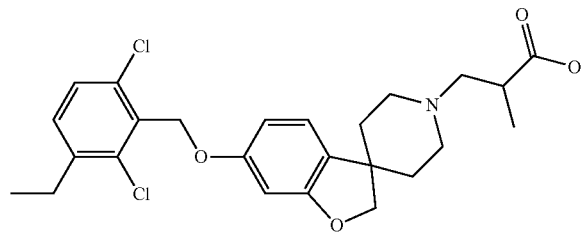 [SMILES: CCc1ccc(Cl)c(COc2ccc3c(c2)OCC32CCN(CC(C)C(=O)O)CC2)c1Cl]
100
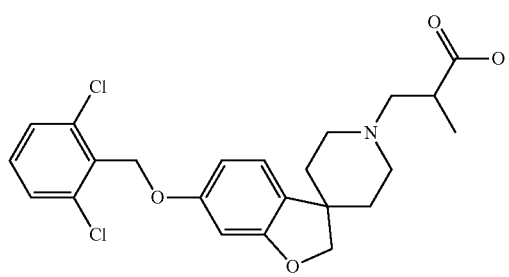 [SMILES: CC(CN1CCC2(CC1)COc1cc(OCc3c(Cl)cccc3Cl)ccc12)C(=O)O]
101
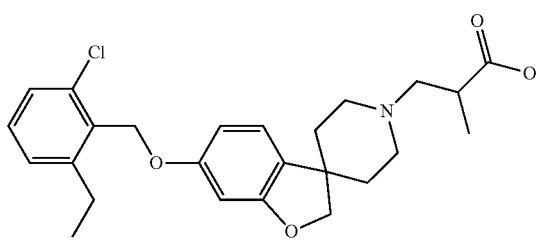 [SMILES: CCc1cccc(Cl)c1COc1ccc2c(c1)OCC21CCN(CC(C)C(=O)O)CC1]
102
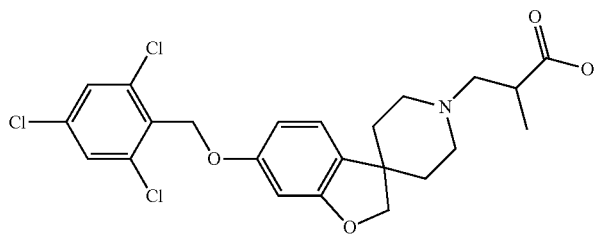 [SMILES: CC(CN1CCC2(CC1)COc1cc(OCc3c(Cl)cc(Cl)cc3Cl)ccc12)C(=O)O]
103
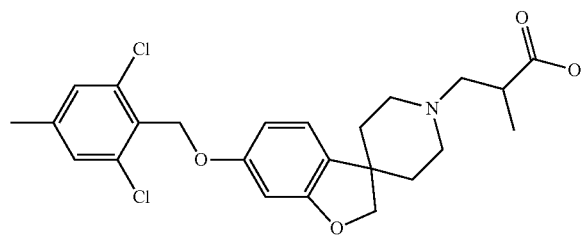 [SMILES: Cc1cc(Cl)c(COc2ccc3c(c2)OCC32CCN(CC(C)C(=O)O)CC2)c(Cl)c1]
104
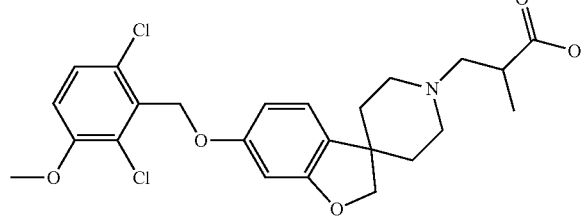

-continued
105
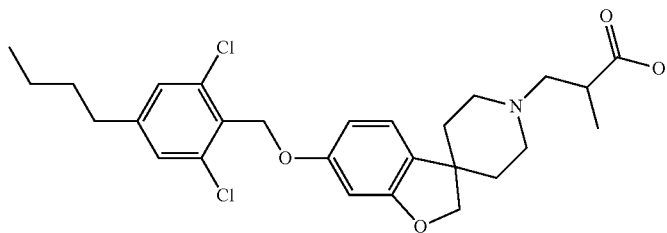 [SMILES: CCCCc1cc(Cl)c(COc2ccc3c(c2)OCC32CCN(CC(C)C(=O)O)CC2)c(Cl)c1]
106
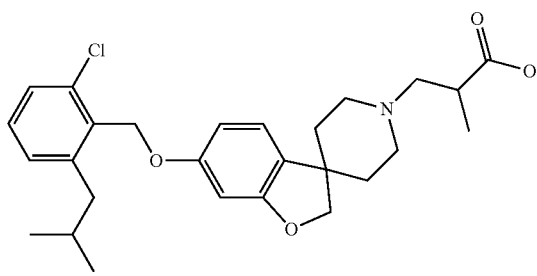 [SMILES: CC(C)Cc1cccc(Cl)c1COc1ccc2c(c1)OCC21CCN(CC(C)C(=O)O)CC1]
107
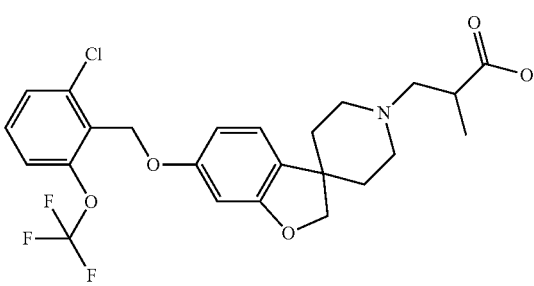 [SMILES: CC(CN1CCC2(CC1)COc1cc(OCc3c(Cl)cccc3OC(F)(F)F)ccc12)C(=O)O]
108
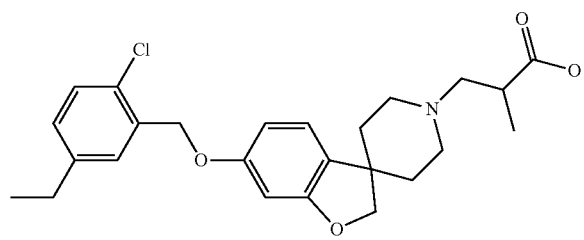 [SMILES: CCc1ccc(Cl)c(COc2ccc3c(c2)OCC32CCN(CC(C)C(=O)O)CC2)c1]
109
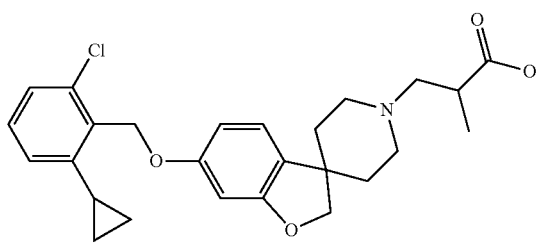 [SMILES: CC(CN1CCC2(CC1)COc1cc(OCc3c(Cl)cccc3C3CC3)ccc12)C(=O)O]
110
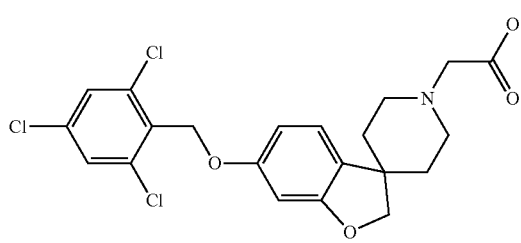 [SMILES: O=C(O)CN1CCC2(CC1)COc1cc(OCc3c(Cl)cc(Cl)cc3Cl)ccc12]

-continued
| 111 | 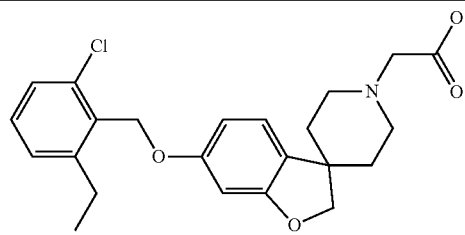 |
| 112 | 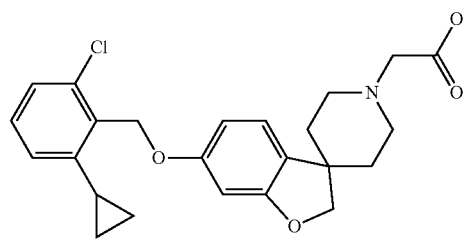 [SMILES: O=C(O)CN1CCC2(CC1)COc1cc(OCc3c(Cl)cccc3C3CC3)ccc12] |
| 113 | 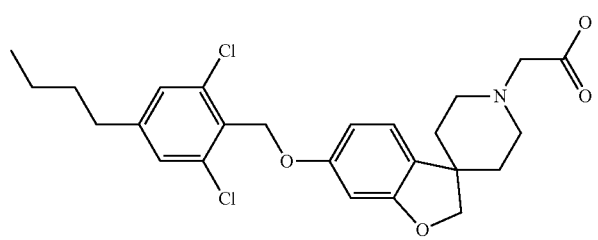 [SMILES: CCCCc1cc(Cl)c(COc2ccc3c(c2)OCC32CCN(CC(=O)O)CC2)c(Cl)c1] |
| 114 | 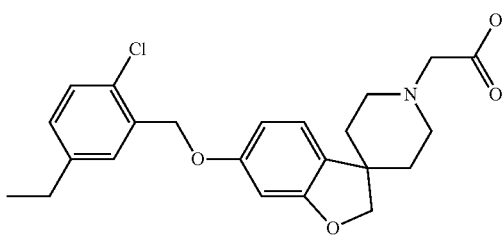 [SMILES: CCc1ccc(Cl)c(COc2ccc3c(c2)OCC32CCN(CC(=O)O)CC2)c1] |
| 115 | 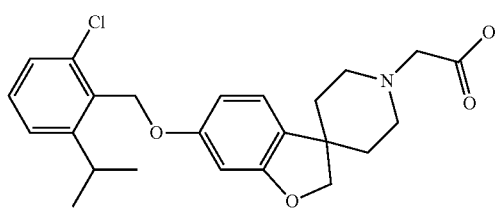 [SMILES: CC(C)c1cccc(Cl)c1COc1ccc2c(c1)OCC21CCN(CC(=O)O)CC1] |
| 116 | 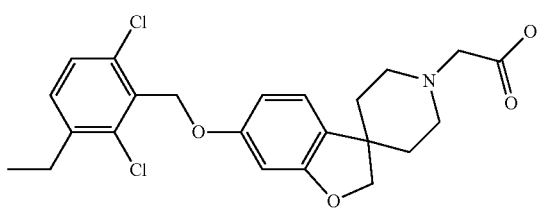 [SMILES: CCc1ccc(Cl)c(COc2ccc3c(c2)OCC32CCN(CC(=O)O)CC2)c1Cl] |
| 117 | 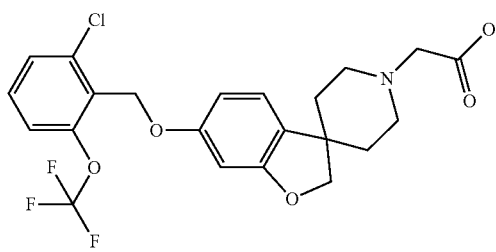 [SMILES: O=C(O)CN1CCC2(CC1)COc1cc(OCc3c(Cl)cccc3OC(F)(F)F)ccc12] |

-continued
118 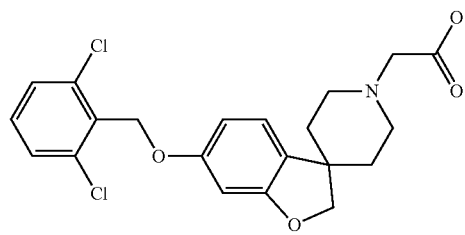 [SMILES: O=C(O)CN1CCC2(CC1)COc1cc(OCc3c(Cl)cccc3Cl)ccc12]
119 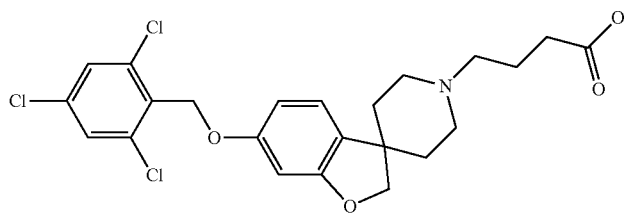 [SMILES: O=C(O)CCCN1CCC2(CC1)COc1cc(OCc3c(Cl)cc(Cl)cc3Cl)ccc12]
120 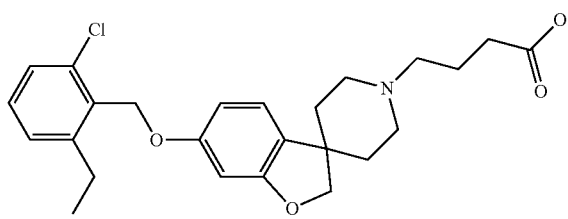 [SMILES: CCc1cccc(Cl)c1COc1ccc2c(c1)OCC21CCN(CCCC(=O)O)CC1]
121 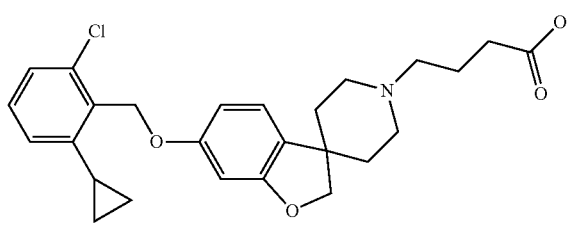 [SMILES: O=C(O)CCCN1CCC2(CC1)COc1cc(OCc3c(Cl)cccc3C3CC3)ccc12]
122 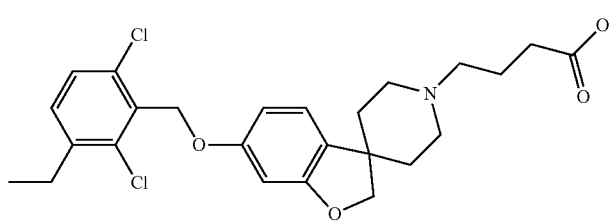 [SMILES: CCc1ccc(Cl)c(COc2ccc3c(c2)OCC32CCN(CCCC(=O)O)CC2)c1Cl]
123 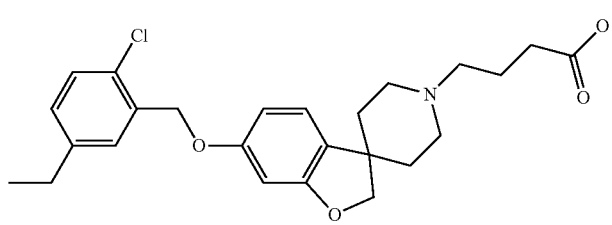 [SMILES: CCc1ccc(Cl)c(COc2ccc3c(c2)OCC32CCN(CCCC(=O)O)CC2)c1]
124 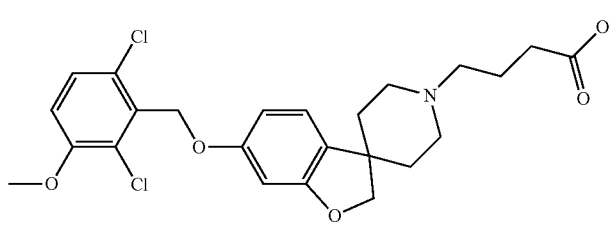 [SMILES: COc1ccc(Cl)c(COc2ccc3c(c2)OCC32CCN(CCCC(=O)O)CC2)c1Cl]

-continued
125
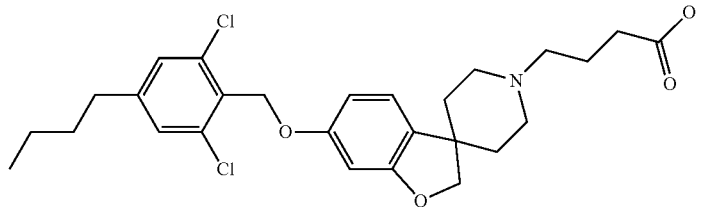 [SMILES: CCCCc1cc(Cl)c(COc2ccc3c(c2)OCC32CCN(CCCC(=O)O)CC2)c(Cl)c1]
126
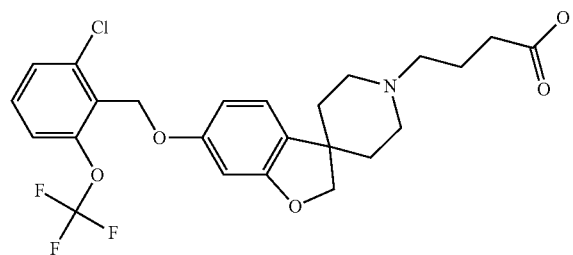 [SMILES: O=C(O)CCCN1CCC2(CC1)COc1cc(OCc3c(Cl)cccc3OC(F)(F)F)ccc12]
127
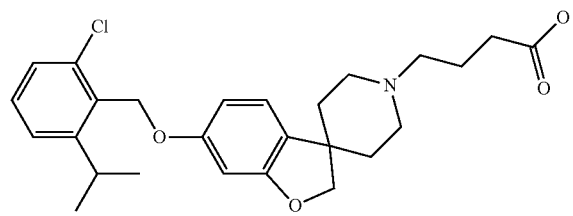 [SMILES: CC(C)c1cccc(Cl)c1COc1ccc2c(c1)OCC21CCN(CCCC(=O)O)CC1]
128
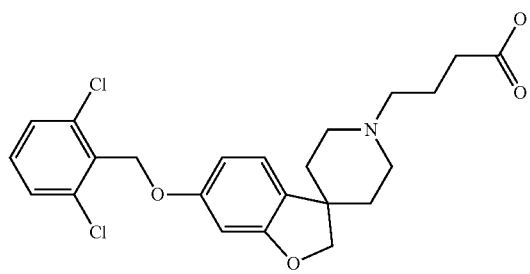 [SMILES: O=C(O)CCCN1CCC2(CC1)COc1cc(OCc3c(Cl)cccc3Cl)ccc12]
129
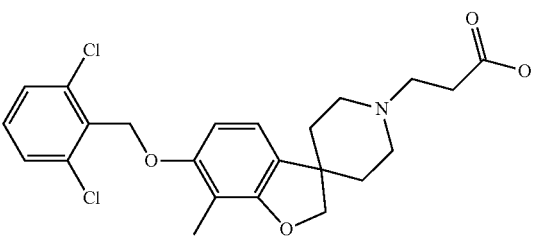 [SMILES: Cc1c(OCc2c(Cl)cccc2Cl)ccc2c1OCC21CCN(CCC(=O)O)CC1]
130
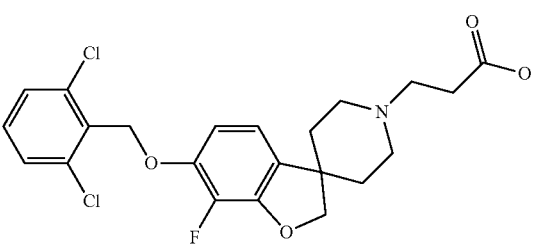 [SMILES: O=C(O)CCN1CCC2(CC1)COc1c2ccc(OCc2c(Cl)cccc2Cl)c1F]

-continued
131
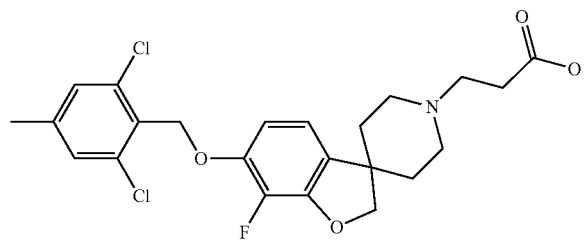 [SMILES: Cc1cc(Cl)c(COc2ccc3c(c2F)OCC32CCN(CCC(=O)O)CC2)c(Cl)c1]
132
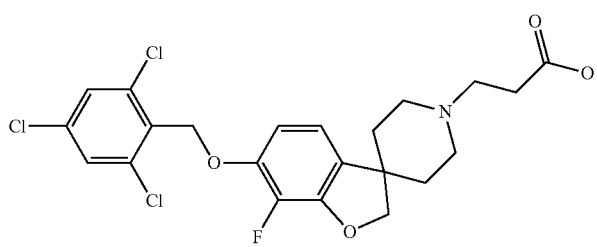 [SMILES: O=C(O)CCN1CCC2(CC1)COc1c2ccc(OCc2c(Cl)cc(Cl)cc2Cl)c1F]
133
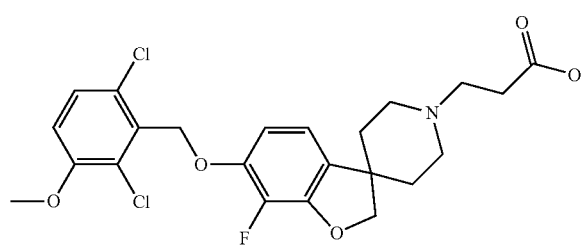 [SMILES: COc1ccc(Cl)c(COc2ccc3c(c2F)OCC32CCN(CCC(=O)O)CC2)c1Cl]
134
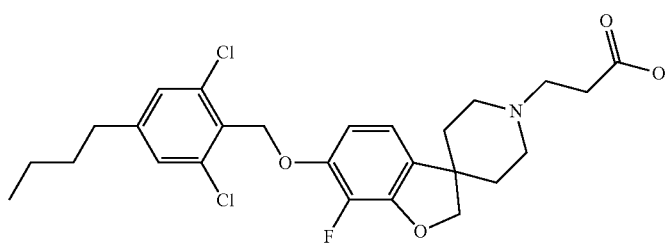 [SMILES: CCCCc1cc(Cl)c(COc2ccc3c(c2F)OCC32CCN(CCC(=O)O)CC2)c(Cl)c1]
135
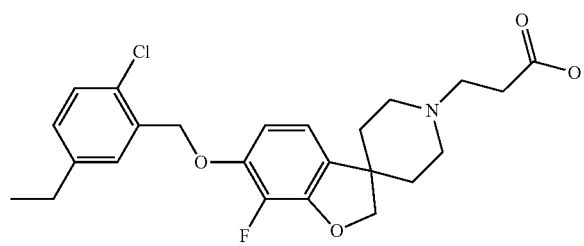 [SMILES: CCc1ccc(Cl)c(COc2ccc3c(c2F)OCC32CCN(CCC(=O)O)CC2)c1]
136
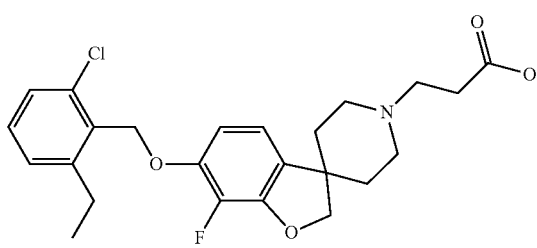

-continued
137
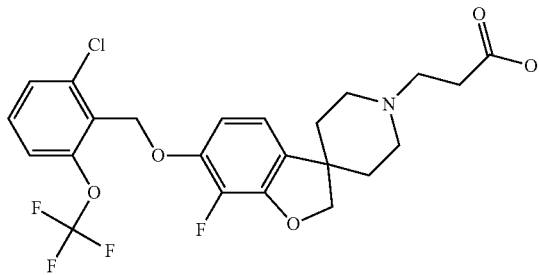 [SMILES: O=C(O)CCN1CCC2(CC1)COc1c2ccc(OCc2c(Cl)cccc2OC(F)(F)F)c1F]
138
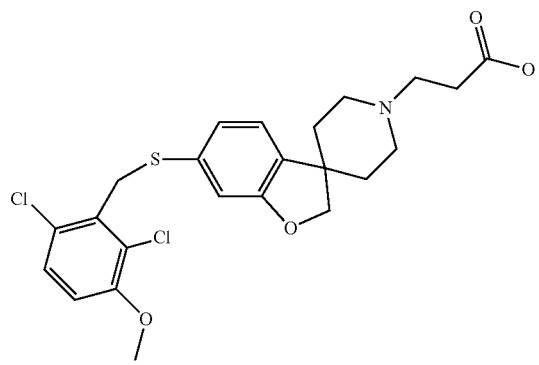 [SMILES: COc1ccc(Cl)c(CSc2ccc3c(c2)OCC32CCN(CCC(=O)O)CC2)c1Cl]
139
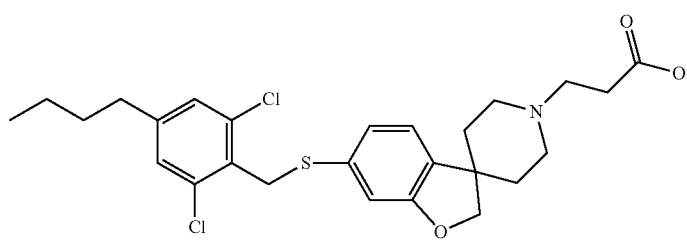 [SMILES: CCCCc1cc(Cl)c(CSc2ccc3c(c2)OCC32CCN(CCC(=O)O)CC2)c(Cl)c1]
140
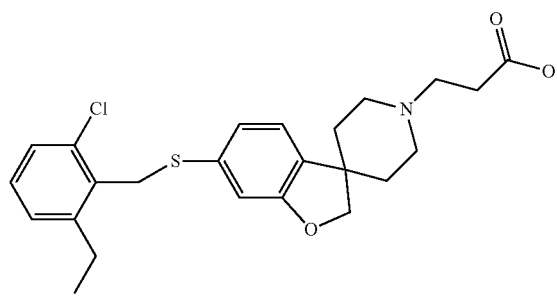 [SMILES: CCc1cccc(Cl)c1CSc1ccc2c(c1)OCC21CCN(CCC(=O)O)CC1]
141
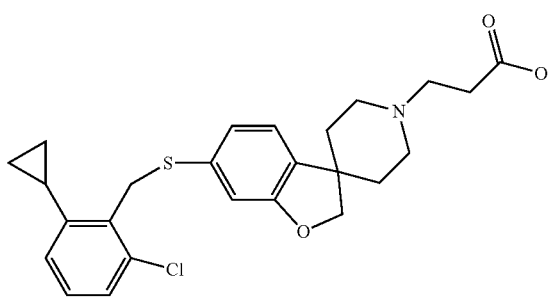 [SMILES: O=C(O)CCN1CCC2(CC1)COc1cc(SCc3c(Cl)cccc3C3CC3)ccc12]

-continued
| | |
|---|---|
| 142 | 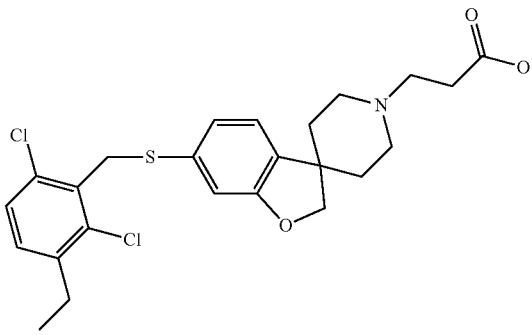 [SMILES: CCc1ccc(Cl)c(CSc2ccc3c(c2)OCC32CCN(CCC(=O)O)CC2)c1Cl] |
| 143 | 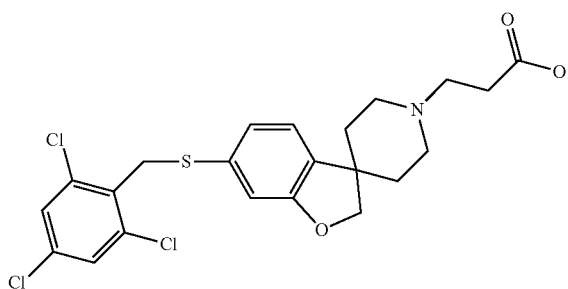 [SMILES: O=C(O)CCN1CCC2(CC1)COc1cc(SCc3c(Cl)cc(Cl)cc3Cl)ccc12] |
| 144 | 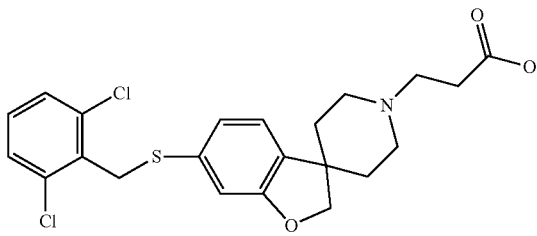 [SMILES: O=C(O)CCN1CCC2(CC1)COc1cc(SCc3c(Cl)cccc3Cl)ccc12] |
| 145 | 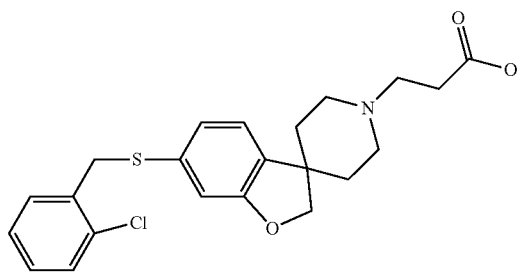 [SMILES: O=C(O)CCN1CCC2(CC1)COc1cc(SCc3ccccc3Cl)ccc12] |
| 146 | 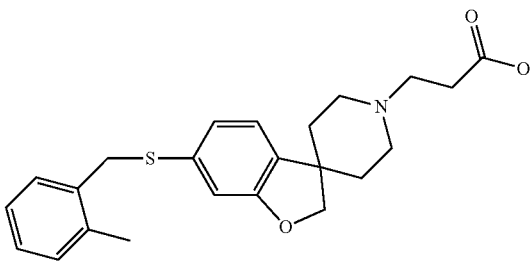 [SMILES: Cc1ccccc1CSc1ccc2c(c1)OCC21CCN(CCC(=O)O)CC1] |

-continued
147
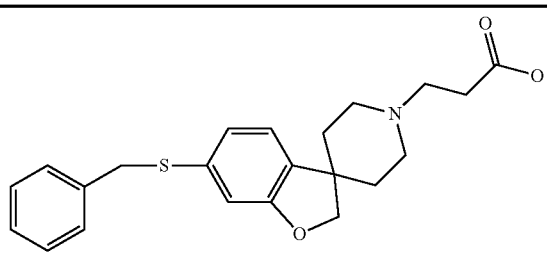
148
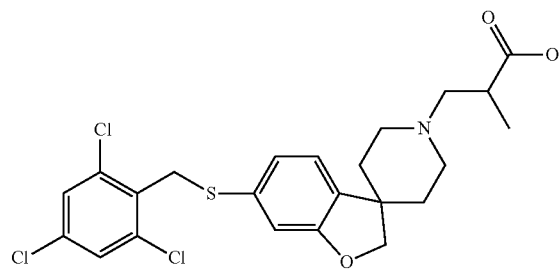 [SMILES: CC(CN1CCC2(CC1)COc1cc(SCc3c(Cl)cc(Cl)cc3Cl)ccc12)C(=O)O]
149
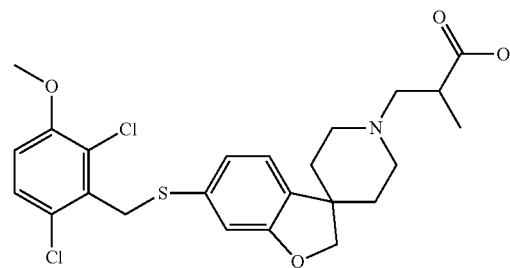 [SMILES: COc1ccc(Cl)c(CSc2ccc3c(c2)OCC32CCN(CC(C)C(=O)O)CC2)c1Cl]
150
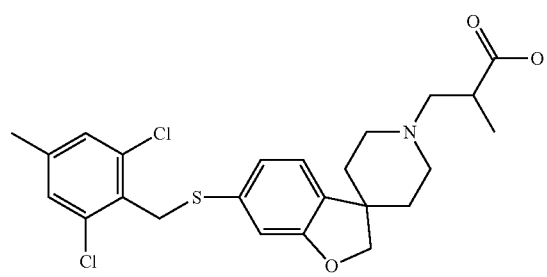 [SMILES: Cc1cc(Cl)c(CSc2ccc3c(c2)OCC32CCN(CC(C)C(=O)O)CC2)c(Cl)c1]
151
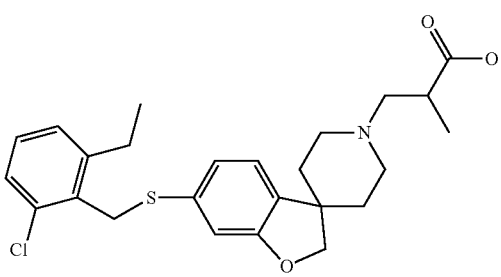 [SMILES: CCc1cccc(Cl)c1CSc1ccc2c(c1)OCC21CCN(CC(C)C(=O)O)CC1]
152
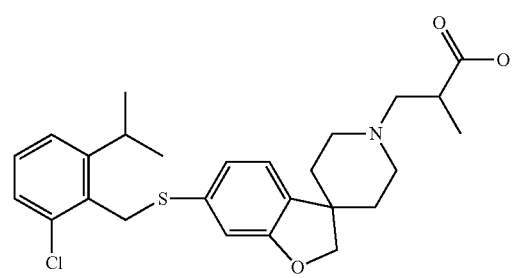 [SMILES: CC(CN1CCC2(CC1)COc1cc(SCc3c(Cl)cccc3C(C)C)ccc12)C(=O)O]

153 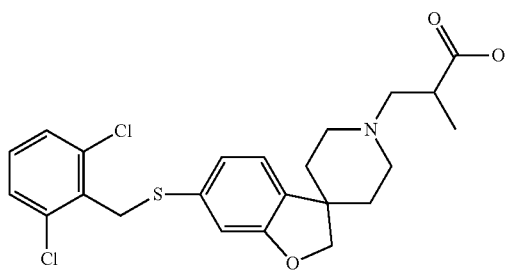 [SMILES: CC(CN1CCC2(CC1)COc1cc(SCc3c(Cl)cccc3Cl)ccc12)C(=O)O]
154 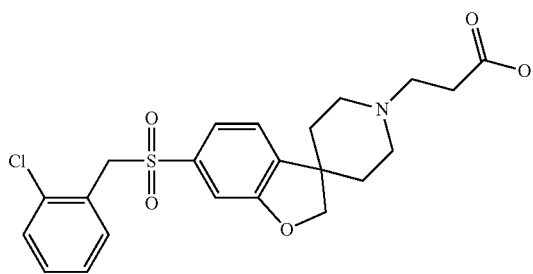 [SMILES: O=C(O)CCN1CCC2(CC1)COc1cc(S(=O)(=O)Cc3ccccc3Cl)ccc12]
155 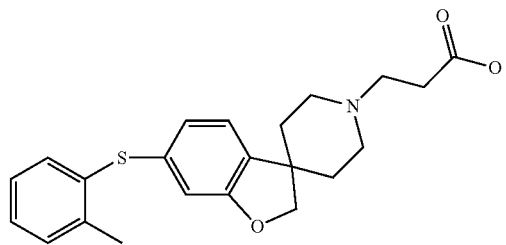 [SMILES: Cc1ccccc1Sc1ccc2c(c1)OCC21CCN(CCC(=O)O)CC1]
156 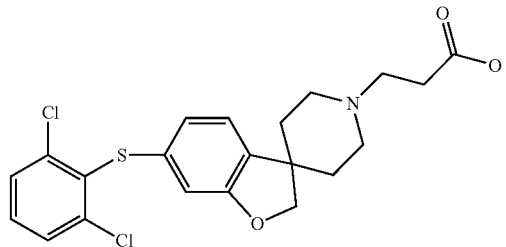 [SMILES: O=C(O)CCN1CCC2(CC1)COc1cc(Sc3c(Cl)cccc3Cl)ccc12]
157 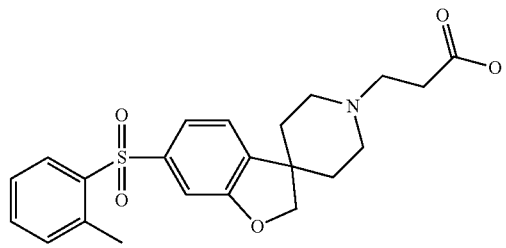 [SMILES: Cc1ccccc1S(=O)(=O)c1ccc2c(c1)OCC21CCN(CCC(=O)O)CC1]
158 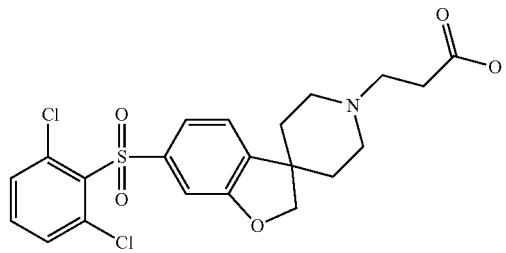 [SMILES: O=C(O)CCN1CCC2(CC1)COc1cc(S(=O)(=O)c3c(Cl)cccc3Cl)ccc12]

-continued
159
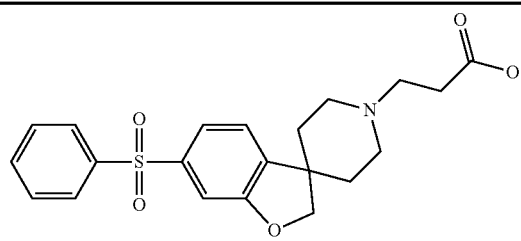
160
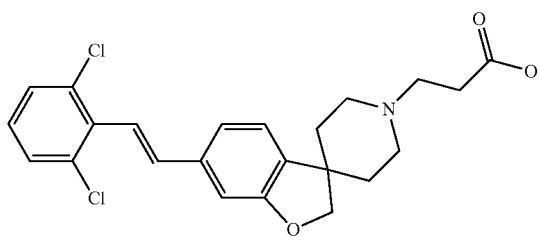 [SMILES: O=C(O)CCN1CCC2(CC1)COc1cc(/C=C/c3c(Cl)cccc3Cl)ccc12]
161
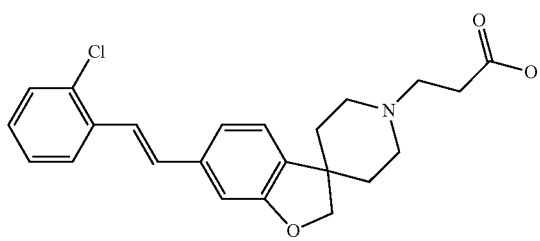 [SMILES: O=C(O)CCN1CCC2(CC1)COc1cc(/C=C/c3ccccc3Cl)ccc12]
162
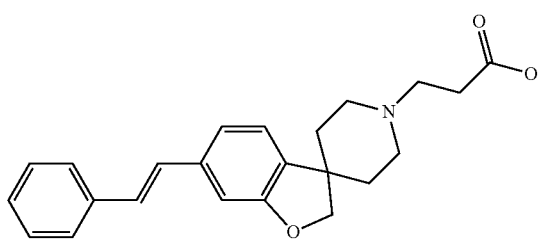 [SMILES: O=C(O)CCN1CCC2(CC1)COc1cc(/C=C/c3ccccc3)ccc12]
163
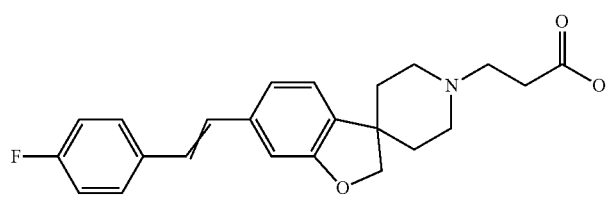 [SMILES: O=C(O)CCN1CCC2(CC1)COc1cc(C=Cc3ccc(F)cc3)ccc12]
164
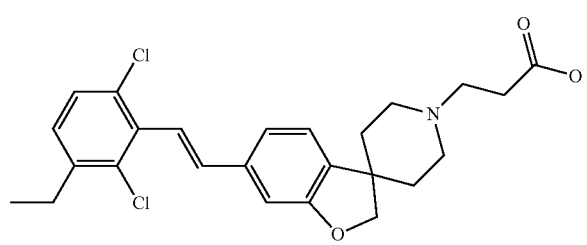 [SMILES: CCc1ccc(Cl)c(/C=C/c2ccc3c(c2)OCC32CCN(CCC(=O)O)CC2)c1Cl]
165
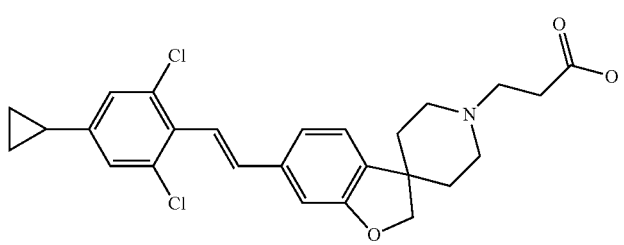 [SMILES: O=C(O)CCN1CCC2(CC1)COc1cc(/C=C/c3c(Cl)cc(C4CC4)cc3Cl)ccc12]

166
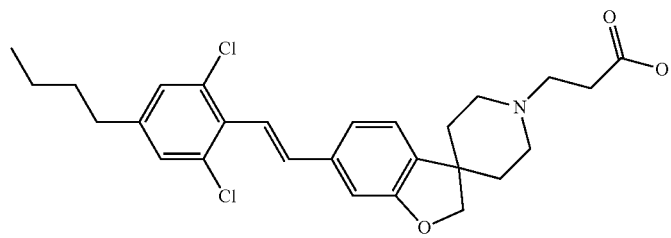 [SMILES: CCCCc1cc(Cl)c(/C=C/c2ccc3c(c2)OCC32CCN(CCC(=O)O)CC2)c(Cl)c1]
167
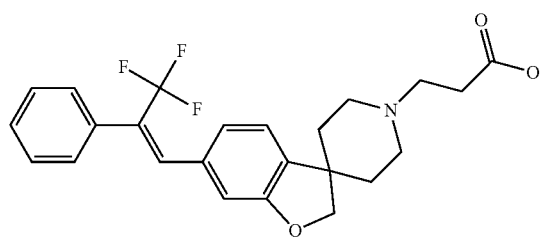 [SMILES: O=C(O)CCN1CCC2(CC1)COc1cc(/C=C(/c3ccccc3)C(F)(F)F)ccc12]
168
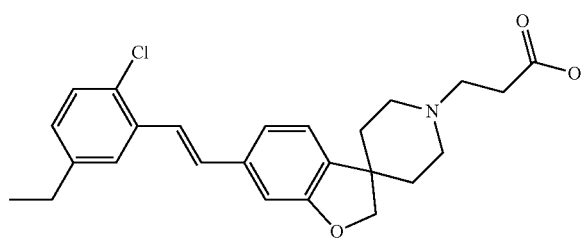 [SMILES: CCc1ccc(Cl)c(/C=C/c2ccc3c(c2)OCC32CCN(CCC(=O)O)CC2)c1]
169
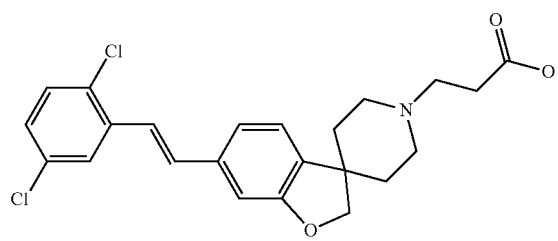 [SMILES: O=C(O)CCN1CCC2(CC1)COc1cc(/C=C/c3cc(Cl)ccc3Cl)ccc12]
170
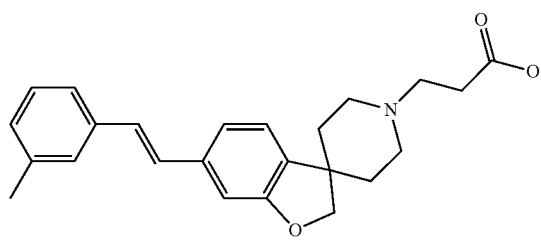 [SMILES: Cc1cccc(/C=C/c2ccc3c(c2)OCC32CCN(CCC(=O)O)CC2)c1]
171
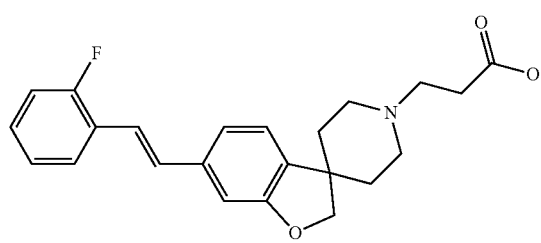

-continued
| | |
|---|---|
| 172 | 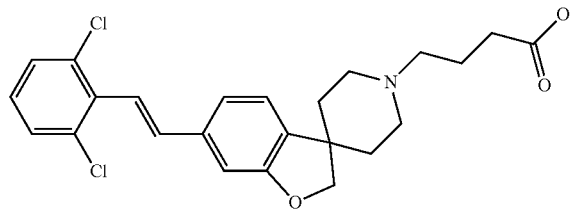 [SMILES: O=C(O)CCCN1CCC2(CC1)COc1cc(/C=C/c3c(Cl)cccc3Cl)ccc12] |
| 173 | 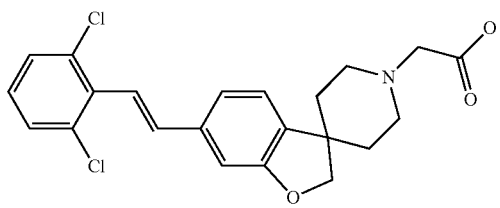 [SMILES: O=C(O)CN1CCC2(CC1)COc1cc(/C=C/c3c(Cl)cccc3Cl)ccc12] |
| 174 | 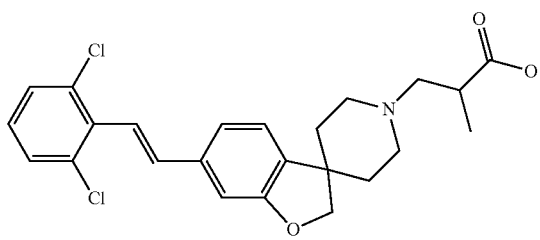 [SMILES: CC(CN1CCC2(CC1)COc1cc(/C=C/c3c(Cl)cccc3Cl)ccc12)C(=O)O] |
| 175 | 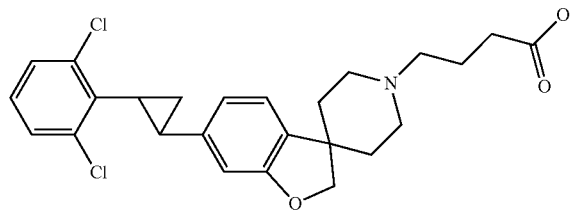 [SMILES: O=C(O)CCCN1CCC2(CC1)COc1cc(C3CC3c3c(Cl)cccc3Cl)ccc12] |
| 176 | 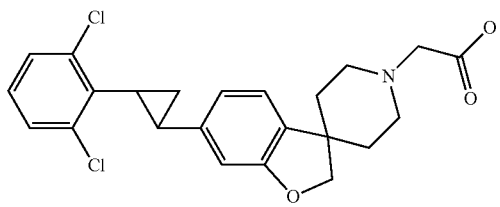 [SMILES: O=C(O)CN1CCC2(CC1)COc1cc(C3CC3c3c(Cl)cccc3Cl)ccc12] |
| 177 | 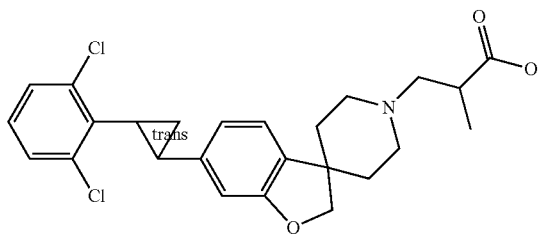 [SMILES: CC(CN1CCC2(CC1)COc1cc(C3CC3c3c(Cl)cccc3Cl)ccc12)C(=O)O] |
| 178 | 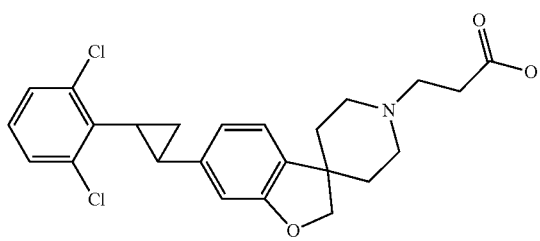 [SMILES: O=C(O)CCN1CCC2(CC1)COc1cc(C3CC3c3c(Cl)cccc3Cl)ccc12] |

| | |
|---|---|
| 179 | 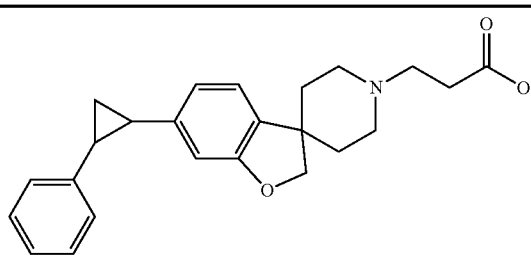 |
| 180 | 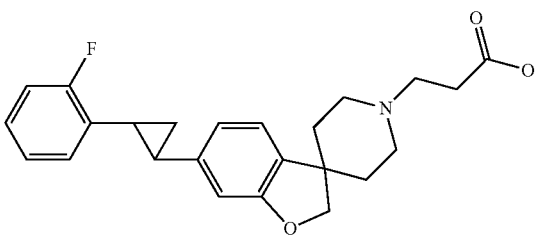 [SMILES: O=C(O)CCN1CCC2(CC1)COc1cc(C3CC3c3ccccc3F)ccc12] |
| 181 | 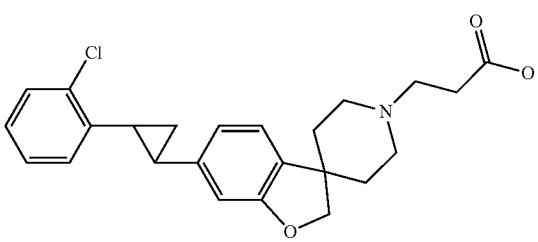 [SMILES: O=C(O)CCN1CCC2(CC1)COc1cc(C3CC3c3ccccc3Cl)ccc12] |
| 182 | 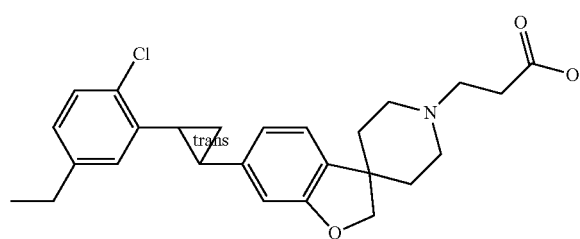 [SMILES: CCc1ccc(Cl)c(C2CC2c2ccc3c(c2)OCC32CCN(CCC(=O)O)CC2)c1] |
| 183 | 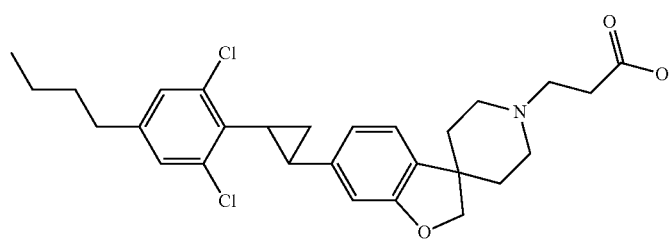 [SMILES: CCCCc1cc(Cl)c(C2CC2c2ccc3c(c2)OCC32CCN(CCC(=O)O)CC2)c(Cl)c1] |
| 184 | 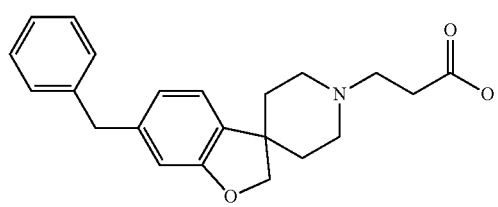 [SMILES: O=C(O)CCN1CCC2(CC1)COc1cc(Cc3ccccc3)ccc12] |
| 185 | 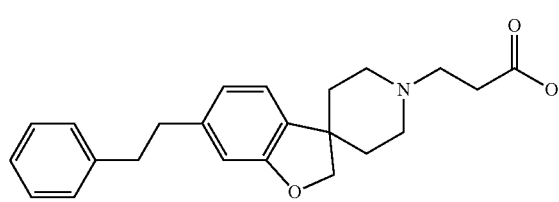 [SMILES: O=C(O)CCN1CCC2(CC1)COc1cc(CCc3ccccc3)ccc12] |

US 10,179,791 B2
235                                                                    236
-continued
186
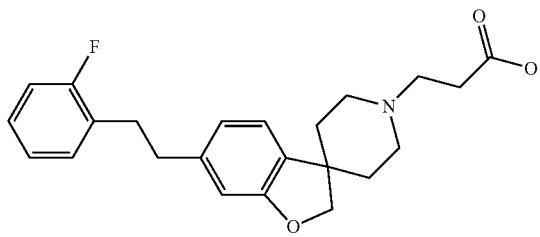 [SMILES: O=C(O)CCN1CCC2(CC1)COc1cc(CCc3ccccc3F)ccc12]
187
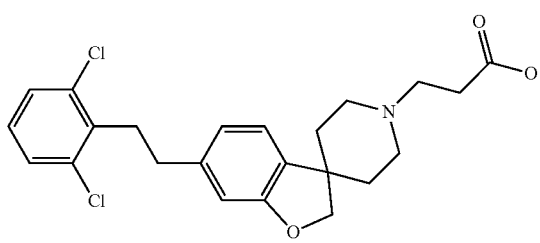 [SMILES: O=C(O)CCN1CCC2(CC1)COc1cc(CCc3c(Cl)cccc3Cl)ccc12]
188
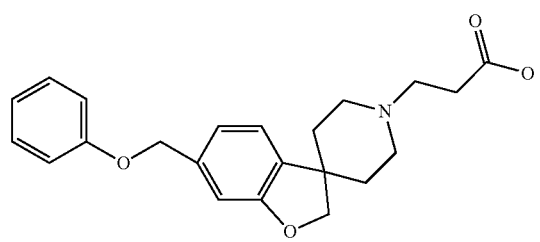 [SMILES: O=C(O)CCN1CCC2(CC1)COc1cc(COc3ccccc3)ccc12]
189
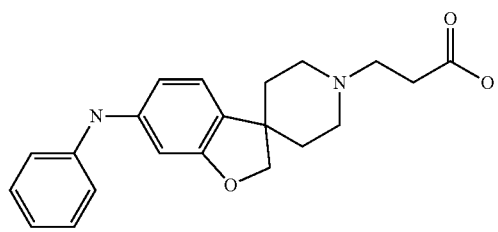 [SMILES: O=C(O)CCN1CCC2(CC1)COc1cc(Nc3ccccc3)ccc12]
190
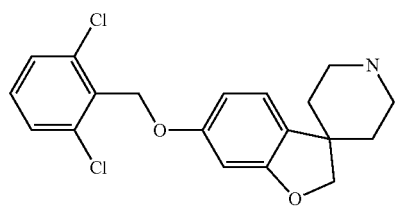 [SMILES: Clc1cccc(Cl)c1COc1ccc2c(c1)OCC21CCNCC1]
191
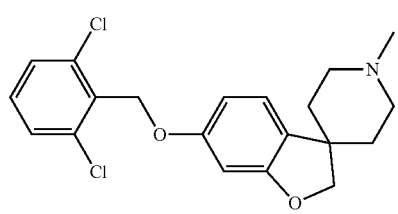 [SMILES: CN1CCC2(CC1)COc1cc(OCc3c(Cl)cccc3Cl)ccc12]

-continued
| | |
|---|---|
| 192 | 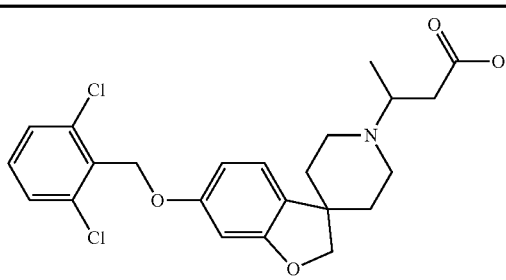 |
| 193 | 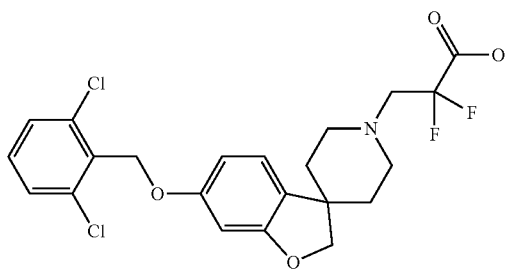 [SMILES: O=C(O)C(F)(F)CN1CCC2(CC1)COc1cc(OCc3c(Cl)cccc3Cl)ccc12] |
| 194 | 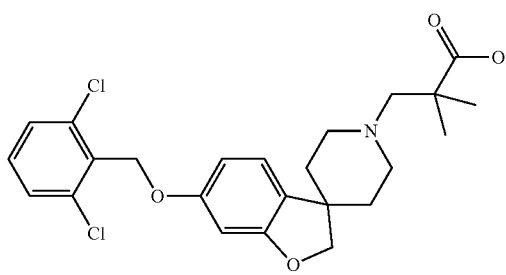 [SMILES: CC(C)(CN1CCC2(CC1)COc1cc(OCc3c(Cl)cccc3Cl)ccc12)C(=O)O] |
| 195 | 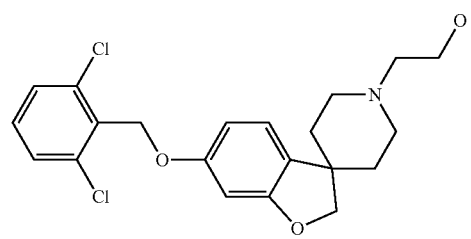 [SMILES: OCCN1CCC2(CC1)COc1cc(OCc3c(Cl)cccc3Cl)ccc12] |
| 196 | 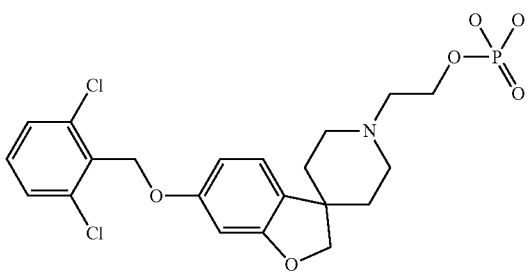 |
| 197 | 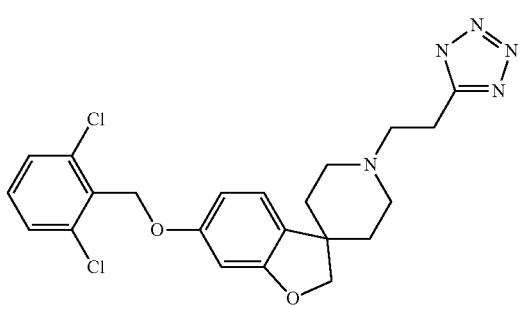 [SMILES: Clc1cccc(Cl)c1COc1ccc2c(c1)OCC21CCN(CCc2nnn[nH]2)CC1] |

198
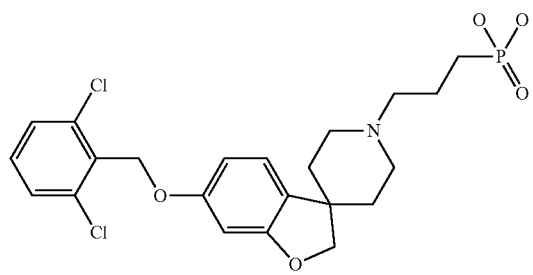 [SMILES: O=P(O)(O)CCCN1CCC2(CC1)COc1cc(OCc3c(Cl)cccc3Cl)ccc12]
199
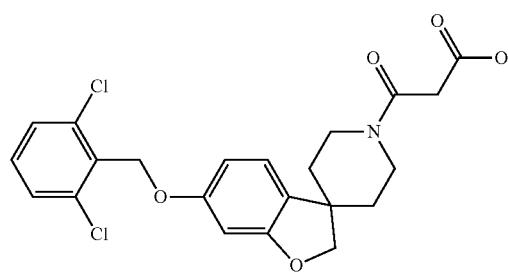 [SMILES: O=C(O)CC(=O)N1CCC2(CC1)COc1cc(OCc3c(Cl)cccc3Cl)ccc12]
200
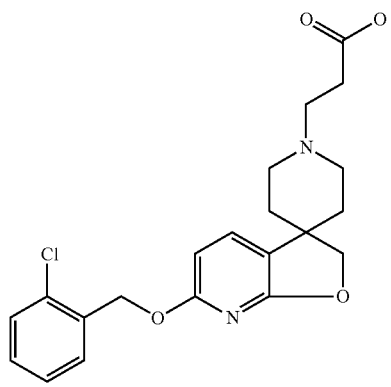 [SMILES: O=C(O)CCN1CCC2(CC1)COc1nc(OCc3ccccc3Cl)ccc12]
201
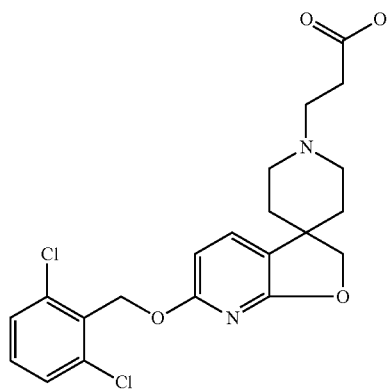 [SMILES: O=C(O)CCN1CCC2(CC1)COc1nc(OCc3c(Cl)cccc3Cl)ccc12]

-continued
202
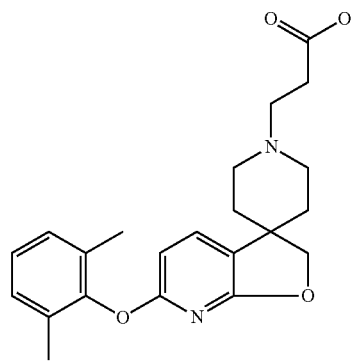 [SMILES: Cc1cccc(C)c1Oc1ccc2c(n1)OCC21CCN(CCC(=O)O)CC1]
203
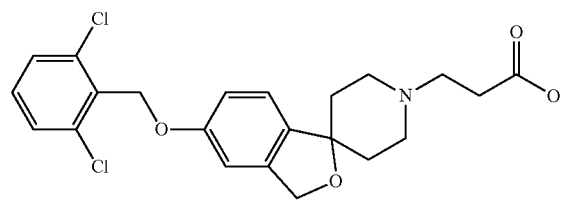 [SMILES: O=C(O)CCN1CCC2(CC1)OCc1cc(OCc3c(Cl)cccc3Cl)ccc12]
204
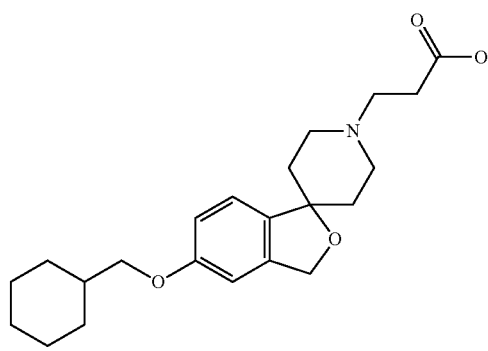 [SMILES: O=C(O)CCN1CCC2(CC1)OCc1cc(OCC3CCCCC3)ccc12]
205
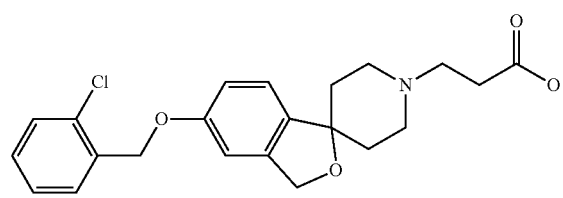 [SMILES: O=C(O)CCN1CCC2(CC1)OCc1cc(OCc3ccccc3Cl)ccc12]
206
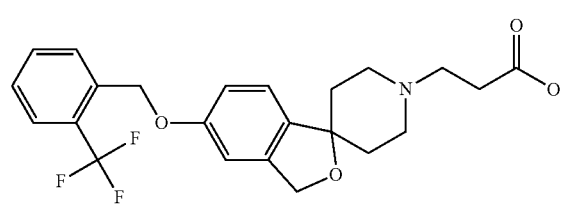 [SMILES: O=C(O)CCN1CCC2(CC1)OCc1cc(OCc3ccccc3C(F)(F)F)ccc12]
207
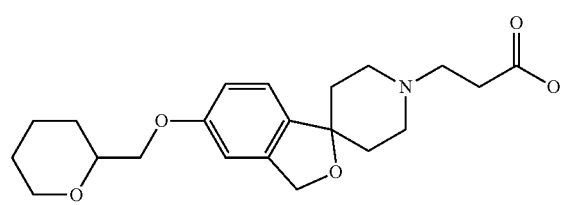 [SMILES: O=C(O)CCN1CCC2(CC1)OCc1cc(OCC3CCCCO3)ccc12]

-continued
208 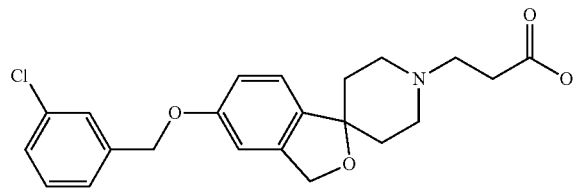 [SMILES: O=C(O)CCN1CCC2(CC1)OCc1cc(OCc3cccc(Cl)c3)ccc12]
209 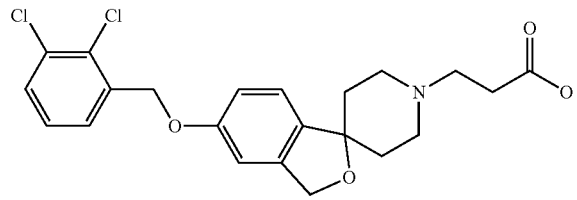 [SMILES: O=C(O)CCN1CCC2(CC1)OCc1cc(OCc3cccc(Cl)c3Cl)ccc12]
210 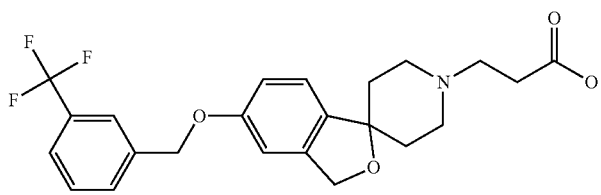 [SMILES: O=C(O)CCN1CCC2(CC1)OCc1cc(OCc3cccc(C(F)(F)F)c3)ccc12]
211 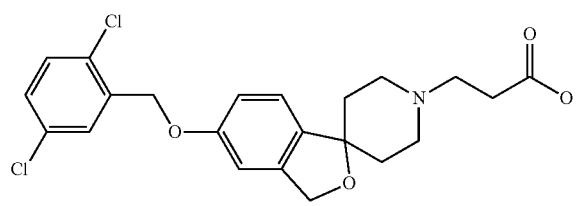 [SMILES: O=C(O)CCN1CCC2(CC1)OCc1cc(OCc3cc(Cl)ccc3Cl)ccc12]
212 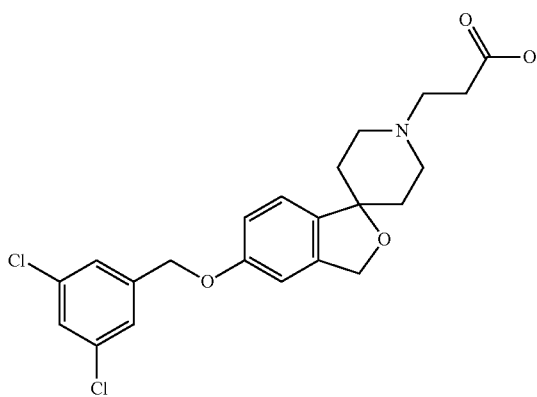 [SMILES: O=C(O)CCN1CCC2(CC1)OCc1cc(OCc3cc(Cl)cc(Cl)c3)ccc12]
213 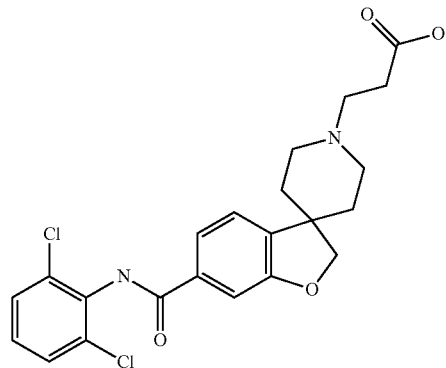 [SMILES: O=C(O)CCN1CCC2(CC1)COc1cc(C(=O)Nc3c(Cl)cccc3Cl)ccc12]

-continued
214
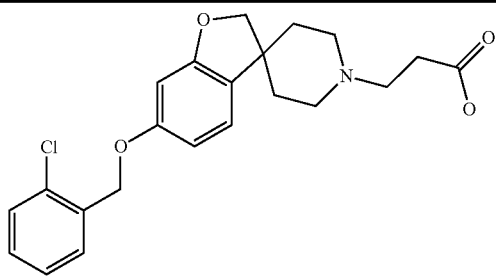
215
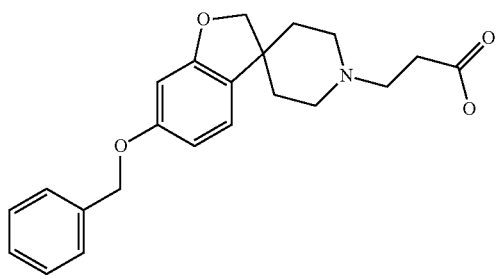 [SMILES: O=C(O)CCN1CCC2(CC1)COc1cc(OCc3ccccc3)ccc12]
216
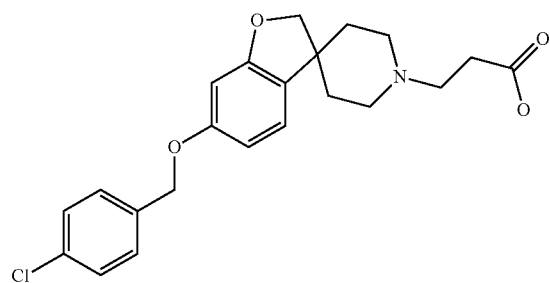 [SMILES: O=C(O)CCN1CCC2(CC1)COc1cc(OCc3ccc(Cl)cc3)ccc12]
217
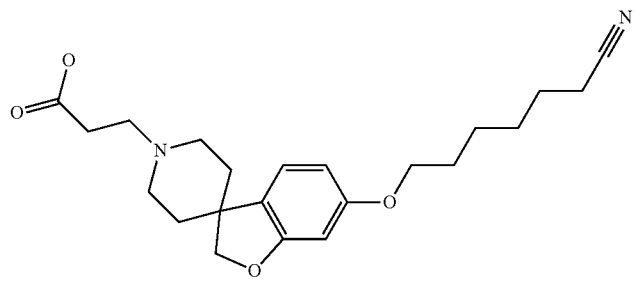 [SMILES: N#CCCCCCCOc1ccc2c(c1)OCC21CCN(CCC(=O)O)CC1]
218
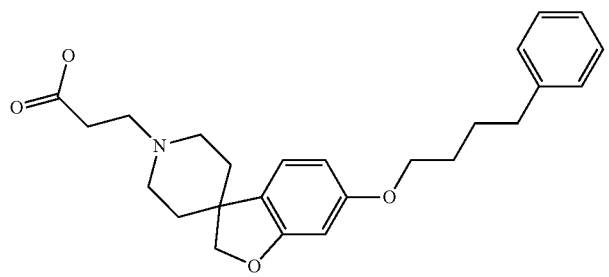 [SMILES: O=C(O)CCN1CCC2(CC1)COc1cc(OCCCCc3ccccc3)ccc12]
219
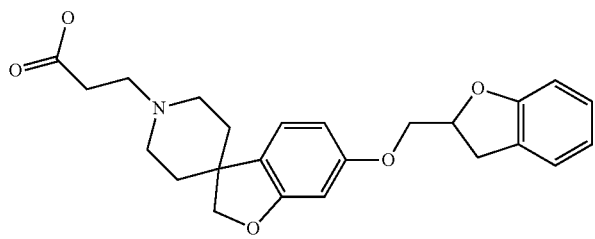 [SMILES: O=C(O)CCN1CCC2(CC1)COc1cc(OCC3Cc4ccccc4O3)ccc12]

-continued
| 220 | 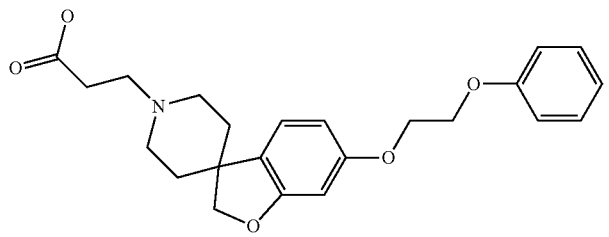 |
| 221 | 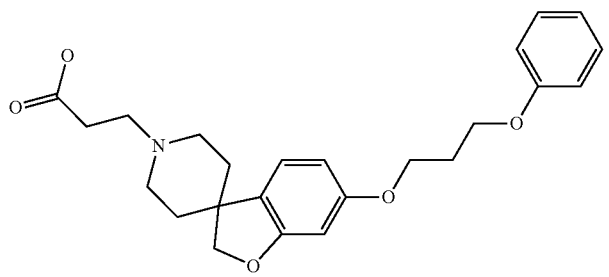 [SMILES: O=C(O)CCN1CCC2(CC1)COc1cc(OCCCOc3ccccc3)ccc12] |
| 222 | 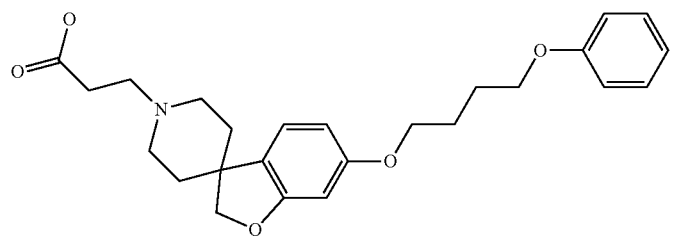 [SMILES: O=C(O)CCN1CCC2(CC1)COc1cc(OCCCCOc3ccccc3)ccc12] |
| 223 | 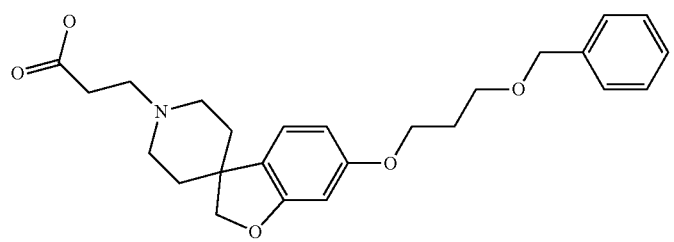 [SMILES: O=C(O)CCN1CCC2(CC1)COc1cc(OCCCOCc3ccccc3)ccc12] |
| 224 | 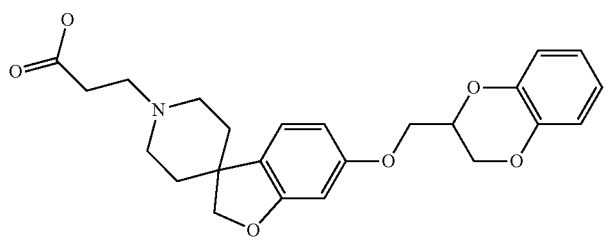 [SMILES: O=C(O)CCN1CCC2(CC1)COc1cc(OCC3COc4ccccc4O3)ccc12] |
| 225 | 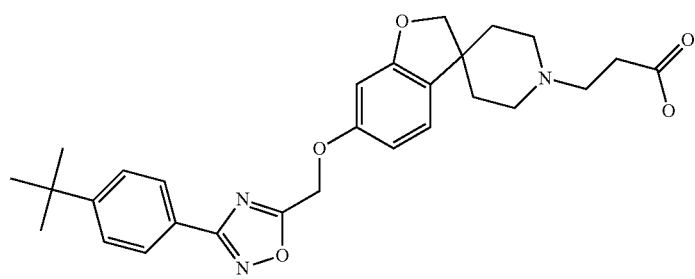 [SMILES: CC(C)(C)c1ccc(-c2noc(COc3ccc4c(c3)OCC43CCN(CCC(=O)O)CC3)n2)cc1] |

-continued
| 226 | 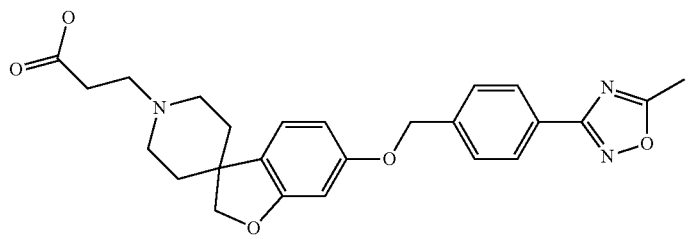 [SMILES: Cc1nc(-c2ccc(COc3ccc4c(c3)OCC43CCN(CCC(=O)O)CC3)cc2)no1] |
| --- | --- |
| 227 | 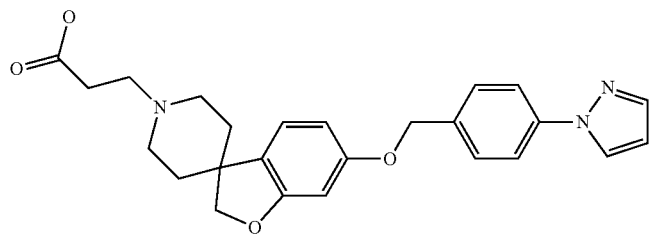 [SMILES: O=C(O)CCN1CCC2(CC1)COc1cc(OCc3ccc(-n4cccn4)cc3)ccc12] |
| 228 | 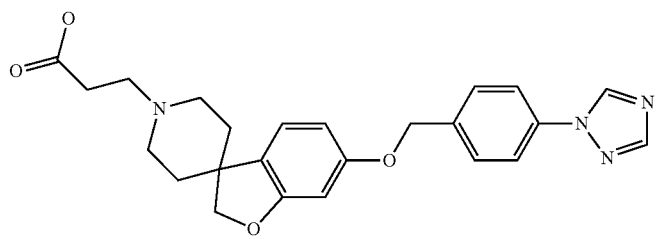 [SMILES: O=C(O)CCN1CCC2(CC1)COc1cc(OCc3ccc(-n4cncn4)cc3)ccc12] |
| 229 | 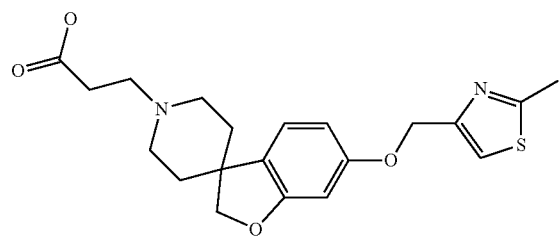 [SMILES: Cc1nc(COc2ccc3c(c2)OCC32CCN(CCC(=O)O)CC2)cs1] |
| 230 | 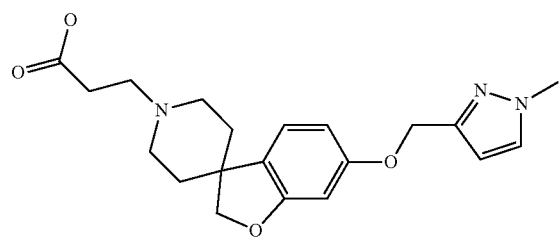 [SMILES: Cn1ccc(COc2ccc3c(c2)OCC32CCN(CCC(=O)O)CC2)n1] |
| 231 | 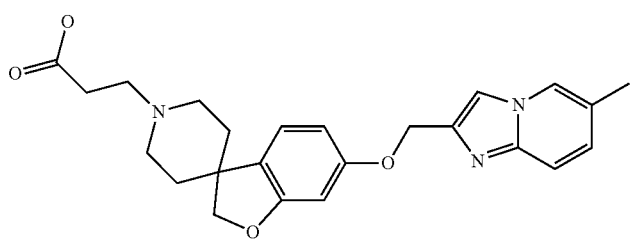 [SMILES: Cc1ccc2nc(COc3ccc4c(c3)OCC43CCN(CCC(=O)O)CC3)cn2c1] |

-continued
| | |
|---|---|
| 232 | 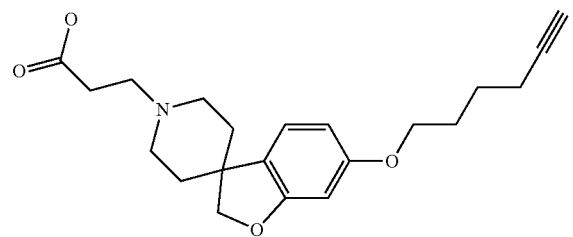 [SMILES: C#CCCCCOc1ccc2c(c1)OCC21CCN(CCC(=O)O)CC1] |
| 233 | 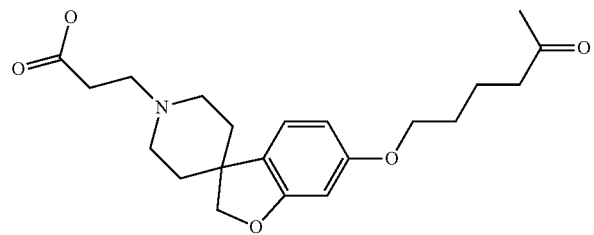 [SMILES: CC(=O)CCCCOc1ccc2c(c1)OCC21CCN(CCC(=O)O)CC1] |
| 234 | 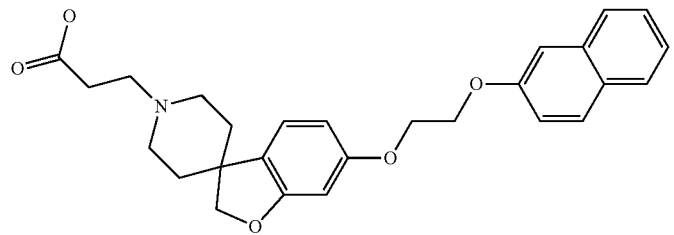 [SMILES: O=C(O)CCN1CCC2(CC1)COc1cc(OCCOc3ccc4ccccc4c3)ccc12] |
| 235 | 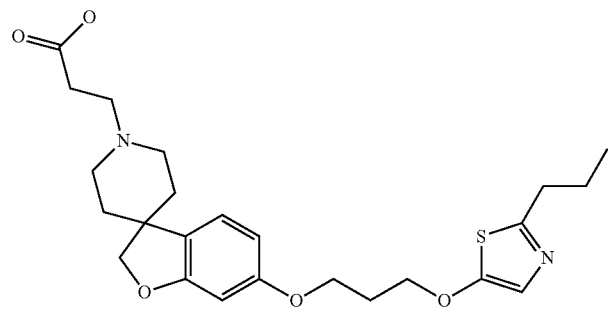 [SMILES: CCCc1ncc(OCCCOc2ccc3c(c2)OCC32CCN(CCC(=O)O)CC2)s1] |
| 236 | 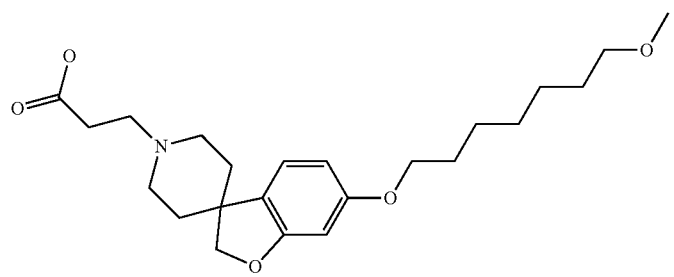 [SMILES: COCCCCCCCOc1ccc2c(c1)OCC21CCN(CCC(=O)O)CC1] |
| 237 | 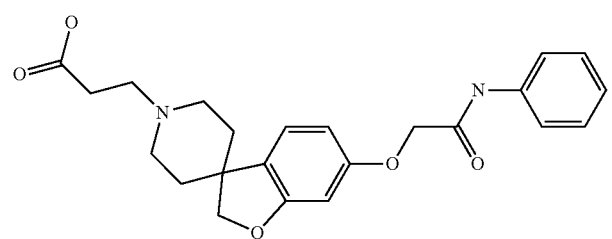 [SMILES: O=C(O)CCN1CCC2(CC1)COc1cc(OCC(=O)Nc3ccccc3)ccc12] |

-continued
238
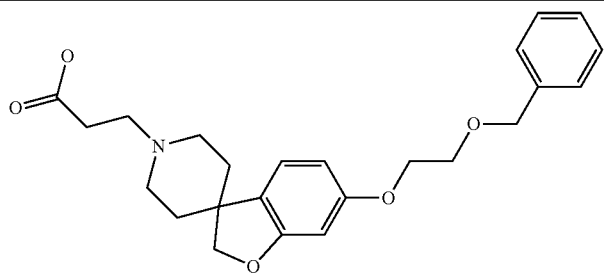
239
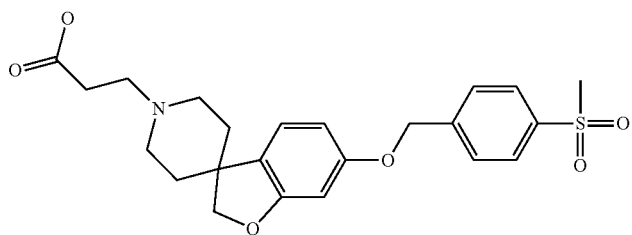 [SMILES: CS(=O)(=O)c1ccc(COc2ccc3c(c2)OCC32CCN(CCC(=O)O)CC2)cc1]
240
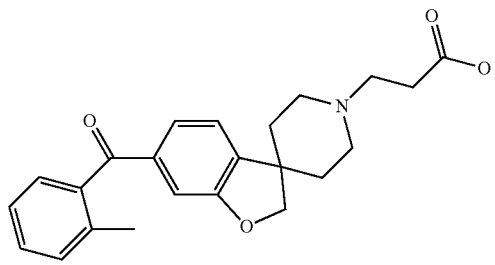 [SMILES: Cc1ccccc1C(=O)c1ccc2c(c1)OCC21CCN(CCC(=O)O)CC1]
241
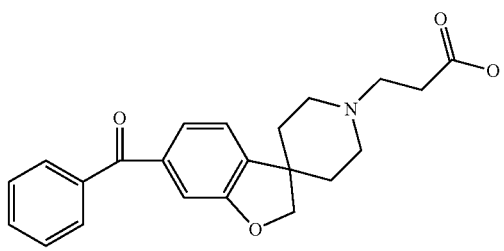 [SMILES: O=C(O)CCN1CCC2(CC1)COc1cc(C(=O)c3ccccc3)ccc12]
242
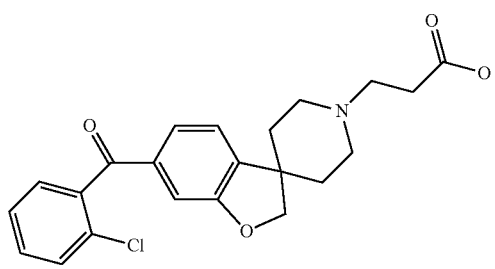 [SMILES: O=C(O)CCN1CCC2(CC1)COc1cc(C(=O)c3ccccc3Cl)ccc12]
243
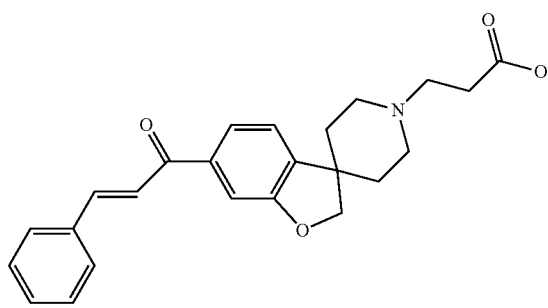 [SMILES: O=C(O)CCN1CCC2(CC1)COc1cc(C(=O)/C=C/c3ccccc3)ccc12]

-continued
244
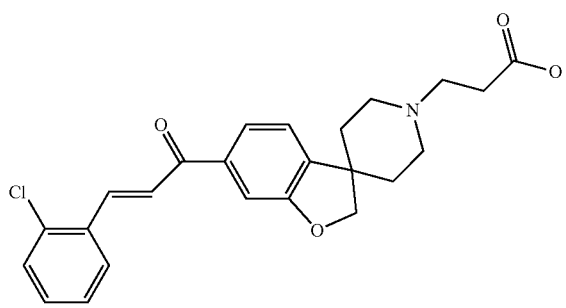 [SMILES: O=C(O)CCN1CCC2(CC1)COc1cc(C(=O)/C=C/c3ccccc3Cl)ccc12]
245
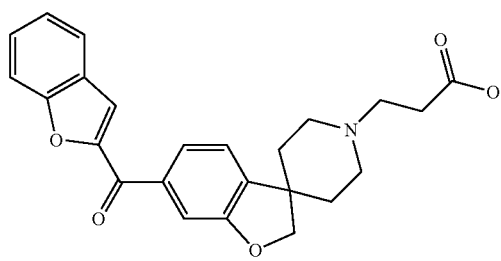 [SMILES: O=C(O)CCN1CCC2(CC1)COc1cc(C(=O)c3cc4ccccc4o3)ccc12]
246
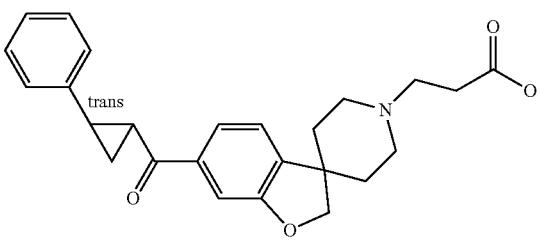 [SMILES: O=C(O)CCN1CCC2(CC1)COc1cc(C(=O)C3CC3c3ccccc3)ccc12]
247
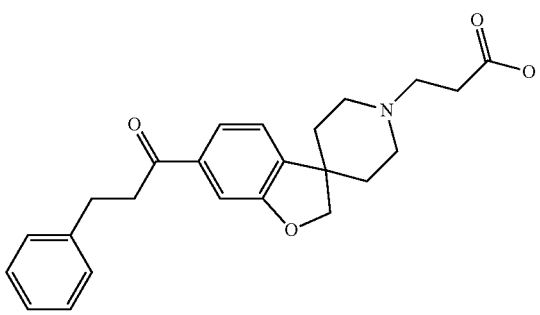 [SMILES: O=C(O)CCN1CCC2(CC1)COc1cc(C(=O)CCc3ccccc3)ccc12]
248
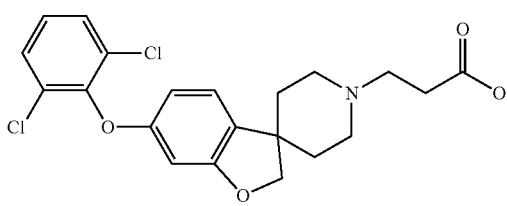 [SMILES: O=C(O)CCN1CCC2(CC1)COc1cc(Oc3c(Cl)cccc3Cl)ccc12]
249
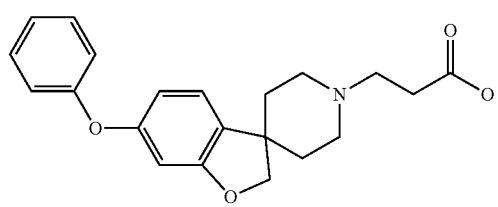

-continued
| 250 | 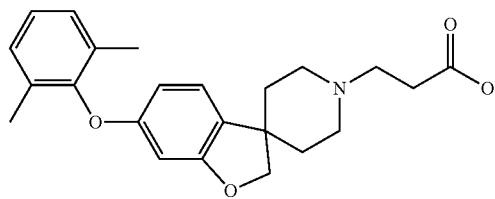 [SMILES: Cc1cccc(C)c1Oc1ccc2c(c1)OCC21CCN(CCC(=O)O)CC1] |
| 251 | 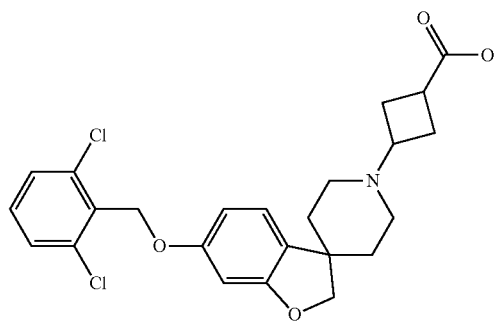 [SMILES: O=C(O)C1CC(N2CCC3(CC2)COc2cc(OCc4c(Cl)cccc4Cl)ccc23)C1] |
| 252 | 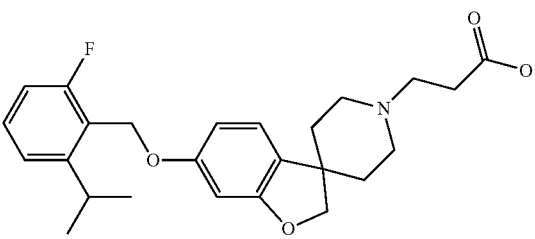 [SMILES: CC(C)c1cccc(F)c1COc1ccc2c(c1)OCC21CCN(CCC(=O)O)CC1] |
| 253 | 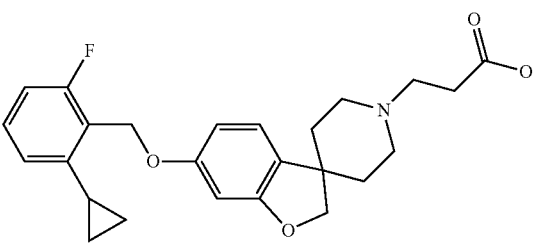 |
| 254 | 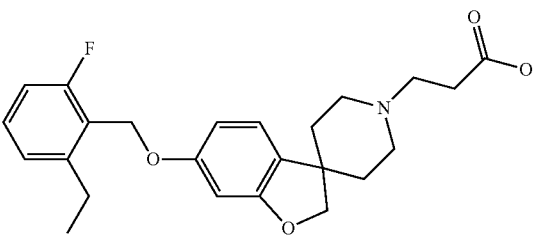 [SMILES: CCc1cccc(F)c1COc1ccc2c(c1)OCC21CCN(CCC(=O)O)CC1] |
| 255 | 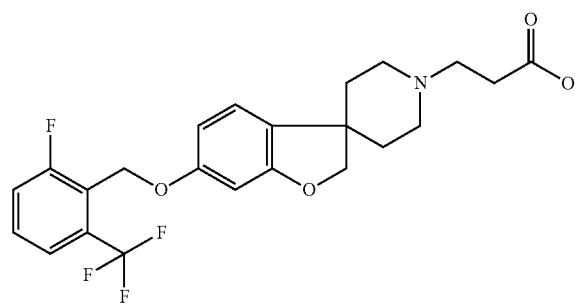 [SMILES: O=C(O)CCN1CCC2(CC1)COc1cc(OCc3c(F)cccc3C(F)(F)F)ccc12] |

256
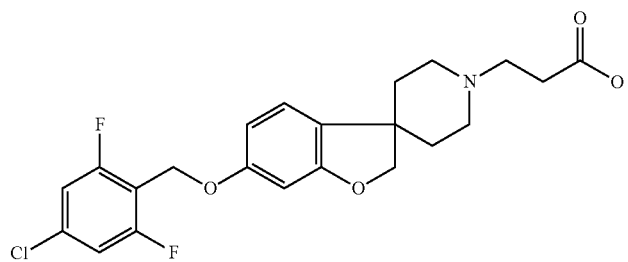 [SMILES: O=C(O)CCN1CCC2(CC1)COc1cc(OCc3c(F)cc(Cl)cc3F)ccc12]
257
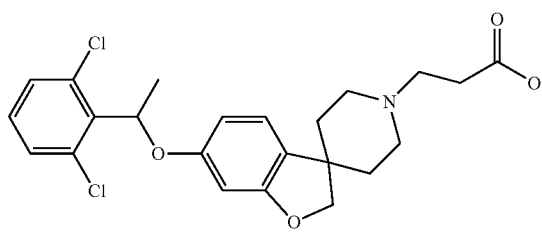 [SMILES: CC(Oc1ccc2c(c1)OCC21CCN(CCC(=O)O)CC1)c1c(Cl)cccc1Cl]
258
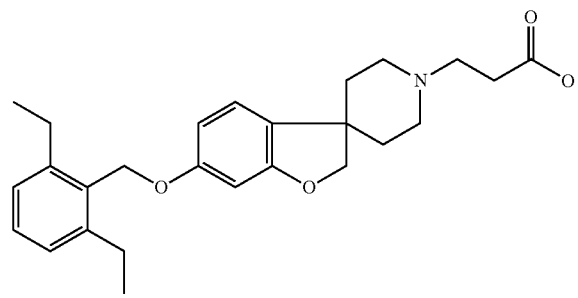 [SMILES: CCc1cccc(CC)c1COc1ccc2c(c1)OCC21CCN(CCC(=O)O)CC1]
259
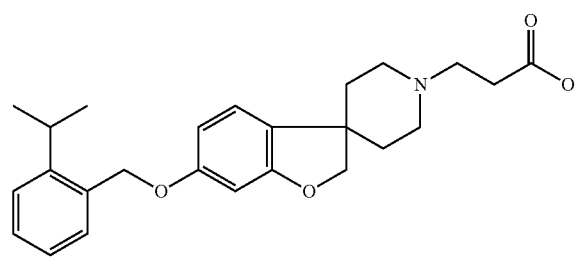 [SMILES: CC(C)c1ccccc1COc1ccc2c(c1)OCC21CCN(CCC(=O)O)CC1]
260
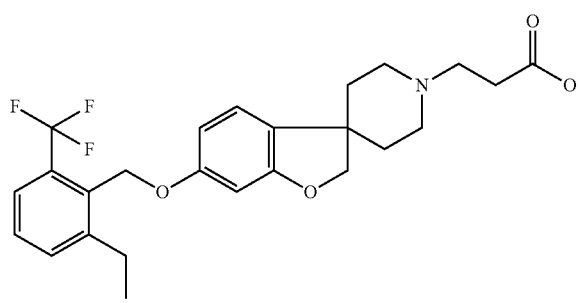 [SMILES: CCc1cccc(C(F)(F)F)c1COc1ccc2c(c1)OCC21CCN(CCC(=O)O)CC1]

261 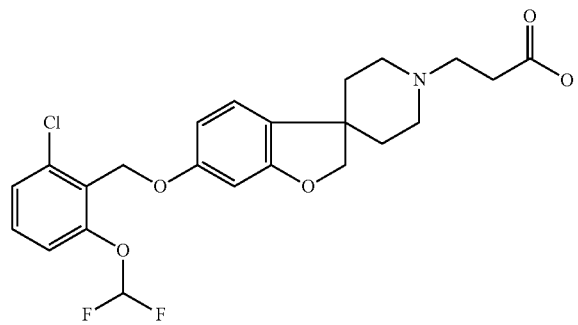 [SMILES: O=C(O)CCN1CCC2(CC1)COc1cc(OCc3c(Cl)cccc3OC(F)F)ccc12]
262 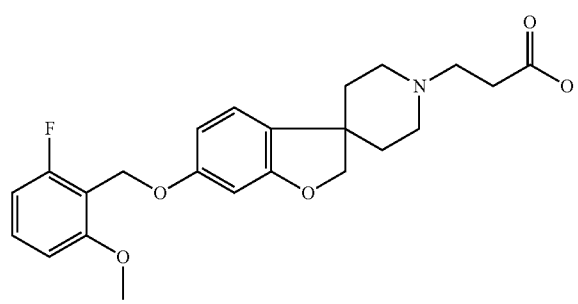 [SMILES: COc1cccc(F)c1COc1ccc2c(c1)OCC21CCN(CCC(=O)O)CC1]
263 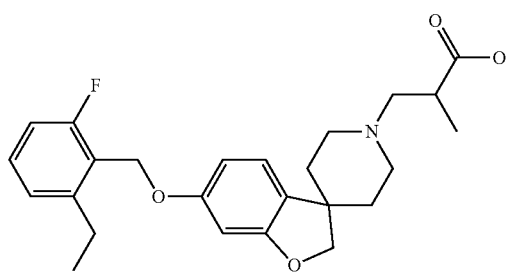 [SMILES: CCc1cccc(F)c1COc1ccc2c(c1)OCC21CCN(CC(C)C(=O)O)CC1]
264 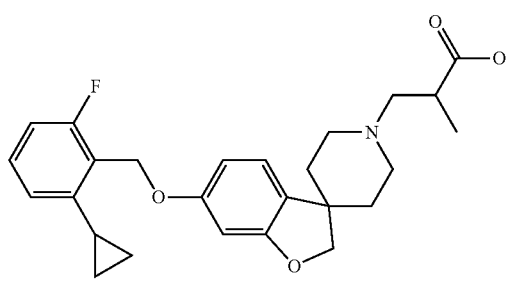 [SMILES: CC(CN1CCC2(CC1)COc1cc(OCc3c(F)cccc3C3CC3)ccc12)C(=O)O]
265 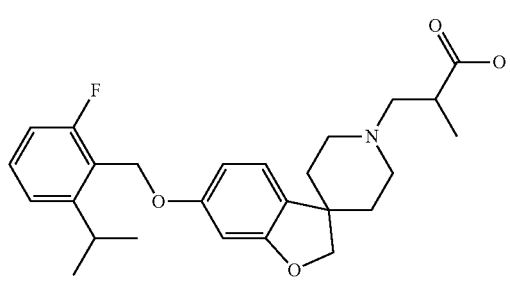 [SMILES: CC(CN1CCC2(CC1)COc1cc(OCc3c(F)cccc3C(C)C)ccc12)C(=O)O]

-continued
| 266 | 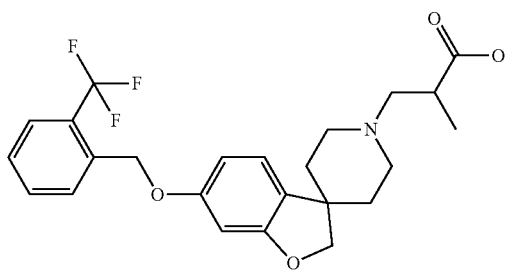 [SMILES: CC(CN1CCC2(CC1)COc1cc(OCc3ccccc3C(F)(F)F)ccc12)C(=O)O] |
| 267 | 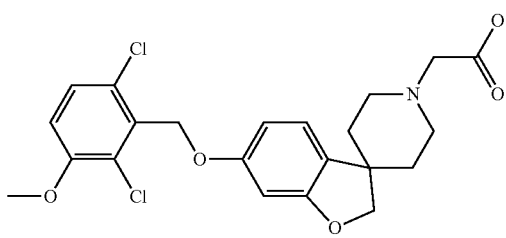 [SMILES: COc1ccc(Cl)c(COc2ccc3c(c2)OCC32CCN(CC(=O)O)CC2)c1Cl] |
| 268 | 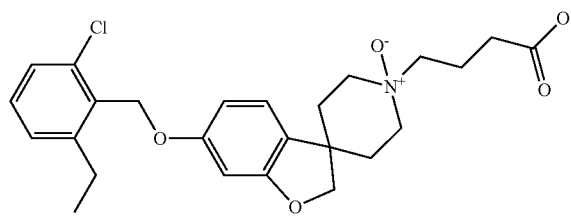 [SMILES: CCc1cccc(Cl)c1COc1ccc2c(c1)OCC21CC[N+]([O-])(CCCC(=O)O)CC1] |
| 269 | 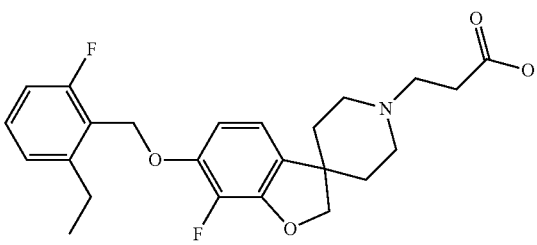 |
| 270 | 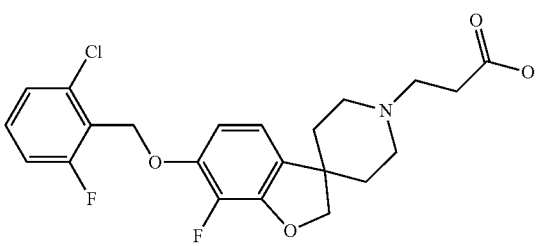 |
| 271 | 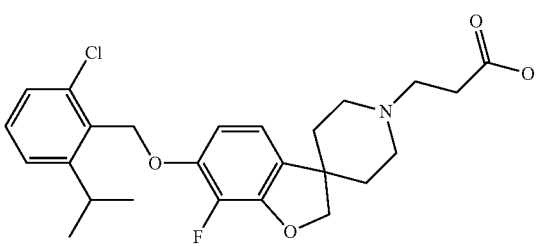 [SMILES: CC(C)c1cccc(Cl)c1COc1ccc2c(c1F)OCC21CCN(CCC(=O)O)CC1] |

-continued
| | |
|---|---|
| 272 | 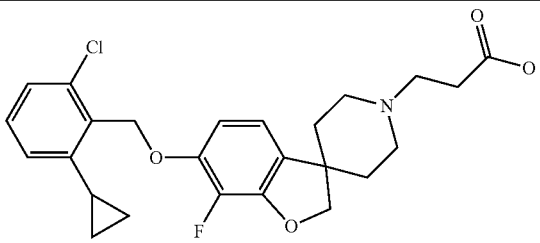 |
| 273 | 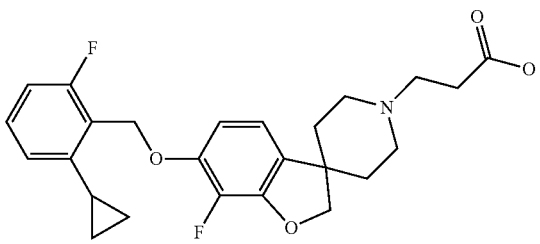 [SMILES: O=C(O)CCN1CCC2(CC1)COc1c2ccc(OCc2c(F)cccc2C2CC2)c1F] |
| 274 | 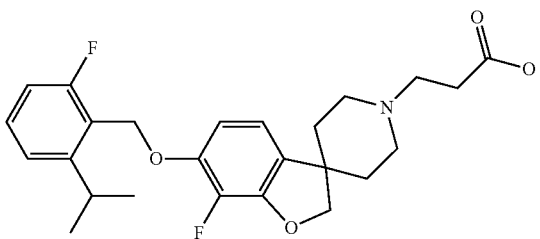 [SMILES: CC(C)c1cccc(F)c1COc1ccc2c(c1F)OCC21CCN(CCC(=O)O)CC1] |
| 275 | 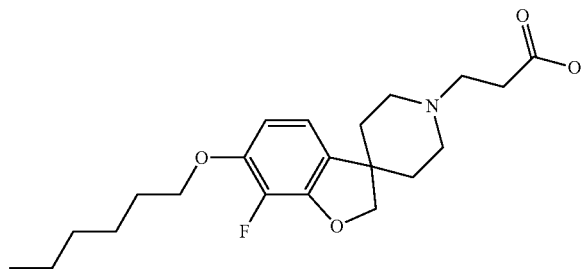 [SMILES: CCCCCCOc1ccc2c(c1F)OCC21CCN(CCC(=O)O)CC1] |
| 276 | 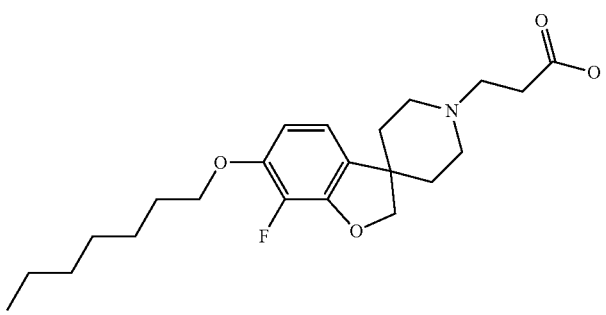 [SMILES: CCCCCCCOc1ccc2c(c1F)OCC21CCN(CCC(=O)O)CC1] |
| 277 | 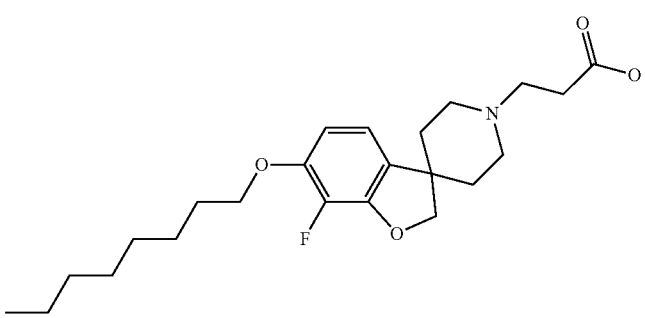 [SMILES: CCCCCCCCOc1ccc2c(c1F)OCC21CCN(CCC(=O)O)CC1] |

278 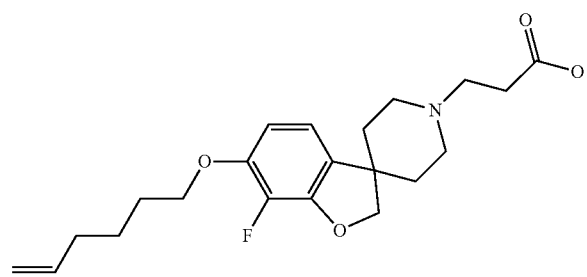 [SMILES: C=CCCCCOc1ccc2c(c1F)OCC21CCN(CCC(=O)O)CC1]
279 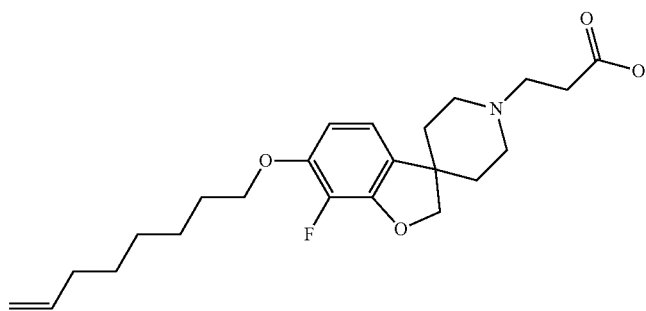
280 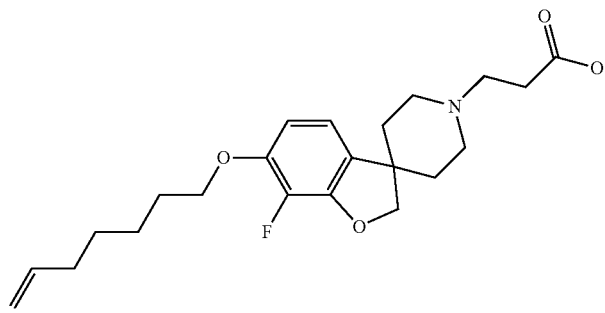 [SMILES: C=CCCCCCOc1ccc2c(c1F)OCC21CCN(CCC(=O)O)CC1]
281 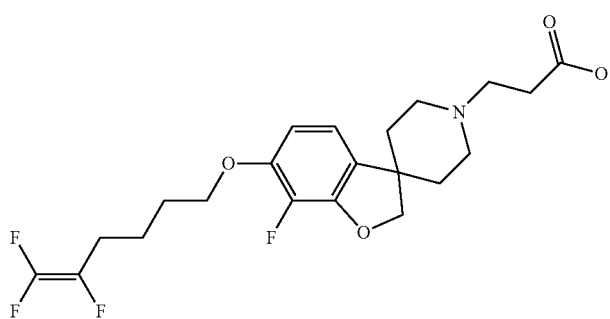 [SMILES: O=C(O)CCN1CCC2(CC1)COc1c2ccc(OCCCCC(F)=C(F)F)c1F]
282 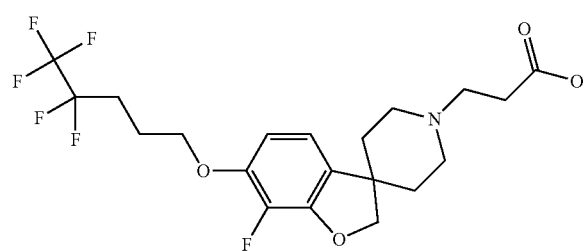 [SMILES: O=C(O)CCN1CCC2(CC1)COc1c2ccc(OCCCC(F)(F)C(F)(F)F)c1F]

283
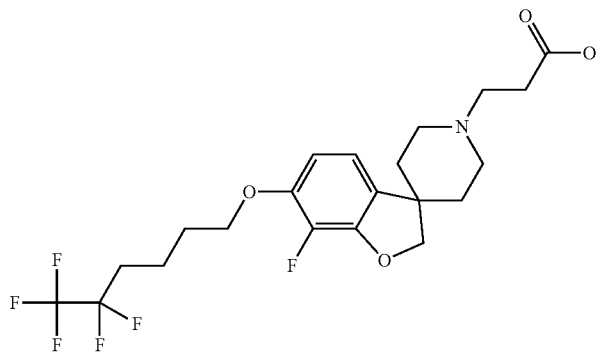 [SMILES: O=C(O)CCN1CCC2(CC1)COc1c2ccc(OCCCCC(F)(F)C(F)(F)F)c1F]
284
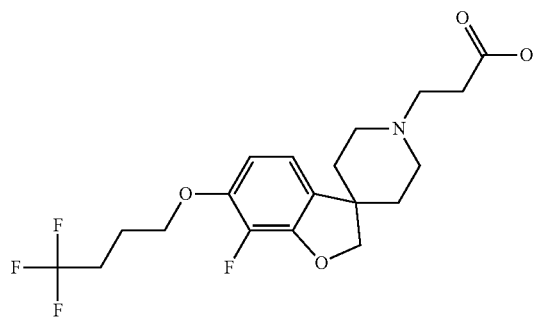 [SMILES: O=C(O)CCN1CCC2(CC1)COc1c2ccc(OCCCC(F)(F)F)c1F]
285
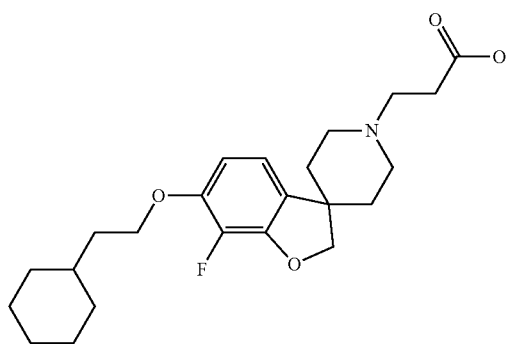 [SMILES: O=C(O)CCN1CCC2(CC1)COc1c2ccc(OCCC2CCCCC2)c1F]
286
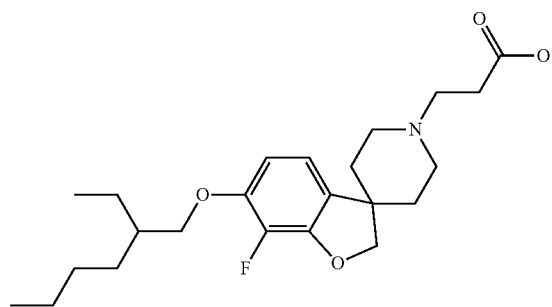 [SMILES: CCCCC(CC)COc1ccc2c(c1F)OCC21CCN(CCC(=O)O)CC1]

287
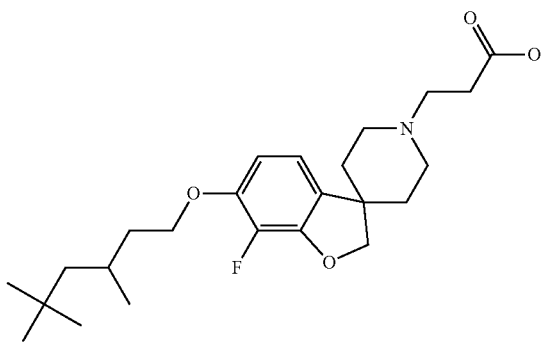 [SMILES: CC(CCOc1ccc2c(c1F)OCC21CCN(CCC(=O)O)CC1)CC(C)(C)C]
288
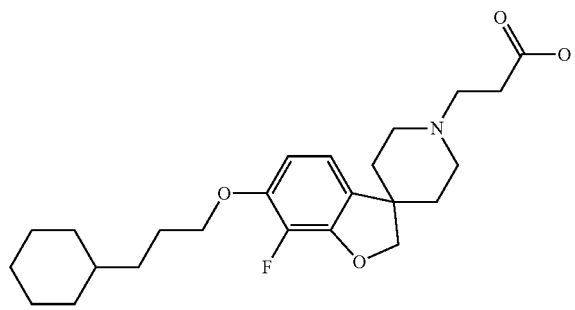 [SMILES: O=C(O)CCN1CCC2(CC1)COc1c2ccc(OCCCC2CCCCC2)c1F]
289
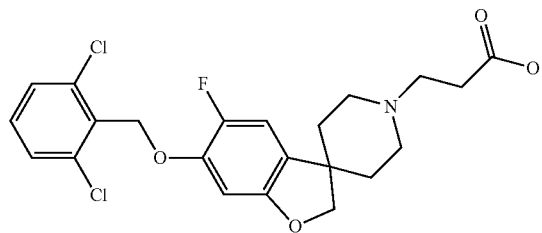 [SMILES: O=C(O)CCN1CCC2(CC1)COc1cc(OCc3c(Cl)cccc3Cl)c(F)cc12]
290
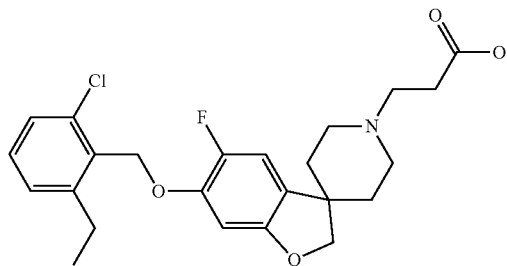 [SMILES: CCc1cccc(Cl)c1COc1cc2c(cc1F)C1(CCN(CCC(=O)O)CC1)CO2]
291
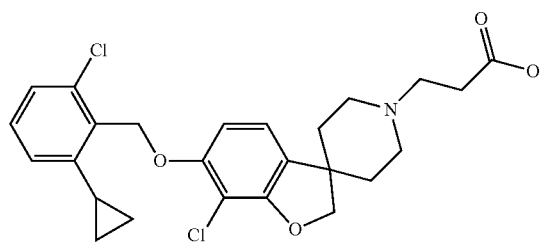 [SMILES: O=C(O)CCN1CCC2(CC1)COc1c2ccc(OCc2c(Cl)cccc2C2CC2)c1Cl]

| | |
|---|---|
| 292 | 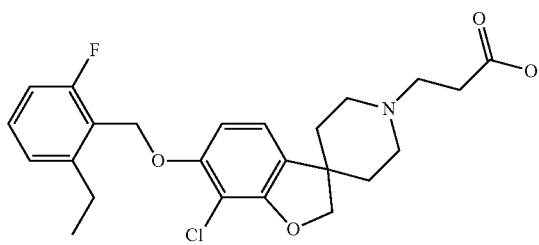 |
| 293 | 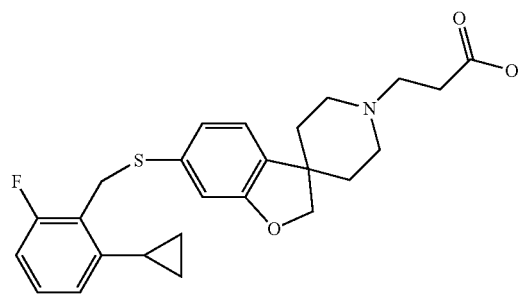 [SMILES: O=C(O)CCN1CCC2(CC1)COc1cc(SCc3c(F)cccc3C3CC3)ccc12] |
| 294 | 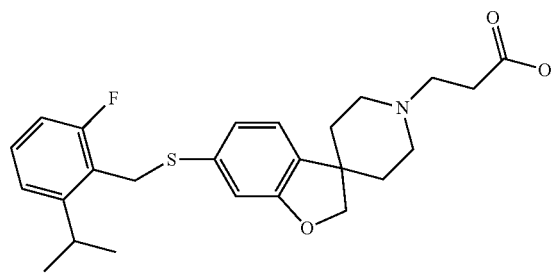 [SMILES: CC(C)c1cccc(F)c1CSc1ccc2c(c1)OCC21CCN(CCC(=O)O)CC1] |
| 295 | 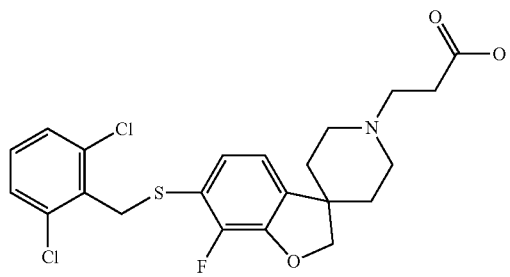 [SMILES: O=C(O)CCN1CCC2(CC1)COc1c2ccc(SCc2c(Cl)cccc2Cl)c1F] |
| 296 | 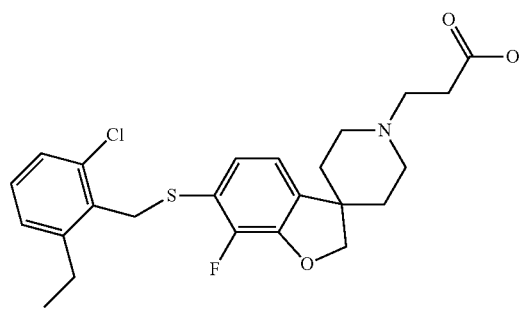 [SMILES: CCc1cccc(Cl)c1CSc1ccc2c(c1F)OCC21CCN(CCC(=O)O)CC1] |

-continued
297
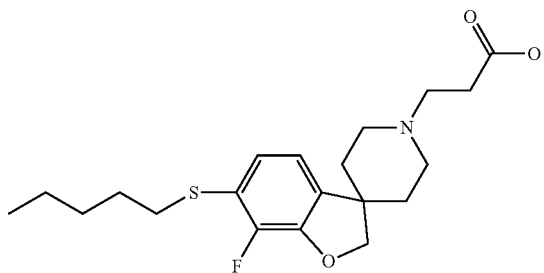 [SMILES: CCCCCSc1ccc2c(c1F)OCC21CCN(CCC(=O)O)CC1]
298
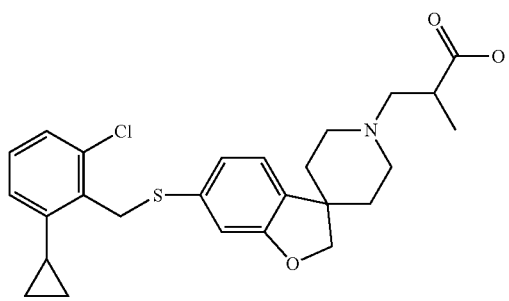 [SMILES: CC(CN1CCC2(CC1)COc1cc(SCc3c(Cl)cccc3C3CC3)ccc12)C(=O)O]
299
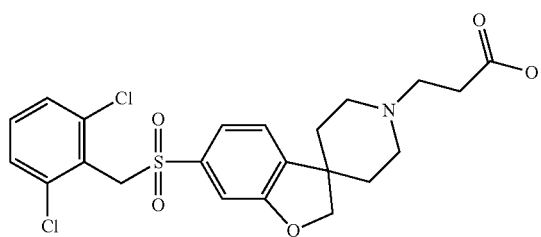 [SMILES: O=C(O)CCN1CCC2(CC1)COc1cc(S(=O)(=O)Cc3c(Cl)cccc3Cl)ccc12]
300
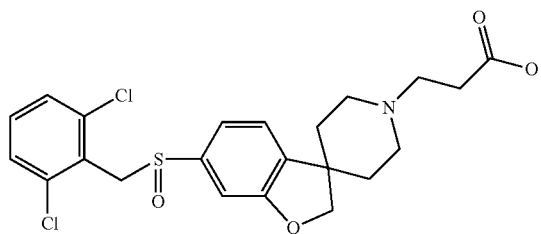 [SMILES: O=C(O)CCN1CCC2(CC1)COc1cc(S(=O)Cc3c(Cl)cccc3Cl)ccc12]
301
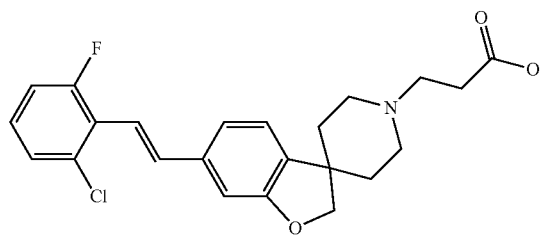 [SMILES: O=C(O)CCN1CCC2(CC1)COc1cc(/C=C/c3c(F)cccc3Cl)ccc12]
302
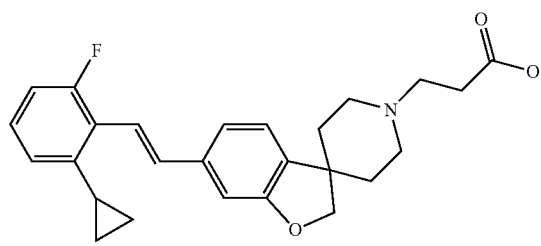 [SMILES: O=C(O)CCN1CCC2(CC1)COc1cc(/C=C/c3c(F)cccc3C3CC3)ccc12]

303 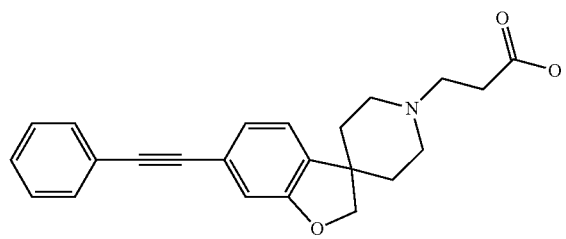 [SMILES: O=C(O)CCN1CCC2(CC1)COc1cc(C#Cc3ccccc3)ccc12]
304 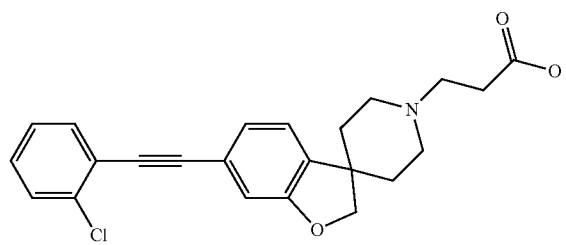 [SMILES: O=C(O)CCN1CCC2(CC1)COc1cc(C#Cc3ccccc3Cl)ccc12]
305 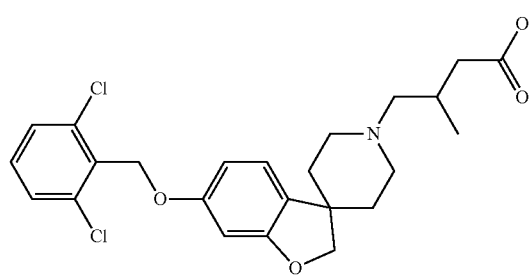 [SMILES: CC(CC(=O)O)CN1CCC2(CC1)COc1cc(OCc3c(Cl)cccc3Cl)ccc12]
306 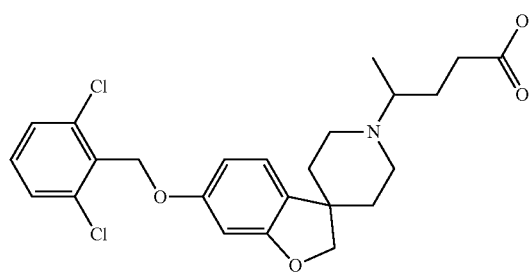 [SMILES: CC(CCC(=O)O)N1CCC2(CC1)COc1cc(OCc3c(Cl)cccc3Cl)ccc12]
307 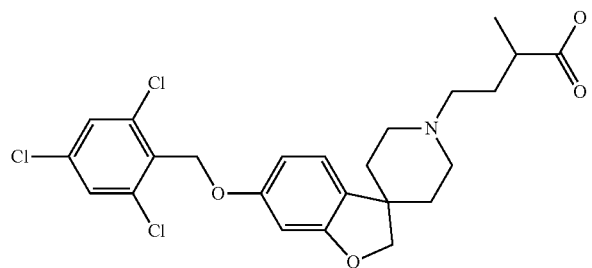 [SMILES: CC(CCN1CCC2(CC1)COc1cc(OCc3c(Cl)cc(Cl)cc3Cl)ccc12)C(=O)O]
308 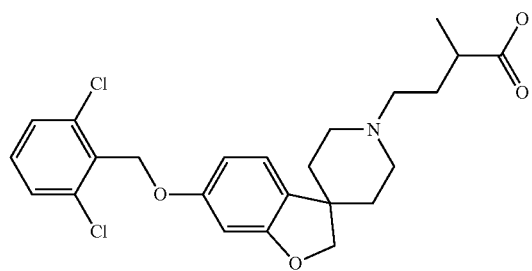

-continued
| 309 | 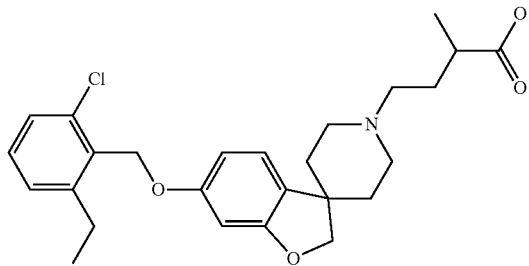 [SMILES: CCc1cccc(Cl)c1COc1ccc2c(c1)OCC21CCN(CCC(C)C(=O)O)CC1] |
| --- | --- |
| 310 | 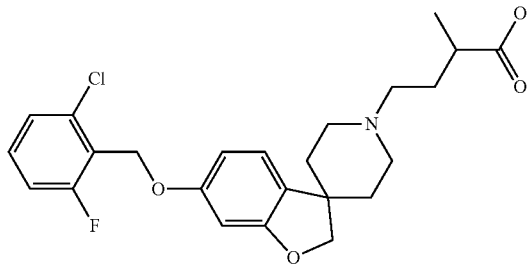 [SMILES: CC(CCN1CCC2(CC1)COc1cc(OCc3c(F)cccc3Cl)ccc12)C(=O)O] |
| 311 | 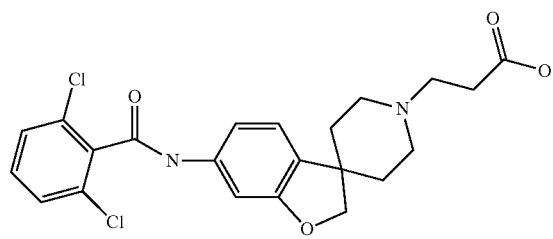 [SMILES: O=C(O)CCN1CCC2(CC1)COc1cc(NC(=O)c3c(Cl)cccc3Cl)ccc12] |
| 312 | 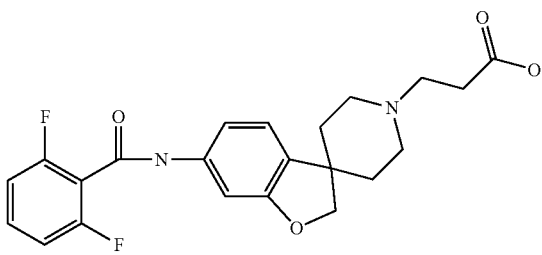 [SMILES: O=C(O)CCN1CCC2(CC1)COc1cc(NC(=O)c3c(F)cccc3F)ccc12] |
| 313 | 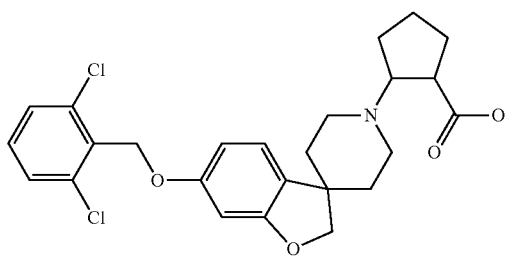 [SMILES: O=C(O)C1CCCC1N1CCC2(CC1)COc1cc(OCc3c(Cl)cccc3Cl)ccc12] |
| 314 | 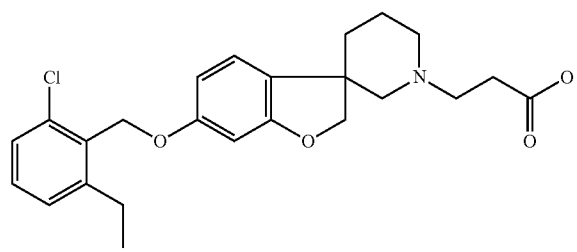 [SMILES: CCc1cccc(Cl)c1COc1ccc2c(c1)OCC21CCCN(CCC(=O)O)C1] |

-continued
| | |
|---|---|
| 315 | 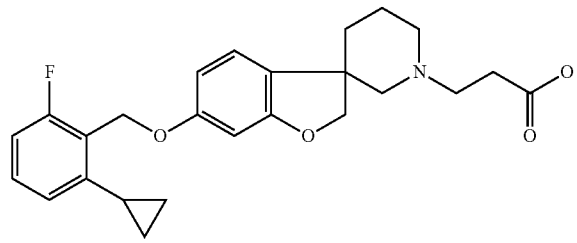 [SMILES: O=C(O)CCN1CCCC2(COc3cc(OCc4c(F)cccc4C4CC4)ccc32)C1] |
| 316 | 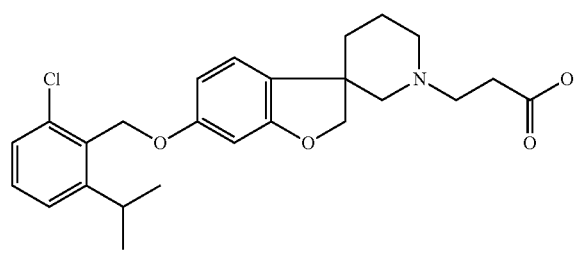 [SMILES: CC(C)c1cccc(Cl)c1COc1ccc2c(c1)OCC21CCCN(CCC(=O)O)C1] |
| 317 | 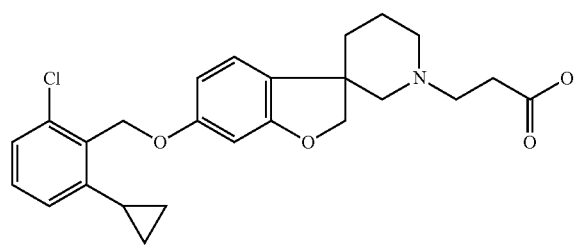 [SMILES: O=C(O)CCN1CCCC2(COc3cc(OCc4c(Cl)cccc4C4CC4)ccc32)C1] |
| 318 | 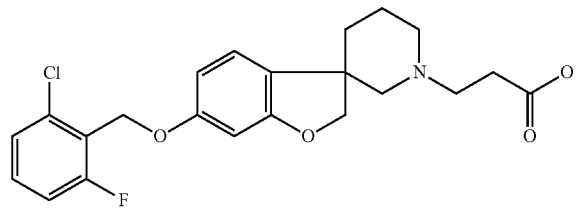 [SMILES: O=C(O)CCN1CCCC2(COc3cc(OCc4c(F)cccc4Cl)ccc32)C1] |
| 319 | 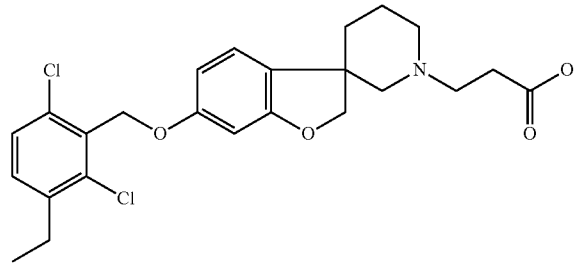 [SMILES: CCc1ccc(Cl)c(COc2ccc3c(c2)OCC32CCCN(CCC(=O)O)C2)c1Cl] |
| 320 | 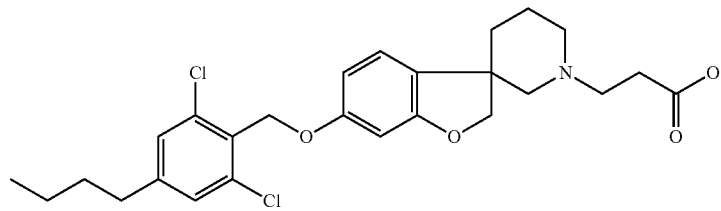 [SMILES: CCCCc1cc(Cl)c(COc2ccc3c(c2)OCC32CCCN(CCC(=O)O)C2)c(Cl)c1] |

| | |
|---|---|
| 321 | 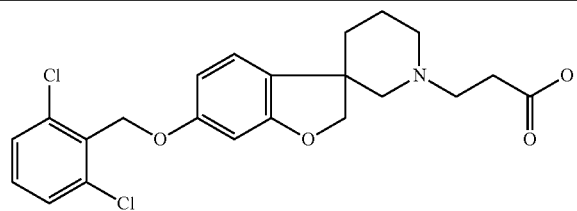 |
| 322 | 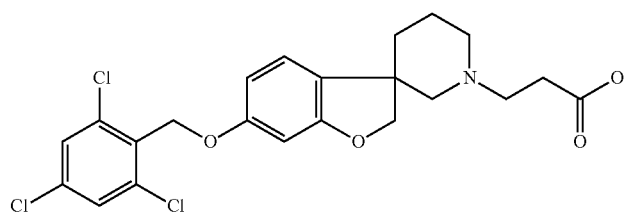 [SMILES: O=C(O)CCN1CCCC2(COc3cc(OCc4c(Cl)cc(Cl)cc4Cl)ccc32)C1] |
| 323 | 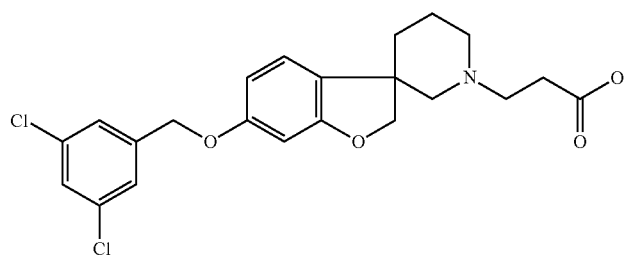 [SMILES: O=C(O)CCN1CCCC2(COc3cc(OCc4cc(Cl)cc(Cl)c4)ccc32)C1] |
| 324 | 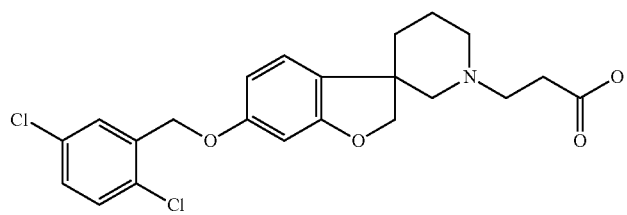 [SMILES: O=C(O)CCN1CCCC2(COc3cc(OCc4cc(Cl)ccc4Cl)ccc32)C1] |
| 325 | 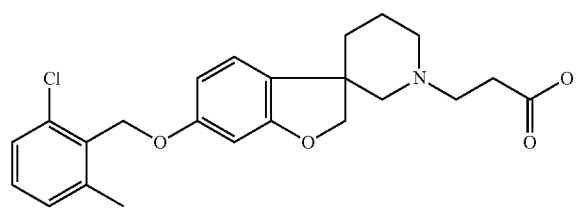 [SMILES: Cc1cccc(Cl)c1COc1ccc2c(c1)OCC21CCCN(CCC(=O)O)C1] |
| 326 | 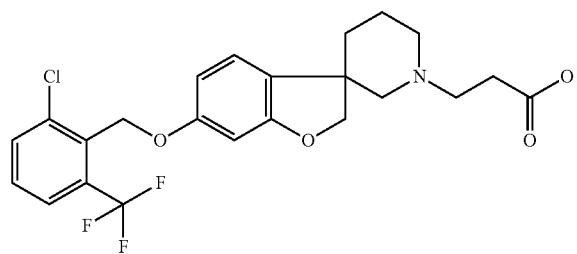 [SMILES: O=C(O)CCN1CCCC2(COc3cc(OCc4c(Cl)cccc4C(F)(F)F)ccc32)C1] |
| 327 | 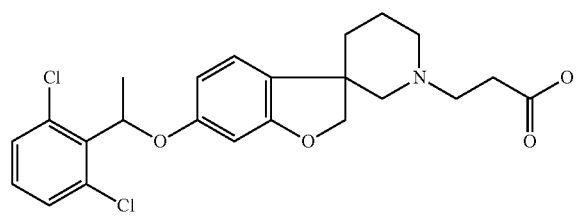 [SMILES: CC(Oc1ccc2c(c1)OCC21CCCN(CCC(=O)O)C1)c1c(Cl)cccc1Cl] |

-continued
| | |
|---|---|
| 328 | 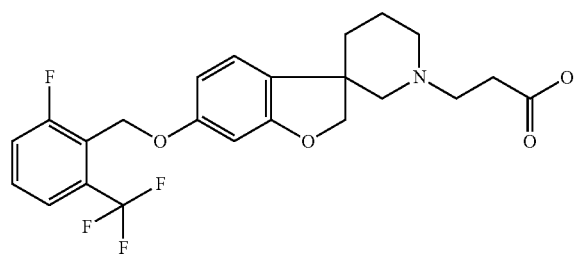 [SMILES: O=C(O)CCN1CCCC2(COc3cc(OCc4c(F)cccc4C(F)(F)F)ccc32)C1] |
| 329 | 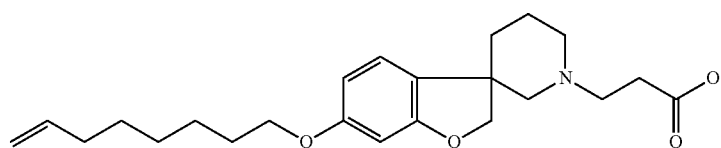 [SMILES: C=CCCCCCCOc1ccc2c(c1)OCC21CCCN(CCC(=O)O)C1] |
| 330 | 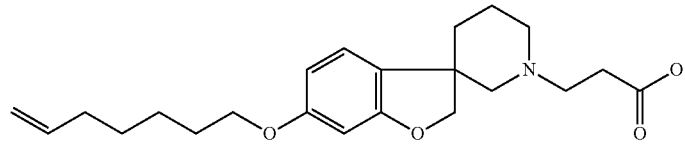 [SMILES: C=CCCCCCOc1ccc2c(c1)OCC21CCCN(CCC(=O)O)C1] |
| 331 | 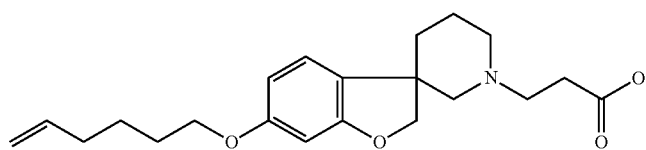 [SMILES: C=CCCCCOc1ccc2c(c1)OCC21CCCN(CCC(=O)O)C1] |
| 332 | 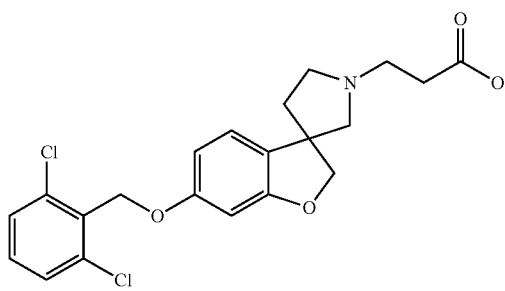 [SMILES: O=C(O)CCN1CCC2(COc3cc(OCc4c(Cl)cccc4Cl)ccc32)C1] |
| 333 | 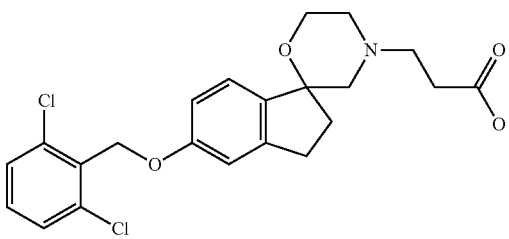 [SMILES: O=C(O)CCN1CCOC2(CCc3cc(OCc4c(Cl)cccc4Cl)ccc32)C1] |
| 334 | 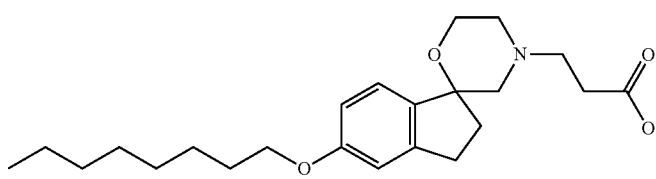 [SMILES: CCCCCCCCOc1ccc2c(c1)CCC21CN(CCC(=O)O)CCO1] |

335

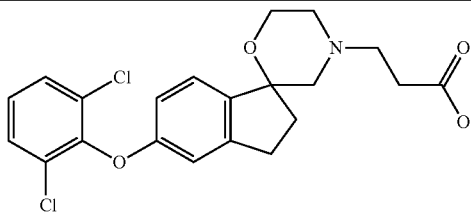

336

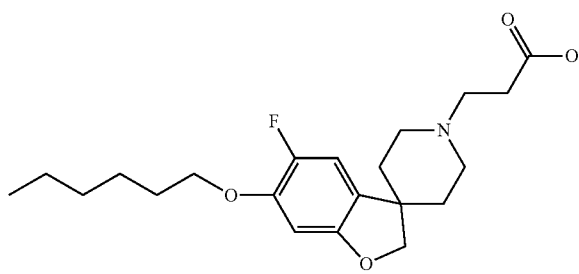 [SMILES: CCCCCCOc1cc2c(cc1F)C1(CCN(CCC(=O)O)CC1)CO2]

§ 5. PHARMACOLOGICAL TESTS & DATA

In Vitro Functional Activity (Agonism) on Human S1P5 Receptors

The CHO-human-S1P5-Aeqorin assay was bought from Euroscreen, Brussels (Euroscreen, Technical dossier, Human Lysophospholid S1P5 (Edg8) receptor, DNA clone and CHO AequoScreen™ recombinant cell-line, catalog no: ES-593-A, September 2006). Human-S1P5-Aequorin cells express mitochondrial targeted apo-Aequorin. Cells have to be loaded with coelanterazine, in order to reconstitute active Aequorin. After binding of agonists to the human S1P5 receptor the intracellular calcium concentration increases and binding of calcium to the apo-Aequorin/coelenterazine complex leads to an oxidation reaction of coelenterazine, which results in the production of apo-Aequorin, coelenteramide, $CO_2$ and light ($\square_{max}$ 469 nm). This luminescent response is dependent on the agonist concentration. Luminescence is measured using the MicroBeta Jet (Perkin Elmer). Agonistic effects of compounds are expressed as $pEC_{50}$. Compounds were tested at a 10 points half log concentration range, and 3 independent experiments were performed in single point's measurements.

In Vitro Functional Activity (Agonism) on Human S1P3 Receptors

The CHO-human-S1P3-Aeqorin assay (CHO/Gα16/AEQ/h-S1P3) was established at Solvay Pharmaceuticals. The plasmid DNA coding for the S1P3 receptor (accession number in GenBank NM_005226 was purchased from UMR cDNA resource Centre (Rolla, Mo.). The pcDNA3.1/hS1P3 construct carrying the mitochondrially targeted apo-Aeqorin and Gal6 protein was transfected in CHO $K_1$ cell-line.

Human-S1P3-Aequorin cells express mitochondrial targeted apo-Aequorin. Cells have to be loaded with coelanterazine, in order to reconstitute active Aequorin. After binding of agonists to the human S1P3 receptor the intracellular calcium concentration increases and binding of calcium to the apo-Aequorin/coelenterazine complex leads to an oxidation reaction of coelenterazine, which results in the production of apo-Aequorin, coelenteramide, $CO_2$ and light ($\square_{max}$ 469 nm). This luminescent response is dependent on the agonist concentration. Luminescence is measured using the MicroBeta Jet (Perkin Elmer). Agonistic effects of compounds are expressed as $pEC_{50}$. Compounds were tested at a 10 points half log concentration range, and 3 independent experiments were performed in single point's measurements.

In Vitro Functional Activity (Agonism) on Human S1P1 Receptors (Method A)

The CHO-K1-human-S1P1-Aeqorin assay was bought from Euroscreen Fast, Brussels (Euroscreen, Technical dossier, Human S1P1 (Edg1) receptor, DNA clone and CHO-K1 AequoScreen™ recombinant cell-line, catalog no: FAST-0197L, February 2010). Human-S1P1-Aequorin cells express mitochondrial targeted apo-Aequorin. Cells have to be loaded with coelanterazine, in order to reconstitute active Aequorin. After binding of agonists to the human S1P1 receptor the intracellular calcium concentration increases and binding of calcium to the apo-Aequorin/coelenterazine complex leads to an oxidation reaction of coelenterazine, which results in the production of apo-Aequorin, coelenteramide, $CO_2$ and light ($\square_{max}$ 469 nm). This luminescent response is dependent on the agonist concentration. Luminescence is measured using the MicroBeta Jet (Perkin Elmer). Agonistic effects of compounds are expressed as $pEC_{50}$. Compounds were tested at a 10 points half log concentration range, and 2 independent experiments were performed in single point's measurements.

In Vitro Functional Activity (Agonism) on Human S1P1 Receptors (Method B)

The CHO-K1-Human S1P1-c-AMP assay was performed at Euroscreenfast, Brussels (Euroscreen, Human S1P1 coupling $G_{i/o}$, (Edg1) receptor, catalog no: FAST-0197C, December 2009).

Recombinant CHO-K1 cells expressing human S1P1, grown to mid-log Phase in culture media without antibiotics, detached, centrifuged and re-suspended. For agonist testing cells are mixed with compound and Forskolin and incubated at room temperature. Cells are lyses and cAMP concentration are estimated, according to the manufacturer specification, With the HTRF kit from CIS-BIO International (cat no 62AM2PEB).

Agonistic effects of compounds are expressed as a percentage of the activity of the reference compound at its $EC_{100}$ concentration, $EC_{50}$ is calculated and results are reported as $pEC_{50}$. Compounds were tested at a 10 points half log concentration range duplicated in 1 experiment.

Pharmacological Data (Receptor Agonism) for Selected Compounds:

| Compound | S1P5 pEC$_{50}$ | S1P1$^A$ pEC$_{50}$ | S1P1$^B$ pEC$_{50}$ | S1P3 pEC$_{50}$ |
|---|---|---|---|---|
| 29 | 7 | <5.0 | | <4.5 |
| 38 | 6.7 | | <5.5 | <5.0 |
| 51 | 6.6 | | <5.5 | <5.0 |
| 59 | 7.8 | | <5.5 | <5.0 |
| 68 | 7.5 | | <5.5 | <5.0 |
| 74 | 7.6 | | <5.5 | nd |
| 75 | 7.7 | 5.6 | | <5.0 |
| 77 | 7.6 | 5.2 | | <5.0 |
| 79 | 7.2 | | 5.7 | <5.0 |
| 100 | 7 | | <5.5 | <5.0 |
| 102 | 7.8 | 6.2 | | nd |
| 110 | 7.8 | <5.0 | | 5.7 |
| 111 | 7.6 | <5.0 | | 5.7 |
| 121 | 7.1 | 5.3 | | <5.0 |
| 127 | 6.9 | 5.1 | | 5.6 |
| 128 | 7.6 | | <5.5 | <5.0 |
| 129 | 7.5 | | <5.5 | <5.0 |
| 132 | 8.3 | <4.5 | | 5.7 |
| 136 | 8 | 5.9 | | <5.0 |
| 140 | 8.5 | 6.8 | | <5.0 |
| 141 | 8.2 | 6.5 | | <5.0 |
| 143 | 7.5 | <5.0 | | nd |
| 153 | 7.9 | 6 | | nd |
| 160 | 7.7 | | <5.5 | <5.0 |
| 171 | 6.5 | | <5.5 | <5.0 |
| 176 | 7.6 | <4.5 | | <5.0 |
| 178 | 7.1 | | <5.5 | 5.5 |
| 182 | 7.4 | | <5.5 | <5.0 |
| 203 | 6.7 | <5.0 | | <5.0 |
| 248 | 6.5 | | <5.5 | <5.0 |
| 252 | 7.3 | 5.3 | | 5.3 |
| 253 | 7.7 | 5.6 | | <5.0 |
| 258 | 7.8 | 5.6 | | <5.0 |
| 276 | 7.1 | <4.5 | | <5.0 |
| 277 | 7.8 | 7.1 | | <5.0 |
| 289 | 7.5 | <4.5 | | <5.0 |
| 296 | 8.7 | 7.4 | | <5.0 |
| 299 | 6 | <4.5 | | <5.0 |
| 303 | 7.6 | <4.5 | | <5.0 |
| 317 | 7 | <4.5 | | <5.0 |
| 321 | 7.1 | <4.5 | | <5.0 |
| 326 | 7.3 | <4.5 | | <5.0 |

S1P1$^A$: determined using method A
S1P1$^B$: determined using method B
nd = not determined.

In Vivo Therapeutic Model; T-Maze

Age-related memory deficits occur in humans and rodents. Spontaneous alternation is the innate tendency of rodents to alternate free choices in a T-maze over a series of successive runs. This sequential procedure relies on working memory and is sensitive to various pharmacological manipulations affecting memory processes (*Aging and the physiology of spatial memory*. Barnes C. A. *Neurobiol. Aging* 1988:563-8; Dember W N, Fowler H. *Spontaneous alternation behavior. Psychol. Bull.* 1958, 55(6):412-427; Gerlai R. *A new continuous alternation task in T-maze detects hippocampal dysfunction in mice. A strain comparison and lesion study. Behav Brain Res* 1998 95(1):91-101).

For this study, male C57BL/6J mice of 2 months or 12 months old were used in the spontaneous alternation task in the T-maze. In short, mice were subjected to 1 session containing 15 trials, consisting of 1 "forced-choice" trial, followed by 14 "free-choice" trials. The animal was considered as entering one of the arms of the maze when all four paws are placed within this arm. A session is terminated and the animal is removed from the maze as soon as 14 free-choice trials have been performed or 15 min have elapsed, whatever event occurs first. The percentage of alternation over the 14 free-choice trials was determined for each mouse and was used as an index of working memory performance. A compound of the invention was administrated p.o. for 21 days prior the T-maze assay and on the day of the T-maze at t=−30 min. It was found that compounds of the invention at doses ranging from of 0.01-15 mg/kg/day reverse the age-related cognitive decline in the 12-month old C57BL6J mice with up to 100%. Thus, treated 12 month old mice were identical in their performance as 2 months old vehicle-treated mice. (See FIG. 1)

Conclusion: compounds of the present invention have a positive effect on age related cognitive decline.

The invention claimed is:

1. A compound of the formula (I)

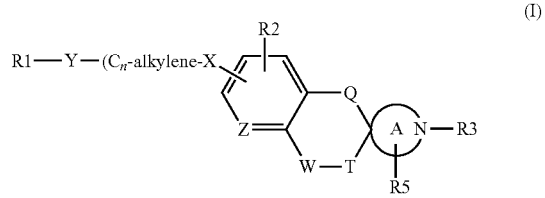

or a pharmaceutically acceptable salt, solvate, or hydrate thereof, or an N-oxide of any of the foregoing, wherein
R1 is
a (3-6C)cycloalkyl group, a (4-6C)cycloalkenyl group, or a (8-10C)bicyclic group,
wherein the group is optionally substituted with at least one substituent independently selected from the group consisting of a halogen atom and (1-4C)alkyl;
a phenyl group or a naphthyl group,
wherein the group is optionally substituted with at least one substituent independently selected from the group consisting of
a halogen atom,
cyano,
(1-6C)alkyl optionally substituted with at least one fluoro atom,
(1-6C)alkoxy optionally substituted with at least one fluoro atom,
amino,
di(1-4C)alkylamino, and
(3-6C)cycloalkyl optionally substituted with a phenyl group, wherein the phenyl group is optionally substituted with a substituent selected from the group consisting of (1-4C)alkyl and a halogen atom; or
wherein the phenyl group is optionally substituted with phenoxy, benzyl, benzyloxy, phenylethyl or monocyclic heterocycle,
wherein the phenoxy, benzyl, benzyloxy, phenylethyl or monocyclic heterocycle is optionally substituted with (1-4C)alkyl optionally substituted with at least one fluoro atom;
a monocyclic heterocycle optionally substituted with a substituent selected from the group consisting of
a halogen atom,
(1-6C)alkyl optionally substituted with at least one fluoro atom,
(3-6C)cycloalkyl, and phenyl optionally substituted with a substituent selected from the group consisting of (1-4C)alkyl and a halogen atom; or
a bicyclic heterocycle optionally substituted with a halogen atom or (1-4C)alkyl optionally substituted with at least one fluoro atom;

—Y—($C_n$-alkylene)-X— is a linking group wherein
Y is attached to R1 and is selected from the group consisting of a bond, —O—, —CO—, —S—, —SO—, —$SO_2$—, —CH=CH—, —C($CF_3$)=CH—, —C≡C—, $CH_2$—O—, —O—CO—, —CO—O—, —CO—NH—, —NH—CO—, and a trans-cyclopropylene;
n is an integer from 0 to 10; and
X is attached to the phenylene/pyridyl moiety and is selected from the group consisting of a bond, —O—, —S—, —SO—, —$SO_2$—, —NH—, —CO—, —CH=CH—, and a trans-cyclopropylene;
R2 is H, a halogen atom, (1-4C)alkoxy, or (1-4C)alkyl optionally substituted with at least one fluoro atom;
R3 is
(1-4C)alkylene-R4 wherein
the alkylene group is onally substituted with at least one halogen atom
or
the alkylene group is optionally substituted with a ($CH_2$)$_2$ to form a cyclopropyl moiety, or
(3-6C)cycloalkylene-R4, —$CH_2$-(3-6C)cycloalkylene-R4, (3-6C)cycloalkylene-CH2-R4, or —CO—$CH_2$-R4,
wherein R4 is selected from the group consisting of —$PO_3H_2$, —$OPO_3H_2$, —COOH, —COO(1-4C)alkyl, and tetrazol-5-yl;
Q is a bond;
—W-T- is —O—$CH_2$—;
R5 is H or a halogen atom;
Z is CH or CR2; and
A is a morpholine ring structure or piperidinyl.

2. The compound of claim 1, wherein R3 is selected from the group consisting of —$CH_2$—COOH, —($CH_2$)$_2$—COOH, —($CH_2$)$_3$—COOH, —$CH_2$—$CHCH_3$—COOH, —$CH_2$-C($CH_3$)$_2$—COOH, —$CHCH_3$—$CH_2$—COOH, —$CH_2$—$CF_2$—COOH, —CO—$CH_2$—COOH, 1,3-cyclobutylene-COOH, —($CH_2$)$_2$—$PO_3H_2$, —($CH_2$)$_3$—$PO_3H_2$, —($CH_2$)$_2$—$OPO_3H_2$, —($CH_2$)$_3$—$OPO_3H_2$, —$CH_2$-tetrazol-5-yl, —($CH_2$)$_2$-tetrazol-5-yl, and —($CH_2$)$_3$tetrazol-5-yl.

3. The compound of claim 1, wherein R2 is selected from the group consisting of H, methyl, chloro, and fluoro.

4. The compound of claim 1, wherein R5 is H.

5. The compound of claim 1, wherein Y is selected from the group consisting of a bond, —O—, —CO—, —CH=CH—, —C($CF_3$)=CH—, —C≡C—, and a trans-cyclopropylene; and n is an integer from 0 to 6.

6. The compound of claim 1, wherein
R1 is
cyclohexyl, cyclohexenyl, or biphenyl, each of which is optionally substituted with at least one halogen atom;
a phenyl optionally substituted with one, two or three substituents independently selected from the group consisting of
halogen,
(1-4C)alkyl,
trifluoromethyl,
(1-4C)alkoxy,
trifluoromethoxy, and
cyclopropyl optionally substituted with phenyl, thienyl, pyridyl, or tetrahydropyranyl, wherein the phenyl, thienyl, pyridyl, or tetrahydropyranyl is optionally substituted with halogen, (1-4C)alkyl, cyclopropyl or phenyl optionally substituted with halogen; or
indolyl dihydrobenzofuranyl, or benzdioxanyl, each of which is optionally substituted with a halogen atom or (1-4C)alkyl.

7. The compound of claim 1, wherein
R1 is phenyl, optionally substituted with at least one substituent independently selected from the group consisting of
a halogen atom,
(1-4C)alkyl,
a cyclopropyl, and
a trifluoromethyl; and
the group —Y—($C_n$-alkylene)-X— is selected from the group consisting of
—$CH_2$O—,
—$CH_2$-S—, and
—CH=CH—.

8. The compound of claim 1, wherein A is piperidinyl.

9. The compound of claim 1, having the formula (II):

(II)

R1—Y—($C_n$-alkylene)-X— [structure with R2, Q, N—R3, Z, W—T, R5]

10. The compound of claim 1, wherein R1 is 2,6-dichlorophenyl and R3 is —($CH_2$)$_2$—COOH.

11. The compound of claim 1, wherein the compound is selected from the group consisting of:
3-(5-{[2-(Trifluoromethyl)phenyl]methoxy}-2H-spiro[1-benzofuran-3,4'-piperidine]-1'-yl)propanoic acid,
3-(5-(Cyclohexylmethoxy)-2H-spiro[1-benzofuran-3,4'-piperidine]-1'-yl]propanoic acid,
3-(5-{[3-(Trifluoromethyl)phenyl]methoxy}-2H-spiro[1-benzofuran-3,4'-piperdine]-1'-yl)propanoic acid,
3-{5-[(2,6-Dichlorophenyl)methoxy]-2H-spiro[1-benzofuran-3,4'-piperidine]-1'-yl}propanoic acid,
3-{5-[(3,5-Dichlorophenyl)methoxy]-2H-spiro[-1-benzofuran-3,4'-piperidine]-1'-yl}propanoic acid,
3-{5-[(2,6-Difluorophenyl)methoxy]-2H-spiro[1-benzofuran-3,4'-piperidine]-1'-yl}propanoic acid,
3-{5-[(2-Chlorophenyl)methoxy]-2H-spiro[1-benzofuran-3,4'-piperidine]-1'-yl}propanoic acid,
3-{5-[(2,4,6-Trichlorophenyl)methoxy]-2H-spiro[1-benzofuran-3,4'-piperidine]-1'-yl}propanoic acid,
3-{5-[(2-Chloro-6-methylphenyl)methoxy]-2H-spiro[1-benzofuran-3,4'-piperidine]-1'-yl}propanoic acid,
3-[5(Phenylamino)-2H-spiro[1-benzofuran-3,4'-piperidine]-1'-yl]propanoic acid,
3-{6-[(2,6-Dichlorophenyl)methoxy]-2H-spiro[1-benzofuran-3,4'-piperidine]-1'-yl}propanoic acid,
3-{6-[(4-Phenylpentyl)oxy]-2H-spiro[1-benzofuran-3,4'-piperidine]-1'-yl}propanoic acid,
3-{6-[(3-Chlorophenyl)methoxy]-2H-spiro[1-benzofuran-3,4'-piperidine]-1'-yl}propanoic acid, 3-[6-(Cyclohexylmethoxy)-2H-spiro[1-benzofuran-3,4'-piperidine]-1'-yl]propanoic acid,
3-[6-(Oxan-2ylmethoxy)-2H-spiro[1-benzofuran-3,4'-piperidine]-1'-yl]propanoic acid,
3-{6-[(2,5Dichlorophenyl)methoxy]-2H-spiro[1-benzofuran-3,4'-piperidine]-1'-yl}propanoic acid,
3-(6-{[3-(Trifluoromethyl)phenyl]methoxy}-2H-spiro[1-benzofuran-3,4'-piperidine]-1'-yl)propanoic acid,
3-(6{[2-(Trifluoromethyl)phenyl]methoxy}-2H-Spiro[1-benzofuran-3,4'-piperidine]-1'-yl)propanoic acid,
3-{6-[2,3-Dichlorophenyl)methoxy]-2H-spiro[1-benzofuran-3,4'-piperidine]-1'-yl}propanoic acid,
3-{6-[(2-Chloro-6-fluorphenyl)methoxy]-2H-spiro[1-benzofuran-3,4'-piperidine]-1'-yl}propanoic acid,
3-[6-(Benzyloxy)-2H-spiro[1-benzofuran-3,4'-piperidine]-1'-yl]-propanoic acid,
3-{6-[(2,4-Dichlorophenyl)methoxy]-2H-spiro[1-benzofuran-3,4'-piperidine]-1'-yl}propanoic acid,
3-(6-{[2-Chloro-6-(trifluoromethyl)phenyl]methoxy}-2H-spiro[1-benzofuran-3,4'-piperidine]-1'-yl)propanoic acid,
3-[6(Cyclohex-3-en-1ylmethoxy)-2H-spiro[1-benzofuran-3,4'-piperidine]-1'-yl]propanoic acid,
3-{6-[(3,5-Dichloropyridin-4-yl)methoxy]-2H-spiro[1-benzofuran-3,4'-piperidine]-1'-yl}propanoic acid,
3-{6-[(2,4-Dichloropyridin-3-yl)methoxy]-2H-spiro[1-benzofuran-3,4'-piperidine]-1'-yl}propanoic acid,
3-{6-[(2,4,6-Trichloroplienyl)methoxy]-2H-spiro[1-benzofuran-3,4'-piperidine]-1'-yl]propanoic acid,
3-{6-[(2,6-Dichloro-4-iodophenyl)methoxy]-2H-spiro[1-benzofuran-3,4'-piperidine]-1'-yl}propanoic acid,
3-{6-[(2,6-Difluorophenyl)methoxy]-2H-spiro[1-benzofuran-3,4'-piperidine]-1'-yl}propanoic acid,
3-{6-[2-(2,6-Dichlorphenyl)ethoxy]-2H-spiro[1-benzofuran-3,4'-piperidine]-1'-yl}propanoic acid,
3-{6[2-(2-Fluororphenyl)ethoxy]-2H-spiro[1-benzofuran-3,4'-piperidine]-1'-yl}propanoic acid,
3-{6-[(2-Chloro-5-methylphenyl)methoxy]-2H-spiro[1-benzofuran-3,4'-piperidine]-1'-yl}propanoic acid,
3-{6-[(2-Chloro-5-ethylphenyl)methoxy]-2H-spiro[1-benzofuran-3,4'-piperidine]-1'-yl}propanoic acid,
3-{6-[(2-Chloro-5-propylphenyl)metboxy]-2H-spiro[1-benzofuran-3,4'-piperidine]-1'-yl}propanoic acid,
3-{6-[3(2-Fluorophenyl)propoxyl-2H-spiro[1-benzofuran-3,4'-piperidine]-1'-yl}propanoic acid,
3-{6-[3-(2-Chlorophenyl)propoxy]-2H-spiro[1-benzofuran-3,4'-piperidine]- 1'-yl}propanoic acid,
3-[6-(3-Phenylpropoxy)-2H-spiro[1-benzofuran-3,4'-piperidine]-1'-yl]propanoic acid,
3-{6-[2-(2,4-Dichlorophenyl)ethoxy]-2H-spiro[1-benzofuran-3,4'-piperidine]-1'-yl}propanoic acid,
3-{6-[2-(2-Chlorophenyl)ethoxy]-2H-spiro[1-benzofuran-3,4'-piperidine]-1'-yl}propanoic acid,
3-(6-{[2,6-Dichloro-4-(trifluoromethyl)phenyl]methoxy}-2H-spiro[1-benzofuran-3,4'-piperidine]-1'-yl)propanoic acid,
3-{6-[(2,6-Dichloro-4-methylphenyl)methoxy]-2H-spiro[1-benzofuran-3,4'-piperidine]-1'-yl}propanoic acid,
3-{6-[(5-Bromo-2-chlorophenyl)methoxy]-2H-spiro[1-benzofuran-3,4'-piperidine]-1'-yl}propanoic acid,
3-{6-[(2-Chloro-6-methylphenyl)methoxy]-2H-spiro[1-benzofuran-3,4'-piperidine]-1'-yl}propanoic acid,
3-(6-{3-[2-(Trifluoromethyl)phenyl]propoxy}-2H-spiro[1-benzofuran-3,4'-piperidine]-1'-yl)propanoic acid,
3-{6-[3(2,3-Difluorophenyl)propoxy]-2H-spiro[1-benzofuran-3,4'-piperidine]-1'-yl}propanoic acid,
3-{6[3-(2-Chloro-6-fluorophenyl)propoxy]-2H-spiro[1-benzofuran-3,4'-piperidine]-1'-yl}propanoic acid,
3-{6-[3-(2,6-Dichlorophenyl,propoxy]-2H-spiro[1-benzofuran-3,4'-piperidine]-1'-yl}-propanoic acid,
3-{6-[3-(4-Chlorophenyl)propoxy]-2H-spiro[1-benzofuran-3,4'-piperidine]-1'-yl}propanoic acid,
3-{6-[(2-Chloro-5-phenylphenyl)methoxy]-2H-spiro[1-benzofuran-3,4'-piperidine]-1'-yl}propanoic acid,
3-{6-[(2,6-Dichloro-3-ethylphenyl)methoxy]2H-spiro[1-benzofuran-3,4'-piperdine]-1'-yl}propanoic acid,
3-{6[(4-Butyl-2,6-dichlorophenyl)methoxy]-2H-spiro[1-benzofuran-3,4'-pipetidine]-1'-yl}propanoic acid,
3-{6-[(2,6-Dichloro-4-cyclorpropylphenyl)methoxy]-2H-spiro[1-benzofuran-3,4'-piperidine]-1'-yl}propanoic acid,
3-{6-[(2-Chloro-5-cyclopropylphenyl)methoxy]-2H-spiro[1-benzofuran-3,4'-piperidine]-1'-yl}propanoic acid,
3[6-({2-Chloro-5[2-plienylcyclopropyl]phenyl}methoxy)-2H-spiro[1-benzofuran-3,4'-piperidine]-1'-yl]propanoic acid,
3-{6-[(2-Chloro-6-ethylphenyl)methoxy]-2H-spiro[1-benzofuran-3,4'-piperidine]-1'-yl}propanoic acid,
3-(6-{[2-Chloro-6-(propan-2-yl)phenyl]methoxy}-2H-spiro[1-benzofuran-3,4'-piperidine]-1'-yl)propanoic acid,
3-{6-[(2-Chloro-6-cyclopropylphenyl)methoxy]-2H-spiro[1-benzofuran-3,4'-piperidine]-1'-yl}propanoic acid,
3-{6-[(2,6-Dichloro-3-methoxyphenyl)methoxy]-2H-spiro[1-benzofuran-3,4'-piperidine]-1'-yl}propanoic acid,
3-(6-{[2-Chloro-6-(trifluoromethoxy)phenyl]methoxy}-2H-spiro[1-benzofuran-3,4'-piperidine]-1'-yl)propanoic acid,
3-(6-{[2-Chloro-6-(2-methylpropyl)phenyl]methoxy}-2H-spiro[1-benzofuran-3,4'-piperidine]-1'-yl)propanoic acid,
3-{6-[(5,7-Dichloro-2,3-dihydro-1H-inden-1-yl)oxy]-2H-spiro[1-benzofuran-3,4'-piperidine]-1'-yl}propanoic acid,
3-{6-[(5,7-Difluoro-2,3dihydro-1H-inden-1-yl)oxy]-2H-spiro[1-benzofuran-3,4'-piperidine]-1'-yl}propanoic acid,
3-{6-[(1R)-(2,3dihydro-1H-inden-1-yl)oxy]-2H-spiro[1-benzofuran-3,4'-piperidine]-1'-yl}propanoic acid,
3-{6-[(1S)-(2,3-dihydro-1H-inden-1-yl)oxy]-2H-spiro[1-benzofuran-3,4'-piperidine]-1'-yl}propanoic acid,
3-(6-{[(2E)-3(4-Chlorophenyl)prop-2-en-1-yl]oxy}-2H-spiro[1-benzofuran-3,4'-piperidine]-1'-yl)propanoic acid,
3-{6-[(3-Phenyl)prop-2-yn-1-yl]oxy-2H-spiro[1-benzofuran-3,4'-piperidine]-1'-yl]-propanoic acid,
3-[6-(2,3Dihydro-1-benzoluran-3yloxy)-2H-spiro[1-benzofuran-3,4'-piperidine]-1'-yl]propanoic acid,
3-(6-{[(2E)-3-(2,6-dichlorophenyl)prop-2-en-1-yl]}-2H-spiro[1-benzofuran-3,4'-piperidine]-1'-yl)propanoic acid,
3-(6-{[(2E)-3phenylprop-2-en-1-yl]oxy}-2H-spiro[1-benzofuran-3,4'-piperidine]-1'-yl)propanoic acid,
3-{6[(7-Chloro-2,3-dihydro-1H-inden-1-yl)oxy]-2H-spiro[1-benzofuran-3,4'-piperidine]-1'-yl}propanoic acid,
3-(6-{[3-(4-Chlorophenyl)prop-2-yn-1-yl]oxy}-2H-spiro[1-benzofuran-3,4'-piperidine]-1'-yl)propanoic acid, 3-(6-{[(2E)-3-(2-fluororophenyl)prop-2-en-1-yl]oxy}-2H-spiro[1-benzofuran-3,4'-piperidine]-1'-yl)propanoic acid,
3-{6-[(4-Bromothiophen-2yl)methoxy]-2H-spiro[1-benzofuran-3,4'-piperidine]-1'-yl}propanoic acid,
3-{6-[(4-Butylthiophen-2yl)methoxy]-2H-spiro[1-benzofuran-3,4'-piperidine]-1'-yl}-propanoic acid,
3-(6-{[4-(2-Fluorophenyl)thiophen-2methoxy}-2H-spiro[1-benzofuran-3,4'-piperidine]-1'-yl)propanoic acid,
3-{6-[(4-Phenyithiophen-2yl)methoxy]-2H-spiro[1-benzofuran-3,4-piperidine]-1'-yl}propanoic acid,
3-{6-[(4-Bromo-3-methylthiophen-2yl)methoxy]-2H-spiro[1-benzofuran-3,4'-piperidine]-1'-yl}propanoic acid,
3{6-[(4-Cyclopropylmethylthiophen-2yl)methoxy]-2H-spiro[1-benzfuran-3,4'-piperidine]-1'-yl}propanoic acid,
3-{6-[(3Methyl-4-phenylthiophen-2yl)methoxy]-2H-spiro[1-benzofuran-3,4'-piperidine]-1'-yl}propanoic acid,
3-{6-[(4-Butyl-3-methylthiophen-2yl)methoxy]-2H-spiro[1-benzofuran-3,4'-piperidine]-1'-yl}propanoic acid,
3-{6-[(2,6-Dichloro-3-ethylphenyl)methoxy]-2H-spiro[1-benzofuran-3,4'-piperidine]1'-yl}-2-methylpropanoic acid,
3-{6-[(2,6-Dichlorophenyl)methoxy]-2H-spiro[1-benzofuran-3,4'-piperdine]-1'-yl}-2-methylpropanoic acid,
3-{6-[(2-Chloro-6-ethylphenyl)methoxy]-2H-spiro[1-benzofuran-3,4'-piperidine]-1'-yl}-2-methylpropanoic acid,
2-Methyl-3-{(6-[(2,4,6-trichlorophenyl)methoxy]-2H-spiro[1-benzofuran-3,4'-piperidine]-1'-yl}propanoic acid,
3-{6-[(2,6-Dichloro-4-methylphenyl)methoxy]-2H-spiro[1-benzofuran-3,4'-piperidine]-1'-yl}-2-methylpropanoic acid,
3-{(6-[(2,6-Dichloro-3methoxyphenyl)methoxy]-2H-spiro[1-benzofuran-3,4'-piperidine]-1'-yl}-2-methylpropanoic acid,
3-{6-[(4-Butyl-2,6-dichlorophenyl)methoxy]-2H-spiro[1-benzoluran-3,4'-piperidine]-1'-yl}-2-methylpropanoic acid,
3-(6-{[2-Chloro-6-(2-methpropyl)phenyl]methoxy}-2H-spiro[1-benzofuran-3,4'-piperidine]-1'-yl)-2-methylpropanoic acid,
3-(6-{[2-Chloro-6-(trifluoromethoxy)phenyl]methoxy}-2H-Spiro[1-benzofuran-3,4'-piperidine]-1'-yl)-2-methylpropanoic acid,
3-{6-[(2-Chloro-5-ethylphenyl)methoxy]-2H-spiro[1-benzofuran-3,4'-piperidine]-1'-yl}-2-methylpropanoic acid,
3-{6-[(2-Chloro-6-cyclopropylphenyl)methoxy]-2H-spiro[1-benzofuran-3,4'-piperidine]-1'-yl}-2-methylpropanoic acid,
2-{(6-[(2,4,6-Trichlorophenyl)methoxy]-2H-spiro[1-benzofuran-3,4'-piperidine]-1'-yl}acetic acid,
2-{6-[(2-Chloro-6-ethylphenyl)methoxy]-2H-spiro[1-benzofuran-3,4'-piperidine]-1'-yl}acetic acid,
2-{6-[(2-Chloro-6-cyclopropylphenyl)methoxy]-2H-spiro[1-benzofuran-3,4'-piperidine]-1'-yl}acetic acid,
2-{(6-[(4-Butyl-2,6-dichlorophenyl)methoxy]-2H-spiro[1-benzofuran-3,4'-piperidine]-1'-yl}acetic acid,
2-{6-[(2-Chloro-5-ethylpheny)methoxy]-2H-spiro[1-benzofuran-3,4'-piperidine]-1'-yl}acetic acid,
2-(6-{[2-Chloro-6-(propan-2-yl)phenyl]methoxy}2H-spiro[1-benzofuran-3,4'-piperidine]-1'-yl)acetic acid,
2-{6-[2,6Dichloro-3-ethylphenyl)methoxy]-2H-spiro[1-benzofuran-3,4'-piperidine]-1'-yl}acetic acid,
2-(6-{[2-Chloro-6-(trifluoromethoxy)phenyl]methoxy}-2H-spiro[1-benzofuran-3,4'-piperidine]-1'-yl)acetic acid,
2-{6-[(2,6-Dichlorophenyl)methoxy]-2H-spiro[1-benzofuran-3,4'-piperidine]-1'-yl}acetic acid,
4-{6-[(2,4,6-Trichlorophenyl)methoxy]-2H-spiro[1-benzofuran-3,4'-piperidine]-1'-yl}butanoic acid,
4-{6-[(2-Chloro-6-ethylphenyl)methoxy]-2H-spiro[1-benzofuran-3,4'-piperidine]-1'-yl}butanoic acid,
4-{6-[(2-Chloro-6-cyclopropylphenyl)methoxy]-2H-spiro[1-benzofuran-3,4'-piperidine]-1'-yl}butanoic acid,
4-{6-[(2,6-Dicbloro-3ethylphenyl)methoxy]-2H-spiro[1-benzofuran-3,4'-piperidine]-1'-yl}butanoic acid,
4-{6-[(2-Chloro-5-ethylphenyl)methoxy]-2H-spiro[1-benzofuran-3,4'-piperidine]-1'-yl}butanoic acid,
4-{6-[(2,6-Dichloro-3methoxyphenyl)methoxy]-2H-spiro[1-benzofuran-3,4'-piperidine]-1'-yl}butanoic acid,
4-{6-[(4-Butyl-2,6-dichlorophenyl)methoxy]-2H-spiro[1-benzofuran-3,4'-piperidine]-1'-yl}butanoic acid,
4-(6-{[2-Chloro-6-(trifluoromethoxy)phenyl]methoxy}-2H-spiro[1-benzofuran-3,4'-piperidine]-1'-yl)butanoic acid,
4-(6-{[2-Chloro-6-(propan-2-yl)phenyl]methoxy)}-2H-spiro[1-benzofuran-3,4'-piperidine]-1'-yl)butanoic acid,
4-{6-[(2,6-Dichlorophenyl)methoxy]-2H-spiro[1-benzofuran-3,4'-piperidine]-1'-yl}butanoic acid,
3{6-[2,6-Dichlorophenyl)methox]-7-methyl-2H-spiro[1-benzofuran-3,4'-piperidine]-1'-yl}propanoic acid,
3-{6-[(2,6-Dichlorophenyl)methoxy]-7-fluor-2H-spiro[1-benzofuran-3,4'-piperidine]-1'-yl}propanoic acid,
3-{6-[(2,6-Dichloro-4-methyiphenyl)methoxy]-7-fluoro-2H-spiro[1-benzofuran-3,4'-piperidine]-1'-yl}propanoic acid,
3-{7-Fluoro-6-[(2,4,6-trichlorophenyl)methoxy]-2H-spiro[1-benzofuran-3,4'-piperidine]-1'-yl}propanoic acid,
3-{6-[(2,6-Dichloro-3-methoxyphenyl)methoxy]-7-fluor-2H-spiro[1-benzofuran-3,4'-piperidine]-1'-yl}propanoic acid,
3-{6-[(4-Butyl-2,6-dichiorophenyl) methoxy]-7-fluor-2H-spiro[1-benzofuran-3,4'-piperidine]-1'-yl}propanoic acid,
3-{6-[(2-Chloro-5-ethylphenyl)methoxyl]-7-fluoro-2H-spiro[1-benzofuran-3,4'-piperidine]-1'-yl}propanoic acid,
3-{6-[(2-Chloro-6-ethylphenyl)methoxy]-7-fluoro-2H-spiro[1-benzofuran-3,4'-piperidine]-1'-yl}propanoic acid,
3-(6-{[2-Chloro-6-(trifluoromethoxy)phenyl]methoxy}-7-fluoro-2H-spiro[1-benzofuran-3,4'-piperidine]-1'-yl)propanoic acid,
3-(6-{[2,6-Dichloro-3methoxyphenyl)methyl]sulfanyl}-2H-spiro[1-benzofuran-3,4'-piperidine]-1'-yl)propanoic acid,
3-(6-{[(4-Butyl-2,6-dichlorophenyl)methyl]sulfanyl}-2H-spiro[1-benzofuran-3,4'-piperidine]-1'-yl)propanoic acid,
3-(6{[(2-Chloro-6-ethylphenyl)methyl]sulfanyl}-2H-spiro[1-benzofuran-3,4'-piperidine]-1'-yl)propanoic acid, 3(6-{[(2-Chloro-6-cyclopropylphenyl)methyl]sulfanyl}-2H-spiro[1-benzoluran-3,4'-piperidine]-1'-yl)propanoic acid, 3(6-{[(2,6-Dichloro-3ethylphenyl)methyl]sulfanyl}-2H-spiro[1-benzofuran-3,4'-piperidine]-1'-yl)propanoic acid, 3(6-{[(2,4,6-Trichlorophenyl)methyl]sulfanyl}-2H-spiro[1-benzofuran-3,4'-piperidine]-1'-yl)propanoic acid, 3-(6-{[(2,6-Dichlorophenyl)methyl]sulfanyl}-2H-spiro[1-benzofuran-3,4'-piperidine]-1'-yl)propanoic acid, 3-(6-{[(2-Chloroplienyl)methyl]sulfanyl}-2H-spiro[1-benzofuran-3,4'-piperidine]-1'-yl)propanoic acid, 3-(6-{[(2-Methylphenyl)methyl]sulfanyl}-2H-spiro[1-benzofuran-3,4'-piperdine]-1'-yl)propanoic acid, 3-[6-(Benzylsulfanyl)-2H-spiro[1-benzoluran-3,4'-piperidine]-1'-yl]propanoic acid, 2-Methyl-3-(6-{[(2,4,6-trichlorophenyl)methyl]sulfanyl}-2H-spiro[1-benzofuran-3,4'-piperidine]-1'-yl)propanoic acid, 3-(6-{[(2,6-Dichloro-3-methoxyphenyl)methyl]sulfanyl}-2H-spiro[1-benzofuran-3,4'-piperidine]-1'-yl)-2-methylpropanoic acid, 3-(6-{[(2,6-Dichloro-4-methylphenyl)methyl]sulfanyl}-2H-spiro[1-benzofuran-3,4'-piperidine]-1'-yl)-2-methylpropanoic acid, 3-(6-{[(2-Chloro-6-ethylphenyl)methyl]sulfanyl}-2H-spiro[1-benzofuran-3,4'-piperidine]-1'-yl)-2-methylpropanoic acid, 3-[6-({[2-Chloro-6-(propan-2-yl)phenyl]methnyl})sulfany)-2H-spiro[1-benzofuran-3,4'-piperidine]-1'-yl]-2-methylpropanoic acid, 3-(6-{[(2,6-Dichlorophenypmethyl)methyl]sulfanyl}-2H-spiro[1-benzofuran-3,4'-piperidine]-1'-yl)-2-methylpropanoic acid, 3-(6-{[(2-Chlorophenyl)methane]sulfonyl}-2H-spiro[1-benzofuran-3,4'-piperidine]-1'-yl)propanoic acid, 3{6-[(2-Methylphenyl)sulfanyl]-2H-spiro[1-benzofuran-3,4'-pipetidine]-1'-yl}propanoic acid, 3-{6-[2,6-Dichlorophenyl)sulfanyl]-2H-spiro[1-benzofuran-3,4'-)piperidine]-1'-yl}propanoic acid, 3-{6-[(2-Methylbenzene)sulfonyl]-2H-spiro[1-benzofuran-3,4'-piperidine]-1'-yl}propanoic acid, 3-{6-[(2,6-Dichlorobenzene)sulfonyl]-2H-spiro[1-benzofuran-3,4'piperdine]-1-yl}-propanoic acid, 3-[6-(Benzenesulfonyl)-2H-spiro[1-benzofuran-3,4'-piperidine]-1-propanoic acid, 3-{6-[(E)-2-(2,6-Dichloropheny)ethenyl]-2H-spiro[1-benzofuran-3,4'-piperidine]-1'-yl}propanoic acid, 3-{6-[(E)-2-(2-Chlorophenyl)ethenyl]-2H-spiro[1-benzofuran-3,4'-piperidine]-1'-yl}propanoic acid, 3-{6-[(E)-2-Phenylethenyl]-2H-spiro[1-benzofuran-3,4'-piperidine]-1'-yl}-propanoic acid, 3-{6-[(E)-2-(4-Fluorphenyl)ethenyl]-2H-spiro[1-benzofuran-3,4'-piperidine]-1'-yl}-propanoic acid, 3-{6-[(E)-2-(2,6-Dichloro-3ethylphenyl)ethenyl]-2H-spiro[1-benzofuran-3,4'-piperidine]-1'-yl}propanoic acid, 3-{6-[(E)-2-(2,6-Dichloro-4-cyclopropylphenyl)ethenyl]-2H-spiro[1-benzofuran-3,4'-piperidine]-1'-yl}propanoic acid, 3-{6-[(E)-2-(4-Butyl-2,6-dichlorophenyl)ethenyl]-2H-spiro[1-benzofuran-3,4'-piperidine]-1'-yl}propanoic acid, 3-{6-[(1Z)-3,3,3-Trifluoro-2-phenylprop-1-en-1-yl]-2H-spiro[1-benzofuran-3,4'-piperidine]-1'-yl}propanoic acid, 3-{6-[(E)-2-(2-Chloro-5-ethylphenyl)ethenyl]-2H-spiro[1-benzofuran-3,4'-piperidine]-1'-yl}propanoic acid, 3-{6-[(E)-2-(2,5-Dichlorophenyl)ethenyl]-2H-spiro[1-benzofuran-3,4'-piperidine]-1'-yl}propanoic acid, 3-{6-[(E)-2-(3-Methylphenyl)ethenyl]-2H-spiro[1-benzofuran-3,4'-piperidine]-1'-yl}propanoic acid, 3-{6-[(E)-2-(2-Fluorophenyl)ethenyl]-2H-spiro[1-benzofuran-3,4-piperidine]-1'-yl}propanoic acid, 4-{6-[(E)-2-(2,6-Dichlorophenyl)ethenyl]-2H-spiro[1-benzofuran-3,4'-piperidine]-1'-yl}butanoic acid, 2-{6-[(E)-2-(2,6-Dichlorophenyl)ethenyl]-2H-spiro[1-benzofuran-3,4'-piperidine]-1'-yl}acetic acid, 3-{6-[(E)-2-(2,6-Dichlorophenyl)ethenyl]-2H-spiro[1-benzofuran-3,4'-piperidine]-1'-yl}-2-methylpropanoic acid, 4-{6-[2-(2,6-Diehlorophenyl)cyclopropyl]2H-spiro[1-benzofuran-3,4'-piperidine]-1'-yl}butanoic acid, 2-{6[2-(2,6-Dichlorophenyl)cyclopropyl]-2H-spiro[1-benzofuran-3,4'-piperidine]-1'-yl}acetic acid, 3-{6-[2-(2,6-Dichlorophenyl)cyclopropyl]-2H-spiro[1-benzofuran-3,4'-piperidine]-1'-yl}-2-methylpropanoic acid, 3-{6-[2-(2,6-Diehlorophenyl)cyclopropyl]-2H-spiro[1-benzofuran-3,4'-piperidine]-1'-yl}propanoic acid, 3[6-(2-Phenylcyclopropyl)-2H-spiro[1-benzofuran-3,4'-piperidine]-1'-yl]propanoic acid, 3-{6[2-(2-Fluorophenyl)cyclopropyl]-2H-spiro[1-benzofuran-3,4'-piperidine]-1'-yl}propanoic acid, 3-{6-[2-(2-Chlorophenyl)cyclopropyl]-2H-spiro[1-benzofuran-3,4'-piperidine]-1'-yl}propanoic acid, 3-{6-[2-(2-Chloro-5-ethylphenyl)cyclopropyl]-2H-spiro[1-benzofuran-3,4'-piperidine]-1'-yl}propanoic acid, 3-{6[2-(4-Butyl-2,6-dichlorophenyl)cyclopropyl]-2H-spiro[1-benzofuran-3,4'-piperidine]-1'-yl}propanoic acid, 3-{6-Benzyl-2H-spiro[1-benzofuran-3,4'-piperidine]-1'-yl}propanoic acid, 3-[6-(2-Phenylethyl)-2H-spiro[1-benzofuran-3,4'-piperidine]-1'-yl]propanoic acid, 3-{6-[2-(2,6-Diehlorophenyl)ethyl]-2H-spiro[1-benzofuran-3,4'-piperidine]-1'-yl}propanoic acid, 3-{6[2-(2-Fluorophenyl)ethyl]-2H-spiro[1-benzofuran-3,4'-piperidine]-1'-yl}propanoic acid, 3-[6-(Phenoxymethyl)-2H-spiro[1-benzofuran-3,4'-piperidine]-1'-yl]propanoic acid, 3-[6-(Phenylamino)-2H-spiro[1-benzofuran-3,4'-piperidine]-1'-yl]propanoic acid, 3-{6-[(2,6-Dichlorophenyl)methoxy]-2H-spiro[1-benzofuran-3,4'-piperidine]-1'-yl}butanoic acid, 3-{6-[(2,6-Dichlorophenyl)methoxy]-2H-spiro[1-benzofuran-3,4'-piperidine]-1'-yl}-2,2-difluoropropanoic acid, 3-{6-[(2,6-Dichlorophenyl)methoxy]-2H-spiro[1-benzofuran-3,4'-piperidine]-1'-yl}-2,2-dimethylpropanoic acid, (2-{(6-[(2,6-Dichlorophenyl)methoxy]-2H-spiro[1-benzofuran-3,4'-piperidine]-1'-yl}-ethoxy)phosphonic acid, 6-[(2,6-Dichlorophenyl)methoxy]-1'-(1H-1,2,3,4-tetrazol-5-yl)ethyl]-2H-spiro[1-benzofuran-3,4'-piperidine], (3-{6-[(2,6-Dichlorophenyl)methoxy]-2H-spiro[1-benzofuran-3,4'-piperidine]-1'-yl}-propyl)phosphonic acid, 3-{6-[(2,6-Dichlorophenyl)methoxy]-2H-spiro[1-benzofuran-3,4'-piperidine]-1'-yl}-3-oxopropanoic acid, 3-{6-[((2,6-Dichlorophenyl)carbamoyl)]-2H-spiro[1-benzofuran-3,4'-piperidine]-1'-yl}propanoic acid, 3-{6-[(2-Chlorophenyl)methoxy]-2H-spiro[1-benzofuran-3,4'-piperidine]-1'-yl}propanoic acid,
3-[6-(Benzyloxy)-2H-spiro[1-benzofuran-3,4'-piperidine]-1'-yl]propanoic acid,
3-{6-[(4-Chlorophenyl)methoxy]-2H-spiro[1-benzofuran-3,4'-piperidine]-1'-yl}propanoic acid,
3-[6-(4-Phenylbutoxy)-2H-spiro[1-benzofuran-3,4'-pipetidine]-1'-yl]propanoic acid,
3-[6-(2,3Dihydro-1-benzofuran-2-ylmethoxy)-2H-spiro[1-benzofuran-3,4'-piperidine]-1'-yl]propanoic acid,
3-[6-(2-Phenoxyethoxy)-2H-spiro[1-benzofuran-3,4'-piperidine]-1'-yl]propanoic acid,
3-[6-(2-Phenoxypropoxy)-2H-spiro[1-benzofuran-3,4'-piperidine]-1'-yl]propanoic acid,
3-[6-(2-Phenoxybutoxy)-2H-spiro[1-benzofuran-3,4'-piperidine]-1'-yl]propanoic acid,
Tert-butyl 3-{6-[3(Benzyloxy)propoxy]-2H-spiro[1-benzofuran-3,4'-piperidine]-1'-yl}-propanoic acid,
3-[6-(2-,3-Dihydro-1,4-benzodioxin-2-ylmethoxy)-2H-spiro[1-benzofuran-3,4'-piperidine]-1'-yl]propanoic acid,
3-(6-{[3-(4-Tert-butylphenyl)-1,2,4-oxadiazol-5-yl]methoxy}-2H-spiro[1-benzofuran -3,4'-piperidine]-1'-yl)propanoic acid,
3-(6-{[4-(5-Methy-1,2,4-oxadiazol-3yl)phenyl]methoxy}-2H-spiro[1-benzofuran-3,4'-piperidine]-1'-yl)propanoic acid,
3-(6-{[4-(1H-Pyrazol-1-yl)phenyl]methoxy}-2H-spiro[1-benzofuran-3,4'-piperidine]-1'-yl)propanoic acid,
3-(6-{[4-(1H-1,2,4-Triazol-1-yl)phenyl]methoxy}-2H-spiro[1-benzofuran-3,4'-piperidine]-1'-yl)propanoic acid,
3-{6-[(2-Methyl-1,3-thiazo1-4-yl)methoxy]-2H-spiro[1-benzofuran-3,4'-piperidine]-1'-yl}propanoic acid,
3-{6-[(1-Methyl-1H-pyrazol-3yl)methoxy]-2H-spiro[1-benzofuran-3,4'-piperidine]-1'-yl}propanoic acid,
3-[6-({6-Methylimidazol[1,2-a]pyridin-2yl}methoxy)-2H-spiro[1-benzofuran-3,4'-piperidine]-1'-yl]propanoic acid,
3-{6[2-(Naphtalen-2-yloxy)ethoxy]-2H-spiro[1-benzofuran-3,4'-piperidine]-1'-yl}propanoic acid,
3-(6-{3-[(2-Propyl- 1,3-thiazol -5-yl)oxy]propoxy}-2H-Spiro[1-benzofuran-3,4'-piperidine]-1'-yl)propanoic acid,
3-{6-[(Phenylcarbamoyl)methoxy]-2H-spiro[1-benzofuran-3,4'-piperidine]-1'-yl}propanoic acid,
3-{6[2-(Benzyloxy)ethoxy]-2H-spiro[1-benzofuran-3,4'-pipetidine]-1'-yl}propanoic acid,
3-{6-[(4-Methanesulfonylphenyl)methoxy]-2H-spiro[1-benzofuran-3,4'-piperidine]-1'yl}-propanoic acid,
3-{6-[(2-Methylphenyl)carbonyl]-2H-spiro[1-benzofuran-3,4'-piperidine]-1'-yl}propanoic acid,
3-{6-Benzoyl-2H-spiro[1-benzofuran-3,4'-piperidine]-1'-yl}propanoic acid,
3{6-[(2-Chlorophenyl)carbonl]-2H-spiro[1-benzofuran-3,4'-piperidine]-1'-yl}propanoic acid,
3-{6-[(2E)-3Phenylprop-2-enoyl]-2H-spiro[1-benzofuran-3,4'-piperdine]-1'-yl}propanoic acid,
3-{6-[(2E)-3-(2-Chlorophenyl)prop-2-enoyl]-2H-Spiro[1-benzofuran-3,4'-piperdine]-1'-yl}propanoic acid,
3-{6-[(1Benzofuran-2-yl)carbonyl]-2H-spiro[1-benzofuran-3,4'-piperidine]-1'-yl}propanoic acid,
3-{6-[(2-Phenylcyclopropyl)carbonyl]-2H-spiro[1-benzofuran-3,4'-piperidine]-1'-yl}propanoic acid,
3-[6-(3phenylpropanoyl)-2H-spiro[1-benzofuran-3,4'-piperidine]-1'-yl]propanoic acid,
3-[6-(2,6-Dichlorophenoxy)-2H-spiro[1-benzofuran-3,4'-piperidine]-1'-yl]propanoic acid,
3-{(6-Phenoxy)-2H-spiro[1-benzofuran-3,4'-piperidine]-1'-yl}propanoic acid,
3-[6-(2,6-Dimethylphenoxy)-2H-spiro[1-benzofiiran-3,4'-piperidine]-1'-yl]propanoic acid,
3-{6-[(2,6-Dichlorophenyl)methoxy]-2H-spiro[1-benzofuran-3,4'-piperidine]-1'-yl}cyclobutane-1-carboxylic acid,
3-(6-{[2-fluoro-6-(propan-2-yl)phenyl]methoxy}-2H-spiro[1-benzofuran-3,4'-piperidine]-1'-yl)propanoic acid,
3-{6-[(2-cyclopropyl-6-fluoroplienyl)methoxy]-2H-spiro[1-benzofuran-3,4'-piperidine]-1'-yl}propanoic acid,
3-{6-[(2-ethyl-6-fluorophenyl)methoxyl]-2H-spiro[1-benzofuran-3,4'-piperidine]-1'-yl}propanoic acid,
3-(6-{[2-fluoro-6-(trifluoroimethyl)phenyl ]methoxy}-2H-spirol[1-benzofuran-3,4'-piperidine]-1'-yl)propanoic acid,
3-{6-[(4-chloro-2,6-difluorophenyl)methoxy]-2H-spiro[1-benzofuran-3,4'-piperidine]-1'-yl}propanoic acid,
3-{6-[1-(2,6-dichlorophenyl)ethoxyl-2H-spiro[1-benzofuran-3,4'-piperidine]-1'-yl}propanoic acid,
3-{6-[(2,6-diethylphenyl)methoxy]-2H-spiro[1-benzofuran-3,4'-piperidine]1'-yl}propanoic acid,
3-(6-{[2-(propan-2-yl)phenyl]methoxy}-2H-spiro[1-benzofuran-3,4'-piperidine]-1'-yl)propanoic acid,
3-(6-{[2-ethyl-6-(trifluoromethyl)phenyl]methoxy}-2H-spiro[1-benzofuran-3,4'-piperidine]-1'-yl)propanoic acid,
3-(6-{[2-Chloro-6-(difluoromethoxy)phenyl]methoxy}-2H-spiro[1-benzofuran-3,4'-piperidine]-1'-yl)propanoic acid,
3-{6-[(2-Fluoro-6-methoxyphenyl)methoxy]-2H-spiro[1-benzofuran-3,4'-piperidine]-1'-yl}propanoic acid,
3-{6-[(2-ethyl-6-fluorophenyl)methoxy]-2H-spiro[1-benzofuran-3,4'-piperdine]-1'-yl}-2-methylpropanoic acid,
3-{6-[(2-cyclopropyl-6-fluorophenyl)methoxy]-2H-spiro[1-benzofuran-3,4'-piperidine]-1'-yl}-2-methylpropanoic acid,
3-(6-{[2-fluoro-6-(propan-2-yl)phenyl]methoxy}-2H-spiro[1-benzofuran-3,4'-piperidine]-1'-yl)-2-methylpropanoic acid,
2-methyl-3-(6-{[2-(trifluorornethyl)phenyl]methoxy}-2H-spiro[1-benzofuran-3,4'-piperidine]-1'-yl)propanoic acid,
2-{6-[(2,6-dichloro-3methoxyphenyl)methoxy]-2H-spiro[1-benzofuran-3,4'-piperidine]-1'-yl}acetic acid,
1'-(3Carboxypropyl)-6-[(2-Chloro-6-ethylphenyl)methoxy]-2H-spiro[1-benzofuran -3,4'-piperidin]-1'-ium-1'olate,
3-{6-[(2-Chloro-6-ethylophenyl)methoxy]-7-fluoro-2H-spiro[1-benzofuran-3,4'-piperidine]-1'-yl}propanoic acid,
3-{6-[(2-Chloro-6-fluorophenyl)methoxy]-7-fluoro-2H-spiro[1-benzofuran-3,4'-piperidine]-1'-yl}propanoic acid,
3-{6-[(2-Chloro-6-(propan-2-yl)phenyl)methoxy[-7-fluoro-2H-spiro[1-benzofuran-3,4'-piperidine]-1'-yl}propanoic acid,
3-{6-[(2-Chloro-6-cyclopropylphenyl)methoxy]-7-fluoro-2H-spiro[1-benzofuran-3,4'-piperidine]-1'-yl}propanoic acid,
3-{6-[(2-Cyclopropyl-6-fluorophenyl)methoxy[-7-fluoro-2H-spiro[1-benzofuran- 3,4'-piperidine]-1'-yl}propanoic acid, 3-(7-fluoro-6-{[2-fluoro-6-(propan-2-yl)phenyl] methoxy}-2H-spiro[1-benzofuran-3,4'-piperidine]-1'-yl)propanoic acid,
3-[6-(Cyclohexylethoxy)-7-fluoro-2H-spiro[1-benzofuran-3,4'-piperidine]-1'-yl]propanoic acid,
3-[6-(3Cyclohexylpropoxy)-7-fluoro-2H-spiro[1-benzofuran-3,4'-piperidine]-1'-yl]propanoic acid,
3-{6-[(2,6-Dichlorophenyl)methoxy]-5-fluoro-2H-spiro[1-benzofuran-3,4'-piperidine]-1'-yl}propanoic acid,
3-{6-[(2-Chloro-6-ethylphenyl)methoxy]-5-fluoro-2H-spiro[1-benzofuran-3,4'-piperidine]-1'-yl}propanoic acid,
3-{7-Chloro-6-[(2-chloro-6-cyclopropylphenyl) methoxy]-2H-spiro[1-benzofuran-3,4'-piperidine]-1'-yl}propanoic acid,
3-(7-Chloro-6-{[2-fluoro-6-(propan-2-yl)phenyl] methoxy}-2H-spiro[1-benzofuran-3,4'-piperidine]-1'-yl)propanoic acid,
3-(6-{[(2-Cyclopropyl-6-fluorophenyl)methyl]sulfanyl}-2H-spiro[1-benzofuran-3,4'-piperidine]-1'-yl)propanoic acid,
3-[6-({[2-Fluoro-6-(propan-2-yl)phenyl] methyl}sulfanyl)-2H-spiro[1-benzofuran-3,4'-piperidine]-1'-yl]propanoic acid,
3-(6-{[(2,6-Dichlorophenyl)methyl]sulfany}-2H-spiro[1-benzafuran-3,4'-piperidin]-1'-yl)propanoic acid,
3-(6-{[(2-Chloro-6-ethylphenyl)methyl]sulfanyl}-2H-spiro[1-benzofuran-3,4'-piperidine]-1'-yl)propanoic acid,
3-(6-{[(2-Chloro-6-cyclopropylphenyl)methyl]sulfanyl}-2H-spiro[1-benzofuran-3,4'-piperidine]-1'-yl)-2-methylpropanoic acid,
3-(6-{[(2,6-Dichlorophenyl)methane]sulfonyl}-2H-spiro[1-benzofuran-3,4'-piperidine]-1'-yl)propanoic acid,
3-(6-{[(2,6-Dichlorophenyl)methane]sulfinyl}-2H-spiro[1-benzofuran-3,4'-piperidine]-1'-yl)propanoic acid,
3-{6-[(E)-2-(2Chloro-6-fluorophenyl)ethenyl]-2H-spiro[1-benzofuran-3,4'-piperidine]-1'-yl}propanoic acid,
3-{6-[(E)-2-(2-Cyclopropyl-6-fluorophenyl)ethenyl]-2H-spiro[1-benzofuran-3,4'-piperidine]-1'-yl}propanoic acid,
3-[6-(2-Phenylethynyl)-2H-spiro[1-benzofuran-3,4'-piperidine]-1'-yl]propanoic acid,
3-{6[2-(2-Chlorophenyl)ethynyl]-2H-spiro[1-benzofuran-3,4'-piperidine]-1'-yl}propanoic acid,
4-{6-(2,6-Dichlorophenyl)methoxy]-2H-spiro[1-benzofuran-3,4'-piperdine]-1'-yl}-3-methylbutanoic acid,
4-{6-[(2,6-Dichlorophenyl)methoxy]-2H-spiro[1-benzofuran-3,4'-piperidine]-1'-yl}pentanoic acid,
2-Methyl-4-{6-[(2,4,6-trichlorophenyl)methoxy]-2H-spiro[1-benzofuran-3,4'-piperidine]-1'-yl}butanoic acid,
4-{6-[(2,6-Dichlorophenyl)methoxy]-2H-spiro[1-benzofuran-3,4'-piperidine]-1'-yl}-2-methylbutanoic acid,
4-{6-[(2-Chloro-6-ethylphenyl)methoxyl]-2H-spiro[1-benzofuran-3,4'-piperidine]-1'-yl}-yl}-2-methylbutanoic acid,
4-{6-[(2-Chloro-6-fluorophenyl)methoxy]-2H-spiro[1-benzofuran-3,4'-piperidine]-1'-yl}-2-methylbutanoic acid,
3-{6-[(2,6-Dichlorobenzene)amido]-2H-spiro[1-benzofuran-3,4'-piperdine]-1'-yl}propanoic acid,
3-{6-[(2,6-Difluorobenzene)amido]-2H-spiro[1-benzofuran-3,4'-piperidine]-1'-yl}propanoic acid,
2-{6[(2-Dichlorophenyl)methoxy]-2H-spiro[1-benzofuran-3,4'-piperidine]-1'-yl}cyclopentane-1-carboxylic acid,
3-{6-[(2-Chloro-6-ethylphenyl)methoxy]-2H-spiro[1-benzofuran-3,3'-piperdine]-1'-yl}propanoic acid,
3-{6-[(2-Cyclopropyl-6-fluorophenyl)methoxy]-2H-spiro[1-benzofuran-3,3'-piperidine]-1'-yl}propanoic acid,
3-(6-{[2-Chloro-6-(propan-2-y)phenyl]methoxy}-2H-spiro[1-benzofuran-3,3'-piperidine]-1'-yl)propanoic acid,
3-{6[(2-Chloro-6-cycoprylphenyl)methoxy]-2H-spiro[1-benxofuran-3,3'-piperidine]-1'-yl}propanoic acid,
3-{6-[(2-Chloro-6-fluorophenyl)methoxy]-2H-spiro[1-benzofuran-3,3'-piperidine]-1'-yl}propanoic acid,
3-{6-[(2,6-Dichloro-3ethylphenyl)methoxy]-2H-spiro[-benzofuran-3,3'-piperidine]-1'-yl}propanoic acid,
3-{6-[(4-Butyl-2,6-dichlorophenyl)methoxyl]-2H-spiro[1-benzofuran-3,3'-piperidine]-1'-yl}propanoic acid,
3-{6-[(2,6-Dichlorophenyl)methoxy]-2H-spiro[1-benzofuran-3,3'-piperidine]-1'-yl}propanoic acid,
3-{6-[(2,4,6-Trichlorophenyl)methoxy]-2H-spiro[1-benzofuran-3,3'-piperidine]-1'-yl}propanoic acid,
3-{6-[(3,5-Dichlorophenyl)methoxy]-2H-spiro[1-benzofuran-3,3'-piperidine]-1'-yl}propanoic acid,
3-{6-[(2,5-Dichlorophenyl)methoxy]2H-spiro[1-benzofuran-3,3'-piperidine]-1'-yl}propanoic acid,
3-{6-[(2-Chloro-6-methylphenyl)methoxy]-2H-spiro[1-benzofuran-3,3'-piperidine]-1'-yl}propanoic acid,
3-(6-{[2-Chloro-6-(trifluoromethyl)phenyl]methoxy}-2H-spiro[1-benzofuran-3,3'-piperidine]-1'-yl)propanoic acid,
3-{6[1-(2,6-Dichlorophenyl)ethoxy]-2H-spiro[-benzofuran-3,3'-piperidine]-1'-yl}propanoic acid, and
3-(6-{[2-Fluoro-6-(trifluoromethyl)phenyl]methoxy}-2H-spiro[1-benzofuran-3,3'-piperidine]-1'-yl)propanoic acid, or a pharmaceutically acceptable salt, solvate, or hydrate thereof, or an N-oxide of any of the foregoing.

12. A method of treating and/or alleviating a disease and/or condition selected from the group consisting of age-related cognitive decline, Alzheimer's disease, dementia, Niemann Pick disease, cognitive deficits in schizophrenia, obsessive-compulsive behavior, major depression, autism, multiple sclerosis, and pain, the method comprising administering to a patient in need thereof a compound according to claim 1, or a pharmaceutically acceptable salt, solvate, or hydrate thereof, or an N-oxide of any of the foregoing.

13. The method of claim 12 wherein the dementia is vascular dementia.

14. A pharmaceutical composition comprising the compound of claim 1 and at least one pharmaceutically acceptable auxiliary.

15. A method of treating and/or alleviating a disease and/or condition selected from the group consisting of age-related cognitive decline, Alzheimer's disease, dementia, Niemann Pick disease, cognitive deficits in schizophrenia, obsessive-compulsive behavior, major depression, autism, multiple sclerosis, and pain, the method comprising administering to a patient in need thereof the pharmaceutical composition according to claim 14.

16. The method of claim 15, wherein the dementia is vascular dementia.

17. A process for the preparation of a compound according to claim 1 having formula (I), wherein ring A is a piperidiny, R2 is H or one or two substituents selected from the group consisting of a fluoro atom, (1-4C)alkyl, and (1-4C)alkoxy; —W-T- is —O—CH2-; and Z is selected from the group consisting of CH and CR2, said process comprising an intramolecular Heck cyclization step wherein a compound of formula (V),

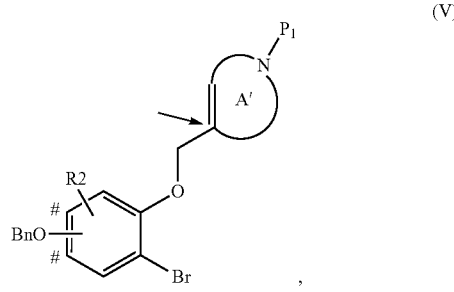

wherein A' represents a 6- membered cyclic amine with a double bond at the carbon atom indicated with an arrow, P1 is a protecting group selected from the group consisting of —CO$_2$-benzyl and —CO$_2$-(1-4C)alkyl, Bn is benzyl and the BnO-group may be attached at one of the sites indicated with #,
is converted in a suitable solvent at elevated temperature, in the presence of silver carbonate and a Herrmann-Beller catalyst, into a compound of formula (VI),

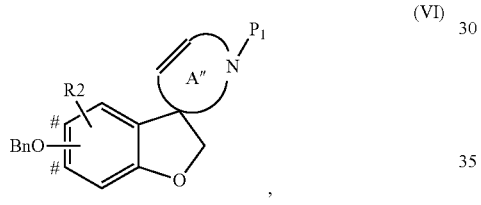

wherein A" represents a 6- membered cyclic amine with a double bond at a position shifted one or two positions, depending on the position of the nitrogen atom in the ring, with regard to ring A' of the compound of formula (V), whereafter the compound of formula (VI) is deprotected and substituted with R3 and R1-Y—(C$_n$-alkylene)-X as defined in claim 1 to produce the compound of formula (I).

18. The compound of claim 1, which is 3-{6-[(2-Chloro-6-ethylphenyl)methoxy]-2H-spiro[1-benzofuran-3,4'-piperidine]-1'-yl}-2-methylpropanoic acid, or a pharmaceutically acceptable salt, solvate, or hydrate thereof, or an N-oxide of any of the foregoing.

19. The compound of claim 1, which is 3-{6-[(E)-2-(2,6-Dichlorophenyl)ethenyl]-2H-spiro[1-benzofuran-3,4'-piperidine]-1'-yl}propanoic acid, or a pharmaceutically acceptable salt, solvate, or hydrate thereof, or an N-oxide of any of the foregoing.

20. The compound of claim 1, which is 3-{6-[(E)-2-(2,6-Dichorophenyl)ethenyl]-2H-spiro[1-benzofuran-3,4'-piperidine]-1'-yl}-2-methylpropanoic acid,
or a pharmaceutically acceptable salt, solvate, or hydrate thereof, or an N-oxide of any of the foregoing.

21. The compound of claim 1, which is 3-[6-(2-Phenylethynyl)-2H-spiro [1-benzofuran-3,4'-piperidine]-1'-yl]propanoic acid, or a pharmaceutically acceptable salt, solvate, or hydrate thereof, or an N-oxide of any of the foregoing.

22. A compound selected from the group consisting of:
6-[(2,6-Dichlorophenyl)methoxy]-2H-spiro[1-benzofuran-3,4'-piperidine],
6-[(2,6-Dichlorophenyl)methoxy]-1'-methyl-2H-spiro[1-benzofuran-3,4'-piperidine],
2-{6-[(2,6-Dichlorophenyl)methoxy]-2H-spiro[1-benzofuran-3,4'-piperidine]-1'-yl}ethan-1-ol, and
3-{6-[(2,6-Dichlorophenyl)methoxy]-2H-spiro[1-benzofuran-3,3'-pyrrolidine]-1'-yl}propanoic acid,
or a pharmaceutically acceptable salt, solvate, and hydrate thereof, or an N-oxide of any of the foregoing.

* * * * *